US010695414B2

(12) United States Patent
Kew et al.

(10) Patent No.: US 10,695,414 B2
(45) Date of Patent: Jun. 30, 2020

(54) MODULATION OF REPLICATIVE FITNESS BY DEOPTIMIZATION OF SYNONYMOUS CODONS

(71) Applicant: The Government of the USA as represented by the Secretary of the Dept. of Health and Human Services, Atlanta, GA (US)

(72) Inventors: Olen M. Kew, Alpharetta, GA (US); Cara Carthel Burns, Avondale Estates, GA (US); Jing Shaw, Decatur, GA (US); Raymond Campagnoli, Decatur, GA (US); Jacqueline Quay, Chapel Hill, NC (US)

(73) Assignee: The Government of the United States of America as represented by the Secretary of the Department of Health and Human Services, Center for Disease Control and Prevention, Atlanta, GA (US)

( * ) Notice: Subject to any disclaimer, the term of this patent is extended or adjusted under 35 U.S.C. 154(b) by 0 days.

(21) Appl. No.: 15/994,074

(22) Filed: May 31, 2018

(65) Prior Publication Data

US 2018/0264098 A1 Sep. 20, 2018

Related U.S. Application Data

(62) Division of application No. 15/684,355, filed on Aug. 23, 2017, which is a division of application No. 14/464,619, filed on Aug. 20, 2014, now abandoned, which is a division of application No. 11/576,941, filed as application No. PCT/US2005/036241 on Oct. 7, 2005, now Pat. No. 8,846,051.

(60) Provisional application No. 60/617,545, filed on Oct. 8, 2004.

(51) Int. Cl.

| | |
|---|---|
| ***A61K 39/04*** | (2006.01) |
| ***A61K 39/108*** | (2006.01) |
| ***A61K 39/00*** | (2006.01) |
| ***C07K 14/245*** | (2006.01) |
| ***C12N 15/67*** | (2006.01) |
| ***C12N 7/00*** | (2006.01) |

(52) U.S. Cl.

CPC .......... *A61K 39/0258* (2013.01); *A61K 39/00* (2013.01); *C07K 14/245* (2013.01); *C12N 7/00* (2013.01); *C12N 15/67* (2013.01); *A61K 2039/522* (2013.01); *A61K 2039/5254* (2013.01); *C12N 2710/16162* (2013.01); *C12N 2710/16662* (2013.01); *C12N 2710/16762* (2013.01); *C12N 2760/16162* (2013.01); *C12N 2760/18462* (2013.01); *C12N 2760/18562* (2013.01); *C12N 2770/20062* (2013.01); *C12N 2770/24162* (2013.01); *C12N 2770/32162* (2013.01); *C12N 2770/32762* (2013.01); *C12N 2770/36262* (2013.01); *Y02A 50/466* (2018.01); *Y02A 50/472* (2018.01); *Y02A 50/476* (2018.01)

(58) Field of Classification Search

None

See application file for complete search history.

(56) References Cited

FOREIGN PATENT DOCUMENTS

| | | |
|---|---|---|
| WO | WO 95/09249 | 4/1995 |
| WO | WO 02/077183 | 10/2002 |
| WO | WO 02/095363 | 11/2002 |

OTHER PUBLICATIONS

Agashe et al., "Good Codons, Bad Transcript: Large Reductions in Gene Expression and Fitness Arising from Synonymous Mutations in a Key Enzyme," *Mol. Biol. Evol.*, vol. 30, No. 3, pp. 549-560, 2012.

Amino Acid and Codon Table (pdf); www.cbs.dtu.dk/courses/27619/codon.html; downloaded from internet by sws; Apr. 26, 2012.

Baltimore System Group IV viruses (pdf); copied from www.virology.net/Big_Virology/BVFamilyGroup.html#IV; created Aug. 26, 2012 by sws.

Baltimore System Group IV Viruses (pdf); downloaded from internet by ses; Apr. 26, 2012.

Bennetzen and Hall, "Codon Selection in Yeast," *J. Biol. Chem.* 257:3026-3031, 1982.

Bonekamp et al., "Translation Rates of Individual Codons Are Not Correlated with tRNA Abundances or with Frequencies of Utilization in *Escherichia coli," Journal of Bacteriology*, vol. 171, No. 11, pp. 5812-5816, 1989.

Bradel-Tretheway et al., "Effects of codon-optimization on protein expression by the human herpesvirus 6 and 7 U51 open reading frame," *Journal of Virological Methods*, vol. 111, pp. 145-156, 2003.

Burns et al., "Modulation of Poliovirus Replicative Fitness in HeLa Cells by Deoptimization of Synonymous Codon Usage in the Capsid Region," *J. Virol.* vol. 80, pp. 3259-3272, 2006.

Carlini and Stephan, "In Vivo Introduction of Unpreferred Synonymous Codons into the *Drosophila* Adh Gene Results in Reduced Levels of ADH Protein," *Genetics* vol. 163, pp. 239-243, 2003.

(Continued)

*Primary Examiner* — Jennifer E Graser

(74) *Attorney, Agent, or Firm* — Klarquist Sparkman, LLP

(57) ABSTRACT

Methods of producing a pathogen with reduced replicative fitness are disclosed, as are attenuated pathogens produced using the methods. In particular examples, the method includes deoptimizing one or more codons in a coding sequence, thereby reducing the replicative fitness of the pathogen. Methods of using the attenuated pathogens as immunogenic compositions are also disclosed.

17 Claims, 63 Drawing Sheets

Specification includes a Sequence Listing.

(56) References Cited

OTHER PUBLICATIONS

Carter et al., "Transcription Attenuation in *Salmonella typhimurium*: The Significance of Rare Leucine Codons in the leu Leader," *Proc. Natl. Acad. Sci. USA*, vol. 83, No. 21, pp. 8127-8131, 1986.
Cherkasova et al., "Long-Term Circulation of Vaccine-Derived Poliovirus that Causes Paralytic Disease," *J. Virol.* vol. 76, pp. 6791-6799, 2002.
Christodoulou et al., "Mapping of Mutations Associated with Neurovirulence in Monkeys Infected with Sabin 1 Poliovirus Revertants Selected at High Temperature," *J. Virol.* vol. 64, pp. 4922-4929, 1990.
Dejiang et al., "Silencing of potato virus X coat protein gene in transgenic tobaccos by codon replacement that confers resistance to PVX infection," *Chinese Science Bulletin*, vol. 48, No. 15, pp. 1592-1598, 2003.
Eriani et al., "Isolation and Characterization of the Gene Coding for *Escherichia coli* arginyl-tRNA synthetase," *Nucl. Acids Res.*, vol. 17, No. 14, pp. 5725-5736, 1989.
Gavrilin et al., "Evolution of Circulating Wild Poliovirus and of Vaccine-Derived Poliovirus in an Immunodeficient Patient: a Unifying Model," *J. Virol.* vol. 74, pp. 7381-7390, 2000.
Georgescu et al., "Mapping of Mutations Contributing to the Temperature Sensitivity of the Sabin 1 Vaccine Strain of Poliovirus," *J. Virol.* vol. 69, pp. 5278-5286, 1995.
Hoekema et al., "Codon Replacement in the PKG1 Gene of *Saccharomyces cerevisiae*: Experimental Approach to Study the Role of Biased Codon Usage in Gene Expression," *Mol. Cell. Biol.* vol. 7, pp. 2914-2924, 1987.
Ikemura, "Codon Usage and tRNA Content in Unicellular and Multicellular Organisms," *Molecular Biology and Evolution*, vol. 2, No. 1, pp. 13-34, 1985.
Kew et al., "Prolonged Replication of a Type 1 Vaccine-Derived Poliovirus in an Immunodeficient Patient," *J Clin. Microbial*, vol. 36, No. 10, pp. 2893-2899, 1998.
Khetsuriani et al., "Persistence of Vaccine-Derived Polioviruses among Immunodeficient Persons with Vaccine-Associated Paralytic Poliomyelitis," *J. Infect. Dis.*, vol. 188, pp. 1845-1852, 2003.
Kinney et al., "Construction of Infectious cDNA Clones for Dengue 2 Virus: Strain 16681 and Its Attenuated Vaccine Derivative, Strain PDK-53," *Virology*, vol. 230, pp. 300-308, 1997.
Lamonica et al., "Mapping of Sequences Required for Mouse Neurovirulence of Poliovirus Type 2 Lansing," *J. Virol.*, vol. 57, No. 2, pp. 515-525, 1986.
Lee et al., "Novel Design Architecture for Genetic Stability of Recombinant Poliovirus: the Manipulation of G/C Contents and their Distribution Patterns Increases the Genetic Stability of Inserts in a Poliovirus-Based RPS-Vax Vector System," *J. Virol.*, vol. 76, pp. 1649-1662, 2002.
Lemm et al., "Mutations Which Alter the Level or Structure of nsP4 Can Affect the Efficiency of Sindbis Virus Replication in a Host-Dependent Manner," *J. Virol.*, vol. 64, pp. 3001-3011, 1990.
Macadam et al., "Genetic Basis of Attenuation of the Sabin Type 2 Vaccine Strain of Poliovirus in Primates," *Virology*, vol. 192, pp. 18-26, 1993.
Mueller et al., "Reduction of the rate of poliovirus protein synthesis through large-scale codon deoptimization causes attenuation of viral virulence by lowering specific infectivity," *J. Virol*, vol. 80, pp. 9687-9696, 2006.
Pevear et al., "Localization of genomic regions specific for the attenuated, mouse-adapted poliovirus type 2 strain W-2," *J. Gen. Virol.*, vol. 71, pp. 43-52, 1990.
Ramakrishna et al., "Codon Optimization of the Tat Antigen of Human Immunodeficiency Virus Type 1 Generates Strong Immune Responses in Mice Following Genetic Immunization," *J. Virol.*, vol. 78, pp. 9174-9189, 2004.
Ren et al., "Identification of Two Determinants that Attenuate Vaccine-Related Type 2 Poliovirus," *J. Virol.*, vol. 65, pp. 1377-1382, 1991.
Robinson et al., "Codon Usage Can Affect Efficiency of Translation of Genes in *Escherichia coli*," *Nucl. Acids Res.*, vol. 12, pp. 6663-6671, 1984.
Rothberg and Wimmer, "Mononucleotide and Dinucleotide Frequencies, and Codon Usage in Poliovirion RNA," *Nucl. Acids Res.*, vol. 9, pp. 6221-6229, 1981.
Sharp and Li, "The codon adaptation index—a measure of directional synonymous codon usage bias and its potential applications," *Nucl. Acids Res.*, vol. 15, No. 3, 1987.
Song et al., "High-level Expression of Codon Optimized Foot-and-Mouth Disease Virus Complex Epitopes and Cholera Toxin B Subunit Chimera in *Hansenula polymorpha,*" *Biochem. Biophys. Res. Commun.*, vol. 315, pp. 235-239, 2004.
Statford et al., "Influence of Codon Usage on the Immunogenicity of a DNA Vaccine Against Tetanus," *Vaccine*, vol. 19, pp. 810-815, 2000.
Stenico et al., "Codon usage in Caenorhabditis elegans: delineation of translational selection and mutational biases," *Nucl. Acids Res.*, vol. 22, No. 13, pp. 2437-2446, 1994.
Tatem et al., "A Mutation Present in the Amino Terminus of Sabin 3 Poliovirus VP1 Protein is Attenuating," *J. Virol.*, vol. 66, pp. 3194-3197, 1992.
Wilmes-Riesenberg et al., "An Altered rpoS Allele Contributes to the Avirulence of *Salmonella typhimurium* LT2," *Infection and Immunity*, vol. 65, No. 1, pp. 203-210, 1997.
Zhou et al., "Papillomavirus Capsid Protein Expression Level Depends on the Match between Codon Usage and tRNA Availability," *J. Virol.*, vol. 73, pp. 4972-4982, 1999.
Zhu et al., "The Relationship Between the Gene Expression Level of Classical Swine Fever Virus and the Synonymous Codon Usage," *J. Wuhan Univ.* vol. 49, pp. 252-256, 2003 (including English translation).

FIG. 1B

```
                           ↓ BstZ17I
       GAG TGT TGT GTC AGG TAT ACA ACT GTT TGT TGG AAC CAC TGT GTT AGC TTT ACT TCT CAT TTA ACC AAT TAA TCA
640    --- --- --- -+- --- --- --+ --- --- --- +-- --- --- -+- --- --- --+ --- --- --- +-- --- --- -+- ---   714

                                                   → VP4
       AAA ACA ATA CGA GGA TAA AAC AAC AAT ACT ACA ATG GGC GCC CAA GTT TCA TCA CAG AAA GTT GGA GCC CAC GAA
715    --- --+ --- --- --- +-- --- --- -+- --- --- --+ --- --- --- +-- --- --- -+- --- --- --+ --- --- ---   789
                                                         T   G       C AGC AGC           C   T   G
                                                   M   G   A   Q   V   S   S   Q   K   V   G   A   H   E

       AAT TCA AAC AGA GCC TAT GGC GGG TCC ACC ATC AAT TAC ACT ACA ATC AAT TAC TAT AGG GAC TCT GCA AGC AAT
790    +-- --- --- -+- --- --- --+ --- --- --- +-- --- --- -+- --- --- --+ --- --- --- +-- --- --- -+- ---   864
           AGC     C G   G       T   T AG    G               G   G                 C       AGC   G
       N   S   N   R   A   Y   G   G   S   T   I   N   Y   T   T   I   N   Y   Y   R   D   S   A   S   N

       GCA GCA AGC AAG CAA GAT TTT GCA CAA GAT CCG TCC AAG TTC ACC GAA CCC ATT AAG GAC GTC CTT ATT AAG ACC
865    --- --+ --- --- --- +-- --- --- -+- --- --- --+ --- --- --- +-- --- --- -+- --- --- --+ --- --- ---   939
         G   G                       G             AG            G       G   C                   C       G
       A   A   S   K   Q   D   F   A   Q   D   P   S   K   F   T   E   P   I   K   D   V   L   I   K   T
                           → VP2
       GCT CCC ATG CTA AAC TCC CCA AAC ATT GAG GCG TGT GGT TAT AGT GAC AGG GTA ATG CAG CTA ACT CTG GGC AAT
940    +-- --- --- -+- --- --- --+ --- --- --- +-- --- --- -+- --- --- --+ --- --- --- +-- --- --- -+- ---   1014
         G   G       T     AG    G       C                       C     C     C           T   G   T   T
       A   P   M   L   N   S   P   N   I   E   A   C   G   Y   S   D   R   V   M   Q   L   T   L   G   N

       TCA ACG ATC ACC ACC CAA GAA GCG GCC AAT TCT GTT GTT GCC TAC GGT AGA TGG CCT GAA TAC ATC AGA GAT ACC
1015   --- --+ --- --- --- +-- --- --- -+- --- --- --+ --- --- --- +-- --- --- -+- --- --- --+ --- --- ---   1089
       AGC               G               G     AGC   C   C   G         C G       G             C G       G
       S   T   I   T   T   Q   E   A   A   N   S   V   V   A   Y   G   R   W   P   E   Y   I   R   D   T

       GAG GCA AAT CCT GTA GAC CAA CCA ACC GAG CCC GAT GTA GCC GCG TGC AGG TTC TAC ACA TTA GAT ACC GTC ACT
1090   +-- --- --- -+- --- --- --+ --- --- --- +-- --- --- -+- --- --- --+ --- --- --- +-- --- --- -+- ---   1164
             G       G               G   G       G       C   G         C             G C T       G       G
       E   A   N   P   V   D   Q   P   T   E   P   D   V   A   A   C   R   F   Y   T   L   D   T   V   T

       TGG CGC AAG GAG TCC AGA GGG TGG TGG TGG AAA CTA CCA GAC GCT TTA AAA GAC ATG GGG TTA TTT GGT CAA AAC
1165   --- --+ --- --- --- +-- --- --- -+- --- --- --+ --- --- --- +-- --- --- -+- --- --- --+ --- --- ---   1239
             G         AG  C G   T                   T   G       G C T               T C T
       W   R   K   E   S   R   G   W   W   W   K   L   P   D   A   L   K   D   M   G   L   F   G   Q   N

       ATG TTT TAT CAC TAT CTT GGG AGG GCT GGC TAC ACA GTG CAC GTA CAG TGC AAT GCT TCA AAG TTT CAT CAA GGA
1240   +-- --- --- -+- --- --- --+ --- --- --- +-- --- --- -+- --- --- --+ --- --- --- +-- --- --- -+- ---   1314
                                 T C     G   T       G   C       C               G AGC                   T
       M   F   Y   H   Y   L   G   R   A   G   Y   T   V   H   V   Q   C   N   A   S   K   F   H   Q   G
           ↓ AvrII
       GCT CTA GGG GTG TTT GCA GTT CCA GAA ATG TGT TTA GCT GGT GAT AGC ACA ACT CAC ATG TTC ACA AAG TAC GAG
1315   --- --+ --- --- --- +-- --- --- -+- --- --- --+ --- --- --- +-- --- --- -+- --- --- --+ --- --- ---   1389
         C           C       G   C   G             C T   G               G   G               G
       A   L   G   V   F   A   V   P   E   M   C   L   A   G   D   S   T   T   H   M   F   T   K   Y   E

       AAT GCG AAT CCA GGC GAA AAA GGA GGT GAA TTC AAA GGG AGT TTC ACC CTT GAT ACC AAC GCC ACT AAC CCT GCA
1390   +-- --- --- -+- --- --- --+ --- --- --- +-- --- --- -+- --- --- --+ --- --- --- +-- --- --- -+- ---   1464
                     G   T           T                   T   C       G           G       G   G       G   G
       N   A   N   P   G   E   K   G   G   E   F   K   G   S   F   T   L   D   T   N   A   T   N   P   A

       CGG AAC TTC TGC CCA GTT GAT TAC CTC TTC GGG AGT GGA GTG CTG GTA GGG AAT GCA TTT GTT TAT CCA CAT CAA
1465   --- --+ --- --- --- +-- --- --- -+- --- --- --+ --- --- --- +-- --- --- -+- --- --- --+ --- --- ---   1539
                         G   C           T       T   C   T   C   T   C   T       G       C       G
       R   N   F   C   P   V   D   Y   L   F   G   S   G   V   L   V   G   N   A   F   V   Y   P   H   Q

       ATA ATA AAC CTG CGC ACT AAC AAC TGT GCT ACG CTA GTA TTG CCC TAT GTA AAC TCA CTC TCA ATA GAT AGC ATG
1540   +-- --- --- -+- --- --- --+ --- --- --- +-- --- --- -+- --- --- --+ --- --- --- +-- --- --- -+- ---   1614
         C   C       T   G   G               G       T   C C T   G       C     AGC   T AGC   C
       I   I   N   L   R   T   N   N   C   A   T   L   V   L   P   Y   V   N   S   L   S   I   D   S   M

       ACA AAG CAC AAC AAC TGG GGG ATC GCT ATC CTC CCC CTG GCG CCA CTA GAC TTT GCC ACT GAA TCT TCC ACT GAG
1615   --- --+ --- --- --- +-- --- --- -+- --- --- --+ --- --- --- +-- --- --- -+- --- --- --+ --- --- ---   1689
         G                       T       G       T   G   T       G   T           G   G     AGC AG    G
       T   K   H   N   N   W   G   I   A   I   L   P   L   A   P   L   D   F   A   T   E   S   S   T   E

       ATA CCC ATT ACA CTG ACC ATT GCT CCC ATG TGC TGC GAA TTC AAT GGT TTA CGC AAC ATC ACT GTG CCA AGA ACC
1690   +-- --- --- -+- --- --- --+ --- --- --- +-- --- --- -+- --- --- --+ --- --- --- +-- --- --- -+- ---   1764
         C   G   C   G   T   G   C   G   G                             C T   G           G   C   G C G   G
       I   P   I   I   L   T   I   A   P   M   C   C   E   F   N   G   L   R   N   I   T   V   P   R   T
           → VP3
       CAA GGA TTA CCA GTC CTG AAC ACT CCA GGG AGT AAC CAG TAC CTG ACC GCA GAC AAT TAC CAG TCT CCG TGT GCG
1765   --- --+ --- --- --- +-- --- --- -+- --- --- --+ --- --- --- +-- --- --- -+- --- --- --+ --- --- ---   1839
             T C T   G       T       G   G   T   C               T   G   G                 AGC
       Q   G   L   P   V   L   N   T   P   G   S   N   Q   Y   L   T   A   D   N   Y   Q   S   P   C   A

       ATA CCT GAG TTT GAT GTC ACT CCA CCC ATA GAC ATA CCA GGG GAG GTG CGC AAC ATG ATG GAA TTG GCG GAA ATA
1840   +-- --- --- -+- --- --- --+ --- --- --- +-- --- --- -+- --- --- --+ --- --- --- +-- --- --- -+- ---   1914
         C   G                   G   G   G   C       C   G   T       C   G                 C T           C
       I   P   E   F   D   V   T   P   P   I   D   I   P   G   E   V   R   N   M   M   E   L   A   E   I

       GAC ACC ATG ATA CCC CTC AAC TTG ACA AGT CAA CGC AAG AAC ACA ATG GAC ATG TAT AGA GTC GAG TTG AGC GAC
1915   --- --+ --- --- --- +-- --- --- -+- --- --- --+ --- --- --- +-- --- --- -+- --- --- --+ --- --- ---   1989
             G       C   G   T     C T   G   C       G           G                 C G         C T
       D   T   M   I   P   L   N   L   T   S   Q   R   K   N   T   M   D   M   Y   R   V   E   L   S   D
```

FIG. 1C

```
     ACG GCT CAC TCT GAC ACG CCG ATC TTG TGT CTC TCG TTG TCC CCC GCT TCA GAC CCC AGA TTG GCA CAC ACT ATG
1990 +-- --- --- -+- --- --- --+ --- --- --- +-- --- --- -+- --- --- --+ --- --- --- +-- --- --- -+- ---  2064
           G     AGC                 C T       T AGC     AG    G   G AGC       G C G C T   G       G
     T   A   H   S   D   T   P   I   L   C   L   S   L   S   P   A   S   D   P   R   L   A   H   T   M
                                                       ↓ PpuMI
     TTG GGT GAG ATA TTA AAT TAC TAC ACA CAC TGG GCA GGG TCC TTG AAA TTT ACC TTT CTC TTT TGC GGC TCA ATG
2065 --- --+ --- --- --- +-- --- --- -+- --- --- --+ --- --- --- +-- --- --- -+- --- --- --+ --- --- ---  2139
     C T           C C T               G           G                       G       T           T AGC
     L   G   E   I   L   N   Y   Y   T   H   W   A   G   S   L   K   F   T   F   L   F   C   G   S   M

     ATG GCC ACC GGA AAG TTA TTG GTT TCT TAC GCA CCA CCC GGA GCA GAG GCC CCC AAG AGT CGC AAA GAA GCA ATG
2140 +-- --- --- -+- --- --- --+ --- --- --- +-- --- --- -+- --- --- --+ --- --- --- +-- --- --- -+- ---  2214
           G   G   T         C T   C AGC       G   G   G   T   G       G   G       C   G           G
     M   A   T   G   K   L   L   V   S   Y   A   P   P   G   A   E   A   P   K   S   R   K   E   A   M

     CTT GGG ACA CAT GTG ATA TGG GAC ATT GGG TTG CAG TCT TCA TGC ACT ATG GTG GTA CCT TGG ATC AGT AAT ACC
2215 --- --+ --- --- --- +-- --- --- -+- --- --- --+ --- --- --- +-- --- --- -+- --- --- --+ --- --- ---  2289
           T   G       C   C           C   T C T     AGC AGC       G       C   C   G           C       G
     L   G   T   H   V   I   W   D   I   G   L   Q   S   S   C   T   M   V   V   P   W   I   S   N   T

     ACA TAC AGA CAA ACC ATC AAC GAT AGT TTC ACA GAA GGT GGC TAC ATT AGC ATG TTC TAT CAA ACT AGG GTT GTT
2290 +-- --- --- -+- --- --- --+ --- --- --- +-- --- --- -+- --- --- --+ --- --- --- +-- --- --- -+- ---  2364
       G     C G       G               C       G           T       C                       G C     C   C
     T   Y   R   Q   T   I   N   D   S   F   T   E   G   G   Y   I   S   M   F   Y   Q   T   R   V   V

     GTC CCG TTG TCC ACA CCC AGA AAG ATG GAC ATC CTG GGT TTT GTG TCA GCT TGC AAT GAC TTC AGT GTG CGC TTA
2365 --- --+ --- --- --- +-- --- --- -+- --- --- --+ --- --- --- +-- --- --- -+- --- --- --+ --- --- ---  2439
             C T AG    G   G C G                   T           C AGC   G                   C   C   G C T
     V   P   L   S   T   P   R   K   M   D   I   L   G   F   V   S   A   C   N   D   F   S   V   R   L
                                                             → VP1
     CTG CGA GAT ACA ACA CAC ATT AGT CAA GAG GCT ATG CCA CAA GGA ATT GGT GAC ATG ATT GAG GGG GCC GTT GAA
2440 +-- --- --- -+- --- --- --+ --- --- --- +-- --- --- -+- --- --- --+ --- --- --- +-- --- --- -+- ---  2514
       T   G       G   G       C   C           G       G       T   C               C       T   G   C
     L   R   D   T   T   H   I   S   Q   E   A   M   P   Q   G   I   G   D   M   I   E   G   A   V   E

     GGG ATT ACT AAA AAT GCA TTG GTT CCC CCG ACT TCC ACC AAT AGC CTG CCT GAC ACA AAG CCG AGC GGT CCA GCC
2515 --- --+ --- --- --- +-- --- --- -+- --- --- --+ --- --- --- +-- --- --- -+- --- --- --+ --- --- ---  2589
       T   C   G           G C T   C   G       G AG    G           T   G       G                   G   G
     G   I   T   K   N   A   L   V   P   P   T   S   T   N   S   L   P   D   T   K   P   S   G   P   A
                                       ↓ EagI
     CAC TCC AAG GAG ATA CCT GCA TTG ACA GCC GTG GAG ACA GGG GCT ACC AAT CCG TTG GTG CCT TCG GAC ACC GTG
2590 +-- --- --- -+- --- --- --+ --- --- --- +-- --- --- -+- --- --- --+ --- --- --- +-- --- --- -+- ---  2664
         AG            C   G   G C T   G       C       G   T   G   G         C T   C   G AGC         G   C
     R   S   K   E   I   P   A   L   T   A   V   E   T   G   A   T   N   P   L   V   P   S   D   T   V

     CAA ACG CGC CAT GTC ATC CAG AGA CGA ACG CGA TCA GAG TCC ACG GTT GAG TCA TTC TTT GCA AGA GGG GCT TGC
2665 --- --+ --- --- --- +-- --- --- -+- --- --- --+ --- --- --- +-- --- --- -+- --- --- --+ --- --- ---  2739
               G                 C G   G       G AGC     AG        C     AGC           G C G   T   G
     Q   T   R   H   V   I   Q   R   R   T   R   S   E   S   T   V   E   S   F   F   A   R   G   A   C

     GTG GCT ATC ATT GAG GTG GAC AAT GAT GCA CCG ACA AAG CGC GCC AGC AGA TTG TTT TCG GTT TGG AAA ATA ACT
2740 +-- --- --- -+- --- --- --+ --- --- --- +-- --- --- -+- --- --- --+ --- --- --- +-- --- --- -+- ---  2814
       C   G       C                       G       G       G   G     C G C T     AGC   C           C   G
     V   A   I   I   E   V   D   N   D   A   P   T   K   R   A   S   R   L   F   S   V   W   K   I   T

     TAC AAA GAT ACT GTT CAA CTG AGA CGC AAA CTG GAA TTT TTC ACA TAT TCG AGA TTT GAC ATG GAG TTC ACT TTT
2815 --- --+ --- --- --- +-- --- --- -+- --- --- --+ --- --- --- +-- --- --- -+- --- --- --+ --- --- ---  2889
                   G   C       T C G   G       T               G     AGC C G                       G
     Y   K   D   T   V   Q   L   R   R   K   L   E   F   F   T   Y   S   R   F   D   M   E   F   T   F

     GTG GTC ACC TCA AAC TAC ATT GAT GCA AAT AAC GGA CAT GCA TTG AAC CAA GTT TAT CAG ATA ATG TAT ATA CCA
2890 +-- --- --- -+- --- --- --+ --- --- --- +-- --- --- -+- --- --- --+ --- --- --- +-- --- --- -+- ---  2964
       C       G AGC           C       G           T       G C T           C           C           C   G
     V   V   T   S   N   Y   I   D   A   N   N   G   H   A   L   N   Q   V   Y   Q   I   M   Y   I   P

     CCC GGA GCA CCT ATC CCT GGT AAA TGG AAT GAC TAT ACG TGG CAG ACG TCC TCT AAC CCG TCG GTG TTT TAC ACC
2965 --- --+ --- --- --- +-- --- --- -+- --- --- --+ --- --- --- +-- --- --- -+- --- --- --+ --- --- ---  3039
       G   T   G   G       G                                             AGC         AGC   C           G
     P   G   A   P   I   P   G   K   W   N   D   Y   T   W   Q   T   S   S   N   P   S   V   F   Y   T

     TAT GGG GCG CCC CCA GCA AGA ATA TCA GTG CCC TAC GTG GGA ATT GCT AAT GCG TAT TCC CAC TTT TAT GAT GGG
3040 +-- --- --- -+- --- --- --+ --- --- --- +-- --- --- -+- --- --- --+ --- --- --- +-- --- --- -+- ---  3114
           T       G   G   G C G   C AGC   C   G       C   T   C   G             AG                    T
     Y   G   A   P   P   A   R   I   S   V   P   Y   V   G   I   A   N   A   Y   S   H   F   Y   D   G

     TTT GCA AAA GTA CCA CTA GCG GGT CAA GCC TCA ACT GAA GGC GAT TCG TTG TAC GGT GCT GCC TCA CTG AAT GAT
3115 --- --+ --- --- --- +-- --- --- -+- --- --- --+ --- --- --- +-- --- --- -+- --- --- --+ --- --- ---  3189
           G       C   G   T               G AGC   G       T     AGC C T           G   G AGC   T
     F   A   K   V   P   L   A   G   Q   A   S   T   E   G   D   S   L   Y   G   A   A   S   L   N   D

     TTT GGA TCA CTG GCT GTT CGC GTG GTA AAT GAT CAC AAC CCC ACG CGG CTC ACC TCC AAG ATC AGA GTG TAC ATG
3190 +-- --- --- -+- --- --- --+ --- --- --- +-- --- --- -+- --- --- --+ --- --- --- +-- --- --- -+- ---  3264
           T AGC   T   G   C   G   C   C                   G           T   G AG          C G   C
     F   G   S   L   A   V   R   V   V   N   D   H   N   P   T   R   L   T   S   K   I   R   V   Y   M
```

FIG. 1D

```
                                                          ↓ XhoI
      AAG CCA AAG CAT GTC AGA GTC TGG TGC CCA CGA CCT CCA CGA GCA GTC CCA TAC TTC GGA CCA GGT GTT GAT TAT
3265  --- --+ --- --- --- +-- --- --- -+- --- --- --+ --- --- --- +-- --- --- -+- --- --- --+ --- --- ---   3339
           G              C G                 G   G     T
      K   P   K   H   V   R   V   W   C   P   R   P   P   R   A   V   P   Y   F   G   P   G   V   D   Y

      AAA GAT GGG CTC ACC CCA CTA CCA GAA AAG GGA TTA ACG ACT TAT
3340  +-- --- --- -+- --- --- --+ --- --- --- +-- --- --- -+- ---   3384

      K   D   G   L   T   P   L   P   E   K   G   L   T   T   Y
```

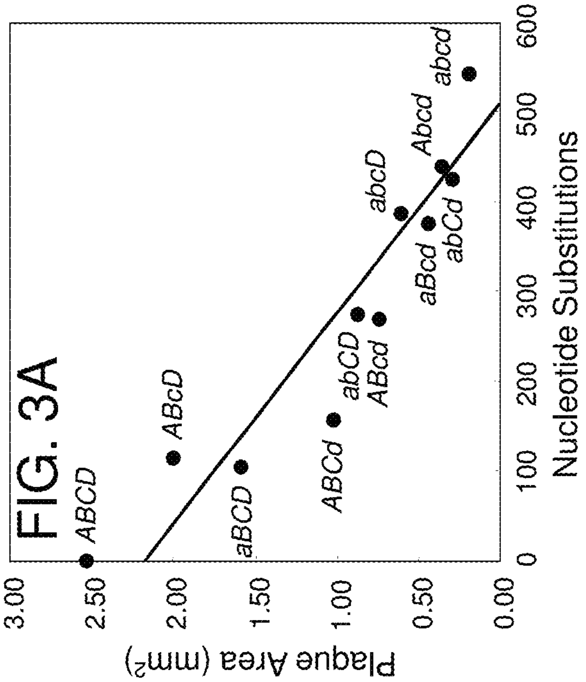
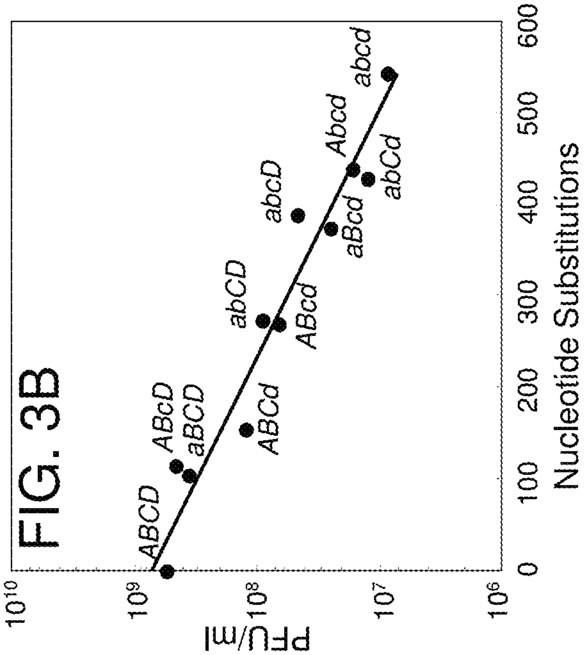
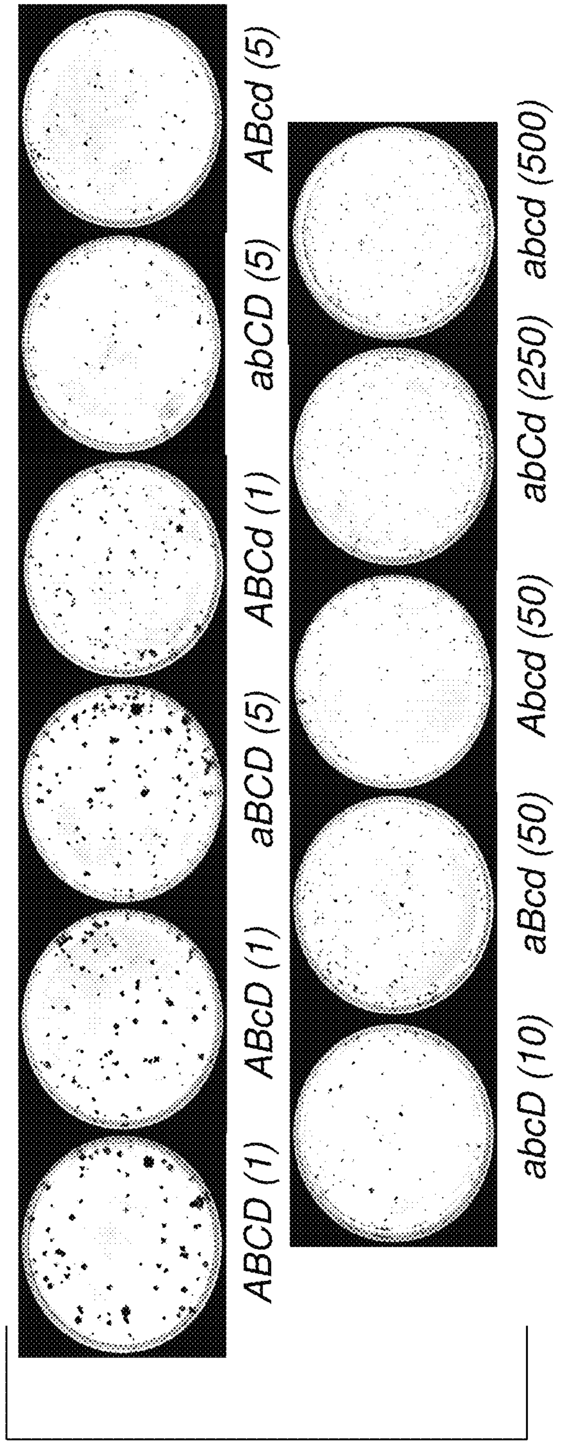
FIG. 3C

FIG. 9A

Poliovirus type 2, strain MEF1, complete open reading frame: all Arginine changed to CGG;
90 of 2207 (4.1%) codons changed, 139 of 6621 (2.1%) nucleotides changed (no change nt 4479 in cre element)
Sequence from MEF1 GenBank AY082677 (VP1 only from CDC)
Numbering (nt 748-7368) from GenBank AY238473 MEF1 (complete genome with 4 nt 1 aa different than CDC MEF1)

```
748
¦
ATG GGC GCC CAA GTC TCA TCA CAG AAA GTT GGA GCC CAT GAG AAT TCA AAC AGA GCT TAT GGC GGA TCC ACC ATT
                                                                    C G
M   G   A   Q   V   S   S   Q   K   V   G   A   H   E   N   S   N   R   A   Y   G   G   S   T   I

AAT TAC ACT ACT ATT AAT TAT TAC AGG GAT TCT GCG AGC AAT GCC GCT AGT AAG CAG GAC TTT GCA CAA GAC CCA
                                C
N   Y   T   T   I   N   Y   Y   R   D   S   A   S   N   A   A   S   K   Q   D   F   A   Q   D   P

TCC AAG TTC ACT GAA CCT ATT AAA GAT GTT CTC ATT AAG ACC GCT CCC ACG CTA AAC TCT CCT AAT ATC GAG GCG

S   K   F   T   E   P   I   K   D   V   L   I   K   T   A   P   T   L   N   S   P   N   I   E   A

TGT GGG TAT AGC GAC AGA GTG ATG CAA CTA ACC CTA GGC AAT TCC ACC ATT ACC ACA CAG GAG GCG GCC AAT TCT
                    C G
C   G   Y   S   D   R   V   M   Q   L   T   L   G   N   S   T   I   T   T   Q   E   A   A   N   S

GTC GTT GCA TAC GGC CGG TGG CCC GAG TAC ATC AAG GAC TCA GAA GCA AAT CCT GTG GAC CAG CCA ACT GAA CCG

V   V   A   Y   G   R   W   P   E   Y   I   K   D   S   E   A   N   P   V   D   Q   P   T   E   P

GAC GTT GCC GCG TGC AGG TTT TAC ACA CTA GAC ACT GTT ACT TGG CGC AAG GAG TCC AGA GGG TGG TGG TGG AAA
                    C                                             G             C G
D   V   A   A   C   R   F   Y   T   L   D   T   V   T   W   R   K   E   S   R   G   W   W   W   K

CTG CCT GAT GCA CTA AAG GAC ATG GGA TTA TTC GGC CAG AAC ATG TTC TAC CAC TAC CTC GGG AGG GCT GGC TAT
                                                                                    C
L   P   D   A   L   K   D   M   G   L   F   G   Q   N   M   F   Y   H   Y   L   G   R   A   G   Y

ACT GTG CAC GTA CAG TGT AAT GCT TCA AAG TTT CAC CAG GGC GCC CTC GGG GTA TTC GCA GTT CCA GAA ATG TGC

T   V   H   V   Q   C   N   A   S   K   F   H   Q   G   A   L   G   V   F   A   V   P   E   M   C

CTG GCA GGC GAC AGC ACA ACC CAC ATG TTT ACA AAA TAT GAG AAT GCA AAT CCG GGT GAG AAA GGG GGT GAA TTC

L   A   G   D   S   T   T   H   M   F   T   K   Y   E   N   A   N   P   G   E   K   G   G   E   F

AAA GGG AGT TTT ACT CTG GAT ACT AAC GCT ACC AAC CCT GCA CGC AAC TTT TGT CCC GTT GAT TAT CTC TTC GGG
                                                          G
K   G   S   F   T   L   D   T   N   A   T   N   P   A   R   N   F   C   P   V   D   Y   L   F   G

AGC GGA GTA CTG GCG GGA AAT GCG TTT GTT TAC CCA CAT CAG ATA ATT AAT CTG CGC ACC AAC AAC TGT GCC ACG
                                                                          G
S   G   V   L   A   G   N   A   F   V   Y   P   H   Q   I   I   N   L   R   T   N   N   C   A   T

TTG GTG CTG CCA TAC GTT AAT TCA CTT TCC ATA GAC AGC ATG ACA AAA CAC AAC AAT TGG GGA ATT GCT ATC CTT

L   V   L   P   Y   V   N   S   L   S   I   D   S   M   T   K   H   N   N   W   G   I   A   I   L

CCG CTG GCA CCA CTT GAC TTT GCC ACC GAG TCC TCC ACT GAG ATA CCC ATT ACT CTA ACT ATT GCC CCT ATG TGT

P   L   A   P   L   D   F   A   T   E   S   S   T   E   I   P   I   T   L   T   I   A   P   M   C

TGT GAA TTC AAT GGG TTG CGC AAC ATC ACT GTA CCC AGA ACT CAA GGG TTG CCA GTC TTA AAC ACT CCA GGA AGC
                          G                     C G
C   E   F   N   G   L   R   N   I   T   V   P   R   T   Q   G   L   P   V   L   N   T   P   G   S

AAC CAG TAC TTA ACA GCA GAC AAC TAT CAA TCC CCA TGT GCG ATA CCC GAG TTT GAT GTA ACA CCA CCC ATA GAC

N   Q   Y   L   T   A   D   N   Y   Q   S   P   C   A   I   P   E   F   D   V   T   P   P   I   D

ATC CCG GGG GAA GTG CGC AAC ATG ATG GAA TTG GCA GAG ATA GAC ACC ATG ATA CCT CTC AAT CTG ACG AAC CAG
                      G
I   P   G   E   V   R   N   M   M   E   L   A   E   I   D   T   M   I   P   L   N   L   T   N   Q

CGC AAG AAC ACC ATG GAT ATG TAC AGA GTC GAA CTG AAT GAT GCG GCT CAC TCT GAC ACA CCA ATA TTG TGT CTC
  G                             C G
R   K   N   T   M   D   M   Y   R   V   E   L   N   D   A   A   H   S   D   T   P   I   L   C   L

TCA CTG TCT CCA GCA TCA GAT CCT AGG CTA GCA CAC ACT ATG CTA GGT GAA ATA CTG AAC TAC TAC ACA CAC TGG
                                C
S   L   S   P   A   S   D   P   R   L   A   H   T   M   L   G   E   I   L   N   Y   Y   T   H   W
```

FIG. 9B

```
GCA GGG TCA TTG AAG TTC ACA TTT CTC TTC TGC GGC TCA ATG ATG GCC ACT GGT AAA TTG CTA GTG TCC TAT GCA

A   G   S   L   K   F   T   F   L   F   C   G   S   M   M   A   T   G   K   L   L   V   S   Y   A

CCT CCT GGT GCG GAA GCC CCT AAA AGC CGC AAA GAA GCG ATG CTC GGC ACC CAC GTG ATC TGG GAC ATC GGA TTA
                                      G
P   P   G   A   E   A   P   K   S   R   K   E   A   M   L   G   T   H   V   I   W   D   I   G   L

CAG TCA TCA TGC ACT ATG GTG GTA CCT TGG ATT AGC AAC ACC ACA TAC AGA CAA ACC ATC AAC GAT AGC TTC ACA
                                                                C G
Q   S   S   C   T   M   V   V   P   W   I   S   N   T   T   Y   R   Q   T   I   N   D   S   F   T

GAA GGA GGG TAC ATC AGT ATG TTT TAC CAA ACT AGA GTT GTT GTG CCA TTG TCC ACC CCT AGA AAG ATG GAC ATA
                                            C G                                 C G
E   G   G   Y   I   S   M   F   Y   Q   T   R   V   V   V   P   L   S   T   P   R   K   M   D   I

TTG GGC TTT GTG TCA GCC TGC AAT GAC TTC AGT GTG CGC CTG TTG CGT GAC ACG ACG CAC ATA AGC CAA GAG GCT
                                                  G           G
L   G   F   V   S   A   C   N   D   F   S   V   R   L   L   R   D   T   T   H   I   S   Q   E   A

ATG CCA CAA GGA TTG GGT GAT TTA ATT GAA GGG GTT GTT GAG GGA GTC ACG AGA AAT GCC TTG ACA CCA CTG ACA
                                                                    C G
M   P   Q   G   L   G   D   L   I   E   G   V   V   E   G   V   T   R   N   A   L   T   P   L   T

CCT GCC AAC AAC TTG CCT GAT ACA CAA TCT AGC GGC CCA GCC CAC TCT AAG GAA ACA CCA GCG CTA ACA GCC GTA

P   A   N   N   L   P   D   T   Q   S   S   G   P   A   H   S   K   E   T   P   A   L   T   A   V

GAG ACA GGG GCC ACC AAC CCA TTG GTG CCT TCA GAC ACG GTA CAA ACT CGT CAC GTC ATC CAA AAG CGG ACG CGG
                                                                  G
E   T   G   A   T   N   P   L   V   P   S   D   T   V   Q   T   R   H   V   I   Q   K   R   T   R

TCG GAG TCT ACG GTT GAG TCT TTC TTC GCA AGA GGA GCT TGT GTG GCC ATT ATT GAA GTG GAT AAT GAT GCT CCA
                                        C G
S   E   S   T   V   E   S   F   F   A   R   G   A   C   V   A   I   I   E   V   D   N   D   A   P

ACA AAG CGT GCC AGT AAA TTA TTT TCA GTC TGG AAG ATA ACT TAC AAA GAC ACC GTT CAG TTA AGA CGT AAG TTG
          G                                                                         C G   G
T   K   R   A   S   K   L   F   S   V   W   K   I   T   Y   K   D   T   V   Q   L   R   R   K   L

GAG TTC TTT ACA TAT TCA AGG TTT GAC ATG GAG TTC ACC TTT GTG GTT ACA TCC AAT TAT ACC GAT GCA AAC AAT
                        C
E   F   F   T   Y   S   R   F   D   M   E   F   T   F   V   V   T   S   N   Y   T   D   A   N   N

GGG CAC GCA CTA AAT CAA GTT TAC CAG ATA ATG TAC ATA CCA CCT GGG GCA CCG ATC CCT GGC AAG TGG AAT GAT

G   H   A   L   N   Q   V   Y   Q   I   M   Y   I   P   P   G   A   P   I   P   G   K   W   N   D

TAC ACA TGG CAA ACG TCA TCT AAC CCA TCA GTG TTT TAC ACT TAC GGG GCA CCT CCA GCT AGA ATA TCA GTG CCC
                                                                                    C G
Y   T   W   Q   T   S   S   N   P   S   V   F   Y   T   Y   G   A   P   P   A   R   I   S   V   P

TAC GTG GGC ATT GCC AAT GCA TAT TCT CAT TTT TAC GAT GGG TTT GCC AAA GTA CCA CTA GCA GGC CAA GCC TCA

Y   V   G   I   A   N   A   Y   S   H   F   Y   D   G   F   A   K   V   P   L   A   G   Q   A   S

ACA GAG GGT GAC TCG CTG TAT GGA GCG GCT TCA TTG AAT GAC TTC GGA TCA CTG GCT GTT CGA GTG GTG AAT GAC
                                                                                      G
T   E   G   D   S   L   Y   G   A   A   S   L   N   D   F   G   S   L   A   V   R   V   V   N   D

CAC AAC CCT ACG AAA CTC ACT TCA AAA ATC AGA GTG TAC ATG AAA CCA AAG CAC GTC AGA GTG TGG TGT CCG CGA
                                        C G                                     C G               G
H   N   P   T   K   L   T   S   K   I   R   V   Y   M   K   P   K   H   V   R   V   W   C   P   R

CCC CCT CGA GCA GTC CCA TAC TAC GGA CCA GGG GTT GAC TAC AAG GAT GGA CTA GCC CCA CTG CCA GAG AAA GGC
          G
P   P   R   A   V   P   Y   Y   G   P   G   V   D   Y   K   D   G   L   A   P   L   P   E   K   G

TTG ACA ACC TAT GGT TTT GGC CAC CAA AAT AAG GCA GTG TAC ACG GCA GGT TAC AAA ATT TGC AAT TAC CAC CTC

L   T   T   Y   G   F   G   H   Q   N   K   A   V   Y   T   A   G   Y   K   I   C   N   Y   H   L

GCC ACC CAG GAA GAC TTA CAA AAT GCG GTA AAC ATT ATG TGG ATT AGA GAC CTT TTA GTA GTG GAA TCC AAA GCC
                                                            C G
A   T   Q   E   D   L   Q   N   A   V   N   I   M   W   I   R   D   L   L   V   V   E   S   K   A

CAA GGC ATA GAC TCA ATT GCT AGA TGT AAC TGC CAC ACT GGA GTG TAC TAC TGT GAA TCC AGG AGG AAG TAC TAC
                            C G                                                     C   C
Q   G   I   D   S   I   A   R   C   N   C   H   T   G   V   Y   Y   C   E   S   R   R   K   Y   Y

CCG GTC TCT TTT ACT GGC CCC ACC TTT CAG TAC ATG GAA GCA AAT GAG TAC TAT CCA GCC CGA TAC CAA TCC CAC
                                                                                  G
P   V   S   F   T   G   P   T   F   Q   Y   M   E   A   N   E   Y   Y   P   A   R   Y   Q   S   H
```

FIG. 9C

```
ATG TTA ATT GGC CAT GGT TTT GCA TCT CCA GGG GAC TGT GGT GGG ATT CTC AGG TGC CAA CAT GGA GTA ATT GGA
                                                                    C
M   L   I   G   H   G   F   A   S   P   G   D   C   G   G   I   L   R   C   Q   H   G   V   I   G

ATC ATT ACA GCT GGA GGA GAA GGC CTA GTC GCT TTC TCG GAC ATC AGA GAT CTG TAC GCA TAC GAG GAG GAG GCT
                                                            C G
I   I   T   A   G   G   E   G   L   V   A   F   S   D   I   R   D   L   Y   A   Y   E   E   E   A

ATG GAG CAG GGA GTC TCC AAC TAT ATT GAG TCC CTT GGG GCT GCA TTT GGG AGT GGA TTC ACC CAG CAA ATA GGA

M   E   Q   G   V   S   N   Y   I   E   S   L   G   A   A   F   G   S   G   F   T   Q   Q   I   G

AAC AAA ATT TCA GAA CTC ACT AGC ATG GTC ACC AGC ACT ATA ACT GAG AAA CTA CTA AAG AAT CTC ATT AAA ATA

N   K   I   S   E   L   T   S   M   V   T   S   T   I   T   E   K   L   L   K   N   L   I   K   I

ATT TCA TCC CTT GTT ATC ATC ACC AGA AAC TAT GAA GAC ACG ACC ACA GTG CTG GCT ACC CTT GCT CTC CTC GGT
                                C G
I   S   S   L   V   I   I   T   R   N   Y   E   D   T   T   T   V   L   A   T   L   A   L   L   G

TGT GAT GCG TCC CCA TGG CAA TGG CTA AAG AAG AAA GCC TGT GAC ATC TTG GAA ATC CCC TAC ATC ATG CGA CAG
                                                                                             G
C   D   A   S   P   W   Q   W   L   K   K   K   A   C   D   I   L   E   I   P   Y   I   M   R   Q

GGC GAT AGC TGG TTG AAG AAG TTT ACA GAG GCA TGC AAT GCA GCC AAG GGA TTG GAA TGG GTG TCT AAT AAA ATA

G   D   S   W   L   K   K   F   T   E   A   C   N   A   A   K   G   L   E   W   V   S   N   K   I

TCC AAA TTT ATT GAC TGG CTC AAA GAG AAG ATC ATT CCA CAG GCT AGA GAC AAG CTA GAG TTT GTT ACC AAA CTG
                                                            C G
S   K   F   I   D   W   L   K   E   K   I   I   P   Q   A   R   D   K   L   E   F   V   T   K   L

AAG CAA CTA GAA ATG TTG GAG AAC CAA ATT GCA ACC ATT CAT CAA TCG TGC CCA AGT CAG GAG CAT CAA GAA ATC

K   Q   L   E   M   L   E   N   Q   I   A   T   I   H   Q   S   C   P   S   Q   E   H   Q   E   I

CTG TTC AAT AAC GTG AGA TGG TTA TCC ATA CAG TCA AAG AGA TTT GCC CCG CTC TAT GCG GTT GAG GCT AAG AGA
                    C G                             C G                                         C G
L   F   N   N   V   R   W   L   S   I   Q   S   K   R   F   A   P   L   Y   A   V   E   A   K   R

ATA CAA AAG TTA GAG CAC ACG ATT AAC AAC TAC GTA CAG TTC AAG AGC AAA CAC CGT ATT GAA CCA GTA TGT TTG

I   Q   K   L   E   H   T   I   N   N   Y   V   Q   F   K   S   K   H   R   I   E   P   V   C   L

TTG GTG CAC GGT AGC CCA GGC ACG GGC AAG TCA GTT GCC ACC AAT TTA ATT GCC AGA GCA ATA GCA GAG AAG GAG
                                                                        C G
L   V   H   G   S   P   G   T   G   K   S   V   A   T   N   L   I   A   R   A   I   A   E   K   E

AAC ACC TCC ACA TAC TCA CTA CCA CCA GAT CCC TCC CAT TTC GAT GGG TAC AAG CAA CAA GGT GTG GTG ATC ATG

N   T   S   T   Y   S   L   P   P   D   P   S   H   F   D   G   Y   K   Q   Q   G   V   V   I   M

GAT GAT TTG AAT CAG AAC CCA GAC GGA GCA GAC ATG AAG CTG TTT TGT CAG ATG GTC TCC ACT GTA GAA TTC ATA

D   D   L   N   Q   N   P   D   G   A   D   M   K   L   F   C   Q   M   V   S   T   V   E   F   I

CCA CCA ATG GCT TCG CTA GAA GAA AAG GGT ATT TTG TTC ACA TCT AAT TAC GTT TTG GCC TCA ACC AAT TCC AGT

P   P   M   A   S   L   E   E   K   G   I   L   F   T   S   N   Y   V   L   A   S   T   N   S   S

CGC ATC ACC CCA CCA ACT GTT GCG CAC AGC GAT GCC CTA GCC AGG CGC TTT GCA TTT GAC ATG GAC ATA CAA ATC
 G                                                      C     G
R   I   T   P   P   T   V   A   H   S   D   A   L   A   R   R   F   A   F   D   M   D   I   Q   I

ATG AGC GAG TAT TCT AGA GAT GGA AAA TTG AAC ATG GCG ATG GCA ACT GAA ATG TGT AAG AAC TGT CAT CAA CCA
                    C G
M   S   E   Y   S   R   D   G   K   L   N   M   A   M   A   T   E   M   C   K   N   C   H   Q   P

GCA AAC TTC AAG AGA TGT TGC CCA TTG GTG TGT GGC AAA GCC ATC CAG CTG ATG GAC AAA TCT TCC AGA GTC AGA
                C G                                                                     C G     C G
A   N   F   K   R   C   C   P   L   V   C   G   K   A   I   Q   L   M   D   K   S   S   R   V   R

TAT AGT ATA GAT CAG ATT ACT ACC ATG ATT ATT AAT GAG AGG AAC AGA AGA TCA AGT ATC GGT AAT TGC ATG GAG
                                                    C       C G C G
Y   S   I   D   Q   I   T   T   M   I   I   N   E   R   N   R   R   S   S   I   G   N   C   M   E

GCA CTT TTC CAA GGT CCT CTT CAA TAC AAA GAC CTG AAA ATA GAC ATT AAG ACC ACA CCT CCT CCT GAG TGC ATC

A   L   F   Q   G   P   L   Q   Y   K   D   L   K   I   D   I   K   T   T   P   P   P   E   C   I

AAT GAT TTG CTC CAA GCA GTT GAT TCT CAA GAG GTA AGA GAC TAC TGT GAG AAG AAG GGT TGG ATA GTA GAC ATC
                                                C G
N   D   L   L   Q   A   V   D   S   Q   E   V   R   D   Y   C   E   K   K   G   W   I   V   D   I
```

FIG. 9D

```
ACT AGT CAG GTG CAA ACC GAA AGA AAC ATC AAT AGA GCA ATG ACT ATT CTT CAG GCG GTC ACC ACA TTT GCC GCA
                            C G             C G
T   S   Q   V   Q   T   E   R   N   I   N   R   A   M   T   I   L   Q   A   V   T   T   F   A   A

GTT GCT GGA GTG GTG TAT GTG ATG TAC AAA CTC TTT GCA GGG CAT CAA GGA GCG TAT ACA GGG CTT CCC AAT AAG

V   A   G   V   V   Y   V   M   Y   K   L   F   A   G   H   Q   G   A   Y   T   G   L   P   N   K

AGA CCC AAT GTC CCC ACC ATC AGG ACT GCC AAG GTT CAG GGC CCA GGA TTT GAC TAC GCA GTG GCA ATG GCC AAA
C G                         C
R   P   N   V   P   T   I   R   T   A   K   V   Q   G   P   G   F   D   Y   A   V   A   M   A   K

AGA AAC ATT CTT ACG GCA ACT ACC ATT AAG GGA GAG TTC ACA ATG CTC GGA GTG CAT GAT AAT GTG GCC ATT CTA
C G
R   N   I   L   T   A   T   T   I   K   G   E   F   T   M   L   G   V   H   D   N   V   A   I   L

CCA ACC CAC GCA TCA CCG GGT GAA ACA ATA GTC ATT GAT GGC AAG GAA GTA GAG GTA CTG GAT GCT AAA GCC CTG

P   T   H   A   S   P   G   E   T   I   V   I   D   G   K   E   V   E   V   L   D   A   K   A   L

GAG GAC CAG GCC GGG ACC AAC CTA GAA ATC ACC ATT GTC ACT CTT AAG AGA AAT GAG AAG TTC AGG GAC ATC AGA
                                                                C G                 C           C G
E   D   Q   A   G   T   N   L   E   I   T   I   V   T   L   K   R   N   E   K   F   R   D   I   R

CCA CAC ATC CCC ACT CAA ATC ACT GAG ACA AAT GAT GGA GTT TTA ATT GTG AAC ACT AGT AAG TAC CCC AAC ATG

P   H   I   P   T   Q   I   T   E   T   N   D   G   V   L   I   V   N   T   S   K   Y   P   N   M

TAT GTT CCT GTC GGT GCT GTG ACT GAA CAG GGG TAT CTC AAT CTC GGT GGA CGC CAA ACT GCT CGT ACT TTA ATG
                                                                      G               G
Y   V   P   V   G   A   V   T   E   Q   G   Y   L   N   L   G   G   R   Q   T   A   R   T   L   M

TAC AAC TTT CCA ACG AGA GCA GGT CAA TGT GGT GGA GTT ATC ACC TGC ACT GGC AAG GTC ATC GGG ATG CAT GTT
                    C G
Y   N   F   P   T   R   A   G   Q   C   G   G   V   I   T   C   T   G   K   V   I   G   M   H   V

GGT GGG AAC GGT TCA CAT GGG TTC GCA GCA GCC CTG AAG CGA TCC TAT TTC ACT CAG AGT CAA GGT GAA ATC CAG
                                                      G
G   G   N   G   S   H   G   F   A   A   A   L   K   R   S   Y   F   T   Q   S   Q   G   E   I   Q

TGG ATG AGA CCA TCA AAA GAA GTG GGC TAC CCC GTT ATT AAT GCT CCA TCT AAA ACT AAA CTG GAA CCC AGT GCA
        C G
W   M   R   P   S   K   E   V   G   Y   P   V   I   N   A   P   S   K   T   K   L   E   P   S   A

TTC CAT TAT GTG TTT GAA GGT GTC AAG GAA CCA GCT GTG CTC ACC AAA AGT GAC CCC AGA TTG AAG ACA GAT TTT
                                                                            C G
F   H   Y   V   F   E   G   V   K   E   P   A   V   L   T   K   S   D   P   R   L   K   T   D   F

GAA GAG GCT ATC TTT TCC AAG TAT GTG GGA AAT AAG ATT ACT GAA GTG GAT GAG TAC ATG AAA GAA GCT GTC GAT

E   E   A   I   F   S   K   Y   V   G   N   K   I   T   E   V   D   E   Y   M   K   E   A   V   D

CAT TAC GCA GGC CAG CTC ATG TCA CTA GAC ATC AAC ACA GAA CAA ATG TGC CTT GAG GAT GCA ATG TAT GGC ACT

H   Y   A   G   Q   L   M   S   L   D   I   N   T   E   Q   M   C   L   E   D   A   M   Y   G   T

GAC GGT CTC GAA GCT CTA GAC CTC AGT ACC AGT GCT GGG TAT CCC TAT GTG GCA ATG GGG AAA AAG AAA AGA GAC
                                                                                            C G
D   G   L   E   A   L   D   L   S   T   S   A   G   Y   P   Y   V   A   M   G   K   K   K   R   D

ATT TTG AAT AAG CAA ACC AGA GAC ACA AAG GAA ATG CAA AGG CTT CTG GAC ACC TAT GGT ATT AAT TTA CCT TTA
                        C G                         C
I   L   N   K   Q   T   R   D   T   K   E   M   Q   R   L   L   D   T   Y   G   I   N   L   P   L

GTC ACC TAT GTG AAA GAT GAG CTT AGA TCC AAG ACC AAA GTG GAA CAG GGC AAG TCC AGG CTA ATT GAG GCC TCA
                                C G                                         C
V   T   Y   V   K   D   E   L   R   S   K   T   K   V   E   Q   G   K   S   R   L   I   E   A   S

AGT CTC AAT GAC TCT GTC GCC ATG AGG ATG GCT TTT GGC AAC TTG TAC GCA GCA TTC CAC AAG AAC CCA GGT GTA
                                C
S   L   N   D   S   V   A   M   R   M   A   F   G   N   L   Y   A   A   F   H   K   N   P   G   V

GTG ACA GGA TCG GCT GTT GGC TGT GAC CCA GAT TTG TTT TGG AGT AAA ATA CCA GTC CTC ATG GAG GAA AAA CTC

V   T   G   S   A   V   G   C   D   P   D   L   F   W   S   K   I   P   V   L   M   E   E   K   L

TTT GCA TTT GAT TAC ACG GGT TAT GAT GCT TCA CTA AGC CCC GCC TGG TTT GAG GCT CTC AAG ATG GTT CTA GAG

F   A   F   D   Y   T   G   Y   D   A   S   L   S   P   A   W   F   E   A   L   K   M   V   L   E

AAA ATT GGG TTT GGT GAC AGA GTG GAT TAC ATT GAT TAT CTG AAT CAC TCG CAC CAT CTA TAT AAA AAT AAG ACA
                        C G
K   I   G   F   G   D   R   V   D   Y   I   D   Y   L   N   H   S   H   L   Y   K   N   K   T
```

FIG. 9E

```
TAT TGT GTT AAG GGC GGC ATG CCA TCT GGC TGC TCT GGC ACC TCA ATT TTT AAT TCA ATG ATT AAT AAT CTA ATA

Y   C   V   K   G   G   M   P   S   G   C   S   G   T   S   I   F   N   S   M   I   N   N   L   I

ATC AGG ACT CTC TTA CTG AAA ACC TAC AAG GGC ATA GAT TTA GAC CAC CTG AAG ATG ATA GCC TAT GGT GAT GAT
    C
I   R   T   L   L   L   K   T   Y   K   G   I   D   L   D   H   L   K   M   I   A   Y   G   D   D

GTA ATT GCT TCC TAC CCC CAT GAG GTT GAT GCT AGT CTC CTA GCC CAA TCA GGA AAA GAC TAT GGA CTA ACC ATG

V   I   A   S   Y   P   H   E   V   D   A   S   L   L   A   Q   S   G   K   D   Y   G   L   T   M

ACA CCA GCT GAC AAA TCA GCC ACC TTT GAA ACA GTC ACA TGG GAG AAT GTA ACA TTC TTG AAA AGA TTC TTT AGA
                                                                                    C G         C G
T   P   A   D   K   S   A   T   F   E   T   V   T   W   E   N   V   T   F   L   K   R   F   F   R

GCA GAT GAA AAG TAT CCC TTT CTG GTA CAT CCA GTG ATG CCA ATG AAA GAA ATT CAC GAA TCA ATT AGA TGG ACT
                                                                                        C G
A   D   E   K   Y   P   F   L   V   H   P   V   M   P   M   K   E   I   H   E   S   I   R   W   T

AAA GAT CCC AGA AAC ACT CAG GAT CAT GTT CGC TCA CTG TGC TTA TTG GCT TGG CAC AAT GGC GAG GAA GAG TAC
            C G                           G
K   D   P   R   N   T   Q   D   H   V   R   S   L   C   L   L   A   W   H   N   G   E   E   E   Y

AAT AAA TTT TTA GCT AAG ATT AGA AGT GTG CCA ATC GGA AGA GCA TTA CTG CTC CCT GAG TAC TCC ACA TTG TAC
                            C G                     C G
N   K   F   L   A   K   I   R   S   V   P   I   G   R   A   L   L   L   P   E   Y   S   T   L   Y

CGC CGT TGG CTC GAC TCA TTT
  G   G                   |
R   R   W   L   D   S   F ?368
```

FIG. 10A

Foot-and Mouth Disease Virus, serotype O, strain UKG/35/2001, complete capsid, codons for 9 amino acids modified GenBank AJ539141 1695-3896, 2202 nt, 734 aa

```
GGC GCC GGG CAA TCC AGC CCG GCG ACT GGG TCA CAG AAC CAG TCA GGC AAC ACT GGA AGC ATT ATC AAC AAT TAC
  G   G           G               G       G               G   G       G   G       A   A
G   A   G   Q   S   S   P   A   T   G   S   Q   N   Q   S   G   N   T   G   S   I   I   N   N   Y

TAC ATG CAG CAG TAC CAG AAC TCC ATG GAC ACG CAG CTT GGT GAC AAC GCT ATT AGC GGA GGC TCC AAC GAG GGG
                              G                   A   G           G   A       G   G   G
Y   M   Q   Q   Y   Q   N   S   M   D   T   Q   L   G   D   N   A   I   S   G   G   S   N   E   G

TCC ACG GAC ACC ACC TCC ACT CAC ACA ACC AAC ACT CAG AAC AAT GAC TGG TTT TCA AAG CTG GCC AGT TCC GCT
  G           G   G   G   G       G   G       G                           G       A   G TCG   G   G
S   T   D   T   T   S   T   H   T   T   N   T   Q   N   N   D   W   F   S   K   L   A   S   S   A

TTT AGC GGT CTT TTC GGC GCT CTT CTT GCT GAC AAG AAA ACC GAG GAG ACC ACT CTT CTC GAG GAC CGC ATC CTC
          G   A       G   G   A   A   G               G           G   G   A   A           A   A   A
F   S   G   L   F   G   A   L   L   A   D   K   K   T   E   E   T   T   L   L   E   D   R   I   L

ACT ACC CGC AAC GGA CAC ACG ACC TCG ACA ACC CAG TCG AGC GTT GGA GTC ACT TAC GGG TAC GCA ACA GCT GAG
  G   G   A       G           G       G   G               A   G   A   G               G   G   G
T   T   R   N   G   H   T   T   S   T   T   Q   S   S   V   G   V   T   Y   G   Y   A   T   A   E

GAC TTT GTG AGC GGA CCA AAC ACA TCT GGG CTT GAG ACC AGG GTT GTG CAG GCA GAG CGG TTC TTC AAA ACC CAC
          A       G   G       G   G       A       G C A   A   A       G       A               G
D   F   V   S   G   P   N   T   S   G   L   E   T   R   V   V   Q   A   E   R   F   F   K   T   H

TTG TTC GAC TGG GTC ACC AGT GAC CCG TTT GGA CGG TGC TAT CTG CTG GAA CTC CCA ACT GAC CAC AAA GGT GTC
C A               A   G TCG               G   A           A   A       A   G   G               G   A
L   F   D   W   V   T   S   D   P   F   G   R   C   Y   L   L   E   L   P   T   D   H   K   G   V

TAC GGC AGC CTG ACC GAC TCT TAT GCT TAC ATG AGA AAC GGT TGG GAT GTT GAG GTC ACC GCA GTG GGA AAT CAG
      G       A   G       G       G       C           G           A       A   G   G   A   G
Y   G   S   L   T   D   S   Y   A   Y   M   R   N   G   W   D   V   E   V   T   A   V   G   N   Q

TTC AAC GGA GGA TGT CTG TTG GTG GCC ATG GTG CCA GAA CTT TGC TCT ATT GAC AAG AGA GAG CTG TAC CAG CTC
          G   G       A C A   A   G       A   G       A       G   A         C         A           A
F   N   G   G   C   L   L   V   A   M   V   P   E   L   C   S   I   D   K   R   E   L   Y   Q   L

ACG CTC TTT CCC CAC CAG TTC ATC AAC CCC CGG ACG AAC ATG ACG GCG CAC ATC ACT GTG CCC TTT GTT GGC GTC
      A       G               A       G   A                           A   G   A   G       A   G   A
T   L   F   P   H   Q   F   I   N   P   R   T   N   M   T   A   H   I   T   V   P   F   V   G   V

AAC CGC TAC GAC CAG TAC AAG GTA CAC AAA CCT TGG ACC CTC GTG GTT ATG GTT GTG GCC CCG CTG ACT GTC AAC
      A                                   G       G   A   A   A       A   A   G       A   G   A
N   R   Y   D   Q   Y   K   V   H   K   P   W   T   L   V   V   M   V   V   A   P   L   T   V   N

ACC GAA GGT GCC CCA CAG ATC AAG GTC TAT GCC AAC ATC GCC CCT ACC AAC GTG CAC GTT GCG GGT GAG TTC CCT
  G       G   G   G       A       A       G       A   G   G   G       A       A       G           G
T   E   G   A   P   Q   I   K   V   Y   A   N   I   A   P   T   N   V   H   V   A   G   E   F   P

TCT AAG GAA GGG ATC TTC CCC GTG GCA TGT AGC GAC GGT TAC GGT GGT CTG GTG ACC ACT GAC CCA AAG ACG GCT
  G               A       G   A   G               G       G   G   A   A   G   G       G           G
S   K   E   G   I   F   P   V   A   C   S   D   G   Y   G   G   L   V   T   T   D   P   K   T   A

GAC CCC GCC TAC GGG AAA GTG TTC AAT CCA CCT CGC AAC ATG TTG CCG GGG CGG TTC ACC AAC TTC CTT GAT GTG
      G   G               A           G   G   A           C A         A       G           A       A
D   P   A   Y   G   K   V   F   N   P   P   R   N   M   L   P   G   R   F   T   N   F   L   D   V

GCT GAG GCG TGC CCT ACG TTT CTG CAC TTT GAG GGT GGC GTG CCG TAC GTG ACC ACA AAG ACG GAC TCA GAC AGG
  G               G           A               G   G   A           A   G   G               G     C A
A   E   A   C   P   T   F   L   H   F   E   G   G   V   P   Y   V   T   T   K   T   D   S   D   R

GTG CTC GCC CAG TTC GAC TTG TCT CTG GCA GCA AAG CAC ATG TCA AAC ACC TTC CTG GCA GGT CTC GCC CAG TAC
  A   A   G             C A   G   A   G   G               G       G       A   G   G   A   G
V   L   A   Q   F   D   L   S   L   A   A   K   H   M   S   N   T   F   L   A   G   L   A   Q   Y

TAC ACA CAG TAC AGC GGC ACC ATC AAC CTG CAC TTC ATG TTC ACA GGA CCC ACT GAC GCG AAA GCG CGT TAC ATG
      G               G   G   A       A                   G   G   G   G                   A
Y   T   Q   Y   S   G   T   I   N   L   H   F   M   F   T   G   P   T   D   A   K   A   R   Y   M

ATT GCA TAC GCC CCC CCT GGT ATG GAG CCG CCC AAA ACA CCT GAG GCG GCC GCC CAC TGC ATT CAT GCG GAG TGG
  A   G       G   G   G   G               G       G   G           G   G           A
I   A   Y   A   P   P   G   M   E   P   P   K   T   P   E   A   A   A   H   C   I   H   A   E   W

GAC ACA GGG TTG AAT TCA AAA TTC ACA TTT TCA ATC CCT TAC CTT TCG GCG GCT GAT TAC GCG TAC ACC GCG TCT
      G     C A       G           G       G   A   G       A           G                   G       G
D   T   G   L   N   S   K   F   T   F   S   I   P   Y   L   S   A   A   D   Y   A   Y   T   A   S
```

FIG. 10B

```
GAC GCT GCG GAG ACC ACA AAT GTA CAG GGA TGG GTT TGC CTG TTT CAA ATT ACA CAC GGG AAG GCT GAC GGC GAC
      G           G   G               G       A       A           A   G               G       G
D   A   A   E   T   T   N   V   Q   G   W   V   C   L   F   Q   I   T   H   G   K   A   D   G   D

GCA CTG GTC GTT CTA GCT AGC GCC GGT AAG GAC TTT GAG CTG CGT CTG CCA GTT GAC GCT CGC ACG CAG ACC ACC
  G   A   A   A       G       G   G                   A   A   A   G   A       G   A           G   G
A   L   V   V   L   A   S   A   G   K   D   F   E   L   R   L   P   V   D   A   R   T   Q   T   T

TCC GCA GGT GAG TCG GCT GAC CCC GTG ACT GCC ACT GTT GAG AAC TAC GGT GGT GAG ACA CAG GTC CAG AGA CGC
  G   G   G           G       G   A   G   G   G   A               G   G       G       A     C     A
S   A   G   E   S   A   D   P   V   T   A   T   V   E   N   Y   G   G   E   T   Q   V   Q   R   R

CAA CAC ACG GAT GTC TCG TTC ATA TTA GAC AGA TTT GTG AAA GTA ACA CCA AAA GAC CAA ATT AAT GTG TTG GAC
                  A             C       C         A           G   G               A       A C A
Q   H   T   D   V   S   F   I   L   D   R   F   V   K   V   T   P   K   D   Q   I   N   V   L   D

CTG ATG CAA ACC CCT GCA CAC ACT TTG GTA GGC GCG CTC CTC CGT ACT GCC ACC TAC TAC TTC GCA GAT CTA GAA
  A           G   G   G       G C A       G       A   A   A   G   G   G               G
L   M   Q   T   P   A   H   T   L   V   G   A   L   L   R   T   A   T   Y   Y   F   A   D   L   E

GTG GCA GTG AAA CAC GAG GGG AAC CTT ACC TGG GTC CCG AAT GGG GCG CCC GAG ACA GCG TTG GAC AAC ACC ACC
  A   G   A                       A   G       A                   G       G     C A           G   G
V   A   V   K   H   E   G   N   L   T   W   V   P   N   G   A   P   E   T   A   L   D   N   T   T

AAT CCA ACG GCT TAC CAC AAG GCA CCG CTC ACC CGG CTT GCA CTG CCT TAC ACG GCA CCG CAC CGT GTC TTG GCT
      G       G               G       A   G   A   A   G   A   G           G           A   A C A   G
N   P   T   A   Y   H   K   A   P   L   T   R   L   A   L   P   Y   T   A   P   H   R   V   L   A

ACT GTT TAC AAC GGG AAC TGC AAG TAT GGC GAG AGC CCC GTG ACC AAT GTG AGA GGT GAC CTG CAA GTA TTG GCC
  G   A                               G           G   A   G       A C     G       A         C A   G
T   V   Y   N   G   N   C   K   Y   G   E   S   P   V   T   N   V   R   G   D   L   Q   V   L   A

CAA AAG GCG GCA AGA ACG CTG CCT ACC TCC TTC AAT TAC GGT GCC ATC AAA GCC ACT CGG GTG ACT GAA CTG CTT
              G C         A   G   G   G               G   G   A       G   G   A   A   G       A   A
Q   K   A   A   R   T   L   P   T   S   F   N   Y   G   A   I   K   A   T   R   V   T   E   L   L

TAC CGC ATG AAG AGG GCC GAA ACA TAC TGC CCC CGG CCT CTT TTG GCT ATT CAC CCA AGC GAA GCT AGA CAC AAA
      A         C A   G       G           G   A   G   A C A   G   A       G           G C
Y   R   M   K   R   A   E   T   Y   C   P   R   P   L   L   A   I   H   P   S   E   A   R   H   K

CAA AAG ATT GTT GCG CCT GTG AAA CAG
          A   A       G   A
Q   K   I   V   A   P   V   K   Q
```

FIG. 11A

SARS coronavirus, strain Urbani, GenBank AY278741

S (spike) glycoprotein, nt 21,492-25,256

```
21,492
|
ATG TTT ATT TTC TTA TTA TTT CTT ACT CTC ACT AGT GGT AGT GAC CTT GAC CGG TGC ACC ACT TTT GAT GAT GTT
          C     C G C G       G   G   G   G TCG   G TCG       G               G   G               C
M   F   I   F   L   L   F   L   T   L   T   S   G   S   D   L   D   R   C   T   T   F   D   D   V

CAA GCT CCT AAT TAC ACT CAA CAT ACT TCA TCT ATG AGG GGG GTT TAC TAT CCT GAT GAA ATT TTT AGA TCA GAC
      G   G           G           G   G   G     C         C           G           C     C G   G
Q   A   P   N   Y   T   Q   H   T   S   S   M   R   G   V   Y   Y   P   D   E   I   F   R   S   D

ACT CTT TAT TTA ACT CAG GAT TTA TTT CTT CCA TTT TAT TCT AAT GTT ACA GGG TTT CAT ACT ATT AAT CAT ACG
  G   G     C G   G         C G       G   G           G       C   G               G   C
T   L   Y   L   T   Q   D   L   F   L   P   F   Y   S   N   V   T   G   F   H   T   I   N   H   T

TTT GGC AAC CCT GTC ATA CCT TTT AAG GAT GGT ATT TAT TTT GCT GCC ACA GAG AAA TCA AAT GTT GTC CGT GGT
      G       G       C   G               G   C           G   G   G           G       C       G   G
F   G   N   P   V   I   P   F   K   D   G   I   Y   F   A   A   T   E   K   S   N   V   V   R   G

TGG GTT TTT GGT TCT ACC ATG AAC AAC AAG TCA CAG TCG GTG ATT ATT ATT AAC AAT TCT ACT AAT GTT GTT ATA
      C       G   G   G                   G           C   C   C   C           G   G       C   C   C
W   V   F   G   S   T   M   N   N   K   S   Q   S   V   I   I   I   N   N   S   T   N   V   V   I

CGA GCA TGT AAC TTT GAA TTG TGT GAC AAC CCT TTC TTT GCT GTT TCT AAA CCC ATG GGT ACA CAG ACA CAT ACT
  G   G                 C                 G           G   C   G       G       G   G       G       G
R   A   C   N   F   E   L   C   D   N   P   F   F   A   V   S   K   P   M   G   T   Q   T   H   T

ATG ATA TTC GAT AAT GCA TTT AAT TGC ACT TTC GAG TAC ATA TCT GAT GCC TTT TCG CTT GAT GTT TCA GAA AAG
      C               G               G               C   G       G           G       C   G
M   I   F   D   N   A   F   N   C   T   F   E   Y   I   S   D   A   F   S   L   D   V   S   E   K

TCA GGT AAT TTT AAA CAC TTA CGA GAG TTT GTG TTT AAA AAT AAA GAT GGG TTT CTC TAT GTT TAT AAG GGC TAT
  G   G                 C G   G           C                               G       C           G
S   G   N   F   K   H   L   R   E   F   V   F   K   N   K   D   G   F   L   Y   V   Y   K   G   Y

CAA CCT ATA GAT GTA GTT CGT GAT CTA CCT TCT GGT TTT AAC ACT TTG AAA CCT ATT TTT AAG TTG CCT CTT GGT
      G   C       C   C   G       G   G   G   G           G C         G   C         C     G   G   G
Q   P   I   D   V   V   R   D   L   P   S   G   F   N   T   L   K   P   I   F   K   L   P   L   G

ATT AAC ATT ACA AAT TTT AGA GCC ATT CTT ACA GCC TTT TCA CCT GCT CAA GAC ATT TGG GGC ACG TCA GCT GCA
  C       C   G         C G   G   C   G   G   G       G   G   G           C       G       G   G   G
I   N   I   T   N   F   R   A   I   L   T   A   F   S   P   A   Q   D   I   W   G   T   S   A   A

GCC TAT TTT GTT GGC TAT TTA AAG CCA ACT ACA TTT ATG CTC AAG TAT GAT GAA AAT GGT ACA ATC ACA GAT GCT
  G           C   G     C G       G   G   G           G                       G   G       G       G
A   Y   F   V   G   Y   L   K   P   T   T   F   M   L   K   Y   D   E   N   G   T   I   T   D   A

GTT GAT TGT TCT CAA AAT CCA CTT GCT GAA CTC AAA TGC TCT GTT AAG AGC TTT GAG ATT GAC AAA GGA ATT TAC
  C           G           G   G   G       G           G   C     TCG           C           G   C
V   D   C   S   Q   N   P   L   A   E   L   K   C   S   V   K   S   F   E   I   D   K   G   I   Y

CAG ACC TCT AAT TTC AGG GTT GTT CCC TCA GGA GAT GTT GTG AGA TTC CCT AAT ATT ACA AAC TTG TGT CCT TTT
      G   G         C     C   C   G   G   G       C   C C G       G       C   G     C         G
Q   T   S   N   F   R   V   V   P   S   G   D   V   V   R   F   P   N   I   T   N   L   C   P   F

GGA GAG GTT TTT AAT GCT ACT AAA TTC CCT TCT GTC TAT GCA TGG GAG AGA AAA AAA ATT TCT AAT TGT GTT GCT
  G       C           G   G           G   G           G         C G           C   G           C   G
G   E   V   F   N   A   T   K   F   P   S   V   Y   A   W   E   R   K   K   I   S   N   C   V   A

GAT TAC TCT GTG CTC TAC AAC TCA ACA TTT TTT TCA ACC TTT AAG TGC TAT GGC GTT TCT GCC ACT AAG TTG AAT
          G   C   G           G   G           G   G                   G   C   G   G   G     C
D   Y   S   V   L   Y   N   S   T   F   F   S   T   F   K   C   Y   G   V   S   A   T   K   L   N

GAT CTT TGC TTC TCC AAT GTC TAT GCA GAT TCT TTT GTA GTC AAG GGA GAT GAT GTA AGA CAA ATA GCG CCA GGA
      G           G               G       G       C           G           C C G       C       G   G
D   L   C   F   S   N   V   Y   A   D   S   F   V   V   K   G   D   D   V   R   Q   I   A   P   G

CAA ACT GGT GTT ATT GCT GAT TAT AAT TAT AAA TTG CCA GAT GAT TTC ATG GGT TGT GTC CTT GCT TGG AAT ACT
      G   G   C   C   G                     C     G                   G           G   G           G
Q   T   G   V   I   A   D   Y   N   Y   K   L   P   D   D   F   M   G   C   V   L   A   W   N   T

AGG AAC ATT GAT GCT ACT TCA ACT GGT AAT TAT AAT TAT AAA TAT AGG TAT CTT AGA CAT GGC AAG CTT AGG CCC
C         C       G   G   G   G   G                         C         G C G       G       G C     G
R   N   I   D   A   T   S   T   G   N   Y   N   Y   K   Y   R   Y   L   R   H   G   K   L   R   P

TTT GAG AGA GAC ATA TCT AAT GTG CCT TTC TCC CCT GAT GGC AAA CCT TGC ACC CCA CCT GCT CTT AAT TGT TAT
        C G       C   G       C   G       G   G       G       G       G   G   G   G   G
F   E   R   D   I   S   N   V   P   F   S   P   D   G   K   P   C   T   P   P   A   L   N   C   Y

TGG CCA TTA AAT GAT TAT GGT TTT TAC ACC ACT ACT GGC ATT GGC TAC CAA CCT TAC AGA GTT GTA GTA CTT TCT
      G C G               G           G   G   G   G   C   G           G     C G   C   C   C   G   G
W   P   L   N   D   Y   G   F   Y   T   T   T   G   I   G   Y   Q   P   Y   R   V   V   V   L   S
```

FIG. 11B

```
TTT GAA CTT TTA AAT GCA CCG GCC ACG GTT TGT GGA CCA AAA TTA TCC ACT GAC CTT ATT AAG AAC CAG TGT GTC
          G C G       G       G       C       G   G     C G   G   G       G   C
F   E   L   L   N   A   P   A   T   V   C   G   P   K   L   S   T   D   L   I   K   N   Q   C   V

AAT TTT AAT TTT AAT GGA CTC ACT GGT ACT GGT GTG TTA ACT CCT TCT TCA AAG AGA TTT CAA CCA TTT CAA CAA
                      G   G   G   G   G   G   C C G   G   G   G   G     C G           G
N   F   N   F   N   G   L   T   G   T   G   V   L   T   P   S   S   K   R   F   Q   P   F   Q   Q

TTT GGC CGT GAT GTT TCT GAT TTC ACT GAT TCC GTT CGA GAT CCT AAA ACA TCT GAA ATA TTA GAC ATT TCA CCT
      G   G       C   G           G       G   C   G       G       G   G       C C G       C   G   G
F   G   R   D   V   S   D   F   T   D   S   V   R   D   P   K   T   S   E   I   L   D   I   S   P

TGC TCT TTT GGG GGT GTA AGT GTA ATT ACA CCT GGA ACA AAT GCT TCA TCT GAA GTT GCT GTT CTA TAT CAA GAT
      G           G   C TCG   C   C   G   G   G   G       G   G   G       C   G   C   G
C   S   F   G   G   V   S   V   I   T   P   G   T   N   A   S   S   E   V   A   V   L   Y   Q   D

GTT AAC TGC ACT GAT GTT TCT ACA GCA ATT CAT GCA GAT CAA CTC ACA CCA GCT TGG CGC ATA TAT TCT ACT GGA
  C           G       C   G   G   G   C       G           G   G   G   G       G   C       G   G   G
V   N   C   T   D   V   S   T   A   I   H   A   D   Q   L   T   P   A   W   R   I   Y   S   T   G

AAC AAT GTA TTC CAG ACT CAA GCA GGC TGT CTT ATA GGA GCT GAG CAT GTC GAC ACT TCT TAT GAG TGC GAC ATT
          C           G       G   G       G   C   G   G                   G   G                   C
N   N   V   F   Q   T   Q   A   G   C   L   I   G   A   E   H   V   D   T   S   Y   E   C   D   I

CCT ATT GGA GCT GGC ATT TGT GCT AGT TAC CAT ACA GTT TCT TTA TTA CGT AGT ACT AGC CAA AAA TCT ATT GTG
  G   C   G   G   G   C       G TCG           G   C   G C G C G   G TCG   G TCG           G   C   C
P   I   G   A   G   I   C   A   S   Y   H   T   V   S   L   L   R   S   T   S   Q   K   S   I   V

GCT TAT ACT ATG TCT TTA GGT GCT GAT AGT TCA ATT GCT TAC TCT AAT AAC ACC ATT GCT ATA CCT ACT AAC TTT
  G       G       G C G   G   G     TCG   G   C   G       G           G   C   G   C   G   G
A   Y   T   M   S   L   G   A   D   S   S   I   A   Y   S   N   N   T   I   A   I   P   T   N   F

TCA ATT AGC ATT ACT ACA GAA GTA ATG CCT GTT TCT ATG GCT AAA ACC TCC GTA GAT TGT AAT ATG TAC ATC TGC
  G   C TCG   C   G   G       C       G   C   G       G       G   G   C
S   I   S   I   T   T   E   V   M   P   V   S   M   A   K   T   S   V   D   C   N   M   Y   I   C

GGA GAT TCT ACT GAA TGT GCT AAT TTG CTT CTC CAA TAT GGT AGC TTT TGC ACA CAA CTA AAT CGT GCA CTC TCA
  G       G   G           G     C     G   G           G TCG           G       G       G   G   G   G
G   D   S   T   E   C   A   N   L   L   L   Q   Y   G   S   F   C   T   Q   L   N   R   A   L   S

GGT ATT GCT GCT GAA CAG GAT CGC AAC ACA CGT GAA GTG TTC GCT CAA GTC AAA CAA ATG TAC AAA ACC CCA ACT
  G   C   G   G               G       G   G       C       G                               G   G   G
G   I   A   A   E   Q   D   R   N   T   R   E   V   F   A   Q   V   K   Q   M   Y   K   T   P   T

TTG AAA TAT TTT GGT GGT TTT AAT TTT TCA CAA ATA TTA CCT GAC CCT CTA AAG CCA ACT AAG AGG TCT TTT ATT
C                 G   G               G       C C G   G       G   G       G   G     C     G       C
L   K   Y   F   G   G   F   N   F   S   Q   I   L   P   D   P   L   K   P   T   K   R   S   F   I

GAG GAC TTG CTC TTT AAT AAG GTG ACA CTC GCT GAT GCT GGC TTC ATG AAG CAA TAT GGC GAA TGC CTA GGT GAT
        C     G               C   G   G   G       G   G                       G           G   G
E   D   L   L   F   N   K   V   T   L   A   D   A   G   F   M   K   Q   Y   G   E   C   L   G   D

ATT AAT GCT AGA GAT CTC ATT TGT GCG CAG AAG TTC AAT GGA CTT ACA GTG TTG CCA CCT CTG CTC ACT GAT GAT
  C       G C G       G   C                           G   G   G   C C     G   G       G   G
I   N   A   R   D   L   I   C   A   Q   K   F   N   G   L   T   V   L   P   P   L   L   T   D   D

ATG ATT GCT GCC TAC ACT GCT GCT CTA GTT AGT GGT ACT GCC ACT GCT GGA TGG ACA TTT GGT GCT GGC GCT GCT
      C   G   G       G   G   G   G   C TCG   G   G   G   G   G   G       G       G   G   G   G   G
M   I   A   A   Y   T   A   A   L   V   S   G   T   A   T   A   G   W   T   F   G   A   G   A   A

CTT CAA ATA CCT TTT GCT ATG CAA ATG GCA TAT AGG TTC AAT GGC ATT GGA GTT ACC CAA AAT GTT CTC TAT GAG
  G       C   G       G               G     C             G   C   G   C   G           C   G
L   Q   I   P   F   A   M   Q   M   A   Y   R   F   N   G   I   G   V   T   Q   N   V   L   Y   E

AAC CAA AAA CAA ATC GCC AAC CAA TTT AAC AAG GCG ATT AGT CAA ATT CAA GAA TCA CTT ACA ACA ACA TCA ACT
                      G                           C TCG       C           G   G   G   G   G   G   G
N   Q   K   Q   I   A   N   Q   F   N   K   A   I   S   Q   I   Q   E   S   L   T   T   T   S   T

GCA TTG GGC AAG CTG CAA GAC GTT GTT AAC CAG AAT GCT CAA GCA TTA AAC ACA CTT GTT AAA CAA CTT AGC TCT
  G C     G                   C   C               G       G C G       G   G   C           G TCG   G
A   L   G   K   L   Q   D   V   V   N   Q   N   A   Q   A   L   N   T   L   V   K   Q   L   S   S

AAT TTT GGT GCA ATT TCA AGT GTG CTA AAT GAT ATC CTT TCG CGA CTT GAT AAA GTC GAG GCG GAG GTA CAA ATT
          G   G   C   G TCG   C   G               G       G   G                           C       C
N   F   G   A   I   S   S   V   L   N   D   I   L   S   R   L   D   K   V   E   A   E   V   Q   I

GAC AGG TTA ATT ACA GGC AGA CTT CAA AGC CTT CAA ACC TAT GTA ACA CAA CAA CTA ATC AGG GCT GCT GAA ATC
    C   C G   C   G   G C G   G     TCG   G       G       C   G           G     C     G   G
D   R   L   I   T   G   R   L   Q   S   L   Q   T   Y   V   T   Q   Q   L   I   R   A   A   E   I

AGG GCT TCT GCT AAT CTT GCT GCT ACT AAA ATG TCT GAG TGT GTT CTT GGA CAA TCA AAA AGA GTT GAC TTT TGT
C     G   G   G       G   G   G   G           G           C   G   G       G     C G   C
R   A   S   A   N   L   A   A   T   K   M   S   E   C   V   L   G   Q   S   K   R   V   D   F   C
```

FIG. 11C

```
GGA AAG GGC TAC CAC CTT ATG TCC TTC CCA CAA GCA GCC CCG CAT GGT GTT GTC TTC CTA CAT GTC ACG TAT GTG
  G       G           G       G       G       G   G           G   C           G                   C
G   K   G   Y   H   L   M   S   F   P   Q   A   A   P   H   G   V   V   F   L   H   V   T   Y   V

CCA TCC CAG GAG AGG AAC TTC ACC ACA GCG CCA GCA ATT TGT CAT GAA GGC AAA GCA TAC TTC CCT CGT GAA GGT
  G   G         C             G   G       G   G   C               G       G           G   G       G
P   S   Q   E   R   N   F   T   T   A   P   A   I   C   H   E   G   K   A   Y   F   P   R   E   G

GTT TTT GTG TTT AAT GGC ACT TCT TGG TTT ATT ACA CAG AGG AAC TTC TTT TCT CCA CAA ATA ATT ACT ACA GAC
  C       C           G   G   G           C   G     C                 G   G       C   C   G   G
V   F   V   F   N   G   T   S   W   F   I   T   Q   R   N   F   F   S   P   Q   I   I   T   T   D

AAT ACA TTT GTC TCA GGA AAT TGT GAT GTC GTT ATT GGC ATC ATT AAC AAC ACA GTT TAT GAT CCT CTG CAA CCT
      G           G   G                   C   C   G       C           G   C           G           G
N   T   F   V   S   G   N   C   D   V   V   I   G   I   I   N   N   T   V   Y   D   P   L   Q   P

GAG CTC GAC TCA TTC AAA GAA GAG CTG GAC AAG TAC TTC AAA AAT CAT ACA TCA CCA GAT GTT GAT CTT GGC GAC
      G       G                                                   G   G   G       C       G   G
E   L   D   S   F   K   E   E   L   D   K   Y   F   K   N   H   T   S   P   D   V   D   L   G   D

ATT TCA GGC ATT AAC GCT TCT GTC GTC AAC ATT CAA AAA GAA ATT GAC CGC CTC AAT GAG GTC GCT AAA AAT TTA
  C   G   G   C       G   G               C               C       G   G               G       C G
I   S   G   I   N   A   S   V   V   N   I   Q   K   E   I   D   R   L   N   E   V   A   K   N   L

AAT GAA TCA CTC ATT GAC CTT CAA GAA TTG GGA AAA TAT GAG CAA TAT ATT AAA TGG CCT TGG TAT GTT TGG CTC
          G   G   C       G         C     G                       C           G           C       G
N   E   S   L   I   D   L   Q   E   L   G   K   Y   E   Q   Y   I   K   W   P   W   Y   V   W   L

GGC TTC ATT GCT GGA CTA ATT GCC ATC GTC ATG GTT ACA ATC TTG CTT TGT TGC ATG ACT AGT TGT TGC AGT TGC
  G       C   G   G   G   C   G               C   G     C     G               G TCG         TCG
G   F   I   A   G   L   I   A   I   V   M   V   T   I   L   L   C   C   M   T   S   C   C   S   C

CTC AAG GGT GCA TGC TCT TGT GGT TCT TGC TGC AAG TTT GAT GAG GAT GAC TCT GAG CCA GTT CTC AAG GGT GTC
  G       G   G       G       G   G                                   G       G   C   G       G
L   K   G   A   C   S   C   G   S   C   C   K   F   D   E   D   D   S   E   P   V   L   K   G   V

AAA TTA CAT TAC ACA TAA
    C G           G
K   L   H   Y   T ¦ stop
                  ¦
                  25,256
```

FIG. 12A

```
CAAT GGG AGC TAT CGG ACC TCG CTT AGG ACT CCT ATT CCC ATG GAG AGA CTC CTA GAT GAG GTT CTT GCC CCC GGT
                                                                 T A T             A T A   A   A   A
                                                     M   E   R   L   L   D   E   V   L   A   P   G

GGG CCT TAT AAC TTA ACC GTC GGC AGT TGG GTA AGA GAC CAC GTC CGC TCA ATT GTC GAG GGC GCG TGG GAA GTG
  A   A               A   A   A TCA                       A A A           A       A   A           A
G   P   Y   N   L   T   V   G   S   W   V   R   D   H   V   R   S   I   V   E   G   A   W   E   V

CGC GAT GTT GTT TCC GCT GCC CAA AAG CGG GCC ATC GTA GCC GTG ATA CCC AGA CCT GTG TTC ACG CAG ATG CAG
A A       A   A   A   A   A         A A   A           A   A       A       A   A   A       A
R   D   V   V   S   A   A   Q   K   R   A   I   V   A   V   I   P   R   P   V   F   T   Q   M   Q

GTC AGT GAT CAC CCA GCA CTC CAC GCA ATT TCG CGG TAT ACC CGC CGC CAT TGG ATC GAG TGG GGC CCT AAA GAA
  A TCA                 T A               A A A       A A A A A                       A   A
V   S   D   H   P   A   L   H   A   I   S   R   Y   T   R   R   H   W   I   E   W   G   P   K   E

GCC CTA CAC GTC CTC ATC GAC CCA AGC CCG GGC CTG CTC CGC GAG GTC GCT CGC GTT GAG CGC CGC TGG GTC GCA
  A T         A T A           TCA   A   A T A T A A A       A   A A A   A     A A A A       A
A   L   H   V   L   I   D   P   S   P   G   L   L   R   E   V   A   R   V   E   R   R   W   V   A

CTG TGC CTC CAC AGG ACG GCA CGC AAA CTC GCC ACC GCC CTG GCC GAG ACG GCC AGC GAG GCG TGG CAC GCT GAC
T A   T T A       A   A     A A     T A   A   A   A T A   A       A   A TCA       A           A
L   C   L   H   R   T   A   R   K   L   A   T   A   L   A   E   T   A   S   E   A   W   H   A   D

TAC GTG TGC GCG CTG CGT GGC GCA CCG AGC GGC CCC TTC TAC GTC CAC CCT GAG GAC GTC CCG CAC GGC GGT CGC
  T   A   T   A T A A A   A       A TCA   A   A       T   A       A           A   A       A   A A A
Y   V   C   A   L   R   G   A   P   S   G   P   F   Y   V   H   P   E   D   V   P   H   G   G   R

GCC GTG GCG GAC AGA TGC TTG CTC TAC TAC ACA CCC ATG CAG ATG TGC GAG CTG ATG CGT ACC ATT GAC GCC ACC
  A   A   A           T   A T A   T   T       A               T     T A     A A   A           A   A
A   V   A   D   R   C   L   L   Y   Y   T   P   M   Q   M   C   E   L   M   R   T   I   D   A   T

CTG CTC GTG GCG GTC GAC TTG TGG CCG GTC GCC CTT GCG GCC CAC GTC GGC GAC GAC TGG GAC GAC CTG GGC ATT
T A T A   A   A   A       A       A   A   A T A   A   A       A   A                     T A   A
L   L   V   A   V   D   L   W   P   V   A   L   A   A   H   V   G   D   D   W   D   D   L   G   I

GCC TGG CAT CTC GAC CAT GAC GGC GGT TGC CCC GCC GAT TGC CGC GGA GCC GGC GCT GGG CCC ACG CCC GGC TAC
  A         T A               A   A   T   A   A       T A A       A   A   A   A   A   A   A   A   T
A   W   H   L   D   H   D   G   G   C   P   A   D   C   R   G   A   G   A   G   P   T   P   G   Y

ACC CGC CCC TGC ACC ACA CGC ATC TAC CAA GTC CTG CCG GAC ACC GCC CAC CCC GGG CGC CTC TAC CGG TGC GGG
  A A A   A   T   A     A A       T       A T A   A       A   A       A   A A A T A   T A A   T   A
T   R   P   C   T   T   R   I   Y   Q   V   L   P   D   T   A   H   P   G   R   L   Y   R   C   G

CCC CGC CTG TGG ACG CGC GAT TGC GCC GTG GCC GAA CTC TCA TGG GAG GTT GCC CAA CAC TGC GGG CAC CAG GCG
  A A A T A       A A A       T   A   A   A     T A               A   A           T   A           A
P   R   L   W   T   R   D   C   A   V   A   E   L   S   W   E   V   A   Q   H   C   G   H   Q   A

CGC GTG CGC GCC GTG CGG TGC ACC CTC CCT ATC CGC CAC GTG CGC AGC CTC CAA CCC AGC GCG CGG GTC CGA CTC
A A   A A A   A   A A A   T   A T A   A     A A       A A A TCA T A       A TCA   A A A   A A   T A
R   V   R   A   V   R   C   T   L   P   I   R   H   V   R   S   L   Q   P   S   A   R   V   R   L

CCG GAC CTC GTC CAT CTC GCC GAG GTG GGC CGG TGG CGG TGG TTC AGC CTC CCC CGC CCC GTG TTC CAG CGC ATG
  A     T A   A     T A   A       A   A A A     A A         TCA T A   A A A   A   A         A A
P   D   L   V   H   L   A   E   V   G   R   W   R   W   F   S   L   P   R   P   V   F   Q   R   M

CTG TCC TAC TGC AAG ACC CTG AGC CCC GAC GCG TAC TAC AGC GAG CGC GTG TTC AAG TTC AAG AAC GCC CTG AGC
T A   A   T   T       A T A TCA   A       A   T   T TCA     A A   A                       A T A TCA
L   S   Y   C   K   T   L   S   P   D   A   Y   Y   S   E   R   V   F   K   F   K   N   A   L   S

CAC AGC ATC ACG CTC GCG GGC AAT GTG CTG CAA GAG GGG TGG AAG GGC ACG TGC GCC GAG GAA GAC GCG CTG TGC
    TCA       A T A   A   A       A T A           A           A   A   T   A               A T A   T
H   S   I   T   L   A   G   N   V   L   Q   E   G   W   K   G   T   C   A   E   E   D   A   L   C

GCA TAC GTA GCC TTC CGC GCG TGG CAG TCT AAC GCC AGG TTG GCG GGG ATT ATG AAA AGC GCG AAG CGC TGC GCC
      T       A     A A   A           A       A   A   A   A   A             TCA   A     A A   T   A
A   Y   V   A   F   R   A   W   Q   S   N   A   R   L   A   G   I   M   K   S   A   K   R   C   A

GCC GAC TCT TTG AGC GTG GCC GGC TGG CTG GAC ACC ATT TGG GGC GCC ATT AAG CGG TTC TTC GGC AGC GTG CCC
  A       A   A TCA   A   A   A     T A       A           A   A         A A           A TCA   A   A
A   D   S   L   S   V   A   G   W   L   D   T   I   W   G   A   I   K   R   F   F   G   S   V   P

CTC GCC GAG CGC ATG GAG GAG TGG GAA CAG GAC GCC GCG GTC GCC GCC TTC GAC CGC GGC CCC CTC GAG GAC GGC
T A   A     A A                               A   A   A   A   A         A A   A   A T A           A
L   A   E   R   M   E   E   W   E   Q   D   A   A   V   A   A   F   D   R   G   P   L   E   D   G
```

FIG. 12B

```
GGG CGC CAC TTG GAC ACC GTG CAA CCC CCA AAA TCG CCG CCC CGC CCT GAG ATC GCC GCG ACC TGG ATC GTC CAC
  A A A       A       A   A       A           A   A   A A A   A           A   A   A           A
G   R   H   L   D   T   V   Q   P   P   K   S   P   P   R   P   E   I   A   A   T   W   I   V   H

GCA GCC AGC GCA GAC CGC CAT TGT GCG TGC GCT CCC CGC TGC GAC GTC CCG CGC GAA CGT CCT TCC GCG CCC GCC
      A TCA         A A           A   T   A   A A A   T       A   A A A     A A   A   A   A   A   A
A   A   S   A   D   R   H   C   A   C   A   P   R   C   D   V   P   R   E   R   P   S   A   P   A

GGC CCG CCG GAT GAC GAG GCG CTC ATC CCG CCG TGG CTG TTC GCC GAG CAC CGT GCC CTC CGC TGC CGC GAG TGG
  A   A   A               A T A       A   A     T A       A         A A   A T A A A   T A A
G   P   P   D   D   E   A   L   I   P   P   W   L   F   A   E   H   R   A   L   R   C   R   E   W

GAT TTC GAG GTT CTC CGC GCG CGC GCC GAT ACG GCG GCC GCG CCC GCC CCG CTG GCT CCA CGC CCT GCG CGG TAC
              A T A A A   A A A   A       A   A   A   A   A   A   A T A   A     A A   A   A A A   T
D   F   E   V   L   R   A   R   A   D   T   A   A   A   P   A   P   L   A   P   R   P   A   R   Y

CCC ACC GTG CTC TAC CGC CAC CCC GCC CAC CAC GGT CCG TGG CTC ACC CTT GAC GAG CCG GGC GAG GCT GAC GCG
  A   A   A T A   T A A       A   A           A   A     T A   A T A           A   A       A       A
P   T   V   L   Y   R   H   P   A   H   H   G   P   W   L   T   L   D   E   P   G   E   A   D   A

GCC CTG GTC CTA TGC GAC CCA CTT GGC CAG CCG CTC CGG GGC CCT GAA CGC CAC TTC GCC GCC GGC GCG CAT ATG
  A T A   A T     T         T A   A       A T A A A   A   A     A A           A   A   A   A
A   L   V   L   C   D   P   L   G   Q   P   L   R   G   P   E   R   H   F   A   A   G   A   H   M

TGC GCG CAG GCG CGG GGG CTC CAG GCT TTT GTC CGT GTC GTG CCT CCA CCC GAG CGC CCC TGG GCC GAC GGG GGC
  T   A       A A A   A T A       A       A A A   A   A   A       A     A A   A       A       A   A
C   A   Q   A   R   G   L   Q   A   F   V   R   V   V   P   P   P   E   R   P   W   A   D   G   G

GCC AGA GCG TGG GCG AAG TTC TTC CGC GGC TGC GCC TGG GCG CAG CGC TTG CTC GGC GAG CCA GCA GTT ATG CAC
  A       A       A             A A   A   T   A       A     A A   A T A   A               A
A   R   A   W   A   K   F   F   R   G   C   A   W   A   Q   R   L   L   G   E   P   A   V   M   H

CTC CCA TAC ACC GAT GGC GAC GTG CCA CAG CTG ATC GCA CTG GCT TTG CGC ACG CTG GCC CAA CAG GGG GCC GCC
T A       T   A       A       A         T A         T A   A   A A A   A T A   A           A   A   A
L   P   Y   T   D   G   D   V   P   Q   L   I   A   L   A   L   R   T   L   A   Q   Q   G   A   A

TTG GCA CTC TCG GTG CGT GAC CTG CCC GGG GGT GCA GCG TTC GAC GCA AAC GCG GTC ACC GCC GCC GTG CGC GCT
  A     T A   A   A A A     T A   A   A   A       A                   A   A   A   A   A   A A A   A
L   A   L   S   V   R   D   L   P   G   G   A   A   F   D   A   N   A   V   T   A   A   V   R   A

GGC CCC GGC CAG TCC GCG GCC ACG TCA TCG CCA CCC GGC GAC CCC CCG CCG CCG CGC TGC GCA CGG CGA TCG CAA
  A   A   A       A   A   A   A       A       A   A       A   A   A   A A A   T     A A A     A
G   P   G   Q   S   A   A   T   S   S   P   P   G   D   P   P   P   P   R   C   A   R   R   S   Q

CGG CAC TCG GAC GCC CGC GGC ACT CCG CCC CCC GCG CCT GCG CGC GAC CCG CCG CCG CCC GCC CCC AGC CCG CCC
A A       A       A A A   A   A   A   A   A   A   A   A A A       A   A   A   A   A   A TCA   A   A
R   H   S   D   A   R   G   T   P   P   P   A   P   A   R   D   P   P   P   P   A   P   S   P   P

GCG CCA CCC CGC GCG GGT GAC CCG GTC CCT CCC ACT TCC GCG GGG CCG GCG GAT CGC GCG CGT GAC GCC GAG CTG
  A       A A A   A   A       A   A   A   A   A   A   A   A   A   A     A A   A A A       A     T A
A   P   P   R   A   G   D   P   V   P   P   T   S   A   G   P   A   D   R   A   R   D   A   E   L

GAG GTC GCC TAC GAA CCG AGC GGC CCC CCC ACG TCA ACC AAG GCA GAC CCA GAC AGC GAC ATC GTT GAA AGT TAC
      A   A   T       A TCA   A   A   A   A       A                     TCA           A     TCA   T
E   V   A   Y   E   P   S   G   P   P   T   S   T   K   A   D   P   D   S   D   I   V   E   S   Y

GCC CGC GCC GCC GGA CCC GTG CAC CTC CGA GTC CGC GAC ATC ATG GAC CCA CCG CCC GGC TGC AAG GTC GTG GTC
  A A A   A   A       A   A     T A A     A A A                       A   A   A   T       A   A   A
A   R   A   A   G   P   V   H   L   R   V   R   D   I   M   D   P   P   P   G   C   K   V   V   V

AAC GCC GCC AAC GAG GGG CTG CTG GCC GGC TCT GGC GTG TGC GGT GCC ATC TTT GCC AAC GCC ACG GCG GCC CTC
      A   A           A T A T A   A   A   A   A   A   T   A   A           A       A   A   A   A T A
N   A   A   N   E   G   L   L   A   G   S   G   V   C   G   A   I   F   A   N   A   T   A   A   L

GCT GCA GAC TGC CGG CGC CTC GCC CCA TGC CCC ACC GGC GAG GCA GTG GCG ACA CCC GGC CAC GGC TGC GGG TAC
  A           T A A A A T A   A       T   A   A   A           A   A       A   A       A   T   A   T
A   A   D   C   R   R   L   A   P   C   P   T   G   E   A   V   A   T   P   G   H   G   C   G   Y

ACC CAC ATC ATC CAC GCC GTC GCG CCG CGG CGT CCT CGG GAC CCC GCC GCC CTC GAG GAG GGC GAA GCG CTG CTC
  A                   A   A   A   A A A A A   A A A       A   A   A T A           A       A T A T A
T   H   I   I   H   A   V   A   P   R   R   P   R   D   P   A   A   L   E   E   G   E   A   L   L

GAG CGC GCC TAC CGC AGC ATC GTC GCG CTA GCC GCC GCG CGT CGG TGG GCG CGT GTC GCG TGC CCC CTC CTC GGC
    A A   A   T A A TCA       A   A T     A   A   A A A A A       A A A   A   A   T   A T A T A   A
E   R   A   Y   R   S   I   V   A   L   A   A   A   R   R   W   A   R   V   A   C   P   L   L   G

GCT GGC GTC TAC GGC TGG TCT GCT GCG GAG TCC CTC CGA GCC GCG CTC GCG GCT ACG CGC ACC GAG CCC GCC GAG
  A   A   A   T   A       A   A   A       A T A A     A   A T A   A   A   A A A   A       A   A
A   G   V   Y   G   W   S   A   A   E   S   L   R   A   A   L   A   A   T   R   T   E   P   A   E

CGC GTG AGC CTG CAC ATC TGC CAT CCC GAC CGC GCC ACG CTG ACG CAC GCC TCC GTG CTC GTC GGC GCG GGG CTC
A A   A TCA T A           T       A     A A   A   A T A   A       A   A   A T A   A   A   A   A T A
R   V   S   L   H   I   C   H   P   D   R   A   T   L   T   H   A   S   V   L   V   G   A   G   L
```

FIG. 12C

```
GCT GCC AGG CGC GTC AGT CCT CCT CCG ACC GAG CCC CTC GCA TCT TGC CCC GCC GGT GAC CCG GGC CGA CCG GCT
  A   A   A A A   A TCA   A   A   A   A       A T A       A   T   A   A   A       A   A A     A   A
A   A   R   R   V   S   P   P   P   T   E   P   L   A   S   C   P   A   G   D   P   G   R   P   A

CAG CGC AGC GCG TCG CCC CCA GCG ACC CCC CTT GGG GAT GCC ACC GCG CCC GAG CCC CGC GGA TGC CAG GGG TGC
    A A TCA   A   A   A       A   A   A T A   A       A   A   A   A       A A A       T       A   T
Q   R   S   A   S   P   P   A   T   P   L   G   D   A   I   A   P   E   P   R   G   C   Q   G   C

GAA CTC TGC CGG TAC ACG CGC GTC ACC AAT GAC CGC GCC TAT GTC AAC CTG TGG CTC GAG CGC GAC CGC GGC GCC
    T A   T A A   T   A A A   A   A         A A   A       A     T A     T A     A A     A A   A   A
E   L   C   R   Y   T   R   V   T   N   D   R   A   Y   V   N   L   W   L   E   R   D   R   G   A

ACC AGC TGG GCC ATG CGC ATT CCC GAG GTG GTT GTC TAC GGG CCG GAG CAC CTC GCC ACG CAT TTT CCA TTA AAC
  A TCA       A     A A       A       A   A   A   T   A   A         T A   A   A
T   S   W   A   M   R   I   P   E   V   V   V   Y   G   P   E   H   L   A   T   H   F   P   L   N

CAC TAC AGT GTG CTC AAG CCC GCG GAG GTC AGG CCC CCG CGA GGC ATG TGC GGG AGT GAC ATG TGG CGC TGC CGC
      T TCA   A T A       A   A       A   A   A   A A     A       T   A TCA             A A   T A A
H   Y   S   V   L   K   P   A   E   V   R   P   P   R   G   M   C   G   S   D   M   W   R   C   R

GGC TGG CAG GGC GTG CCG CAG GTG CGG TGC ACC CCC TCC AAC GCT CAC GCC GCC CTG TGC CGC ACA GGC GTG CCC
  A           A   A   A       A A A   T   A   A   A       A       A   A T A   T A A       A   A   A
G   W   Q   G   V   P   Q   V   R   C   T   P   S   N   A   H   A   A   L   C   R   T   G   V   P

CCT CGG GTG AGC ACG CGA GGC GGC GAG CTA GAC CCA AAC ACC TGC TGG CTC CGC GCC GCC GCC AAC GTT GCG CAG
  A A A   A TCA   A A     A   A     T                 A   T     T A A A   A   A   A       A   A
P   R   V   S   T   R   G   G   E   L   D   P   N   T   C   W   L   R   A   A   A   N   V   A   Q

GCT GCG CGC GCC TGC GGC GCC TAC ACG AGT GCC GGG TGC CCC AGG TGC GCC TAC GGC CGC GCC CTG AGC GAA GCC
  A   A A A   A   T   A   A   T   A TCA   A   A   T   A   A   T   A   T   A A A   A T A TCA       A
A   A   R   A   C   G   A   Y   T   S   A   G   C   P   R   C   A   Y   G   R   A   L   S   E   A

CGC ACT CAT AAG GAC TTC GCC GCG CTG AGC CAG CGG TGG AGC GCG AGC CAC GCC GAT GCC TCC TCT GAC GGC ACC
A A   A                   A   A T A TCA     A A     TCA   A TCA       A       A   A   A       A   A
R   T   H   K   D   F   A   A   L   S   Q   R   W   S   A   S   H   A   D   A   S   S   D   G   T

GGA GAT CCC CTC GAC CCC CTG ATG GAG ACC GTG GGA TGC GCC TGT TCG CGC GTG TGG GTC GGC TCC GAG CAC GAG
          A T A       A T A           A   A       T   A       A A A   A       A   A   A
G   D   P   L   D   P   L   M   E   T   V   G   C   A   C   S   R   V   W   V   G   S   E   H   E

GCC CCG CCC GAC CAC CTC CTG GTG TCC CTC CAC CGT GCC CCA AAT GGT CCG TGG GGC GTA GTG CTC GAG GTG CGT
  A   A   A         T A T A   A   A T A     A A   A           A   A       A       A T A       A A A
A   P   P   D   H   L   L   V   S   L   H   R   A   P   N   G   P   W   G   V   V   L   E   V   R

GCG CGC CCC GAG GGG GGC AAC CCC ACC GGC CAC TTC GTC TGC GCG GTC GGC GGC GGC CCA CGC CGC GTC TCG GAC
  A A A   A       A   A       A   A   A           A   T   A   A   A   A   A     A A A A   A   A
A   R   P   E   G   G   N   P   T   G   H   F   V   C   A   V   G   G   G   P   R   R   V   S   D

CGC CCC CAC CTT TGG CTC GCG GTC CCC CTG TCT CGG GGC GGT GGC ACC TGT GCC GCG ACC GAC GAG GGG CTG GCC
A A   A     T A     T A   A   A   A T A   A A A   A   A   A   A       A   A   A           A T A   A
R   P   H   L   W   L   A   V   P   L   S   R   G   G   G   T   C   A   A   T   D   E   G   L   A

CAG GCG TAC TAC GAC GAC CTC GAG GTG CGC CGC CTC GGG GAT GAC GCC ATG GCC CGG GCG GCC CTC GCA TCA GTC
      A   T   T         T A       A A A A A T A   A           A       A A A   A   A T A           A
Q   A   Y   Y   D   D   L   E   V   R   R   L   G   D   D   A   M   A   R   A   A   L   A   S   V

CAA CGC CCT CGC AAA GGC CCT TAC AAT ATC AGG GTA TGG AAC ATG GCC GCA GGC GCT GGC AAG ACC ACC CGC ATC
    A A   A A A       A   A   T           A                   A       A   A   A       A   A A A
Q   R   P   R   K   G   P   Y   N   I   R   V   W   N   M   A   A   G   A   G   K   T   T   R   I

CTC GCT GCC TTC ACG CGC GAA GAC CTT TAC GTC TGC CCC ACC AAT GCG CTC CTG CAC GAG ATC CAG GCC AAA CTC
T A   A   A       A A A         T A   T   A   T   A   A       A T A T A                   A     T A
L   A   A   F   T   R   E   D   L   Y   V   C   P   T   N   A   L   L   H   E   I   Q   A   K   L

CGC GCG CGC GAT ATC GAG ATC AAG AAC GCC GCC ACC TAC GAG CGC GCG CTG ACG AAA CCG CTC GCC GCC TAC CGC
A A   A A A                           A   A   A   T     A A   A T A   A       A T A   A   A   T A A
R   A   R   D   I   E   I   K   N   A   A   T   Y   E   R   A   L   T   K   P   L   A   A   Y   R

CGC ATC TAC ATC GAT GAG GCG TTC ACT CTC GGC GGC GAG TAC TGC GCG TTC GTT GCC AGC CAA ACC ACC GCG GAG
A A       T               A       A T A   A   A       T   T   A       A   A TCA       A   A   A
R   I   Y   I   D   E   A   F   T   L   G   G   E   Y   C   A   F   V   A   S   Q   T   T   A   E

GTG ATC TGC GTC GGT GAT CGG GAC CAG TGC GGC CCA CAC TAC GCC AAT AAC TGC CGC ACC CCC GTC CCT GAC CGC
  A       T   A   A     A A           T   A           T   A           T A A   A   A   A   A     A A
V   I   C   V   G   D   R   D   Q   C   G   P   H   Y   A   N   N   C   R   T   P   V   P   D   R

TGG CCT ACC GAG CGC TCG CGC CAC ACT TGG CGC TTC CCC GAC TGC TGG GCG GCC CGC CTG CGC GCG GGG CTC GAT
      A   A     A A   A A A       A     A A       A       T       A   A A A T A A A   A   A T A
W   P   T   E   R   S   R   H   T   W   R   F   P   D   C   W   A   A   R   L   R   A   G   L   D

TAT GAC ATC GAG GGC GAG CGC ACC GGC ACC TTC GCC TGC AAC CTT TGG GAC GGC CGC CAG GTC GAC CTT CAC CTC
                  A     A A   A   A   A       A   T     T A           A A A       A     T A     T A
Y   D   I   E   G   E   R   T   G   T   F   A   C   N   L   W   D   G   R   Q   V   D   L   H   L
```

FIG. 12D

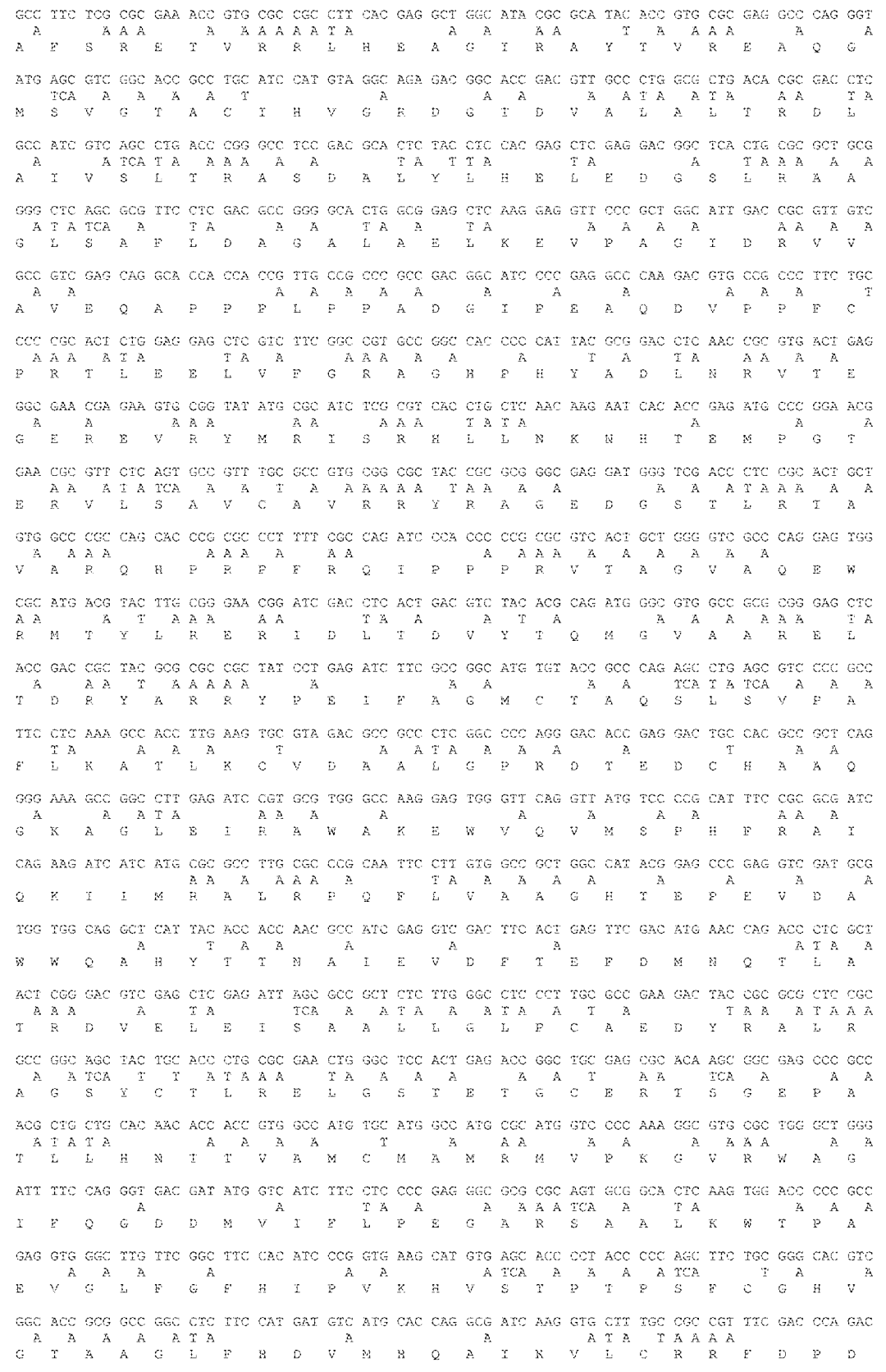

GCC TTC TCG CGC GAA ACC GTG CGC CGC CTT CAC GAG GCT GGC ATA CGC GCA TAC ACC GTG CGC GAG GCC CAG GGT
A A A A A A A A A A T A A A A A T A A A A A A
A F S R E T V R R L H E A G I R A Y T V R E A Q G

ATG AGC GTC GGC ACC GCC TGC ATC CAT GTA GGC AGA GAC GGC ACC GAC GTT GCC CTG GCG CTG ACA CGC GAC CTC
TCA A A A A T A A A A A T A A T A A A T A
M S V G T A C I H V G R D G T D V A L A L T R D L

GCC ATC GTC AGC CTG ACC CGG GCC TCC GAC GCA CTC TAC CTC CAC GAG CTC GAG GAC GGC TCA CTG CGC GCT GCG
A A TCA T A A A A A A T A T T A T A A T A A A A A
A I V S L T R A S D A L Y L H E L E D G S L R A A

GGG CTC AGC GCG TTC CTC GAC GCC GGG GCA CTG GCG GAG CTC AAG GAG GTT CCC GCT GGC ATT GAC CGC GTT GTC
A T A TCA A T A A A T A A T A A A A A A A A A
G L S A F L D A G A L A E L K E V P A G I D R V V

GCC GTC GAG CAG GCA CCA CCA CCG TTG CCG CCC GCC GAC GGC ATC CCC GAG GCC CAA GAC GTG CCG CCC TTC TGC
A A A A A A A A A A A A A T
A V E Q A P P P L P P A D G I P E A Q D V P P F C

CCC CGC ACT CTG GAG GAG CTC GTC TTC GGC CGT GCC GGC CAC CCC CAT TAC GCG GAC CTC AAC CGC GTG ACT GAG
A A A A T A T A A A A A A A A T A T A A A A A
P R T L E E L V F G R A G H P H Y A D L N R V T E

GGC GAA CGA GAA GTG CGG TAT ATG CGC ATC TCG CGT CAC CTG CTC AAC AAG AAT CAC ACC GAG ATG CCC GGA ACG
A A A A A A A A A A T A T A A A A
G E R E V R Y M R I S R H L L N K N H T E M P G T

GAA CGC GTT CTC AGT GCC GTT TGC GCC GTG CGG CGC TAC CGC GCG GGC GAG GAT GGG TCG ACC CTC CGC ACT GCT
A A A T A TCA A A T A A A A A A T A A A A A A A T A A A A A A
E R V L S A V C A V R R Y R A G E D G S T L R T A

GTG GCC CGC CAG CAC CCG CGC CCT TTT CGC CAG ATC CCA CCC CCG CGC GTC ACT GCT GGG GTC GCC CAG GAG TGG
A A A A A A A A A A A A A A A A A A A
V A R Q H P R P F R Q I P P P R V T A G V A Q E W

CGC ATG ACG TAC TTG CGG GAA CGG ATC GAC CTC ACT GAC GTC TAC ACG CAG ATG GGC GTG GCC GCG CGG GAG CTC
A A A T A A A A A T A A A T A A A A A A A T A
R M T Y L R E R I D L T D V Y T Q M G V A A R E L

ACC GAC CGC TAC GCG CGC CGC TAT CCT GAG ATC TTC GCC GGC ATG TGT ACC GCC CAG AGC CTG AGC GTC CCC GCC
A A A T A A A A A A A A A A TCA T A TCA A A A
T D R Y A R R Y P E I F A G M C T A Q S L S V P A

TTC CTC AAA GCC ACC TTG AAG TGC GTA GAC GCC GCC CTC GGC CCC AGG GAC ACC GAG GAC TGC CAC GCC GCT CAG
T A A A A T A A T A A A A A T A A
F L K A T L K C V D A A L G P R D T E D C H A A Q

GGG AAA GCC GGC CTT GAG ATC CGT GCG TGG GCC AAG GAG TGG GTT CAG GTT ATG TCC CCG CAT TTC CGC GCG ATC
A A A T A A A A A A A A A A A A A
G K A G L E I R A W A K E W V Q V M S P H F R A I

CAG AAG ATC ATC ATG CGC GCC TTG CGC CCG CAA TTC CTT GTG GCC GCT GGC CAT ACG GAG CCC GAG GTC GAT GCG
A A A A A A A T A A A A A A A A A
Q K I I M R A L R P Q F L V A A G H T E P E V D A

TGG TGG CAG GCT CAT TAC ACC ACC AAC GCC ATC GAG GTC GAC TTC ACT GAG TTC GAC ATG AAC CAG ACC CTC GCT
A T A A A A A A T A A
W W Q A H Y T T N A I E V D F T E F D M N Q T L A

ACT CGG GAC GTC GAG CTC GAG ATT AGC GCC GCT CTC TTG GGC CTC CCT TGC GCC GAA GAC TAC CGC GCG CTC CGC
A A A A T A TCA A A T A A A T A A T A T A A A T A A A
T R D V E L E I S A A L L G L P C A E D Y R A L R

GCC GGC AGC TAC TGC ACC CTG CGC GAA CTG GGC TCC ACT GAG ACC GGC TGC GAG CGC ACA AGC GGC GAG CCC GCC
A A TCA T T A T A A A T A A A A A A T A A TCA A A A
A G S Y C T L R E L G S T E T G C E R T S G E P A

ACG CTG CTG CAC AAC ACC ACC GTG GCC ATG TGC ATG GCC ATG CGC ATG GTC CCC AAA GGC GTG CGC TGG GCT GGG
A T A T A A A A A T A A A A A A A A A A A
T L L H N T T V A M C M A M R M V P K G V R W A G

ATT TTC CAG GGT GAC GAT ATG GTC ATC TTC CTC CCC GAG GGC GCG CGC AGT GCG GCA CTC AAG TGG ACC CCC GCC
A A T A A A A A A TCA A T A A A A
I F Q G D D M V I F L P E G A R S A A L K W T P A

GAG GTG GGC TTG TTC GGC TTC CAC ATC CCG GTG AAG CAT GTG AGC ACC CCT ACC CCC AGC TTC TGC GGG CAC GTC
A A A A A A A TCA A A A A TCA T A A
E V G L F G F H I P V K H V S T P T P S F C G H V

GGC ACC GCG GCC GGC CTC TTC CAT GAT GTC ATG CAC CAG GCG ATC AAG GTG CTT TGC CGC CGT TTC GAC CCA GAC
A A A A A T A A A A T A T A A A A
G T A A G L F H D V M H Q A I K V L C R R F D P D

FIG. 12E

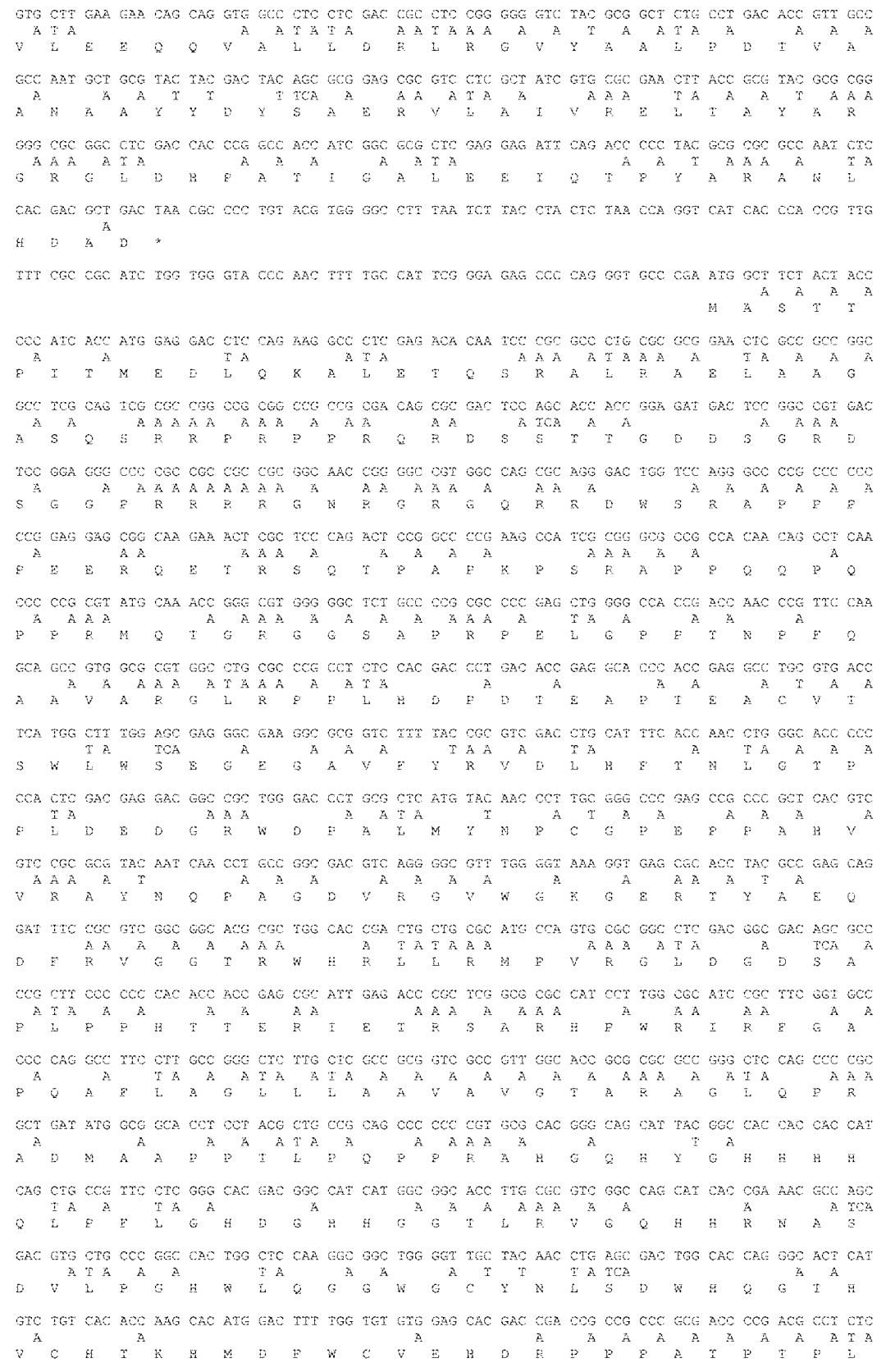

```
GTG CTT GAA GAA CAG CAG GTG GCC CTC CTC GAC CGC CTC CGG GGG GTC TAC GCG GCT CTG CCT GAC ACC GTT GCC
  A T A                   A   A T A T A     A A T A A A   A   A   T   A   A T A   A       A   A   A
V   L   E   E   Q   Q   V   A   L   L   D   R   L   R   G   V   Y   A   A   L   P   D   T   V   A

GCC AAT GCT GCG TAC TAC GAC TAC AGC GCG GAG CGC GTC CTC GCT ATC GTG CGC GAA CTT ACC GCG TAC GCG CGG
  A       A   A   T   T       T TCA   A     A A   A T A   A       A A A     T A   A   A   T   A A A
A   N   A   A   Y   Y   D   Y   S   A   E   R   V   L   A   I   V   R   E   L   T   A   Y   A   R

GGG CGC GGC CTC GAC CAC CCG GCC ACC ATC GGC GCG CTC GAG GAG ATT CAG ACC CCC TAC GCG CGC GCC AAT CTC
  A A A   A T A           A   A   A       A   A T A                   A   A   T   A A A   A     T A
G   R   G   L   D   H   P   A   T   I   G   A   L   E   E   I   Q   T   P   Y   A   R   A   N   L

CAC GAC GCT GAC TAA CGC CCC TGT ACG TGG GGC CTT TAA TCT TAC CTA CTC TAA CCA GGT CAT CAC CCA CCG TTG
          A
H   D   A   D   *

TTT CGC CGC ATC TGG TGG GTA CCC AAC TTT TGC CAT TCG GGA GAG CCC CAG GGT GCC CGA ATG GCT TCT ACT ACC
                                                                                      A   A   A   A
                                                                                M   A   S   T   T

CCC ATC ACC ATG GAG GAC CTC CAG AAG GCC CTC GAG ACA CAA TCC CGC GCC CTG CGC GCG GAA CTC GCC GCC GGC
  A       A             T A           A T A               A A A   A T A A A   A     T A   A   A   A
P   I   T   M   E   D   L   Q   K   A   L   E   T   Q   S   R   A   L   R   A   E   L   A   A   G

GCC TCG CAG TCG CGC CGG CCG CGG CCG CCG CGA CAG CGC GAC TCC AGC ACC ACC GGA GAT GAC TCC GGC CGT GAC
  A   A       A A A A A   A A A   A   A A       A A       A TCA   A   A               A   A A A
A   S   Q   S   R   R   P   R   P   P   R   Q   R   D   S   S   T   T   G   D   D   S   G   R   D

TCC GGA GGG CCC CGC CGC CGC CGC GGC AAC CGG GGC CGT GGC CAG CGC AGG GAC TGG TCC AGG GCC CCG CCC CCC
  A       A   A A A A A A A A A   A     A A   A A A   A     A A   A           A   A   A   A   A   A
S   G   G   P   R   R   R   R   G   N   R   G   R   G   Q   R   R   D   W   S   R   A   P   P   P

CCG GAG GAG CGG CAA GAA ACT CGC TCC CAG ACT CCG GCC CCG AAG CCA TCG CGG GCG CCG CCA CAA CAG CCT CAA
  A         A A           A A A   A       A   A   A   A           A A A   A   A               A
P   E   E   R   Q   E   T   R   S   Q   T   P   A   P   K   P   S   R   A   P   P   Q   Q   P   Q

CCC CCG CGT ATG CAA ACC GGG CGT GGG GGC TCT GCC CCG CGC CCC GAG CTG GGG CCA CCG ACC AAC CCG TTC CAA
  A   A A A           A   A A A   A   A   A   A   A A A   A     T A   A       A   A       A
P   P   R   M   Q   T   G   R   G   G   S   A   P   R   P   E   L   G   P   P   T   N   P   F   Q

GCA GCC GTG GCG CGT GGC CTG CGC CCG CCT CTC CAC GAC CCT GAC ACC GAG GCA CCC ACC GAG GCC TGC GTG ACC
      A   A   A A A   A T A A A   A   A T A           A       A           A   A       A   T   A   A
A   A   V   A   R   G   L   R   P   P   L   H   D   P   D   T   E   A   P   T   E   A   C   V   T

TCA TGG CTT TGG AGC GAG GGC GAA GGC GCG GTC TTT TAC CGC GTC GAC CTG CAT TTC ACC AAC CTG GGC ACC CCC
        T A     TCA       A       A   A   A       T A A   A     T A           A     T A   A   A   A
S   W   L   W   S   E   G   E   G   A   V   F   Y   R   V   D   L   H   F   T   N   L   G   T   P

CCA CTC GAC GAG GAC GGC CGC TGG GAC CCT GCG CTC ATG TAC AAC CCT TGC GGG CCC GAG CCG CCC GCT CAC GTC
    T A               A A A           A   A T A       T       A   T   A   A       A   A   A       A
P   L   D   E   D   G   R   W   D   P   A   L   M   Y   N   P   C   G   P   E   P   P   A   H   V

GTC CGC GCG TAC AAT CAA CCT GCC GGC GAC GTC AGG GGC GTT TGG GGT AAA GGT GAG CGC ACC TAC GCC GAG CAG
  A A A   A   T           A   A   A       A   A   A   A       A       A     A A   A   T   A
V   R   A   Y   N   Q   P   A   G   D   V   R   G   V   W   G   K   G   E   R   T   Y   A   E   Q

GAT TTC CGC GTC GGC GGC ACG CGC TGG CAC CGA CTG CTG CGC ATG CCA GTG CGC GGC CTC GAC GGC GAC AGC GCC
        A A   A   A   A   A A A         A   T A T A A A           A A A   A T A       A     TCA   A
D   F   R   V   G   G   T   R   W   H   R   L   L   R   M   P   V   R   G   L   D   G   D   S   A

CCG CTT CCC CCC CAC ACC ACC GAG CGC ATT GAG ACC CGC TCG GCG CGC CAT CCT TGG CGC ATC CGC TTC GGT GCC
  A T A   A   A       A   A     A A           A A A   A   A A A       A     A A     A A       A   A
P   L   P   P   H   T   T   E   R   I   E   T   R   S   A   R   H   P   W   R   I   R   F   G   A

CCC CAG GCC TTC CTT GCC GGG CTC TTG CTC GCC GCG GTC GCC GTT GGC ACC GCG CGC GCC GGG CTC CAG CCC CGC
  A       A     T A   A   A T A   A T A   A   A   A   A   A   A   A A A   A   A T A           A A A
P   Q   A   F   L   A   G   L   L   L   A   A   V   A   V   G   T   A   R   A   G   L   Q   P   R

GCT GAT ATG GCG GCA CCT CCT ACG CTG CCG CAG CCC CCC CGT GCG CAC GGG CAG CAT TAC GGC CAC CAC CAC CAT
  A           A       A   A   A T A   A       A   A A A   A       A           T   A
A   D   M   A   A   P   P   T   L   P   Q   P   P   R   A   H   G   Q   H   Y   G   H   H   H   H

CAG CTG CCG TTC CTC GGG CAC GAC GGC CAT CAT GGC GGC ACC TTG CGC GTC GGC CAG CAT CAC CGA AAC GCC AGC
    T A   A     T A   A           A           A   A   A   A A A   A   A             A         A TCA
Q   L   P   F   L   G   H   D   G   H   H   G   G   T   L   R   V   G   Q   H   H   R   N   A   S

GAC GTG CTG CCC GGC CAC TGG CTC CAA GGC GGC TGG GGT TGC TAC AAC CTG AGC GAC TGG CAC CAG GGC ACT CAT
      A T A   A   A         T A       A   A       A   T   T     T A TCA                   A   A
D   V   L   P   G   H   W   L   Q   G   G   W   G   C   Y   N   L   S   D   W   H   Q   G   T   H

GTC TGT CAC ACC AAG CAC ATG GAC TTT TGG TGT GTG GAG CAC GAC CGA CCG CCG CCC GCG ACC CCG ACG CCT CTC
  A           A                               A             A     A   A   A   A   A   A   A   A T A
V   C   H   T   K   H   M   D   F   W   C   V   E   H   D   R   P   P   P   A   T   P   T   P   L
```

FIG. 12F

```
ACC ACC GCG GCG AAC TCC ACG ACC GCC GCC ACC CCC GCC ACT GCG CCG GCC CCC TGC CAC GCC GGC CTC AAT GAC
  A   A   A   A       A   A   A   A   A   A   A   A   A   A   A   A   A   T       A   A T A
T   T   A   A   N   S   T   T   A   A   T   P   A   T   A   P   A   P   C   H   A   G   L   N   D

AGC TGC GGC GGC TTC TTG TCT GGG TGC GGG CCG ATG CGC CTG CGC CAC GGC GCT GAC ACC CGG TGC GGT CGG TTG
TCA   T   A   A       A   A   A   T   A   A     A A T A A A       A   A       A A A   T   A A A   A
S   C   G   G   F   L   S   G   C   G   P   M   R   L   R   H   G   A   D   T   R   C   G   R   L

ATC TGC GGG CTG TCT ACC ACC GCC CAG TAC CCG CCT ACC CGG TTT GGC TGC GCT ATG CGG TGG GGC CTT CCC CCC
      T   A T A   A   A   A   A       T   A   A   A A A       A   T   A     A A       A T A   A   A
I   C   G   L   S   T   T   A   Q   Y   P   P   T   R   F   G   C   A   M   R   W   G   L   P   P

TGG GAA CTG GTC GTC CTT ACC GCC CGC CCC GAA GAC GGC TGG ACT TGC CGC GGC GTG CCC GCC CAC CCA GGC ACC
        T A   A   A T A   A   A A A   A           A       A   T A A   A   A   A   A           A   A
W   E   L   V   V   L   T   A   R   P   E   D   G   W   T   C   R   G   V   P   A   H   P   G   T

CGC TGC CCC GAA CTG GTG AGC CCC ATG GGA CGC GCG ACT TGC TCC CCA GCC TCG GCC CTC TGG CTC GCC ACA GCG
A A   T   A     T A   A TCA   A         A A   A   A   T   A       A   A   A T A     T A   A       A
R   C   P   E   L   V   S   P   M   G   R   A   T   C   S   P   A   S   A   L   W   L   A   T   A

AAC GCG CTG TCT CTT GAT CAC GCC CTC GCG GCC TTC GTC CTG CTG GTC CCG TGG GTC CTG ATA TTC ATG GTG TGC
      A T A   A T A           A T A   A   A       A T A T A   A   A       A T A               A   T
N   A   L   S   L   D   H   A   L   A   A   F   V   L   L   V   P   W   V   L   I   F   M   V   C

CGC CGC ACC TGT CGC CGC CGC GGC GCC GCC GCC GCC CTC ACC GCG GTC GTC CTG CAG GGG TAC AAC CCC CCC GCC
A A A A   A     A A A A A A   A   A   A   A   A T A   A   A   A   A T A       A   T       A   A   A
R   R   T   C   R   R   R   G   A   A   A   A   L   T   A   V   V   L   Q   G   Y   N   P   P   A

TAT GGC GAG GAG GCT TTC ACC TAC CTC TGC ACT GCA CCG GGG TGC GCC ACT CAA GCA CCT GTC CCC GTG CGC CTC
      A           A       A   T T A   T   A       A   A   T   A   A           A   A   A   A A A T A
Y   G   E   E   A   F   T   Y   L   C   T   A   P   G   C   A   T   Q   A   P   V   P   V   R   L

GCT GGC GTC CGC TTT GAG TCC AAG ATT GTG GAC GGC GGC TGC TTT GCC CCA TGG GAC CTC GAG GCC ACT GGA GCC
  A   A   A A A           A           A       A   A   T       A             T A       A   A       A
A   G   V   R   F   E   S   K   I   V   D   G   G   C   F   A   P   W   D   L   E   A   T   G   A

TGC ATT TGC GAG ATC CCC ACT GAT GTC TCG TGC GAG GGC TTG GGG GCC TGG GTA CCC ACA GCC CCT TGC GCG CGC
  T       T           A   A       A   A   T       A   A   A   A           A       A   A   T   A A A
C   I   C   E   I   P   T   D   V   S   C   E   G   L   G   A   W   V   P   T   A   P   C   A   R

ATC TGG AAT GGC ACA CAG CGC GCG TGC ACC TTC TGG GCT GTC AAC GCC TAC TCC TCT GGC GGG TAC GCG CAG CTG
              A         A A   A   T   A           A   A       A   T   A   A   A   A   T   A     T A
I   W   N   G   T   Q   R   A   C   T   F   W   A   V   N   A   Y   S   S   G   G   Y   A   Q   L

GCC TCT TAC TTC AAC CCT GGC GGC AGC TAC TAC AAG CAG TAC CAC CCT ACC GCG TGC GAG GTT GAA CCT GCC TTC
  A   A   T           A   A   A TCA   T   T           T       A   A   A   T       A       A   A
A   S   Y   F   N   P   G   G   S   Y   Y   K   Q   Y   H   P   T   A   C   E   V   E   P   A   F

GGA CAC AGC GAC GCG GCC TGC TGG GGC TTC CCC ACC GAC ACC GTG ATG AGC GTG TTC GCC CTT GCT AGC TAC GTC
        TCA       A   A   T       A       A   A       A   A     TCA   A       A T A   A TCA   T   A
G   H   S   D   A   A   C   W   G   F   P   T   D   T   V   M   S   V   F   A   L   A   S   Y   V

CAG CAC CCT CAC AAG ACC GTC CGG GTC AAG TTC CAT ACA GAG ACC AGG ACC GTC TGG CAA CTC TCC GTT GCT GGC
          A           A   A A A   A                       A   A   A   A         T A   A   A   A   A
Q   H   P   H   K   T   V   R   V   K   F   H   T   E   T   R   T   V   W   Q   L   S   V   A   G

GTG TCG TGC AAC GTC ACC ACT GAA CAC CCG TTC TGC AAC ACG CCG CAC GGA CAA CTC GAG GTC CAG GTC CCG CCC
  A   A   T       A   A   A           A       T       A   A             T A       A       A   A   A
V   S   C   N   V   T   T   E   H   P   F   C   N   T   P   H   G   Q   L   E   V   Q   V   P   P

GAC CCC GGG GAC CTG GTT GAG TAC ATT ATG AAC CAC ACC GGC AAT CAG CAG TCC CGG TGG GGC CTC GGG AGC CCG
      A   A     T A   A       T                   A   A               A A A       A T A   A TCA   A
D   P   G   D   L   V   E   Y   I   M   N   H   T   G   N   Q   Q   S   R   W   G   L   G   S   P

AAT TGC CAT GGC CCC GAT TGG GCC TCC CCG GTT TGC CAA CGC CAT TCC CCT GAC TGC TCG CGG CTT GTG GGG GCT
      T       A   A           A   A   A   A   T     A A       A   A       T   A A A T A   A   A   A
N   C   H   G   P   D   W   A   S   P   V   C   Q   R   H   S   P   D   C   S   R   L   V   G   A

ACG CCA GAG CGT CCC CGG CTG CGC CTG GTC GAC GCC GAC GAC CCC CTG CTG CGC ACT GCC CCT GGG CCC GGC GAG
  A         A A   A A A T A A A T A   A       A           A T A T A A A   A   A   A   A   A   A
T   P   E   R   P   R   L   R   L   V   D   A   D   D   P   L   L   R   T   A   P   G   P   G   E

GTG TGG GTC ACG CCT GTC ATA GGC TCT CAG GCG CGC AAG TGC GGA CTC CAC ATA CGC GCT GGA CCG TAC GGC CAT
  A       A   A   A   A       A   A       A A A       T     T A         A A   A       A   T   A
V   W   V   T   P   V   I   G   S   Q   A   R   K   C   G   L   H   I   R   A   G   P   Y   G   H

GCT ACC GTC GAA ATG CCC GAG TGG ATC CAC GCC CAC ACC ACC AGC GAC CCC TGG CAC CCA CCG GGC CCC TTG GGG
  A   A   A           A                   A       A   A TCA       A               A   A   A   A   A
A   T   V   E   M   P   E   W   I   H   A   H   T   T   S   D   P   W   H   P   P   G   P   L   G

CTG AAG TTC AAG ACA GTT CGC CCG GTG GCC CTG CCA CGC ACG TTA GCG CCA CCC CGC AAT GTG CGT GTG ACC GGG
T A                   A A A   A   A   A T A     A A   A       A       A A A       A A A   A   A   A
L   K   F   K   T   V   R   P   V   A   L   P   R   T   L   A   P   P   R   N   V   R   V   T   G
```

FIG. 12G

```
TGC TAC CAG TGC GGT ACC CCC GCG CTG GTG GAA GGC CTT GCC CCC GGG GGA GGG AAT TGC CAT CTC ACC GTC AAT
  T   T       T   A   A   A   A T A   A       A T A   A   A   A       A       T     T A   A   A
C   Y   Q   C   G   T   P   A   L   V   E   G   L   A   P   G   G   G   N   C   H   L   T   V   N

GGC GAG GAT CTC GGC GCC TTC CCC CCT GGG AAG TTC GTC ACC GCC GCC CTC CTC AAC ACC CCC CCG CCC TAC CAA
  A         T A   A   A       A   A   A           A   A   A   A T A T A       A   A   A   A   T
G   E   D   L   G   A   F   P   P   G   K   F   V   T   A   A   L   L   N   T   P   P   P   Y   Q

GTC AGC TGC GGG GGC GAG AGC GAT CGC GCG AGC GCG CGG GTC ATT GAC CCC GCC GCG CAA TCG TTT ACC GGC GTG
  A TCA   T   A   A     TCA     A A   A TCA   A A A   A           A   A   A       A       A   A   A
V   S   C   G   G   E   S   D   R   A   S   A   R   V   I   D   P   A   A   Q   S   F   T   G   V

GTG TAT GGC ACA CAC ACC ACT GCT GTG TCG GAG ACC CGG CAG ACC TGG GCG GAG TGG GCT GCT GCC CAT TGG TGG
  A       A           A   A   A   A   A       A A A       A       A           A   A   A
V   Y   G   T   H   T   T   A   V   S   E   T   R   Q   T   W   A   E   W   A   A   A   H   W   W

CAG CTC ACT CTG GGC GCC ATT TGC GCC CTC CTA CTC GCT GGC TTA CTC GCT TGC TGT GCC AAA TGC TTG TAC TAC
    T A   A T A   A   A       T   A T A T   T A   A   A     T A   A   T       A       T   A   T   T
Q   L   T   L   G   A   I   C   A   L   L   L   A   G   L   L   A   C   C   A   K   C   L   Y   Y

TTG CGC GGC GCT ATA GCG CCG CGC TAG TGG GCC CCC GCG CGA AAC CCG CAC TAG CCC ACT AGA TTC CCG CAC CTG
  A A A   A   A       A   A A A
L   R   G   A   I   A   P   R   *

TTG CTG CAT AG
```

FIG. 13A

Varicella-zoster Virus, Human Herpesvirus 3
gH and gE genes attenuated; 9 amino acid codons modified
Oka vaccine strain (V-Oka)GenBank AB097932
Oka parental strain (P-Oka) GenBank AB097933
The two strains are identical in the gH and gE ORFs.

gH

```
65,959 V-Oka
65,935 P-Oka
|
ATG TTT GCG CTA GTT TTA GCG GTG GTA ATT CTT CCT CTT TGG ACC ACG GCT AAT AAA TCT TAC GTA ACA CCA ACC
          T       C C     T   C   C   C   A       A       T   T             AG        C   T   T   T
M   F   A   L   V   L   A   V   V   I   L   P   L   W   T   T   A   N   K   S   Y   V   T   P   T

CCT GCG ACT CGC TCT ATC GGA CAT ATG TCT GCT CTT CTA CGA GAA TAT TCC GAC CGT AAT ATG TCT CTG AAA TTA
      T     A G AG        C         AG        A     A G         AGT     A G         AG    A     C
P   A   T   R   S   I   G   H   M   S   A   L   L   R   E   Y   S   D   R   N   M   S   L   K   L

GAA GCC TTT TAT CCT ACT GGT TTC GAT GAA GAA CTC ATT AAA TCA CTT CAC TGG GGA AAT GAT AGA AAA CAC GTT
      T                   C                   A   C     AGT   A           C           G           C
E   A   F   Y   P   T   G   F   D   E   E   L   I   K   S   L   H   W   G   N   D   R   K   H   V

TTC TTG GTT ATT GTT AAG GTT AAC CCT ACA ACA CAC GAA GGA GAC GTC GGG CTG GTT ATA TTT CCA AAA TAC TTG
    C A   C   C   C       C           T   T           C           C   A   C   C       T         C A
F   L   V   I   V   K   V   N   P   T   T   H   E   G   D   V   G   L   V   I   F   P   K   Y   L

TTA TCG CCA TAC CAT TTC AAA GCA GAA CAT CGA GCA CCG TTT CCT GCT GGA CGT TTT GGA TTT CTT AGT CAC CCT
C   AGT   T                   T         A G   T   T               C A G       C       A
L   S   P   Y   H   F   K   A   E   H   R   A   P   F   P   A   G   R   F   G   F   L   S   H   P

GTG ACA CCC GAC GTG AGC TTC TTT GAC AGT TCG TTT GCG CCG TAT TTA ACT ACG CAA CAT CTT GTT GCG TTT ACT
  C   T   T       C   T                 AGT       T   T     C         T           A   C   T
V   T   P   D   V   S   F   F   D   S   S   F   A   P   Y   L   T   T   Q   H   L   V   A   F   T

ACG TTC CCA CCA AAC CCC CTT GTA TGG CAT TTG GAA AGA GCT GAG ACC GCA GCA ACT GCA GAA AGG CCG TTT GGG
  T       T   T       T   A   C         C A       G           T   T   T       T           T       C
T   F   P   P   N   P   L   V   W   H   L   E   R   A   E   T   A   A   T   A   E   R   P   F   G

GTA AGT CTT TTA CCC GCT CGC CCA ACA GTC CCC AAG AAT ACT ATT CTT GAA CAT AAA GCG CAT TTT GCT ACA TGG
  C       A C     T     A G   T   T       T               C   A               T               T
V   S   L   L   P   A   R   P   T   V   P   K   N   T   I   L   E   H   K   A   H   F   A   T   W

GAT GCC CTT GCC CGA CAT ACT TTT TTT TCT GCC GAA GCA ATT ATC ACC AAC TCA ACG TTG AGA ATA CAC GTT CCC
      T   A   T A G                 AG    T       T   C       T     AGT   T C A   G   C       C   T
D   A   L   A   R   H   T   F   F   S   A   E   A   I   I   T   N   S   T   L   R   I   H   V   P

CTT TTT GGG TCG GTA TGG CCA ATT CGA TAC TGG GCC ACC GGT TCG GTG CTT CTC ACA AGC GAC TCG GGT CGT GTG
  A       C AGT   C       T   C A G           T   T   C AGT   C   A   A   T   T     AGT   C A G   C
L   F   G   S   V   W   P   I   R   Y   W   A   T   G   S   V   L   L   T   S   D   S   G   R   V

GAA GTA AAT ATT GGT GTA GGA TTT ATG AGC TCG CTC ATT TCT TTA TCC TCT GGA CTA CCG ATA GAA TTA ATT GTT
      C       C   C   C   C           T AGT   A   C AG  C   AGT AG    C       T   C     C     C   C
E   V   N   I   G   V   G   F   M   S   S   L   I   S   L   S   S   G   L   P   I   E   L   I   V

GTA CCA CAT ACA GTA AAA CTG AAC GCG GTT ACA AGC GAC ACC ACA TGG TTC CAG CTA AAT CCA CCG GGT CCG GAT
  C   T       T   C       A       T   C   T   T       T   T                       T   T   C   T
V   P   H   T   V   K   L   N   A   V   T   S   D   T   T   W   F   Q   L   N   P   P   G   P   D

CCG GGG CCA TCT TAT CGA GTT TAT TTA CTT GGA CGT GGG TTG GAT ATG AAT TTT TCA AAG CAT GCT ACG GTC GAT
  T   C   T AG      A G   C     C     A   C A G   C C A                 AGT               T
P   G   P   S   Y   R   V   Y   L   L   G   R   G   L   D   M   N   F   S   K   H   A   T   V   D

ATA TGC GCA TAT CCC GAA GAG AGT TTG GAT TAC CGC TAT CAT TTA TCC ATG GCC CAC ACG GAG GCT CTG CGG ATG
  C       T       T             C A         A G         C   AGT       T       T           A A
I   C   A   Y   P   E   E   S   L   D   Y   R   Y   H   L   S   M   A   H   T   E   A   L   R   M

ACA ACG AAG GCG GAT CAA CAT GAC ATA AAC GAG GAA AGC TAT TAC CAT ATC GCC GCA AGA ATA GCC ACA TCA ATT
  T   T       T                   C               T                   T   T   G   C   T   T AGT   C
T   T   K   A   D   Q   H   D   I   N   E   E   S   Y   Y   H   I   A   A   R   I   A   T   S   I

TTT GCG TTG TCG GAA ATG GGC CGT ACC ACA GAA TAT TTT CTG TTA GAT GAG ATC GTA GAT GTT CAG TAT CAA TTA
      T C A AGT             A G   T   T               A C                 C       C             C
F   A   L   S   E   M   G   R   T   T   E   Y   F   L   L   D   E   I   V   D   V   Q   Y   Q   L

AAA TTC CTT AAT TAC ATT TTA ATG CGG ATA GGA GCA GGA GCT CAT CCC AAC ACT ATA TCC GGA ACC TCG GAT CTG
          A           C C       A     C   C   T   C           T           C AGT   C   T AGT       A
K   F   L   N   Y   I   L   M   R   I   G   A   G   A   H   P   N   T   I   S   G   T   S   D   L
```

FIG. 13B

```
ATC TTT GCC GAT CCA TCG CAG CTT CAT GAC GAA CTT TCA CTT CTT TTT GGT CAG GTA AAA CCC GCA AAT GTC GAT
          T       T AGT       A               A AGT   A   A       C       C       T   T
I   F   A   D   P   S   Q   L   H   D   E   L   S   L   L   F   G   Q   V   K   P   A   N   V   D

TAT TTT ATT TCA TAT GAT GAA GCC CGT GAT CAA CTA AAG ACC GCA TAC GCG CTT TCC CGT GGT CAA GAC CAT GTG
          C AGT               T A G                   T   T       T   A AGT A G   C               C
Y   F   I   S   Y   D   E   A   R   D   Q   L   K   T   A   Y   A   L   S   R   G   Q   D   H   V

AAT GCA CTT TCT CTC GCC AGG CGT GTT ATA ATG AGC ATA TAC AAG GGG CTG CTT GTG AAG CAA AAT TTA AAT GCT
      T   A AG    A   T     A G   C   C       T   C           C   A   A   C             C
N   A   L   S   L   A   R   R   V   I   M   S   I   Y   K   G   L   L   V   K   Q   N   L   N   A

ACA GAG AGG CAG GCT TTA TTT TTT GCC TCA ATG ATT TTA TTA AAT TTC CGC GAA GGA CTA GAA AAT TCA TCT CGG
  T                 C             T AGT       C C   C           A G       C             AGT AG  A
T   E   R   Q   A   L   F   F   A   S   M   I   L   L   N   F   R   E   G   L   E   N   S   S   R

GTA TTA GAC GGT CGC ACA ACT TTG CTT TTA ATG ACA TCC ATG TGT ACG GCA GCT CAC GCC ACG CAA GCA GCA CTT
  C C         C A G   T     C A   A C         T AGT           T   T           T   T       T   T   A
V   L   D   G   R   T   T   L   L   L   M   T   S   M   C   T   A   A   H   A   T   Q   A   A   L

AAC ATA CAA GAA GGC CTG GCA TAC TTA AAT CCT TCA AAA CAC ATG TTT ACA ATA CCA AAC GTA TAC AGT CCT TGT
      C               A   T     C           AGT                   T   C   T       C
N   I   Q   E   G   L   A   Y   L   N   P   S   K   H   M   F   T   I   P   N   V   Y   S   P   C

ATG GGT TCC CTT CGT ACA GAC CTC ACG GAA GAG ATT CAT GTT ATG AAT CTC CTG TCG GCA ATA CCA ACA CGC CCA
      C AGT   A A G   T       A   T           C       C           A   A AGT   T   C   T   T A G   T
M   G   S   L   R   T   D   L   T   E   E   I   H   V   M   N   L   L   S   A   I   P   T   R   P

GGA CTT AAC GAG GTA TTG CAT ACC CAA CTA GAC GAA TCT GAA ATA TTC GAC GCG GCA TTT AAA ACC ATG ATG ATT
  C   A           C C A       T                 AG        C           T   T           T           C
G   L   N   E   V   L   H   T   Q   L   D   E   S   E   I   F   D   A   A   F   K   T   M   M   I

TTT ACC ACA TGG ACT GCC AAA GAT TTG CAT ATA CTC CAC ACC CAT GTA CCA GAA GTA TTT ACG TGT CAA GAT GCA
      T   T           T         C A     C   A       T       C   T       C       T               T
F   T   T   W   T   A   K   D   L   H   I   L   H   T   H   V   P   E   V   F   T   C   Q   D   A

GCC GCG CGT AAC GGA GAA TAT GTG CTC ATT CTT CCA GCT GTC CAG GGA CAC AGT TAT GTG ATT ACA CGA AAC AAA
  T   T A G       C           C   A   C   A   T               C               C   C   T A G
A   A   R   N   G   E   Y   V   L   I   L   P   A   V   Q   G   H   S   Y   V   I   T   R   N   K

CCT CAA AGG GGT TTG GTA TAT TCC CTG GCA GAT GTG GAT GTA TAT AAC CCC ATA TCC GTT GTT TAT TTA AGC AAG
              C C A   C     AGT   A   T       C       C           T   C AGT   C   C     C     T
P   Q   R   G   L   V   Y   S   L   A   D   V   D   V   Y   N   P   I   S   V   V   Y   L   S   K

GAT ACT TGC GTG TCT GAA CAT GGT GTC ATA GAG ACG GTC GCA CTG CCC CAT CCG GAC AAT TTA AAA GAA TGT TTG
              C AG            C       C       T       T   A   T       T         C               C A
D   T   C   V   S   E   H   G   V   I   E   T   V   A   L   P   H   P   D   N   L   K   E   C   L

TAT TGC GGA AGT GTT TTT CTT AGG TAT CTA ACC ACG GGG GCG ATT ATG GAT ATA ATT ATT ATT GAC AGC AAA GAT
          C       C       A               T   T   C   T   C           C   C   C   C       T
Y   C   G   S   V   F   L   R   Y   L   T   T   G   A   I   M   D   I   I   I   I   D   S   K   D

ACA GAA CGA CAA CTA GCC GCT ATG GGA AAC TCC ACA ATT CCA CCC TTC AAT CCA GAC ATG CAC GGG GAT GAC TCT
  T     A G           T           C     AGT   T   C   T   T           T               C         AG
T   E   R   Q   L   A   A   M   G   N   S   T   I   P   P   F   N   P   D   M   H   G   D   D   S

AAG GCT GTG TTG TTG TTT CCA AAC GGA ACT GTG GTA ACG CTT CTA GGA TTC GAA CGA CGA CAA GCC ATA CGA ATG
          C C A C A       T       C       C   C   T   A       C         A G A G       T   C A G
K   A   V   L   L   F   P   N   G   T   V   V   T   L   L   G   F   E   R   R   Q   A   I   R   M

TCG GGA CAA TAC CTT GGG GCC TCT TTA GGA GGG GCG TTT CTG GCG GTA GTG GGG TTT GGT ATT ATC GGA TGG ATG
AGT   C           A   C   T AG  C     C   C   T       A   T   C   C   C       C   C       C
S   G   Q   Y   L   G   A   S   L   G   G   A   F   L   A   V   V   G   F   G   I   I   G   W   M

TTA TGT GGA AAT TCC CGC CTT CGA GAA TAT AAT AAA ATA CCT CTG ACA TAA
C         C     AGT A G   A A G                   C       A   T
L   C   G   N   S   R   L   R   E   Y   N   K   I   P   L   T ¦ stop
                                                              68,484 V-Oka
                                                              68,460 P-Oka
```

FIG. 14A gE

```
115,901 V-Oka
115,913 P-Oka
|
ATG GGG ACA GTT AAT AAA CCT GTG GTG GGG GTA TTG ATG GGG TTC GGA ATT ATC ACG GGA ACG TTG CGT ATA ACG
      C   T   C               C   C   C   C C A       C       C   C       T   C   T C A A G   C   T
M   G   T   V   N   K   P   V   V   G   V   L   M   G   F   G   I   I   T   G   T   L   R   I   T

AAT CCG GTC AGA GCA TCC GTC TTG CGA TAC GAT GAT TTT CAC ATC GAT GAA GAC AAA CTG GAT ACA AAC TCC GTA
      T       G   T AGT     C A A G                                           A       T     AGT   C
N   P   V   R   A   S   V   L   R   Y   D   D   F   H   I   D   E   D   K   L   D   T   N   S   V

TAT GAG CCT TAC TAC CAT TCA GAT CAT GCG GAG TCT TCA TGG GTA AAT CGG GGA GAG TCT TCG CGA AAA GCG TAC
                        AGT           T     AG  AGT       C     A     C     AG  AGT A G       T
Y   E   P   Y   Y   H   S   D   H   A   E   S   S   W   V   N   R   G   E   S   S   R   K   A   Y

GAT CAT AAC TCA CCT TAT ATA TGG CCA CGT AAT GAT TAT GAT GGA TTT TTA GAG AAC GCA CAC GAA CAC CAT GGG
            AGT           C       T A G                   C     C             T                   C
D   H   N   S   P   Y   I   W   P   R   N   D   Y   D   G   F   L   E   N   A   H   E   H   H   G

GTG TAT AAT CAG GGC CGT GGT ATC GAT AGC GGG GAA CGG TTA ATG CAA CCC ACA CAA ATG TCT GCA CAG GAG GAT
  C                 A G   C           T   C     A   C             T   T         AG    T
V   Y   N   Q   G   R   G   I   D   S   G   E   R   L   M   Q   P   T   Q   M   S   A   Q   E   D

CTT GGG GAC GAT ACG GGC ATC CAC GTT ATC CCT ACG TTA AAC GGC GAT GAC AGA CAT AAA ATT GTA AAT GTG GAC
  A   C           T               C           T C                     G           C   C       C
L   G   D   D   T   G   I   H   V   I   P   T   L   N   G   D   D   R   H   K   I   V   N   V   D

CAA CGT CAA TAC GGT GAC GTG TTT AAA GGA GAT CTT AAT CCA AAA CCC CAA GGC CAA AGA CTC ATT GAG GTG TCA
    A G           C       C           C       A       T       T               G   A   C       C AGT
Q   R   Q   Y   G   D   V   F   K   G   D   L   N   P   K   P   Q   G   Q   R   L   I   E   V   S

GTG GAA GAA AAT CAC CCG TTT ACT TTA CGC GCA CCG ATT CAG CGG ATT TAT GGA GTC CGG TAC ACC GAG ACT TGG
  C                   T         C   A G   T   T   C     A     C       C     A         T
V   E   E   N   H   P   F   T   L   R   A   P   I   Q   R   I   Y   G   V   R   Y   T   E   T   W

AGC TTT TTG CCG TCA TTA ACC TGT ACG GGA GAC GCA GCG CCC GCC ATC CAG CAT ATA TGT TTA AAA CAT ACA ACA
  T     C A   T AGT C     T       T   C       T   T   T   T               C     C             T   T
S   F   L   P   S   L   T   C   T   G   D   A   A   P   A   I   Q   H   I   C   L   K   H   T   T

TGC TTT CAA GAC GTG GTG GTG GAT GTG GAT TGC GCG GAA AAT ACT AAA GAG GAT CAG TTG GCC GAA ATC AGT TAC
                  C   C   C       C           T                             C A   T
C   F   Q   D   V   V   V   D   V   D   C   A   E   N   T   K   E   D   Q   L   A   E   I   S   Y

CGT TTT CAA GGT AAG AAG GAA GCG GAC CAA CCG TGG ATT GTT GTA AAC ACG AGC ACA CTG TTT GAT GAA CTC GAA
A G           C               T           T       C   C   C       T   T   T   A               A
R   F   Q   G   K   K   E   A   D   Q   P   W   I   V   V   N   T   S   T   L   F   D   E   L   E

TTA GAC CCC CCC GAG ATT GAA CCG GGT GTC TTG AAA GTA CTT CGG ACA GAA AAA CAA TAC TTG GGT GTG TAC ATT
C         T   T       C       T   C     C A       C   A A     T                 C A   C   C       C
L   D   P   P   E   I   E   P   G   V   L   K   V   L   R   T   E   K   Q   Y   L   G   V   Y   I

TGG AAC ATG CGC GGC TCC GAT GGT ACG TCT ACC TAC GCC ACG TTT TTG GTC ACC TGG AAA GGG GAT GAA AAA ACA
            A G     AGT       C   T AG    T       T   T     C A       T           C               T
W   N   M   R   G   S   D   G   T   S   T   Y   A   T   F   L   V   T   W   K   G   D   E   K   T

AGA AAC CCT ACG CCC GCA GTA ACT CCT CAA CCA AGA GGG GCT GAG TTT CAT ATG TGG AAT TAC CAC TCG CAT GTA
  G           T   T   T   C               T   G   C                                     AGT       C
R   N   P   T   P   A   V   T   P   Q   P   R   G   A   E   F   H   M   W   N   Y   H   S   H   V

TTT TCA GTT GGT GAT ACG TTT AGC TTG GCA ATG CAT CTT CAG TAT AAG ATA CAT GAA GCG CCA TTT GAT TTG CTG
    AGT   C   C       T       T C A   T           A               C           T   T         C A   A
F   S   V   G   D   T   F   S   L   A   M   H   L   Q   Y   K   I   H   E   A   P   F   D   L   L

TTA GAG TGG TTG TAT GTC CCC ATC GAT CCT ACA TGT CAA CCA ATG CGG TTA TAT TCT ACG TGT TTG TAT CAT CCC
C           C A           T               T           T     A   C       AG    T     C A           T
L   E   W   L   Y   V   P   I   D   P   T   C   Q   P   M   R   L   Y   S   T   C   L   Y   H   P

AAC GCA CCC CAA TGC CTC TCT CAT ATG AAT TCC GGT TGT ACA TTT ACC TCG CCA CAT TTA GCC CAG CGT GTT GCA
      T   T           A AG              AGT   C       T       T AGT   T     C     T     A G   C   T
N   A   P   Q   C   L   S   H   M   N   S   G   C   T   F   T   S   P   H   L   A   Q   R   V   A

AGC ACA GTG TAT CAA AAT TGT GAA CAT GCA GAT AAC TAC ACC GCA TAT TGT CTG GGA ATA TCT CAT ATG GAG CCT
  T   T   C                           T               T   T           A   C   C AG
S   T   V   Y   Q   N   C   E   H   A   D   N   Y   T   A   Y   C   L   G   I   S   H   M   E   P
```

FIG. 14B

```
AGC TTT GGT CTA ATC TTA CAC GAC GGG GGC ACC ACG TTA AAG TTT GTA GAT ACA CCC GAG AGT TTG TCG GGA TTA
  T       C         C             C       T   T C             C       T   T         C A AGT   C C
S   F   G   L   I   L   H   D   G   G   T   T   L   K   F   V   D   T   P   E   S   L   S   G   L

TAC GTT TTT GTG GTG TAT TTT AAC GGG CAT GTT GAA GCC GTA GCA TAC ACT GTT GTA TCC ACA GTA GAT CAT TTT
      C       C   C               C       C       T   C   T           C   C AGT   T   C
Y   V   F   V   V   Y   F   N   G   H   V   E   A   V   A   Y   T   V   V   S   T   V   D   H   F

GTA AAC GCA ATT GAA GAG CGT GGA TTT CCG CCA ACG GCC GGT CAG CCA CCG GCG ACT ACT AAA CCC AAG GAA ATT
  C       T   C         A G   C       T   T   T   T   C       T   T   T               T           C
V   N   A   I   E   E   R   G   F   P   P   T   A   G   Q   P   P   A   T   T   K   P   K   E   I

ACC CCC GTA AAC CCC GGA ACG TCA CCA CTT CTA CGA TAT GCC GCA TGG ACC GGA GGG CTT GCA GCA GTA GTA CTT
  T   T   C       T   C   T AGT   T   A     A G       T   T       T   C   C   A   T   T   C   C   A
T   P   V   N   P   G   T   S   P   L   L   R   Y   A   A   W   T   G   G   L   A   A   V   V   L

TTA TGT CTC GTA ATA TTT TTA ATC TGT ACG GCT AAA CGA ATG AGG GTT AAA GCC TAT AGG GTA GAC AAG TCC CCG
C         A   C   C     C             T         A G           C       T           C         AGT   T
L   C   L   V   I   F   L   I   C   T   A   K   R   M   R   V   K   A   Y   R   V   D   K   S   P

TAT AAC CAA AGC ATG TAT TAC GCT GGC CTT CCA GTG GAC GAT TTC GAG GAC TCG GAA TCT ACG GAT ACG GAA GAA
              T                       A   T   C                     AGT     AG    T       T
Y   N   Q   S   M   Y   Y   A   G   L   P   V   D   D   F   E   D   S   E   S   T   D   T   E   E

GAG TTT GGT AAC GCG ATT GGA GGG AGT CAC GGG GGT TCG AGT TAC ACG GTG TAT ATA GAT AAG ACC CGG TGA
          C       T   C   C   C           C   C AGT           T   C       C           T A ¦
E   F   G   N   A   I   G   G   S   H   G   G   S   S   Y   T   V   Y   I   D   K   T   R ¦ stop
                                                                                    V-Oka 117,772
                                                                                    P-Oka 117,784
```

FIG. 15A

```
AGGG CCA AGG AAC ATA CAC ACC CAA CAG AAC CCA GAC CCC GGC CCA CGG CGC CGC GCC CCC AAC CCC CGA CAA CCA

GAG GGA GCC CCC AAC CAA TCC CGC CGG CTC CCC CGG TGC CCA CAG GCA GGG ACA CCA ACC CCC GAA CAG ACC CAG

CAC CCA ACC ATC GAC AAT CCA AGA CGG GGG GGC CCC CCC AAA AAA AGG CCC CCA GGG GCC GAC AGC CAG CAC CGC

GAG GAA GCC CAC CCA CCC CAC ACA CGA CCA CGG CAA CCA AAC CAG AAC CCA GAC CAC CCT GGG CCA CCA GCT CCC

AGA CTC GGC CAT CAC CCC GCA GAA AGG AAA GGC CAC AAC CCG CGC ACC CCA GCC CCG ATC CGG CGG GGA GCC ACC

CAA CCC GAA CCA GCA CCC AAG AGC GAT CCC CGA AGG ACC CCC GAA CCG CAA AGG ACA TCA GTA TCC CAC AGC CTC

TCC AAG TCC CCC GGT CTC CTC CTC TTC TCG AAG GGA CCA AAA GAT CAA TCC ACC ACA CCC GAC GAC ACT CAA CTC

CCC ACC CCT AAA GGA GAC ACC GGG AAT CCC AGA ATC AAG ACT CAT CCA ATG TCC ATC ATG GGT CTC AAG GTG AAC
                                                                      G           C   T       A
                                                                M   S   I   M   G   L   K   V   N

GTC TCT GCC ATA TTC ATG GCA GTA CTG TTA ACT CTC CAA ACA CCC ACC GGT CAA ATC CAT TGG GGC AAT CTC TCT
  A   G   G               G       T C T   G   T       G   G   G   C                           T   G
V   S   A   I   F   M   A   V   L   L   T   L   Q   T   P   T   G   Q   I   H   W   G   N   L   S

AAG ATA GGG GTG GTA GGA ATA GGA AGT GCA AGC TAC AAA GTT ATG ACT CGT TCC AGC CAT CAA TCA TTA GTC ATA
          C   A       C       C TCG   G TCG           A       G   C   G TCG           G C T   A
K   I   G   V   V   G   I   G   S   A   S   Y   K   V   M   T   R   S   S   H   Q   S   L   V   I

AAA TTA ATG CCC AAT ATA ACT CTC CTC AAT AAC TGC ACG AGG GTA GAG ATT GCA GAA TAC AGG AGA CTA CTG AGA
    C T       G           G   T   T                 C C               G         C C C C   T   T C C
K   L   M   P   N   I   T   L   L   N   N   C   T   R   V   E   I   A   E   Y   R   R   L   L   R

ACA GTT TTG GAA CCA ATT AGA GAT GCA CTT AAT GCA ATG ACC CAG AAT ATA AGA CCG GTT CAG AGT GTA GCT TCA
  G   A C T       G     C C       G           G       G             C C       A     TCG       G   G
T   V   L   E   P   I   R   D   A   L   N   A   M   T   Q   N   I   R   P   V   Q   S   V   A   S

AGT AGG AGA CAC AAG AGA TTT GCG GGA GTA GTC CTG GCA GGT GCG GCC CTA GGC GTT GCC ACA GCT GCT CAG ATA
TCG C C C C         C C           C       A   T   G   C       G   T       A   G   G   G   G
S   R   R   H   K   R   F   A   G   V   V   L   A   G   A   A   L   G   V   A   T   A   A   Q   I

ACA GCC GGC ATT GCA CTT CAC CAG TCC ATG CTG AAC TCT CAA GCC ATC GAC AAT CTG AGA GCG AGC CTG GAA ACT
  G   G           G               G       T       G       G               T C C     TCG   T       G
T   A   G   I   A   L   H   Q   S   M   L   N   S   Q   A   I   D   N   L   R   A   S   L   E   T

ACT AAT CAG GCA ATT GAG ACA ATC AGA CAA GCA GGG CAG GAG ATG ATA TTG GCT GTT CAG GGT GTC CAA GAC TAC
  G           G           G     C C       G   C                 C T   G   A       C   A
T   N   Q   A   I   E   T   I   R   Q   A   G   Q   E   M   I   L   A   V   Q   G   V   Q   D   Y

ATC AAT AAT GAG CTG ATA CCG TCT ATG AAC CAA CTA TCT TGT GAT TTA ATC GGC CAG AAG CTC GGG CTC AAA TTG
                  T           G               T   G         C T                   T   C   T     C T
I   N   N   E   L   I   P   S   M   N   Q   L   S   C   D   L   I   G   Q   K   L   G   L   K   L

CTC AGA TAC TAT ACA GAA ATC CTG TCA TTA TTT GGC CCC AGT TTA CGG GAC CCC ATA TCT GCG GAG ATA TCT ATC
  T C C           G           T   G C T           G TCG C T   C       G       G               G
L   R   Y   Y   T   E   I   L   S   L   F   G   P   S   L   R   D   P   I   S   A   E   I   S   I

CAG GCT TTG AGC TAT GCG CTT GGA GGA GAC ATC AAT AAG GTG TTA GAA AAG CTC GGA TAC AGT GGA GGT GAT TTA
      G C T TCG               C   C                   A C T           T   C     TCG   C   C     C T
Q   A   L   S   Y   A   L   G   G   D   I   N   K   V   L   E   K   L   G   Y   S   G   G   D   L

CTG GGC ATC TTA GAG AGC GGA GGA ATA AAG GCC CGG ATA ACT CAC GTC GAC ACA GAG TCC TAC TTC ATT GTC CTC
  T         C T     TCG   C   C           G   C       G       A       G       G               A   T
L   G   I   L   E   S   G   G   I   K   A   R   I   T   H   V   D   T   E   S   Y   F   I   V   L

AGT ATA GCC TAT CCG ACG CTG TCC GAG ATT AAG GGG GTG ATT GTC CAC CGG CTA GAG GGG GTC TCG TAC AAC ATA
TCG       G               T   G               C   A       A       C   T       C   A
S   I   A   Y   P   T   L   S   E   I   K   G   V   I   V   H   R   L   E   G   V   S   Y   N   I

GGC TCT CAA GAG TGG TAT ACC ACT GTG CCC AAG TAT GTT GCA ACC CAA GGG TAC CTT ATC TCG AAT TTT GAT GAG
      G                   G   G   A   G           A   G   G       C
G   S   Q   E   W   Y   T   T   V   P   K   Y   V   A   T   Q   G   Y   L   I   S   N   F   D   E

TCA TCG TGT ACT TTC ATG CCA GAG GGG ACT GTG TGC AGC CAA AAT GCC TTG TAC CCG ATG AGT CCT CTG CTC CAA
  G           G           G       C   G   A     TCG           G C T             TCG   G   T   T
S   S   C   T   F   M   P   E   G   T   V   C   S   Q   N   A   L   Y   P   M   S   P   L   L   Q

GAA TGC CTC CGG GGG TAC ACC AAG TCC TGT GCT CGT ACA CTC GTA TCC GGG TCT TTT GGG AAC CGG TTC ATT TTA
          T   C   C       G       G       G   C   G   T       G   C   G       C       C         C T
E   C   L   R   G   Y   T   K   S   C   A   R   T   L   V   S   G   S   F   G   N   R   F   I   L

TCA CAA GGG AAC CTA ATA GCC AAT TGT GCA TCA ATC CTT TGC AAG TGT TAC ACA ACA GGA ACG ATC ATT AAT CAA
  G       C       T       G           G   G                           G   G   C
S   Q   G   N   L   I   A   N   C   A   S   I   L   C   K   C   Y   T   T   G   T   I   I   N   Q
```

FIG. 15B

```
GAC CCT GAC AAG ATC CTA ACA TAC ATT GCT GCC GAT CAC TGC CCG GTA GTC GAG GTG AAC GGC GTG ACC ATC CAA
      G               T   G           G   G                       A       A           A   G
D   P   D   K   I   L   T   Y   I   A   A   D   H   C   P   V   V   E   V   N   G   V   T   I   Q

GTC GGG AGC AGG AGG TAT CCA GAC GCT GTG TAC TTG CAC AGA ATT GAC CTC GGT CCT CCC ATA TCA TTG GAG AGG
  A   C TCG C C C C       G       G   A     C T     C C           T   C   G   G       G C T     C C
V   G   S   R   R   Y   P   D   A   V   Y   L   H   R   I   D   L   G   P   P   I   S   L   E   R

TTG GAC GTA GGG ACA AAT CTG GGG AAT GCA ATT GCT AAG TTG GAG GAT GCC AAG GAA TTG TTG GAG TCA TCG GAC
C T           C   G       T   C       G       G     C T           G         C T C T       G
L   D   V   G   T   N   L   G   N   A   I   A   K   L   E   D   A   K   E   L   L   E   S   S   D

CAG ATA TTG AGG AGT ATG AAA GGT TTA TCG AGC ACT AGC ATA GTC TAC ATC CTG ATT GCA GTG TGT CTT GGA GGG
        C T C C TCG           C C T     TCG   G TCG       A           T       G   A           C   C
Q   I   L   R   S   M   K   G   L   S   S   T   S   I   V   Y   I   L   I   A   V   C   L   G   G

TTG ATA GGG ATC CCC GCT TTA ATA TGT TGC TGC AGG GGG CGT TGT AAC AAA AAG GGA GAA CAA GTT GGT ATG TCA
C T       C       G   G C T                 C C   C   C                   C           A   C       G
L   I   G   I   P   A   L   I   C   C   C   R   G   R   C   N   K   K   G   E   Q   V   G   M   S

AGA CCA GGC CTA AAG CCT GAT CTT ACG GGA ACA TCA AAA TCC TAT GTA AGG TCG CTC TGA TCC TCT ACA ACT CTT
C C   G       T       G               C   G   G       G         C C       T
R   P   G   L   K   P   D   L   T   G   T   S   K   S   Y   V   R   S   L

GAA ACA CAA ATG TCC CAC AAG TCT CCT CTT CGT CAT CAA GCA ACC ACC GCA CCC AGC ATC AAG CCC ACC TGA AAT

TAT CTC CGG CTT CCC TCT GGC CGA ACA ATA TCG GTA GTT AAT CAA AA
```

FIG. 16A

```
AGGGT GCA AGA TCA TCC ACA ATG TCA CCA CAA CGA GAC CGG ATA AAT GCC TTC TAC AAA GAT AAC CCC CAT CCC AAG
                                G   G       C       C           G                       G       G
                          M   S   P   Q   R   D   R   I   N   A   F   Y   K   D   N   P   H   P   K

  GGA AGT AGG ATA GTC ATT AAC AGA GAA CAT CTT ATG ATT GAT AGA CCT TAT GTT TTG CTG GCT GTT CTG TTT GTC
    C TCG C C       A         C C                         C C   G       A C T   T   G   A   T       A
  G   S   R   I   V   I   N   R   E   H   L   M   I   D   R   P   Y   V   L   L   A   V   L   F   V

  ATG TTT CTG AGC TTG ATC GGG TTG CTA GCC ATT GCA GGC ATT AGA CTT CAT CGG GCA GCC ATC TAC ACC GCA GAG
            T TCG C T       C C T   T   G       G         C C           C   G   G           G   G
  M   F   L   S   L   I   G   L   L   A   I   A   G   I   R   L   H   R   A   A   I   Y   T   A   E

  ATC CAT AAA AGC CTC AGC ACC AAT CTA GAT GTA ACT AAC TCA ATC GAG CAT CAG GTC AAG GAC GTG CTG ACA CCA
              TCG   T TCG   G       T           G       G                   A           A   T   G   G
  I   H   K   S   L   S   T   N   L   D   V   T   N   S   I   E   H   Q   V   K   D   V   L   T   P

  CTC TTC AAA ATC ATC GGT GAT GAA GTG GGC CTG AGG ACA CCT CAG AGA TTC ACT GAC CTA GTG AAA TTA ATC TCT
    T                   C           A       T C C   G   G     C C       G       T   A     C T       G
  L   F   K   I   I   G   D   E   V   G   L   R   T   P   Q   R   F   T   D   L   V   K   L   I   S

  GAC AAG ATT AAA TTC CTT AAT CCG GAT AGG GAG TAC GAC TTC AGA GAT CTC ACT TGG TGT ATC AAC CCG CCA GAG
                                      C C                 C C       T   G                       G
  D   K   I   K   F   L   N   P   D   R   E   Y   D   F   R   D   L   T   W   C   I   N   P   P   E

  AGA ATC AAA TTG GAT TAT GAT CAA TAC TGT GCA GAT GTG GCT GCT GAA GAG CTC ATG AAT GCA TTG GTG AAC TCA
  C C         C T                           G       A   G   G           T           G C T   A       G
  R   I   K   L   D   Y   D   Q   Y   C   A   D   V   A   A   E   E   L   M   N   A   L   V   N   S

  ACT CTA CTG GAG ACC AGA ACA ACC AAT CAG TTC CTA GCT GTC TCA AAG GGA AAC TGC TCA GGG CCC ACT ACA ATC
    G   T   T       G C C   G   G               T   G   A   G       C           G   C   G   G   G
  T   L   L   E   T   R   T   T   N   Q   F   L   A   V   S   K   G   N   C   S   G   P   T   T   I

  AGA GGT CAA TTC TCA AAC ATG TCG CTG TCC CTG TTA GAC TTG TAT TTA GGT CGA GGT TAC AAT GTG TCA TCT ATA
  C C   C           G               T   G   T C T     C T     C T   C   C   C           A   G   G
  R   G   Q   F   S   N   M   S   L   S   L   L   D   L   Y   L   G   R   G   Y   N   V   S   S   I

  GTC ACT ATG ACA TCC CAG GGA ATG TAT GGG GGA ACT TAC CTA GTG GAA AAG CCT AAT CTG AGC AGC AAA AGG TCA
    A   G       G   G       C           C   C   G       T   A           G       T TCG TCG     C C   G
  V   T   M   T   S   Q   G   M   Y   G   G   T   Y   L   V   E   K   P   N   L   S   S   K   R   S

  GAG TTG TCA CAA CTG AGC ATG TAC CGA GTG TTT GAA GTA GGT GTT ATC AGA AAT CCG GGT TTG GGG GCT CCG GTG
      C T   G       T TCG           C   A               C   A     C C           C C T   C   G       A
  E   L   S   Q   L   S   M   Y   R   V   F   E   V   G   V   I   R   N   P   G   L   G   A   P   V

  TTC CAT ATG ACA AAC TAT CTT GAG CAA CCA GTC AGT AAT GAT CTC AGC AAC TGT ATG GTG GCT TTG GGG GAG CTC
                G                       G   A TCG           T TCG               A   G C T   C       T
  F   H   M   T   N   Y   L   E   Q   P   V   S   N   D   L   S   N   C   M   V   A   L   G   E   L

  AAA CTC GCA GCC CTT TGT CAC GGG GAA GAT TCT ATC ACA ATT CCC TAT CAG GGA TCA GGG AAA GGT GTC AGC TTC
        T   G   G               C           G       G       G           C   G   C       C   A TCG
  K   L   A   A   L   C   H   G   E   D   S   I   T   I   P   Y   Q   G   S   G   K   G   V   S   F

  CAG CTC GTC AAG CTA GGT GTC TGG AAA TCC CCA ACC GAC ATG CAA TCC TGG GTC CCC TTA TCA ACG GAT GAT CCA
        T   A       T   C   A           G   G   G               G       A   G C T   G               G
  Q   L   V   K   L   G   V   W   K   S   P   T   D   M   Q   S   W   V   P   L   S   T   D   D   P

  GTG ATA GAC AGG CTT TAC CTC TCA TCT CAC AGA GGT GTT ATC GCT GAC AAT CAA GCA AAA TGG GCT GTC CCG ACA
    A         C C           T   G   G     C C   C   A       G               G           G   A       G
  V   I   D   R   L   Y   L   S   S   H   R   G   V   I   A   D   N   Q   A   K   W   A   V   P   T

  ACA CGA ACA GAT GAC AAG TTG CGA ATG GAG ACA TGC TTC CAA CAG GCG TGT AAG GGT AAA ATC CAA GCA CTC TGC
    G   C   G             C T   C           G                               C               G   T
  T   R   T   D   D   K   L   R   M   E   T   C   F   Q   Q   A   C   K   G   K   I   Q   A   L   C

  GAG AAT CCC GAG TGG GCA CCA TTG AAG GAT AAC AGG ATT CCT TCA TAC GGG GTC TTG TCT GTT GAT CTG AGT CTG
            G           G   G C T             C C       G   G       C   A C T   G   A       T TCG   T
  E   N   P   E   W   A   P   L   K   D   N   R   I   P   S   Y   G   V   L   S   V   D   L   S   L

  ACA GTT GAG CTT AAA ATC AAA ATT GCT TCG GGA TTC GGG CCA TTG ATC ACA CAC GGT TCA GGG ATG GAC CTA TAC
    G   A                           G       C       C   G C T       G       C   G   C           T
  T   V   E   L   K   I   K   I   A   S   G   F   G   P   L   I   T   H   G   S   G   M   D   L   Y

  AAA TCC AAC CAC AAC AAT GTG TAT TGG CTG ACT ATC CCG CCA ATG AAG AAC CTA GCC TTA GGT GTA ATC AAC ACA
        G                   A           T   G           G               T   G C T   C               G
  K   S   N   H   N   N   V   Y   W   L   T   I   P   P   M   K   N   L   A   L   G   V   I   N   T

  TTG GAG TGG ATA CCG AGA TTC AAG GTT AGT CCC TAC CTC TTC ACT GTC CCA ATT AAG GAA GCA GGC GAA GAC TGC
  C T                 C C           A TCG   G       T       G   A   G               G
  L   E   W   I   P   R   F   K   V   S   P   Y   L   F   T   V   P   I   K   E   A   G   E   D   C

  CAT GCC CCA ACA TAC CTA CCT GCG GAG GTG GAT GGT GAT GTC AAA CTC AGT TCC AAT CTG GTG ATT CTA CCT GGT
        G   G   G       T   G           A       C       A       T TCG   G       T   A       T   G   C
  H   A   P   T   Y   L   P   A   E   V   D   G   D   V   K   L   S   S   N   L   V   I   L   P   G
```

FIG. 16B

```
CAA GAT CTC CAA TAT GTT TTG GCA ACC TAC GAT ACT TCC AGG GTT GAA CAT GCT GTG GTT TAT TAC GTT TAC AGC
          T           A C T   G   G           G   G C C   A           G   A   A           A     TCG
Q   D   L   Q   Y   V   L   A   T   Y   D   T   S   R   V   E   H   A   V   V   Y   Y   V   Y   S

CCA AGC CGC TCA TTT TCT TAC TTT TAT CCT TTT AGG TTG CCT ATA AAG GGG GTC CCC ATC GAA TTA CAA GTG GAA
  G TCG       G       G               G     C C C T   G           C   A   G         C T       A
P   S   R   S   F   S   Y   F   Y   P   F   R   L   P   I   K   G   V   P   I   E   L   Q   V   E

TGC TTC ACA TGG GAC CAA AAA CTC TGG TGC CGT CAC TTC TGT GTG CTT GCG GAC TCA GAA TCT GGT GGA CAT ATC
          G                   T           C               A               G       G   C   C
C   F   T   W   D   Q   K   L   W   C   R   H   F   C   V   L   A   D   S   E   S   G   G   H   I

ACT CAC TCT GGG ATG GTG GGC ATG GGA GTC AGC TGC ACA GTC ACC CGG GAA GAT GGA ACC AAT CGC AGA TAG GGC
  G       G   C       A           C   A TCG       G   A   G   C           C   G         C C
T   H   S   G   M   V   G   M   G   V   S   C   T   V   T   R   E   D   G   T   N   R   R

TGC TAG TGA ACC AAT CAC ATG ATG TCA CCC AGA CAT CAG GCA TAC CCA CTA GTG TGA AAT AGA CAT CAG AAT TAA

GAA AAA
```

FIG. 17A

```
GGGG CAA ATA ACA ATG GAG TTG CTA ATC CTC AAA GCA AAT GCA ATT ACC ACA ATC CTC ACT GCA GTC ACA TTT TGT
                         C     G       G       G       G       G   G       G   G   G       G
                 M   E   L   L   I   L   K   A   N   A   I   T   T   I   L   T   A   V   T   F   C

TTT GCT TCT GGT CAA AAC ATC ACT GAA GAA TTT TAT CAA TCA ACA TGC AGT GCA GTT AGC AAA GGC TAT CTT AGT
      G   G   G               G   G   G               G   G     TCG   G     TCG       G       G TCG
F   A   S   G   Q   N   I   T   E   E   F   Y   Q   S   T   C   S   A   V   S   K   G   Y   L   S

GCT CTG AGA ACT GGT TGG TAT ACC AGT GTT ATA ACT ATA GAA TTA AGT AAT ATC AAG GAA AAT AAG TGT AAT GGA
  G     C G   G   G           G TCG           G       G C G TCG               G                   G
A   L   R   T   G   W   Y   T   S   V   I   T   I   E   L   S   N   I   K   E   N   K   C   N   G

ACA GAT GCT AAG GTA AAA TTG ATA AAA CAA GAA TTA GAT AAA TAT AAA AAT GCT GTA ACA GAA TTG CAG TTG CTC
  G       G             C                 G C G                       G       G   G C       C     G
T   D   A   K   V   K   L   I   K   Q   E   L   D   K   Y   K   N   A   V   T   E   L   Q   L   L

ATG CAA AGC ACA CCA GCA ACA AAC AAT CGA GCC AGA AGA GAA CTA CCA AGG TTT ATG AAT TAT ACA CTC AAC AAT
        TCG   G   G   G   G           G   G C G C G   G   G   G C                     G   G
M   Q   S   T   P   A   T   N   N   R   A   R   R   E   L   P   R   F   M   N   Y   T   L   N   N

GCC AAA AAA ACC AAT GTA ACA TTA AGC AAG AAA AGG AAA AGA AGA TTT CTT GGT TTT TTG TTA GGT GTT GGA TCT
  G           G           G C G TCG         C       C G C G       G   G     C   C G   G       G   G
A   K   K   T   N   V   T   L   S   K   K   R   K   R   R   F   L   G   F   L   L   G   V   G   S

GCA ATC GCC AGT GGC GTT GCT GTA TCT AAG GTC CTG CAC CTA GAA GGG GAA GTG AAC AAG ATC AAA AGT GCT CTA
  G       G TCG   G       G       G                   G   G       G                     TCG   G   G
A   I   A   S   G   V   A   V   S   K   V   L   H   L   E   G   E   V   N   K   I   K   S   A   L

CTA TCC ACA AAC AAG GCT GTA GTC AGC TTA TCA AAT GGA GTT AGT GTC TTA ACC AGC AAA GTG TTA GAC CTC AAA
  G   G   G           G         TCG C G   G       G     TCG     C G   G TCG         C G       G
L   S   T   N   K   A   V   V   S   L   S   N   G   V   S   V   L   T   S   K   V   L   D   L   K

AAC TAT ATA GAT AAA CAA TTG TTA CCT ATT GTG AAC AAG CAA AGC TGC AGC ATA TCA AAT ATA GCA ACT GTG ATA
                        C   C G   G                     TCG     TCG       G           G   G
N   Y   I   D   K   Q   L   L   P   I   V   N   K   Q   S   C   S   I   S   N   I   A   T   V   I

GAG TTC CAA CAA AAG AAC AAC AGA CTA CTA GAG ATT ACC AGG GAA TTT AGT GTT AAT GCA GGT GTA ACT ACA CCT
                            C G   G   G           G C     G     TCG           G   G       G   G   G
E   F   Q   Q   K   N   N   R   L   L   E   I   T   R   E   F   S   V   N   A   G   V   T   T   P

GTA AGC ACT TAC ATG TTA ACT AAT AGT GAA TTA TTG TCA TTA ATC AAT GAT ATG CCT ATA ACA AAT GAT CAG AAA
    TCG   G         C G   G     TCG   G C G C     G C G                   G       G
V   S   T   Y   M   L   T   N   S   E   L   L   S   L   I   N   D   M   P   I   T   N   D   Q   K

AAG TTA ATG TCC AAC AAT GTT CAA ATA GTT AGA CAG CAA AGT TAC TCT ATC ATG TCC ATA ATA AAA GAG GAA GTC
    C G       G                         C G         TCG       G           G                   G
K   L   M   S   N   N   V   Q   I   V   R   Q   Q   S   Y   S   I   M   S   I   I   K   E   E   V

TTA GCA TAT GTA GTA CAA TTA CCA CTA TAT GGT GTT ATA GAT ACA CCC TGT TGG AAA CTA CAC ACA TCC CCT CTA
C G   G                 C G   G   G       G               G   G               G       G   G   G   G
L   A   Y   V   V   Q   L   P   L   Y   G   V   I   D   T   P   C   W   K   L   H   T   S   P   L

TGT ACA ACC AAC ACA AAA GAA GGG TCC AAC ATC TGT TTA ACA AGA ACT GAC AGA GGA TGG TAC TGT GAC AAT GCA
      G   G       G       G       G             C G   G C G   G     C G   G                       G
C   T   T   N   T   K   E   G   S   N   I   C   L   T   R   T   D   R   G   W   Y   C   D   N   A

GGA TCA GTA TCT TTC TTC CCA CAA GCT GAA ACA TGT AAA GTT CAA TCA AAT CGA GTA TTT TGT GAC ACA ATG AAC
  G   G       G           G       G   G   G                   G       G                   G
G   S   V   S   F   F   P   Q   A   E   T   C   K   V   Q   S   N   R   V   F   C   D   T   M   N

AGT TTA ACA TTA CCA AGT GAA GTA AAT CTC TGC AAT GTT GAC ATA TTC AAC CCC AAA TAT GAT TGT AAA ATT ATG
TCG C G   G C G   G TCG   G           G                               G
S   L   T   L   P   S   E   V   N   L   C   N   V   D   I   F   N   P   K   Y   D   C   K   I   M

ACT TCA AAA ACA GAT GTA AGC AGC TCC GTT ATC ACA TCT CTA GGA GCC ATT GTG TCA TGC TAT GGC AAA ACT AAA
  G   G       G         TCG TCG   G           G   G   G   G   G           G           G       G
T   S   K   T   D   V   S   S   S   V   I   T   S   L   G   A   I   V   S   C   Y   G   K   T   K

TGT ACA GCA TCC AAT AAA AAT CGT GGA ATC ATA AAG ACA TTT TCT AAC GGG TGC GAT TAT GTA TCA AAT AAA GGG
      G   G   G               G   G               G       G                           G
C   T   A   S   N   K   N   R   G   I   I   K   T   F   S   N   G   C   D   Y   V   S   N   K   G

GTG GAC ACT GTG TCT GTA GGT AAC ACA TTA TAT TAT GTA AAT AAG CAA GAA GGT AAA AGT CTC TAT GTA AAA GGT
          G       G       G       G C G                           G   G     TCG   G               G
V   D   T   V   S   V   G   N   T   L   Y   Y   V   N   K   Q   E   G   K   S   L   Y   V   K   G

GAA CCA ATA ATA AAT TTC TAT GAC CCA TTA GTA TTC CCC TCT GAT GAA TTT GAT GCA TCA ATA TCT CAA GTC AAC
  G   G                           G C G           G   G       G           G   G       G
E   P   I   I   N   F   Y   D   P   L   V   F   P   S   D   E   F   D   A   S   I   S   Q   V   N

GAG AAG ATT AAC CAG AGC CTA GCA TTT ATT CGT AAA TCC GAT GAA TTA TTA CAT AAT GTA AAT GCT GGT AAA TCC
                    TCG   G   G           G       G       G C G C G                   G   G       G
E   K   I   N   Q   S   L   A   F   I   R   K   S   D   E   L   L   H   N   V   N   A   G   K   S
```

FIG. 17B

```
ACC ATA AAT ATC ATG ATA ACT ACT ATA ATT ATA GTG ATT ATA GTA ATA TTG TTA TCA TTA ATT GCT GTT GGA CTG
 G                        G   G                                 C   C G   G C G       G       G
T   I   N   I   M   I   T   T   I   I   I   V   I   I   V   I   L   L   S   L   I   A   V   G   L

CTC TTA TAC TGT AAG GCC AGA AGC ACA CCA GTC ACA CTA AGC AAA GAT CAA CTG AGT GGT ATA AAT AAT ATT GCA
  G C G               G C G TCG   G   G       G   G TCG                 TCG   G                   G
L   L   Y   C   K   A   R   S   T   P   V   T   L   S   K   D   Q   L   S   G   I   N   N   I   A

TTT AGT AAC TAA ATA AAA ATA GCA CCT AAT CAT GTT CTT ACA ATG GTT TAC TAT CTG CTC ATA GAC AAC CCA TCT
    TCG
F   S   N

GTC ATT GGA TTT TCT TAA AAT CTG AAC TTC ATC GAA ACT CTC ATC TAT AAA CCA TCT CAC TTA CAC TAT TTA AGT

AGA TTC CTA GTT TAT AGT TAT ATA AAA
```

FIG. 18

```
GGG GCA AAT GCA AAC ATG TCC AAA AAC AAG GAC CAA CGC ACC GCT AAG ACA TTA GAA AGG ACC TGG GAC ACT CTC
                          G                       G   G   G       G C G   G C     G           G   G
                    M   S   K   N   K   D   Q   R   T   A   K   T   L   E   R   T   W   D   T   L

AAT CAT TTA TTA TTC ATA TCA TCG TGC TTA TAT AAG TTA AAT CTT AAA TCT GTA GCA CAA ATC ACA TTA TCC ATT
        C G C G           G         C G         C G       G       G       G           G C G   G
N   H   L   L   F   I   S   S   C   L   Y   K   L   N   L   K   S   V   A   Q   I   T   L   S   I

CTG GCA ATG ATA ATC TCA ACT TCA CTT ATA ATT GCA GCC ATC ATA TTC ATA GCC TCG GCA AAC CAC AAA GTC ACA
      G               G   G   G   G           G   G                   G       G                   G
L   A   M   I   I   S   T   S   L   I   I   A   A   I   I   F   I   A   S   A   N   H   K   V   T

CCA ACA ACT GCA ATC ATA CAA GAT GCA ACA AGC CAG ATC AAG AAC ACA ACC CCA ACA TAC CTC ACC CAG AAT CCT
  G   G   G   G                   G   G TCG                   G   G   G   G       G   G           G
P   T   T   A   I   I   Q   D   A   T   S   Q   I   K   N   T   T   P   T   Y   L   T   Q   N   P

CAG CTT GGA ATC AGT CCC TCT AAT CCG TCT GAA ATT ACA TCA CAA ATC ACC ACC ATA CTA GCT TCA ACA ACA CCA
      G   G     TCG   G   G           G   G       G   G           G   G       G   G   G   G   G   G
Q   L   G   I   S   P   S   N   P   S   E   I   T   S   Q   I   T   T   I   L   A   S   T   T   P

GGA GTC AAG TCA ACC CTG CAA TCC ACA ACA GTC AAG ACC AAA AAC ACA ACA ACA ACT CAA ACA CAA CCC AGC AAG
  G           G   G           G   G   G           G           G   G   G   G       G       G TCG
G   V   K   S   T   L   Q   S   T   T   V   K   T   K   N   T   T   T   T   Q   T   Q   P   S   K

CCC ACC ACA AAA CAA CGC CAA AAC AAA CCA CCA AGC AAA CCC AAT AAT GAT TTT CAC TTT GAA GTG TTC AAC TTT
  G   G   G           G               G   G TCG       G                           G
P   T   T   K   Q   R   Q   N   K   P   P   S   K   P   N   N   D   F   H   F   E   V   F   N   F

GTA CCC TGC AGC ATA TGC AGC AAC AAT CCA ACC TGC TGG GCT ATC TGC AAA AGA ATA CCA AAC AAA AAA CCA GGA
      G     TCG         TCG           G   G           G             C G       G               G   G
V   P   C   S   I   C   S   N   N   P   T   C   W   A   I   C   K   R   I   P   N   K   K   P   G

AAG AAA ACC ACT ACC AAG CCC ACA AAA AAA CCA ACC CTC AAG ACA ACC AAA AAA GAT CCC AAA CCT CAA ACC ACT
          G   G   G       G   G           G   G   G       G   G               G       G       G   G
K   K   T   T   T   K   P   T   K   K   P   T   L   K   T   T   K   K   D   P   K   P   Q   T   T

AAA TCA AAG GAA GTA CCC ACC ACC AAG CCC ACA GAA GAG CCA ACC ATC AAC ACC ACC AAA ACA AAC ATC ATA ACT
      G       G       G   G   G       G   G   G       G   G           G   G       G               G
K   S   K   E   V   P   T   T   K   P   T   E   E   P   T   I   N   T   T   K   T   N   I   I   T

ACA CTA CTC ACC TCC AAC ACC ACA GGA AAT CCA GAA CTC ACA AGT CAA ATG GAA ACC TTC CAC TCA ACT TCC TCC
  G   G   G   G   G       G   G   G       G   G   G   G TCG           G   G           G   G   G   G
T   L   L   T   S   N   T   T   G   N   P   E   L   T   S   Q   M   E   T   F   H   S   T   S   S

GAA GGC AAT CCA AGC CCT TCT CAA GTC TCT ACA ACA TCC GAG TAC CCA TCA CAA CCT TCA TCT CCA CCC AAC ACA
  G   G       G TCG   G   G           G   G   G   G           G   G       G   G   G   G   G       G
E   G   N   P   S   P   S   Q   V   S   T   T   S   E   Y   P   S   Q   P   S   S   P   P   N   T

CCA CGC CAG TAG TTA CTT AAA AA
  G   G
P   R   Q
```

FIG. 19

```
CAA AAA CTT CCC GGA AAT GAC AAC AGC ACG GCA ACG CTG TGC CTT GGG CAC CAT GCA GTA CCA AAC GGA ACG ATT
        T A   G   C             TCG       G     T A     T A   C           G       G       C       C
Q   K   L   P   G   N   D   N   S   T   A   T   L   C   L   G   H   H   A   V   P   N   G   T   I

GTG AAA ACA ATC ACG AAT GAC CAA ATT GAA GTT ACT AAT GCT ACT GAG CTG GTT CAG AGT TCC TCA ACA GGT GGA
          G                       C           G           G     T A         TCG   G   G   G   C   C
V   K   T   I   T   N   D   Q   I   E   V   T   N   A   T   E   L   V   Q   S   S   S   T   G   G

ATA TGC GAC AGT CCT CAT CAG ATC CTT GAT GGA GAA AAC TGC ACA CTA ATA GAT GCT CTA TTG GGA GAC CCT CAG
  C         TCG   G             T A       C               G T     C         T     A   C       G
I   C   D   S   P   H   Q   I   L   D   G   E   N   C   T   L   I   D   A   L   L   G   D   P   Q

TGT GAT GGC TTC CAA AAT AAG AAA TGG GAC CTT TTT GTT GAA CGC AGC AAA GCC TAC AGC AAC TGT TAC CCT TAT
                                        T A                 TCG       G     TCG               G
C   D   G   F   Q   N   K   K   W   D   L   F   V   E   R   S   K   A   Y   S   N   C   Y   P   Y

GAT GTG CCG GAT TAT GCC TCC CTT AGG TCA CTA GTT GCC TCA TCC GGC ACA CTG GAG TTT AAC AAT GAA AGC TTC
                      G   G T A C C   G T         G   G   G       G T A                     TCG
D   V   P   D   Y   A   S   L   R   S   L   V   A   S   S   G   T   L   E   F   N   N   E   S   F

AAT TGG ACT GGA GTC ACT CAG AAT GGA ACA AGC TCT GCT TGC AAA AGG AGA TCT AAT AAA AGT TTC TTT AGT AGA
          G   C       G           C   G TCG   G             C C C C   G         TCG         TCG C C
N   W   T   G   V   T   Q   N   G   T   S   S   A   C   K   R   R   S   N   K   S   F   F   S   R

TTG AAT TGG TTG ACC CAT TTA AAA TAC AAA TAC CCA GCA TTG AAC GTG ACT ATG CCA AAC AAT GAA AAA TTT GAC
  A           A   G                           G   G   A           G       G
L   N   W   L   T   H   L   K   Y   K   Y   P   A   L   N   V   T   M   P   N   N   E   K   F   D

AAA TTG TAC ATT TGG GGG GTT CAC CAC CCG GGT ACG GAC AGT GAC CAA ATC AGC CTA TAT GCT CAA GCA TCA GGA
      A       C       C                   C         TCG             TCG T                 G   G   C
K   L   Y   I   W   G   V   H   H   P   G   T   D   S   D   Q   I   S   L   Y   A   Q   A   S   G

AGA ATC ACA GTC TCT ACC AAA AGA AGC CAA CAA ACT GTA ATC CCG AAT ATC GGA TCT AGA CCC AGG GTA AGG GAT
C C       G       G   G     C C TCG           G                       C   G C C   G C C     C C
R   I   T   V   S   T   K   R   S   Q   Q   T   V   I   P   N   I   G   S   R   P   R   V   R   D

GTC TCC AGC AGA ATA AGC ATC TAT TGG ACA ATA GTA AAA CCG GGA GAC ATA CTT TTG ATT AAC AGC ACA GGG AAT
      G TCG C C   C TCG               G   C               C       C T A   A   C     TCG   G   C
V   S   S   R   I   S   I   Y   W   T   I   V   K   P   G   D   I   L   L   I   N   S   T   G   N

CTA ATT GCT CCT AGG GGT TAC TTC AAA ATA CGA AGT GGG AAA AGC TCA ATA ATG AGA TCA GAT GCA CCC ATT GGC
T     C       G C C   C               C   C TCG   C     TCG   G   C     C C   G       G   G   C
L   I   A   P   R   G   Y   F   K   I   R   S   G   K   S   S   I   M   R   S   D   A   P   I   G

AAA TGC AAT TCT GAA TGC ATC ACT CCA AAT GGA AGC ATT CCC AAT GAC AAA CCA TTT CAA AAT GTA AAC AGG ATC
              G               G   G       C TCG   C   G               G                     C C
K   C   N   S   E   C   I   T   P   N   G   S   I   P   N   D   K   P   F   Q   N   V   N   R   I

ACA TAT GGG GCC TGT CCC AGA TAT GTT AAG CAA AAC ACT CTG AAA TTG GCA ACA GGG ATG CGA AAT GTA CCA GAG
  G       C   G       G C C                       G T A       A   G   G   C       C           G
T   Y   G   A   C   P   R   Y   V   K   Q   N   T   L   K   L   A   T   G   M   R   N   V   P   E

AAA CAA ACT AGA GGC ATA TTT GGC GCA ATC GCG GGT TTC ATA GAA AAT GGT TGG GAG GGA ATG GTG G
          G C C       C           G           C       C           C           C
K   Q   T   R   G   I   F   G   A   I   A   G   F   I   E   N   G   W   E   G   M   V
```

FIG. 20

```
AAA GCA GGA GTG AAn ATG AAT CCA AAT CAA AAG ATA ATA ACG ATT GGC TCT GTT TCT CTC ACC ATT TCC ACA ATA
      G   C                   G               C   C       C       G       G T A   G   C   G   G   C
K   A   G   V   X   M   N   P   N   Q   K   I   I   T   I   G   S   V   S   L   T   I   S   T   I

TGC TTC TTC ATG CAA ATT GCC ATC CTG ATA ACT ACT GTA ACA TTG CAT TTC AAG CAA TAT GAA TTC AAC TCC CCC
                      C   G     T A   C   G   G       G   A                                   G   G
C   F   F   M   Q   I   A   I   L   I   T   T   V   T   L   H   F   K   Q   Y   E   F   N   S   P

CCA AAC AAC CAA GTG ATG CTG TGT GAA CCA ACA ATA ATA GAA AGA AAC ATA ACA GAG ATA GTG TAT CTG ACC AAC
  G                     T A           G   G   C   C     C C       C   G       C         T A   G
P   N   N   Q   V   M   L   C   E   P   T   I   I   E   R   N   I   T   E   I   V   Y   L   T   N

ACC ACC ATA GAG AAG GAA ATA TGC CCC AAA CTA GCA GAA TAC AGA AAT TGG TCA AAG CCG CAA TGT AAC ATT ACA
  G   G   C               C       G     T     G         C C           G                       C   G
T   T   I   E   K   E   I   C   P   K   L   A   E   Y   R   N   W   S   K   P   Q   C   N   I   T

GGA TTT GCA CCT TTT TCT AAG GAC AAT TCG ATT CGG CTT TCC GCT GGT GGG GAC ATC TGG GTG ACA AGA GAA CCT
  C       G   G       G                   C   C T A   G   G   C   C                   G C C       G
G   F   A   P   F   S   K   D   N   S   I   R   L   S   A   G   G   D   I   W   V   T   R   E   P

TAT GTG TCA TGC GAT CCT GAC AAG TGT TAT CAA TTT GCC CTT GGA CAG GGA ACA ACA CTA AAC AAC GTG CAT TCA
          G           G                           G T A   C       C   G   G T                     G
Y   V   S   C   D   P   D   K   C   Y   Q   F   A   L   G   Q   G   T   T   L   N   N   V   H   S

AAT GAC ACA GTA CAT GAT AGG ACC CCT TAT CGG ACC CTA TTG ATG AAT GAG TTG GGT GTT CCA TTT CAT CTG GGG
          G             C C   G   G       C   G T     A               A   C       G     T A       C
N   D   T   V   H   D   R   T   P   Y   R   T   L   L   M   N   E   L   G   V   P   F   H   L   G

ACC AAG CAA GTG TGC ATA GCA TGG TCC AGC TCA AGT TGT CAC GAT GGA AAG GCA TGG CTG CAT GTT TGT GTA ACG
  G                   C   G       G TCG   G TCG               C       G     T A
T   K   Q   V   C   I   A   W   S   S   S   S   C   H   D   G   K   A   W   L   H   V   C   V   T

GGG GAT GAT GAA AAT GCA ACT GCT AGC TTC ATT TAC AAT GGG AGG CTT GTA GAT AGT ATT GTT TCA TGG TCC AAA
  C                   G   G   G TCG       C           C C C T A         TCG   C       G       G
G   D   D   E   N   A   T   A   S   F   I   Y   N   G   R   L   V   D   S   I   V   S   W   S   K

AAA ATC CTC AGG ACC CAG GAG TCA GAA TGC GTT TGT ATC AAT GGA ACT TGT ACA GTA GTA ATG ACT GAT GGG AGT
        T A C C   G           G                           C   G       G               G       C TCG
K   I   L   R   T   Q   E   S   E   C   V   C   I   N   G   T   C   T   V   V   M   T   D   G   S

GCT TCA GGA AAA GCT GAT ACT AAA ATA CTA TTC ATT GAG GAG GGG AAA ATC GTT CAT ACT AGC ACA TTG TCA GGA
  G   G   C       G       G       C T         C           C                   G TCG   G   A   G   C
A   S   G   K   A   D   T   K   I   L   F   I   E   E   G   K   I   V   H   T   S   T   L   S   G

AGT GCT CAG CAT GTC GAG GAG TGC TCC TGT TAT CCT CGA TAT CCT GGT GTC AGA TGT GTC TGC AGA GAC AAC TGG
TCG   G                           G           G   C       G   C     C C             C C
S   A   Q   H   V   E   E   C   S   C   Y   P   R   Y   P   G   V   R   C   V   C   R   D   N   W

AAA GGC TCC AAT AGG CCC ATC GTA GAT ATA AAC ATA AAG GAT TAT AGC ATT GTT TCC AGT TAT GTG TGC TCA GGA
          G     C C   G               C       C             TCG   C       G TCG                 G   C
K   G   S   N   R   P   I   V   D   I   N   I   K   D   Y   S   I   V   S   S   Y   V   C   S   G

CTT GTT GGA GAC ACA CCC AGA AAA AAC GAC AGC TCC AGC AGT AGC CAT TGC TTG GAT CCA AAC AAT GAG GAA GGT
T A       C       G   G C C             TCG   G TCG TCG TCG           A       G                   C
L   V   G   D   T   P   R   K   N   D   S   S   S   S   S   H   C   L   D   P   N   N   E   E   G

GGT CAT GGA GTG AAA GGC TGG GCC TTT GAT GAT GGA AAT GAC GTG TGG ATG GGA AGA ACG ATC AGC GAG AAG TTA
  C       C                   G               C                       C C C         TCG
G   H   G   V   K   G   W   A   F   D   D   G   N   D   V   W   M   G   R   T   I   S   E   K   L

CGC TCA GGA TAT GAA ACC TTC AAA GTC ATT GAA GGC TGG TCC AAC CCT AAC TCC AAA TTG CAG ATA AAT AGG CAA
      G   C           G               C               G       G       G       A       C     C C
R   S   G   Y   E   T   F   K   V   I   E   G   W   S   N   P   N   S   K   L   Q   I   N   R   Q

GTC ATA GTT GAC AGA GGT AAT AGG TCC GGT TAT TCT GGT ATT TTC TCT GTT GAA GGC AAA AGC TGC ATC AAT CGG
      C         C C   C     C C   G   C       G   C   C       G                 TCG               C
V   I   V   D   R   G   N   R   S   G   Y   S   G   I   F   S   V   E   G   K   S   C   I   N   R

TGC TTT TAT GTG GAG TTG ATA AGG GGA AGA AAA CAA GAA ACT GAA GTC TTG TGG ACC TCA AAC AGT ATT GTT GTG
                      A   C C C   C C C               G           A       G   G     TCG   C
C   F   Y   V   E   L   I   R   G   R   K   Q   E   T   E   V   L   W   T   S   N   S   I   V   V

TTT TGT GGC ACC TCA GGT ACA TAT GGA ACA GGC TCA TGG CCT GAT GGG GCG GAC ATC AAT CTC ATG CCT ATA TAA
              G   G   C   G       C   G       G       G       C                 T A     G   C
F   C   G   T   S   G   T   Y   G   T   G   S   W   P   D   G   A   D   I   N   L   M   P   I   *

GCT TTC GCA ATT TTA GAA AAA ACT CCT TGT TTC C
  G       G C               G   G
A   F   A   I   L   E   K   T   P   C   F
```

FIG. 21A

```
ATG AGA GTG ATG GGG ATA TTG AAG AAT TAT CAG CAA TGG TGG ATG TGG GGC ATC TTA GGC TTT TGG ATG TTA ATA
    C T   C       T     C C                                       T     C C   T             C C
M   R   V   M   G   I   L   K   N   Y   Q   Q   W   W   M   W   G   I   L   G   F   W   M   L   I

ATT AGT AGT GTG GTA GGA AAC TTG TGG GTC ACA GTC TAT TAT GGG GTA CCT GTG TGG AAA GAA GCA AAA ACT ACT
    TCG TCG   C   C   T     C C           G               T   C   G   C               G       G   G
I   S   S   V   V   G   N   L   W   V   T   V   Y   Y   G   V   P   V   W   K   E   A   K   T   T

CTA TTC TGT ACA TCA GAT GCT AAA GCA TAT GAG ACA GAG GTG CAT AAT GTC TGG GCT ACA CAT GCC TGT GTA CCC
  C           G   G       G       G           G       C                   G   G       G       C   G
L   F   C   T   S   D   A   K   A   Y   E   T   E   V   H   N   V   W   A   T   H   A   C   V   P

ACA GAC CCC AAC CCA CAA GAA ATA GTT TTG GAA AAT GTA ACA GAA AAT TTT AAC ATG TGG AAA AAT GAC ATG GTG
  G       G       G               C C C           C   G                                           C
T   D   P   N   P   Q   E   I   V   L   E   N   V   T   E   N   F   N   M   W   K   N   D   M   V

GAT CAG ATG CAT GAG GAT ATA ATC AGT TTA TGG GAC CAA AGC CTA AAG CCA TGT GTA AAG TTG ACC CCA CTC TGT
                                TCG C C             TCG   C       G       C     C C   G   G
D   Q   M   H   E   D   I   I   S   L   W   D   Q   S   L   K   P   C   V   K   L   T   P   L   C

GTC ACT TTA AAA TGT AGA AAT GTT AAT GCT ACC AAC AAT ATT AAT AGC ATG ATT GAT AAC AGT AAT AAG GGA GAA
      G C C         C T       C       G   G                 TCG                 TCG           T
V   T   L   K   C   R   N   V   N   A   T   N   N   I   N   S   M   I   D   N   S   N   K   G   E

ATG AAA AAT TGC TCT TTC AAT GTA ACC ACA GAA CTA AGA GAT AGG AAA CAG GAA GTA CAT GCA CTT TTT TAT AGA
                  G           C   G   G       C C T     C T               C       G   C         C T
M   K   N   C   S   F   N   V   T   T   E   L   R   D   R   K   Q   E   V   H   A   L   F   Y   R

CTT GAT GTA GTA CCA CTT CAG GGC AAC AAC TCT AAT GAG TAT AGA TTA ATA AAT TGT AAT ACG TCA GCC ATA ACA
  C       C   C   G   C       T           G             C T C C                       G   G       G
L   D   V   V   P   L   Q   G   N   N   S   N   E   Y   R   L   I   N   C   N   T   S   A   I   T

CAA GCC TGT CCA AAG GTC TCT TTT GAT CCA ATT CCT ATA CAT TAT TGT ACT CCA GCT GGT TAT GCG ATT CTA AAG
      G       G           G           G       G                   G   G   G                   C
Q   A   C   P   K   V   S   F   D   P   I   P   I   H   Y   C   T   P   A   G   Y   A   I   L   K

TGT AAT AAT CAG ACA TTC AAT GGG ACA GGA CCA TGC AAT AAT GTC AGC TCA GTA CAA TGT GCA CAT GGA ATT AAG
                  G           T   G   T   G                 TCG   G   C           G       T
C   N   N   Q   T   F   N   G   T   G   P   C   N   N   V   S   S   V   Q   C   A   H   G   I   K

CCA GTG GTA TCA ACT CAG CTA CTG TTA AAT GGT AGC GTA GCA AAA GGA GAG ATA ATA ATT AGA TCT GAA AAT CTG
  G   C   C   G   G       C   C C C         TCG   C   G       T                 C T   G           C
P   V   V   S   T   Q   L   L   L   N   G   S   V   A   K   G   E   I   I   I   R   S   E   N   L

ACA AAC AAT GCC AAA ATA ATA ATA GTA CAA CTT AAT AAA CCT GTA AAA ATT GTG TGT GTA AGG CCT AAC AAT AAT
  G           G                   C       C           G   C           C       C C T   G
T   N   N   A   K   I   I   I   V   Q   L   N   K   P   V   K   I   V   C   V   R   P   N   N   N

ACA AGA AAA AGT GTA AGG ATA GGA CCA GGA CAA ACA TTC TAT GCA ACA GGA GAA ATA ATA GGA GAC ATA AGA CAA
  G C T     TCG   C C T       T   G   T       G           G   G   T               T         C T
T   R   K   S   V   R   I   G   P   G   Q   T   F   Y   A   T   G   E   I   I   G   D   I   R   Q

GCA TAT TGT ATC ATT AAT AAA ACT GAA TGG AAT AGC ACT TTA CAA GGG GTA AGT AAA AAA TTA GAA GAA CAC TTC
  G                           G             TCG   G C C       T   C TCG         C C
A   Y   C   I   I   N   K   T   E   W   N   S   T   L   Q   G   V   S   K   K   L   E   E   H   F

TCT AAA AAA GCA ATA AAA TGT GAA CCG TCA TCA GGA GGG GAC CTA GAA ATT ACA ACA CAT AGC TTT AAT TGT AGA
  G           G                       G   G   T   T       C           G   G     TCG             C T
S   K   K   A   I   K   C   E   P   S   S   G   G   D   L   E   I   T   T   H   S   F   N   C   R

GGA GAA TTT TTC TAT TGC GAC ACA TCA CAA CTG TTT AAT AGT ACA TAC AGT CCC AGT TTT AAT GGT ACA GAA AAT
  T                           G   G       C         TCG   G     TCG   G TCG               G
G   E   F   F   Y   C   D   T   S   Q   L   F   N   S   T   Y   S   P   S   F   N   G   T   E   N

AAA TTA AAC GGG ACC ATC ACA ATC ACA TGT AGA ATA AAA CAA ATT ATA AAC ATG TGG CAA AAG GTA GGA AGA GCA
    C C       T   G       G       G     C T                                           C   T C T   G
K   L   N   G   T   I   T   I   T   C   R   I   K   Q   I   I   N   M   W   Q   K   V   G   R   A

ATG TAT GCC CCT CCC ATT GCA GGA AAC CTA ACA TGT GAA TCA GAT ATC ACA GGA TTA CTA TTG ACA CGT GAT GGA
          G   G   G       G   T       C   G           G           G   T C C   C C C   G           T
M   Y   A   P   P   I   A   G   N   L   T   C   E   S   D   I   T   G   L   L   L   T   R   D   G

GGA AAA ACA GGT CCA AAT GAC ACA GAG ATA TTC AGA CCT GGA GGA GGG GAT ATG AGG GAC AAC TGG AGA AAT GAA
  T       G       G           G             C T   G   T   T   T         C T             C T
G   K   T   G   P   N   D   T   E   I   F   R   P   G   G   G   D   M   R   D   N   W   R   N   E

TTA TAT AAA TAT AAA GTA GTA GAA ATT AAG CCA TTG GGA GTA GCA CCC ACT GAG GCA AAA AGG AGA GTG GTG GAG
C C                   C   C               G C C   T   C   G   G   G       G     C T C T   C   C
L   Y   K   Y   K   V   V   E   I   K   P   L   G   V   A   P   T   E   A   K   R   R   V   V   E

AGA GAA AAA AGA GCA GTG GGA ATA GGA GCT GTG TGC CTT GGG TTC TTG GGA GCA GCT GGA AGC ACT ATG GGC GCG
C T         C T   G   C   T       T   G   C       C   T     C C   T   G   G   T TCG   G       T
R   E   K   R   A   V   G   I   G   A   V   C   L   G   F   L   G   A   A   G   S   T   M   G   A
```

FIG. 21B

```
GCG TCA ATA ACG CTG ACG GTA CAG GCC AGA CTA TTG TTG TCT GGT ATA GTG CAG CAG CAA AAC AAT CTG CTG AGG
      G           C       C       G C T   C C C C C   G           C                       C   C C T
A   S   I   T   L   T   V   Q   A   R   L   L   L   S   G   I   V   Q   Q   Q   N   N   L   L   R

GCT ATA GAG GCG CAA CAG CAT CTG TTG CAA CTC ACA GTC TGG GGC ATT AAG CAG CTC CAG ACA AGA ATC TTG GCT
  G                           C C C           G           T                       G C T     C C   G
A   I   E   A   Q   Q   H   L   L   Q   L   T   V   W   G   I   K   Q   L   Q   T   R   I   L   A

GTA GAA AGA TAC CTA AAG GAT CAA CAG CTC CTA GGG ATT TGG GGC TGC TCT GGA AAA CTC ATC TGC ACC ACT GCT
  C     C T       C                       C   T           T       G   T                   G   G   G
V   E   R   Y   L   K   D   Q   Q   L   L   G   I   W   G   C   S   G   K   L   I   C   T   T   A

GTG CCT TGG AAC TCC AGT TGG AGT AAT AGA TCT CAT GAT GAG ATT TGG GAT AAC ATG ACC TGG ATG CAG TGG GAT
  C   G           G TCG     TCG     C T   G                                   G
V   P   W   N   S   S   W   S   N   R   S   H   D   E   I   W   D   N   M   T   W   M   Q   W   D

AGA GAA ATT AAT AAT TAC ACA GAC ACA ATA TAC AGG TTG CTT GAA GAA TCA CAA AAC CAG CAG GAG AAA AAT GAA
C T                       G       G         C T C C   C           G
R   E   I   N   N   Y   T   D   T   I   Y   R   L   L   E   E   S   Q   N   Q   Q   E   K   N   E

AAG GAT TTA TTA GCA TTG GAC AGT TGG CAA AAT CTG TGG AAT TGG TTT AGC ATA ACA AAT TGG CTG TGG TAT ATA
        C C C C   G C C     TCG               C                 TCG       G           C
K   D   L   L   A   L   D   S   W   Q   N   L   W   N   W   F   S   I   T   N   W   L   W   Y   I

AAA ATA TTC ATA ATG ATA GTA GGA GGC TTG ATA GGT TTA AGA ATA ATT TTT GCT GTG CTT TCT ATA GTG AAT AGA
                          C   T   T C C         C C C T               G   C   C   G       C     C T
K   I   F   I   M   I   V   G   G   L   I   G   L   R   I   I   F   A   V   L   S   I   V   N   R

GTT AGG CAG GGA TAC TCA CCT CTG CCG TTT CAG ACC CTT ACC CCG AAC CCA AGG GAA CCC GAC AGG CTC GGA AGA
  C C T       T       G   G   C               G   C   G           G C T       G     C T       T C T
V   R   Q   G   Y   S   P   L   P   F   Q   T   L   T   P   N   P   R   E   P   D   R   L   G   R

ATC GAA GAA GAA GGT GGA GAG CAA GAC AGA GGC AGA TCC ATT CGC TTA GTG AGC GGA TTC TTA GCG CTT GCC TGG
                      T             C T   T C T   G       T C C   C TCG   T     C C       C   G
I   E   E   E   G   G   E   Q   D   R   G   R   S   I   R   L   V   S   G   F   L   A   L   A   W

GAC GAC CTG CGG AGC CTG TGC CTT TTC AGC TAC CAC CGA TTG AGA GAC TTC ATA TTG ATT GCA GCA AGA GTG TTG
          C   T TCG   C       C     TCG           T C C C T             C C       G   G C T   C C C
D   D   L   R   S   L   C   L   F   S   Y   H   R   L   R   D   F   I   L   I   A   A   R   V   L

GAA CTT CTG GGA CAG AGG GGG TGG GAA GCC CTT AAA TAT CTG GGA AGC CTT GTG CAG TAT TGG GGT CTA GAG CTA
      C   C   T     C T   T           G   C           C   T TCG   C   C                   C       C
E   L   L   G   Q   R   G   W   E   A   L   K   Y   L   G   S   L   V   Q   Y   W   G   L   E   L

AAA AAG AGT GCT ATT AGT CTG CTT GAT ACC ATA GCA ATA GCA GTA GCT GAA GGA ACA GAT AGG ATT ATA GAA TTC
        TCG   G     TCG   C   C       G       G       G   C   G       T   G     C T
K   K   S   A   I   S   L   L   D   T   I   A   I   A   V   A   E   G   T   D   R   I   I   E   F

ATA CAA AGA ATT TGT AGA GCT ATT CGC AAC ATA CCT AGA AGA ATA AGA CAG GGC TTT GAA GCA GCT TTG CAA TAA
        C T         C T   G       T           G C T C T     C T       T           G   G C C
I   Q   R   I   C   R   A   I   R   N   I   P   R   R   I   R   Q   G   F   E   A   A   L   Q
```

FIG. 22A

```
GTG AAT ATT CAG GCT CTT CTC TCA GAA AAA GTC CGT CAG GCC ATG ATT GCG GCA GGC GCG CCT GCG GAT TGC GAA
                                            A G
V   N   I   Q   A   L   L   S   E   K   V   R   Q   A   M   I   A   A   G   A   P   A   D   C   E

CCG CAG GTT CGT CAG TCA GCA AAA GTT CAG TTC GGC GAC TAT CAG GCT AAC GGC ATG ATG GCA GTT GCT AAA AAA
            A G
P   Q   V   R   Q   S   A   K   V   Q   F   G   D   Y   Q   A   N   G   M   M   A   V   A   K   K

CTG GGT ATG GCA CCG CGA CAA TTA GCA GAG CAG GTG CTG ACT CAT CTG GAT CTT AAC GGT ATC GCC AGC AAA GTT
                    A G
L   G   M   A   P   R   Q   L   A   E   Q   V   L   T   H   L   D   L   N   G   I   A   S   K   V

GAG ATC GCC GGT CCA GGC TTT ATC AAC ATT TTC CTT GAT CCG GCA TTC CTG GCT GAA CAT GTT CAG CAG GCG CTG

E   I   A   G   P   G   F   I   N   I   F   L   D   P   A   F   L   A   E   H   V   Q   Q   A   L

GCG TCC GAT CGT CTC GGT GTT GCT ACG CCA GAA AAA CAG ACC ATT GTG GTT GAC TAC TCT GCG CCA AAC GTG GCG
            A G
A   S   D   R   L   G   V   A   T   P   E   K   Q   T   I   V   V   D   Y   S   A   P   N   V   A

AAA GAG ATG CAT GTC GGT CAC CTG CGC TCT ACC ATT ATT GGT GAC GCA GCA GTG CGT ACT CTG GAG TTC CTC GGT
                                A G                                     A G
K   E   M   H   V   G   H   L   R   S   T   I   I   G   D   A   A   V   R   T   L   E   F   L   G

CAC AAA GTG ATT CGC GCA AAC CAC GTC GGC GAC TGG GGC ACT CAG TTC GGT ATG CTG ATT GCA TGG CTG GAA AAG
                A G
H   K   V   I   R   A   N   H   V   G   D   W   G   T   Q   F   G   M   L   I   A   W   L   E   K

CAG CAG CAG GAA AAC GCC GGT GAA ATG GAG CTG GCT GAC CTT GAA GGT TTC TAC CGC GAT GCG AAA AAG CAT TAC
                                                                        A G
Q   Q   Q   E   N   A   G   E   M   E   L   A   D   L   E   G   F   Y   R   D   A   K   K   H   Y

GAT GAA GAT GAA GAG TTC GCC GAG CGC GCA CGT AAC TAC GTG GTA AAA CTG CAA AGC GGT GAC GAA TAT TTC CGC
                                A G     A G                                                     A G
D   E   D   E   E   F   A   E   R   A   R   N   Y   V   V   K   L   Q   S   G   D   E   Y   F   R

GAG ATG TGG CGC AAA CTG GTC GAC ATC ACC ATG ACG CAG AAC CAG ATC ACC TAC GAT CGT CTC AAC GTG ACG CTG
            A G                                                             A G
E   M   W   R   K   L   V   D   I   T   M   T   Q   N   Q   I   T   Y   D   R   L   N   V   T   L

ACC CGT GAT GAC GTG ATG GGC GAA AGC CTC TAC AAC CCG ATG CTG CCA GGA ATT GTG GCG GAT CTC AAA GCC AAA
    A G
T   R   D   D   V   M   G   E   S   L   Y   N   P   M   L   P   G   I   V   A   D   L   K   A   K

GGT CTG GCA GTA GAA AGC GAA GGG GCG ACC GTC GTA TTC CTT GAT GAG TTT AAA AAC AAG GAA GGC GAA CCG ATG

G   L   A   V   E   S   E   G   A   T   V   V   F   L   D   E   F   K   N   K   E   G   E   P   M

GGC GTG ATC ATT CAG AAG AAA GAT GGC GGC TAT CTC TAC ACC ACC ACT GAT ATC GCC TGT GCG AAA TAT CGT TAT
                                                                                            A G
G   V   I   I   Q   K   K   D   G   G   Y   L   Y   T   T   T   D   I   A   C   A   K   Y   R   Y

GAA ACA CTG CAT GCC GAT CGC GTG CTG TAT TAC ATC GAC TCC CGT CAG CAT CAA CAC CTG ATG CAG GCA TGG GCG
                        A G                             A G
E   T   L   H   A   D   R   V   L   Y   Y   I   D   S   R   Q   H   Q   H   L   M   Q   A   W   A

ATC GTC CGT AAA GCA GGC TAT GTA CCG GAA TCC GTA CCG CTG GAA CAC CAC ATG TTC GGC ATG ATG CTG GGT AAA
        A G
I   V   R   K   A   G   Y   V   P   E   S   V   P   L   E   H   H   M   F   G   M   M   L   G   K

GAC GGC AAA CCG TTC AAA ACC CGC GCG GGT GGT ACA GTG AAA CTG GCC GAT CTG CTG GAT GAA GCC CTG GAA CGT
                            A G                                                                 A G
D   G   K   P   F   K   T   R   A   G   G   T   V   K   L   A   D   L   L   D   E   A   L   E   R

GCA CGC CGT CTG GTG GCA GAA AAG AAC CCG GAT ATG CCA GCC GAC GAG CTG GAA AAA CTG GCT AAC GCG GTT GGT
    A G A G
A   R   R   L   V   A   E   K   N   P   D   M   P   A   D   E   L   E   K   L   A   N   A   V   G

ATT GGT GCG GTG AAA TAT GCG GAT CTC TCC AAA AAC CGC ACC ACG GAC TAC ATC TTC GAC TGG GAC AAC ATG CTG
                                                A G
I   G   A   V   K   Y   A   D   L   S   K   N   R   T   T   D   Y   I   F   D   W   D   N   M   L

GCG TTT GAG GGT AAT ACC GCG CCA TAC ATG CAG TAT GCA TAC ACG CGT GTA TTG TCC GTG TTC CGT AAA GCA GAA
                                                            A G                     A G
A   F   E   G   N   T   A   P   Y   M   Q   Y   A   Y   T   R   V   L   S   V   F   R   K   A   E

ATT GAC GAA GAG CAA CTG GCT GCA GCT CCG GTT ATC ATC CGT GAA GAT CGT GAA GCG CAA CTG GCA GCT CGC CTG
                                                    A G         A G                         A G
I   D   E   E   Q   L   A   A   A   P   V   I   I   R   E   D   R   E   A   Q   L   A   A   R   L

CTG CAG TTT GAA GAA ACC CTC ACC GTG GTT GCC CGT GAA GGC ACG CCG CAT GTA ATG TGT GCT TAC CTG TAC GAT
                                            A G
L   Q   F   E   E   T   L   T   V   V   A   R   E   G   T   P   H   V   M   C   A   Y   L   Y   D
```

FIG. 22B

```
CTG GCC GGT CTG TTC TCT GGC TTC TAC GAG CAC TGC CCG ATC CTC AGC GCA GAA AAC GAA GAA GTG CGT AAC AGC
                                                                                        A G
L   A   G   L   F   S   G   F   Y   E   H   C   P   I   L   S   A   E   N   E   E   V   R   N   S

CGT CTA AAA CTG GCA CAA CTG ACG GCG AAG ACG CTG AAG CTG GGT CTG GAT ACG CTG GGT ATT GAG ACT GTA GAG
A G
R   L   K   L   A   Q   L   T   A   K   T   L   K   L   G   L   D   T   L   G   I   E   T   V   E

CGT ATG TAA
A G
R   M   *
```

FIG. 23

```
GTG TCT AAA GAA AAA TTT GAA CGT ACA AAA CCG CAC GTT AAC GTT GGT ACT ATC GGC CAC GTT GAC CAC GGT AAA
                            A G
V   S   K   E   K   F   E   R   T   K   P   H   V   N   V   G   T   I   G   H   V   D   H   G   K

ACT ACT CTG ACC GCT GCA ATC ACC ACC GTA CTG GCT AAA ACC TAC GGC GGT GCT GCT CGT GCA TTC GAC CAG ATC
                                                                            A G
T   T   L   T   A   A   I   T   T   V   L   A   K   T   Y   G   G   A   A   R   A   F   D   Q   I

GAT AAC GCG CCG GAA GAA AAA GCT CGT GGT ATC ACC ATC AAC ACT TCT CAC GTT GAA TAC GAC ACC CCG ACC CGT
                                A G                                                             A G
D   N   A   P   E   E   K   A   R   G   I   T   I   N   T   S   H   V   E   Y   D   T   P   T   R

CAC TAC GCA CAC GTA GAC TGC CCG GGG CAC GCC GAC TAT GTT AAA AAC ATG ATC ACC GGT GCT GCT CAG ATG GAC

H   Y   A   H   V   D   C   P   G   H   A   D   Y   V   K   N   M   I   T   G   A   A   Q   M   D

GGC GCG ATC CTG GTA GTT GCT GCG ACT GAC GGC CCG ATG CCG CAG ACT CGT GAG CAC ATC CTG CTG GGT CGT CAG
                                                                A G                         A G
G   A   I   L   V   V   A   A   T   D   G   P   M   P   Q   T   R   E   H   I   L   L   G   R   Q

GTA GGC GTT CCG TAC ATC ATC GTG TTC CTG AAC AAA TGC GAC ATG GTT GAT GAC GAA GAG CTG CTG GAA CTG GTT

V   G   V   P   Y   I   I   V   F   L   N   K   C   D   M   V   D   D   E   E   L   L   E   L   V

GAA ATG GAA GTT CGT GAA CTT CTG TCT CAG TAC GAC TTC CCG GGC GAC GAC ACT CCG ATC GTT CGT GGT TCT GCT
                A G                                                                 A G
E   M   E   V   R   E   L   L   S   Q   Y   D   F   P   G   D   D   T   P   I   V   R   G   S   A

CTG AAA GCG CTG GAA GGC GAC GCA GAG TGG GAA GCG AAA ATC CTG GAA CTG GCT GGC TTC CTG GAT TCT TAT ATT

L   K   A   L   E   G   D   A   E   W   E   A   K   I   L   E   L   A   G   F   L   D   S   Y   I

CCG GAA CCA GAG CGT GCG ATT GAC AAG CCG TTC CTG CTG CCG ATC GAA GAC GTA TTC TCC ATC TCC GGT CGT GGT
                A G                                                                         A G
P   E   P   E   R   A   I   D   K   P   F   L   L   P   I   E   D   V   F   S   I   S   G   R   G

ACC GTT GTT ACC GGT CGT GTA GAA CGC GGT ATC ATC AAA GTT GGT GAA GAA GTT GAA ATC GTT GGT ATC AAA GAG
                    A G         A G
T   V   V   T   G   R   V   E   R   G   I   I   K   V   G   E   E   V   E   I   V   G   I   K   E

ACT CAG AAG TCT ACC TGT ACT GGC GTT GAA ATG TTC CGC AAA CTG CTG GAC GAA GGC CGT GCT GGT GAG AAC GTA
                                                A G                         A G
T   Q   K   S   T   C   T   G   V   E   M   F   R   K   L   L   D   E   G   R   A   G   E   N   V

GGT GTT CTG CTG CGT GGT ATC AAA CGT GAA GAA ATC GAA CGT GGT CAG GTA CTG GCT AAG CCG GGC ACC ATC AAG
                A G             A G                 A G
G   V   L   L   R   G   I   K   R   E   E   I   E   R   G   Q   V   L   A   K   P   G   T   I   K

CCG CAC ACC AAG TTC GAA TCT GAA GTG TAC ATT CTG TCC AAA GAT GAA GGC GGC CGT CAT ACT CCG TTC TTC AAA
                                                                        A G
P   H   T   K   F   E   S   E   V   Y   I   L   S   K   D   E   G   G   R   H   T   P   F   F   K

GGC TAC CGT CCG CAG TTC TAC TTC CGT ACT ACT GAC GTG ACT GGT ACC ATC GAA CTG CCG GAA GGC GTA GAG ATG
        A G                     A G
G   Y   R   P   Q   F   Y   F   R   T   T   D   V   T   G   T   I   E   L   P   E   G   V   E   M

GTA ATG CCG GGC GAC AAC ATC AAA ATG GTT GTT ACC CTG ATC CAC CCG ATC GCG ATG GAC GAC GGT CTG CGT TTC
                                                                                            A G
V   M   P   G   D   N   I   K   M   V   V   T   L   I   H   P   I   A   M   D   D   G   L   R   F

GCA ATC CGT GAA GGC GGC CGT ACC GTT GGC GCG GGC GTT GTT GCT AAA GTT CTG GGC TAA
        A G             A G
A   I   R   E   G   G   R   T   V   G   A   G   V   V   A   K   V   L   G   *
```

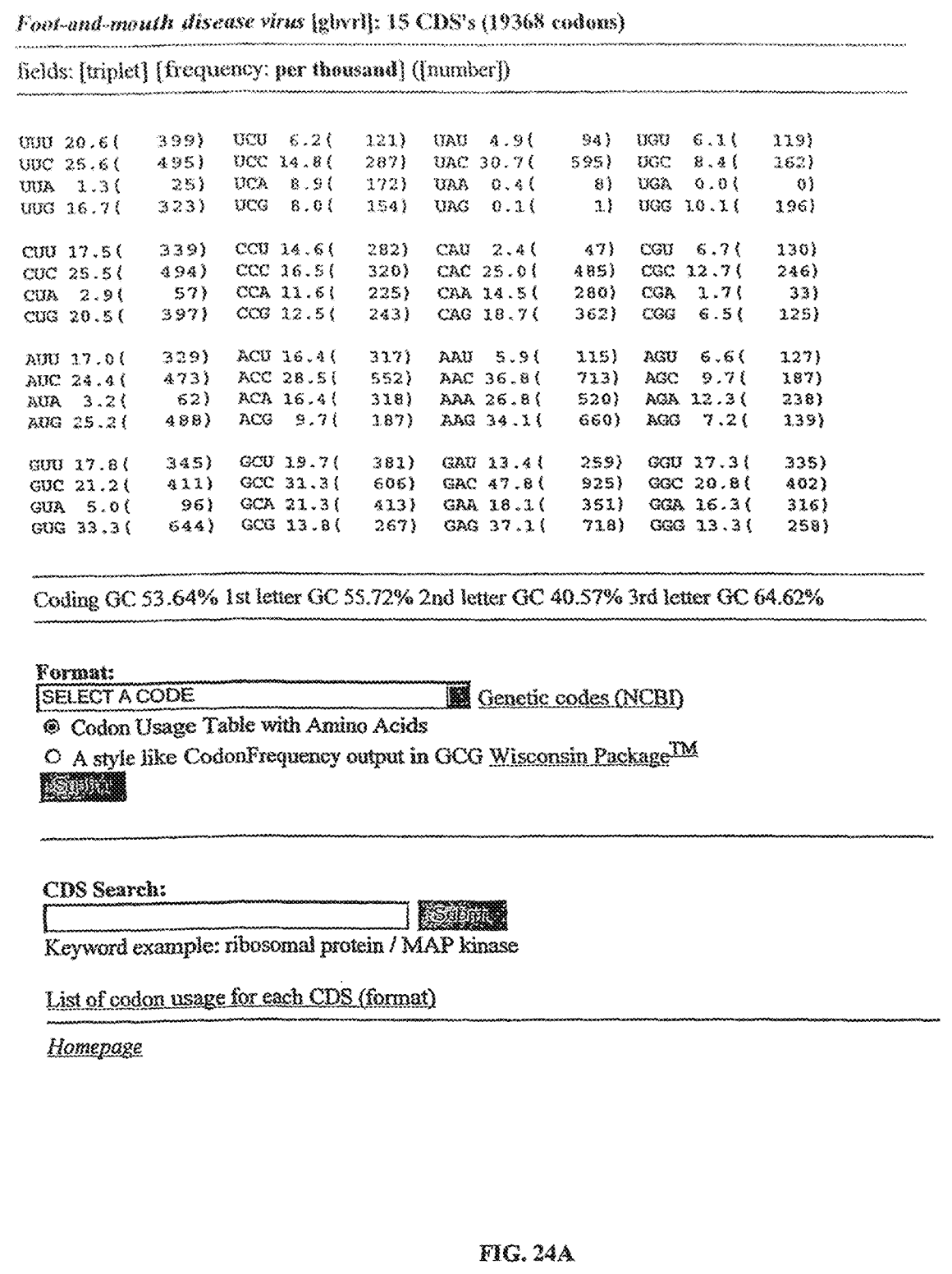

*Foot-and-mouth disease virus* [gbvrl]: 15 CDS's (19368 codons)

fields: [triplet] [frequency: per thousand] ([number])

| | | | |
|---|---|---|---|
| UUU 20.6( 399) | UCU 6.2( 121) | UAU 4.9( 94) | UGU 6.1( 119) |
| UUC 25.6( 495) | UCC 14.8( 287) | UAC 30.7( 595) | UGC 8.4( 162) |
| UUA 1.3( 25) | UCA 8.9( 172) | UAA 0.4( 8) | UGA 0.0( 0) |
| UUG 16.7( 323) | UCG 8.0( 154) | UAG 0.1( 1) | UGG 10.1( 196) |
| CUU 17.5( 339) | CCU 14.6( 282) | CAU 2.4( 47) | CGU 6.7( 130) |
| CUC 25.5( 494) | CCC 16.5( 320) | CAC 25.0( 485) | CGC 12.7( 246) |
| CUA 2.9( 57) | CCA 11.6( 225) | CAA 14.5( 280) | CGA 1.7( 33) |
| CUG 20.5( 397) | CCG 12.5( 243) | CAG 18.7( 362) | CGG 6.5( 125) |
| AUU 17.0( 329) | ACU 16.4( 317) | AAU 5.9( 115) | AGU 6.6( 127) |
| AUC 24.4( 473) | ACC 28.5( 552) | AAC 36.8( 713) | AGC 9.7( 187) |
| AUA 3.2( 62) | ACA 16.4( 318) | AAA 26.8( 520) | AGA 12.3( 238) |
| AUG 25.2( 488) | ACG 9.7( 187) | AAG 34.1( 660) | AGG 7.2( 139) |
| GUU 17.8( 345) | GCU 19.7( 381) | GAU 13.4( 259) | GGU 17.3( 335) |
| GUC 21.2( 411) | GCC 31.3( 606) | GAC 47.8( 925) | GGC 20.8( 402) |
| GUA 5.0( 96) | GCA 21.3( 413) | GAA 18.1( 351) | GGA 16.3( 316) |
| GUG 33.3( 644) | GCG 13.8( 267) | GAG 37.1( 718) | GGG 13.3( 258) |

Coding GC 53.64% 1st letter GC 55.72% 2nd letter GC 40.57% 3rd letter GC 64.62%

Format:

SELECT A CODE Genetic codes (NCBI)

◉ Codon Usage Table with Amino Acids

○ A style like CodonFrequency output in GCG Wisconsin Package™

Submit

CDS Search:

Submit

Keyword example: ribosomal protein / MAP kinase

List of codon usage for each CDS (format)

*Homepage*

FIG. 24A

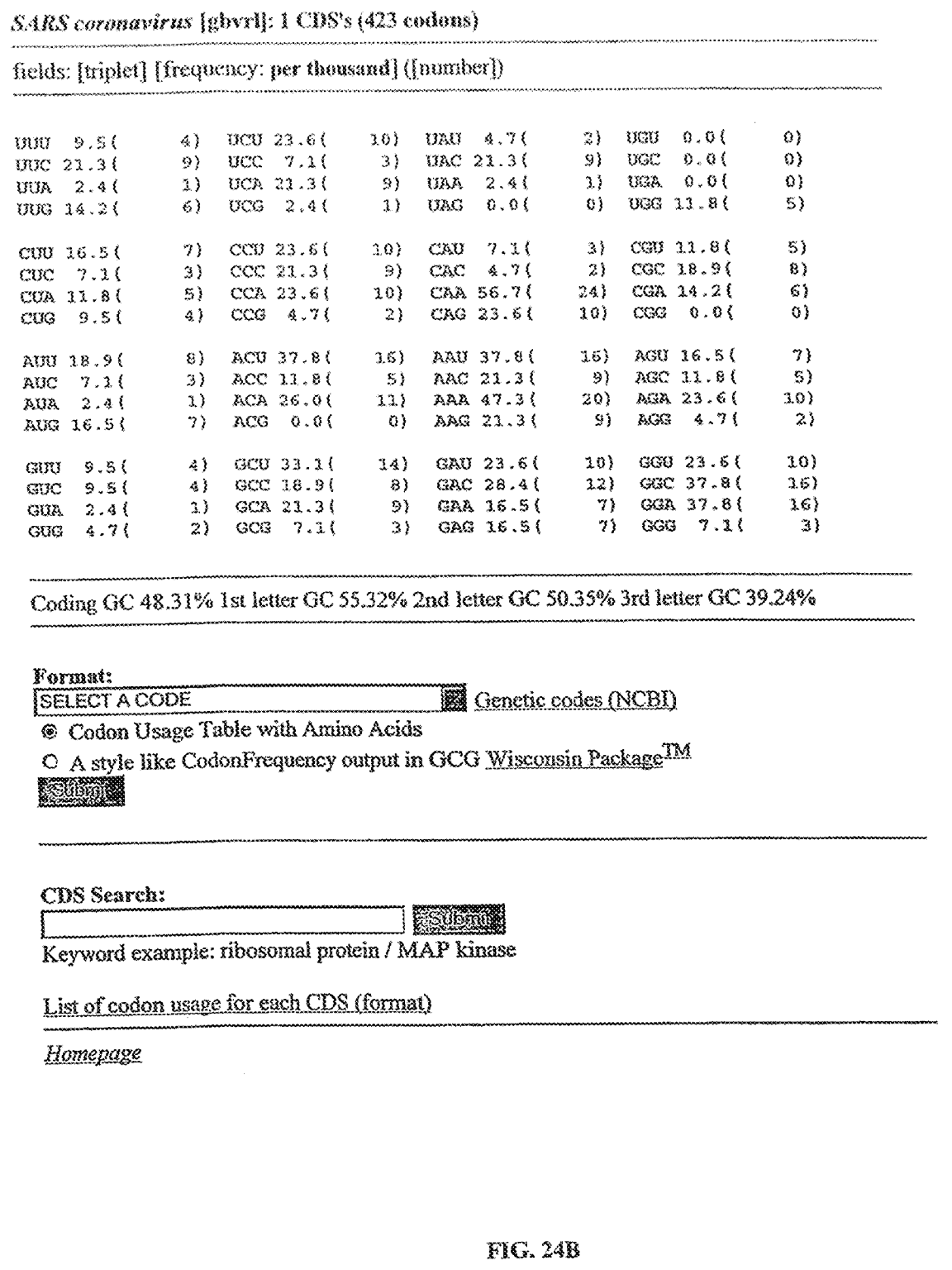

*SARS coronavirus* [gbvrl]: 1 CDS's (423 codons)

fields: [triplet] [frequency: per thousand] ([number])

| | | | | | | | | | | | |
|---|---|---|---|---|---|---|---|---|---|---|---|
| UUU | 9.5( | 4) | UCU | 23.6( | 10) | UAU | 4.7( | 2) | UGU | 0.0( | 0) |
| UUC | 21.3( | 9) | UCC | 7.1( | 3) | UAC | 21.3( | 9) | UGC | 0.0( | 0) |
| UUA | 2.4( | 1) | UCA | 21.3( | 9) | UAA | 2.4( | 1) | UGA | 0.0( | 0) |
| UUG | 14.2( | 6) | UCG | 2.4( | 1) | UAG | 0.0( | 0) | UGG | 11.8( | 5) |
| CUU | 16.5( | 7) | CCU | 23.6( | 10) | CAU | 7.1( | 3) | CGU | 11.8( | 5) |
| CUC | 7.1( | 3) | CCC | 21.3( | 9) | CAC | 4.7( | 2) | CGC | 18.9( | 8) |
| CUA | 11.8( | 5) | CCA | 23.6( | 10) | CAA | 56.7( | 24) | CGA | 14.2( | 6) |
| CUG | 9.5( | 4) | CCG | 4.7( | 2) | CAG | 23.6( | 10) | CGG | 0.0( | 0) |
| AUU | 18.9( | 8) | ACU | 37.8( | 16) | AAU | 37.8( | 16) | AGU | 16.5( | 7) |
| AUC | 7.1( | 3) | ACC | 11.8( | 5) | AAC | 21.3( | 9) | AGC | 11.8( | 5) |
| AUA | 2.4( | 1) | ACA | 26.0( | 11) | AAA | 47.3( | 20) | AGA | 23.6( | 10) |
| AUG | 16.5( | 7) | ACG | 0.0( | 0) | AAG | 21.3( | 9) | AGG | 4.7( | 2) |
| GUU | 9.5( | 4) | GCU | 33.1( | 14) | GAU | 23.6( | 10) | GGU | 23.6( | 10) |
| GUC | 9.5( | 4) | GCC | 18.9( | 8) | GAC | 28.4( | 12) | GGC | 37.8( | 16) |
| GUA | 2.4( | 1) | GCA | 21.3( | 9) | GAA | 16.5( | 7) | GGA | 37.8( | 16) |
| GUG | 4.7( | 2) | GCG | 7.1( | 3) | GAG | 16.5( | 7) | GGG | 7.1( | 3) |

Coding GC 48.31% 1st letter GC 55.32% 2nd letter GC 50.35% 3rd letter GC 39.24%

Format:

SELECT A CODE [Genetic codes (NCBI)]

◉ Codon Usage Table with Amino Acids

○ A style like CodonFrequency output in GCG Wisconsin Package™

Submit

CDS Search:

Submit

Keyword example: ribosomal protein / MAP kinase

List of codon usage for each CDS (format)

*Homepage*

FIG. 24B

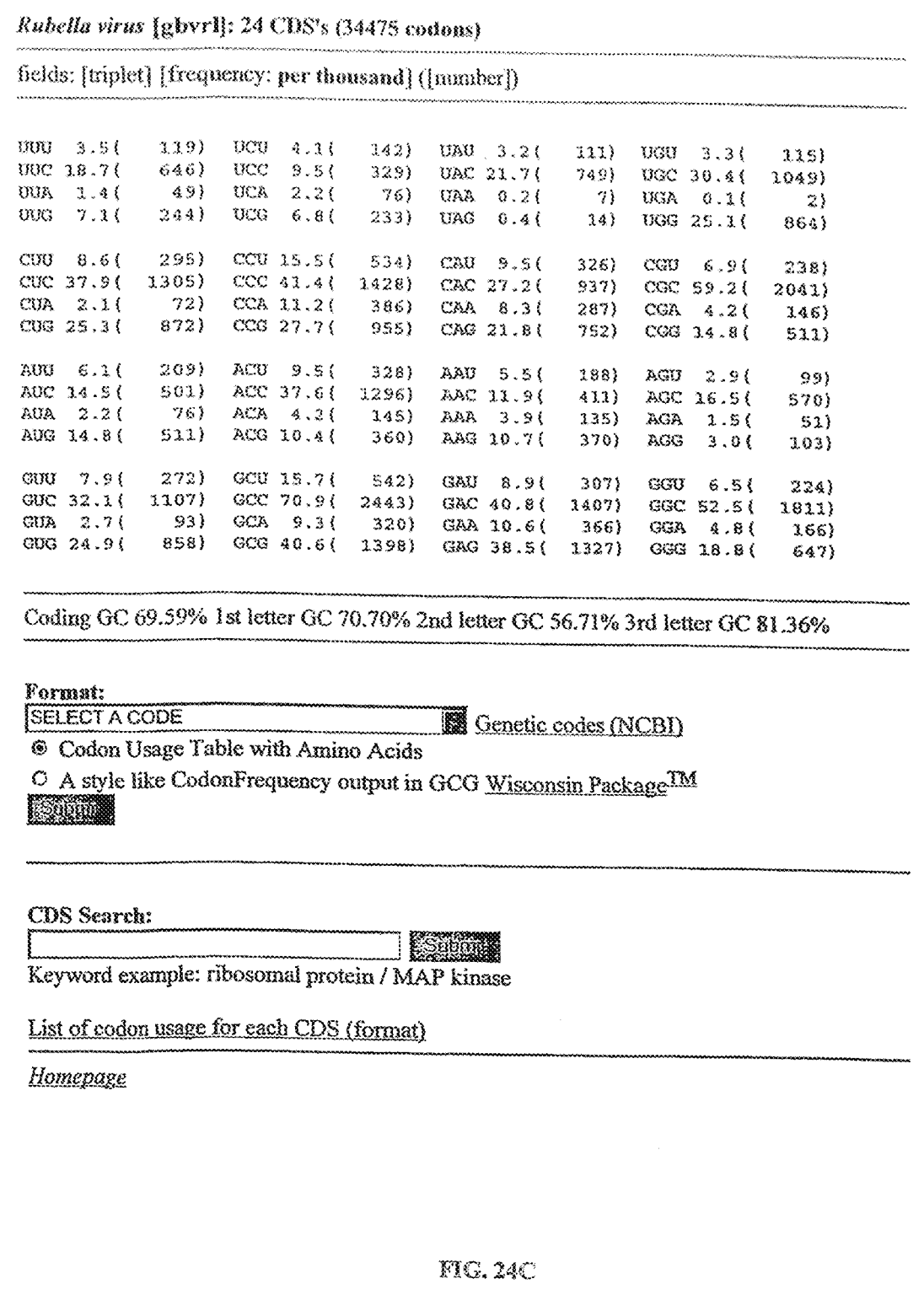

*Rubella virus* [gbvrl]: 24 CDS's (34475 codons)

fields: [triplet] [frequency: per thousand] ([number])

```
UUU  3.5(  119)   UCU  4.1(  142)   UAU  3.2(  111)   UGU  3.3(  115)
UUC 18.7(  646)   UCC  9.5(  329)   UAC 21.7(  749)   UGC 30.4( 1049)
UUA  1.4(   49)   UCA  2.2(   76)   UAA  0.2(    7)   UGA  0.1(    2)
UUG  7.1(  244)   UCG  6.8(  233)   UAG  0.4(   14)   UGG 25.1(  864)

CUU  8.6(  295)   CCU 15.5(  534)   CAU  9.5(  326)   CGU  6.9(  238)
CUC 37.9( 1305)   CCC 41.4( 1428)   CAC 27.2(  937)   CGC 59.2( 2041)
CUA  2.1(   72)   CCA 11.2(  386)   CAA  8.3(  287)   CGA  4.2(  146)
CUG 25.3(  872)   CCG 27.7(  955)   CAG 21.8(  752)   CGG 14.8(  511)

AUU  6.1(  209)   ACU  9.5(  328)   AAU  5.5(  188)   AGU  2.9(   99)
AUC 14.5(  501)   ACC 37.6( 1296)   AAC 11.9(  411)   AGC 16.5(  570)
AUA  2.2(   76)   ACA  4.2(  145)   AAA  3.9(  135)   AGA  1.5(   51)
AUG 14.8(  511)   ACG 10.4(  360)   AAG 10.7(  370)   AGG  3.0(  103)

GUU  7.9(  272)   GCU 15.7(  542)   GAU  8.9(  307)   GGU  6.5(  224)
GUC 32.1( 1107)   GCC 70.9( 2443)   GAC 40.8( 1407)   GGC 52.5( 1811)
GUA  2.7(   93)   GCA  9.3(  320)   GAA 10.6(  366)   GGA  4.8(  166)
GUG 24.9(  858)   GCG 40.6( 1398)   GAG 38.5( 1327)   GGG 18.8(  647)
```

Coding GC 69.59% 1st letter GC 70.70% 2nd letter GC 56.71% 3rd letter GC 81.36%

Format:
[SELECT A CODE] Genetic codes (NCBI)
● Codon Usage Table with Amino Acids
○ A style like CodonFrequency output in GCG Wisconsin Package™
[Submit]

CDS Search:
[        ] [Submit]
Keyword example: ribosomal protein / MAP kinase List of codon usage for each CDS (format)

*Homepage*

FIG. 24C

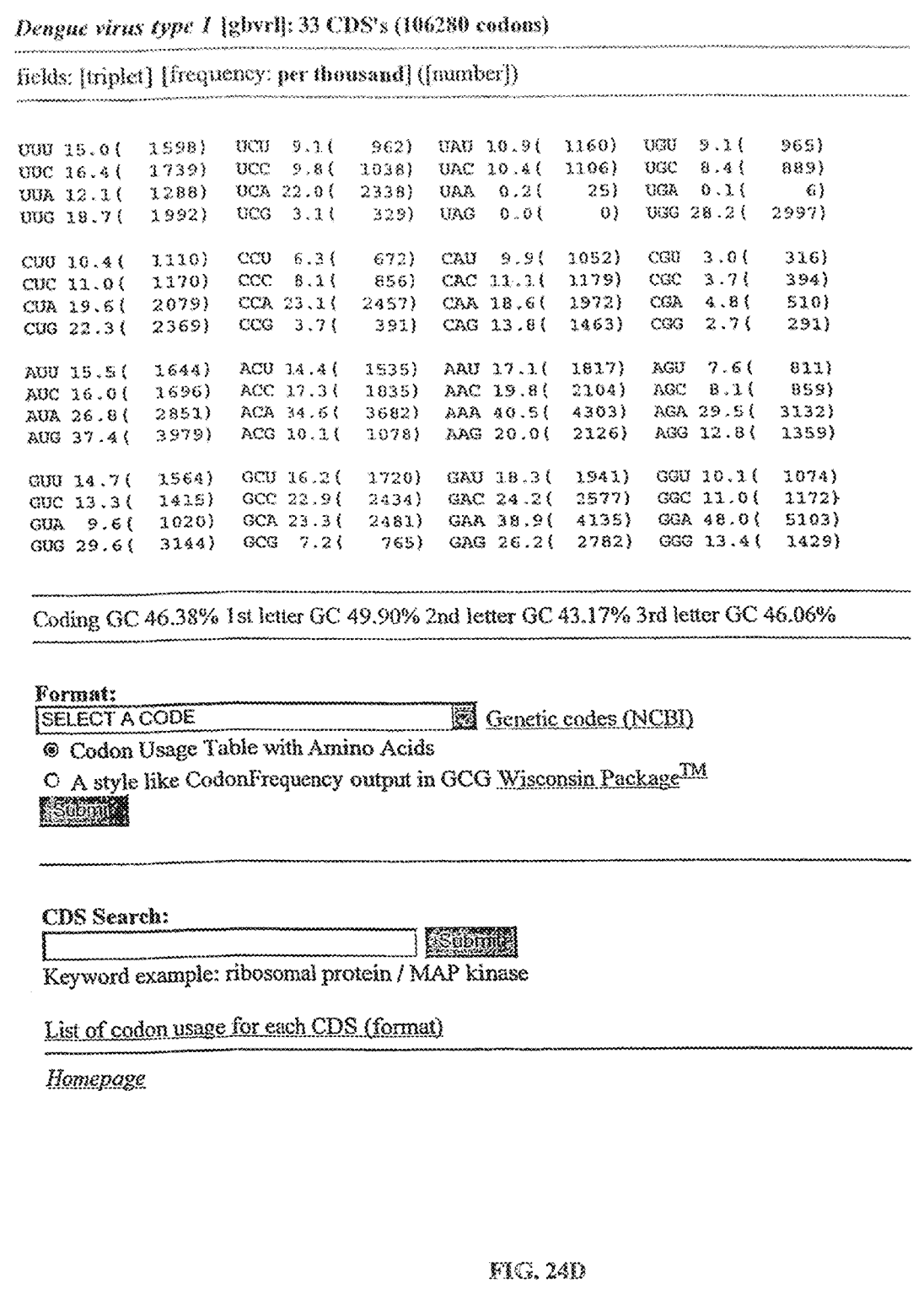

*Dengue virus type 1* [gbvrl]: 33 CDS's (106280 codons)

fields: [triplet] [frequency: per thousand] ([number])

| | | | |
|---|---|---|---|
| UUU 15.0( 1598) | UCU 9.1( 962) | UAU 10.9( 1160) | UGU 9.1( 965) |
| UUC 16.4( 1739) | UCC 9.8( 1038) | UAC 10.4( 1106) | UGC 8.4( 889) |
| UUA 12.1( 1288) | UCA 22.0( 2338) | UAA 0.2( 25) | UGA 0.1( 6) |
| UUG 18.7( 1992) | UCG 3.1( 329) | UAG 0.0( 0) | UGG 28.2( 2997) |
| CUU 10.4( 1110) | CCU 6.3( 672) | CAU 9.9( 1052) | CGU 3.0( 316) |
| CUC 11.0( 1170) | CCC 8.1( 856) | CAC 11.1( 1179) | CGC 3.7( 394) |
| CUA 19.6( 2079) | CCA 23.1( 2457) | CAA 18.6( 1972) | CGA 4.8( 510) |
| CUG 22.3( 2369) | CCG 3.7( 391) | CAG 13.8( 1463) | CGG 2.7( 291) |
| AUU 15.5( 1644) | ACU 14.4( 1535) | AAU 17.1( 1817) | AGU 7.6( 811) |
| AUC 16.0( 1696) | ACC 17.3( 1835) | AAC 19.8( 2104) | AGC 8.1( 859) |
| AUA 26.8( 2851) | ACA 34.6( 3682) | AAA 40.5( 4303) | AGA 29.5( 3132) |
| AUG 37.4( 3979) | ACG 10.1( 1078) | AAG 20.0( 2126) | AGG 12.8( 1359) |
| GUU 14.7( 1564) | GCU 16.2( 1720) | GAU 18.3( 1941) | GGU 10.1( 1074) |
| GUC 13.3( 1415) | GCC 22.9( 2434) | GAC 24.2( 2577) | GGC 11.0( 1172) |
| GUA 9.6( 1020) | GCA 23.3( 2481) | GAA 38.9( 4135) | GGA 48.0( 5103) |
| GUG 29.6( 3144) | GCG 7.2( 765) | GAG 26.2( 2782) | GGG 13.4( 1429) |

Coding GC 46.38% 1st letter GC 49.90% 2nd letter GC 43.17% 3rd letter GC 46.06%

Format:
SELECT A CODE Genetic codes (NCBI)
◉ Codon Usage Table with Amino Acids
○ A style like CodonFrequency output in GCG Wisconsin Package™
Submit

CDS Search:
Submit
Keyword example: ribosomal protein / MAP kinase

List of codon usage for each CDS (format)

*Homepage*

FIG. 24D

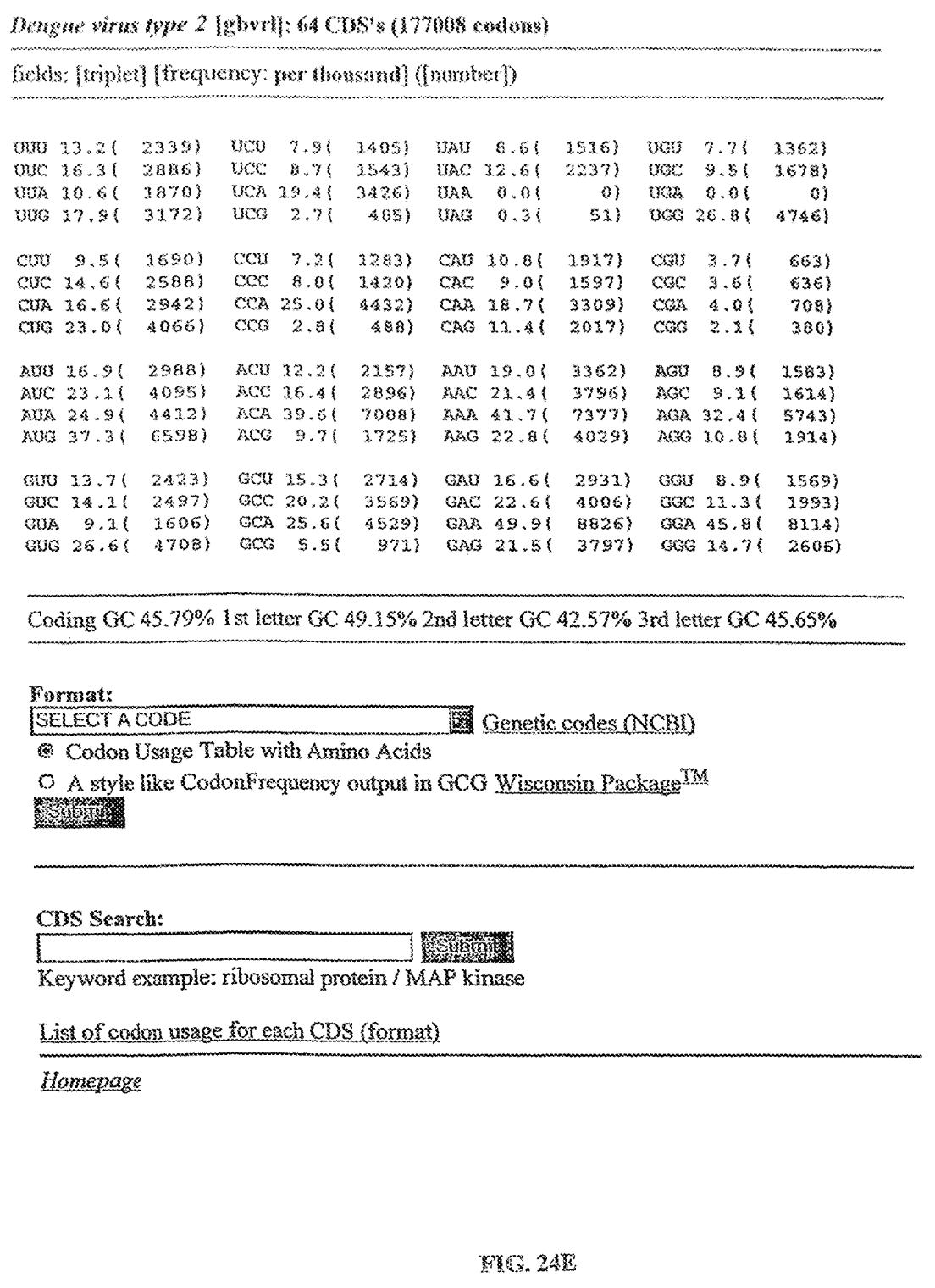

*Dengue virus type 2* [gbvrl]: 64 CDS's (177008 codons)

fields: [triplet] [frequency: per thousand] ([number])

```
UUU 13.2( 2339)  UCU  7.9( 1405)  UAU  8.6( 1516)  UGU  7.7( 1362)
UUC 16.3( 2886)  UCC  8.7( 1543)  UAC 12.6( 2237)  UGC  9.5( 1678)
UUA 10.6( 1870)  UCA 19.4( 3426)  UAA  0.0(    0)  UGA  0.0(    0)
UUG 17.9( 3172)  UCG  2.7(  485)  UAG  0.3(   51)  UGG 26.8( 4746)

CUU  9.5( 1690)  CCU  7.2( 1283)  CAU 10.8( 1917)  CGU  3.7(  663)
CUC 14.6( 2588)  CCC  8.0( 1420)  CAC  9.0( 1597)  CGC  3.6(  636)
CUA 16.6( 2942)  CCA 25.0( 4432)  CAA 18.7( 3309)  CGA  4.0(  708)
CUG 23.0( 4066)  CCG  2.8(  488)  CAG 11.4( 2017)  CGG  2.1(  380)

AUU 16.9( 2988)  ACU 12.2( 2157)  AAU 19.0( 3362)  AGU  8.9( 1583)
AUC 23.1( 4095)  ACC 16.4( 2896)  AAC 21.4( 3796)  AGC  9.1( 1614)
AUA 24.9( 4412)  ACA 39.6( 7008)  AAA 41.7( 7377)  AGA 32.4( 5743)
AUG 37.3( 6598)  ACG  9.7( 1725)  AAG 22.8( 4029)  AGG 10.8( 1914)

GUU 13.7( 2423)  GCU 15.3( 2714)  GAU 16.6( 2931)  GGU  8.9( 1569)
GUC 14.1( 2497)  GCC 20.2( 3569)  GAC 22.6( 4006)  GGC 11.3( 1993)
GUA  9.1( 1606)  GCA 25.6( 4529)  GAA 49.9( 8826)  GGA 45.8( 8114)
GUG 26.6( 4708)  GCG  5.5(  971)  GAG 21.5( 3797)  GGG 14.7( 2606)
```

Coding GC 45.79% 1st letter GC 49.15% 2nd letter GC 42.57% 3rd letter GC 45.65%

Format:

SELECT A CODE   Genetic codes (NCBI)

◉ Codon Usage Table with Amino Acids

○ A style like CodonFrequency output in GCG Wisconsin Package™

Submit

CDS Search:

Submit

Keyword example: ribosomal protein / MAP kinase

List of codon usage for each CDS (format)

*Homepage*

FIG. 24E

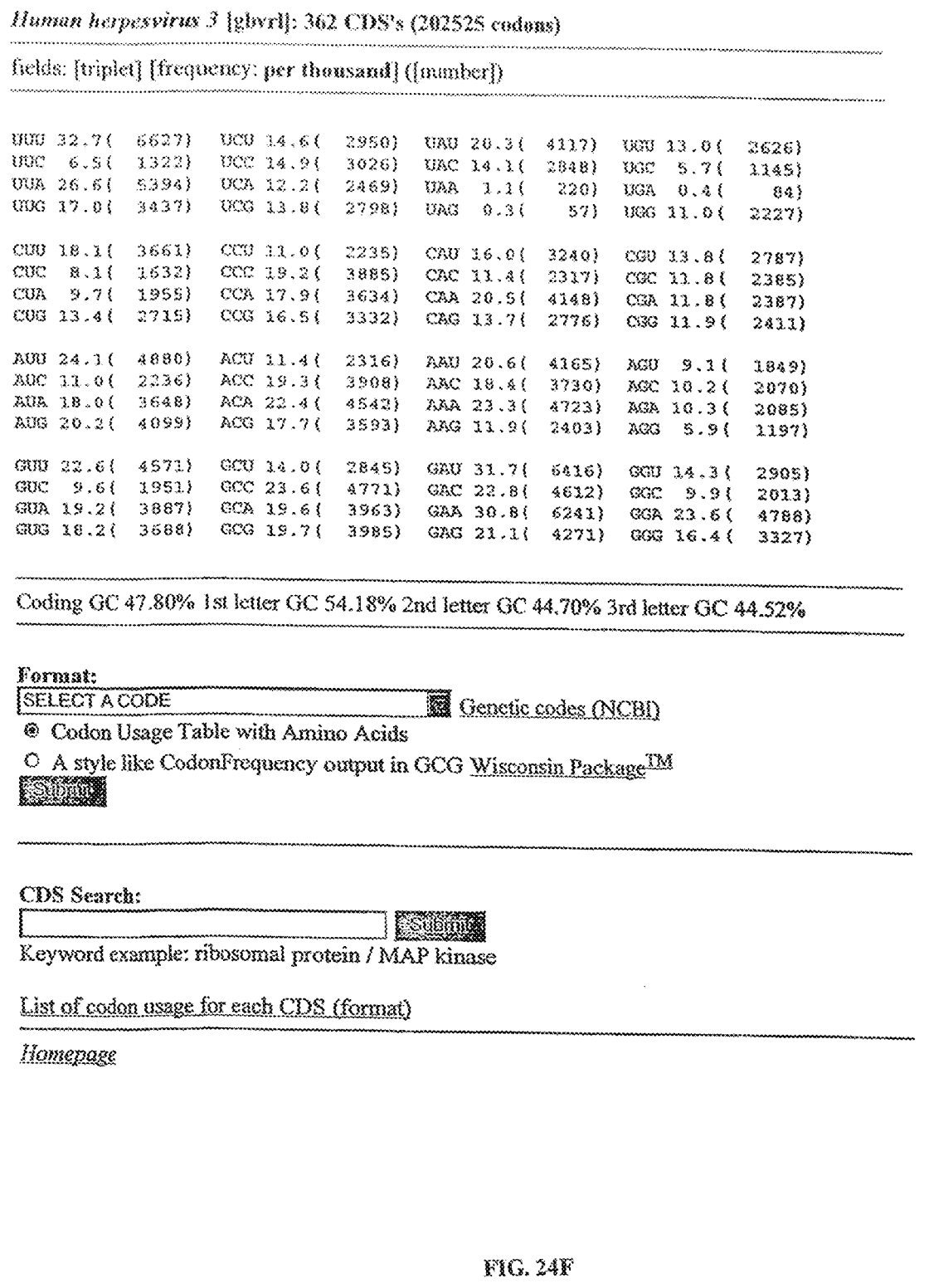

*Human herpesvirus 3* [gbvrl]: 362 CDS's (202525 codons)

fields: [triplet] [frequency: per thousand] ([number])

| | | | |
|---|---|---|---|
| UUU 32.7( 6627) | UCU 14.6( 2950) | UAU 20.3( 4117) | UGU 13.0( 2626) |
| UUC 6.5( 1322) | UCC 14.9( 3026) | UAC 14.1( 2848) | UGC 5.7( 1145) |
| UUA 26.6( 5394) | UCA 12.2( 2469) | UAA 1.1( 220) | UGA 0.4( 84) |
| UUG 17.0( 3437) | UCG 13.8( 2798) | UAG 0.3( 57) | UGG 11.0( 2227) |
| CUU 18.1( 3661) | CCU 11.0( 2235) | CAU 16.0( 3240) | CGU 13.8( 2787) |
| CUC 8.1( 1632) | CCC 19.2( 3885) | CAC 11.4( 2317) | CGC 11.8( 2385) |
| CUA 9.7( 1955) | CCA 17.9( 3634) | CAA 20.5( 4148) | CGA 11.8( 2387) |
| CUG 13.4( 2715) | CCG 16.5( 3332) | CAG 13.7( 2776) | CGG 11.9( 2411) |
| AUU 24.1( 4880) | ACU 11.4( 2316) | AAU 20.6( 4165) | AGU 9.1( 1849) |
| AUC 11.0( 2236) | ACC 19.3( 3908) | AAC 18.4( 3730) | AGC 10.2( 2070) |
| AUA 18.0( 3648) | ACA 22.4( 4542) | AAA 23.3( 4723) | AGA 10.3( 2085) |
| AUG 20.2( 4099) | ACG 17.7( 3593) | AAG 11.9( 2403) | AGG 5.9( 1197) |
| GUU 22.6( 4571) | GCU 14.0( 2845) | GAU 31.7( 6416) | GGU 14.3( 2905) |
| GUC 9.6( 1951) | GCC 23.6( 4771) | GAC 22.8( 4612) | GGC 9.9( 2013) |
| GUA 19.2( 3887) | GCA 19.6( 3963) | GAA 30.8( 6241) | GGA 23.6( 4788) |
| GUG 18.2( 3688) | GCG 19.7( 3985) | GAG 21.1( 4271) | GGG 16.4( 3327) |

Coding GC 47.80% 1st letter GC 54.18% 2nd letter GC 44.70% 3rd letter GC 44.52%

Format:

SELECT A CODE   Genetic codes (NCBI)

◉ Codon Usage Table with Amino Acids

○ A style like CodonFrequency output in GCG Wisconsin Package™

Submit

CDS Search:

Submit

Keyword example: ribosomal protein / MAP kinase

List of codon usage for each CDS (format)

*Homepage*

FIG. 24F

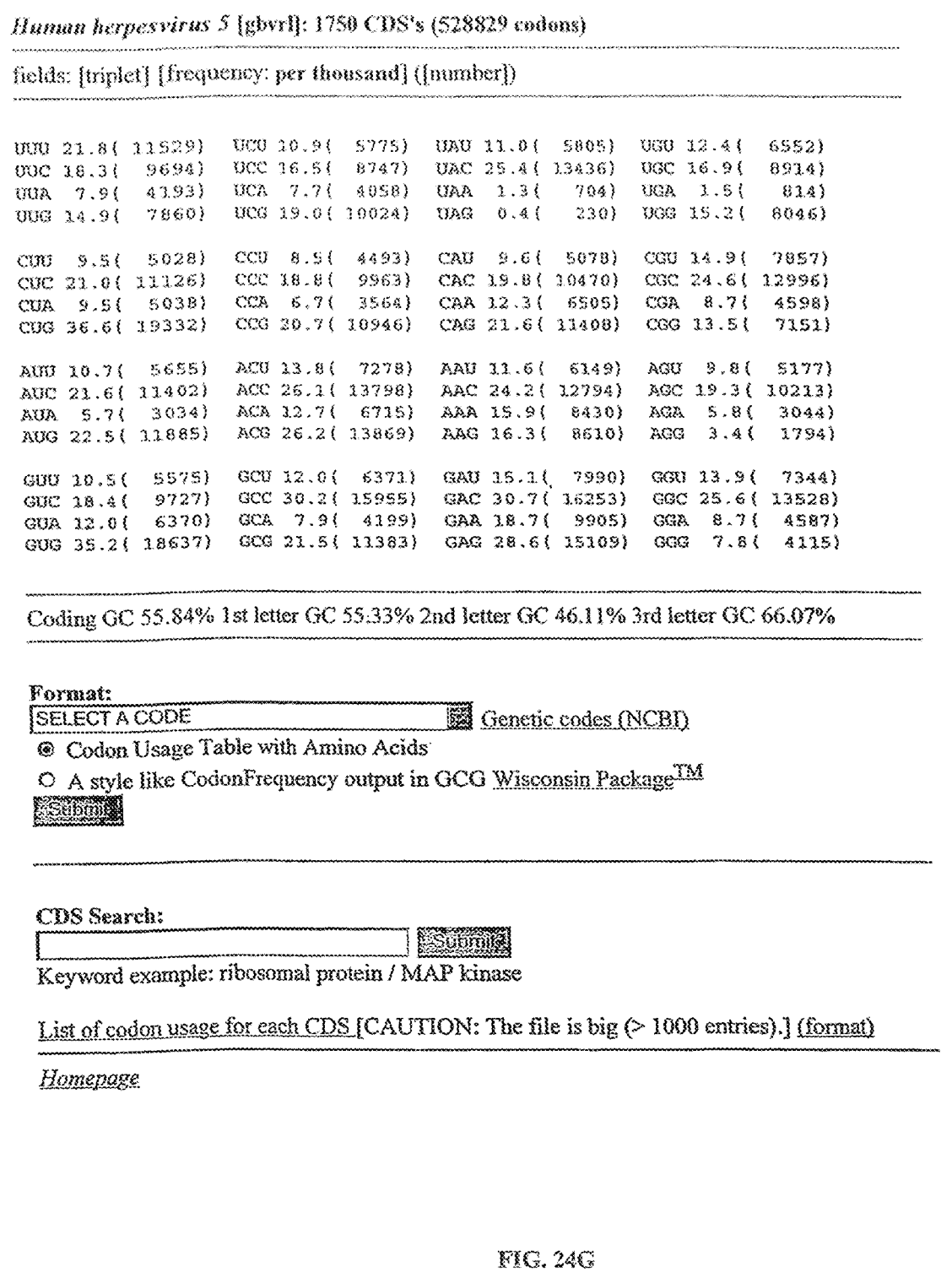

*Human herpesvirus 5* [gbvrl]: 1750 CDS's (528829 codons)

fields: [triplet] [frequency: per thousand] ([number])

```
UUU 21.8( 11529)  UCU 10.9(  5775)  UAU 11.0(  5805)  UGU 12.4(  6552)
UUC 18.3(  9694)  UCC 16.5(  8747)  UAC 25.4( 13436)  UGC 16.9(  8914)
UUA  7.9(  4193)  UCA  7.7(  4058)  UAA  1.3(   704)  UGA  1.5(   814)
UUG 14.9(  7860)  UCG 19.0( 10024)  UAG  0.4(   230)  UGG 15.2(  8046)

CUU  9.5(  5028)  CCU  8.5(  4493)  CAU  9.6(  5078)  CGU 14.9(  7857)
CUC 21.0( 11126)  CCC 18.8(  9963)  CAC 19.8( 10470)  CGC 24.6( 12996)
CUA  9.5(  5038)  CCA  6.7(  3564)  CAA 12.3(  6505)  CGA  8.7(  4598)
CUG 36.6( 19332)  CCG 20.7( 10946)  CAG 21.6( 11408)  CGG 13.5(  7151)

AUU 10.7(  5655)  ACU 13.8(  7278)  AAU 11.6(  6149)  AGU  9.8(  5177)
AUC 21.6( 11402)  ACC 26.1( 13798)  AAC 24.2( 12794)  AGC 19.3( 10213)
AUA  5.7(  3034)  ACA 12.7(  6715)  AAA 15.9(  8430)  AGA  5.8(  3044)
AUG 22.5( 11885)  ACG 26.2( 13869)  AAG 16.3(  8610)  AGG  3.4(  1794)

GUU 10.5(  5575)  GCU 12.0(  6371)  GAU 15.1(  7990)  GGU 13.9(  7344)
GUC 18.4(  9727)  GCC 30.2( 15955)  GAC 30.7( 16253)  GGC 25.6( 13528)
GUA 12.0(  6370)  GCA  7.9(  4199)  GAA 18.7(  9905)  GGA  8.7(  4587)
GUG 35.2( 18637)  GCG 21.5( 11383)  GAG 28.6( 15109)  GGG  7.8(  4115)
```

Coding GC 55.84% 1st letter GC 55.33% 2nd letter GC 46.11% 3rd letter GC 66.07%

Format:

SELECT A CODE Genetic codes (NCBI)

◉ Codon Usage Table with Amino Acids

○ A style like CodonFrequency output in GCG Wisconsin Package™

Submit

CDS Search:

Submit

Keyword example: ribosomal protein / MAP kinase

List of codon usage for each CDS [CAUTION: The file is big (> 1000 entries).] (format)

*Homepage*

FIG. 24G

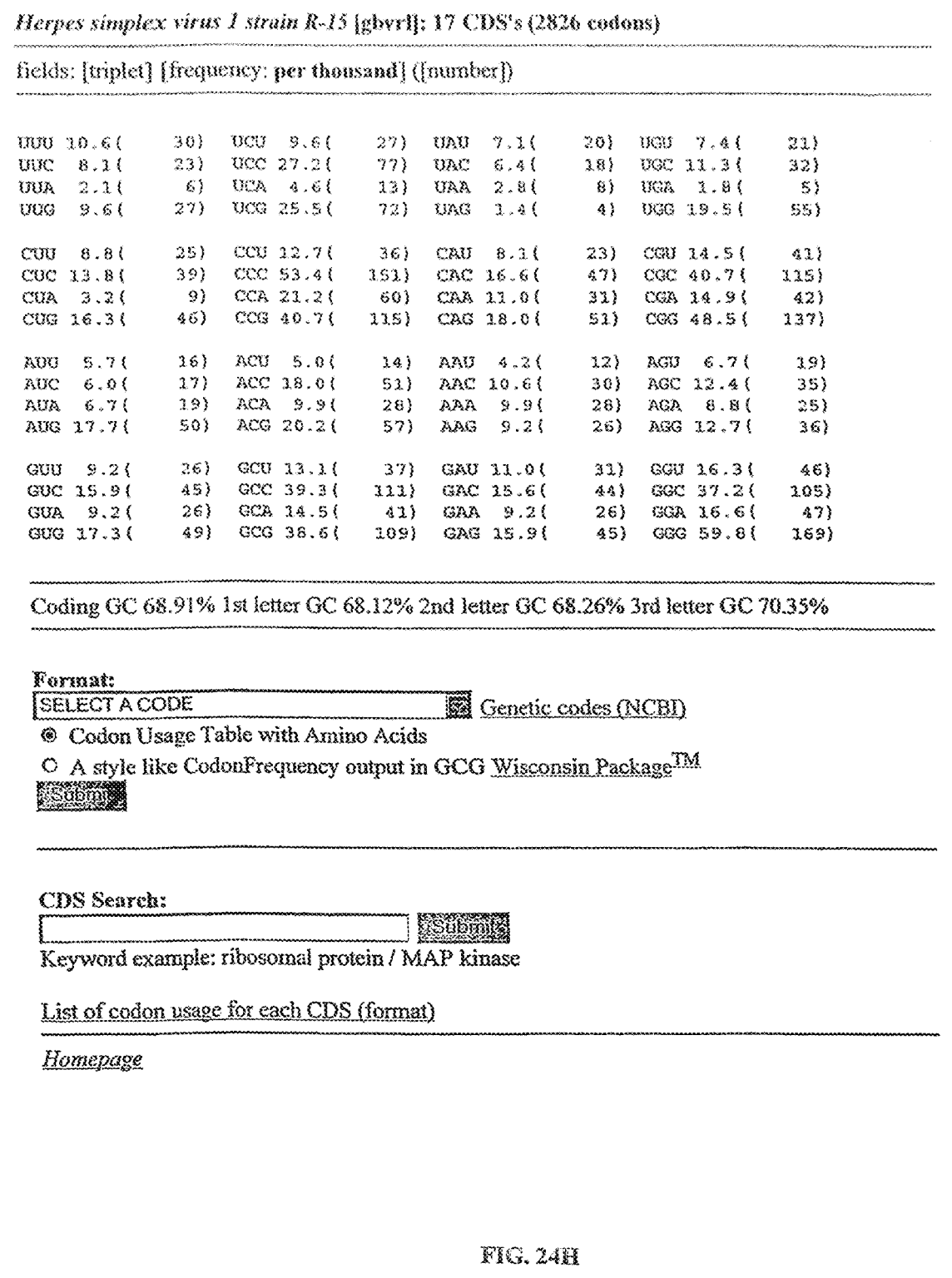

*Herpes simplex virus 1 strain R-15* [gbvrl]: 17 CDS's (2826 codons)

fields: [triplet] [frequency: per thousand] ([number])

```
UUU 10.6(    30)  UCU  9.6(    27)  UAU  7.1(    20)  UGU  7.4(    21)
UUC  8.1(    23)  UCC 27.2(    77)  UAC  6.4(    18)  UGC 11.3(    32)
UUA  2.1(     6)  UCA  4.6(    13)  UAA  2.8(     8)  UGA  1.8(     5)
UUG  9.6(    27)  UCG 25.5(    72)  UAG  1.4(     4)  UGG 19.5(    55)

CUU  8.8(    25)  CCU 12.7(    36)  CAU  8.1(    23)  CGU 14.5(    41)
CUC 13.8(    39)  CCC 53.4(   151)  CAC 16.6(    47)  CGC 40.7(   115)
CUA  3.2(     9)  CCA 21.2(    60)  CAA 11.0(    31)  CGA 14.9(    42)
CUG 16.3(    46)  CCG 40.7(   115)  CAG 18.0(    51)  CGG 48.5(   137)

AUU  5.7(    16)  ACU  5.0(    14)  AAU  4.2(    12)  AGU  6.7(    19)
AUC  6.0(    17)  ACC 18.0(    51)  AAC 10.6(    30)  AGC 12.4(    35)
AUA  6.7(    19)  ACA  9.9(    28)  AAA  9.9(    28)  AGA  8.8(    25)
AUG 17.7(    50)  ACG 20.2(    57)  AAG  9.2(    26)  AGG 12.7(    36)

GUU  9.2(    26)  GCU 13.1(    37)  GAU 11.0(    31)  GGU 16.3(    46)
GUC 15.9(    45)  GCC 39.3(   111)  GAC 15.6(    44)  GGC 37.2(   105)
GUA  9.2(    26)  GCA 14.5(    41)  GAA  9.2(    26)  GGA 16.6(    47)
GUG 17.3(    49)  GCG 38.6(   109)  GAG 15.9(    45)  GGG 59.8(   169)
```

Coding GC 68.91% 1st letter GC 68.12% 2nd letter GC 68.26% 3rd letter GC 70.35%

Format:

SELECT A CODE Genetic codes (NCBI)

◉ Codon Usage Table with Amino Acids

○ A style like CodonFrequency output in GCG Wisconsin Package™

Submit

CDS Search:

Submit

Keyword example: ribosomal protein / MAP kinase

List of codon usage for each CDS (format)

*Homepage*

FIG. 24H

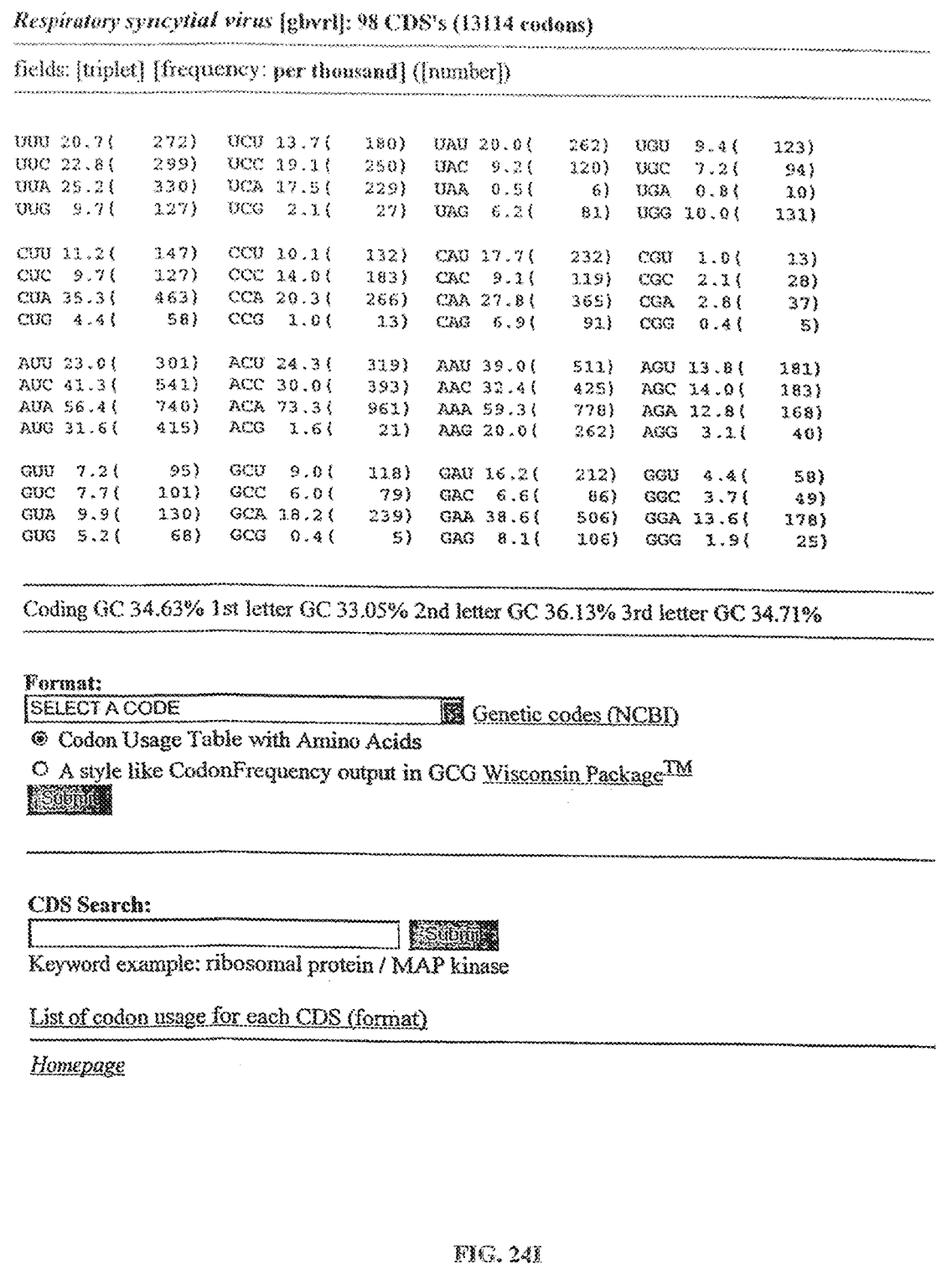

*Respiratory syncytial virus* [gbvrl]: 98 CDS's (13114 codons)

fields: [triplet] [frequency: per thousand] ([number])

| | | | | | | | |
|---|---|---|---|---|---|---|---|
| UUU | 20.7( 272) | UCU | 13.7( 180) | UAU | 20.0( 262) | UGU | 9.4( 123) |
| UUC | 22.8( 299) | UCC | 19.1( 250) | UAC | 9.2( 120) | UGC | 7.2( 94) |
| UUA | 25.2( 330) | UCA | 17.5( 229) | UAA | 0.5( 6) | UGA | 0.8( 10) |
| UUG | 9.7( 127) | UCG | 2.1( 27) | UAG | 6.2( 81) | UGG | 10.0( 131) |
| CUU | 11.2( 147) | CCU | 10.1( 132) | CAU | 17.7( 232) | CGU | 1.0( 13) |
| CUC | 9.7( 127) | CCC | 14.0( 183) | CAC | 9.1( 119) | CGC | 2.1( 28) |
| CUA | 35.3( 463) | CCA | 20.3( 266) | CAA | 27.8( 365) | CGA | 2.8( 37) |
| CUG | 4.4( 58) | CCG | 1.0( 13) | CAG | 6.9( 91) | CGG | 0.4( 5) |
| AUU | 23.0( 301) | ACU | 24.3( 319) | AAU | 39.0( 511) | AGU | 13.8( 181) |
| AUC | 41.3( 541) | ACC | 30.0( 393) | AAC | 32.4( 425) | AGC | 14.0( 183) |
| AUA | 56.4( 740) | ACA | 73.3( 961) | AAA | 59.3( 778) | AGA | 12.8( 168) |
| AUG | 31.6( 415) | ACG | 1.6( 21) | AAG | 20.0( 262) | AGG | 3.1( 40) |
| GUU | 7.2( 95) | GCU | 9.0( 118) | GAU | 16.2( 212) | GGU | 4.4( 58) |
| GUC | 7.7( 101) | GCC | 6.0( 79) | GAC | 6.6( 86) | GGC | 3.7( 49) |
| GUA | 9.9( 130) | GCA | 18.2( 239) | GAA | 38.6( 506) | GGA | 13.6( 178) |
| GUG | 5.2( 68) | GCG | 0.4( 5) | GAG | 8.1( 106) | GGG | 1.9( 25) |

Coding GC 34.63% 1st letter GC 33.05% 2nd letter GC 36.13% 3rd letter GC 34.71%

Format:

SELECT A CODE Genetic codes (NCBI)

◉ Codon Usage Table with Amino Acids

○ A style like CodonFrequency output in GCG Wisconsin Package™

Submit

CDS Search:

Submit

Keyword example: ribosomal protein / MAP kinase

List of codon usage for each CDS (format)

*Homepage*

FIG. 24I

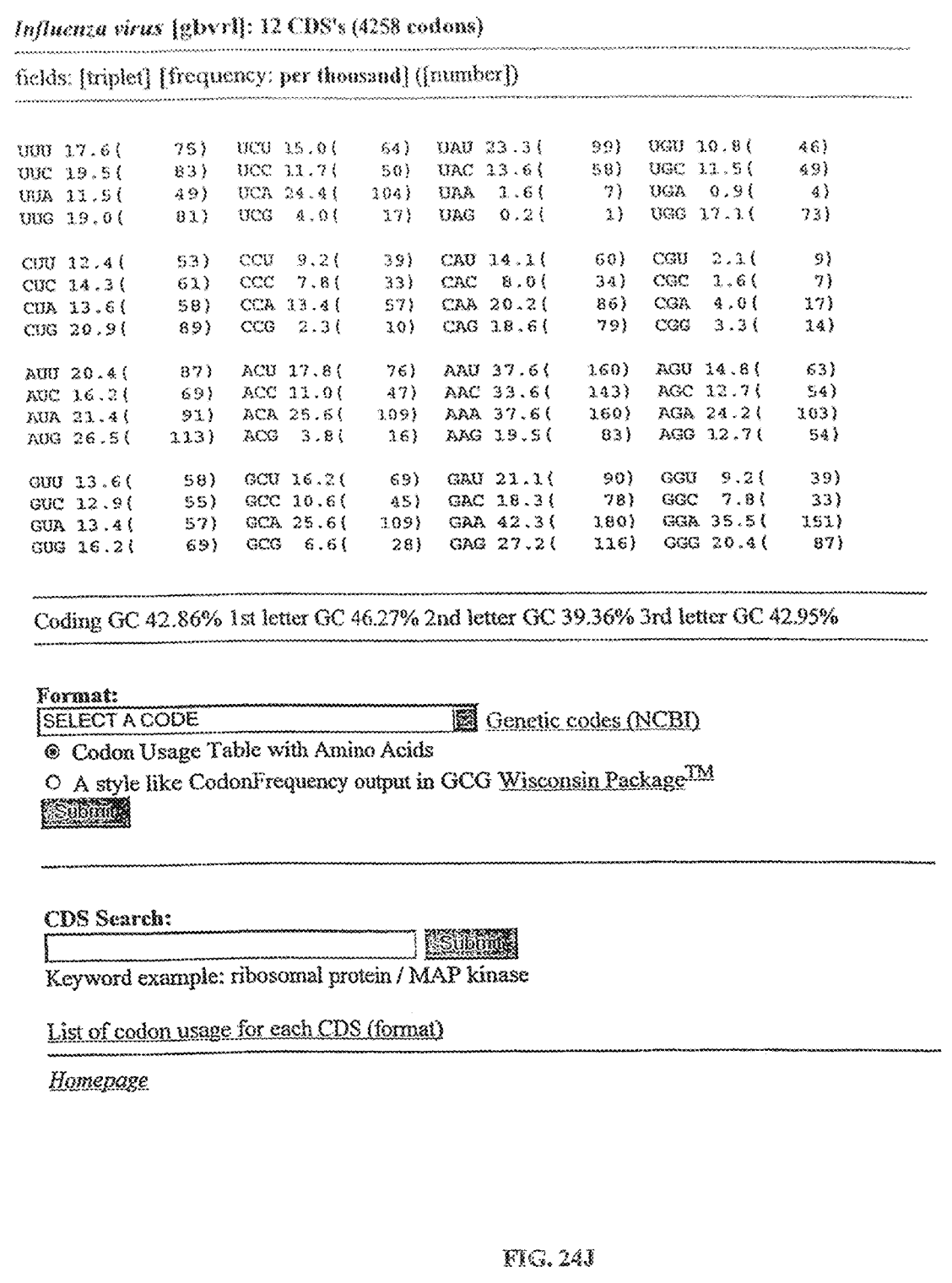

*Influenza virus* [gbvrl]: 12 CDS's (4258 codons)

fields: [triplet] [frequency: per thousand] ([number])

```
UUU 17.6(  75)  UCU 15.0(  64)  UAU 23.3(  99)  UGU 10.8(  46)
UUC 19.5(  83)  UCC 11.7(  50)  UAC 13.6(  58)  UGC 11.5(  49)
UUA 11.5(  49)  UCA 24.4( 104)  UAA  1.6(   7)  UGA  0.9(   4)
UUG 19.0(  81)  UCG  4.0(  17)  UAG  0.2(   1)  UGG 17.1(  73)

CUU 12.4(  53)  CCU  9.2(  39)  CAU 14.1(  60)  CGU  2.1(   9)
CUC 14.3(  61)  CCC  7.8(  33)  CAC  8.0(  34)  CGC  1.6(   7)
CUA 13.6(  58)  CCA 13.4(  57)  CAA 20.2(  86)  CGA  4.0(  17)
CUG 20.9(  89)  CCG  2.3(  10)  CAG 18.6(  79)  CGG  3.3(  14)

AUU 20.4(  87)  ACU 17.8(  76)  AAU 37.6( 160)  AGU 14.8(  63)
AUC 16.2(  69)  ACC 11.0(  47)  AAC 33.6( 143)  AGC 12.7(  54)
AUA 21.4(  91)  ACA 25.6( 109)  AAA 37.6( 160)  AGA 24.2( 103)
AUG 26.5( 113)  ACG  3.8(  16)  AAG 19.5(  83)  AGG 12.7(  54)

GUU 13.6(  58)  GCU 16.2(  69)  GAU 21.1(  90)  GGU  9.2(  39)
GUC 12.9(  55)  GCC 10.6(  45)  GAC 18.3(  78)  GGC  7.8(  33)
GUA 13.4(  57)  GCA 25.6( 109)  GAA 42.3( 180)  GGA 35.5( 151)
GUG 16.2(  69)  GCG  6.6(  28)  GAG 27.2( 116)  GGG 20.4(  87)
```

Coding GC 42.86% 1st letter GC 46.27% 2nd letter GC 39.36% 3rd letter GC 42.95%

Format:

SELECT A CODE Genetic codes (NCBI)

◉ Codon Usage Table with Amino Acids

○ A style like CodonFrequency output in GCG Wisconsin Package™

Submit

CDS Search:

Submit

Keyword example: ribosomal protein / MAP kinase

List of codon usage for each CDS (format)

*Homepage*

FIG. 24J

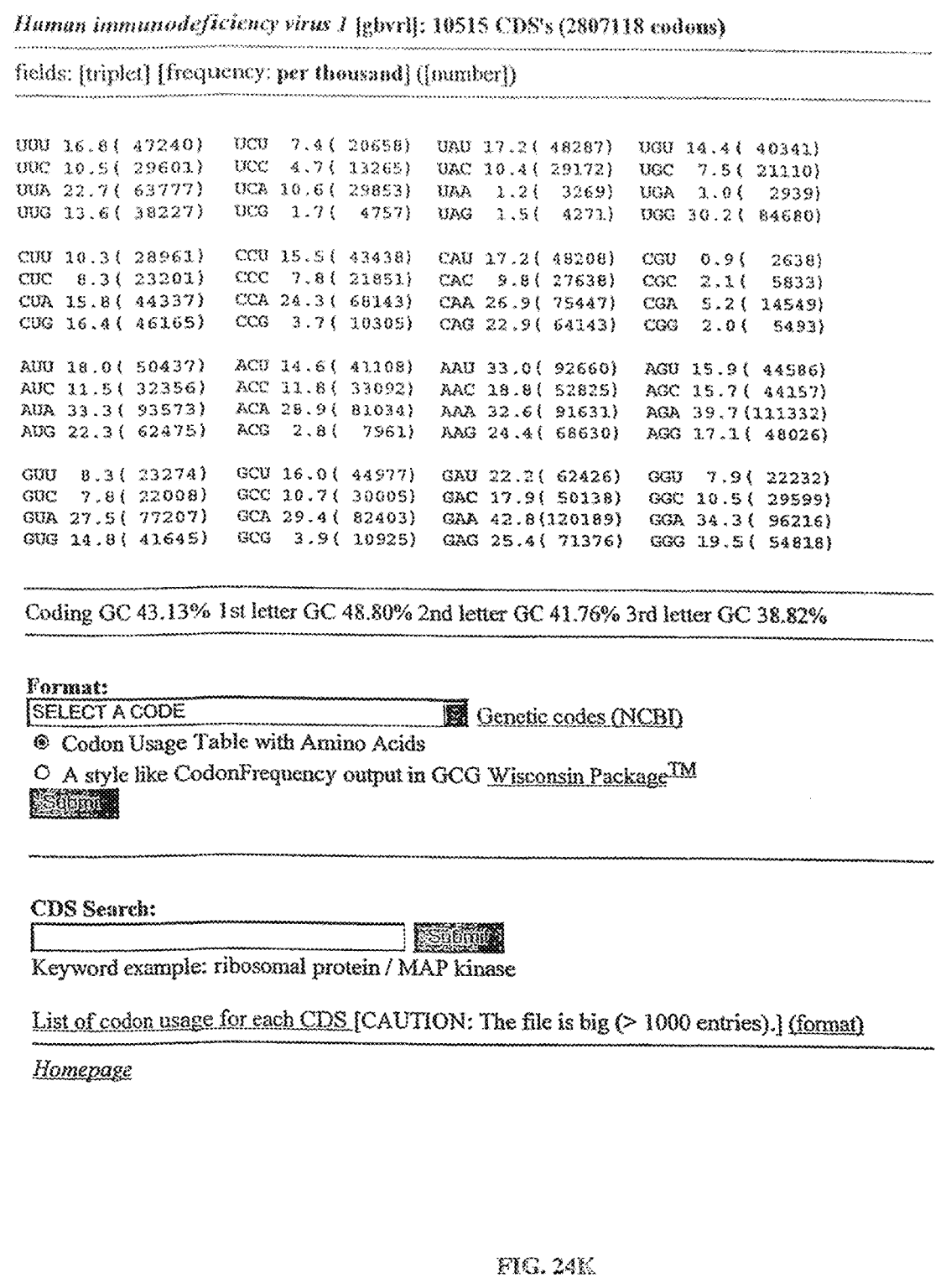

*Human immunodeficiency virus 1* [gbvrl]: 10515 CDS's (2807118 codons)

fields: [triplet] [frequency: per thousand] ([number])

```
UUU 16.8( 47240)  UCU  7.4( 20658)  UAU 17.2( 48287)  UGU 14.4( 40341)
UUC 10.5( 29601)  UCC  4.7( 13265)  UAC 10.4( 29172)  UGC  7.5( 21110)
UUA 22.7( 63777)  UCA 10.6( 29853)  UAA  1.2(  3269)  UGA  1.0(  2939)
UUG 13.6( 38227)  UCG  1.7(  4757)  UAG  1.5(  4271)  UGG 30.2( 84680)

CUU 10.3( 28961)  CCU 15.5( 43438)  CAU 17.2( 48208)  CGU  0.9(  2638)
CUC  8.3( 23201)  CCC  7.8( 21851)  CAC  9.8( 27638)  CGC  2.1(  5833)
CUA 15.8( 44337)  CCA 24.3( 68143)  CAA 26.9( 75447)  CGA  5.2( 14549)
CUG 16.4( 46165)  CCG  3.7( 10305)  CAG 22.9( 64143)  CGG  2.0(  5493)

AUU 18.0( 50437)  ACU 14.6( 41108)  AAU 33.0( 92660)  AGU 15.9( 44586)
AUC 11.5( 32356)  ACC 11.8( 33092)  AAC 18.8( 52825)  AGC 15.7( 44157)
AUA 33.3( 93573)  ACA 28.9( 81034)  AAA 32.6( 91631)  AGA 39.7(111332)
AUG 22.3( 62475)  ACG  2.8(  7961)  AAG 24.4( 68630)  AGG 17.1( 48026)

GUU  8.3( 23274)  GCU 16.0( 44977)  GAU 22.2( 62426)  GGU  7.9( 22232)
GUC  7.8( 22008)  GCC 10.7( 30005)  GAC 17.9( 50138)  GGC 10.5( 29599)
GUA 27.5( 77207)  GCA 29.4( 82403)  GAA 42.8(120189)  GGA 34.3( 96216)
GUG 14.8( 41645)  GCG  3.9( 10925)  GAG 25.4( 71376)  GGG 19.5( 54818)
```

Coding GC 43.13% 1st letter GC 48.80% 2nd letter GC 41.76% 3rd letter GC 38.82%

Format:
[SELECT A CODE] Genetic codes (NCBI)
● Codon Usage Table with Amino Acids
○ A style like CodonFrequency output in GCG Wisconsin Package™
[Submit]

CDS Search:
[_____] [Submit]
Keyword example: ribosomal protein / MAP kinase List of codon usage for each CDS [CAUTION: The file is big (> 1000 entries).] (format)

*Homepage*

FIG. 24K

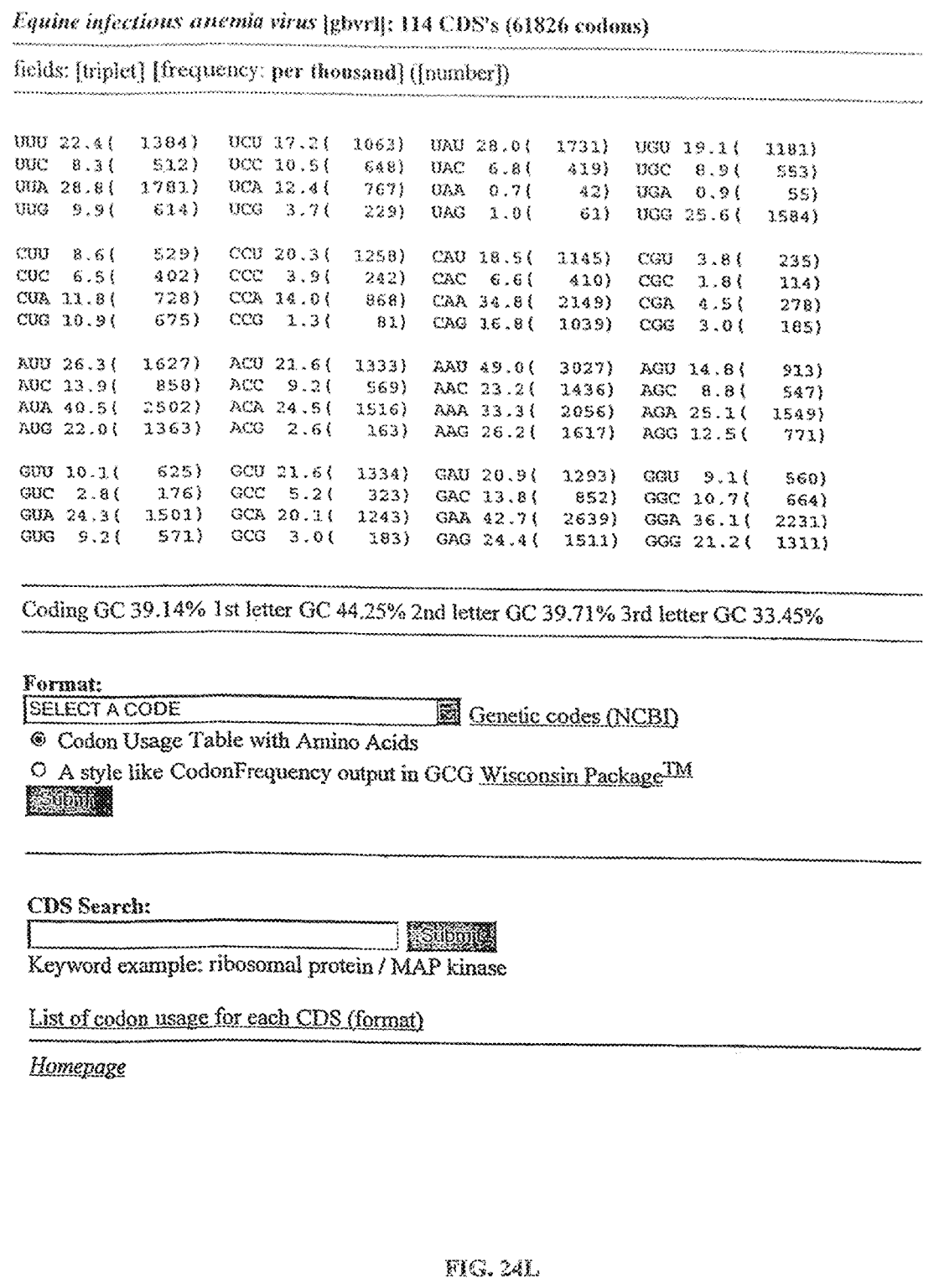

*Equine infectious anemia virus* [gbvrl]: 114 CDS's (61826 codons)

fields: [triplet] [frequency: per thousand] ([number])

| | | | |
|---|---|---|---|
| UUU 22.4( 1384) | UCU 17.2( 1063) | UAU 28.0( 1731) | UGU 19.1( 1181) |
| UUC 8.3( 512) | UCC 10.5( 648) | UAC 6.8( 419) | UGC 8.9( 553) |
| UUA 28.8( 1781) | UCA 12.4( 767) | UAA 0.7( 42) | UGA 0.9( 55) |
| UUG 9.9( 614) | UCG 3.7( 229) | UAG 1.0( 61) | UGG 25.6( 1584) |
| CUU 8.6( 529) | CCU 20.3( 1258) | CAU 18.5( 1145) | CGU 3.8( 235) |
| CUC 6.5( 402) | CCC 3.9( 242) | CAC 6.6( 410) | CGC 1.8( 114) |
| CUA 11.8( 728) | CCA 14.0( 868) | CAA 34.8( 2149) | CGA 4.5( 278) |
| CUG 10.9( 675) | CCG 1.3( 81) | CAG 16.8( 1039) | CGG 3.0( 185) |
| AUU 26.3( 1627) | ACU 21.6( 1333) | AAU 49.0( 3027) | AGU 14.8( 913) |
| AUC 13.9( 858) | ACC 9.2( 569) | AAC 23.2( 1436) | AGC 8.8( 547) |
| AUA 40.5( 2502) | ACA 24.5( 1516) | AAA 33.3( 2056) | AGA 25.1( 1549) |
| AUG 22.0( 1363) | ACG 2.6( 163) | AAG 26.2( 1617) | AGG 12.5( 771) |
| GUU 10.1( 625) | GCU 21.6( 1334) | GAU 20.9( 1293) | GGU 9.1( 560) |
| GUC 2.8( 176) | GCC 5.2( 323) | GAC 13.8( 852) | GGC 10.7( 664) |
| GUA 24.3( 1501) | GCA 20.1( 1243) | GAA 42.7( 2639) | GGA 36.1( 2231) |
| GUG 9.2( 571) | GCG 3.0( 183) | GAG 24.4( 1511) | GGG 21.2( 1311) |

Coding GC 39.14% 1st letter GC 44.25% 2nd letter GC 39.71% 3rd letter GC 33.45%

Format:

SELECT A CODE Genetic codes (NCBI)

◉ Codon Usage Table with Amino Acids

○ A style like CodonFrequency output in GCG Wisconsin Package™

Submit

CDS Search:

Submit

Keyword example: ribosomal protein / MAP kinase

List of codon usage for each CDS (format)

*Homepage*

FIG. 24L

*Escherichia coli* [gbbct]: 13200 CDS's (4030266 codons)

fields: [triplet] [frequency: per thousand] ([number])

```
UUU 22.3( 89985)  UCU 10.8( 43728)  UAU 18.0( 72440)  UGU  5.3( 21431)
UUC 15.8( 63684)  UCC  9.4( 37738)  UAC 12.1( 48758)  UGC  6.0( 24208)
UUA 14.5( 58346)  UCA  9.7( 38904)  UAA  2.0(  7907)  UGA  1.0(  4206)
UUG 12.7( 51140)  UCG  8.5( 34448)  UAG  0.3(  1149)  UGG 13.9( 55921)

CUU 12.3( 49607)  CCU  7.8( 31303)  CAU 12.5( 50496)  CGU 19.3( 77801)
CUC 10.1( 40777)  CCC  5.5( 22191)  CAC  9.0( 36460)  CGC 18.8( 75701)
CUA  4.4( 17639)  CCA  8.6( 34744)  CAA 14.3( 57536)  CGA  4.0( 16167)
CUG 46.9(189204)  CCG 19.8( 79918)  CAG 28.4(114518)  CGG  6.4( 25766)

AUU 29.5(118960)  ACU 10.9( 43846)  AAU 21.8( 87884)  AGU 10.5( 42329)
AUC 23.0( 92826)  ACC 21.7( 87349)  AAC 21.4( 86073)  AGC 15.0( 60556)
AUA  7.8( 31326)  ACA 10.3( 41555)  AAA 35.1(141491)  AGA  4.2( 16943)
AUG 26.0(104652)  ACG 13.8( 55504)  AAG 12.9( 51895)  AGG  2.5( 10033)

GUU 20.0( 80574)  GCU 17.4( 70044)  GAU 32.8(132131)  GGU 25.2(101534)
GUC 14.2( 57354)  GCC 24.0( 96703)  GAC 19.1( 76987)  GGC 26.2(105620)
GUA 11.8( 47387)  GCA 21.5( 86585)  GAA 38.1(153370)  GGA 10.4( 41743)
GUG 23.7( 95503)  GCG 28.6(115274)  GAG 18.8( 75654)  GGG 11.6( 46760)
```

Coding GC 50.20% 1st letter GC 57.14% 2nd letter GC 40.85% 3rd letter GC 52.61%

Format:

SELECT A CODE Genetic codes (NCBI)

◉ Codon Usage Table with Amino Acids

○ A style like CodonFrequency output in GCG Wisconsin Package™

Submit

CDS Search:

Submit

Keyword example: ribosomal protein / MAP kinase

List of codon usage for each CDS [CAUTION: The file is big (> 1000 entries).] (format)

*Homepage*

```
2614 ACA GCC GTG GAG ACA GGG GCT ACC AAT CCG TTG GTG CCT TCG GAC ACC GTG CAA ACG CGC CAT GTC ATC  2682
       G                                   A               A       T           T A A
      T   A   V   E   T   G   A   T   N   P   L   V   P   S   D   T   V   Q   T   R   H   V   I
2683 CAG AGA CGA ACG CGA TCA GAG TCC ACG GTT GAG TCA TTC TTT GCA AGA GGG GCT TGC GTG GCT ATC ATT  2751
             A     T A                 T                                       T
      Q   R   R   T   R   S   E   S   T   V   E   S   F   F   A   R   G   A   C   V   A   I   I
2752 GAG GTG GAC AAT GAT GCA CCG ACA AAG CGC GCC AGC AGA TTG TTT TCG GTT TGG AAA ATA ACT TAC AAA  2820
                               A         A A                       A
      E   V   D   N   D   A   P   T   K   R   A   S   R   L   F   S   V   W   K   I   T   Y   K
2821 GAT ACT GTT CAA CTG AGA CGC AAA CTG GAA TTT TTC ACA TAT TCG AGA TTT GAC ATG GAG TTC ACT TTT  2889
                             A A                               A
      D   T   V   Q   L   R   R   K   L   E   F   F   T   Y   S   R   F   D   M   E   F   T   F
2890 GTG GTC ACC TCA AAC TAC ATT GAT GCA AAT AAC GGA CAT GCA TTG AAC CAA GTT TAT CAG ATA ATG TAT  2958
                                               T
      V   V   T   S   N   Y   I   D   A   N   N   G   H   A   L   N   Q   V   Y   Q   I   M   Y
2959 ATA CCA CCC GGA GCA CCT ATC CCT GGT AAA TGG AAT GAC TAT ACG TGG CAG ACG TCC TCT AAC CCG TCG  3027
               A                                               T           T               A   A
      I   P   P   G   A   P   I   P   G   K   W   N   D   Y   T   W   Q   T   S   S   N   P   S
3028 GTG TTT TAC ACC TAT GGG GCG CCC CCA GCA AGA ATA TCA GTG CCC TAC GTG GGA ATT GCT AAT GCG TAT  3096
                               A                                   T                       A
      V   F   Y   T   Y   G   A   P   P   A   R   I   S   V   P   Y   V   G   I   A   N   A   Y
3097 TCC CAC TTT TAT GAT GGG TTT GCA AAA GTA CCA CTA GCG GGT CAA GCC TCA ACT GAA GGC GAT TCG TTG  3165
                                                       A                           T       A
      S   H   F   Y   D   G   F   A   K   V   P   L   A   G   Q   A   S   T   E   G   D   S   L
3166 TAC GGT GCT GCC TCA CTG AAT GAT TTT GGA TCA CTG GCT GTT CGC GTG GTA AAT GAT CAC AAC CCC ACG  3234
       T                                                     A A                               T
      Y   G   A   A   S   L   N   D   F   G   S   L   A   V   R   V   V   N   D   H   N   P   T
3235 CGG CTC ACC TCC AAG ATC AGA GTG TAC ATG AAG CCA AAG CAT GTC AGA GTC TGG TGC CCA CGA CCT CCA  3303
     A                                                                               A         T
      R   L   T   S   K   I   R   V   Y   M   K   P   K   H   V   R   V   W   C   P   R   P   P
```

FIG. 26

```
2614 ACA GCC GTG GAG ACA GGG GCT ACC AAT CCG TTG GTG CCT TCG GAC ACC GTG CAA ACG CGC CAT GTC ATC  2682
       G                       A           A               A       T           A A A
      T   A   V   E   T   G   A   T   N   P   L   V   P   S   D   T   V   Q   T   R   H   V   I
2683 CAG AGA CGA ACG CGA TCA GAG TCC ACG GTT GAG TCA TTC TTT GCA AGA GGG GCT TGC GTG GCT ATC ATT  2751
             A     A A                 T                                       T       A
      Q   R   R   T   R   S   E   S   T   V   E   S   F   F   A   R   G   A   C   V   A   I   I
2752 GAG GTG GAC AAT GAT GCA CCG ACA AAG CGC GCC AGC AGA TTG TTT TCG GTT TGG AAA ATA ACT TAC AAA  2820
                               A         A A                       A               C
      E   V   D   N   D   A   P   T   K   R   A   S   R   L   F   S   V   W   K   I   T   Y   K
2821 GAT ACT GTT CAA CTG AGA CGC AAA CTG GAA TTT TTC ACA TAT TCG AGA TTT GAC ATG GAG TTC ACT TTT  2889
       C                     A A                               A
      D   T   V   Q   L   R   R   K   L   E   F   F   T   Y   S   R   F   D   M   E   F   T   F
2890 GTG GTC ACC TCA AAC TAC ATT GAT GCA AAT AAC GGA CAT GCA TTG AAC CAA GTT TAT CAG ATA ATG TAT  2958
                                           C   T                                       C       C
      V   V   T   S   N   Y   I   D   A   N   N   G   H   A   L   N   Q   V   Y   Q   I   M   Y
2959 ATA CCA CCC GGA GCA CCT ATC CCT GGT AAA TGG AAT GAC TAT ACG TGG CAG ACG TCC TCT AAC CCG TCG  3027
       T       A           A           A                   C   T           T       A       A   A
      I   P   P   G   A   P   I   P   G   K   W   N   D   Y   T   W   Q   T   S   S   N   P   S
3028 GTG TTT TAC ACC TAT GGG GCG CCC CCA GCA AGA ATA TCA GTG CCC TAC GTG GGA ATT GCT AAT GCG TAT  3096
                               A                   T               T               A       A
      V   F   Y   T   Y   G   A   P   P   A   R   I   S   V   P   Y   V   G   I   A   N   A   Y
3097 TCC CAC TTT TAT GAT GGG TTT GCA AAA GTA CCA CTA GCG GGT CAA GCC TCA ACT GAA GGC GAT TCG TTG  3165
                                           G       G   A                           T       A
      S   H   F   Y   D   G   F   A   K   V   P   L   A   G   Q   A   S   T   E   G   D   S   L
3166 TAC GGT GCT GCC TCA CTG AAT GAT TTT GGA TCA CTG GCT GTT CGC GTG GTA AAT GAT CAC AAC CCC ACG  3234
       T                                                   G A A       G                       A
      Y   G   A   A   S   L   N   D   F   G   S   L   A   V   R   V   V   N   D   H   N   P   T
3235 CGG CTC ACC TCC AAG ATC AGA GTG TAC ATG AAG CCA AAG CAT GTC AGA GTC TGG TGC CCA CGA CCT CCA  3303
     A                                                                               A         T
      R   L   T   S   K   I   R   V   Y   M   K   P   K   H   V   R   V   W   C   P   R   P   P
```

FIG. 27

2614 ACA GCC GTG GAG ACA GGG GCT ACC AAT CCG TTG GTG CCT TCG GAC ACC GTG CAA ACG CGC CAT GTC ATC 2682
G C G C G G C C G C
T A V E T G A T N P L V P S D T V Q T R H V I
2683 CAG AGA CGA ACG CGA TCA GAG TCC ACG GTT GAG TCA TTC TTT GCA AGA GGG GCT TGC GTG GCT ATC ATT 2751
C G G C G C G C C C G C G C
Q R R T R S E S T V E S F F A R G A C V A I I
2752 GAG GTG GAC AAT GAT GCA CCG ACA AAG CGC GCC AGC AGA TTG TTT TCG GTT TGG AAA ATA ACT TAC AAA 2820
C C C G G G TCG C G
E V D N D A P T K R A S R L F S V W K I T Y K
2821 GAT ACT GTT CAA CTG AGA CGC AAA CTG GAA TTT TTC ACA TAT TCG AGA TTT GAC ATG GAG TTC ACT TTT 2889
G C C G C C G C
D T V Q L R R K L E F F T Y S R F D M E F T F
2890 GTG GTC ACC TCA AAC TAC ATT GAT GCA AAT AAC GGA CAT GCA TTG AAC CAA GTT TAT CAG ATA ATG TAT 2958
C G G C C G C G
V V T S N Y I D A N N G H A L N Q V Y Q I M Y
2959 ATA CCA CCC GGA GCA CCT ATC CCT GGT AAA TGG AAT GAC TAT ACG TGG CAG ACG TCC TCT AAC CCG TCG 3027
G C G G G C G G
I P P G A P I P G K W N D Y T W Q T S S N P S
3028 GTG TTT TAC ACC TAT GGG GCG CCC CCA GCA AGA ATA TCA GTG CCC TAC GTG GGA ATT GCT AAT GCG TAT 3096
G C C G G G C G G C C G C
V F Y T Y G A P P A R I S V P Y V G I A N A Y
3097 TCC CAC TTT TAT GAT GGG TTT GCA AAA GTA CCA CTA GCG GGT CAA GCC TCA ACT GAA GGC GAT TCG TTG 3165
G C C C G G C G G G
S H F Y D G F A K V P L A G Q A S T E G D S L
3166 TAC GGT GCT GCC TCA CTG AAT GAT TTT GGA TCA CTG GCT GTT CGC GTG GTA AAT GAT CAC AAC CCC ACG 3234
C G G G C C G C G C C G
Y G A A S L N D F G S L A V R V V N D H N P T
3235 CGG CTC ACC TCC AAG ATC AGA GTG TAC ATG AAG CCA AAG CAT GTC AGA GTC TGG TGC CCA CGA CCT CCA 3303
G G C C G C C C G G T
R L T S K I R V Y M K P K H V R V W C P R P P

FIG. 28

2614 ACA GCC GTG GAG ACA GGG GCT ACC AAT CCG TTG GTG CCT TCG GAC ACC GTG CAA ACG CGC CAT GTC ATC 2682
G C G C G G C C A G T A C A A
T A V E T G A T N P L V P S D T V Q T R H V I
2683 CAG AGA CGA ACG CGA TCA GAG TCC ACG GTT GAG TCA TTC TTT GCA AGA GGG GCT TGC GTG GCT ATC ATT 2751
C T T AGC G C G C G C C C G C G T C
Q R R T R S E S T V E S F F A R G A C V A I I
2752 GAG GTG GAC AAT GAT GCA CCG ACA AAG CGC GCC AGC AGA TTG TTT TCG GTT TGG AAA ATA ACT TAC AAA 2820
C T C C G G G TCG C A A G T
E V D N D A P T K R A S R L F S V W K I T Y K
2821 GAT ACT GTT CAA CTG AGA CGC AAA CTG GAA TTT TTC ACA TAT TCG AGA TTT GAC ATG GAG TTC ACT TTT 2889
G A A C T C T G C C T T G C
D T V Q L R R K L E F F T Y S R F D M E F T F
2890 GTG GTC ACC TCA AAC TAC ATT GAT GCA AAT AAC GGA CAT GCA TTG AAC CAA GTT TAT CAG ATA ATG TAT 2958
C T G G T C C G C G A A
V V T S N Y I D A N N G H A L N Q V Y Q I M Y
2959 ATA CCA CCC GGA GCA CCT ATC CCT GGT AAA TGG AAT GAC TAT ACG TGG CAG ACG TCC TCT AAC CCG TCG 3027
G C G G G C G G
I P P G A P I P G K W N D Y T W Q T S S N P S
3028 GTG TTT TAC ACC TAT GGG GCG CCC CCA GCA AGA ATA TCA GTG CCC TAC GTG GGA ATT GCT AAT GCG TAT 3096
A T G C C G G G C T G A G C T C G C
V F Y T Y G A P P A R I S V P Y V G I A N A Y
3097 TCC CAC TTT TAT GAT GGG TTT GCA AAA GTA CCA CTA GCG GGT CAA GCC TCA ACT GAA GGC GAT TCG TTG 3165
G C C C G G C G G G A
S H F Y D G F A K V P L A G Q A S T E G D S L
3166 TAC GGT GCT GCC TCA CTG AAT GAT TTT GGA TCA CTG GCT GTT CGC GTG GTA AAT GAT CAC AAC CCC ACG 3234
C G G G T C C G C G A C C T G
Y G A A S L N D F G S L A V R V V N D H N P T
3235 CGG CTC ACC TCC AAG ATC AGA GTG TAC ATG AAG CCA AAG CAT GTC AGA GTC TGG TGC CCA CGA CCT CCA 3303
T G G A C C A T G C A C C A G G T
R L T S K I R V Y M K P K H V R V W C P R P P

FIG. 29

```
2614 ACA GCC GTG GAG ACA GGG GCT ACC AAT CCG TTG GTG CCT TCG GAC ACC GTG CAA ACG CGC CAT GTC ATC 2682
       G       C       G   T   G   G         C T   C   G           G   C           G           A
      T   A   V   E   T   G   A   T   N   P   L   V   P   S   D   T   V   Q   T   R   H   V   I
2683 CAG AGA CGA ACG CGA TCA GAG TCC ACG GTT GAG TCA TTC TTT GCA AGA GGG GCT TGC GTG GCT ATC ATT 2751
         C G   G       G   G       G       C       G           G C G   T   G       C   G   A   A
      Q   R   R   T   R   S   E   S   T   V   E   S   F   F   A   R   G   A   C   V   A   I   I
2752 GAG GTG GAC AAT GAT GCA CCG ACA AAG CGC GCC AGC AGA TTG TTT TCG GTT TGG AAA ATA ACT TAC AAA 2820
                           G       G   A   G   G TCG C G C T           C               G
      E   V   D   N   D   A   P   T   K   R   A   S   R   L   F   S   V   W   K   I   T   Y   K
2821 GAT ACT GTT CAA CTG AGA CGC AAA CTG GAA TTT TTC ACA TAT TCG AGA TTT GAC ATG GAG TTC ACT TTT 2889
           G   C       T C G   G       T               G         C G                       G
      D   T   V   Q   L   R   R   K   L   E   F   F   T   Y   S   R   F   D   M   E   F   T   F
2890 GTG GTC ACC TCA AAC TAC ATT GAT GCA AAT AAC GGA CAT GCA TTG AAC CAA GTT TAT CAG ATA ATG TAT 2958
       C       G   G           A       G           T       G C T           C
      V   V   T   S   N   Y   I   D   A   N   N   G   H   A   L   N   Q   V   Y   Q   I   M   Y
2959 ATA CCA CCC GGA GCA CCT ATC CCT GGT AAA TGG AAT GAC TAT ACG TGG CAG ACG TCC TCT AAC CCG TCG 3027
           G   G   T   G   G   A   G                                           G   G
      I   P   P   G   A   P   I   P   G   K   W   N   D   Y   T   W   Q   T   S   S   N   P   S
3028 GTG TTT TAC ACC TAT GGG GCG CCC CCA GCA AGA ATA TCA GTG CCC TAC GTG GGA ATT GCT AAT GCG TAT 3096
       C           G       T       G   G   G C G   C   G   C   G       C   T   C   G
      V   F   Y   T   Y   G   A   P   P   A   R   I   S   V   P   Y   V   G   I   A   N   A   Y
3097 TCC CAC TTT TAT GAT GGG TTT GCA AAA GTA CCA CTA GCG GGT CAA GCC TCA ACT GAA GGC GAT TCG TTG 3165
       G   T               T       G       C   G   T               G   G   G       T         C T
      S   H   F   Y   D   G   F   A   K   V   P   L   A   G   Q   A   S   T   E   G   D   S   L
3166 TAC GGT GCT GCC TCA CTG AAT GAT TTT GGA TCA CTG GCT GTT CGC GTG GTA AAT GAT CAC AAC CCC ACG 3234
               G   G   G   T               T   G   T   G   C   G   C   C           T       G
      Y   G   A   A   S   L   N   D   F   G   S   L   A   V   R   V   V   N   D   H   N   P   T
3235 CGG CTC ACC TCC AAG ATC AGA GTG TAC ATG AAG CCA AAG CAT GTC AGA GTC TGG TGC CCA CGA CCT CCA 3303
           T   G   G   A   A C G   C               G   A         C G               G   G       T
      R   L   T   S   K   I   R   V   Y   M   K   P   K   H   V   R   V   W   C   P   R   P   P
```

FIG. 30

```
2614 ACA GCC GTG GAG ACA GGG GCT ACC AAT CCG TTG GTG CCT TCG GAC ACC GTG CAA ACG CGC CAT GTC ATC 2682
       G       A               C       C   A               A       G   A       T   T   C
      T   A   V   E   T   G   A   T   N   P   L   V   P   S   D   T   V   Q   T   R   H   V   I
2683 CAG AGA CGA ACG CGA TCA GAG TCC ACG GTT GAG TCA TTC TTT GCA AGA GGG GCT TGC GTG GCT ATC ATT 2751
       A       G       G   G       T               T       C           A       T       C   T
      Q   R   R   T   R   S   E   S   T   V   E   S   F   F   A   R   G   A   C   V   A   I   I
2752 GAG GTG GAC AAT GAT GCA CCG ACA AAG CGC GCC AGC AGA TTG TTT TCG GTT TGG AAA ATA ACT TAC AAA 2820
       A       T           T   A           T       T       A       A   C       G
      E   V   D   N   D   A   P   T   K   R   A   S   R   L   F   S   V   W   K   I   T   Y   K
2821 GAT ACT GTT CAA CTG AGA CGC AAA CTG GAA TTT TTC ACA TAT TCG AGA TTT GAC ATG GAG TTC ACT TTT 2889
       C   C       G T A       T   G T     G   C   T           A   G                       C
      D   T   V   Q   L   R   R   K   L   E   F   F   T   Y   S   R   F   D   M   E   F   T   F
2890 GTG GTC ACC TCA AAC TAC ATT GAT GCA AAT AAC GGA CAT GCA TTG AAC CAA GTT TAT CAG ATA ATG TAT 2958
           T   A   C   T   T               C   T   G   C     C A   T           C               C
      V   V   T   S   N   Y   I   D   A   N   N   G   H   A   L   N   Q   V   Y   Q   I   M   Y
2959 ATA CCA CCC GGA GCA CCT ATC CCT GGT AAA TGG AAT GAC TAT ACG TGG CAG ACG TCC TCT AAC CCG TCG 3027
               T   G       G           C   G           T   C   A       A       A           A   A
      I   P   P   G   A   P   I   P   G   K   W   N   D   Y   T   W   Q   T   S   S   N   P   S
3028 GTG TTT TAC ACC TAT GGG GCG CCC CCA GCA AGA ATA TCA GTG CCC TAC GTG GGA ATT GCT AAT GCG TAT 3096
                   T   C       A   T       T                               C       C       A
      V   F   Y   T   Y   G   A   P   P   A   R   I   S   V   P   Y   V   G   I   A   N   A   Y
3097 TCC CAC TTT TAT GAT GGG TTT GCA AAA GTA CCA CTA GCG GGT CAA GCC TCA ACT GAA GGC GAT TCG TTG 3165
       T   T       C               C                   A   C               A   G   T   C     C
      S   H   F   Y   D   G   F   A   K   V   P   L   A   G   Q   A   S   T   E   G   D   S   L
3166 TAC GGT GCT GCC TCA CTG AAT GAT TTT GGA TCA CTG GCT GTT CGC GTG GTA AAT GAT CAC AAC CCC ACG 3234
       T   A   G   T     T         C   C                       A       G       C           T
      Y   G   A   A   S   L   N   D   F   G   S   L   A   V   R   V   V   N   D   H   N   P   T
3235 CGG CTC ACC TCC AAG ATC AGA GTG TAC ATG AAG CCA AAG CAT GTC AGA GTC TGG TGC CCA CGA CCT CCA 3303
               T   A   A                       A           C           G       T   G       C   T
      R   L   T   S   K   I   R   V   Y   M   K   P   K   H   V   R   V   W   C   P   R   P   P
```

MODULATION OF REPLICATIVE FITNESS BY DEOPTIMIZATION OF SYNONYMOUS CODONS

CROSS REFERENCE TO RELATED APPLICATIONS

This is a divisional of co-pending U.S. application Ser. No. 15/684,355, filed Aug. 23, 2017, which is a divisional of U.S. application Ser. No. 14/464,619, filed Aug. 20, 2014, now abandoned, which is a divisional of U.S. application Ser. No. 11/576,941, filed Nov. 19, 2007, now U.S. Pat. No. 8,846,051, issued Sep. 30, 2014, which is the U.S. National Stage of International Application No. PCT/US2005/036241, filed Oct. 7, 2005, which was published in English under PCT Article 21(2), which in turn claims benefit of U.S. Provisional Application No. 60/617,545 filed Oct. 8, 2004. Each application is incorporated by reference in its entirety.

ACKNOWLEDGMENT OF GOVERNMENT SUPPORT

This invention was made by the National Center for Infectious Diseases, Centers for Disease Control and Prevention, an agency of the United States Government. Therefore, the U.S. Government has certain rights in this invention.

FIELD

This disclosure relates to methods of reducing the replicative fitness of a pathogen by deoptimizing codons. Pathogens with deoptimized codons can be used to increase the phenotypic stability of attenuated vaccines.

BACKGROUND

Infections by intracellular pathogens such as viruses, bacteria and parasites, are cleared in most cases after activation of specific T cellular immune responses that recognize foreign antigens and eliminate infected cells. Vaccines against those infectious organisms have been traditionally developed by administration of whole live attenuated or inactivated microorganisms. Although research has been performed using subunit vaccines, the levels of cellular immunity induced are usually low and not capable of eliciting complete protection against diseases caused by intracellular microbes.

One problem encountered when using live attenuated vaccines is the development of adverse events in some patients. Typical reactions associated with live viral and bacterial vaccines, such as measles, mumps, rubella (MMR) and varicella vaccines, often resemble attenuated forms of the disease against which the vaccine is directed. However, more severe adverse affects have been reported. For example, there is an association between the Urabe strain of mumps vaccine and viral meningitis (Dubey and Banerjee, *Indian J. Pediatr.* 70:579-84, 2003). In addition, vaccine associated thrombocytopenia has been reported. Although epidemiological studies do not support a causative link between MMR and autism (Chen et al., *Psychol. Med.* 34:543-53, 2004), the fear remains and likely contributes to poor vaccine acceptance in some regions and sections of society.

In addition, documented safety concerns with vaccines demonstrate the harm that vaccines can cause. For example, the currently available attenuated Sabin oral polio vaccine (OPV) strains are genetically unstable, principally because only 2-5 base substitutions confer the attenuated phenotype (Ren et al. *J. Virol.* 65:1377-82, 1991). This instability is the underlying cause of vaccine-associated paralytic poliomyelitis in immunologically normal (Strebel et al., *Clin. Infect. Dis.* 14:568-79, 1992) and in people with B-cell immunodeficiencies (Kew et al., *J. Clin. Microbiol.* 36:2893-9; Khetsuriani et al., *J. Infect. Dis* 188:1845-52, 2003; Yang et al., *J. Virol.* 79:12623-34), and of outbreaks associated with circulating vaccine-derived polioviruses (Kew et al., *Science* 296: 356-9, 2002; Yang et al., *J. Virol.* 77:8366-77, 2003; Rousset et al., *Emerg. Inf Dis.* 9:885-7, 2003; Kew et al., *Bull. WHO* 82:16-23, 2004; Shimizu et al., *J. Virol.* 78:13512-21, 2004; Kew et al., *Ann. Rev. Microbiol.* 59:587-635, 2005). In addition, the CDC recommended suspending use of the rhesus-human rotavirus reassortant-tetravalent vaccine (RRV-TV) due to cases of intussusception (a bowel obstruction in which one segment of bowel becomes enfolded within another segment) among infants who received the vaccine (*MMWR Morb Mortal Wkly Rep.* 53:786-9, 2004).

Although the primary mode of protective immunity induced by OPV is the production of neutralizing antibody by B-cells, OPV stimulates an immune response similar to that of a natural infection. Immunity against paralytic disease is further enhanced by the production of antibodies in the gastrointestinal tract that limit poliovirus replication, and, thus, person-to-person transmission. The stimulation of intestinal immunity, along with ease of administration, has made OPV the vaccine of choice for global polio eradication (Aylward and Cochi, *Bull. WHO* 82:40-6, 2004). Therefore, there is a need to identify methods of making an attenuated vaccine that reduces the safety concerns with currently available live attenuated vaccines while retaining the advantages of attenuated vaccines.

SUMMARY

The inventors have determined that replacement of one or more natural (or native) codons in a pathogen with synonymous unpreferred codons can decrease the replicative fitness of the pathogen, thereby attenuating the pathogen. The unpreferred synonymous codon(s) encode the same amino acid as the native codon(s), but have nonetheless been found to reduce a pathogen's replicative fitness. The introduction of deoptimized codons into a pathogen can limit the ability of the pathogen to mutate or to use recombination to become virulent. The disclosed compositions and methods can be used in attenuated vaccines having well-defined levels of replicative fitness and enhanced genetic stabilities.

Methods of reducing a pathogen's replicative fitness are disclosed. In some examples, the method includes deoptimizing at least one codon in a coding sequence of the pathogen, thereby generating a deoptimized coding sequence. Such deoptimization reduces replicative fitness of the pathogen. In some examples, more than one coding sequence of the pathogen is deoptimized, such as at least one, at least two, or at least 5 coding sequences, such as deoptimizing 1, 2, 3, 4, 5, 6, 7, 8, 9 or 10 coding sequences of the pathogen.

More than one codon in the one or more coding sequences can be deoptimized, such as at least 15 codons, at least 20 codons, at least 30 codons, at least 40 codons, at least 50 codons, at least 60 codons, at least 70 codons, at least 100 codons, at least 200 codons, at least 500 codons, or even at least 1000 codons, in each coding sequence. In some examples, at least 20% of the coding sequence of each desired gene is deoptimized, such as at least 30%, at least 40%, at least 50%, at least 60%, at least 70%, at least 80%, at least 90%, at least 95%, or even at least 97% deoptimized.

In particular examples, deoptimizing the codon composition alters the G+C content of a coding sequence, such as increases or decreases the G+C content by at least 10%, for example increases the G+C content of a coding sequence by at least 10%, such as at least 20%, at least 30%, at least 40%, at least 50%, at least 60%, at least 70%, at least 80%, or even by at least 90%, or decreases the G+C content of a coding sequence by at least 10%, such as at least 20%, at least 30%, at least 40%, at least 50%, at least 60%, at least 70%, at least 80%, or even by at least 90%. However, the G+C content can be altered in combination with deoptimizing one or more codons in a pathogen sequence. For example, some of the nucleotide substitutions can be made to deoptimize codons (which may or may not alter the G+C content of the sequence), and other nucleotide substitutions can be made to alter the G+C content of the sequence (which may or may result in a deoptimized codon). Altering the G+C content of the sequence may also result in a deoptimized codon, but is not required in all instances.

For example, if the pathogen is a rubella virus, whose RNA genome has a high G+C content and consequently has a high rate of usage of rare codons rich in G+C. Therefore, deoptimization of rubella virus can be achieved by decreasing the G+C content of one or more coding sequences, for example decreasing the G+C content by at least 10%, such as at least 20%, or even by at least 50%. In another example, the pathogen is a poliovirus, and deoptimization can be achieved by increasing the G+C content of one or more coding sequences, for example increasing the G+C content by at least 10%, such as at least 20%, or even by at least 50%.

In some examples, deoptimizing the codon composition alters the frequency of CG dinucleotides, TA dinucleotides, or both, in a coding sequence, such as increases or decreases the frequency of CG or TA dinucleotides by at least 10%, for example increases in the number of CG or TA dinucleotides in a coding sequence by at least 10%, such as at least 20%, at least 30%, at least 40%, at least 50%, at least 60%, at least 100%, at least 200%, or even by at least 300%, or decreases in the number of CG or TA dinucleotides in a coding sequence by at least 10%, such as at least 20%, at least 30%, at least 40%, at least 50%, at least 60%, at least 70%, at least 80%, or even by at least 90%. However, the number of CG or TA dinucleotides can be altered in combination with deoptimizing one or more codons in a pathogen sequence. For example, some of the nucleotide substitutions can be made to deoptimize codons (which may or may not alter the number of CG or TA dinucleotides in the sequence), and other nucleotide substitutions can be made to alter the number of CG or TA dinucleotides in the coding sequence (which may or may result in a deoptimized codon). Altering the number of CG or TA dinucleotides in the sequence may also result in a deoptimized codon, but is not required in all instances.

For example, if the pathogen is a poliovirus or eukaryotic virus, deoptimization can be achieved by increasing the number of CG or TA dinucleotides in one or more coding sequences, for example increasing the number of CG or TA dinucleotides by at least 10%, such as at least 30%, or even by at least 300%. In another example, the pathogen is a bacterium, and deoptimization can be achieved by decreasing the number of CG or TA dinucleotides in one or more coding sequences, for example decreasing the number of CG or TA dinucleotides by at least 10%, such as at least 30%, or even by at least 50%.

In particular examples, methods of reducing the replicative fitness of a pathogen include analysis of a codon usage table for the pathogen to identify amino acids that are encoded by at least 2 different codons, (such as 2 different codons, 3 different codons, 4 different codons, or 6 different codons), and choosing the codon used least frequently (lowest codon usage frequency) of the different codons in the pathogen. The one or more low-frequency codons chosen are used to replace the appropriate one or more codons in the native sequence, for example using molecular biology methods, thereby generating a deoptimized sequence that reduces the replicative fitness of the pathogen. For example, if the pathogen uses the CCU, CCC, CCA and CCG codons to encode for Pro at 12, 19, 21 and 9% frequency respectively, the CCG codon can be used to replace at least one CCU, CCC, or CCA codon in the native pathogen sequence, thereby generating a deoptimized sequence.

In this example, the use of the CCG codon may also increase the number of CG dinucleotides in the sequence, and may also increase the G+C content of the sequence. In examples where the amino acid is encoded by only two different codons, one of the two codons can be selected and used in the deoptimized sequence if the codon usage is highly biased, such as a difference of at least 10%, at least 20%, or at least 30%. For example, if the pathogen uses the codons CAA and CAG to encode for Gln at 60% and 40% frequency respectively, the CAG codon is used to replace at least one CAA codon in the native sequence, thereby generating a deoptimized sequence. In this example, the use of the CAG codon may also increase the G+C content of the sequence.

In some examples, when choosing a low frequency codon, the codon chosen based on its ability to alter the G+C content of the deoptimized sequence or alter the frequency of CG or TA dinucleotides. For example, if the pathogen uses the CCU, CCC, CCA and CCG codons to encode for Pro at 9, 19, 21 and 12% frequency respectively, the CCG codon can be used to replace at least one CCU, CCC, or CCA codon in the native pathogen sequence, if the presence of increased G+C content or increased numbers of CG dinucleotides is desired in the deoptimized sequence. Even though CCG is not the most infrequently used codon, the use of this codon will increase the number of CG dinucleotides in the sequence and may increase the G+C content of the deoptimized sequence. In contrast, if the presence of decreased G+C content or decreased numbers of CG dinucleotides is desired in the deoptimized sequence, the CCU codon could be used to replace at least one CCG, CCC, or CCA codon in the native pathogen sequence.

In some examples, there may be two or more codons used at low frequencies that are similar in value, such as codon usages that are within 0.01-2% of each other (for example within 0.1-2%, 0.5-2% or 1-2% of each other). In this case, one can opt to not choose the codon with the lowest codon usage frequency. In some examples, the codon chosen is one that will alter the G+C content of the deoptimized sequence, such as increase or decrease the G+C content of the sequence. In other examples, the codon chosen is one that increases or decreases the frequency of a specific dinucleotide pair (such as a CG or TA dinucleotide pair) found at low frequencies in that genome (such as no more than 4%, for example no more than 3%). Such dinucleotide pairs can fall across codon boundaries, or be contained within the codon.

The codon usage table used can include codon usage data from the complete genome of the pathogen (or 2 or more genomes, for example from different strains of the pathogen), codon usage data from one or more genes (such as 1 gene, at least 2 genes, at least 3 genes, at least 5 genes, or even at least 10 genes), for example one or more genes involved in the antigenicity of the pathogen.

Specific non-limiting examples of deoptimized coding sequences for several pathogens are disclosed herein. In some examples, a deoptimized coding sequence includes a nucleic acid sequence having at least 90% sequence identity, such as at least 95% sequence identity, to any of SEQ ID NOS: 5, 8, 11, 14, 18, 21, 24, 27, 30, 33, 36, 39, 42, 45, 48, 51, 54, 55, 56, 57, 58, 67, 68, or 69. Sequences that hybridize to any of SEQ ID NOS: 5, 8, 11, 14, 18, 21, 24, 27, 30, 33, 36, 39, 42, 45, 48, 51, 54, 55, 56, 57, 58, 67, 68, or 69, for example under stringent conditions, are also disclosed. In some examples, a deoptimized coding sequence includes a nucleic acid sequence shown in any of SEQ ID NOS: 5, 8, 11, 14, 18, 21, 24, 27, 30, 33, 36, 39, 42, 45, 48, 51, 54, 55, 56, 57, 58, 67, 68, or 69.

In particular examples, more than one coding sequence in the pathogen is deoptimized, such as at least 2 coding sequences, such as at least 3, at least 4, at least 5, at least 6, at least 7, at least 8, at least 9, or even at least 10 coding sequences. Any coding sequence can be deoptimized. In one example, one of the deoptimized coding sequences encodes for a housekeeping gene. Particular examples of coding sequences that can be deoptimized in a pathogen, include, but are not limited to, sequences that encode a viral capsid, a viral spike glycoprotein (for example the gH and gE surface glycoproteins of varicella-zoster virus); glycoprotein B, glycoprotein D, glycoprotein H, and glycoprotein N of human cytomegalovirus; glycoprotein D, tegument protein host shut-off factor, ribonucleotide reductase large subunit of human herpes simplex viruses; the fusion (F) protein and glycoprotein (G) of respiratory syncytial virus; the hemagglutinin (HA) and neuraminidase (NA) glycoproteins of influenza virus; the env protein of human immunodeficiency virus type 1 (HIV-1), ArgS and TufA gene products of *Escherichia coli*, or combinations thereof.

The replicative fitness of the pathogen can be reduced by any amount sufficient to attenuate the pathogen. In some examples, the replicative fitness of the deoptimized pathogen is reduced by at least 20%, such as at least 30%, at least 40%, at least 48%, at least 50%, at least 75%, at least 80%, at least 90%, at least 95%, or even at least 97%, as compared to replicative fitness of a pathogen (of the same species and strain) having a coding sequence with an optimized codon composition.

Any pathogen can be attenuated using the disclosed methods. Particular examples include, but are not limited to, viruses (such as positive-strand RNA viruses, negative-strand RNA viruses, DNA viruses, and retroviruses), bacteria, fungi, and protozoa.

In one specific example, the pathogen is a poliovirus. For example, when the natural codons of the Sabin type 2 (Sabin 2) OPV strain (Sabin and Boulger. *J. Biol. Stand.* 1:115-8; 1973; Toyoda et al., *J. Mol. Biol.* 174:561-85, 1984) were replaced with synonymous unpreferred codons in sequences encoding capsid proteins, virus plaque size and yield in cell culture decreased in proportion to the number of unpreferred codons incorporated into the capsid sequences. The altered codon composition was largely conserved during 25 serial passages in HeLa cells. Fitness for replication in HeLa cells of both the unmodified Sabin 2 and modified constructs increased with higher passage; however, the relative fitness of the modified constructs remained lower than that of the unmodified construct.

Attenuated pathogens produced by the methods disclosed herein are also provided. In one example, immunogenic compositions include an attenuated pathogen produced by the disclosed methods. Such immunogenic compositions can include other agents, such as an adjuvant, a pharmaceutically acceptable carrier, or combinations thereof.

Methods are disclosed for eliciting an immune response against a pathogen in a subject, using the disclosed attenuated pathogens. In one example, the method includes administering an immunologically effective amount of the disclosed attenuated pathogens to a subject, thereby eliciting an immune response in the subject. In particular examples, the disclosed attenuated pathogens are present in an immunogenic composition which is administered to a subject. Subjects include human and veterinary subjects, such as cats, dogs, cattle, sheep, pigs and horses.

The foregoing and other features and advantages of the disclosure will become more apparent from the following detailed description of a several embodiments.

BRIEF DESCRIPTION OF THE FIGURES

FIGS. 1B-1D is a sequence showing original S2R9 Sabin 2 triplets (ABCD, SEQ ID NO: 3) above the codon-replacement residues; the deduced amino acids for both constructs are indicated below the triplets (SEQ ID NO: 4). The fully replaced sequence (abcd, SEQ ID NO: 5) is referred to S2R23.

FIG. 3A is a graph showing mean plaque area in HeLa cells versus the number of nucleotide substitutions in the capsid region. The coefficient of determination ($R^2$) for the regression line was 0.88.

FIG. 3B is a graph showing virus yields (12-hour postinfection) of a single-step growth curve versus the number of nucleotide substitutions in the capsid region. The coefficient of determination ($R^2$) for the regression line was 0.94.

FIG. 3C is a digital image showing plaque phenotypes at 35° C. in HeLa cells.

FIG. 8A is a graph showing mean plaque areas of evolving viruses using a plaque assay of HeLa cells after 60 hours incubation at 35° C.

FIG. 8B is a graph showing virus titers determined by plaque assay of HeLa cells at 35° C. on every fifth passage.

FIGS. 9A-E show an original MEF1 capsid sequence (SEQ ID NO: 6; GenBank Accession No. AY082677) above the codon-replacement residues for an MEF1 de-optimized capsid sequence (SEQ ID NO: 8) (only replaced nucleotides are indicated); the deduced amino acids for both the constructs are indicated below the triplets (SEQ ID NO: 7).

FIGS. 10A-10B show an original FMDV capsid sequence (SEQ ID NO: 9; GenBank Accession No. AJ539141) above the codon-replacement residues for an FMDV de-optimized capsid sequence (SEQ ID NO: 11) (only replaced nucleotides are indicated); the deduced amino acids are indicated below the triplets (SEQ ID NO: 10).

FIGS. 11A-11C show an original SARS spike glycoprotein sequence (SEQ ID NO: 12; GenBank Accession No. AY278741) above the codon-replacement residues for a de-optimized SARS spike glycoprotein sequence (SEQ ID NO: 14) (only replaced nucleotides are indicated); the deduced amino acids are indicated below the triplets (SEQ ID NO: 13).

FIGS. 12A-12G shows an original rubella sequence (SEQ ID NO: 15; GenBank Accession No. L78917) above the codon-replacement residues for a de-optimized rubella sequence (SEQ ID NO: 18) (only replaced nucleotides are indicated); the deduced amino acids are indicated below the triplets (SEQ ID NOS: 16 and 17).

FIGS. 13A-B show an original VZV gH sequence (GenBank Accession No. AB097932, SEQ ID NO: 19) above the codon-replacement residues for a de-optimized VZV gH sequence (SEQ ID NO: 21) (only replaced nucleotides are indicated); the deduced amino acids are indicated below the triplets (SEQ ID NO: 20).

FIGS. 14A-B show an original VZV gE sequence (GenBank Accession No. AB097933, SEQ ID NO: 22) above the codon-replacement residues for a de-optimized VZV gE sequence (SEQ ID NO: 24) (only replaced nucleotides are indicated); the deduced amino acids are indicated below the triplets (SEQ ID NO: 23).

FIGS. 15A-B show an original measles F sequence (SEQ ID NO: 25; GenBank Accession No. AF266287) above the codon-replacement residues for a de-optimized measles F sequence (SEQ ID NO: 27) (only replaced nucleotides are indicated); the deduced amino acids are indicated below the triplets (SEQ ID NO: 26).

FIGS. 16A-B show an original measles hemagglutinin (H) sequence (SEQ ID NO: 28; GenBank Accession No. AF266287) above the codon-replacement residues for a de-optimized measles H sequence (SEQ ID NO: 30) (only replaced nucleotides are indicated); the deduced amino acids are indicated below the triplets (SEQ ID NO: 29).

FIGS. 17A-B show an original RSV F sequence (SEQ ID NO: 31; GenBank Accession No. U63644) above the codon-replacement residues for a de-optimized RSV F sequence (SEQ ID NO: 33) (only replaced nucleotides are indicated); the deduced amino acids are indicated below the triplets (SEQ ID NO: 32).

FIG. 18 shows an original RSV G sequence (SEQ ID NO: 34; GenBank Accession No. U63644) above the codon-replacement residues for a de-optimized RSV G sequence (SEQ ID NO: 36) (only replaced nucleotides are indicated); the deduced amino acids are indicated below the triplets (SEQ ID NO: 35).

FIG. 19 shows an original influenza HA sequence (SEQ ID NO: 37) above the codon-replacement residues for a de-optimized influenza HA sequence (SEQ ID NO: 39) (only replaced nucleotides are indicated); the deduced amino acids are indicated below the triplets (SEQ ID NO: 38).

FIG. 20 shows an original influenza NA sequence (SEQ ID NO: 40) above the codon-replacement residues for a de-optimized influenza NA sequence (SEQ ID NO: 42) (only replaced nucleotides are indicated); the deduced amino acids are indicated below the triplets (SEQ ID NO: 41).

FIGS. 21A-21B show an original HIV-1 env sequence (SEQ ID NO: 43; GenBank Accession No. AF110967) above the codon-replacement residues for a de-optimized HIV-1 env sequence (SEQ ID NO: 45) (only replaced nucleotides are indicated); the deduced amino acids are indicated below the triplets (SEQ ID NO: 44).

FIGS. 22A-22B show an original *E. coli* ArgS sequence (SEQ ID NO: 46; GenBank Accession No. U0096) above the codon-replacement residues for a de-optimized *E. coli* ArgS sequence (SEQ ID NO: 48) (only replaced nucleotides are indicated); the deduced amino acids are indicated below the triplets (SEQ ID NO: 47).

FIG. 23 shows an original *E. coli* TufA sequence (SEQ ID NO: 49; GenBank Accession No. J01690) above the codon-replacement residues for a de-optimized *E. coli* TufA sequence (SEQ ID NO: 51) (only replaced nucleotides are indicated); the deduced amino acids are indicated below the triplets (SEQ ID NO: 50).

FIGS. 24A-24M show exemplary codon usage tables for various pathogens.

FIG. 25 shows a Sabin 2 virus cassette d (VP1 region) sequence that has been altered by reducing the number of CG dinucleotides. The original sequence (nucleotides 1975-2664 of SEQ ID NO: 3) is shown above the codon-replacement residues for an altered Sabin 2 cassette d (VP1 region) sequence (SEQ ID NO: 65) (only replaced nucleotides are indicated); the deduced amino acids are indicated below the triplets (amino acids 623-852 of SEQ ID NO: 4).

FIG. 26 shows a Sabin 2 virus cassette d (VP1 region) sequence that has been altered by decreasing the number of CG and TA dinucleotides. The original sequence (nucleotides 1975-2664 of SEQ ID NO: 3) is shown above the codon-replacement residues for an altered Sabin 2 cassette d (VP1 region) sequence (SEQ ID NO: 66) (only replaced nucleotides are indicated); the deduced amino acids are indicated below the triplets (amino acids 623-852 of SEQ ID NO: 4).

FIG. 27 shows a Sabin 2 virus cassette d (VP1 region) sequence that has been altered by increasing the number of CG dinucleotides. The original sequence (nucleotides 1975-2664 of SEQ ID NO: 3) is shown above the codon-replacement residues for a de-optimized Sabin 2 cassette d (VP1 region) sequence (SEQ ID NO: 67) (only replaced nucleotides are indicated); the deduced amino acids are indicated below the triplets (amino acids 623-852 of SEQ ID NO: 4). Original CG dinucleotides retained after codon changes are underlined.

FIG. 28 shows a Sabin 2 virus cassette d (VP1 region) sequence that has been altered by increasing the number of CG and TA dinucleotides. The original sequence (nucleotides 1975-2664 of SEQ ID NO: 3) is shown above the codon-replacement residues for a de-optimized Sabin 2 cassette d (VP1 region) sequence (SEQ ID NO: 68) (only replaced nucleotides are indicated); the deduced amino acids are indicated below the triplets (amino acids 623-852 of SEQ ID NO: 4). Original CG, TA dinucleotides retained after codon changes are underlined.

FIG. 29 shows a Sabin 2 virus cassette d (VP1 region) sequence having maximum codon deoptimization. The original sequence (nucleotides 1975-2664 of SEQ ID NO: 3) is shown above the codon-replacement residues for the de-optimized Sabin 2 cassette d (VP1 region) sequence (SEQ ID NO: 69) (only replaced nucleotides are indicated); the deduced amino acids are indicated below the triplets (amino acids 623-852 of SEQ ID NO: 4). Original CG dinucleotides retained after codon changes are underlined.

FIG. 30 shows a Sabin 2 virus cassette d (VP1 region) sequence that has MEF1 codons for Sabin 2 amino acids. The original sequence (nucleotides 1975-2664 of SEQ ID NO: 3) is shown above the codon-replacement residues; the deduced amino acids are indicated below the triplets (amino acids 623-852 of SEQ ID NO: 4). The altered Sabin 2 cassette d (VP1 region) sequence (SEQ ID NO: 70) is shown below the original sequence (only replaced nucleotides are indicated). The amino acids that differ between Sabin 2 and MEF-1 are underlined.

SEQUENCE LISTING

Figure 1A:
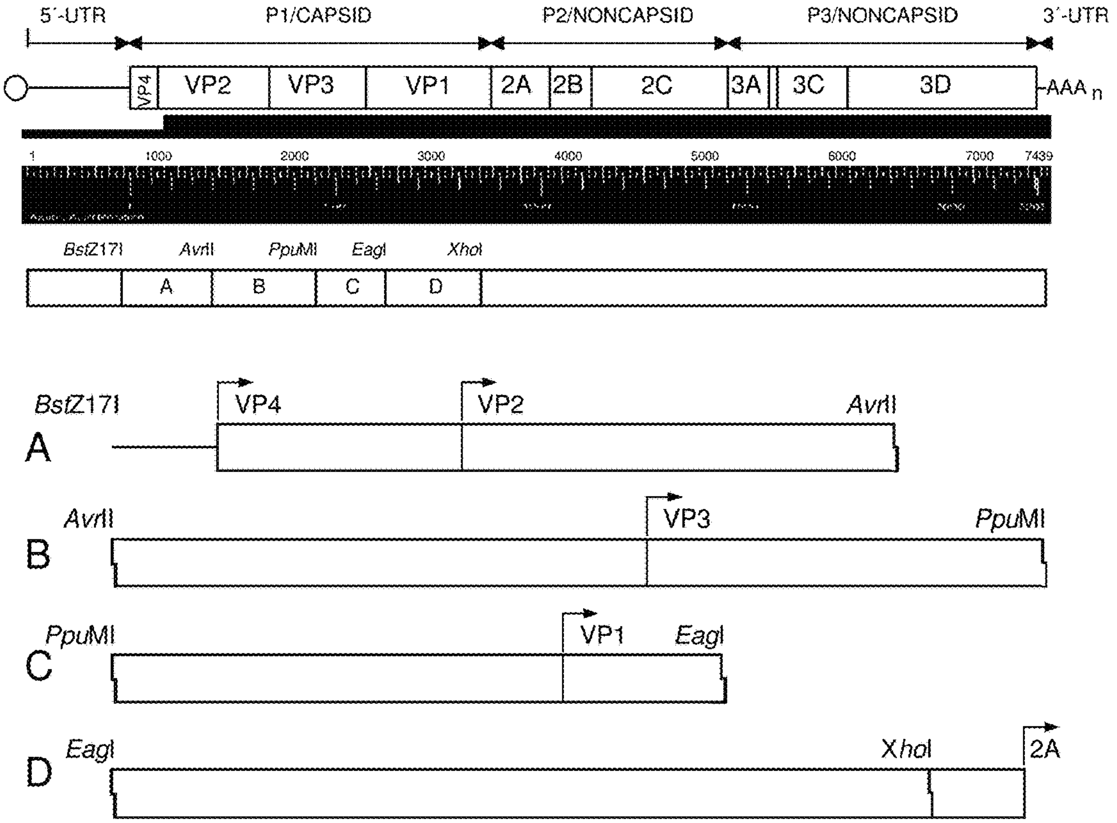
FIG. 1A is a schematic drawing showing the locations of the codon replacement cassettes A-D in the infectious Sabin 2 (S2R9) cDNA clone. The restriction sites used for construction of the codon replacement constructs are indicated at the appropriate positions, in the context of the mature viral proteins.

The nucleic acid and amino acid sequences listed in the accompanying sequence listing are shown using standard letter abbreviations for nucleotide bases, and three-letter code for amino acids. Only one strand of each nucleic acid sequence is shown, but the complementary strand is understood as included by any reference to the displayed strand. The Sequence Listing is submitted as an ASCII text file in the form of the file named Sequence_Listing.txt, which was created on Mar. 5, 2020, and is 592 kilobytes, which is incorporated by reference herein.

SEQ ID NO: 1 is a primer sequence used to reverse transcribe poliovirus cDNA.

SEQ ID NO: 2 is a primer sequence used to long PCR amplify poliovirus cDNA.

SEQ ID NO: 3 is a capsid nucleic acid coding sequence of Sabin 2 (construct S2R9) poliovirus.

SEQ ID NO: 4 is a protein sequence encoded by SEQ ID NO: 3.

SEQ ID NO: 5 is a Sabin 2 codon-deoptimized nucleic acid sequence.

SEQ ID NO: 6 is a capsid nucleic acid coding sequence of MEF1 poliovirus.

SEQ ID NO: 7 is a protein sequence encoded by SEQ ID NO: 6.

SEQ ID NO: 8 is an MEF1 codon-deoptimized nucleic acid sequence.

SEQ ID NO: 9 is a capsid nucleic acid coding sequence of FMDV.

SEQ ID NO: 10 is a protein sequence encoded by SEQ ID NO: 9.

SEQ ID NO: 11 is an FMDV codon-deoptimized capsid nucleic acid sequence.

SEQ ID NO: 12 is a spike glycoprotein nucleic acid coding sequence of SARS coronavirus.

SEQ ID NO: 13 is a protein sequence encoded by SEQ ID NO: 12.

SEQ ID NO: 14 is a SARS coronavirus codon-deoptimized spike glycoprotein nucleic acid sequence.

SEQ ID NO: 15 is a nucleic acid coding sequence of rubella virus.

SEQ ID NOS: 16 and 17 are protein sequences encoded by SEQ ID NO: 15.

SEQ ID NO: 18 is a rubella codon-deoptimized nucleic acid sequence.

SEQ ID NO: 19 is a gH nucleic acid coding sequence of VZV.

SEQ ID NO: 20 is a protein sequence encoded by SEQ ID NO: 18.

SEQ ID NO: 21 is a VZV codon-deoptimized gH nucleic acid sequence.

SEQ ID NO: 22 is a gE nucleic acid coding sequence of VZV.

SEQ ID NO: 23 is a protein sequence encoded by SEQ ID NO: 21.

SEQ ID NO: 24 is a VZV codon-deoptimized gE nucleic acid sequence.

SEQ ID NO: 25 is an F nucleic acid coding sequence of measles virus.

SEQ ID NO: 26 is a protein sequence encoded by SEQ ID NO: 24.

SEQ ID NO: 27 is a measles virus codon-deoptimized F nucleic acid sequence.

SEQ ID NO: 28 is a hemagglutinin (H) nucleic acid coding sequence of measles virus.

SEQ ID NO: 29 is a protein sequence encoded by SEQ ID NO: 27.

SEQ ID NO: 30 is a measles codon-deoptimized H nucleic acid sequence.

SEQ ID NO: 31 is an F nucleic acid coding sequence of RSV.

SEQ ID NO: 32 is a protein sequence encoded by SEQ ID NO: 30.

SEQ ID NO: 33 is a RSV codon-deoptimized F nucleic acid sequence.

SEQ ID NO: 34 is a G nucleic acid coding sequence of RSV.

SEQ ID NO: 35 is a protein sequence encoded by SEQ ID NO: 33.

SEQ ID NO: 36 is a RSV codon-deoptimized G nucleic acid sequence.

SEQ ID NO: 37 is a HA nucleic acid coding sequence of influenza virus.

SEQ ID NO: 38 is a protein sequence encoded by SEQ ID NO: 36.

SEQ ID NO: 39 is an influenza virus codon-deoptimized HA nucleic acid sequence.

SEQ ID NO: 40 is a NA nucleic acid coding sequence of influenza virus.

SEQ ID NO: 41 is a protein sequence encoded by SEQ ID NO: 39.

SEQ ID NO: 42 is an influenza codon-deoptimized NA nucleic acid sequence.

SEQ ID NO: 43 is an env nucleic acid coding sequence of HIV-1.

SEQ ID NO: 44 is a protein sequence encoded by SEQ ID NO: 42.

SEQ ID NO: 45 is an HIV-1 codon-deoptimized env nucleic acid sequence.

SEQ ID NO: 46 is an ArgS nucleic acid coding sequence of *E. coli*.

SEQ ID NO: 47 is a protein sequence encoded by SEQ ID NO: 45.

SEQ ID NO: 48 is an *E. coli* codon-deoptimized ArgS nucleic acid sequence.

SEQ ID NO: 49 is an TufA nucleic acid coding sequence of *E. coli*.

SEQ ID NO: 50 is a protein sequence encoded by SEQ ID NO: 48.

SEQ ID NO: 51 is an *E. coli* codon-deoptimized TufA nucleic acid sequence.

SEQ ID NO: 52 is a nucleic acid sequence showing the sequence of MEF1R1 or uncloned.

SEQ ID NO: 53 is a nucleic acid sequence showing the sequence of MEF1R2.

SEQ ID NO: 54 is a nucleic acid sequence showing the sequence of MEF1R5.

SEQ ID NO: 55 is a nucleic acid sequence showing the sequence of MEF1R6.

SEQ ID NO: 56 is a nucleic acid sequence showing the sequence of MEF1R7.

SEQ ID NO: 57 is a nucleic acid sequence showing the sequence of MEF1R8.

SEQ ID NO: 58 is a nucleic acid sequence showing the sequence of MEF1R9.

SEQ ID NOS: 59-60 are primer sequences used to amplify the $3D^{pol}$ region of Sabin 2.

SEQ ID NO: 61 is a TaqMan probe used to detect the yield of amplicon generated using SEQ ID NOS: 59 and 60.

SEQ ID NOS: 62-63 are primer sequences used to amplify the $3D^{pol}$ region of MEF1.

SEQ ID NO: 64 is a TaqMan probe used to detect the yield of amplicon generated using SEQ ID NOS: 62 and 63.

SEQ ID NO: 65 is a Sabin 2 cassette d (VP1 region) sequence with a reduced number of CG dinucleotides.

SEQ ID NO: 66 is a Sabin 2 cassette d (VP1 region) sequence with a reduced number of CG and TA dinucleotides.

SEQ ID NO: 67 is a Sabin 2 cassette d (VP1 region) sequence with an increased number of CG dinucleotides.

SEQ ID NO: 68 is a Sabin 2 cassette d (VP1 region) sequence with an increased number of CG and TA dinucleotides.

SEQ ID NO: 69 is an exemplary deoptimized Sabin 2 cassette d (VP1 region) sequence.

SEQ ID NO: 70 is a Sabin 2 cassette d (VP1 region) sequence that uses MEF1 codons for Sabin 2 amino acids.

DETAILED DESCRIPTION OF SEVERAL EMBODIMENTS

Abbreviations and Terms

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. For example, the term "comprising a nucleic acid molecule" includes single or plural nucleic acid molecules and is considered equivalent to the phrase "comprising at least one nucleic acid molecule." The term "or" refers to a single element of stated alternative elements or a combination of two or more elements, unless the context clearly indicates otherwise. As used herein, "comprises" means "includes." Thus, "comprising an alteration in the number of TA or CG dinucleotides," means "including an alteration in the number of TA dinucleotides, the number of CG dinucleotides, or the number of CG and TA dinucleotides," without excluding additional elements.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting.

OPV: oral poliovirus vaccine

PV: poliovirus

VAPP: vaccine-associated paralytic poliomyelitis

VDPV: vaccine-derived poliovirus

Adjuvant: A compound, composition, or substance that when used in combination with an immunogenic agent augments or otherwise alters or modifies a resultant immune response. In some examples, an adjuvant increases the titer of antibodies induced in a subject by the immunogenic agent. In another example, if the antigenic agent is a multivalent antigenic agent, an adjuvant alters the particular epitopic sequences that are specifically bound by antibodies induced in a subject.

Exemplary adjuvants include, but are not limited to, Freund's Incomplete Adjuvant (IFA), Freund's complete adjuvant, B30-MDP, LA-15-PH, montanide, saponin, aluminum salts such as aluminum hydroxide (Amphogel, Wyeth Laboratories, Madison, N.J.), alum, lipids, keyhole limpet protein, hemocyanin, the MF59 microemulsion, a mycobacterial antigen, vitamin E, non-ionic block polymers, muramyl dipeptides, polyanions, amphipatic substances, ISCOMs (immune stimulating complexes, such as those disclosed in European Patent EP 109942), vegetable oil, Carbopol, aluminium oxide, oil-emulsions (such as Bayol F or Marcol 52), *E. coli* heat-labile toxin (LT), Cholera toxin (CT), and combinations thereof.

In one example, an adjuvant includes a DNA motif that stimulates immune activation, for example the innate immune response or the adaptive immune response by T-cells, B-cells, monocytes, dendritic cells, and natural killer cells. Specific, non-limiting examples of a DNA motif that stimulates immune activation include CG oligodeoxynucleotides, as described in U.S. Pat. Nos. 6,194,388; 6,207,646; 6,214,806; 6,218,371; 6,239,116; 6,339,068; 6,406,705; and 6,429,199, and IL-2 or other immunomodulators.

Administration: To provide or give a subject an agent, such as an immunogenic composition disclosed herein, by any effective route. Exemplary routes of administration include, but are not limited to, oral, injection (such as subcutaneous, intramuscular, intradermal, intraperitoneal, and intravenous), sublingual, rectal, transdermal, intranasal, vaginal, intraocular, and inhalation routes.

Agent: Any substance, including, but not limited to, a chemical compound, molecule, peptidomimetic, pathogen, or protein.

Antibody: A molecule including an antigen binding site which specifically binds (immunoreacts with) an antigen. Examples include polyclonal antibodies, monoclonal antibodies, humanized monoclonal antibodies, or immunologically effective portions thereof.

Includes immunoglobulin molecules and immunologically active portions thereof.

Immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

Antigen: A compound, composition, or substance that can stimulate the production of antibodies or a T-cell response in an animal, including compositions that are injected or absorbed into an animal. An antigen reacts with the products of specific humoral or cellular immunity, including those induced by heterologous immunogens. The term "antigen" includes all related antigenic epitopes. In one example, an antigen is an attenuated pathogen.

Attenuated pathogen: A pathogen with a decreased or weakened ability to produce disease while retaining the ability to stimulate an immune response like that of the natural pathogen. In one example, a live pathogen is attenuated by deoptimizing one or more codons in one or more genes, such as an immunogenic surface antigen or a housekeeping gene. In another example, a pathogen is attenuated by selecting for avirulent variants under certain growth conditions (for example see Sabin and Boulger. *J. Biol. Stand.* 1:115-8; 1973; Sutter et al., 2003. Poliovirus vaccine—live, p. 651-705. In S. A. Plotkin and W. A. Orenstein (ed.), Vaccines, Fourth ed. W.B. Saunders Company, Philadelphia).

Codons can be deoptimized, for example, by manipulating the nucleic acid sequence using molecular biology methods. Attenuated pathogens, such as an attenuated virus or bacterium, can be used in an immune composition to stimulate an immune response in a subject. For example, attenuated pathogens can be used in an attenuated vaccine to produce an immune response without causing the severe effects of the disease. Particular examples of attenuated vaccines include, but are not limited to, measles, mumps, rubella, polio, typhoid, yellow fever, and varicella vaccines.

cDNA (complementary DNA): A piece of DNA lacking internal, non-coding segments (introns) and regulatory sequences that determine transcription. cDNA can be synthesized in the laboratory by reverse transcription from messenger RNA or viral extracted from cells or purified viruses.

Cellular immunity: An immune response mediated by cells or the products they produce, such as cytokines, rather than by an antibody. It includes, but is not limited to, delayed type hypersensitivity and cytotoxic T cells.

CG dinucleotide: A cytosine nucleotide immediately followed by a guanine in a nucleic acid sequence. Similarly, a TA (or UA) dinucleotide is a thymine (or uracil) nucleotide immediately followed by a adenine in a nucleic acid sequence. For example, the sequence G<u>TA</u>GT<u>CG</u>ACT (nucleotides 1-10 of SEQ ID NO: 2) has one CG dinucleotide and one TA dinucleotide (underlined).

Codon: A specific sequence of three adjacent nucleotide bases on a strand of DNA or RNA that provides genetic code information for a particular amino acid or a termination signal.

Conservative substitution: One or more amino acid substitutions for amino acid residues having similar biochemical properties. Typically, conservative substitutions have little to no impact on the activity of a resulting polypeptide. For example, a conservative substitution is an amino acid substitution in an antigenic epitope of a pathogenic peptide that does not substantially affect the ability of an antibody that specifically binds to the unaltered epitope to specifically bind the epitope including the conservative substitution. Thus, in some examples, a conservative variant of an epitope is also a functional variant of the epitope.

Methods which can be used to determine the amount of recognition by a variant epitope are disclosed herein. In addition, an alanine scan can be used to identify which amino acid residues in a pathogenic epitope can tolerate an amino acid substitution. In one example, recognition is not decreased by more than 25%, for example not more than 20%, for example not more than 10%, when an alanine, or other conservative amino acid (such as those listed below), is substituted for one or more native amino acids. Similarly, an ELISA assay can be used that compares a level of specific binding of an antibody that specifically binds a particular antigenic peptide to a level of specific binding of the antibody to a corresponding peptide with the substitution(s) to determine if the substitution(s) does not substantially affect specific binding of the substituted peptide to the antibody.

In one example, one, two, three, five, or ten conservative substitutions are included in the peptide. In another example, 1-10 conservative substitutions are included in the peptide. In a further embodiment, at least 2 conservative substitutions are included in the peptide. A peptide can be produced to contain one or more conservative substitutions by manipulating the nucleotide sequence that encodes that polypeptide using, for example, standard procedures such as site-directed mutagenesis or PCR. Alternatively, a polypeptide can be produced to contain one or more conservative substitutions by using standard peptide synthesis methods.

Substitutional variants are those in which at least one residue in the amino acid sequence has been removed and a different residue inserted in its place. Conservative substitution tables providing functionally similar amino acids are well known in the art. Examples of amino acids which may be substituted for an original amino acid in a protein and which are regarded as conservative substitutions include: Ser for Ala; Lys for Arg; Gin or His for Asn; Glu for Asp; Ser for Cys; Asn for Gln; Asp for Glu; Pro for Gly; Asn or Gin for His; Leu or Val for Ile; Ile or Val for Leu; Arg or Gln for Lys; Leu or Ile for Met; Met, Leu or Tyr for Phe; Thr for Ser; Ser for Thr; Tyr for Trp; Trp or Phe for Tyr; and Ile or Leu for Val.

Further information about conservative substitutions can be found, among other sources, Ben-Bassat et al., (*J. Bacteriol.* 169:751-7, 1987), O'Regan et al., (*Gene* 77:237-51, 1989), Sahin-Toth et al., (*Protein Sci.* 3:240-7, 1994), Hochuli et al., (*Bio/Technology* 6:1321-5, 1988) and in standard textbooks of genetics and molecular biology.

DNA (deoxyribonucleic acid): A long chain polymer which includes the genetic material of most living organisms (many viruses have genomes containing only ribonucleic acid, RNA). The repeating units in DNA polymers are four different nucleotides, each of which includes one of the four bases, adenine, guanine, cytosine and thymine bound to a deoxyribose sugar to which a phosphate group is attached. Triplets of nucleotides, referred to as codons, in DNA molecules code for amino acid in a polypeptide. The term codon is also used for the corresponding (and complementary) sequences of three nucleotides in the mRNA into which the DNA sequence is transcribed.

Degenerate variant: A nucleic acid sequence encoding a peptide that includes a sequence that is degenerate as a result of the genetic code. There are 20 natural amino acids, most of which are specified by more than one of the 61 codons of the "universal" genetic code used by most cells and viruses. For example, the amino acid Ala is encoded by four codon triplets: GCU, GCG, GCA, and GCC. Therefore, all degenerate nucleotide sequences are included as long as the amino acid sequence of the peptide encoded by the nucleotide sequence is unchanged.

Deoptimization of a codon: To replace a preferred codon in a nucleic acid sequence with a synonymous codon (one that codes for the same amino acid) less frequently used (unpreferred) in the organism. Each organism has a particular codon usage bias for each amino acid, which can be determined from publicly available codon usage tables (for example see Nakamura et al., *Nucleic Acids Res.* 28:292, 2000 and references cited therein; Sharp et al., *Nucleic Acids Res.* 16:8207-11, 1988; Chou and Zhang, *AIDS Res. Hum. Retroviruses*. December; 8(12):1967-76, 1992; West and Iglewski et al., *Nucleic Acids Res.* 16:9323-35, 1988, Rothberg and Wimmer, *Nucleic Acids Res.* 9:6221-9, 1981; Jenkins et al., *J. Mol. Evol.* 52:383-90, 2001; and Watterson, *Mol. Biol. Evol.* 9:666-77, 1992; all herein incorporated by reference). In addition, codon usage tables are available for several organisms on the internet at GenBank's website.

For example, if an organism has a codon usage for the amino acid Val of 15% for GUU, 10% for GUC, 50% for GUA, and 25% for GUG, the "least frequently used codon" is GUC. Therefore, to deoptimize a Val codon, the codon GUC could be used to replace one or more of the codons GUU, GUA, or GUG in a native sequence. Similarly, the codon GUU is a "less frequently used codon" than the GUA codon, and therefore, GUU could be used to replace GUA.

In some examples, the choice of the less frequently used codon is made depending on whether the codon will alter the G+C content, the number of CG dinucleotides, the number of TA(UA) dinucleotides, or combinations thereof, in the deoptimized sequence. For example, if an organism has a codon usage for the amino acid Val of 50% for GUU, 10% for GUC, 15% for GUA, and 25% for GUG, the codon GUA is a "less frequently used codon" than the GUU codon, and could be used to replace GUU, for example if it was desired to increase the number of UA (TA) dinucleotides in the deoptimized sequence. Similarly, the codon GUG is a "less frequently used codon" than the GUU codon, and could be used to replace GUU, for example if it was desired to increase the G+C content of the deoptimized sequence.

Deoptimized pathogen: A pathogen having a nucleic acid coding sequence with one or more deoptimized codons, which decrease the replicative fitness of the pathogen. In some examples, refers to the isolated deoptimized nucleic acid sequence itself, independent of the pathogenic organism.

Epitope: An antigenic determinant. Chemical groups or peptide sequences on a molecule that are antigenic, that is, that elicit a specific immune response. An antibody binds a particular antigenic epitope, or a T-cell reacts with a particular antigenic epitope bound to a specific MHC molecule. In some examples, an epitope has a minimum sequence of 6-8 amino acids, and a maximum sequence of about 100 amino acids, for example, about 50, 25 or 18 amino acids in length.

Functional variant: Sequence alterations in a peptide, wherein the peptide with the sequence alterations retains a function or property (such as immunogenicity) of the unaltered peptide. For example, a functional variant of an epitope can specifically bind an antibody that binds an unaltered form of the epitope or stimulates T-cell proliferation to an extent that is substantially the same as the unaltered form of the epitope. Sequence alterations that provide functional variants can include, but are not limited to, conservative substitutions, deletions, mutations, frameshifts, and insertions. Assays for determining antibody binding and T-cell reactivity are well known in the art.

Screens for immunogenicity can be performed using well known methods such as those described in Harlow and Lane, *Antibodies: A Laboratory Manual*, Cold Spring Harbor Laboratory, 1988, or in Paul, *Fundamental Immunology*, 3rd ed., 243-247 (Raven Press, 1993) and references cited therein. For example, a peptide can be immobilized on a solid support and contacted with subject sera to allow binding of antibodies within the sera to the immobilized polypeptide. Unbound sera may then be removed and bound antibodies detected using, for example, $^{125}$I-labeled Protein A. The ability of a functional variant to react with antigen-specific antisera may be unchanged relative to original epitope, or may be enhanced or diminished by less than 30%, for example, less than 20%, such as less than 10%, relative to the unaltered epitope.

G+C content: The amount of guanine (G) and cytosine (C) in a nucleic acid sequence (such as a pathogen coding sequence). In particular examples, the amount can be expressed in mole fraction or percentage of total number of bases in the sequence. For example, the sequence GTAGTCGACT (nucleotides 1-10 of SEQ ID NO: 2) would be said to have a G+C content of 50% (5 of the 10 bases are guanine and cytosine).

Humoral immunity: Immunity that can be transferred with immune serum from one subject to another. Typically, humoral immunity refers to immunity resulting from the introduction of specific antibodies or stimulation of the production of specific antibodies, for example by administration of one or more of the pathogens with decreased replicative fitness disclosed herein.

Hybridization: The binding of a nucleic acid molecule to another nucleic acid molecule, for example the binding of a single-stranded DNA or RNA to another nucleic acid, thereby forming a duplex molecule. The ability of one nucleic acid molecule to bind to another nucleic acid molecule can depend upon the complementarity between the nucleotide sequences of two nucleic acid molecules, and the stringency of the hybridization conditions.

Methods of performing hybridization are known in the art (such as those described in sections 7.39-7.52 of Sambrook et al., (1989) Molecular Cloning, second edition, Cold Spring Harbor Laboratory, Plainview, N.Y.). For example, Southern or Northern analysis can be used to determine if one nucleic acid sequence hybridizes to another nucleic acid sequence.

Deoptimized nucleic acid molecules are disclosed herein, such as SEQ ID NOs: 5, 8, 11, 14, 18, 21, 24, 27, 30, 33, 36, 39, 42, 45, 48, 51, 54, 55, 56, 57, 58, 67, 68, and 69. However, the present disclosure encompasses other deoptimized nucleic acid molecules that can hybridize to any of SEQ ID NOs: 5, 8, 11, 14, 18, 21, 24, 27, 30, 33, 36, 39, 42, 45, 48, 51, 54, 55, 56, 57, 58, 67, 68, or 69, under moderate or high stringent conditions. In some examples, sequences that can hybridize to any of SEQ ID NOs: 5, 8, 11, 14, 18, 21, 24, 27, 30, 33, 36, 39, 42, 45, 48, 51, 54, 55, 56, 57, 58, 67, 68, or 69 are at least 100 nucleotides in length (such as at least 500, at least 750, at least 1000, at least 2500, or at least 5000 nucleotides in length) and hybridize, under moderate or high hybridization conditions, to the sense or antisense strand of any of SEQ ID NOs: 5, 8, 11, 14, 18, 21, 24, 27, 30, 33, 36, 39, 42, 45, 48, 51, 54, 55, 56, 57, 58, 67, 68, or 69.

Moderately stringent hybridization conditions are when the hybridization is performed at about 42° C. in a hybridization solution containing 25 mM $KPO_4$ (pH 7.4), 5×SSC, 5×Denhart's solution, 50 μg/mL denatured, sonicated salmon sperm DNA, 50% formamide, 10% Dextran sulfate, and 1-15 ng/mL probe (about $5\times10^7$ cpm/μg), while the washes are performed at about 50° C. with a wash solution containing 2×SSC and 0.1% sodium dodecyl sulfate.

Highly stringent hybridization conditions are when the hybridization is performed at about 42° C. in a hybridization solution containing 25 mM $KPO_4$ (pH 7.4), 5×SSC, 5×Denhart's solution, 50 μg/mL denatured, sonicated salmon sperm DNA, 50% formamide, 10% Dextran sulfate, and 1-15 ng/mL probe (about $5\times10^7$ cpm/μg), while the washes are performed at about 65° C. with a wash solution containing 0.2×SSC and 0.1% sodium dodecyl sulfate.

Immune response: A response of a cell of the immune system, such as a B-cell, T-cell, macrophage, monocyte, or polymorphonucleocyte, to an immunogenic agent (such as the disclosed pathogens having decreased replicative fitness or sequences therefrom) in a subject. An immune response can include any cell of the body involved in a host defense response, such as an epithelial cell that secretes interferon or a cytokine. An immune response includes, but is not limited to, an innate immune response or inflammation.

The response can be specific for a particular antigen (an "antigen-specific response"). In a particular example, an immune response is a T cell response, such as a CD4+ response or a CD8+ response. In another example, the response is a B cell response, and results in the production of specific antibodies to the immunogenic agent.

In some examples, such an immune response provides protection for the subject from the immunogenic agent or the source of the immunogenic agent. For example, the response can protect a subject, such as a human or veterinary subject, from infection by a pathogen, or interfere with the progression of an infection by a pathogen. An immune response can be active and involve stimulation of the subject's immune system, or be a response that results from passively acquired immunity.

Immunity: The state of being able to mount a protective response upon exposure to an immunogenic agent (such as the disclosed pathogens having decreased replicative fitness or sequences therefrom). Protective responses can be antibody-mediated or immune cell-mediated, and can be directed toward a particular pathogen. Immunity can be acquired actively (such as by exposure to an immunogenic agent, either naturally or in a pharmaceutical composition) or passively (such as by administration of antibodies).

Immunogen: An agent (such as a compound, composition, or substance) that can stimulate or elicit an immune response by a subject's immune system, such as stimulating the production of antibodies or a T-cell response in a subject. Immunogenic agents include, but are not limited to, pathogens (such as the disclosed pathogens having decreased replicative fitness or sequences therefrom) and their corresponding proteins. One specific example of an immunogenic composition is a vaccine.

Immunogenic carrier: An immunogenic macromolecule to which an antigenic molecule (such as a pathogen with decreased replicative fitness) is bound. When bound to a carrier, the bound molecule becomes more immunogenic, such as an increase of at least 5%, at least 10%, at least 20%, or even at least 50%. Carriers can be used to increase the immunogenicity of the bound molecule or to elicit antibodies against the carrier which are diagnostically, analytically, or therapeutically beneficial. Covalent linking of a molecule to a carrier confers enhanced immunogenicity and T-cell dependence (Pozsgay et al., *PNAS* 96:5194-97, 1999; Lee et al., *J. Immunol.* 116:1711-18, 1976; Dintzis et al., *PNAS* 73:3671-75, 1976). Exemplary carriers include polymeric carriers, which can be natural (for example, polysaccharides, polypeptides or proteins from bacteria or viruses), semi-synthetic or synthetic materials containing one or more functional groups to which a reactant moiety can be attached.

Examples of bacterial products for use as carriers include, but are not limited to, bacterial toxins, such as *B. anthracis* PA (including fragments that contain at least one antigenic epitope and analogs or derivatives capable of eliciting an immune response), LF and LeTx, and other bacterial toxins and toxoids, such as tetanus toxin/toxoid, diphtheria toxin/toxoid, *P. aeruginosa* exotoxin/toxoid/, *pertussis* toxin/toxoid, and *C. perfringens* exotoxin/toxoid. Viral proteins, such as hepatitis B surface antigen and core antigen can also be used as carriers, as well as proteins from higher organisms such as keyhole limpet hemocyanin, horseshoe crab hemocyanin, edestin, mammalian serum albumins, and mammalian immunoglobulins. Additional bacterial products for use as carriers include, but are not limited to, bacterial wall proteins and other products (for example, streptococcal or staphylococcal cell walls and lipopolysaccharide (LPS)).

Immunogenicity: The ability of an agent to induce a humoral or cellular immune response. Immunogenicity can be measured, for example, by the ability to bind to an appropriate MHC molecule (such as an MHC Class I or II molecule) and to induce a T-cell response or to induce a B-cell or antibody response, for example, a measurable cytotoxic T-cell response or a serum antibody response to a given epitope. Immunogenicity assays are well-known in the art and are described, for example, in Paul, *Fundamental Immunology,* 3rd ed., 243-247 (Raven Press, 1993) and references cited therein.

Immunologically Effective Dose: A therapeutically effective amount of an immunogen (such as the disclosed pathogens having decreased replicative fitness or sequences therefrom) that will prevent, treat, lessen, or attenuate the severity, extent or duration of a disease or condition, for example, infection by a pathogen.

Isolated: An "isolated" biological component (such as, a nucleic acid molecule or protein) has been substantially separated, produced apart from, or purified away from other biological components in the cell of the organism in which the component occurs, for example, other chromosomal and extra-chromosomal DNA and RNA, and proteins. Nucleic acid molecules and proteins which have been "isolated" include nucleic acid molecules and proteins purified by standard purification methods. The term also embraces nucleic acid molecules and proteins prepared by recombinant expression in a host cell as well as chemically synthesized proteins and nucleic acids. Samples of isolated biological components include samples of the biological component wherein the biological component represents greater than 90% (for example, greater than 95%, such as greater than 98%) of the sample.

An "isolated" microorganism (such as a virus, bacterium, fungus, or protozoa) has been substantially separated or purified away from microorganisms of different types, strains, or species. Microorganisms can be isolated by a variety of techniques, including serial dilution and culturing.

Lymphocytes: A type of white blood cell involved in the immune defenses of the body. There are two main types of lymphocytes: B-cells and T-cells.

Mimetic: A molecule (such as an organic chemical compound) that mimics the activity of another molecule.

Nucleic acid molecule: A deoxyribonucleotide or ribonucleotide polymer including, without limitation, cDNA, mRNA, genomic DNA, genomic RNA, and synthetic (such as chemically synthesized) DNA. Includes nucleic acid sequences that have naturally-occurring, modified, or non-naturally-occurring nucleotides linked together by naturally-occurring or non-naturally-occurring nucleotide linkages. Nucleic acid molecules can be modified chemically or biochemically and can contain non-natural or derivatized nucleotide bases. Such modifications include, for example, labels, methylation, substitution of one or more of the naturally occurring nucleotides with analogs, and internucleotide linkage modifications.

Nucleic acid molecules can be in any topological conformation, including single-stranded, double-stranded, partially duplexed, triplexed, hairpinned, circular, linear, and padlocked conformations. Where single-stranded, a nucleic acid molecule can be the sense strand or the antisense strand. Also included are synthetic molecules that mimic polynucleotides in their ability to bind to a designated sequence via hydrogen bonding and other chemical interactions. Such molecules are known and include, for example, molecules in which peptide linkages are substituted for phosphate linkages in the backbone.

The disclosure includes isolated nucleic acid molecules that include specified lengths of a nucleotide sequence. Such molecules can include at least 10, at least 15, at least 20, at least 25, at least 30, at least 35, at least 40, at least 45, at least 50, at least 100, at least 300 or at least 500 nucleotides of these sequences or more, and can be obtained from any region of a nucleic acid molecule.

Nucleotide: A subunit of DNA or RNA including a nitrogenous base (adenine, guanine, thymine, or cytosine in DNA; adenine, guanine, uracil, or cytosine in RNA), a phosphate molecule, and a sugar molecule (deoxyribose in DNA and ribose in RNA).

Passive immunity: Immunity acquired by the introduction by immune system components into a subject rather than by stimulation.

Pathogen: A disease-producing agent. Examples include, but are not limited to microbes such as viruses, bacteria, fungi, and protozoa.

Peptide, polypeptide, and protein: Polymers of amino acids (typically L-amino acids) or amino acid mimetics linked through peptide bonds or peptide bond mimetic to form a chain. The terminal amino acid at one end of the chain typically has a free amino group (the amino-terminus), while the terminal amino acid at the other end of the chain typically has a free carboxyl group (the carboxy terminus). Encompasses any amino acid sequence and includes modified sequences such as glycoproteins. The terms cover naturally occurring proteins, as well as those which are recombinantly or synthetically produced.

As used herein, the terms are interchangeable since they all refer to polymers of amino acids (or their analogs) regardless of length. Non-natural combinations of naturally- or non-naturally occurring sequences of amino acids may also be referred to as "fusion proteins."

Pharmaceutically Acceptable Carriers: The pharmaceutically acceptable carriers (vehicles) useful in this disclosure are conventional. *Remington's Pharmaceutical Sciences*, by E. W. Martin, Mack Publishing Co., Easton, Pa., 15th Edition (1975), describes compositions and formulations suitable for pharmaceutical delivery of one or more therapeutic compounds or molecules, such as one or more nucleic acid molecules, proteins or immunogenic compositions disclosed herein.

In general, the nature of the carrier will depend on the particular mode of administration being employed. For instance, parenteral formulations can include injectable fluids that include pharmaceutically and physiologically acceptable fluids such as water, physiological saline, balanced salt solutions, aqueous dextrose, glycerol or the like as a vehicle. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate, sodium lactate, potassium chloride, calcium chloride, and triethanolamine oleate.

Poliovirus (PV): An enterovirus of the Picornaviridae family that is the causative agent of poliomyelitis (polio).

Purified: The term purified does not require absolute purity; rather, it is intended as a relative term. Thus, for example, a purified peptide preparation is one in which the peptide is more enriched than the peptide is in its natural environment within a cell or cell extract. In one example, a preparation is purified such that the purified peptide represents at least 50% of the total peptide content of the preparation. In other examples, a peptide is purified to represent at least 90%, such as at least 95%, or even at least 98%, of all macromolecular species present in a purified preparation prior to admixture with other formulation ingredients, such as a pharmaceutical carrier, excipient, buffer, absorption enhancing agent, stabilizer, preservative, adjuvant or other co-ingredient. In some examples, the purified preparation is be essentially homogeneous, wherein other macromolecular species are not detectable by conventional techniques.

Such purified preparations can include materials in covalent association with the active agent, such as glycoside residues or materials admixed or conjugated with the active agent, which may be desired to yield a modified derivative or analog of the active agent or produce a combinatorial therapeutic formulation, conjugate, fusion protein or the like. The term purified thus includes such desired products as peptide and protein analogs or mimetics or other biologically active compounds wherein additional compounds or moieties are bound to the active agent in order to allow for the attachment of other compounds or provide for formulations useful in therapeutic treatment or diagnostic procedures.

Quantitating: Determining a relative or absolute quantity of a particular component in a sample. For example, in the context of quantitating antibodies in a sample of a subject's blood to detect infection by a pathogen, quantitating refers to determining the quantity of antibodies using an antibody assay, for example, an ELISA-assay or a T-cell proliferation assay.

Recombinant: A recombinant nucleic acid molecule is one that has a sequence that is not naturally occurring or has a sequence that is made by an artificial combination of two otherwise separated segments of sequence. This artificial combination can be accomplished by chemical synthesis or by the artificial manipulation of isolated segments of nucleic acids, for example, by genetic engineering techniques such as those described in Sambrook et al. (ed.), *Molecular Cloning: A Laboratory Manual,* $2^{nd}$ ed., vol. 1-3, Cold Spring Harbor Laboratory Press, Cold Spring Harbor, N.Y., 1989. The term recombinant includes nucleic acid molecules that have been altered solely by addition, substitution, or deletion of a portion of the nucleic acid molecule. Similarly, a recombinant protein is one encoded for by a recombinant nucleic acid molecule.

Replicative fitness: The ability of a pathogen to produce mature infectious progeny. In some examples, introduction of one or more deoptimized codons into a pathogen reduces the replicative fitness of the pathogen, as compared to a pathogen containing native codons. In particular examples, introduction of one or more deoptimized codons into a pathogen, in combination with altering the G+C content or altering the number of CG or TA dinucleotides in a coding sequence, reduces the replicative fitness of the pathogen, as compared to a pathogen containing native codons. In some examples, such replicative fitness is reduced by at least 10%, such as at least 20%, at least 50%, or even at least 90% as compared to a pathogen containing native codons.

Methods that can be used to determine replicative fitness are disclosed herein and are known in the art. For example, to determine the replicative fitness of a virus, plaque size can be determined, infectious center assays can be used, viral titer by TCID50 (tissue-culture infectious doses 50%) or plaque assay, replication in single-step growth curves, temperature-sensitivity or cold-sensitivity of plaques determined, unusual host range observed, or competition assays with a related virus can be determined. To determine the replicative fitness of a bacterium or fungus, exemplary replicative fitness assays include assays for colony-forming activity, temperature-sensitivity, cold-sensitivity, slow growth under certain conditions, increased or rapid bacterial death, reduced ability of the bacteria or fungi to survive various stress conditions (such as nutrient deprivation), altered host range, enzymatic assays indicating reduced activity of a key enzyme, or assays for reduced pathogenicity due to decreased expression of an important protein (such as LPS).

Specific Binding Agent: An agent that binds substantially only to a defined target. Thus a protein-specific binding agent binds substantially only the defined protein, or to a specific region within the protein. As used herein, a specific binding agent includes antibodies and other agents that bind substantially to a specified peptide.

The determination that a particular agent binds substantially only to a specific peptide can readily be made by using or adapting routine procedures. One suitable in vitro assay makes use of the Western blotting procedure (described in many standard texts, including Harlow and Lane, *Using Antibodies: A Laboratory Manual*, CSHL, New York, 1999).

Specifically bind: Refers to the ability of a particular agent (a "specific binding agent") to specifically react with a particular analyte, for example to specifically immunoreact with an antibody, or to specifically bind to a particular peptide sequence. The binding is a non-random binding reaction, for example between an antibody molecule and an antigenic determinant. Binding specificity of an antibody is typically determined from the reference point of the ability of the antibody to differentially bind the specific antigen and an unrelated antigen, and therefore distinguish between two different antigens, particularly where the two antigens have unique epitopes. An antibody that specifically binds to a particular epitope is referred to as a "specific antibody".

In particular examples, two compounds are said to specifically bind when the binding constant for complex formation between the components exceeds about $10^4$ L/mol, for example, exceeds about $10^6$ L/mol, exceeds about $10^8$ L/mol, or exceeds about $10^{10}$ L/mol. The binding constant for two components can be determined using methods that are well known in the art.

Subject: Living multi-cellular organisms, a category that includes human and non-human mammals, as well as other veterinary subjects such as fish and birds.

Therapeutically effective amount: An amount of a therapeutic agent (such as an immunogenic composition) that alone, or together with an additional therapeutic agent(s), induces the desired response, such as a protective immune response or therapeutic response to a pathogen. In one example, it is an amount of immunogen needed to increase resistance to, prevent, ameliorate, or treat infection and disease caused by a pathogenic infection in a subject. Ideally, a therapeutically effective amount of an immunogen is an amount sufficient to increase resistance to, prevent, ameliorate, or treat infection and disease caused by a pathogen without causing a substantial cytotoxic effect in the subject. The preparations disclosed herein are administered in therapeutically effective amounts.

In general, an effective amount of a composition administered to a human or veterinary subject will vary depending upon a number of factors associated with that subject, for example whether the subject previously has been exposed to the pathogen. An effective amount of a composition can be determined by varying the dosage of the product and measuring the resulting immune or therapeutic responses, such as the production of antibodies. Effective amounts also can be determined through various in vitro, in vivo or in situ immunoassays. The disclosed therapeutic agents can be administered in a single dose, or in several doses, as needed to obtain the desired response. However, the effective amount of can be dependent on the source applied, the subject being treated, the severity and type of the condition being treated, and the manner of administration.

The disclosed therapeutic agents can be administered alone, or in the presence of a pharmaceutically acceptable carrier, or in the presence of other agents, for example an adjuvant.

In one example, a desired response is to increase an immune response in response to infection with a pathogen. For example, the therapeutic agent can increase the immune response by a desired amount, for example by at least 5%, at least 10%, at least 15%, at least 20%, at least 25%, at least 30%, at least 50%, at least 75%, or even at least 90%, as compared to an immune response in the absence of the therapeutic agent. This increase can result in decreasing or slowing the progression of, a disease or condition associated with a pathogenic infection.

In another example, a desired response is to decrease the incidence of vaccine-associated paralytic poliomyelitis in response to an attenuated Sabin oral polio vaccine. The incidence of vaccine-associated paralytic poliomyelitis does not need to be completely eliminated for a therapeutic agent, such as a pharmaceutical preparation that includes an immunogen, to be effective. For example, the therapeutic agent (such as a codon-deoptimized oral polio vaccine) can decrease the incidence of vaccine-associated paralytic poliomyelitis or the emergence of circulating vaccine-derived polioviruses by a desired amount, for example by at least 5%, at least 10%, at least 15%, at least 20%, at least 25%, at least 30%, at least 50%, at least 75%, or even at least 90%, as compared to the incidence of vaccine-associated paralytic poliomyelitis or the emergence of circulating vaccine-derived polioviruses in the presence of a oral polio vaccine containing native codons.

Treating a disease: "Treatment" refers to a therapeutic intervention that ameliorates a sign or symptom of a disease or pathological condition related to a disease, even if the underlying pathophysiology is not affected. Reducing a sign or symptom associated with a pathogenic infection can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Treatment can also induce remission or cure of a condition, such as a pathogenic infection or a pathological condition associated with such an infection. In particular examples, treatment includes preventing a disease, for example by inhibiting or even avoiding altogether the full development of a disease or condition, such as a disease associated with a pathogen, such as polio. Thus, prevention of pathogenic disease can include reducing the number of subjects who acquire a disease associated with a pathogenic infection (such as the development of polio or poliomyelitis by the polio virus or development of rabies by the rabies virus) in a population of subjects receiving a preventative treatment (such as vaccination) relative to an untreated control population, or delaying the appearance of such disease in a treated population versus an untreated control population. Prevention of a disease does not require a total absence of disease. For example, a decrease of at least 50% can be sufficient.

Unit dose: A physically discrete unit containing a predetermined quantity of an active material calculated to individually or collectively produce a desired effect such as an immunogenic effect. A single unit dose or a plurality of unit doses can be used to provide the desired effect, such as an immunogenic effect. In one example, a unit dose includes a desired amount of one or more of the disclosed pathogens having reduced replicative fitness.

Vaccine: An immunogenic composition that can be administered to an animal or a human to confer immunity, such as active immunity, to a disease or other pathological condition. Vaccines can be used prophylactically or therapeutically. Thus, vaccines can be used reduce the likelihood of infection or to reduce the severity of symptoms of a disease or condition or limit the progression of the disease or condition. In one example, a vaccine includes one or more of the disclosed pathogens having reduced replicative fitness.

Vector: A nucleic acid molecule as introduced into a host cell, thereby producing a transformed host cell. A vector can include nucleic acid sequences that permit it to replicate in the host cell, such as an origin of replication. A vector can also include one or more therapeutic genes or selectable marker genes and other genetic elements known in the art. A vector can transduce, transform or infect a cell, thereby causing the cell to express nucleic acid molecules or proteins other than those native to the cell. A vector optionally includes materials to aid in achieving entry of the nucleic acid into the cell, such as a viral particle, liposome, protein coating or the like. In one example, a vector is a viral vector. Viral vectors include, but are not limited to, retroviral and adenoviral vectors.

Deoptimizing Codon Usage to Decrease Replicative Fitness

This disclosure provides methods of decreasing the replicative fitness of a pathogen by deoptimizing codon usage in one or more genes of the pathogen. Such methods can be used to increase the genetic stability of the attenuated phenotype of currently available attenuated vaccines, as well as to generate new attenuated pathogens that can be used in immunogenic compositions. For example, the attenuated Sabin oral polio vaccine (OPV) strains are genetically unstable. This instability is the underlying cause of vaccine-associated paralytic poliomyelitis and the emergence of circulating vaccine-derived polioviruses. Therefore, the disclosed compositions and methods can be used to reduce the incidence of vaccine-associated paralytic poliomyelitis and other disorders caused by currently available live attenuated vaccines. The disclosed methods and compositions increase the genetic stability of pathogens by distributing attenuating mutations over many sites within the pathogen's genome.

Codon usage bias, the use of synonymous codons at unequal frequencies, is ubiquitous among genetic systems (Ikemura, *J. Mol. Biol.* 146:1-21, 1981; Ikemura, *J. Mol. Biol.* 158:573-97, 1982). The strength and direction of codon usage bias is related to genomic G+C content and the relative abundance of different isoaccepting tRNAs (Akashi, *Curr. Opin. Genet. Dev.* 11:660-6, 2001; Duret, *Curr. Opin. Genet. Dev.* 12:640-9, 2002; Osawa et al., *Microbiol. Rev.* 56:229-64, 1992). Codon usage can affect the efficiency of gene expression. In *Escherichia coli* (Ikemura, *J. Mol. Biol.* 146:1-21, 1981; Xia *Genetics* 149:37-44, 1998), *Saccharomyces cerevisiae* (Bennetzen and Hall, *J. Biol. Chem.* 257:3026-31, 1982; Ikemura, *J. Mol. Biol.* 158:573-97, 1982), *Caenorhabditis elegans* (Duret, *Curr. Opin. Genet. Dev.* 12:640-9, 2002), *Drosophila melanogaster* (Moriyama and Powell, *J. Mol. Evol.* 45:514-23, 1997), and *Arabidopsis thaliana* (Chiapello et al. *Gene* 209:GC1-GC38, 1998) the most highly expressed genes use codons matched to the most abundant tRNAs (Akashi and Eyre-Walker, *Curr.*

*Opin. Genet. Dev.* 8:688-93, 1998). By contrast, in humans and other vertebrates, codon usage bias is more strongly correlated with the G+C content of the isochore where the gene is located (Musto et al., *Mol. Biol. Evol.* 18:1703-7, 2001; Urrutia and Hurst, *Genetics* 159:1191-9, 2001) than with the breadth or level of gene expression (Duret, *Curr. Opin. Genet. Dev.* 12:640-9, 2002) or the number of tRNA genes (Kanaya et al., *J. Mol. Evol.* 53:290-8, 2001).

The deoptimized nucleic acid sequences of the present application include one or more codons that are degenerate as a result of the genetic code. There are 20 natural amino acids, most of which are specified by more than one codon. However, organisms have codons which are used more frequently, and those that are used less frequently (deoptimized). All possible deoptimized nucleotide sequences are included in the disclosure as long as the deoptimized nucleotide sequence retains the ability to decrease replicative fitness, for example by at least 10%, at least 20%, at least 50% or even at least 75% as compared to the replicative fitness of a pathogen with a codon optimized nucleic acid sequence.

Optimization of codon composition is frequently required for efficient expression of genes in heterologous host systems (André et al., *J. Virol.* 72:1497-503, 1998; Kane, *Curr. Opin. Biotech.* 6:494-500, 1995; Smith, *Biotech. Prog.* 12:417-22, 1996; Yadava and Ockenhouse. *Infect. Immun.* 71:4961-9, 2003). Conversely, engineered codon deoptimization can dramatically decrease the efficiency of gene expression in several organisms (Robinson et al., *Nucleic Acids Res.* 12:6663-71, 1984; Hoekema et al., *Mol. Cell Biol.* 7:2914-24, 1987; Carlini and Stephan. *Genetics* 163: 239-43, 2003; and Zhou et al., *J. Virol.* 73:4972-82, 1999). However, it has not been previously taught or suggested that deoptimization of sequences of a microbial pathogen (such as a housekeeping or antigenic sequence) could be used to systematically reduce the replicative fitness of the pathogen, thereby producing a novel approach for developing attenuated derivatives of the pathogen having well-defined levels of replicative fitness, and increasing the genetic stability of the attenuated phenotype.

Selection of Codons to Deoptimize

The methods provided herein include deoptimizing at least one codon in a coding sequence of a pathogen, thereby generating a deoptimized coding sequence. Such deoptimization reduces replicative fitness of the pathogen. In particular examples, methods of reducing the replicative fitness of a pathogen include identifying one or more amino acids that are encoded by at least 2 different codons in the pathogen (such as 2 different codons, 3 different codons, 4 different codons, or 6 different codons). In some examples, the codon used least frequently (lowest codon usage frequency) for a particular amino acid is incorporated into the sequence of the pathogen (to replace the appropriate one or more codons in the native sequence), thereby deoptimizing the pathogen sequence and reducing the replicative fitness of the pathogen. In other examples, a codon used with a lower frequency than at least one other codon (but not necessarily the codon with the lowest frequency) for a particular amino acid is incorporated into the sequence of the pathogen (to replace the appropriate one or more codons in the native sequence), for example to alter the G+C content of the sequence or alter the number of CG or TA dinucleotides in the sequence, thereby deoptimizing the pathogen sequence and reducing the replicative fitness of the pathogen. Identification of infrequently used codons can be made by analyzing one or more codon usage tables for the pathogen. The codon usage table used can include codon usage data from the complete genome of the pathogen (or 2 or more genomes, for example from different strains of the pathogen), codon usage data from one or more genes (such as 1 gene, at least 2 genes, at least 3 genes, at least 5 genes, or even at least 10 genes), for example one or more genes involved in the antigenicity of the pathogen. Codon usage tables are publicly available for a wide variety of pathogens (for example see Nakamura et al., *Nucleic Acids Res.* 28:292, 2000; Sharp et al., *Nucleic Acids Res.* 16:8207-11, 1988; Chou and Zhang, *AIDS Res. Hum. Retroviruses*. December; 8(12):1967-76, 1992; West and Iglewski et al., *Nucleic Acids Res.* 16:9323-35, 1988, Rothberg and Wimmer, *Nucleic Acids Res.* 9:6221-9, 1981; Jenkins et al., *J. Mol. Evol.* 52:383-90, 2001; and Watterson, *Mol. Biol. Evol.* 9:666-77, 1992; all herein incorporated by reference).

For example, if the pathogen uses the ACU, ACC, ACA, and ACG codons to encode for Thr at 45, 24, 20 and 11% frequency respectively, the ACG codon can be chosen to replace at least one ACU, ACC, or ACA codon sequence of the native pathogen sequence, thereby generating a deoptimized sequence. This selection would also increase the number of CG dinucleotides in the deoptimized sequence. However, if it was desired to decrease the G+C content of the deoptimized sequence, the ACA codon (for example instead of ACG) can be chosen to replace the ACU codon. In examples where the amino acid is encoded by only two different codons, one of the two codons can be selected and used in the deoptimized sequence if the codon usage is highly biased, such as a difference of at least 10%, at least 20%, or at least 30%. For example, if the pathogen uses the codons UAU and UAC to encode for Tyr at 90% and 10% frequency respectively, the UAC codon is used to replace at least one UAU codon of the native pathogen sequence, thereby generating a deoptimized sequence. In contrast, if the pathogen uses the codons UAU and UAC to encode for Tyr at 49% and 51% frequency respectively, Tyr codons would not likely be chosen as the codons to deoptimize.

In some examples, there may be two or more codons used at low frequencies that are similar in value, such as codon usages that are within 0.01-2% of each other (for example within 0.1-2%, 0.5-2% or 1-2% of each other). In some examples, the codon with the lowest codon usage frequency is not chosen to replace a codon more frequently used. In some examples, the codon chosen is one that alters the G+C content of the deoptimized sequence. In other examples, the codon chosen is one that alters the frequency of a specific dinucleotide pair (such as CG or TA) found at low frequencies in that genome (such as no more than 3-4%). One example is the CG dinucleotide, which is strongly suppressed in mammalian genomes and in the genomes of many RNA viruses (Karlin et al., *J. Virol.* 68:2889-2897, 1994). Such dinucleotide pairs can fall across codon boundaries, or be contained within the codon.

Reducing Replicative Fitness

The replicative fitness of a pathogen is the overall replicative capacity of the pathogen to produce mature infectious progeny. By introducing one or more deoptimized codons into a coding region of a pathogen's gene(s), the replicative fitness of the pathogen decreases. In some examples, replicative fitness is decreased by at least 10%, at least 20%, at least 30%, at least 50%, at least 75%, at least 90%, at least 95%, or even at least 98%, as compared to an amount of replicative fitness by the a pathogen of the same species and strain in the absence of deoptimized codons. The disclosed methods can be used for making vaccines because the replicative fitness of the pathogen can be modulated by introducing different numbers of nucleotide changes. This flexibility can allow one to alter systematically the replicative fitness of a candidate vaccine strain in order to allow sufficient replication to induce an immune response, but not enough replication to cause pathogenicity.

Methods that can be used to measure the replicative fitness of a pathogen are known in the art and disclosed herein. For example, to measure the replicative fitness of a virus, plaque size can be measured, infectious center assays can be used, viral titer by TCID50 (tissue-culture infectious doses 50%) or plaque assays can be used, replication in single-step growth curves can be determined, temperature-sensitivity or cold-sensitivity of plaques determined, determination of whether the virus has an unusual host range, or competition assays with a related virus can be determined. To determine the replicative fitness of a bacterium or fungus, exemplary replicative fitness assays include assays for colony-forming activity, temperature-sensitivity, cold-sensitivity, slow growth under certain conditions, increased or rapid bacterial or fungal death, reduced ability of the bacteria or fungi to survive various stress conditions (such as nutrient deprivation), altered host range, enzymatic assays indicating reduced activity of a key enzyme, or assays for reduced pathogenicity due to decreased expression of an important protein (such as LPS). To measure the replicative fitness of a protozoan, exemplary replicative fitness assays include competitive growth assays with unmodified homologues, temperature-sensitivity, cold-sensitivity, slow growth under certain conditions, increased or rapid senescence, reduced ability to survive various stress conditions, altered host range, enzymatic assays indicating reduced activity of a key enzyme, or assays for reduced pathogenicity due to decreased expression of an important protein (such as surface antigens).

This disclosure provides several specific examples of pathogens containing deoptimized codons in various genes, including housekeeping genes and genes encoding proteins that are determinants of immunity. However, one skilled in the art will understand how to use the disclosed methods to deoptimize one or more codons in any pathogen of interest using publicly available codon usage tables and publicly available pathogen sequences In particular examples, a pathogen includes one or more deoptimized codons, for example at least 2, at least 3, at least 4, at least 5, at least 6, at least 7, at least 8, at least 9, at least 10, at least 20, at least 50, at least 100, at least 200, at least 300, at least 400, at least 500, at least 1000, or even at least 2000 deoptimized codons.

In some examples, a pathogen includes deoptimization of at least 5% of the codons in a gene that encode a particular amino acid, such as deoptimization of at least 5% of the codons that encode Ala (or another amino acid such as Leu, Thr, etc.), for example at least 10% of the codons that encode Ala (or another amino acid), at least 20% of the codons that encode Ala (or another amino acid), at least 50% of the codons that encode Ala (or another amino acid), or at least 90% of the codons that encode Ala (or another amino acid) in a gene. In particular examples, a pathogen includes deoptimization of at least 5% of the codons in one or more coding sequences, such as deoptimization of at least 10%, at least 20%, at least 30%, at least 40%, at least 50%, at least 60%, at least 70%, at least 80%, or even at least 90% of the codons in one or more coding sequences.

In one example, viral pathogen sequences are deoptimized in one or more nucleic acid sequences that encode proteins encoding surface antigens which are determinants of immunity, such as a capsid sequences, or spike glycoproteins.

In particular examples, deoptimizing the codon composition results in an altered G+C content of a coding sequence. For example, deoptimizing one or more codons can increase or decrease the G+C content by at least 10%, such as increase the G+C content of a coding sequence by at least 10%, such as at least 20%, at least 30%, at least 40%, at least 50%, at least 60%, at least 70%, at least 80%, or even by at least 90%, or decrease the G+C content of a coding sequence by at least 10%, such as at least 20%, at least 30%, at least 40%, at least 50%, at least 60%, at least 70%, at least 80%, or even by at least 90%. Whether the G+C content is increased or decreased will depend on the sequence of the pathogen of interest.

However, the G+C content can be deliberately altered in combination with deoptimizing one or more codons in a pathogen sequence. For example, some of the nucleotide substitutions can be made to deoptimize codons, and other nucleotide substitutions can be made to alter the G+C content of the sequence. Altering the G+C content of the sequence may also result in a deoptimized codon, but is not required in all instances.

In one example, the pathogen is a rubella virus, whose RNA genome has a high G+C content. Therefore, deoptimization of rubella can be achieved by decreasing the G+C content of one or more coding sequences of rubella, for example decreasing the G+C content by at least 10%, such as at least 20%, or even by at least 50%. In another example, the pathogen is a poliovirus or other eukaryotic virus, and deoptimization can be achieved by increasing the G+C content of one or more coding sequences, for example increasing the G+C content by at least 10%, such as at least 20%, or even by at least 50%. Such changes in G+C content can be achieved as a result of deoptimizing one or more codons, or in addition to deoptimizing one or more codons.

In some examples, deoptimizing the codon composition results in an altered frequency (number) of CG dinucleotides, TA dinucleotides, or both, in a coding sequence. For example, deoptimization of one or more codons may increase or decrease the frequency of CG or TA dinucleotides in the sequence by at least 10%, for example increase the number of CG or TA dinucleotides in a coding sequence by at least 10%, such as at least 20%, at least 30%, at least 40%, at least 50%, at least 60%, at least 100%, at least 200%, or even by at least 300%, or decrease in the number of CG or TA dinucleotides in a coding sequence by at least 10%, such as at least 20%, at least 30%, at least 40%, at least 50%, at least 60%, at least 70%, at least 80%, or even by at least 90%. Whether the number of CG or TA dinucleotides is increased or decreased will depend on the sequence of the pathogen of interest.

However, the number of CG or TA dinucleotides can be deliberately altered in combination with deoptimizing one or more codons in a pathogen sequence. For example, some of the nucleotide substitutions can be made to deoptimize codons, and other nucleotide substitutions can be made to alter the number of CG or TA dinucleotides in the coding sequence. Altering the number of CG or TA dinucleotides in the sequence may also result in a deoptimized codon, but is not required in all instances.

In one example, the pathogen is a poliovirus or eukaryotic virus, and deoptimization can be achieved by increasing the number of CG or TA dinucleotides in one or more coding sequences, for example increasing the number of CG or TA dinucleotides by at least 10%, such as at least 30%, or even by at least 300%. In another example, the pathogen is a bacterium, and deoptimization can be achieved by decreasing the number of CG or TA dinucleotides in one or more coding sequences, for example decreasing the number of CG or TA dinucleotides by at least 10%, such as at least 30%, or even by at least 50%.

In a particular example, the pathogen is a bacterium. Several methods can be used to deoptimize one or more codons in bacterial coding sequences. For example, one or more codons can be deoptimized such that a single rare codon (such as AGG) is used to force exclusive AGG usage in the mRNA encoding the arginyl tRNA synthetase, potentially limiting the pools of charged arginyl-tRNAs in the cell, and therefore synergistically further limiting the production of arginyl tRNA synthetase. In another example, one or more codons are deoptimized (for example by exclusively using AGG to encode for Arg residues) in one or more of the most highly expressed essential genes (such as translation factors). In yet another example, the distribution of codon-deoptimized genes along the genome is chosen to reduce the likelihood that all deoptimized genes could be exchanged out by any single natural recombination event.

Exemplary Pathogens

Any pathogen can be attenuated by deoptimizing one or more codons in one or more coding sequences. Exemplary pathogens include, but are not limited to, viruses, bacteria, fungi, and protozoa. For example, viruses include positive-strand RNA viruses and negative-strand RNA viruses. Exemplary positive-strand RNA viruses include, but are not limited to: Picornaviruses (such as Aphthoviridae [for example foot-and-mouth-disease virus (FMDV)]), Cardioviridae; Enteroviridae (such as Coxsackie viruses, Echoviruses, Enteroviruses, and Polioviruses); Rhinoviridae (Rhinoviruses)); Hepataviridae (Hepatitis A viruses); Togaviruses (examples of which include rubella; alphaviruses (such as Western equine encephalitis virus, Eastern equine encephalitis virus, and Venezuelan equine encephalitis virus)); Flaviviruses (examples of which include Dengue virus, West Nile virus, and Japanese encephalitis virus); and Coronaviruses (examples of which include SARS coronaviruses, such as the Urbani strain). Exemplary negative-strand RNA viruses include, but are not limited to: Orthomyxyoviruses (such as the influenza virus), Rhabdoviruses (such as Rabies virus), and Paramyxoviruses (examples of which include measles virus, respiratory syncytial virus, and parainfluenza viruses).

Polioviruses are small (28 nm diameter), non-enveloped viruses whose single-stranded genome is enclosed in a capsid of 60 identical subunits arranged in icosahedral symmetry. Their positive-stranded genomes (~7500 nt) can serve directly as a messenger RNA, which is translated as a large (~250 kD) polyprotein from a single ORF. The polyprotein is post-translationally processed in a proteolytic cascade catalyzed by virus-encoded proteases, producing at least 10 distinct final cleavage products. Polioviruses grow rapidly in a wide variety of cultured human and simian cells, yielding $10^3$ to $10^4$ infectious particles per infected cell in ~8 hours. As with other RNA viruses, the poliovirus replicase lacks proofreading activity and consequently has a very high rate of base misincorporation (~$10^-$ base substitution per base pair per replication; see Domingo et al. 2002. Error frequencies of picornavirus RNA polymerases: evolutionary implications for virus populations, p. 285-298. In B. L. Semler and E. Wimmer (ed.), Molecular Biology of Picornaviruses. ASM Press, Washington, D.C.; Drake and Holland, *Proc. Natl. Acad. Sci. USA* 96:13910-13, 1999). Polioviruses exist as three stable serotypes, and for each serotype strains with reduced replicative fitness (the "attenuated" Sabin oral poliovirus vaccine [OPV] strains) have been used throughout the world as live virus vaccines; see Sutter et al., 2003. Poliovirus vaccine—live, p. 651-705. In S. A. Plotkin and W. A. Orenstein (ed.), Vaccines, Fourth ed. W.B. Saunders Company, Philadelphia).

Viruses also include DNA viruses. DNA viruses include, but are not limited to: Herpesviruses (such as Varicella-zoster virus, for example the Oka strain; cytomegalovirus; and Herpes simplex virus (HSV) types 1 and 2), Adenoviruses (such as Adenovirus type 1 and Adenovirus type 41), Poxviruses (such as Vaccinia virus), and Parvoviruses (such as Parvovirus B19).

Another group of viruses includes Retroviruses. Examples of retroviruses include, but are not limited to: human immunodeficiency virus type 1 (HIV-1), such as subtype C, HIV-2; equine infectious anemia virus; feline immunodeficiency virus (FIV); feline leukemia viruses (FeLV); simian immunodeficiency virus (SIV); and avian sarcoma virus.

Another type of pathogen are bacteria. Bacteria can be classified as gram-negative or gram-positive. Exemplary gram-negative bacteria include, but are not limited to: *Escherichia coli* (K-12 and O157:H7), *Shigella dysenteriae*, and *Vibrio cholerae*. Exemplary gram-positive bacteria include, but are not limited to: *Bacillus anthracis, Staphylococcus aureus*, pneumococcus, gonococcus, and streptococcal meningitis.

Protozoa, nematodes, and fungi are also types of pathogens. Exemplary protozoa include, but are not limited to, *Plasmodium, Leishmania, Acanthamoeba, Giardia, Entamoeba, Cryptosporidium, Isospora, Balantidium, Trichomonas, Trypanosoma, Naegleria*, and *Toxoplasma*. Exemplary fungi include, but are not limited to, *Coccidiodes immitis* and *Blastomyces dermatitidis*. There is a great need for effective vaccines against protozoan pathogens. No effective vaccines for fungal pathogens have yet been identified.

Exemplary Genes which can be Deoptimized

The gene(s) (for example its corresponding coding sequence) chosen for codon deoptimization can vary depending on the pathogen of interest. In one example, one of the coding sequences deoptimized is a single copy gene that is important for survival of the pathogen, such as a "housekeeping" gene. In some examples, one of the coding sequences deoptimized is a determinant of immunity, such as a viral capsid coding sequence.

In one example, the virus is a positive strand virus, such as a picornavirus, for example a poliovirus, (for example the Sabin type 2 OPV strain or the MEF1 reference strain used in the inactivated poliovirus vaccine [IPV]) or foot-and-mouth-disease virus (FMDV) (such as serotype O), having one or more codons deoptimized in the capsid region of the virus. In one example, one or more of the Arg codons (such as all of the Arg codons in a reading frame) are replaced with a rare Arg codon, such as CGG. Such CGG-deoptimized picornaviruses can be used to produce inactivated poliovirus vaccine (IPV) in Vero cells expressing elevated levels of the corresponding rare tRNA. Such CGG-deoptimized IPV seed strains are less likely to infect workers in IPV production facilities, enhancing poliovirus containment after global polio eradication.

In one example, the positive strand virus is a togavirus, such as a rubella virus or alphavirus. In a particular example, the complete genome of such a virus is de-optimized. However, particular coding sequences can be de-optimized, such as envelope (E) protein E1, E2 or core protein.

In a specific example, the positive strand virus is a flavivirus, such as a dengue virus, West Nile virus, or Japanese encephalitis virus, and one or more codons in the coding sequence of a surface glycoprotein gene deoptimized (such as 8 different amino acid codons).

In a specific example, the positive strand virus is a coronavirus, such as the SARS coronaviruses (for example the Urbani strain). Such viruses can have one or more codons deoptimized in the coding sequence of a spike glycoprotein region (such as at least 5 different amino acid codons deoptimized).

In one example, the pathogen is an RNA virus, such as a negative-strand RNA virus. In a specific example, the virus is an orthomyxyovirus, such as an influenza virus (such as strain H3N2), having one or more codons deoptimized in a hemagglutinin (HA) or neuraminidase (NA) coding sequence. In one example, the virus is a paramyxovirus, such as a measles virus having one or more codons deoptimized in a fusion (F) or hemagglutinin (H) coding sequence, or a respiratory syncytial virus having one or more codons deoptimized in a fusion (F) or glycoprotein (G) coding sequence.

In one example, the pathogen is a retrovirus, such as HIV-1 or HIV-2, and one or more codons are deoptimized in an envelope (env) or group antigen (gag) coding sequence.

In one example, the pathogen is a DNA virus, such as herpesviruses. In a specific example, the virus is a varicella zoster virus (such as the Oka strain), and one or more codons are deoptimized in a glycoprotein E or H coding sequence. In another specific example, the virus is a cytomegalovirus, and one or more codons are deoptimized in a glycoprotein B, H, or N coding sequence. In yet another specific example, the virus is herpes simplex virus types 1 or 2, and one or more codons are deoptimized in genes encoding surface glycoprotein B, glycoprotein D, integument protein, or the large subunit of ribonucleotide reductase.

In one example, the pathogen is a bacterium, such as gram-positive or gram-negative bacteria. In one gram-negative example, the bacterium is *Escherichia coli* (such as strains K-12 or O157:H7), and one or more Arg codons (such as all Arg codons) are replaced with the rare codon AGG in the ArgS gene (arginyl synthetase gene) and the highly expressed TufA gene (translation factor U). In another example, the bacterium is a *Shigella dysenteriae*, and one or more Arg codons (such as all Arg codons) are replaced with AGG in the RdsB gene. In one gram-positive example, the bacterium is *Staphylococcus aureus*, and one or more Arg codons (such as all Arg codons) are replaced with AGG in the RplB and FusA genes.

Pathogens with Deoptimized Codon Sequences as Immunogenic Compositions

The disclosed attenuated pathogens having a nucleic acid coding sequence with one or more deoptimized codons can be used in an immunogenic composition. In some examples, the deoptimized pathogens are further attenuated, for example by passage at suboptimal growth temperatures. Such immunogenic compositions can be used to produce an immune response against the pathogen in a subject, for example to treat a subject infected with the pathogen, decrease or inhibit infection by the pathogen, or reduce the incidence of the development of clinical disease.

In forming a composition for generating an immune response in a subject, or for vaccinating a subject, a purified, diluted, or concentrated pathogen can be utilized.

Compositions Including a Deoptimized Pathogen

In one example, purified or concentrated (or diluted) deoptimized pathogens that have one or more codons deoptimized are provided. In some examples, the immunogenic compositions are composed of non-toxic components, suitable for infants, children of all ages, and adults. Also disclosed are methods for the preparation of a vaccine, which include admixing a deoptimized pathogen of the disclosure and a pharmaceutically acceptable carrier. Although particular examples of deoptimized sequences are provided herein, one skilled in the art will appreciate that further modifications to the nucleic acid or protein sequence of the pathogen can be made without substantially altering the reduced replicative fitness due to the deoptimized codons. Examples of such further modifications include one or more deletions, substitutions, insertions, or combinations thereof, in the nucleic acid or protein sequence. In one example, such further modifications to a deoptimized pathogenic sequence do not increase the replicative fitness of the deoptimized pathogenic sequence by more than 5%, such as no more than 10%, as compared to an amount of replicative fitness by the deoptimized pathogen.

In one example, deoptimized pathogen sequences that include additional amino acid deletions, amino acid replacements, isostereomer (a modified amino acid that bears close structural and spatial similarity to the original amino acid) substitutions, isostereomer additions, and amino acid additions can be utilized, so long as the modified sequences do not increase the replicative fitness of the deoptimized pathogenic sequence by more than 5%, and retain the ability to stimulate an immune response against the pathogen. In another example, deoptimized pathogen sequences that include nucleic acid deletions, nucleic acid replacements, and nucleic acid additions can be utilized, so long as the modified sequences do not increase the replicative fitness of the deoptimized pathogenic sequence by more than 5%, and retains the ability to stimulate an immune response against the pathogen.

In one example, the deoptimized pathogenic nucleic acid sequences are recombinant.

The deoptimized pathogens can be replicated by methods known in the art. For example, pathogens can be transferred into a suitable host cell, thereby allowing the pathogen to replicate. The cell can be prokaryotic or eukaryotic.

The disclosed deoptimized pathogens can be used as immunogenic compositions, such as a vaccine. In one example, an immunogenic composition includes an immunogenically effective amount (or therapeutic amount) of an attenuated deoptimized pathogen of the disclosure, such as a viral, bacterial, fungal, or protozoan deoptimized pathogen. Immunogenically effective refers to the amount of attenuated deoptimized pathogen (live or inactive) administered at vaccination sufficient to induce in the host an effective immune response against virulent forms of the pathogen. An effective amount can being readily determined by one skilled in the art, for example using routine trials establishing dose response curves. In one example, the deoptimized pathogen can range from about 1% to about 95% (w/w) of the composition, such as at least 10%, at least 50%, at least 75%, or at least 90% of the composition.

Pharmaceutical compositions that include a deoptimized pathogen can also include other agents, such as one or more pharmaceutically acceptable carriers or other therapeutic ingredients (for example, antibiotics). In one example, a composition including an immunogenically effective amount of attenuated deoptimized pathogen also includes a pharmaceutically acceptable carrier. Particular examples of pharmaceutically acceptable carriers include, but are not limited to, water, culture fluid in which the pathogen was cultured, physiological saline, proteins such as albumin or casein, and protein containing agents such as serum. Other agents that can be included in the disclosed pharmaceutical compositions, such as vaccines, include, but are not limited to, pH control agents (such as arginine, sodium hydroxide, glycine, hydrochloric acid, citric acid, and the like), local anesthetics (for example, benzyl alcohol), isotonizing agents (for example, sodium chloride, mannitol, sorbitol), adsorption inhibitors (for example, Tween 80), solubility enhancing agents (for example, cyclodextrins and derivatives thereof), stabilizers (for example, serum albumin, magnesium chloride, and carbohydrates such as sorbitol, mannitol, starch, sucrose, glucose, and dextran), emulsifiers, preservatives, (such as chlorobutanol and benzalkonium chloride), wetting agents, and reducing agents (for example, glutathione).

When the immunogenic composition is a liquid, the tonicity of the formulation, as measured with reference to the tonicity of 0.9% (w/v) physiological saline solution taken as unity, can be adjusted to a value at which no substantial, irreversible tissue damage will be induced at the site of administration. Generally, the tonicity of the solution is adjusted to a value of about 0.3 to about 3.0, such as about 0.5 to about 2.0, or about 0.8 to about 1.7.

DNA Immunogenic Compositions

In one example, an immunogenic composition includes a deoptimized nucleic acid coding sequence instead of (or in addition to) the entire deoptimized pathogen. In particular examples, the sequence includes a sequence having at least 90%, at least 95%, or 100% sequence identity to any of SEQ ID NOS: 5, 8, 11, 14, 18, 21, 24, 27, 30, 33, 36, 39, 42, 45, 48, 51, 54, 55, 56, 57, 58, 67, 68, or 69. In some examples, an immunogenic composition includes a full-length deoptimized genome, for example a deoptimized poliovirus genome. However, one skilled in the art will appreciate that fragments of the deoptimized full-length genome can also be used (and in some examples ligated together). The DNA including the deoptimized coding sequence can be part of a vector, such as a plasmid, which is administered to the subject. Such DNA immunogenic compositions can be used to stimulate an immune response using the methods disclosed herein.

In one example, a deoptimized nucleic acid coding sequence from a pathogen is present in a colloidal dispersion system. Colloidal dispersion systems include macromolecule complexes, nanocapsules, microspheres, beads, and lipid-based systems including oil-in-water emulsions, micelles, mixed micelles, and liposomes. Large uni-lamellar vesicles (LUV), which range in size from 0.2-4.0 m can encapsulate a substantial percentage of an aqueous buffer containing large macromolecules. RNA, DNA and intact virions can be encapsulated within the aqueous interior and be delivered to cells in a biologically active form (Fraley et al., *Trends Biochem. Sci.* 6:77, 1981).

The composition of a liposome is usually a combination of phospholipids, particularly high-phase-transition-temperature phospholipids, usually in combination with steroids, such as cholesterol. Examples of lipids useful in liposome production include phosphatidyl compounds, such as phosphatidylglycerol, phosphatidylcholine, phosphatidylserine, phosphatidylethanolamine, sphingolipids, cerebrosides, and gangliosides. Particularly useful are diacylphosphatidyl-glycerols, where the lipid moiety contains from 14-18 carbon atoms, such as 16-18 carbon atoms, and is saturated. Illustrative phospholipids include egg phosphatidylcholine, dipalmitoylphosphatidylcholine and distearoylphosphatidylcholine.

Inducing an Immune Response

Methods are disclosed for stimulating an immune response in a subject using the disclosed deoptimized pathogens (such as a pathogen that includes a sequence having at least 90%, at least 95% or 100% sequence identity to any of SEQ ID NOS: 5, 8, 11, 14, 18, 21, 24, 27, 30, 33, 36, 39, 42, 45, 48, 51, 54, 55, 56, 57, 58, 67, 68, or 69) and immunogenic compositions. The method includes administering to a subject an immunologically effective amount of a deoptimized pathogen having a nucleic acid coding sequence with one or more deoptimized codons, which reduce the replicative fitness of the pathogen (for example by at least 20%, at least 50%, or even at least 99%). Such administration can be broadly effective for treatment and prevention of disease caused by a pathogen, and one or more associated symptoms thereof. In one example, the immunogenic compositions and methods are designed to confer specific immunity against infection with a pathogen, and to induce antibodies specific to the pathogen. The deoptimized pathogens can be delivered to a subject in a manner consistent with conventional methodologies associated with management of the disorder for which treatment or prevention is sought.

In selected examples, one or more symptoms or associated effects of exposure to or infection with a pathogen is prevented or treated by administration to a subject at risk of being infected by the pathogen, or presenting with one or more symptoms associated with infection by the pathogen, of an effective amount of a deoptimized pathogen of the disclosure. Therapeutic compositions and methods of the disclosure for prevention or treatment of toxic or lethal effects of pathogen infection are applicable to a wide spectrum of infectious agents.

Administration of Deoptimized Pathogens

For administration to animals or humans, the immunogenic compositions of the present disclosure, including vaccines, can be given by any method determined appropriate by a clinician. In addition, the immunogenic compositions disclosed herein can be administered locally or systemically. Types of administration include, but are not limited to, intramuscular, subcutaneous, oral, intravenous, intra-atrial, intra-articular, intraperitoneal, parenteral, intraocular, and by a variety of mucosal administration modes, including by oral, rectal, intranasal, intrapulmonary, or transdermal delivery, or by topical delivery to other surfaces.

The disclosed methods include administering a therapeutically effective amount of an attenuated pathogen having one or more deoptimized codon sequences (a deoptimized pathogen) to generate an immune response against the pathogen. Specific, non-limiting examples of an immune response are a B cell or a T cell response. Upon administration of the deoptimized pathogen, the immune system of the subject responds to the immunogenic composition (such as a vaccine) by producing antibodies, both secretory and serum, specific for one or more pathogen epitopes. Such a response signifies that an immunologically effective dose of the deoptimized pathogen was delivered. An immunologically effective dosage can be achieved by single or multiple administrations. In some examples, as a result of the vaccination, the subject becomes at least partially or completely immune to infection by the pathogen, resistant to developing moderate or severe pathogen infection, or protected from disease associated with infection by the pathogen. For example, an effective dose can be measured by detection of a protective antibody titer in the subject.

Typical subjects that can be treated with the compositions and methods of the present disclosure include humans, as well as veterinary subjects such as dogs, cats, horses, chickens, cows, fish, sheep, and pigs. To identify subjects for treatment according to the methods of the disclosure, accepted screening methods can be employed to determine risk factors associated with a targeted or suspected disease of condition (for example, polio) as discussed herein, or to determine the status of an existing disease or condition in a subject. These screening methods include, for example, conventional work-ups to determine environmental, familial, occupational, and other such risk factors that may be associated with the targeted or suspected disease or condition, as well as diagnostic methods, such as various ELISA and other immunoassay methods, which are available and well known in the art to detect or characterize disease-associated markers, such as antibodies present in the serum of a subject indicating that they were previously infected with a particular pathogen. The vaccines can also be administered as part of a routine health maintenance program in at risk individuals, such as the administration of meningococcal vaccines in children and pneumococcal or influenza vaccines in the elderly. These and other routine methods allow a clinician to select subjects in need of therapy using the methods and pharmaceutical compositions of the disclosure. In accordance with these methods and principles, a deoptimized pathogen can be administered using the methods disclosed herein as an independent prophylaxis or treatment program, or as a follow-up, adjunct or coordinate treatment regimen to other treatments, such as surgery, vaccination, or immunotherapy.

The compositions including deoptimized pathogens can be used for therapeutic purposes, such as prophylactically. When provided prophylactically, deoptimized pathogens are provided in advance of any symptom associated with the pathogen against which the prophylaxis is provided. The prophylactic administration of deoptimized pathogens serves to prevent or ameliorate any subsequent infection. When provided therapeutically, deoptimized pathogens are provided at (or shortly after) the onset of a symptom of disease or infection. The disclosed deoptimized pathogens can thus be provided prior to the anticipated exposure to a particular pathogen, so as to attenuate the anticipated severity, duration or extent of an infection or associated disease symptoms, after exposure or suspected exposure to the pathogen, or after the actual initiation of an infection.

The deoptimized pathogens disclosed herein can be administered to the subject in a single bolus delivery, via continuous delivery (for example, continuous transdermal, mucosal, or intravenous delivery) over an extended time period, or in a repeated administration protocol (for example, by an hourly, daily, weekly, or monthly repeated administration protocol). In one example, administration of a daily dose can be carried out both by single administration in the form of an individual dose unit or else several smaller dose units and also by multiple administrations of subdivided doses at specific intervals.

The therapeutically effective dosage of a deoptimized pathogen can be provided as repeated doses within a prolonged prophylaxis or treatment regimen that will yield clinically significant results to alleviate one or more symptoms or detectable conditions associated with a targeted disease or condition as set forth herein. Determination of effective dosages are typically based on animal model studies followed up by human clinical trials and is guided by administration protocols that significantly reduce the occurrence or severity of targeted disease symptoms or conditions in the subject. Various considerations are described, e.g., in Gilman et al., eds., *Goodman and Gilman: The Pharmacological Bases of Therapeutics,* 8th ed., Pergamon Press, 1990; and *Remington's Pharmaceutical Sciences,* $17^{th}$ ed., Mack Publishing Co., Easton, Pa., 1990, each of which is herein incorporated by reference. Suitable models in this regard include, for example, murine, rat, porcine, feline, non-human primate, and other accepted animal model subjects known in the art.

Immunologically effective dosages can also be determined using in vitro models (for example, immunologic and histopathologic assays). Using such models, only ordinary calculations and adjustments are used to determine an appropriate concentration and dose to administer a therapeutically effective amount of the deoptimized pathogen (for example, amounts that are effective to elicit a desired immune response or alleviate one or more symptoms of a targeted disease). In some examples, amounts administered are those amounts adequate to achieve tissue concentrations at the site of action which have been found to achieve the desired effect in vitro. In alternative examples, an effective amount or effective dose of the deoptimized pathogens can decrease or enhance one or more selected biological activities correlated with a disease or condition.

For example, deoptimized pathogens of the present application can be tested using in vitro and in vivo models to confirm adequate attenuation, genetic stability, and immunogenicity for vaccine use. In a particular example, an in vitro assay is used to determine the attenuation and genetic stability of a deoptimized pathogen, for example using the plaque assays and virus yield, single-step growth assays described herein. In another example, deoptimized pathogens are further tested in animal models of infection, for example using the methods described herein. For example, a deoptimized pathogen can be administered to an animal model, and an amount of immunogenic response to the deoptimized pathogen determined, for example by analyzing antibody, T-cell or B-cell production. In some examples, the animal is further exposed to the pathogen, and resistance to infection determined.

The actual dosage of the deoptimized pathogen can vary according to factors such as the disease indication and particular status of the subject (for example, the subject's age, weight, fitness, extent of symptoms, susceptibility factors, and the like), time and route of administration, the type of pathogen against which vaccination is sought, other drugs or treatments being administered concurrently, as well as the specific pharmacology of the deoptimized pathogens for eliciting the desired activity or biological response in the subject. Dosage regimens can be adjusted to provide an optimum prophylactic or therapeutic response. A therapeutically effective amount is also one in which any toxic or detrimental side effects of a deoptimized pathogen are outweighed in clinical terms by therapeutically beneficial effects.

In one example, an immunogenic composition includes any dose of deoptimized bacteria sufficient to evoke an immune response, such as a range of between $10^3$ and $10^{10}$ bacteria per dose, for example at least $10^3$ bacteria, at least $10^4$ bacteria, at least $10^5$ bacteria, at least $10^8$ bacteria, or at least $10^9$ bacteria per dose. In one example, an immunogenic composition includes any dose of deoptimized virions sufficient to evoke an immune response, such as a range of between $10^3$ to $10^{10}$ plaque forming units (PFU) or more of virus per subject, such as $10^4$ to $10^5$ PFU virus per subject, for example at least $10^3$ PFU virus per subject, at least $10^4$ PFU virus per subject, at least $10^5$ PFU virus per subject, or at least $10^9$ PFU virus per subject. In another example, an immunogenic composition includes any dose of deoptimized protozoa sufficient to evoke an immune response, such as at least $10^2$ infectious units per subject, for example at least $10^3$ infectious units per subject, or a range of between $10^2$ to $10^6$ infectious units per subject. In any event, the immunogenic compositions ideally provide a quantity of deoptimized pathogen sufficient to effectively protect the subject against serious or life-threatening pathogen infection.

For each particular subject, specific dosage regimens can be evaluated and adjusted over time according to the individual need and professional judgment of the person administering or supervising the administration of the deoptimized pathogen. For example, in neonates and infants, multiple administrations can be required to elicit sufficient levels of immunity. In some examples, administration of the disclosed immunogenic compositions begins within the first month of life and continues at intervals throughout childhood, such as at two months, six months, one year and two years, as necessary to maintain sufficient levels of protection against pathogen infection. Similarly, adults who are particularly susceptible to repeated or serious infection by pathogens, such as health care workers, day care workers, elderly individuals, and individuals with compromised cardiopulmonary function, may require multiple immunizations to establish or maintain protective immune responses. Levels of induced immunity can be monitored by measuring amounts of neutralizing secretory and serum antibodies, and dosages adjusted or vaccinations repeated as necessary to maintain desired levels of protection.

The antibody response of a subject administered the compositions of the disclosure can be determined by using effective dosages/immunization protocols. In some examples, it is sufficient to assess the antibody titer in serum or plasma obtained from the subject. Decisions as to whether to administer booster inoculations or to change the amount of the immunogenic composition administered to the individual can be at least partially based on the antibody titer level. The antibody titer level can be based on, for example, an immunobinding assay which measures the concentration of antibodies in the serum which bind to a specific antigen present in the pathogen. The ability to neutralize in vitro and in vivo biological effects of the pathogen of interest can also be assessed to determine the effectiveness of the treatment.

Dosage can be varied by the attending clinician to maintain a desired concentration at a target site. Higher or lower concentrations can be selected based on the mode of delivery. Dosage can also be adjusted based on the release rate of the administered formulation. To achieve the same serum concentration level, for example, slow-release particles with a release rate of 5 nanomolar (under standard conditions) would be administered at about twice the dosage of particles with a release rate of 10 nanomolar.

Kits

The instant disclosure also includes kits, packages and multi-container units containing the herein described deoptimized pathogens, alone or in the presence of a pharmaceutically acceptable carrier, and in some examples, an adjuvant. Such kits can be used in the treatment of pathogenic diseases in subjects. In one example, these kits include a container or formulation that contains one or more of the deoptimized pathogens described herein. In one example, this component is formulated in a pharmaceutical preparation for delivery to a subject. The deoptimized pathogens can be contained in a bulk dispensing container or unit or multi-unit dosage form.

Optional dispensing means can be provided, for example a pulmonary or intranasal spray applicator, or a needle. Packaging materials optionally include a label or instruction indicating for what treatment purposes, or in what manner the pharmaceutical agent packaged therewith can be used.

The subject matter of the present disclosure is further illustrated by the following non-limiting Examples.

Example 1

Codon Usage in Poliovirus

This example describes methods used to determine codon usage in poliovirus.

Mononucleotide and dinucleotides frequencies, and codon usage were analyzed in the original reports of poliovirus genomic sequences (Kitamura et al. 1981. *Nature* 291:547-53; Racaniello and Baltimore. 1981. *Proc. Natl. Acad. Sci. USA* 78:4887-91; Rothberg and Wimmer. 1981. *Nucleic Acids Res.* 9:6221-9; Toyoda et al. 1984. *J. Mol. Biol.* 174:561-85). The mono-, di-, and trinucleotide frequency patterns are similar for the three Sabin strains (Toyoda et al. 1984. *J. Mol. Biol.* 174:561-85) and appear to be conserved across poliovirus genotypes (Hughes et al. 1986. *J. Gen. Virol.* 67:2093-102; Kew et al. 2002. *Science* 296:356-9; La Monica et al. 1986. *J. Virol.* 57:515-25; Liu et al. 2003. *J. Virol.* 77:10994-1005; Martin et al. 2000. *Virology* 278:42-9; Yang et al. 2003. *J. Virol.* 77:8366-77) and human enterovirus species C serotypes (Brown et al. 2003. *J. Virol.* 77:8973-84).

As with other enteroviruses, the component bases in the Sabin 2 ORF are present in approximately equal proportions (24.0% U, 22.9% C, 29.9% A, and 23.1% G; see Rezapkin et al., *Virology* 258:152-60, 1999; Toyoda et al., *J. Mol. Biol.* 174:561-85, 1984), thus permitting a low bias in codon usage (Osawa et al., *Microbiol. Rev.* 56:229-264, 1992). Indeed, all codons are used in poliovirus ORFs (Toyoda et al., *J. Mol. Biol.* 174:561-85, 1984), and the overall degree of codon usage bias is low (Jenkins and Holmes. *Virus Res.* 92:1-7, 2003).

One measure of codon usage bias is the number of effective codons ($N_C$), which can vary from 20 (only one codon used for each amino acid) to 61 (all codons used randomly) (Wright, *Gene* 87:23-9, 1990). The $N_C$ values for Sabin 2 are 56.0 for the capsid region and 54.6 for the complete ORF. As with the genomes of vertebrates and most RNA viruses, the dinucleotide CG is suppressed in the Sabin 2 genome (Toyoda et al., *J. Mol. Biol.* 174:561-85, 1984), and the observed pattern of codon usage reflects this CG suppression (Table 1).

TABLE 1

Codon usage in mutagenized capsid interval and complete ORF in unmodified and deoptimized Sabin 2 genomes.

| | | Codon usage (number) | | | | | |
|---|---|---|---|---|---|---|---|
| | | Capsid interval (nt 748 to 3303) Construct | | | Complete ORF (nt 748 to 7368) Construct | | |
| Amino acid | Codon[a] | ABCD[b] | ABCd[c] | abcd[d] | ABCD | ABCd | abcd |
| Arg | CGA | 4 | 1 | 0 | 7 | 4 | 3 |
| | CGC | 11 | 7 | 0 | 13 | 9 | 2 |
| | **CGG** | 2 | 17 | 39 | 7 | 22 | 44 |
| | CGU | 0 | 0 | 0 | 3 | 3 | 3 |
| | AGA | 17 | 9 | 0 | 45 | 37 | 28 |
| | AGG | 5 | 5 | 0 | 23 | 23 | 18 |

TABLE 1-continued

Codon usage in mutagenized capsid interval and complete ORF in unmodified and deoptimized Sabin 2 genomes.

| | | Codon usage (number) | | | | | |
|---|---|---|---|---|---|---|---|
| | | Capsid interval (nt 748 to 3303) Construct | | | Complete ORF (nt 748 to 7368) Construct | | |
| Amino acid | Codon[a] | ABCD[b] | ABCd[c] | abcd[d] | ABCD | ABCd | abcd |
| Leu | CUA | 7 | 6 | 1 | 33 | 32 | 27 |
| | CUC | 7 | 6 | 0 | 27 | 26 | 20 |
| | CUG | 14 | 10 | 0 | 25 | 21 | 11 |
| | **CUU** | 4 | 14 | 55 | 22 | 32 | 73 |
| | UUA | 9 | 9 | 1 | 25 | 25 | 17 |
| | UUG | 18 | 14 | 2 | 40 | 36 | 24 |
| Ser | UCA | 18 | 11 | 0 | 43 | 36 | 25 |
| | UCC | 14 | 11 | 2 | 33 | 30 | 21 |
| | UCG | 6 | 1 | 0 | 8 | 3 | 2 |
| | UCU | 8 | 7 | 0 | 19 | 18 | 11 |
| | **AGC** | 9 | 25 | 63 | 20 | 36 | 74 |
| | AGU | 10 | 10 | 0 | 26 | 26 | 16 |
| Thr | ACA | 20 | 17 | 0 | 47 | 44 | 27 |
| | ACC | 24 | 19 | 1 | 55 | 50 | 32 |
| | **ACG** | 11 | 23 | 74 | 17 | 29 | 80 |
| | ACU | 20 | 16 | 0 | 47 | 43 | 27 |
| Pro | CCA | 21 | 16 | 0 | 53 | 48 | 32 |
| | CCC | 19 | 15 | 0 | 32 | 28 | 13 |
| | **CCG** | 9 | 21 | 59 | 19 | 31 | 69 |
| | CCU | 12 | 9 | 2 | 18 | 15 | 8 |
| Ala | GCA | 23 | 16 | 0 | 61 | 54 | 38 |
| | GCC | 16 | 13 | 2 | 40 | 37 | 26 |
| | **GCG** | 10 | 26 | 66 | 17 | 33 | 73 |
| | GCU | 19 | 13 | 0 | 49 | 43 | 30 |
| Gly | GGA | 12 | 8 | 0 | 38 | 34 | 26 |
| | GGC | 8 | 7 | 0 | 30 | 29 | 22 |
| | GGG | 20 | 16 | 2 | 37 | 33 | 19 |
| | **GGU** | 14 | 23 | 52 | 42 | 51 | 80 |
| Val | GUA | 10 | 8 | 1 | 24 | 22 | 15 |
| | **GUC** | 10 | 27 | 55 | 21 | 38 | 66 |
| | GUG | 20 | 10 | 1 | 55 | 45 | 36 |
| | GUU | 17 | 12 | 0 | 40 | 35 | 23 |
| Ile | AUA | 16 | 12 | 0 | 30 | 26 | 14 |
| | **AUC** | 15 | 22 | 45 | 47 | 54 | 77 |
| | AUU | 14 | 11 | 0 | 59 | 56 | 45 |
| Lys | AAA | 13 | 13 | 13 | 64 | 64 | 64 |
| | AAG | 18 | 18 | 18 | 58 | 58 | 58 |
| Asn | AAC | 25 | 25 | 25 | 61 | 61 | 61 |
| | AAU | 25 | 25 | 25 | 52 | 52 | 52 |
| Gln | CAA | 18 | 18 | 18 | 47 | 47 | 47 |
| | CAG | 9 | 9 | 9 | 32 | 32 | 32 |
| His | CAC | 12 | 12 | 12 | 30 | 30 | 30 |
| | CAT | 6 | 6 | 6 | 19 | 19 | 19 |
| Glu | GAA | 16 | 16 | 16 | 57 | 57 | 57 |
| | GAG | 19 | 19 | 19 | 56 | 56 | 56 |
| Asp | GAC | 23 | 23 | 23 | 51 | 51 | 51 |
| | GAU | 19 | 19 | 19 | 62 | 62 | 62 |
| Tyr | UAC | 21 | 21 | 21 | 57 | 57 | 57 |
| | UAU | 16 | 16 | 16 | 43 | 43 | 43 |
| Cys | UGC | 10 | 10 | 10 | 20 | 20 | 20 |
| | UGU | 5 | 5 | 5 | 22 | 22 | 22 |
| Phe | UUC | 14 | 14 | 14 | 36 | 36 | 36 |
| | UUU | 21 | 21 | 21 | 48 | 48 | 48 |
| Met | AUG | 26 | 26 | 26 | 67 | 67 | 67 |
| Trp | UGG | 13 | 13 | 13 | 28 | 28 | 28 |

[a]Unpreferred codons used as replacement codons are shown in boldface font.

[b]ABCD represents virus construct S2R9, which differs from the reference Sabin 2 strain sequence at three synonymous third-position sites: $A_{2616} \rightarrow G$ (VP1 region), $A_{3303} \rightarrow T$ (VP1 region), and $T_{5640} \rightarrow A$ ($3C^{pro}$ region).

[c]ABCd represents virus construct S2R19, which has replacement codons across an interval spanning 76% of the VP1 region.

[d]abcd represents virus construct S2R23, which has replacement codons across an interval spanning 97% of the capsid region.

Example 2

Poliovirus Containing a Deoptimized Capsid Region

This example describes methods used to generate a poliovirus containing deoptimized codons in the capsid region. Briefly, the original capsid region codons of the Sabin type 2 oral polio vaccine strain were replaced with synonymous codons less frequently used in poliovirus genomes. An unpreferred synonymous codon was used nearly exclusively to code for each of nine amino acids. Codon changes were introduced into four contiguous intervals spanning 97% of the capsid region.

The strategy for codon replacement was as follows. Despite the low overall bias in codon usage in Sabin 2, some synonymous codons are used at much lower frequencies than others (Table 1). To determine codon usage in Sabin 2, the preferred codons for each of nine amino acids were replaced with a synonymous unpreferred codon (Table 1). The codon replacements shown in Table 1 were introduced only within the capsid sequences, because those sequences uniquely identify a poliovirus serotype, as both noncapsid and 5'-UTR region sequences are exchanged out by recombination with other species C enteroviruses during poliovirus circulation.

Because codon usage bias was very low for most two-fold degenerate codons (except codons for His and Tyr), only six-fold, four-fold, and three-fold degenerate codons were replaced. Synonymous codons for nine amino acids were replaced by a single unpreferred codon: CUU for Leu, AGC for Ser, CGG for Arg, CCG for Pro, GUC for Val, ACG for Thr, GCG for Ala, GGU for Gly, and AUC for Ile (Table 1). Whenever possible, codons with G or C at degenerate positions (the nucleotides that differ within the codons that encode for a particular amino acid) were chosen to increase the G+C content of the modified viral genomes.

For example, as shown in Table 1, the amino acid Leu is encoded by 6 different codons in Sabin 2. However, the codon CUU is used the least frequently of the six. Therefore, it was selected to replace the other five codons. Similarly, the amino acid Pro is encoded by four different codons in Sabin 2. However, the codon CCG is used the least frequently of the four. Therefore, it was selected to replace the other three codons. A similar analysis was performed for the least frequently used codon for Thr and Ala. For the amino acid Ser, although the codon UCG was less frequently used than AGC in Sabin 2, AGC was chosen to deoptimize the sequence because it was the least preferred Ser codon among a larger collection of VP1 sequences of wild polioviruses. Similarly, GGU was the least preferred Gly codon among a larger collection of VP1 sequences of wild polioviruses. Codons CGG and AUC were selected for Arg and Ile, respectively, because they were not preferred and their usage would increase the G+C content of the poliovirus genome.

In addition, some codons did not display a significant amount of bias, and were therefore not selected. For example, the amino acid Asp is encoded in the Sabin 2 capsid region by 19 and 23 GAU and GAC codons, respectively. Similarly, the amino acid Glu is encoded in the Sabin 2 capsid region by 16 and 19 GAA and GAG codons, respectively. Since these values are similar, it is not likely that substitution of one for the other would reduce replicative fitness of the pathogen. Ideally, in the case where there are at least two codons that encode for an amino acid in the pathogen, there is at least a 20% difference between the selected codon and one or more of the other codons that encode the amino acid, such as an at least 30% difference, or an at least 50% difference.

Figure 2:
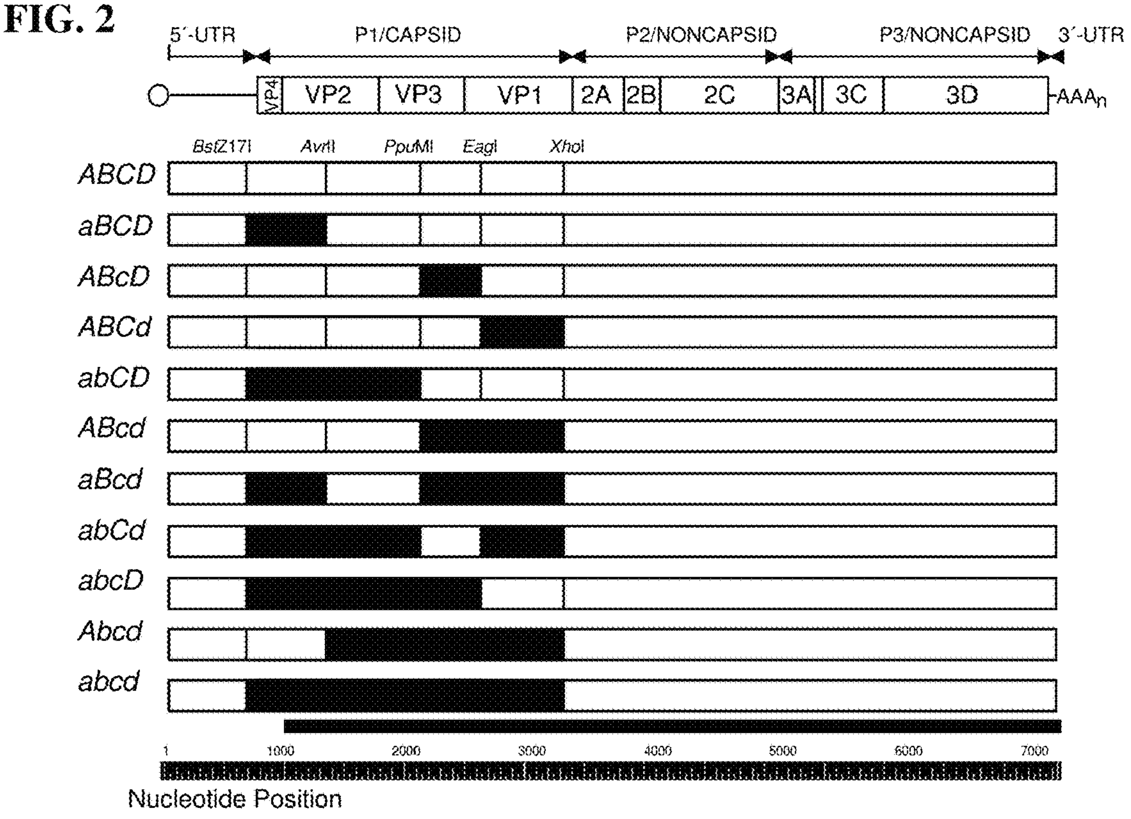
FIG. 2 is a schematic drawing showing exemplary Sabin 2 codon replacement constructs. The Sabin 2 genome is represented with open rectangles. Filled rectangles indicate the locations of individual cassettes, black-filled rectangles indicate cassettes with replacement codons. Unmodified cassettes are indicated by upper case letters; the corresponding cassettes with replacement codons are indicated by lower case letters.

Replacement codons were introduced into a full-length infectious cDNA clone derived from Sabin 2 (construct S2R9) within an interval (nt 748 to 3302) spanning all but the last 27 codons of the capsid region (FIGS. 1A-D). The capsid interval was divided into four mutagenesis cassettes: A (nt 657 to 1317; 661 bp), B (nt 1318 to 2102; 785 bp), C (nt 2103 to 2615; 513 bp), and D (nt 2616 to 3302; 687 bp) (FIG. 1A). Mutagenesis cassette A, bounded by restriction sites BstZ17I and AvrII, includes the last 91 nucleotides of the 5'-UTR, but no 5'-UTR sequences were modified in cassette A. Within each cassette, synonymous codons for the nine amino acids were comprehensively replaced except at 15 positions (replacement at 11 of these positions would have eliminated desirable restriction sites or generated undesirable restriction sites). Unmodified cassettes are identified by uppercase italic letters; the corresponding cassettes with replacement codons are identified by lowercase italic letters. Thus, as shown in FIG. 2, the reference Sabin 2 derivative (derived from cDNA construct S2R9) is identified as ABCD (SEQ ID NO: 3), and the fully modified virus (derived from cDNA construct S2R23) is identified as abcd (SEQ ID NO: 5).

The methods described below were used to generate the deoptimized polioviruses.

Virus and Cells.

The Sabin Original+2 (Sabin and Boulger. *J. Biol. Stand.* 1:115-8, 1973) master seed of the Sabin type 2 oral poliovaccine strain (P712 ch 2ab) was provided by R. Mauler of Behringwerke AG (Marburg, Germany). Virus was grown at 35° C. in suspension cultures as previously described (Rueckert and Pallansch. *Meth. Enzymol.* 78:315-25, 1981) of S3 HeLa cells (human cervical carcinoma cells; ATCC CCL-2.2) or in monolayer cultures of HeLa (ATCC CCL-2), and RD (human rhabdomyosarcoma cells; ATCC CCL-136) cells. Some initial plaque assays were performed in HEp-2C cells (Chen, *Cytogenet. Cell Genet.* 48:19-24, 1988).

Preparation of Infectious Sabin 2 Clones.

Poliovirus RNA was extracted from 250 µl of cell culture lysate (from ~75,000 infected cells) by using TRIZOL LS reagent (Life Technologies, Rockville, Md.) and further purified on CENTRI-SEP columns (Princeton Separations, Adelphia, N.J.). Full-length cDNA was reversed transcribed (42° C. for 2 hours) from ~1 µg of viral RNA in a 20 µl reaction containing 500 µM dNTP (Roche Applied Science, Indianapolis, Ind.), 200 U Superscript II Reverse Transcriptase (Life Technologies), 40 U RNase-inhibitor (Roche), 10 mM dithiothreitol, and 500 ng primer S2-7439A-B [CCTAAGC$(T)_{30}$CCCCGAATTAAAGAAAAATTTACCCCTACA; SEQ ID NO: 1] in Superscript II buffer.

After reverse transcription, 2 U RNase H (Roche) was added and incubated at 37° C. for 40 min. Long PCR amplification of viral cDNA was performed using TaqPlus Precision (Stratagene, La Jolla, Calif.) and AmpliWax PCR Gem 100 beads (Applied Biosystems, Foster City, Calif.) for "hot start" PCR in thin-walled tubes. The bottom mix (50 µl) contained 200 µM each dNTP (Roche) and 250 ng each of primers S2-7439A-B and S2-1S-C(GTAGTCGACTAATACGACTCACTATAGGTTAAAACAGCTCTGGGGTTG; SEQ ID NO: 2) in TaqPlus Precision buffer. A wax bead was added to each tube, and samples were heated at 75° C. for 4 minutes and cooled to room temperature. The top mix (50 µl) contained 2 µl of the cDNA and 10 U TaqPlus Precision in TaqPlus Precision buffer. The samples were incubated in a thermal cycler at 94° C. for 1 minute and then amplified by 30 PCR cycles (94° C. for 30 seconds, 60° C. for 30 seconds, and 72° C. for 8 minutes), followed by a final 94° C. for 1 minute and final extension of 72° C. for 20 minutes.

PCR products were purified using QIAquick PCR purification kit (Qiagen, Valencia, Calif.) and sequentially digested for 2 hours at 37° C. with Sal I and Hind III prior to gel purification. PCR products were ligated to pUC 19 plasmids following standard methods (Sambrook and Russell. 2001. *Molecular Cloning: A Laboratory Manual,* 3rd ed. Cold Spring Harbor Laboratory Press, Cold Spring Harbor, N.Y.) and ligated plasmids were transformed into XL-10 Gold supercompetent *E. coli* cells (Stratagene). Colonies were screened for recombinant plasmids on X-gal indicator plates (Sambrook and Russell. 2001. Molecular Cloning: A Laboratory Manual, 3rd ed. Cold Spring Harbor Laboratory Press, Cold Spring Harbor, N.Y.) and 6 white colonies were transferred to 1.5 ml Luria-Bertani broth containing 50 µg/ml ampicillin (LB/amp) (Roche). Plasmids were purified using QIAprep Spin Miniprep columns and sequences of the inserts were determined by cycle sequencing using an automated DNA sequencer (Applied Biosystems, Foster City, Calif.) (Liu et al., *J. Virol.* 74:11153-61, 2000). The full-length viral insert was sequenced in both orientations using overlapping sense and antisense primers spaced ~500 nt apart. Selected clones were grown in 50 ml LB/amp, and recombinant plasmids were purified using the QIAfilter Plasmid Maxi kit.

Virus Preparation.

Plasmids were linearized with Hind III and purified using QIAquick columns prior to RNA transcription from 1 µg of plasmid DNA using the Megascript T7 In Vitro Transcription kit (Ambion, Austin, Tex.). RNA yields were estimated using DNA Dipsticks (Invitrogen, Carlsbad, Calif.) and RNA chain length was analyzed by electrophoresis on 1% formaldehyde gels prior to transfection. RD cells were transfected with transcripts of viral RNA by using Tfx-20 (Promega, Madison, Wis.). Briefly, semi-confluent RD cells in 12-well cell culture plates were inoculated with 500 µl MEM (MEM incomplete) (Life Technologies) containing 0.1 µg viral RNA transcript and 0.45 µl Tfx-20 Reagent. Plates were incubated for 1 hour at 35° C. prior to addition of 1.5 ml MEM complete [MEM incomplete supplemented with 100 U penicillin and 100 μg streptomycin, 2 mM L-glutamine, 0.075% $NaHCO_3$, 10 μM HEPES (pH 7.5)] (Life Technologies) containing 3% fetal calf serum (FCS; HyClone, Logan, Utah). Negative controls were performed using RNA transcribed from pBluescriptIII SK+(Stratagene) containing a viral insert truncated at base 7200 by digestion with BamHI and transcribed in a reverse orientation from a T3 promoter.

Complete CPE was observed after incubation at 35° C. for 18-20 hours at which time 400 μl from the transfected wells were transferred to a confluent RD cell monolayer in 75 $cm^2$ flasks containing MEM complete. Complete CPE was observed in the second passage after 24 hours at 35° C., and virus was liberated from the infected cells by three freeze-thaw cycles and clarification by centrifugation for 15 minutes at 15,000×g. Control wells were passaged once and monitored for 72 hours post-transfection. The sequences of all virus stocks were verified by RT-PCR amplification of two large overlapping fragments and subsequent sequence analysis of the PCR product.

Site-Directed Mutagenesis.

Single-base substitutions were introduced using the QuikChange Site-Directed Mutagenesis Kit (Stratagene). Briefly, two complementary primers containing the desired mutation were designed for PCR amplification of the plasmid containing the Sabin 2 insert. Amplification was performed using Pfu Turbo DNA polymerase on 5 ng of template DNA for 15 cycles at 95° C. for 30 s, 50° C. for 1 minute, and 68° C. for 23 minutes. PCR products were digested for 1 hour at 37° C. with 10 U of Dpn I prior to transformation in XL-1 Blue Supercompetent cells. Colonies were grown and screened by sequencing as described above.

Assembly PCR. Multiple base substitutions were introduced by assembly PCR using previously described methods (Stemmer et al., *Gene* 164:49-53, 1995). Briefly, primers were designed to span the region of interest with complementary 40-mers overlapping by 10 nt on each end. A first round of assembly (30 PCR cycles of 94° C. for 45 seconds, 52° C. for 45 seconds, and 72° C. for 45 seconds) was performed with a 20 μl reaction mixture containing Taq Plus Precision buffer, 10 U Taq Plus Precision, 5 pmoles of each primer, and 200 μM dNTP. A second round of assembly (25 PCR cycles of 94° C. for 45 seconds, 50° C. for 45 seconds, and 72° C. for 2 minutes) was performed using the outermost sense and antisense primers in a 100 μl reaction mixture in Taq Plus Precision buffer containing 2 μl of product from the first assembly round, 10 U Taq Plus Precision, 200 ng of each primer, and 400 μM dNTP. PCR products were column purified prior to digestion, ligation, and transformation into XL-10 gold supercompetent *E. coli* cells. Clones were grown and screened by sequencing of insert as described.

Construction of Recombinant Clones.

The sequence of the full-length Sabin 2 infectious clone, S2R9, differed from the published sequence of a reference Sabin 2 strain (Rezapkin et al., *Virology* 258:152-60, 1999) at three synonymous third-codon positions: $G_{2616}$ (in VP1 region; A replaced to introduce an EagI restriction site) $T_{3303}$ (in VP1 region; A replaced to introduce a XhoI site), $A_{5640}$ (in $3C^{pro}$ region). The S2R9 construct was used as the reference Sabin 2 strain. Recombinant clones having different combinations of blocks of replacement codons were constructed using standard methods (Kohara et al., *J. Virol.* 53:786-92, 1985).

As shown in Tables 1 and 2, the modifications introduced dramatically altered the mono-, di-, and trinucleotide (codon) frequencies in the capsid region. In the fully modified construct, abcd, nearly half (427/879; 48.6%) of the capsid region codons were replaced, and a total of 544 substitutions (90 first codon position, 44 second position, and 410 third position) were introduced into the 2555 mutagenized capsid region nucleotides. This strategy for codon deoptimization increased the number of CG dinucleotides in the poliovirus templates. CG was the least abundant dinucleotide (181 occurrences) in the unmodified ABCD construct and the most abundant dinucleotide (386 occurrences) in the highly modified abcd construct. Compared with ABCD, the $N_C$ values in the capsid region of abcd fell from 56.2 to 29.8, the number of CG dinucleotides rose from 97 to 302, and the % G+C increased from 48.4% to 56.4% (Table 2). These changes were nearly uniformly distributed over the mutagenized capsid region (Table 2).

TABLE 2

Effective number of codons used ($N_C$), number of CG dinucleotides, and G + C content in mutagenized capsid region sequences.

| | Length of codon- | $N_C$[b] | | | No. of CG dinucleotides[c] | | | % G + C | | |
|---|---|---|---|---|---|---|---|---|---|---|
| Construct[a] | replacement interval (bp) | Replacement interval orig/mod[d] | Complete capsid region[e] | Complete ORF | Replacement interval orig/mod | Complete capsid region | Complete ORF | Replacement interval orig/mod | Complete capsid region | Complete ORF |
| ABCD[f] | 2555[g] | 56.0/56.0 | 56.2 | 54.6 | 94/94 | 97 | 181 | 48.5/48.5 | 48.4 | 46.0 |
| aBCD | 570[g] | 57.3/30.8 | 56.1 | 56.4 | 20/63 | 140 | 224 | 48.1/56.0 | 50.1 | 46.7 |
| AbCD | 785 | 56.0/29.9 | 53.1 | 55.7 | 25/89 | 161 | 245 | 48.4/56.1 | 50.7 | 47.0 |
| ABcD | 513 | 57.7/28.2 | 56.3 | 56.0 | 13/59 | 143 | 227 | 48.3/57.0 | 50.1 | 46.7 |
| ABCd | 687 | 54.0/28.4 | 54.6 | 56.5 | 36/88 | 149 | 233 | 49.1/57.7 | 50.7 | 46.5 |
| abcd | 2555 | 56.0/29.3 | 29.8 | 47.3 | 94/299 | 302 | 386 | 48.5/56.7 | 56.4 | 49.2 |

[a]Constructs correspond to the following infectious cDNA plasmids, clones, and virus derivatives: ABCD, S2R9; aBCD, S2R28; AbCD, not constructed; ABcD, S2R20; ABCd, S2R19; abcd, S2R23; $N_C$, number of CG dinucleotides, and % G + C of all other constructs can be calculated from table.

[b]$N_C$: effective number of codons used (1); one replacement codon spanned the EagI restriction cleavage site and was counted as part of cassette D.

[c]One CG dinucleotide spanned the EagI restriction cleavage site and was counted as part of the cassette D.

[d]orig/mod: original construct/modified codon-replacement construct.

[e]Complete capsid region: nt 748 to 3384.

[f]The S2R9 (ABCD) sequence differs from the reference Sabin 2 sequence at three synonymous third-position sites (see Table 1).

[g]Does not include the 3'-terminal 91 bases of the 5'-UTR at the 5'-end of cassette A (nt 657 to 747) that were not modified.

Example 3

Growth Properties of Codon-Deoptimized Constructs

This example describes methods used to determine the growth properties of the deoptimized Sabin 2 polioviruses generated in Example 2. Similar methods can be used to determine the replicative fitness of any deoptimized virus.

Briefly, RNA transcripts of constructs with different combinations of codon-replacement cassettes (FIG. 2) were transfected into RD cells as described above. Virus obtained from the primary transfection was passaged again in RD cells to increase virus titers as described above. The growth properties of the virus constructs in HeLa cells were measured by plaque assays (FIGS. 3A-E) and single-step growth experiments (FIGS. 4A-B).

Plaque assays were performed by a modification of previously described methods (Yang et al. *J. Virol.* 77:8366-77, 2003). Briefly, confluent HeLa cell monolayers in 100 $cm^2$ cell culture dishes were washed, inoculated with virus in MEM incomplete, and incubated at room temperature for 30 minutes prior to the addition of 0.45% SeaKem LE Agarose (BioWhittaker Molecular, Rockland, Me.) in MEM complete containing 2% FCS. Plates were incubated for 52-60 hours at 35° C., fixed with 0.4% formaldehyde and stained with 3% crystal violet. Plaque size was quantified by scanning plates on a FOTO/Analyst Archiver system (Fotodyne, Hartland, Wis.) and subsequent image analysis using Scion Image for Windows (Scion Corp., Frederick, Md.).

Figure 3D:
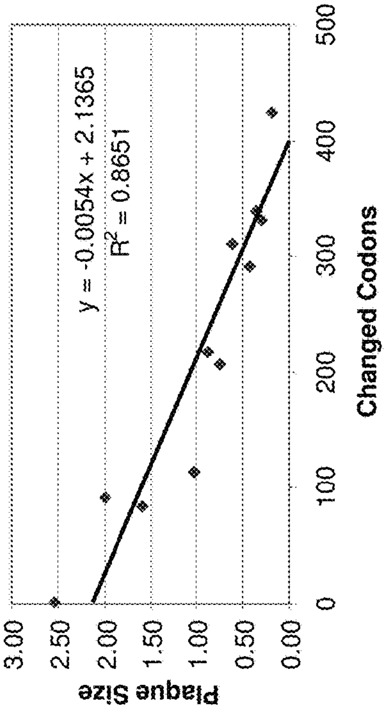
FIG. 3D is a graph showing the inverse linear relationship observed between plaque area and number of replacement codons in Sabin 2.
Figure 3E:
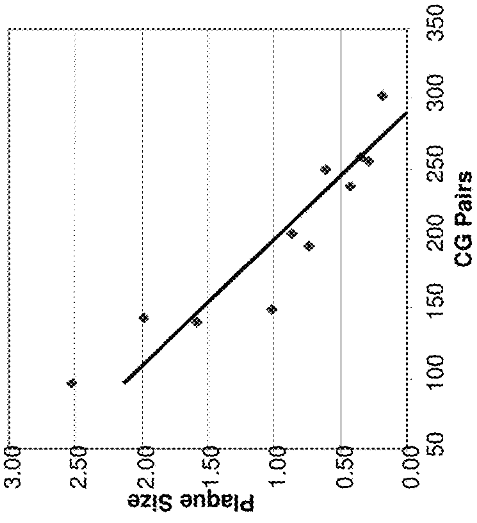
FIG. 3E is a graph showing the inverse linear relationship observed between plaque area and number of CG pairs in Sabin 2.
Figure 4A:
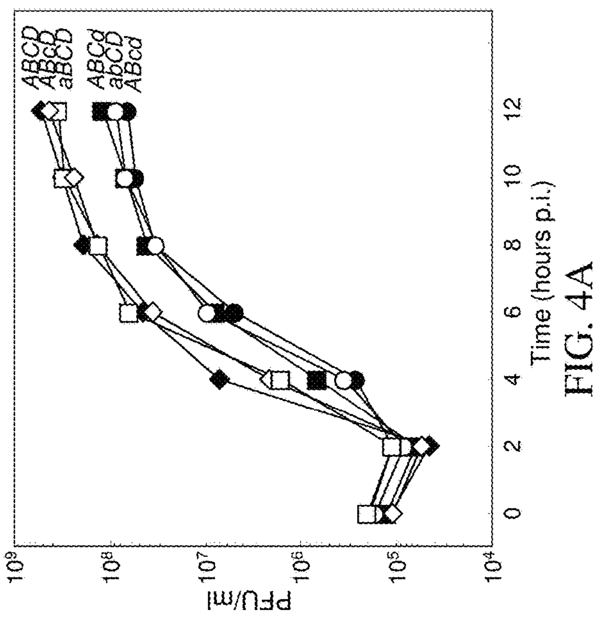
FIGS. 4A and 4B are graphs showing single-step growth curves in HeLa S3 cells at 35° C.
Figure 4B:
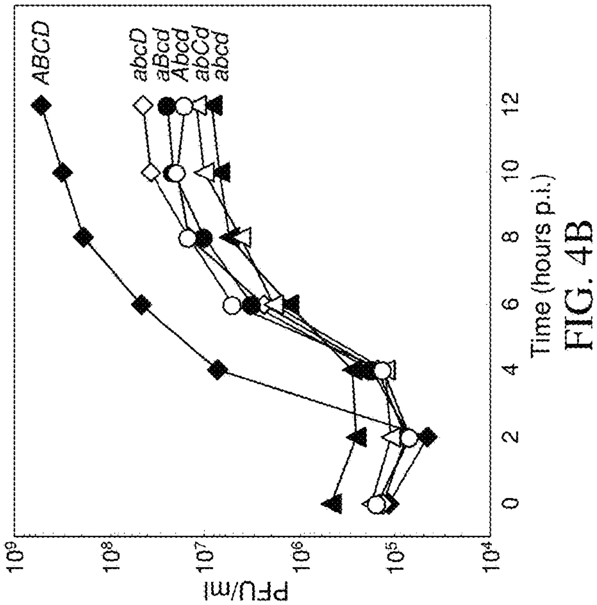

As shown in FIGS. 3A and 3C, an approximately linear inverse relationship was observed between mean plaque area in HeLa cells and the number of nucleotide changes in the capsid region. Similar inverse linear relationships were observed when the abscissa was rescaled to the number of replacement codons (FIG. 3D) or to the number of CG dinucleotides (FIG. 3E). There was no strong polarity to the effects of codon replacement within the capsid region, as introduction of replacement codons into any combination of the four cassettes reduced plaque areas approximately in proportion to the total number of replacement codons. However, replacement of codons into VP1 (cassette D) appeared to have slightly stronger effects than replacement elsewhere. Codon replacement in three or four cassettes generally conferred a minute-plaque phenotype (mean plaque area <25% that of the unmutagenized ABCD prototype), and the mean areas of the observed plaques of the abcd construct were ~9% of the ABCD prototype (FIG. 3C). An exception was the abcD construct, which had a greater mean plaque area (~38% that of the ABCD prototype) than the Abcd, aBcd, and abCd constructs, underscoring the stronger influence upon plaque size of codon replacement within VP1.

Measurement of plaque areas and total plaque number became difficult as plaque size decreased. The diameters of poliovirus plaques are typically heterogeneous, and this heterogeneity was observed with the plaques of all constructs. Precise measurement was most difficult with the smallest of the minute plaques, as was discriminating very minute plaques from other small defects in the cell monolayers. Extended incubation of plaque cultures to 72 hours increased plaque diameters but did not markedly increase the plaque counts. Growth properties of all constructs were also determined by plaque assays and limit dilution infectivity assays in HEp-2(C) cells at 35° C. For some of the constructs (abcd, abCD, AbcD, ABcd, and aBCd), the limit dilution infectivity titer was 2-10 fold higher than the plaque titers. For the other constructs, limit dilution infectivity and plaque titers were similar. The plaque titers might have been underestimated for some constructs because of the difficulty in seeing the tiniest plaques.

A plaque is the result of several cycles of replication, which effectively amplifies any difference in replication rate. To determine the relationship between plaque size, virus growth rates, and virus yield, single-step growth experiments (input MOI: 5 PFU/cell) were performed as follows. S3 HeLa suspension cells ($1\times10^7$) were infected at a multiplicity of infection (MOI) of 5 PFU/cell with stirring for 30 minutes at 25° C. After 30 minutes, cells were sedimented by low-speed centrifugation and resuspended in 2.5 ml warm complete media SMEM containing glutamine, 5% FCS, penicillin-streptomycin, and 25 mM HEPES (pH 7.5). Incubation continued at 35° C. in a water bath with orbital shaking at 300 rpm. Samples were withdrawn at 2-hour intervals from 0 to 14 hours postinfection, and titered by plaque assay in Hep-2(C) cells (35° C., 72 hours).

As shown in FIGS. 3B, 4A and 4B, mean virus yields from the single-step growth assays generally decreased as the number of replacement codons increased. Virus yields were highest (~200 PFU/cell) for the ABCD prototype and constructs ABcD and aBCD. Yields were 4- to 8-fold lower with constructs ABCd, abCD, and ABcd, 12- to 24-fold lower with constructs abcD and aBcd, 30- to 45-fold lower with constructs Abcd and abCd, and ~65-fold lower with construct abcd. Moreover, production of infectious virus appeared to be slower in the codon-replacement constructs than in the unmodified ABCD construct. Although maximum plaque yields were obtained at 10-12 hours for all constructs, proportion of the final yields detected at 4 hours were lower for the codon-deoptimized constructs (FIGS. 4A and 4B).

In summary, although the Sabin 2 OPV strain has a relatively low codon usage bias, its replicative fitness in cell culture was reduced by replacement of preferred codons in the capsid region with synonymous unpreferred codons. The reduction in fitness, as measured by plaque area, was approximately proportional to the length of the interval containing replacement codons. Plaque areas were reduced by ~90% and virus burst yields by ~98% in the abcd construct, in which the replacement interval spanned nearly the entire capsid region. The fitness declines in the replacement codon constructs are not attributable to amino acid substitutions because all constructs encoded the same reference Sabin 2 polyprotein sequence. Virus yields varied over a ~65-fold range in response to the extent of codon deoptimization.

Multiple synonymous capsid codon replacements increase the ability to detect discernible reductions in poliovirus fitness. For example, replacement of 3 to 14 Arg codons in VP1 (0.3% to 1.6% of capsid codons) with CGG (among the least preferred codons in the poliovirus genome) did not result in any apparent reduction in plaque areas. The ability to detect small declines in poliovirus fitness might be improved by replacing the plaque assay, which invariably gives heterogeneous plaques, with a biochemical assay. However, one advantage of the plaque assay and other virus infectivity assays is their high sensitivities to very low levels of biological activity.

Example 4

In Vivo Protein Synthesis by Deoptimized Pathogen Sequences

This example describes methods used to determine if there was a change in the amount of protein synthesis due to the presence of deoptimized codons. Similar methods can be used to measure protein synthesis by any deoptimized pathogen sequence.

Monolayer HeLa cells were plated at $8\times10^5$ per well in a 6-well dish. On the following day, the cells were washed in MEM without serum. Cells were infected at a multiplicity of infection (moi) of 25 in complete MEM with 2% serum. Cells were incubated in a $CO_2$ incubator at 35° C. or 37° C. for 4 hours. Viruses tested were Sabin 2 and MEF1; constructs tested were S2R9 (Sabin 2 prototype genome; ABCD; SEQ ID NO: 3), S2R19 (deoptimized VP3-VP1 genome; ABCd), S2R23 (deoptimized P1/capsid region; abcd; SEQ ID NO: 5), MEF1R2 (MEF1 prototype genome; ABC), MEF1R5 (deoptimized VP3-VP1 genome; ABc), and MEF1R9 (deoptimized P1/capsid region; abc).

Media was removed, and 1.9 ml. of labeling media (200 uCi 35S-met in a mixture of 1 volume regular complete MEM containing 2% serum and 7 volumes of met-deficient complete MEM containing 2% serum) were added. Cultures were incubated in $CO_2$ incubator at 35 or 37° C. for 3 hours. Radioactive media was removed, and cells were rinsed twice with PBS. Cells were lysed in 1 ml lysis buffer (10 mM NaCl, 10 mM Tris-Cl pH 7.5, 1.5 mM $MgCl_2$, containing 1% NP-40) at 35° C. for one minute. The lysed cell-media mixture was transferred to a screw-cap Eppendorf tube on ice. 0.2 ml. lysis buffer was added to the plate, and this lysate was added to the original lysate. The lysate was spun at 2000×g 2 minutes 4° C., and the supernatant was removed to a new tube. SDS was added to the sup to make a final concentration of 1% SDS, and samples were frozen. Samples (4 μl) were run on SDS-10% PAGE gels (Laemmli). Gels were fixed, washed, dried on a vacuum gel drier, and exposed to Kodak BioMax film for 1-3 days at room temperature.

Figure 5A:
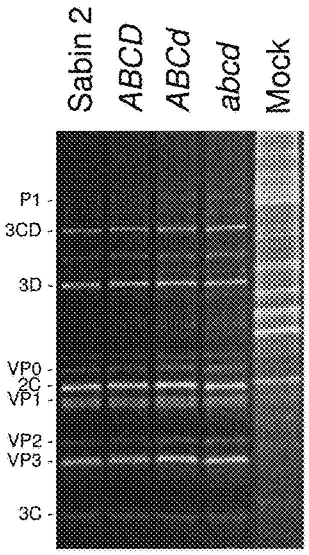
FIGS. 5A and 5B are digital images showing production of intracellular Poliovirus-specific proteins produced by ABCD, ABCd, and abcd viruses in vivo and in vitro. (A) Lysates of infected HeLa cells labeled with [$^{35}$S]methionine at 4 to 7 hours postinfection. (B) In vitro translation products from rabbit reticulocyte lysates programmed with 250 ng of RNA transcripts from cDNAs ABCD, ABCd, and abcd. Noncapsid proteins were identified by their electrophoretic mobilities and band intensities; capsid proteins were identified by their comigration with proteins from purified virions.

Although it was thought that replacement of preferred codons with unpreferred codons would lower replicative fitness primarily by reducing the rate of translation (at the level of polypeptide chain elongation) of viral proteins and potentially disrupting their proteolytic processing in infected cells, unexpectedly, it was observed that the electrophoretic profiles of the labeled virus-specific proteins were similar for all S2R viruses, both in the relative intensities of the labeled viral protein bands and in the total amounts of labeled viral proteins produced in the infected cells (FIG. 5A). The four S2R viruses were similar in the efficiency of shutoff of host cell protein synthesis and in the synthesis and processing of viral proteins in infected HeLa cells. Similar results were obtained with MEF1 viruses (see Example 10, FIG. 5C).

Example 5

In Vitro Translation

This example describes methods used to determine the ability of deoptimized poliovirus RNA transcripts to serve as templates for in vitro translation in rabbit reticulocyte lysates. Similar methods can be used to measure in vitro protein synthesis by any deoptimized pathogen sequence.

For preparation of truncated polio proteins that include the entire capsid protein and terminate in the 2C noncapsid portion of the poliovirus genome, plasmid DNAs were digested with SnaBI. Full-length and partial viral RNAs were transcribed as described herein. In vitro-transcribed RNAs were subjected to phenol/chloroform extraction and two successive ammonium acetate isopropanol precipitations, including 70% ethanol washes. The RNA pellets were air-dried for 5 minutes and then resuspended in a small volume of RNAse-free water. The resuspended RNA was quantitated by measuring $OD_{260}$ absorbance in a spectrophotometer.

In vitro translation was performed using a nuclease-treated rabbit reticulocyte lysate (Promega, Madison, Wis.) supplemented with an uninfected HeLa cell extract (Brown and Ehrenfeld Virology 97: 396-405, 1979), according to the manufacturer's instructions. The HeLa extract has been found to improve the fidelity of initiation of translation. Briefly, 35 μl micrococcal nuclease-treated, supplemented rabbit reticulocyte lysate was mixed with 7 μl HeLa cell extract, 1 μl 1 mM amino acid mix (minus methionine), various amounts of RNA (0.2-1 ug), 30 μCi $^{35}$S-met at 15 mCi/ml, and 1 μl RNasin (40 u/ul) in a final volume of 50 μl. The reactions were incubated at 30° C. for 3 hours. Samples (4 μl) were run on SDS-10% PAGE gels (Laemmli). Gels were fixed, washed, dried on a vacuum gel drier, and exposed to Kodak BioMax film for 1-3 days at room temperature.

Figure 5B:
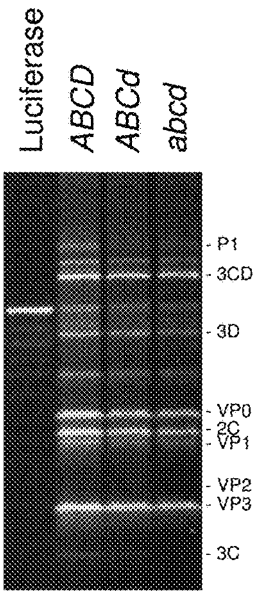
Figure 5C:
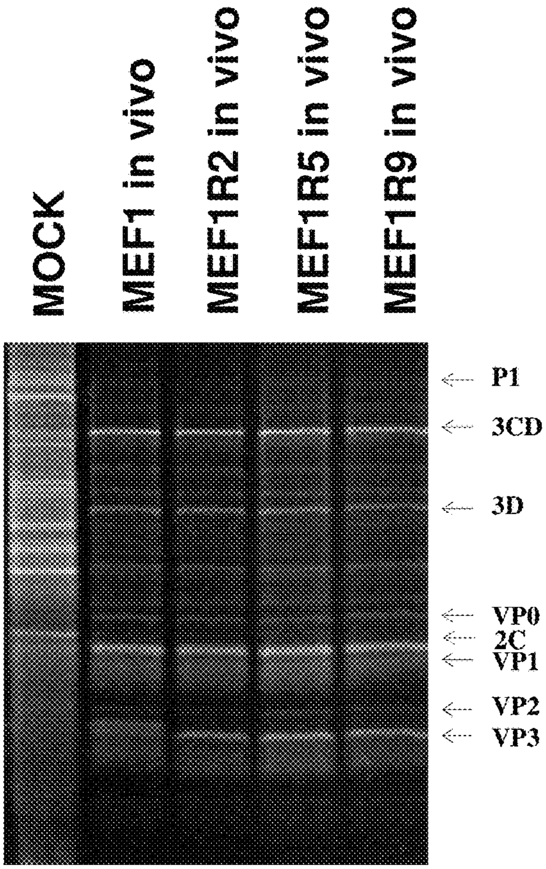
FIGS. 5C and 5D are digital images showing production of intracellular MEF Poliovirus-specific proteins produced by ABC, ABc, and abc viruses in vivo and in vitro. (A) Lysates of infected HeLa cells labeled with [$^{35}$S]methionine at 4 to 7 hours postinfection. (B) In vitro translation products from rabbit reticulocyte lysates programmed with 250 ng of RNA transcripts from cDNAs ABC, ABc, and abc. Noncapsid proteins were identified by their electrophoretic mobilities and band intensities; capsid proteins were identified by their comigration with proteins from purified virions.
Figure 5D:
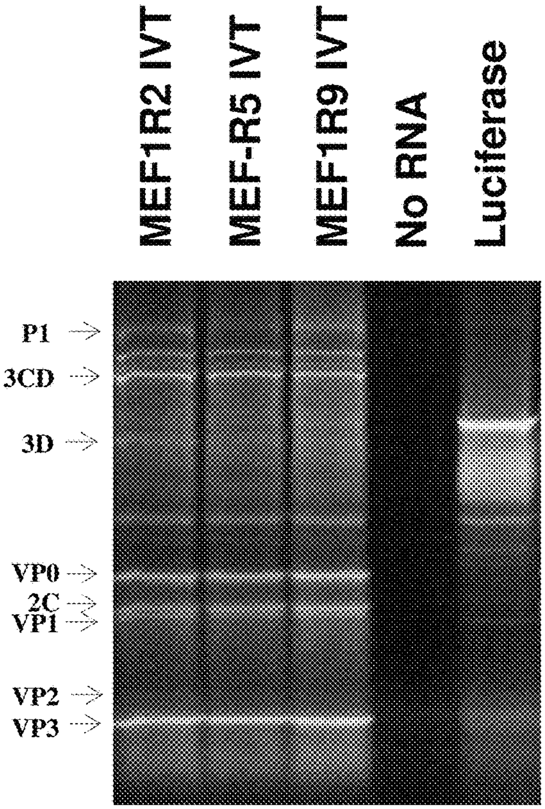

The efficiency of the poliovirus RNA transcripts to serve as templates for in vitro translation in rabbit reticulocytes was similar for all of the viruses tested (S2R9, S2R19, S2R23, MEF1R1, MEF1R2, MEF1R5, and MEF1R9). No decline in translational efficiency was observed with increasing numbers of replacement codons in the in vitro translation systems tested (FIG. 6). The observation that codon replacement had little detectable effect in vivo upon viral protein synthesis and processing was mirrored by the results of in vitro translation experiments in rabbit reticulocyte lysates. Full-length in vitro transcripts from cDNA constructs ABCD, ABCd, and abcd (S2R9, S2R19, S2R23), ABC, ABc and abc (MEF1R2, MEF1R5, and MEF1R9) programmed the in vitro synthesis and processing of virus-specific proteins with nearly equal efficiency (FIGS. 5B and 5D). The in vivo and in vitro protein synthesis results indicate that the reduced replicative fitness of the codon-replacement viruses is not primarily attributable to impairment of translation and processing of viral proteins.

The protein synthesis results are somewhat surprising, since translational effects have been previously observed when unpreferred codons were introduced into the coding region of some genes of bacteria (Barak et al., *J. Mol. Biol.* 256:676-84, 1996), yeast (Hoekema et al., *Mol. Cell Biol.* 7:2914-24, 1987), yeast, and one animal virus (Zhou et al., *J. Virol.* 73:4972-82, 1999). It is possible that translational effects were not observed because some of the codons that are rarely used in poliovirus genomes are used frequently in highly expressed mammalian genes, such that the levels of the tRNAs for these codons may be high and therefore difficult to deplete. Another possible explanation is that poliovirus RNA is not equivalent to a highly expressed gene, as it is not translated as efficiently as mRNAs of the most highly expressed mammalian genes. Polypeptide chain elongation rates are ~220 amino acids per min for poliovirus in HeLa cells at 37° C. (Rekosh, *J. Virol.* 9:479-87, 1972) compared with ~600 amino acids per min for the α-chain of hemoglobin in rabbit reticulocytes (Hunt et al., *J. Mol. Biol.* 43:123-33, 1969). The translation results do not exclude the possibility that there are local conditions in certain cells in an infected person or animal that result in decreased translational efficiency.

Example 6

Specific Infectivities of Virions of Codon-Replacement Viruses

This example describes methods used to measure the infectivity of the deoptimized Sabin viruses described in Example 2. Similar methods can be used to measure the infectivity of any pathogen with one or more deoptimized sequences.

Virus was propagated in RD cells, liberated by freeze-thaw, and concentrated by precipitation with polyethylene glycol 6000 (Nottay et al., *Virology* 108:405-23, 1981). Virions were purified by pelleting, isopycnic centrifugation in CsCl, and repelleting essentially as described by Nottay et al., (*Virology* 108:405-23, 1981). The number of virus particles in each preparation recovered from the CsCl band with a buoyant density of 1.34 g/ml was calculated from the absorbance at 260 nm using the relationship of $9.4\times10^{12}$ virions per $OD_{260}$ unit (Rueckert, R. R. 1976. On the structure and morphogenesis of picornaviruses, p. 131-213. In H. Fraenkel-Conrat and R. R. Wagner (ed.), Comprehensive Virology, vol. 6. Plenum Press, New York.).

The poliovirions produced by HeLa cells infected with viruses ABCD (S2R9), ABCd (S2R19), and abcd (S2R23) were analyzed. Purified infectious virions of all three viruses had similar electrophoretic profiles and the high VP2/VP0 ratios typical of mature capsids. However, the specific infectivities of the purified virions decreased with increased numbers of replacement codons. For example, the particle/PFU ratios increased from 293 (ABCD) to 1221 (ABCd) to 5392 (abcd). The magnitude of the decline in specific infectivity was dependent upon the infectivity assay used, and was steeper with the plaque assay than with the limit dilution assay. This difference arose because the $CCID_{50}$/PFU ratio in HeLa cells increased with the number of replacement codons, from 1.1 (ABCD) to 5.4 (abcd).

Example 7

Measurement of Viral RNA in Infected Cells

Alterations in the primary sequence of the viral genome could affect the levels of RNA in infected HeLa cells by modifying the rates of RNA synthesis or by changing the stabilities of the intracellular viral RNA molecules. This example describes methods used to measure the amount of viral RNA produced in cells infected with the deoptimized viruses described in Example 2. However, one skilled in the art will recognize that similar methods can be used to measure the amount of viral RNA produced in cells infected with any pathogen with one or more deoptimized sequences.

Production of viral RNA in infected HeLa cells during the single-step growth assays described above was measured by quantitative RT-PCR using a Stratagene MX4000 PCR system programmed to incubate at 48° C. for 30 min, 95° C. for 10 min, followed by 60 PCR cycles (95° C. for 15 sec, 60° C. for 1 min). Sequences within the 3' half of the $3D^{pol}$ region of Sabin 2 were amplified using primers S2/7284A (ATTGGCACACTCCTGATTTTAGC; SEQ ID NO: 59) and S2/7195S (CAAAGGATCCCAGAAACACACA; SEQ ID NO: 60), and the amplicon yield measured by the fluorescence at 517 nm of the TaqMan probe S2/7246AB (TTCTTCTTCGCCGTTGTGCCAGG; SEQ ID NO: 61) with FAM attached to the 5' end and BHQ-1 (Biosearch Technologies, Novato, Calif.) attached to the 3' end. Stoichiometric calculations used a value of $2.4\times10^6$ for the molecular weight of Sabin 2 RNA (Kitamura, et al., *Nature* 291:547-53, 1981; Toyoda et al., *J. Mol. Biol.* 174:561-85, 1984).

Figure 6A:
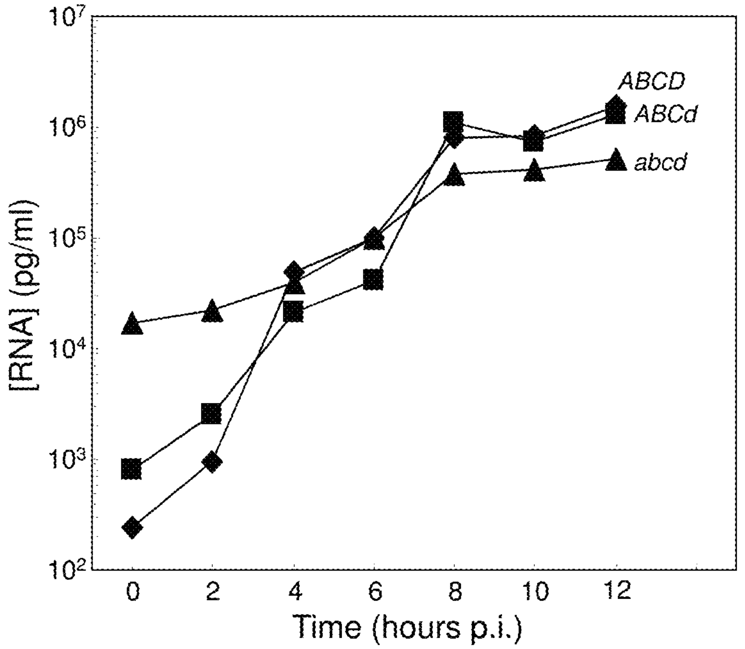
FIGS. 6A and 6B are graphs showing RNA yields from (A) ABCD, ABCd, and abcd Sabin 2 viruses obtained in the single-step growth experiments described in FIGS. 4A and 4B, and for (B) ABC, ABc, and abc MEF1 viruses. RNA levels were determined by quantitative PCR using primers and a probe targeting $3D^{pol}$ region sequences. One pg of poliovirus RNA corresponds to ~250,000 genomes.

Total levels of viral RNA present in infected HeLa cells were measured at 2 h intervals from 0 to 12 hours in the single-step growth experiments described above and shown in FIGS. 4A and 4B. Viral RNA was measured by quantitative PCR using primers targeting $3D^{pol}$ sequences shared among all viruses. After 12 hours, total viral RNA yields were highest (915 ng/ml; equivalent to ~57,000 RNA molecules/cell) for ABCD, lower (569 ng/ml; ~35,000 RNA molecules/cell) for ABCd, and lowest (330 ng/ml; ~20,000 RNA molecules/cell) for abcd (FIG. 6A). Plaque yields, by contrast, had followed a steeper downward trend, from ~130 PFU/cell (ABCD), to ~30 PFU/cell (ABCd), to ~2 PFU/cell (abcd) (FIGS. 3B and 4A-B). Combining these values, the following yields are obtained: ~440 RNA molecules/PFU (ABCD), ~1200 RNA molecules/PFU (ABCd), and ~10,000 RNA molecules/PFU (abcd). Although the RNA molecules/PFU ratios were similar to the particle/PFU ratios determined above for each virus, the number of RNA molecules produced in infected cells is typically about twice the number of virus particles, because only about 50% of the viral RNA product is encapsidated (Hewlett et al., Biochem. 16:2763-7, 1977). Nonetheless, the two sets of values clearly followed similar trends, as RNA yields and specific infectivities declined with increased number of replacement codons.

Because the particle/PFU (or RNA molecule/PFU) ratios were higher for the codon-replacement viruses than for the unmodified ABCD prototype, substantially more ABCd and abcd virion particles were used to initiate the single-step growth infections, even though the input MOIs varied over a narrow (~4-fold) range (FIGS. 4A-B). Consequently, the initial input RNA levels were high for ABCd and very high for abcd, such that the extent of amplification of viral RNA at 12 h was ~4000-fold for ABCD, ~1000-fold for ABCd, and only ~20-fold for abcd (FIG. 6).

The observation that the eclipse phases in the single-step growth experiments were increasingly prolonged as the number of replacement codons increased indicates that codon-replacement viruses were less efficient at completing an early step (or steps) of the infectious cycle. This view is reinforced by the observation that the particle/PFU and RNA molecule/PFU ratios increased sharply with the number of replacement codons. It thus appears that a larger number of codon-replacement virus particles are needed to initiate a replicative cycle, but once the cycle had started the synthesis and processing of viral proteins is nearly normal. Although total viral RNA yield was reduced by only ~3-fold in the most highly modified abcd virus, its viral RNA amplification was only ~20-fold, indicating that impairment of viral RNA synthesis can also contribute to reduced replicative fitness.

Example 8

RNA Secondary Structures of Codon Deoptimized Sequences

This example describes methods used to predict RNA secondary structures of the deoptimized Sabin 2 codon genomes generated in Example 2.

Prediction of the secondary structure of the RNA templates of virus constructs S2R9, S2R19, and S2R23 was performed using the mfold v. 3.1 program (Zuker, *Science* 244: 48-52, 1989; Mathews et al., *J. Mol. Biol.* 288:911-40, 1999; Palmenberg and Sgro, *Semin. Virol.* 8:231-41, 1997) that implements an energy minimization algorithm that finds a structure lying within a percentage (P) of the calculated minimum energy (MinE). Running parameters were set to default except folding temperature (T), which was set to 35° C. The free energy increment (ΔΔG35° C.), dependent on P, is set to 1 kcal/mol or 12 kcal/mol ($SubE_{12}$) when the calculated ΔΔG35° C. values lie below or above these values.

The genomic RNAs of polioviruses and other enteroviruses appear to have relaxed secondary structures outside of the 5'-UTR, the 3'-UTR, and the cre element within the 2C region (Palmenberg and Sgro, *Semin. Virol.* 8:231-41, 1997; Witwer et al., *Nucleic Acids Res.* 29:5079-89, 2001). Accordingly, under physiological conditions, most bases within the ORF can pair with more than one partner, and poliovirus genomes can fold into many different secondary structures having similar thermodynamic stabilities (Palmenberg and Sgro, *Semin. Virol.* 8:231-41, 1997). However, the incorporation of numerous base substitutions into the codon-replacement constructs and the concomitant increase in G+C content might destabilize folding patterns that had been subject to natural selection and stabilize other pairings absent from the unmodified Sabin 2 genome.

Figure 7:
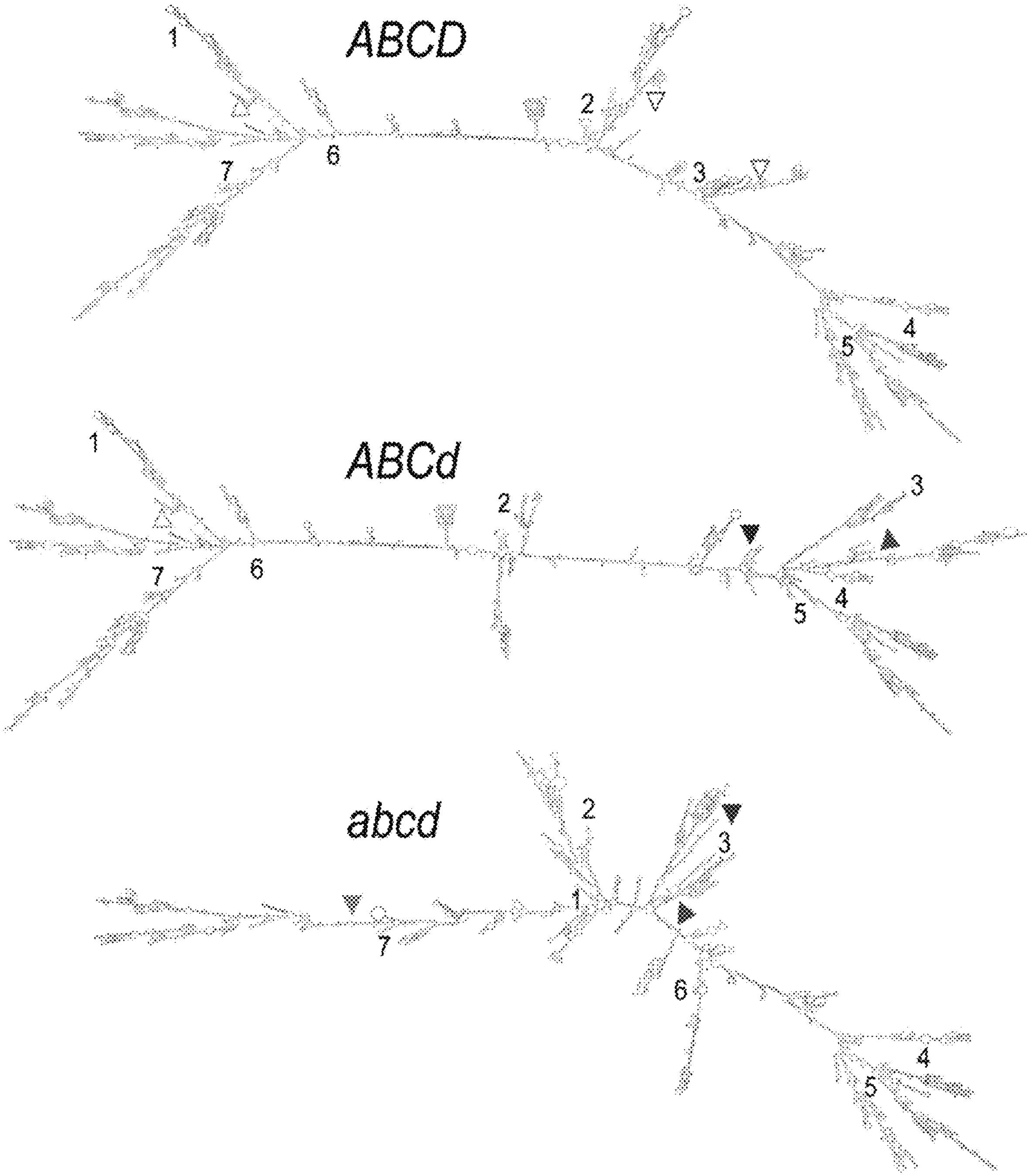
FIG. 7 shows MinE RNA secondary structures for complete genomes of ABCD, ABCd, and abcd viruses calculated by using the mfold algorithm. Base positions are numbered in increments of 1000. Triangles mark boundaries of codon-replacement cassettes: beginning of cassette A (nt 657); beginning of cassette D (nt 2616); end of cassette D (nt 3302). Only intervals bounded by filled triangles had replacement codons.

To determine the effects of codon replacement on RNA folding patterns, the secondary structures of the complete genomes of ABCD, ABCd, and abcd were calculated using the mfold v. 3.1 algorithm. The calculated global thermodynamic stabilities (expressed as minimum free-energy at 35° C. [ΔG35° C.] or MinE) of the RNA secondary structures increased with increasing G+C content (ABCD, ΔG35° C.=−2047 kcal/mol; ABCd, ΔG35° C.=−2078 kcal/mol; abcd, ΔG35° C.=−2191 kcal/mol), and the number of predicted stem structures increased from 546 (ABCD), to 557 (ABCd), to 562 (abcd). The calculated MinE structures for the three viruses also differed (FIG. 7). However, the in vivo pairings are likely to be much more flexible and dynamic than indicated by the static structures shown in FIG. 7, as many alternative structures having nearly equivalent (+12 kcal/mol) MinE values are predicted (SubE12). A more informative measure of structural rigidity is the p-num value, which gives the number of alternative pairings for each base. Unaltered in all viruses were the stable (low p-num values, colored red) secondary structures in the 5'-UTR, the 3'-UTR, and the cre element, as well as the close apposition of the 5' and 3' termini. However, some folding patterns were modified in the codon-replacement viruses, and the structural perturbations extended beyond the boundaries of the modified cassettes. Alterations in stable pairings were most extensive with abcd, where the long P1/capsid region:P3/noncapsid region pairings (nt 1480-1714:nt 5998-5864) predicted for Sabin 2 RNA were destabilized and other pairings formed (FIG. 7).

Example 9

Stability of the Mutant Phenotypes

This example describes methods used to determine the stability of the codon-deoptimized polioviruses during serial passage in HeLa cells.

Three constructs generated as described in Example 2 were examined: ABCD (unmodified prototype), ABCd (modified VP1 region), and abcd (modified P1/capsid region). Poliovirus constructs S2R9 (ABCD), S2R19 (ABCd), and S2R23 (abcd) were serially passaged in HeLa cell monolayers in T75 flasks at 35° C. for 36 hours, at an input MOI ranging from 0.1 PFU/cell to 0.4 PFU/cell. Each virus was passaged 25 times (at 35° C. for 36 hours), wherein each passage represented at least two rounds of replication. At every fifth passage, virus plaque areas, plaque yields, and the genomic sequences of the bulk virus populations were determined, and the MOI was readjusted to ~0.1 PFU/cell.

Figure 8C:
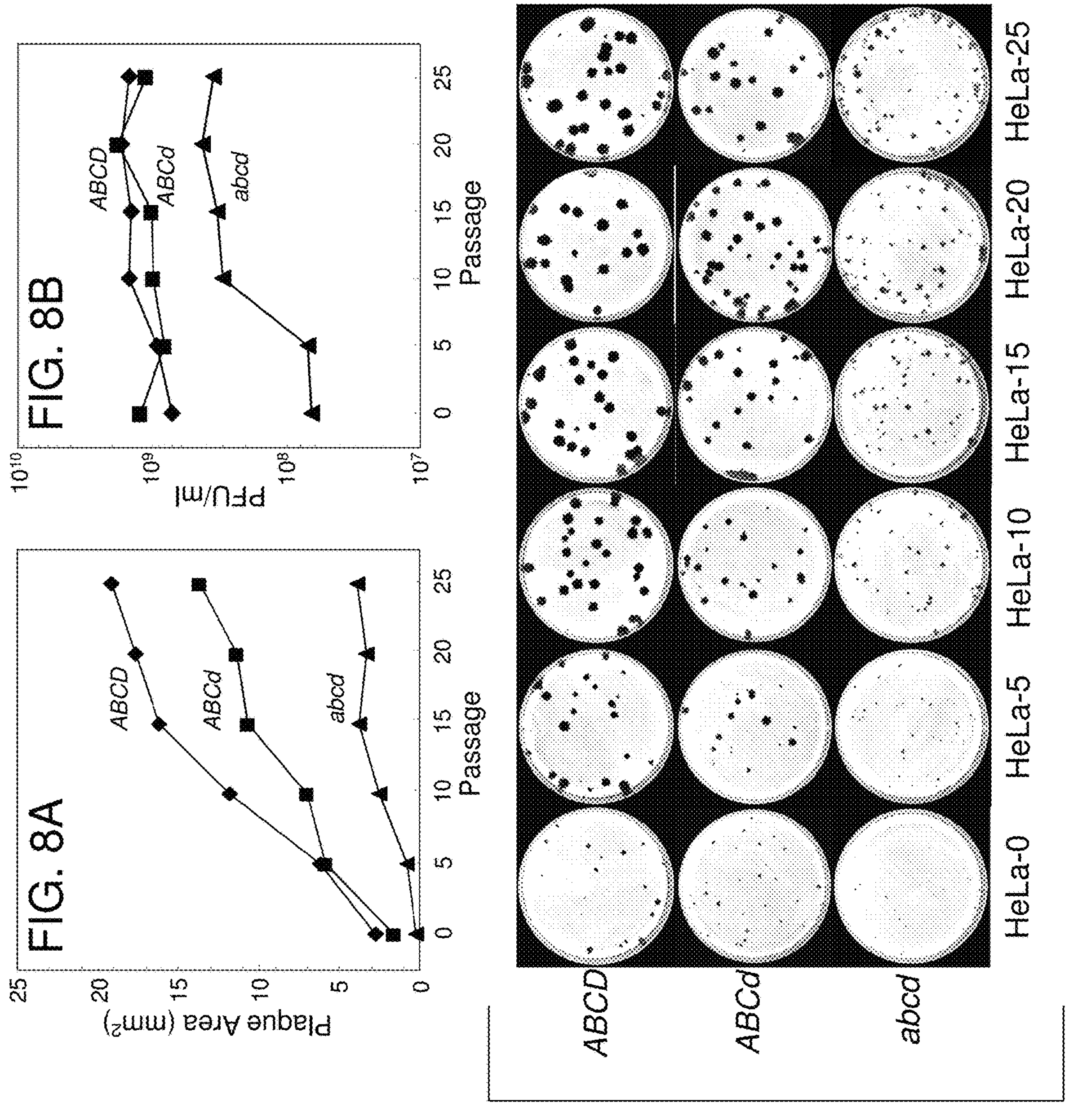
FIG. 8C is a digital image showing plaque phenotypes at 35° C. in HeLa cells (35° C., 60 hours).

All three constructs evolved during serial passage, as measured by increasing plaque size, increasing virus yield, and changing genomic sequences (Table 3; FIGS. 8A-C). Evolution of the ABCD prototype was the least complex. Plaque areas increased ~6-fold from passage 0 to passage 15, and this was accompanied by nucleotide substitutions at 6 sites. By contrast, virus yields increased 2.5-fold over the 25 passages. Two substitutions ($U_{1439}$→C and $C_{2609}$→U) were fixed by passage 10, three more ($U_{3424}$→C, $A_{35}86$→G, and $A_{5501}$→G) by passage 15, and all 6 substitutions were fixed by passage 20. Mixed bases were found at passage 5 ($C_{1439}$>U, $C_{2609}$>U, and $U_{3424}$>C), passage 10 ($C_{3424}$>U, $G_{3586}$>>A, and $G_{5501}$>A) and passage 15 ($A_{5630}$>U). No evidence of back mutation or serial substitutions at a site was observed.

TABLE 3

Nucleotide substitutions in ABCD, ABCd, and abcd during passage.

| | Nt | Nucleotide substitutions | | | | | | -1 | Codon | +4 | Amino acid | | Location in Poly- |
|---|---|---|---|---|---|---|---|---|---|---|---|---|---|
| Virus[a] | Position | RD1 | HeLa5 | HeLa10 | HeLa15 | HeLa20 | HeLa25 | nt[b] | change[c,d,e] | nt[b] | Subst.[d] | Gene | protein[f] |
| ABCD | 1439 | U | C > U | C | C | C | C | C | C**U**U→C**C**U | G | L→P | VP2 | S: NAg-2 |
| | 2609 | C | C > U | U | U | U | U | U | G**C**A→G**U**A | U | A→V | VP1 | I: NC |
| | 3424 | U | U > C | C >> U | C | C | C | C | **U**AC→**C**AC | A | Y→H | 2A | NC |
| | 3586 | A | A | G >> A | G | G | G | G | **A**GA→**G**GA | A | R→G | 2A | NC |
| | 5501 | A | A | G > A | G | G | G | C | A**A**A→A**G**A | G | K→R | 3C | NC |
| | 5630 | A | A | A | A > U | U | U | U | C**A**G→C**U**G | G | Q→L | 3C | NC |
| ABCd | 1456 | A | A >> G | A >> G | A > G | A = G | G > A | U | **A**AC→**G**AC | C | N→D | VP2 | S: NAg-2 |
| | 2776 | A | A | A | A > G | A > G | A > G | G | **A**AG→**G**AG | C | K→E | VP1 | S: NAg-1 |
| | 2780 | G | G >> A | A > G | G > A | G = A | G > A | G | C**G**G↔C**A**G | G | R↔Q | VP1 | S: NAg-1 |
| | 3120[g] | G | G | G | G > A | A > G >> C | A > C >> G | U | GC**G**→GC**A** | A | A | VP1 | I: C |
| | 3377 | C | C | C | C > U | C > U | C > U | A | A**C**G↔A**U**G | A | T↔M | VP1 | I: NC |
| | 3808 | U | U | U | U > C | U > C | U >> C | U | U**A**U→U**G**U | G | Y→R | 2A | NC |
| | 3809 | A | A > G | G >> A | G = A | G > A | G >> A | | | | | | |
| | 4350 | A | A > G | G > A | G = A | G > A | G = A | C | UU**A**↔UU**G** | U | L | 2C | C |
| abcd | 1169 | G | G | G >> A | A >> G | G > A | G > A | G | C**G**G↔C**A**G | A | R↔Q | VP2 | I:C |
| | 1447 | A | A | A | A | A = G | G > A | G | **A**AC→**G**AC | ***G*** | N→D | VP2 | S: NAg-2 |

TABLE 3-continued

Nucleotide substitutions in ABCD, ABCd, and abcd during passage.

| Virus[a] | Nt Position | Nucleotide substitutions | | | | | -1 nt[b] | Codon change[c,d,e] | +4 nt[b] | Amino acid Subst.[d] | Gene | Location in Polyprotein[f] |
|---|---|---|---|---|---|---|---|---|---|---|---|---|
| | | RD1 | HeLa5 | HeLa10 | HeLa15 | HeLa20 | HeLa25 | | | | | |
| | 1608 | U | U | U | U | U = C | C > U | C | GAU→GAC | A | D | VP2 | I: C |
| | 2622 | C | C | C >> U | U >> C | C > U | C | C | GU<u>C</u>↔GU<u>U</u> | G | V | VP1 | I: C |
| | 2633 | C | C | C | U >> C | C >> U | C | U | G<u>CG</u>↔GUG | A | A↔V | VP1 | I: NC |
| | 2903 | A | A | A | A | A = G | G > A | C | AAC→AGC | U | N→S | VP1 | S: NAg-1 |
| | 2915 | C | C | C > U | C >> U | C > U | C >> U | U | G<u>CG</u>↔GUG | A | A↔V | VP1 | ~S: ~NAg-1 |
| | 2986 | A | A | A | A | A = G | G > A | U | AAA→GAA | U | K→E | VP1 | I: V |
| | 3120[g] | G | G > A | G = A | A >> G | A >> G | A >> G | U | G<u>CG</u>→GCA | A | A | VP1 | I: NC |
| | 3121 | A | A | A | A >> C | A > C | A > C | G | AAA→CAA | G | K→Q | VP1 | I: C |
| | 3150 | G | G | G | A > G | G | G | C | A<u>CG</u>→ACA | G | T | VP1 | S: NAg-2 |
| | 3480 | U | U > G | G > U | G >> U | G | G | G | AGU→AGG | G | S→R | 2A | V |
| | 4473 | G | G | G | A > G | A | A | C | AAG→AAA | C | K | 2C | C |

[a]Virus constructs: ABCD, S2R9; ABCd, S2R19; abcd, S2R23.
[b]Nucleotides immediately preceding (-1 nt) and immediately following (+4 nt) codon.
[c]Varying nucleotide is shown in boldface font.
[d]Rightward pointing arrows indicate substitutions that steadily accumulated with increased passage; bidirectional arrows indicate bidirectional fluctuations among substitutions.
[e]CG dinucleotides, including those across codons, are underlined.
[f]Location of amino acid replacements: S, virion surface residue; NAg, neutralizing antigenic site (1, 2); ~NAg, adjacent to neutralizing antigenic site; I, internal capsid residue not exposed to virion surface; NC, non-consensus amino acid; V, variable amino acid.
[g]Represents direct reversion of engineered codon change.

All substitutions mapped to the coding region, and 2 of 6 (33%) mapped to the capsid region, which represents 35.4% of the genome. In distinct contrast to the pattern of poliovirus evolution in humans, where the large majority of base substitutions generate synonymous codons, all six of the observed base substitutions (4 at the second codon position and 2 at the first codon position) generated amino acid replacements (Table 3). None of the substitutions involved loss of a CG dinucleotide.

Evolution of the codon-replacement constructs was more complex and dynamic. In construct ABCd, 4 of the 8 (50%) variable positions mapped to VP1 (12.1% of genome), and 3 of these 4 mapped within the replacement-codon d interval (9.2% of genome) (Table 3). Substitutions at half of the positions involved the apparent loss of CG dinucleotides (6.3% of total genome), although in all instances the loss from the virus population was incomplete. One d interval substitution ($G_{3120}$→A) eliminating a CG dinucleotide represented a back mutation to the original synonymous codon. A second d interval substitution ($G_{2780}$→A) reduced the frequency of a CG dinucleotide by HeLa passage 10, but the CG dinucleotide predominated in the population by HeLa passage 25. Another substitution ($C_{3377}$→U), which resulted in the partial loss of a CG dinucleotide, mapped just downstream from the d interval. Two adjacent substitutions, mapping to positions 3808 and 3809 in 2A, resulted in a complex pattern of substitution involving first and second positions of the same codon. The ABCd construct resembled the ABCD prototype in that substitutions in 6 of the 8 generated amino acid replacements. By contrast, the ABCd construct differed markedly from the ABCD prototype because the dynamics of substitution had apparently not stabilized by passage 25, and mixed bases were found at all 8 positions of variability (Table 3). The active sequence evolution was accompanied by progressively increasing plaque areas over a ~6-fold range, while virus yields fluctuated over a narrow (~2-fold) range (FIGS. 8A-C).

Evolution of the abcd construct was the most dynamic, as determined by expanding plaque areas, increasing virus yields, and nucleotide substitutions. Plaque areas increased ~15-fold from passage 0 to passage 15, and then stabilized (FIGS. 8A-C). Virus yields increased most sharply (~4-fold) between passages 5 and 10, but remained ~4-fold lower than those of the ABCD and ABCd constructs at passage 25 (FIG. 8B). Among the 13 sites of nucleotide variability, most (11/13; 84.6%) mapped to the capsid region, all within the codon-replacement interval, 8 within VP1, 3 within VP2, and none within VP3 (Table 3). As with the other constructs, most (8/13; 61.5%) of the substitutions encoded amino acid replacements. Substitutions at six sites involved partial, transient, or complete loss of CG dinucleotides.

As in the ABCd construct, a $G_{3120}$-A substitution eliminated a CG dinucleotide and restored the original Sabin 2 base. Interestingly, this same reversion was observed in 8 other independent passages of the abcd construct (data not shown). The two variable sites outside of the capsid region (one in 2A, the other in 2C) stabilized with new substitutions by HeLa passage 20, whereas 8 of the 11 variable sites within the capsid region still had mixed bases at passage 25. Apart from the back-mutation at position 3120, all other variable sites differed between the ABCD, ABCd, and abcd constructs. No net changes were observed at site $A_{481}$ (in the 5'-UTR), and $U_{2909}$ (in the VP1 region), known to be strongly selected against when Sabin 2 replicates in the human intestine.

In addition to the elimination of several CG dinucleotides, there was also a net loss (1 lost, 5 partially lost, 1 gained) of UA dinucleotides in the high-passage isolates (Table 3). In the codon-replacement constructs, elimination of UA dinucleotides was incomplete up to passage 25. Most (4 of 6) UA losses involved amino acid replacements. Unlike codons most frequently associated with loss of CG dinucleotides, none of the codons associated with loss of UA dinucleotides were replacement codons. While not as strongly suppressed as CG dinucleotides, UA dinucleotides are underrepresented in poliovirus genomes and human genes.

Most (8 of 13) of the capsid amino acid replacements mapped within or near surface determinants forming neutralizing antigenic sites. For example, four replacements mapped to NAg-1 site and four to NAg-2 site (Table 3). Although surface determinants are generally the most variable, amino acid replacements also occurred in naturally variable non-surface residues in VP1 (Lys-Glu) and $2A^{pro}$ (Ser-Arg). Most of the synonymous mutations mapped to codons for conserved amino acids. However, several of the amino acid replacements, including 5 of the 6 in the ABCD construct, were substitutions to non-consensus residues (Table 3).

Sequence evolution in HeLa cells of the unmodified ABCD virus differed in many respects from the codon-replacement ABCd and abcd viruses. Nucleotide substitutions in the ABCD progeny were dispersed across the ORF, dimorphic variants emerged in the early passages, all 6 mutations were fixed by passage 20, and a single dominant master sequence emerged. By contrast, populations of the ABCd and abcd progeny were complex mixtures of variants at least up to passage 25, and the majority base at the variable sites typically fluctuated from passage to passage. Apparently the incorporation of unpreferred codons into the ABCd and abcd genomes led to an expansion of the mutant spectrum and to the emergence of complex and unstable quasispecies populations.

To identify potential critical codon replacements, substitutions that accumulated in the genomes of codon-replacement viruses upon serial passage in HeLa cells were identified. Only one substitution, G3120-A, a direct back mutation to the original sequence, was shared between derivatives of the ABCd and abcd viruses after serial passage. The 19 other independent substitutions found among the ABCd and abcd high-passage derivatives were associated with 12 different codon triplets. Codon replacement in the VP1 region appeared to have proportionately greater effects on replicative fitness than replacements in other capsid intervals, an observation reinforced by the finding that 8 of the 13 sites that varied upon serial passage of abcd mapped to the VP1 region. Replacement of VP1 region codons in the genome of the unrelated wild poliovirus type 2 prototype strain, MEF1, also had a disproportionately high impact on growth.

The pattern of reversion among high-passage progeny of the codon-replacement virus constructs indicates that increased numbers of CG dinucleotides may contribute to the reductions in fitness. The codon replacements raised the number of CG dinucleotides in the poliovirus complete ORFs from 181 (ABCD) to 386 (abcd). Although the biological basis for CG suppression in RNA viruses is poorly understood (Karlin et al., *J. Virol.* 68:2889-97, 1994), selection against CG dinucleotides during serial passage of ABCd and abcd was sufficiently strong at some sites as to drive amino acid substitutions into the normally well conserved poliovirus capsid proteins. In every instance, the CG suppression was incomplete, and was frequently reversed upon further passage. The most stable trends toward CG suppression involved nucleotide positions 3120 and 3150 and were not associated with amino acid changes.

Although fitness of the ABCd and abcd constructs increased during serial passage in HeLa cells, the virus yields of the ABCd and abcd derivatives were still below that of the unmodified ABCD construct. In addition, the substitutions accumulating in the ABCd and abcd derivatives during cell culture passage were distinct from the Sabin 2 mutations known to accumulate during propagation in cell culture, In summary, replicative fitness of both codon-deoptimized and unmodified viruses increased with passage in HeLa cells. After 25 serial passages (~50 replication cycles), most codon modifications were preserved and the relative fitness of the modified viruses remained below that of the unmodified virus. The increased replicative fitness of high-passage modified virus was associated with the elimination of several CG dinucleotides.

Codon replacement in VP1 appeared to have greater relative effects on replicative fitness than replacements in other capsid intervals, an observation confirmed in similar experiments with the wild poliovirus type 2 prototype strain, MEF1, and reinforced by the finding that 8 of the 13 sites that varied upon serial passage of the abcd construct mapped to VP1.

Example 10

Deoptimized Poliovirus MEF1

This example describes methods used to generate a deoptimized MEF1 virus, and the effects of deoptimizing the sequence.

Methods used were similar to those for Sabin 2 (see Example 2). FIGS. 9A-E show a capsid coding sequence for the poliovirus type 2, strain MEF1 which is deoptimized. The prototype strain is listed on the top (SEQ ID NO: 6), the nucleotide codon change is indicated below that line (SEQ ID NO: 8), and the single-letter amino acid code is included as the third line (SEQ ID NO: 7).

Replacement codons were introduced into an infectious cDNA clone derived from MEF1 (MEF1R2) within an interval (nt. 748 to 3297) spanning all but the last 29 codons of the capsid region.

R5 VIRUS Cassette AfeI-XhoI most of VP1 (SEQ ID NO: 54)

R6 VIRUS Cassette EcoRV-AgeI VP4-VP2 (SEQ ID NO: 55)

R7 VIRUS Cassette AgeI-AfeI VP3-partial VP1 (SEQ ID NO: 56)

R8 VIRUS Cassette EcoRV-AfeI VP4-VP2-VP3-partial VP1 (SEQ ID NO: 57)

R9 VIRUS Cassette EcoRV-XhoI Complete capsid (almost) (SEQ ID NO: 58)

Within each cassette, synonymous codons for the nine amino acids were comprehensively replaced except at 2 positions (replacement at 2 of these positions would have generated undesirable restriction sites). Unmodified cassettes were identified by uppercase italic letters; the corresponding cassettes with modified codons were identified by lowercase italic letters. Thus, the reference MEF1R2 clone was identified as ABC (SEQ ID NO: 53), and the fully modified construct (MEF1R9), was identified as abc (SEQ ID NO: 58).

Figure 9F:
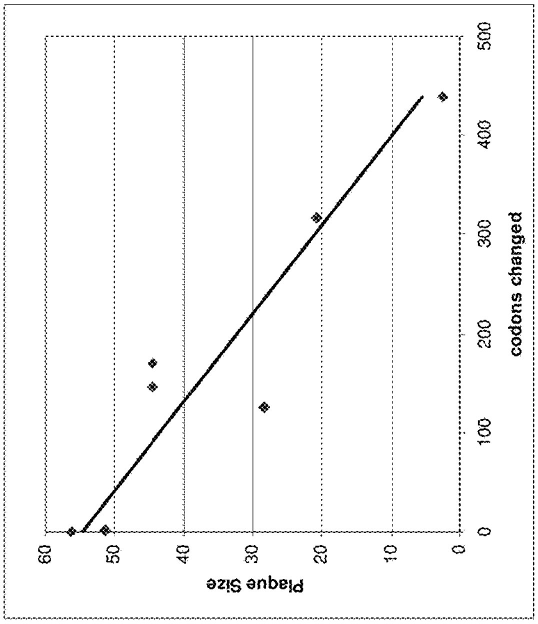
FIG. 9F is a graph showing the inverse linear relationship observed between plaque area and number of replacement codons in MEF1.
Figure 9G:
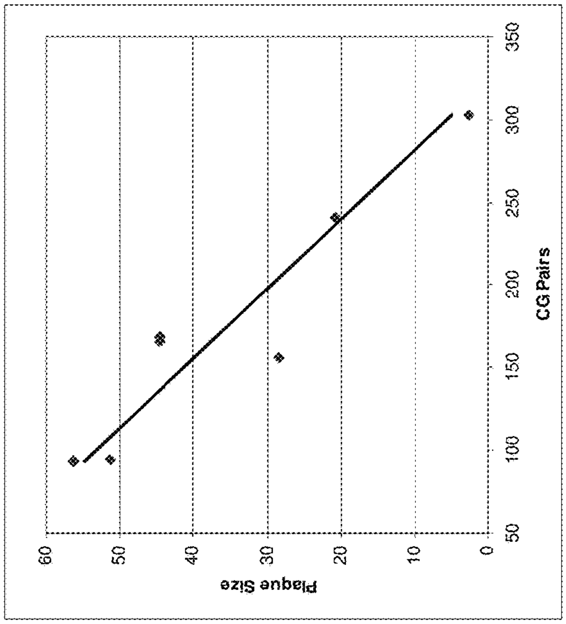
FIG. 9G is a graph showing the inverse linear relationship observed between plaque area and number of CG pairs in MEF1.

The effect of increasing numbers of replacement codons on growth properties was similar to that observed for Sabin 2. An approximately linear inverse relationship was observed between mean plaque area in HeLa cells and the number of nucleotide changes in the capsid region (FIGS. 9F and 9G). Similar inverse linear relationships were observed when the abscissa was rescaled to the number of replacement codons or to the number of CG dinucleotides. There was no strong polarity to the effects of codon replacement within the capsid region, as introduction of replacement codons into any combination of the three cassettes reduced plaque areas approximately in proportion to the total number of replacement codons. However, replacement of codons into VP1 (cassette C) appeared to have slightly stronger effects than replacement elsewhere. Codon replacement across the entire P1/capsid region (construct abc) conferred a minute-plaque phenotype (mean plaque area <25% that of the unmutagenized ABC prototype), and the mean areas of the observed plaques of the abc construct were ~6% of the ABC prototype. Replacements in VP3 and VP4-VP2 that were ~86% of the size of the unmutagenized ABC prototype, underscoring the stronger influence upon plaque size of codon replacement within VP1.

Figure 9I:
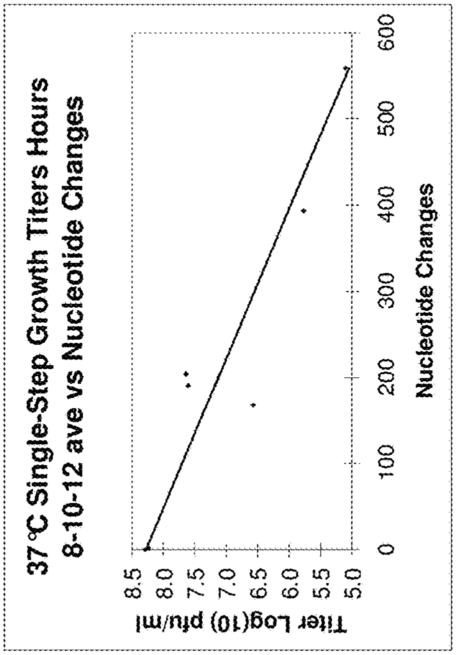
FIG. 9I is a graph showing the inverse linear relationship observed between plaque size and number of nucleotide changes in MEF1.
Figure 9J:
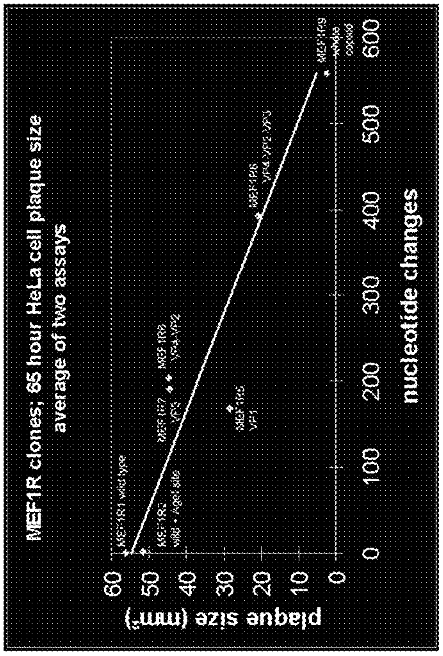
FIG. 9J is a graph showing the inverse linear relationship observed between viral titer and number of nucleotide changes in MEF1.
Figure 9H:
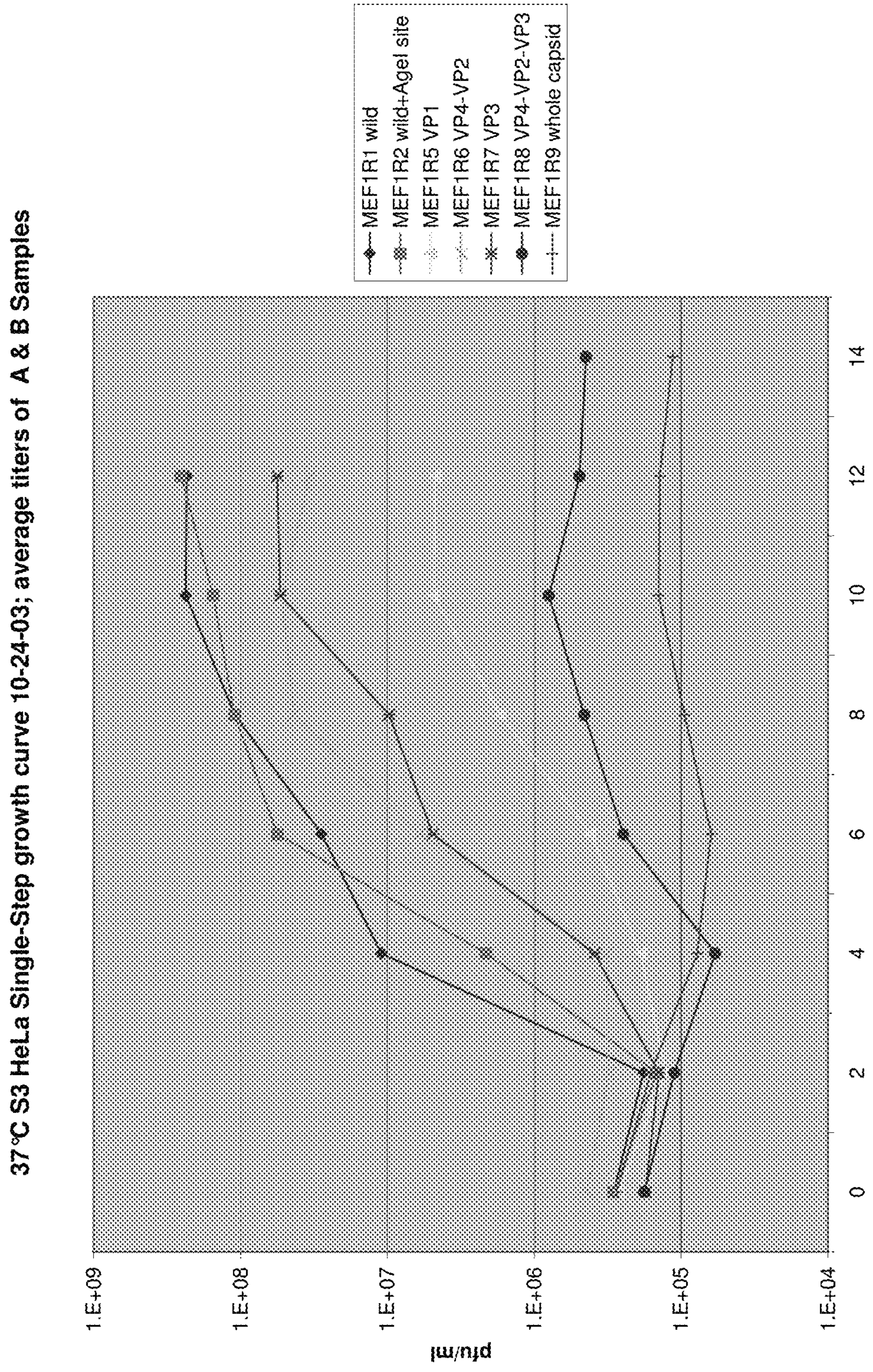
FIG. 9H is a graph showing plaque yields over time for native and deoptimized MEF1 constructs.

Mean virus yields from the single-step growth assays of MEF1 constructs generally decreased as the number of replacement codons increased. As observed for the Sabin 2 codon replacement constructs, production of infectious virus appeared to be slower in the MEF1 codon-replacement constructs than in the unmodified ABC construct. Although maximum plaque yields were obtained at 10-12 hours for all constructs, proportion of the final yields detected at 4 hours were lower for the codon-deoptimized constructs (FIG. 9H). An approximately linear inverse relationship was observed between the log 10 virus yield at 8-12 hours postinfection in the single-step growth curve in HeLa cells and the number of nucleotide changes in the capsid region (FIG. 9I). Plaque size also exhibited a linear inverse relationship with the number of nucleotide changes in the capsid region (FIG. 9J).

The effect on protein translation in vivo and in vitro of the deoptimized MEF viruses was determined using the methods described in Examples 4 and 5. As was observed for the deoptimized Sabin 2 polioviruses, the MEF1 deoptimized viruses had little detectable effect in vivo upon viral protein synthesis and processing (FIG. 5C) or on in vitro translation (FIG. 5D).

Figure 6B:
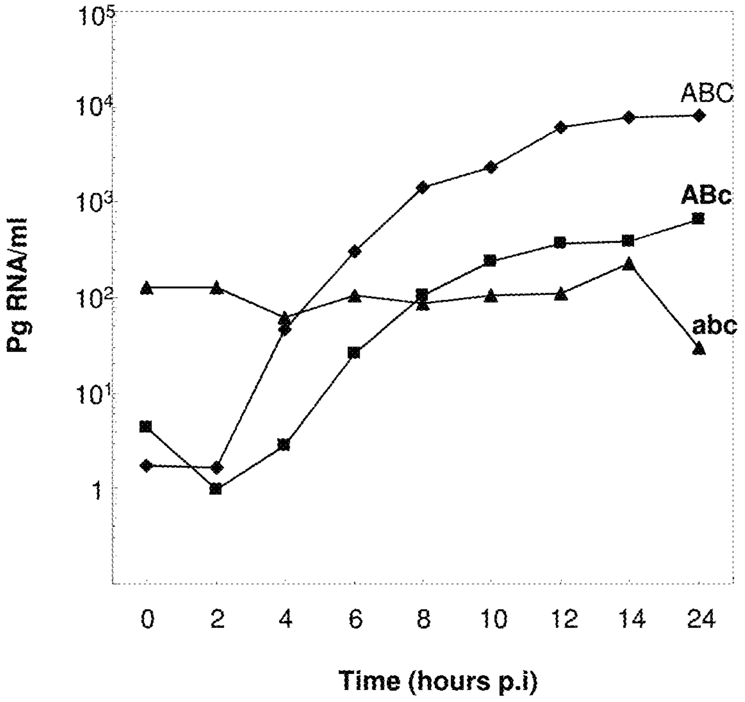

The effect on RNA yields of the deoptimized MEF viruses was determined using the methods described in Example 7, except that the following primers were used to RT-PCR the sequence, CTAAAGATCCCAGAAACACTCA and ATTGGCACACTTCTAATCTTAGC (SEQ ID NOS: 62 and 63), and amplicon yield measured using CTCTTCCTCGCCATTGTGCCAAG (SEQ ID NO: 64). As was observed for the deoptimized Sabin 2 polioviruses, RNA yields declined with increased number of replacement codons. Total viral RNA yields were highest for ABC, lower for ABc, and lowest for abc (MEF1R9) (FIG. 6B). No increase in viral RNA was observed during the s.s. growth curve for MEF1R9 in HeLa S3 cells.

The MEF1 viruses were purified using the methods described in Example 6. In addition to the virus band at 1.34 g/ml, a large amount of material was observed above the virus band. Some of this material was located where empty capsids might be found in the gradient, but the band was diffuse and quite wide. SDS-PAGE analysis of the material revealed VP0, VP1, VP2 and VP3, which is consistent with an immature virus particle.

The ratio of infectivity on RD cells compared to HeLa cells (CCID50) increased as the numbers of nt substitutions increased (Table 4). The ratio for MEF1R2 was 4, whereas the ratio for MEF1R9 was 40. Codon deoptimization had a bigger detrimental effect on the virus titer measured by plaque assay than the virus titer measured by limiting dilution (CCID50) in HeLa cells. For S2R and MEF1R viruses, CCID50 titers were higher than PFU titers (Table 4), with S2R23 and MEF1R9 having the highest ratios of CCID50/PFU. Codon deoptimization had a dramatic effect on the specific infectivity of purified MEF1R viruses, as described for S2R. The particle/HeLa PFU ratios ranged from 182 for MEF1R2 to 18,564 for MEF1R9. The particle/HeLa CCID50s also increased with increased numbers of substitutions, but the effect was more moderate (~4 fold for MEF1R9).

TABLE 4

Infectivity of native and modified polioviruses

| Purified virus | RD CCID50/HeLa CCID50 | CCID50/PFU (HeLa) | Virus particles/HeLa CCID50 | Virus particles/ HeLa PFU |
|---|---|---|---|---|
| MEF1 nonclone | 1 | 3 | 13 | 63 |
| MEF1R1 | 2 | 5 | 15 | 141 |
| MEF1R2 | 4 | 4 | 14 | 182 |
| MEF1R5 | 6 | 4 | 22 | 368 |
| MEF1R8 | 4 | 8 | 34 | 692 |
| MEF1R9 | 40 | 20 | 49 | 18564 |
| S2R9 | 3 | 6 | 16 | 293 |
| S2R19 | 10 | 7 | 25 | 1221 |
| S2R23 | 13 | 16 | 42 | 5392 |

In summary, the replicative fitness of Sabin 2 and MEF1 in cell culture was reduced by replacement of preferred codons in the capsid region with synonymous unpreferred codons. The reduction in fitness, as measured by plaque area, was approximately proportional to the length of the interval containing replacement codons.

Example 11

Additional Deoptimization of Polioviruses

This example describes additional changes that can be made to the Sabin 2 poliovirus capsid sequences disclosed in Example 2, or the MEF1 poliovirus sequences disclosed in Example 10. Such modified sequences can be used in an immunogenic composition In one example, the codon deoptimized Sabin 2 poliovirus capsid sequences disclosed in Example 2 (such as SEQ ID NO: 5), or the codon deoptimized MEF1 poliovirus capsid sequences disclosed in Example 10 (such as SEQ ID NO: 58) can be further deoptimized. For example, additional codon substitutions (for example AUA (Ile), AAA (Lys), and CAU (His)), as well as and redesigned codon substitutions (for example UCG (Ser)) codon substitutions, which are better matched to the least abundant tRNA genes in the human genome (International Human Genome Sequencing Consortium. *Nature* 409:860-921, 2001), can be used to further impair translational efficiency and reduce replicative fitness. Such substitutions can be made using routine molecular biology methods.

Example 12

Additional Methods to Decrease Replicative Fitness

This example describes additional or alternative substitutions that can be made to a pathogen sequence to increase the replicative fitness of a pathogen. In addition to changing codon usage, alterations in G+C content and the frequency of CG or TA dinucleotide pairs can be used to decrease the replicative fitness of a pathogen. For example, a pathogen sequence that includes one or more deoptimized codons can further include an alteration in the overall G+C content of the sequence, such as an increase or decrease of at least 10% in the G+C content in the coding sequence (for example without altering the amino acid sequence of the encoded protein). In another or additional example, a pathogen sequence that includes one or more deoptimized codons can further include an alteration in the number of CG or TA dinucleotides in the sequence, such as an increase or decrease of at least 20% in the number of CG or TA dinucleotides in the coding sequence.

Altering G+C Content

The replicative fitness of a pathogen can be altered by changing the G+C content of a pathogen coding sequence. For example, to increase the G+C content, codons used less frequently by the pathogen that include a "G" or "C" in the third position instead of an "A" or "T" can be incorporated into the deoptimized sequence. Such methods can be used in combination with the other methods disclosed herein for decreasing replicative fitness of a pathogen, for example in combination with deoptimizing codon sequences or altering the frequency of CG or TA dinucleotides.

In one example, the G+C content of a pathogen coding sequence is reduced to decrease replicative fitness. For example, the G+C content of a rubella virus coding sequence can be reduced to decrease replicative fitness of this virus. In one example, the G+C content of a rubella sequence is decreased by at least 10%, at least 20%, or at least 50%, thereby decreasing replicative fitness of the virus. Methods of replacing C and G nucleotides as well as measuring the replicative fitness of the virus are known in the art, and particular examples are provided herein.

In another example, the G+C content of a pathogen coding sequence is increased to decrease replicative fitness. For example, the G+C content of a poliovirus coding sequence can be reduced to decrease replicative fitness of this virus. In one example, the G+C content of a poliovirus sequence is increased by at least 10%, at least 20%, or at least 50%, thereby decreasing replicative fitness of the virus. Methods of replacing A and T nucleotides with C and G nucleotides are known in the art, and particular examples are provided herein.

Altering Frequency of CG or TA Dinucleotides to Decrease Replicative Fitness

The replicative fitness of a pathogen can be altered by changing the number of CG dinucleotides, the TA dinucleotides, or both, in a pathogen coding sequence. For example, to increase the number of CG dinucleotides in a deoptimized sequence, codons used less frequently by the pathogen that include a CG in the second and third position instead of another dinucleotide can be incorporated into the deoptimized sequence. Such methods can be used in combination with the other methods disclosed herein for decreasing replicative fitness of a pathogen, for example in combination with deoptimizing codon sequences.

The dinucleotides CG and TA (UA) are known to be suppressed in poliovirus genomes (Karlin et al., *J. Virol.* 68:2889-97; Kanaya et al., *J. Mol. Evol.* 53, 290-8; Toyoda et al. *J. Mol. Biol.* 174:561-85). The results described herein with the Sabin 2 constructs indicate that increased numbers of CG and TA dinucleotides are associated with reductions in replicative fitness. Therefore, the number of CG or TA dinucleotides can be increased in polio and other eukaryotic viruses (such as those in which CG is strongly suppressed in the genome) to decrease their replicative fitness. In one example, the number of CG or TA dinucleotides in a virus sequence is increased by at least 10%, at least 30%, at least 100%, or at least 300%, thereby decreasing replicative fitness of the virus. The number of CG dinucleotides, TA dinucleotides, or both can be increased in a viral sequence using routine molecular biology methods, and using the methods disclosed herein. For example, additional CG dinucleotides can be incorporated into the ORF by uniform replacement of degenerate third-position bases with C when the first base of the next codon is G. Replacement of codons specifying conserved amino acids can be used to further stabilize the reduced fitness phenotype, as restoration of fitness may strictly require synonymous mutations.

Exemplary Sequences

Provided herein are exemplary modified Sabin 2 sequences that have silent (synonymous) nucleotide substitutions in the cassette d (VP1 region). Such modified sequences can be used in an immunogenic composition SEQ ID NO: 65 (and FIG. 25) show a Sabin 2 sequence with a reduced number of CG dinucleotides (number of CG dinucleotides reduced by 94%). SEQ ID NO: 66 (and FIG. 26) show a Sabin 2 sequence with a reduced number of both CG dinucleotides and UA dinucleotides (number of CG dinucleotides reduced by 94% and number of TA dinucleotides reduced by 57%). These sequences will likely have similar replicative fitness as a native poliovirus, and therefore can be used as a control.

SEQ ID NO: 67 (and FIG. 27) show a Sabin 2 sequence with an increased number of CG dinucleotides (number of CG dinucleotides increased by 389%). SEQ ID NO: 68 (and FIG. 28) show a Sabin 2 sequence with an increased number of both CG dinucleotides and UA dinucleotides, with a priority placed on increasing CG dinucleotides (number of CG dinucleotides increased by 389% and number of TA dinucleotides increased by 203%). These sequences will likely have reduced replicative fitness compared to a native poliovirus, and therefore can be used in immunogenic compositions.

SEQ ID NO: 69 (and FIG. 29) show a Sabin 2 sequence having maximum codon deoptimization. In this sequence, the least favored codons were selected without reference to CG or TA dinucleotides. This sequences will likely have reduced replicative fitness compared to a native poliovirus, and therefore can be used in an immunogenic composition.

SEQ ID NO: 70 (and FIG. 30) show a Sabin 2 sequence using MEF1 codons for Sabin 2 amino acids. This provides a means of using different, naturally occurring codons. This sequences will likely have similar replicative fitness as a native poliovirus, and therefore can be used as a control.

Example 13

Determination of the Replication Steps Altered in Highly Modified Viruses

This example describes methods that can be used to identify the defective replication step in a virus whose coding sequence has been altered to reduce replicative fitness of the virus.

A modified virus, such as a highly modified viruses (for example S2R23 (SEQ ID NO: 5) and MEF1R9 (SEQ ID NO: 58)) can be screened using routine methods in the art. For example, the effects of deoptimizing codons on virus binding, eclipse, uncoating, and particle elution steps can be determined using known methods (Kirkegaard, *J. Virol.* 64:195-206 and Labadie et al. *Virology* 318:66-78, 2004, both herein incorporated by reference as to the methods). Briefly, binding assays (Kirkegaard, *J. Virol.* 64:195-206) could involve determining the percentage of $^3$H-labeled virions onto HeLa or other cells. After incubation with $^3$H-labeled purified poliovirus (such as those shown in SEQ ID NOS: 5 and 58), cells are washed extensively with PBS and the initial and remaining radioactivity counts determined by tricholoroacetic acid precipitation and filtering of the labeled particles.

For conformational alteration assays (Kirkegaard, *J. Virol.* 64:195-206), polioviruses (such as those shown in SEQ ID NOS: 5 and 58) are prebound to a HeLa monolayer at 4° C.

for 60 minutes at MOIs of 0.1 PFU/cell. The monolayers are washed three times with PBS and incubated for various time periods at 35° C. Cells are harvested by scraping, and cytoplasmic extracts are titered by plaque assay on HeLa cells. An alternate method (Pelletier et al., *Virol.* 305:55-65) is to use [$^{35}$S]-methionine-labeled purified virus particles. Infections are synchronized by a 2.5-hour period of adsorption at 0° C., and then conformational transitions initiated by incubation at 37° C. for 3 or 10 minutes. Cell-associated virus particles are separated by centrifugation in sucrose gradients (15-30% w/v) (Pelletier et al., *Cell. Mol. Life Sci.* 54:1385-402, 1998).

For RNA release assays (Kirkegaard, *J. Virol.* 64:195-206), neutral red-containing virus is prepared by harvesting virus (such as those shown in SEQ ID NOS: 5 and 58) from HeLa monolayer grown in the presence of 10 μg of neutral red per ml. Time courses of RNA release are determined by pre-binding approximately 200 PFU of each virus to HeLa monolayers at 4° C. for 60 minutes, followed by washing twice with PBS, and agar overlay. Duplicate plates are irradiated for 8 minutes after various times of incubation at 35° C. The numbers of plaques on the irradiated plates are expressed as a percentage of the number of plaques on the unirradiated control.

Protein synthesis and the kinetics of host cell shutoff of protein synthesis can be determined by using pulse-chase experiments in infected cells and other standard methods. Pactamycin will be used to study translational elongation rates (Rekosh, *J. Virol.* 9:479-487). The spectrum of virus particles produced by highly modified viruses can be characterized using fractions from a CsCl density gradient.

Infectivities in different cell types, such as Vero (African green monkey cell line) and human (and possibly murine) neuroblastoma cell lines, can also be determined using routine methods, such as those disclosed herein.

Example 14

Deoptimized Picornaviruses

Examples 14-17 describe methods that can be used to generate a deoptimized positive-strand RNA virus. This example describes methods that can be used to generate a deoptimized Picornavirus sequence, which can be used in an immunogenic composition. Particular examples of foot-and-mouth disease virus (FMDV) and polioviruses are described. However, one skilled in the art will appreciate that similar (and in some examples the same) substitutions can be made to any Picornavirus.

Sequences for FMDV are publicly available (for example see GenBank Accession Nos: AJ539141; AY333431; NC_003992; NC_011452; NC_004915; NC_004004; NC_002554; AY593852; AY593851; AY593850; and AY593849). Using publicly available FMDV sequences, along with publicly available codon usage tables from FMDV (for example see Sanchez et al., *J. Virol.* 77:452-9, 2003; and Boothroyd et al., *Gene* 17:153-61, 1982, herein incorporated by reference and FIG. 24A), one can generate deoptimized FMDV sequences.

Using the methods described above in Examples 1 and 2, the capsid of FMDV can be deoptimized. FIGS. 10A-B (and SEQ ID NO: 11) show an exemplary FMDV, serotype O strain UKG/35/2001 capsid sequence having codons deoptimized for 9 amino acids (see Table 5). FMDV containing these substitutions can be generated using standard molecular biology methods. In addition, based on the deoptimized codons provided in Table 5, one or more other FMDV coding sequences can be deoptimized. In addition, the methods described in Example 12 can be used to alter the G+C content or the number of CG or TA dinucleotides in an FMDV coding sequence, for example to further decrease the replicative fitness of FMDV.

TABLE 5

Deoptimized FMDV codons

| Amino acid | Deoptimized codon |
|---|---|
| Pro | CCG |
| Val | GTA |
| Gly | GGG |
| Ala | GCG |
| Ile | ATA |
| Thr | ACG |
| Leu | CTA |
| Ser | TCG |
| Arg | CGA |

Sequences for poliovirus are publicly available (for example see GenBank Accession Nos: AF111984; NC_002058; AY560657; AY278553; AY278552; AY278551; AY278550; AY27849; AF538843; AF538842; AF538840; AY177685; AY184221; AY184220; AY184219; and AY238473). Using publicly available human poliovirus sequences, along with publicly available codon usage tables for poliovirus (Rothberg and Wimmer, *Nucleic Acids Res.* 9:6221-9, 1981, as well as the tables disclosed herein), one can generate deoptimized poliovirus sequences.

Using the methods described above (for example see Examples 1 and 2), the capsid of poliovirus can be deoptimized. FIGS. 9A-E (SEQ ID NO: 8) shows an exemplary poliovirus type 2, strain MEF1 capsid sequence having all Arg codons deoptimized to CGG. Poliovirus containing these substitutions can be generated using standard molecular biology methods.

Similarly, using the methods described above (for example, see Examples 1 and 2), poliovirus types 1 and 3 can be deoptimized (for example by deoptimization of the capsid sequence). For example, the neurovirulent wild strains type 1 Mahoney/USA41 (POLIO1B; GenBank Accession No: V01149) and type 3 Leon/USA37 (POL3L37; GenBank Accession No: K01392), and their Sabin strain derivatives LSc 2ab (Sabin type 1) (GenBank Accession No: V01150), and Leon 12 $a_1$b (Sabin type 3) (GenBank Accession No: X00596) can be deoptimized.

Example 15

Deoptimized Coronaviruses

This example describes methods that can be used to generate a deoptimized Coronavirus sequence, which can be used in an immunogenic composition. A particular example of a SARS virus is described. However, one skilled in the art will appreciate that similar (and in some examples the same) substitutions can be made to any Coronavirus.

Sequences for SARS are publicly available (for example, see GenBank Accession Nos: NC_004718; AY654624;

AY595412; AY394850; AY559097; AY559096; AY559095; AY559094; AY559093; AY559092; AY559091; AY559090; AY559089; AY559088; AY274119; and AY278741). Using publicly available SARS sequences, along with publicly available codon usage tables from SARS (for example, see Rota et al., *Science* 300:1394-1399, 2003, herein incorporated by reference, and FIG. 24B), one can generate deoptimized SARS sequences.

Using the methods described above in Examples 1 and 2, the spike glycoprotein of SARS can be deoptimized. FIGS. 11A-C (and SEQ ID NO: 14) shows an exemplary SARS, strain Urbani spike glycoprotein sequence having codons deoptimized for 9 amino acids (see Table 6). SARS containing these substitutions can be generated using standard molecular biology methods. In addition, based on the deoptimized codons provided in Table 6, one or more SARS coding sequences can be deoptimized. Furthermore, the methods described in Example 12 can be used to alter the G+C content or the number of CG or TA dinucleotides in an SARS coding sequence, for example to further decrease the replicative fitness of SARS.

TABLE 6

Deoptimized SARS codons

| Amino acid | Deoptimized codon |
|---|---|
| Pro | CCG |
| Val | GTC |
| Gly | GGG |
| Ala | GCG |
| Ile | ATC |
| Thr | ACG |
| Leu | CTG |
| Ser | TCG |
| Arg | CGG |

Example 16

Deoptimized Togaviruses

This example describes methods that can be used to generate a deoptimized togavirus sequence, which can be used in an immunogenic composition. A particular example of a rubella virus is described. However, one skilled in the art will appreciate that similar (and in some examples the same) substitutions can be made to any togavirus.

Sequences for rubella virus are publicly available (for example see GenBank Accession Nos: L78917; NC_001545; AF435866; AF188704 and AB047329). Using publicly available rubella sequences, along with publicly available codon usage tables from rubella virus (for example see Nakamura et al., *Nucleic Acids Res.* 28:292, 2000 and FIG. 24C), one can generate deoptimized rubella virus sequences. Similar methods can be used to generate a deoptimized sequence for any togavirus.

Using the methods described above in Examples 1 and 2, the coding sequence of a togavirus can be deoptimized. FIGS. 12A-G (and SEQ ID NO: 18) shows an exemplary rubella virus sequence having codons deoptimized for 10 amino acids (see Table 7). Rubella viruses containing the substitutions shown in FIG. 11 can be generated using standard molecular biology methods. In addition, based on the deoptimized codons provided in Table 7, one or more other rubella coding sequences can be deoptimized. Furthermore, the methods described in Example 12 can be used to alter the G+C content or the number of CG or TA dinucleotides in a rubella coding sequence, for example to further decrease the replicative fitness of rubella.

TABLE 7

Deoptimized rubella codons

| Amino acid | Deoptimized codon |
|---|---|
| Gly | GGA |
| Ala | GCA |
| Val | GTA |
| Thr | ACA |
| Cys | TGT |
| Tyr | TAT |
| Leu | TTA |
| Ser | TCA |
| Arg | AGA |
| Pro | CCA |

Example 17

Deoptimized Flaviviruses

This example describes methods that can be used to generate a deoptimized flavivirus sequence, which can be used in an immunogenic composition. Particular examples of a Dengue I and Dengue II viruses are described. However, one skilled in the art will appreciate that similar (and in some examples the same) substitutions can be made to any flavivirus.

Sequences for Dengue type 1 and Dengue type 2 virus are publicly available (for example see GenBank Accession Nos: M87512; U88535 and U88536 for type 1 and M19197; M29095 and AF022434 for type 2). Using publicly available Dengue 1 and Dengue 2 sequences, along with publicly available codon usage tables from Dengue type 1 and Dengue type 2 virus (for example see Nakamura et al., *Nucleic Acids Res.* 28:292, 2000 and FIGS. 22 D and E, respectively), one can generate deoptimized Dengue type I and Dengue type II virus sequences. Similar methods can be used to generate a deoptimized sequence for any flavivirus.

Using the methods described above in Examples 1 and 2, the coding sequence of a flavivirus can be deoptimized. Flaviviruses, such as Dengue type 1 and 2 viruses, containing these substitutions can be generated using standard molecular biology methods, based on the deoptimized codons provided in Tables 8 and 9. Furthermore, the methods described in Example 12 can be used to alter the G+C content or the number of CG or TA dinucleotides in a Flavivirus coding sequence, for example to further decrease the replicative fitness of the Flavivirus.

TABLE 8

| Deoptimized dengue type 1 codons | |
|---|---|
| Amino acid | Deoptimized codon |
| Gly | GGC |
| Ala | GCG |
| Val | GTA |
| Thr | ACG |
| Leu | CTC |
| Ser | TCG |
| Arg | CGG |
| Pro | CCG |

TABLE 9

| Deoptimized dengue type 2 codons | |
|---|---|
| Amino acid | Deoptimized codon |
| Gly | GGT |
| Ala | GCG |
| Val | GTA |
| Thr | ACG |
| Leu | CTT |
| Ser | TCG |
| Arg | CGG |
| Pro | CCG |

Example 18

Deoptimized Herpesviruses

This example describes methods that can be used to generate a deoptimized herpesvirus sequence, which can be used in an immunogenic composition. A particular example of a varicella-zoster virus (human herpesvirus 3) is described. In addition, provided is a list of deoptimized codon sequences that can be used for HSV-1 or HSV-2, as well as human cytomegalovirus (CMV; human herpesvirus 5). However, one skilled in the art will appreciate that similar (and in some examples the same) substitutions can be made to any herpesvirus.

Sequences for varicella-zoster virus are publicly available (for example see GenBank Accession Nos: NC_001348; AY548170; AY548171; AB097932 and AB097933). Using publicly available varicella-zoster virus sequences, along with publicly available codon usage tables from varicella-zoster virus (for example see Nakamura et al., *Nucleic Acids Res.* 28:292, 2000 and FIG. 24F), one can generate deoptimized varicella-zoster virus sequences.

Using the methods described above in Examples 1 and 2, the gH and gE coding sequence of a herpesvirus can be deoptimized. FIGS. 13A-B and 14A-B (and SEQ ID NOS: 21 and 24) show exemplary varicella-zoster virus gH and gE sequences having codons deoptimized for 9 amino acids (see Table 10). Varicella-zoster virus containing these substitutions can be generated using standard molecular biology methods. Using the methods described above in Examples 1 and 2, and standard molecular biology methods, the coding sequence of one or more VZV genes can be deoptimized. In addition, based on the deoptimized codons provided in Table 10, one or more other VZV coding sequences can be deoptimized. Furthermore, the methods described in Example 12 can be used to alter the G+C content or the number of CG or TA dinucleotides in a VZV coding sequence, for example to further decrease the replicative fitness of the VZV.

TABLE 10

| Deoptimized varicella-zoster codons | |
|---|---|
| Amino acid | Deoptimized codon |
| Pro | CCT |
| Val | GTC |
| Gly | GGC |
| Ala | GCT |
| Ile | ATC |
| Thr | ACT |
| Leu | CTA |
| Ser | AGT |
| Arg | AGG |

Sequences for human cytomegalovirus (CMV; human herpesvirus 5) are publicly available (for example see GenBank Accession Nos: AY446894; BK000394; AC146999; NC_001347; and AY315197). Using publicly available CMV sequences, along with publicly available codon usage tables from CMV (for example see Nakamura et al., *Nucleic Acids Res.* 28:292, 2000 and FIG. 24G), one can generate deoptimized CMV sequences.

Table 11 shows CMV deoptimized codon sequences for 9 amino acids. The complete genome of CMV is about 233-236 kb. Using the methods described above in Examples 1 and 2, and standard molecular biology methods, glycoprotein B (UL55), glycoprotein H (UL75), and glycoprotein N (UL73) coding sequences of a CMV can be deoptimized. In addition, based on the deoptimized codons provided in Table 11, one or more other CMV coding sequences can be deoptimized. Furthermore, the methods described in Example 12 can be used to alter the G+C content or the number of CG or TA dinucleotides in a CMV coding sequence, for example to further decrease the replicative fitness of CMV.

TABLE 11

| Deoptimized CMV codons | |
|---|---|
| Amino acid | Deoptimized codon |
| Pro | CCA |
| Val | GTT |
| Gly | GGG |
| Ala | GCA |

TABLE 11-continued

| Deoptimized CMV codons | |
|---|---|
| Amino acid | Deoptimized codon |
| Ile | ATA |
| Thr | ACA |
| Leu | TTA |
| Ser | TCA |
| Arg | AGG |

Sequences for herpes simplex virus 1 and 2 (HSV1 and HSV2) are publicly available (for example see GenBank Accession Nos: X14112 and NC_001806 for HSV1 and NC_001798 for HSV2). Using publicly available HSV1 and HSV2 sequences, along with publicly available codon usage tables from HSV1 and HSV2 (for example see Nakamura et al., *Nucleic Acids Res.* 28:292, 2000 and FIG. 24H), one can generate deoptimized HSV1 and HSV2 sequences.

Table 12 shows HSV1 and HSV2 deoptimized codon sequences for 11 amino acids. The codon choices for HSV1 and 2 are very similar and where there are differences they are small. Therefore, the same codon choices can be used for both HSV1 and HSV2. The complete genome of HSV1 and HSV2 is about 152 kb and 155 kb, respectively. Using the methods described above in Examples 1 and 2, and standard molecular biology methods, glycoprotein B (UL27), glycoprotein D (US6), tegument protein host shut-off factor (UL41; see Geiss, *J. Virol.* 74:11137, 2000), and ribonucleotide reductase large subunit (UL39; see Aurelian, *Clin. Diag. Lab. Immunol.* 11:437-445, 2004) coding sequences of HSV1 or HSV2 can be deoptimized. In addition, based on the deoptimized codons provided in Table 12, one or more other HSV1 or HSV2 coding sequences can be deoptimized. Furthermore, the methods described in Example 12 can be used to alter the G+C content or the number of CG or TA dinucleotides in a HSV1 or HSV2 coding sequence, for example to further decrease the replicative fitness of HSV1 or HSV2.

TABLE 12

| Deoptimized HSV1 and HSV2 codons | | |
|---|---|---|
| Codon | HSV1 | HSV2 |
| Pro | CCT | CCA |
| Val | GTA | GTA |
| Gly | GGA | GGT |
| Ala | GCT | GCA |
| Ile | ATA | ATA |
| Thr | ACT | ACT |
| Leu | TTA | TTA |
| Ser | TCA | TCA |
| Arg | AGA | AGA |
| Asn | AAT | AAT |
| Asp | GAT | GAT |

Example 19

Deoptimized Paramyxoviruses

Examples 19 and 20 describe methods that can be used to generate a deoptimized negative-strand RNA virus. This example describes methods that can be used to generate a deoptimized paramyxovirus sequence, which can be used in an immunogenic composition. Particular examples of measles and respiratory syncytial viruses (RSV) are described. However, one skilled in the art will appreciate that similar (and in some examples the same) substitutions can be made to any paramyxovirus.

Sequences for measles and RSV are publicly available (for example see GenBank Accession Nos: NC_001498; AF266287; AY486084; AF266291; and AF266286 for measles; and NC_001781 (SEQ ID NO: 71); U63644 (SEQ ID NO: 72); AY353550 (SEQ ID NO: 73); NC_001803 (SEQ ID NO: 74); AF013254 (SEQ ID NO: 75), and U39661 (SEQ ID NO: 76) for RSV). Using publicly available measles and RSV sequences, along with publicly available codon usage tables from measles and RSV (for example see Nakamura et al., *Nucleic Acids Res.* 28:292, 2000 and FIG. 24I), one can generate deoptimized measles and RSV sequences. Similar methods can be used to generate a deoptimized sequence for any paramyxovirus.

Using the methods described above in Examples 1 and 2, the fusion (F) or hemagglutinin (H) coding sequence of a paramyxovirus can be deoptimized. FIGS. 15A-B and 16A-B show exemplary measles F and G sequences having codons deoptimized for 8 amino acids (SEQ ID NOS: 27 and 30, respectively). FIGS. 17A-B and 18 (and SEQ ID NOS: 33 and 36) show exemplary RSV F and glycoprotein (G) sequences having codons deoptimized for 8 amino acids (see Tables 13 and 14). Measles and RSV viruses containing these substitutions can be generated using standard molecular biology methods. In addition, based on the deoptimized codons provided in Tables 13 and 14, one or more other measles or RSV coding sequences can be deoptimized. Furthermore, the methods described in Example 12 can be used to alter the G+C content or the number of CG or TA dinucleotides in a RSV coding sequence, for example to further decrease the replicative fitness of RSV.

TABLE 13

| Deoptimized measles codons | |
|---|---|
| Amino acid | Deoptimized codon |
| Gly | GGC |
| Ala | GCG |
| Val | GTA |
| Thr | ACG |
| Leu | CTT |
| Ser | TCG |
| Arg | CGC |
| Pro | CCG |

TABLE 14

| Deoptimized RSV codons | |
|---|---|
| Amino acid | Deoptimized codon |
| Gly | GGG |
| Glu | GAG |
| Ala | GCG |
| Thr | ACG |
| Leu | CTG |
| Ser | TCG |
| Arg | CGG |
| Pro | CCG |

Example 20

Deoptimized Orthomyxyoviruses

This example describes methods that can be used to generate a deoptimized orthomyxyovirus sequence, which can be used in an immunogenic composition. A particular example of an influenza virus is described. However, one skilled in the art will appreciate that similar (and in some examples the same) substitutions can be made to any orthomyxyovirus.

Sequences for influenza virus are publicly available (for example see NC_002204 and AY253754). Using publicly available influenza sequences, along with publicly available codon usage tables from influenza (for example see Nakamura et al., *Nucleic Acids Res.* 28:292, 2000 and FIG. 24J), one can generate deoptimized influenza sequences. Similar methods can be used to generate a deoptimized sequence for any orthomyxyovirus.

Using the methods described above in Examples 1 and 2, the hemagglutinin (HA) or neuraminidase (NA) coding sequences of an orthomyxyovirus can be deoptimized. FIGS. 17 and 18 show an exemplary influenza virus HA (FIG. 19 and SEQ ID NO: 39) and a NA gene (FIG. 20 and SEQ ID NO: 42) sequence having codons deoptimized for 8 amino acids (see Table 15). Influenza viruses containing these substitutions can be generated using standard molecular biology methods. In addition, based on the deoptimized codons provided in Table 15, one or more other influenza coding sequences can be deoptimized. Furthermore, the methods described in Example 12 can be used to alter the G+C content or the number of CG or TA dinucleotides in an influenza coding sequence, for example to further decrease the replicative fitness of influenza.

TABLE 15

| Deoptimized influenza codons | |
|---|---|
| Amino acid | Deoptimized codon |
| Gly | GGC |
| Ala | GCG |
| Ile | ATC |
| Thr | ACG |

TABLE 15-continued

| Deoptimized influenza codons | |
|---|---|
| Amino acid | Deoptimized codon |
| Leu | TTA |
| Ser | TCG |
| Arg | CGC |
| Pro | CCG |

Example 21

Deoptimized Retroviral Codons

This example describes methods that can be used to generate a deoptimized retrovirus sequence, which can be used in an immunogenic composition. Particular examples of an HIV type 1 (HIV-1), subtype C, retrovirus, and a lentivirus, are described. However, one skilled in the art will appreciate that similar (and in some examples the same) substitutions can be made to any retrovirus.

Sequences for HIV-1 are publicly available (for example see GenBank Accession Nos: AF110967; AY322191; AY682547; AY536234; AY536238; AY332236; AY331296 and AY331288). Using publicly available HIV-1 sequences, along with publicly available codon usage tables from HIV-1 (for example see Nakamura et al., *Nucleic Acids Res.* 28:292, 2000; Chou and Zhang, *AIDS Res. Hum. Retroviruses.* 8:1967-76, 1992; Kyprand Mrazek, Nature. 327 (6117):20, 1987, all herein incorporated by reference, and FIG. 24K), one can generate deoptimized HIV-1 sequences. Similar methods can be used to generate a deoptimized sequence for any retrovirus.

Using the methods described above in Examples 1 and 2, the env coding sequence of HIV-1 can be deoptimized. FIGS. 21A-B (and SEQ ID NO: 45) shows an exemplary HIV-1 env sequence having codons deoptimized for 8 amino acids (see Table 16). HIV-1 containing these substitutions can be generated using standard molecular biology methods. In addition, based on the deoptimized codons provided in Table 16, one or more other HIV-1 coding sequences can be deoptimized. Furthermore, the methods described in Example 12 can be used to alter the G+C content or the number of CG or TA dinucleotides in an HIV-1 coding sequence, for example to further decrease the replicative fitness of HIV-1.

TABLE 16

| Deoptimized HIV-1 codons | |
|---|---|
| Amino acid | Deoptimized codon |
| Gly | GGT |
| Ala | GCG |
| Val | GTC |
| Thr | ACG |
| Leu | CTC |
| Ser | TCG |

TABLE 16-continued

| Deoptimized HIV-1 codons | |
|---|---|
| Amino acid | Deoptimized codon |
| Arg | CGT |
| Pro | CCG |

The equine infectious anemia virus (EIAV) is a lentivirus. Sequences for EIAV are publicly available (for example see GenBank Accession Nos: M87581; X16988; NC_001450 and AF327878). Using publicly available EIAV sequences, along with publicly available codon usage tables from EIAV (for example see Nakamura et al., *Nucleic Acids Res.* 28:292, 2000, herein incorporated by reference, and FIG. 24L), one can generate deoptimized EIAV sequences. Similar methods can be used to generate a deoptimized sequence for any lentivirus.

Using the methods described above in Examples 1 and 2, the env coding sequence of EIAV can be deoptimized, for example using the deoptimized codons provided in Table 17. Furthermore, the methods described in Example 12 can be used to alter the G+C content or the number of CG or TA dinucleotides in an EIAV coding sequence, for example to further decrease the replicative fitness of EIAV.

TABLE 17

| Deoptimized equine infectious anaemia virus (EIAV) codons | |
|---|---|
| Amino acid | Deoptimized codon |
| Gly | GGC |
| Ala | GCG |
| Val | GTC |
| Thr | ACG |
| Leu | CTC |
| Ser | TCG |
| Arg | CGC |
| Pro | CCG |

Example 22

Deoptimized Bacterial Codons

This example describes methods that can be used to generate a deoptimized bacterial sequence, which can be used in an immunogenic composition. Particular optimized *E. coli* sequences are described. However, one skilled in the art will appreciate that similar (and in some examples the same) substitutions can be made to any bacterial coding sequence.

Sequences for *E. coli* are publicly available (for example see GenBank Accession Nos: NC_002695; NC_000913; BA000007; NC_004431; and AE014075). Using publicly available *E. coli* sequences, along with publicly available codon usage tables from *E. coli* (for example see Nakamura et al., *Nucleic Acids Res.* 28:292, 2000 and Sharp et al., *Nucleic Acids Res.* 16:8207-11, 1988, all herein incorporated by reference, and FIG. 24M), one can generate deoptimized *E. coli* sequences. Similar methods can be used to generate a deoptimized sequence for any bacterium.

Using the methods described above in Examples 1 and 2, the ArgS or TufA coding sequences of *E. coli* can be deoptimized. FIGS. 22A-B and 23 shows exemplary *E. coli* ArgS and TufA sequences (and SEQ ID NOS: 48 and 51), respectively, having codons deoptimized for 1 amino acid. *E. coli* containing these substitutions can be generated using standard molecular biology methods. In addition, based on the deoptimized codon provided in Table 18, one or more other *E. coli* coding sequences can be deoptimized. Furthermore, the methods described in Example 12 can be used to alter the G+C content or the number of CG or TA dinucleotides in an *E. coli* coding sequence, for example to further decrease the replicative fitness of *E. coli*.

TABLE 18

| Deoptimized *E. coli* K12 codon | |
|---|---|
| Amino acid | Deoptimized codon |
| Arg | AGG |

Example 23

Pharmaceutical Compositions

The disclosed immunogenic deoptimized pathogenic sequences can be incorporated into pharmaceutical compositions (such as immunogenic compositions or vaccines). Pharmaceutical compositions can include one or more deoptimized pathogenic sequences and a physiologically acceptable carrier. Pharmaceutical compositions also can include an immunostimulant. An immunostimulant is any substance that enhances or potentiates an immune response to an exogenous antigen. Examples of immunostimulants include adjuvants, biodegradable microspheres (such as polylactic galactide microspheres) and liposomes (see, for example, U.S. Pat. No. 4,235,877). Vaccine preparation is generally described, for example, in M. F. Powell and M. J. Newman, eds., *Vaccine Design: the subunit and adjuvant approach*, Plenum Press, N Y, 1995. Pharmaceutical compositions within the scope of the disclosure can include other compounds, which may be either biologically active or inactive.

A pharmaceutical composition can include DNA having a deoptimized coding sequence. The DNA can be present within any of a variety of delivery systems known to those of ordinary skill in the art, including nucleic acid expression systems, bacteria and viral expression systems. Numerous gene delivery techniques are well known in the art, including those described by Rolland, *Crit. Rev. Therap. Drug Carrier Systems* 15: 143-198, 1998, and references cited therein. Appropriate nucleic acid expression systems contain DNA sequences for expression in the subject (such as a suitable promoter and terminating signal). Bacterial delivery systems involve the administration of a bacterium (such as Bacillus-Calmette-Guerrin) that expresses the polypeptide on its cell surface or secretes it. In one example, the DNA is introduced using a viral expression system (such as vaccinia or other pox virus, retrovirus, or adenovirus), which can involve the use of a non-pathogenic (defective), replication competent virus. Suitable systems are disclosed, for example, in Fisher-Hoch et al., *Proc. Natl. Acad. Sci., USA* 86:317-21, 1989; Flexner et al., *Ann. N.Y. Acad. Sci.* 569:86-103, 1989; Flexner et al., *Vaccine* 8:17-21, 1990; U.S. Pat. Nos. 4,603, 112, 4,777,127, 4,769,330, and 5,017,487; PCT publications WO 89/01973 and WO 91/02805; Berkner, *Biotechniques* 6:616-27, 1988; Rosenfeld et al., *Science* 252:431-4, 1991; Kolls et al., *Proc. Natl. Acad. Sci. USA* 91:215-9, 1994; Kass-Eisler et al., *Proc. Natl. Acad. Sci. USA* 90:11498-502, 1993; Guzman et al., *Circulation* 88:2838-48, 1993; and Guzman et al., *Cir. Res.* 73:1202-7, 1993. Techniques for incorporating DNA into such expression systems are known. DNA can also be incorporated as "naked DNA," as described, for example, in Ulmer et al., *Science* 259:1745-9, 1993 and Cohen, *Science* 259:1691-2, 1993. Uptake of naked DNA can be increased by coating the DNA onto biodegradable beads.

While any suitable carrier known to those of ordinary skill in the art can be employed in the pharmaceutical compositions, the type of carrier will vary depending on the mode of administration. Pharmaceutical compositions can be formulated for any appropriate manner of administration, including for example, oral (including buccal or sublingual), nasal, rectal, aerosol, topical, intravenous, intraperitoneal, intradermal, intraocular, subcutaneous or intramuscular administration. For parenteral administration, such as subcutaneous injection, exemplary carriers include water, saline, alcohol, fat, wax, buffer, or combinations thereof. For oral administration, any of the above carriers or a solid carrier can be employed. Biodegradable microspheres (such as polylactate polyglycolate) can also be employed as carriers for the pharmaceutical compositions. Suitable biodegradable microspheres are disclosed, for example, in U.S. Pat. Nos. 4,897,268 and 5,075,109.

The disclosed pharmaceutical compositions can also include buffers (such as neutral buffered saline or phosphate buffered saline), carbohydrates (such as glucose, mannose, sucrose or dextrans), mannitol, and additional proteins, polypeptides or amino acids such as glycine, antioxidants, chelating agents such as EDTA or glutathione, and immunostimulants (such as adjuvants, for example, aluminum phosphate) or preservatives.

The compositions of the present disclosure can be formulated as a lyophilizate, or stored at temperatures from about 4° C. to −100° C. Compositions can also be encapsulated within liposomes using well known technology. Furthermore, the compositions can be sterilized, for example, by filtration, radiation, or heat.

Any of a variety of immunostimulants can be employed in the pharmaceutical compositions that include an immunogenically effective amount of attenuated deoptimized pathogen. In some examples, an immunostimulatory composition also includes one or more compounds having adjuvant activity, and can further include a pharmaceutically acceptable carrier.

Adjuvants are non-specific stimulators of the immune system that can enhance the immune response of the host to the immunogenic composition. Some adjuvants contain a substance designed to protect the antigen from rapid catabolism, for example, aluminum hydroxide or mineral oil, and a stimulator of immune responses, such as lipid A, *Bordatella pertussis* or *Mycobacterium tuberculosis* derived proteins. Suitable adjuvants are commercially available as, for example, Merck Adjuvant 65 (Merck and Company, Inc., Rahway, N.J.), TiterMax Gold (TiterMax, Norcross, Ga.), ISA-720 (Seppic, France) ASO-2 (SmithKlineGlaxo, Rixensart, Belgium); aluminum salts such as aluminum hydroxide (for example, Amphogel, Wyeth Laboratories, Madison, N.J.) or aluminum phosphate; salts of calcium, iron or zinc; an insoluble suspension of acylated tyrosine; acylated sugars; cationically or anionically derivatized polysaccharides; polyphosphazenes; biodegradable microspheres; monophosphoryl lipid A and saponins such as quil A and QS-21 (Antigenics, Framingham, Mass.). Cytokines, such as GM-CSF or interleukin-2, -7, or -12, can be used as adjuvants.

The adjuvant composition can be designed to induce an immune response predominantly of the Th1 type. High levels of Th1-type cytokines (such as IFN-γ, TNF-α, IL-2 and IL-12) tend to favor the induction of cell mediated immune responses to an administered antigen. In contrast, high levels of Th2-type cytokines (such as IL-4, IL-5, IL-6 and IL-10) tend to favor the induction of humoral immune responses. Following administration of a pharmaceutical composition as provided herein, a subject may support an immune response that includes Th1- and Th2-type responses. However, in examples where the response is predominantly a Th1-type, the level of Th1-type cytokines increases to a greater extent than the level of Th2-type cytokines. The levels of these cytokines can be readily assessed using standard assays.

Adjuvants for use in eliciting a predominantly Th1-type response include, but are not limited to, a combination of monophosphoryl lipid A, such as 3-de-O-acylated monophosphoryl lipid A (3D-MPL) (Corixa, Hamilton Ind.), together with an aluminum salt. MPL adjuvants are available from Corixa (Seattle, Wash.; see also U.S. Pat. Nos. 4,436,727; 4,877,611; 4,866,034 and 4,912,094). CG-containing oligonucleotides (in which the CG dinucleotide is unmethylated) also induce a predominantly Th1 response. Such oligonucleotides are well known and are described, for example, in PCT publications WO 96/02555 and WO 99/33488. Immunostimulatory DNA sequences are also described, for example, by Sato et al., *Science* 273:352, 1996. Another adjuvant is a saponin such as QS21 (Antigenics, Framingham, Mass.), which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other formulations include an oil-in-water emulsion and tocopherol. An adjuvant formulation involving QS21, 3D-MPL and tocopherol in an oil-in-water emulsion is described in WO 95/17210.

Still further adjuvants include Montanide ISA 720 (Seppic, France), SAF (Chiron, California, United States), ISCOMS (CSL), MF-59 (Chiron), the ASO-2 series of adjuvants (SmithKlineGlaxo, Rixensart, Belgium), Detox (Corixa, Seattle, Wash.), RC-529 (Corixa, Seattle, Wash.), Aminoalkyl glucosaminide 4-phosphates (AGPs), copolymer adjuvants, CG oligonucleotide motifs and combinations of CG oligonucleotide motifs, bacterial extracts (such as mycobacterial extracts), detoxified endotoxins, and membrane lipids. Combinations of two or more adjuvants can also be used.

Still other adjuvants include polymers and co-polymers. For example, copolymers such as polyoxyethylene-polyoxypropylene copolymers and block co-polymers can be used. A particular example of a polymeric adjuvant is polymer P1005.

Adjuvants are utilized in an adjuvant amount, which can vary with the adjuvant, subject, and immunogen. Typical amounts of non-emulsion adjuvants can vary from about 1 ng to about 500 mg per administration, for example, from 10 μg to 800 μg, such as from 50 μg to 500 μg. For emulsion adjuvants (oil-in-water and water-in-oil emulsions) the amount of the oil phase can vary from about 0.1% to about 70%, for example between about 0.5% and 5% oil in an oil-in-water emulsion and between about 30% and 70% oil in a water-in-oil emulsion. Those skilled in the art will appreciate appropriate concentrations of adjuvants, and such amounts can be readily determined.

Any pharmaceutical composition provided herein can be prepared using well known methods that result in a combination of deoptimized pathogen (or deoptimized DNA coding sequence), alone or in the presence of an immunostimulant, carrier or excipient, or combinations thereof. Such compositions can be administered as part of a sustained release formulation (such as a capsule, sponge or gel that includes the deoptimized pathogen) that provides a slow release of the composition following administration. Such formulations can be prepared using well known technology (see, for example, Coombes et al., *Vaccine* 14:1429-38, 1996) and administered by, for example, subcutaneous implantation at the desired target site. Sustained-release formulations can contain a deoptimized pathogen dispersed in a carrier matrix or contained within a reservoir surrounded by a rate controlling membrane.

Carriers for use with the disclosed compositions are biocompatible, and can also be biodegradable, and the formulation can provide a relatively constant level of active component release. Suitable carriers include, but are not limited to, microparticles of poly(lactide-co-glycolide), as well as polyacrylate, latex, starch, cellulose and dextran. Other delayed-release carriers include supramolecular biovectors, which comprise a non-liquid hydrophilic core (such as a cross-linked polysaccharide or oligosaccharide) and, optionally, an external layer comprising an amphiphilic compound, such as a phospholipid (see, for example, U.S. Pat. No. 5,151,254 and PCT publications WO 94/20078, WO/94/23701 and WO 96/06638). The amount of active compound contained within a sustained release formulation depends upon the site of implantation, the rate and expected duration of release and the nature of the condition to be treated or prevented.

Any of a variety of delivery vehicles can be employed with the disclosed pharmaceutical compositions to facilitate production of an antigen-specific immune response to a deoptimized pathogen. Exemplary vehicles include, but are not limited to, hydrophilic compounds having a capacity to disperse the deoptimized pathogen and any additives. The deoptimized pathogen can be combined with the vehicle according to methods known in the art. The vehicle can be a solvent or dispersion medium containing, for example, water, ethanol, polyol (for example, glycerol, propylene glycol, liquid polyethylene glycol, and the like), and suitable mixtures thereof. Other exemplary vehicles include, but are not limited to, copolymers of polycarboxylic acids or salts thereof, carboxylic anhydrides (for example, maleic anhydride) with other monomers (for example, methyl (meth) acrylate, acrylic acid and the like), hydrophilic vinyl polymers, such as polyvinyl acetate, polyvinyl alcohol, polyvinylpyrrolidone, cellulose derivatives, such as hydroxymethylcellulose, hydroxypropylcellulose and the like, and natural polymers, such as chitosan, collagen, sodium alginate, gelatin, hyaluronic acid, and nontoxic metal salts thereof.

A biodegradable polymer can be used as a base or vehicle, such as polyglycolic acids and polylactic acids, poly(lactic acid-glycolic acid) copolymer, polyhydroxybutyric acid, poly(hydroxybutyric acid-glycolic acid) copolymer, and mixtures thereof. Other biodegradable or bioerodible polymers include, but are not limited to, such polymers as poly(epsilon-caprolactone), poly(epsilon-aprolactone-CO-lactic acid), poly(epsilon.-aprolactone-CO-glycolic acid), poly(beta-hydroxy butyric acid), poly(alkyl-2-cyanoacrilate), hydrogels, such as poly(hydroxyethyl methacrylate), polyamides, poly(amino acids) (for example, L-leucine, glutamic acid, L-aspartic acid and the like), poly(ester urea), poly(2-hydroxyethyl DL-aspartamide), polyacetal polymers, polyorthoesters, polycarbonate, polymaleamides, polysaccharides, and copolymers thereof. In some examples, vehicles include synthetic fatty acid esters such as polyglycerin fatty acid esters and sucrose fatty acid esters. Hydrophilic polymers and other vehicles can be used alone or in combination, and enhanced structural integrity can be imparted to the vehicle by partial crystallization, ionic bonding, cross-linking and the like.

The vehicle can be provided in a variety of forms, including, fluid or viscous solutions, gels, pastes, powders, microspheres and films. In one example, pharmaceutical compositions for administering a deoptimized pathogen are formulated as a solution, microemulsion, or other ordered structure suitable for high concentration of active ingredients. Proper fluidity for solutions can be maintained, for example, by the use of a coating such as lecithin, by the maintenance of a desired particle size in the case of dispersible formulations, and by the use of surfactants.

Delivery vehicles include antigen presenting cells (APCs), such as dendritic cells, macrophages, B cells, monocytes and other cells that can be engineered to be efficient APCs. Such cells can, but need not, be genetically modified to increase the capacity for presenting the antigen, to improve activation or maintenance of the T cell response, to have anti-pathogen effects, or to be immunologically compatible with the receiver (matched HLA haplotype). APCs can generally be isolated from any of a variety of biological fluids and organs, including tumor and peritumoral tissues, and may be autologous, allogeneic, syngeneic or xenogeneic cells.

In certain examples, the deoptimized pathogen is administered in a time release formulation. These compositions can be prepared with vehicles that protect against rapid release, and are metabolized slowly under physiological conditions following their delivery (for example in the presence of bodily fluids). Examples include, but are not limited to, a polymer, controlled-release microcapsules, and bioadhesive gels. Many methods for preparing such formulations are well known to those skilled in the art (see, for example, *Sustained and Controlled Release Drug Delivery Systems*, J. R. Robinson, ed., Marcel Dekker, Inc., New York, 1978).

Pharmaceutical compositions can be presented in unit-dose or multi-dose containers, such as sealed ampoules or vials. Such containers are typically hermetically sealed to preserve sterility of the formulation until use. In general, formulations can be stored as suspensions, solutions or as emulsions in oily or aqueous vehicles. Alternatively, a pharmaceutical composition can be stored in a freeze-dried condition requiring only the addition of a sterile liquid carrier immediately prior to use.

The pharmaceutical compositions of the disclosure typically are sterile and stable under conditions of manufacture, storage and use. Sterile solutions can be prepared by incorporating the disclosed deoptimized pathogens (alone or in the presence of a pharmaceutically acceptable carrier, adjuvant, or other biologically active agent) in the desired amount in an appropriate solvent followed by sterilization, such as by filtration. Generally, dispersions are prepared by incorporating the deoptimized pathogen into a sterile vehicle that contains a dispersion medium and other desired ingredients. In the case of sterile powders, methods of preparation include vacuum drying and freeze-drying which yields a powder of the deoptimized pathogen plus any additional desired ingredient from a previously sterile-filtered solution thereof. For vaccine use, the deoptimized pathogens of the disclosure can be used directly in vaccine formulations, or lyophilized, as desired, using lyophilization protocols well known in the art. Lyophilized pathogen is typically be maintained at about 4° C. When ready for use the lyophilized pathogen can be reconstituted in a stabilizing solution (such as saline).

Example 24

Methods of Stimulating an Immune Response

This example describes methods using the disclosed immunogenic compositions that can be used to stimulate an immune response in a subject, such as a human. Methods for inoculation are routine in the art. In some examples, a determination is made as to whether the subject would benefit from administration of a deoptimized pathogen sequence, prior to administering the immunogenic composition. Administration can be achieved by any method known in the art, such as oral administration or inoculation (such as intramuscular, ip, or subcutaneous). In some examples, the deoptimized pathogen is administered, for example an inactivated or live pathogen. In particular examples, the deoptimized nucleic acid molecule or protein molecule is administered. In some examples, combinations of these agents are administered, alone or in the presence of other agents, such as an adjuvant.

The amount of deoptimized pathogen (or part thereof such as DNA sequence) administered is sufficient to induce in the host an effective immune response against virulent forms of the pathogen. An effective amount can being readily determined by one skilled in the art, for example using routine trials establishing dose response curves. The immunogenic compositions disclosed herein can be administered to the subject as needed to confer immunity against the pathogen to the subject. For example, the composition can be administered in a single bolus delivery (which can be followed by one or more booster administrations as needed), via continuous delivery over an extended time period, in a repeated administration protocol (for example, by an hourly, daily, weekly, or monthly repeated administration protocol).

In some examples, a deoptimized viral sequence is administered to a subject. The sequence can be administered as a nucleic acid molecule, the virus itself, or combinations thereof. In one example, a deoptimized DNA sequence is administered to the subject, for example in the presence of a carrier molecule, such as a lipid (for example a liposome). The amount of DNA administered can be determined by routine methods in the art. In some examples, the amount of DNA administered (for example by orally or inoculation) is 0.1 μg-1000 μg DNA, such as 10-100 μg DNA, such as at least 10 μg DNA. In particular examples, a deoptimized virus (live or inactivated, and in some examples lyophilized) is administered to the subject (for example orally or via injection). Exemplary doses of virus, include, but are not limited to, $10^3$ to $10^{10}$ plaque forming units (PFU) or more of virus per dose, such as $10^4$ to $10^5$ PFU virus per dose, for example at least $10^3$ PFU virus per dose, at least $10^4$ PFU virus per dose, at least $10^5$ PFU virus per dose, or at least $10^9$ PFU virus per dose.

In some examples, a deoptimized bacterial sequence is administered to a subject. The sequence can be administered as a nucleic acid molecule, or as the bacterium. In examples wherein a deoptimized bacterial DNA sequence is administered, the methods described above can be used. In particular examples, a deoptimized bacterium (such as an inactivated whole-cell vaccine) is administered to the subject (for example orally or via injection). Exemplary doses of bacteria (as measured by colony-forming units), include, but are not limited to, $10^3$-$10^{10}$ bacteria per dose, for example at least $10^3$ bacteria, at least $10^4$ bacteria, at least $10^5$ bacteria, at least $10^8$ bacteria, or at least $10^9$ bacteria per dose.

In some examples, a deoptimized parasitic sequence is administered to a subject. The sequence can be administered as a nucleic acid molecule, or as the parasite. In examples wherein a deoptimized parasitic DNA sequence is administered, the methods described above can be used. In particular examples, a deoptimized parasite (such as a live or inactivated parasite) is administered to the subject (for example orally or via injection). Exemplary doses of parasites, include, but are not limited to, $10^3$-$10^{10}$ parasites per dose, for example at least $10^3$ parasites, at least $10^4$ bacteria, at least $10^5$ parasites, at least $10^8$ parasites, or at least $10^9$ parasites per dose.

Example 25

Attenuated Poliovirus as an Immunogen

This example describes methods that can be used to demonstrate the ability of an attenuated poliovirus to be used as an immunogen.

Wild-Type Mouse Neurovirulence Using Deoptimized MEF1 Viruses

The method of Ford et al. (*Microbial Pathogenesis* 33:97-107, 2002, herein incorporated by reference) can be used. Wild-type mice are infected with the wild type 2 poliovirus strain MEF1. MEF1 is a mouse-adapted type 2 polio strain that cannot infect mice via the oral route, but can infect via injection. Briefly, wild-type mice (such as six-week old, adult, male Swiss mice (Taconic Labs, Germantown, N.Y.)) are anesthetized with isofluorane and subsequently administered the virus via intramuscular injection (right medial gastrocnoemius) utilizing a 26.5 gauge needle. In some examples, the virus is injected into the brain or spinal cord. Mice each are administered approximately $10^{10}$-$10^{11}$ TCID50 (amount of virus required for 50% infectivity of susceptible cells in tissue culture) of MEF1R2 (an MEF1 clone with an extra silent restriction site; SEQ ID NO: 53), MEF1 (non-clone; SEQ ID NO: 52), MEF1R5 (VP1 alterations; SEQ ID NO: 54), MEF1R9 (SEQ ID NO: 58), or with phospho-buffered saline (PBS) as a negative control.

All inoculated animals are observed daily for signs of disease (paralysis, encephalitis, or death). Paralysis is defined as limb weakness and delineated between spastic/hypertonic and flaccid/hypotonic by a neurologist. Tone is determined by manual manipulation of the limb and compared with normal tone in uninoculated mice. Blood will be collected from mice 21 days after infection. Serum samples are analyzed for the presence of neutralizing antibody to poliovirus. Blood will be collected before euthanasia when necessary.

The following methods can be used to assess immunogenicity of the deoptimized viruses. The presence of neutralizing antibodies can be assessed by using the neutralization test (standard WHO method), as described in Horie et al. (*Appl. Environ. Microbiol.* 68:138-42, 2002). Following immunization, sera is obtained from immunized and non-immunized subjects. About 50 μl of sera dilution series is prepared, in duplicate, in Eagle's minimal essential medium (MEM) supplemented with 2% FCS in a 96-well microtiter plate. Then 50 μl of 100 50% cell culture infectious doses (CCID50) of each isolate, Sabin type 2 vaccine strain, or type 2 wild strain MEF1 is added to each well. After incubation at 36° C. for 2 hours, 100 μl of a cell suspension containing $10^4$ HEp2-C cells in MEM supplemented with 5% FCS are added to each well. The plates are then scored or CPE after 7 days of incubation at 36° C. in a $CO_2$ atmosphere. The calculation of the neutralizing titer of each sample can be determined by the Karber method (see World Health Organization. 1990. Manual for the virological investigation of poliomyelitis. World Health Organization, Expanded Programme on Immunization and Division of Communicable Diseases. W.H.O. publication no. W.H.O./EPI/CDS/POLIO/90.1. World Health Organization, Geneva, Switzerland).

Production of specific neutralizing antibodies when inoculated with codon-deoptimized virus constructs of MEF1 would give evidence of protective immunity. Protection from paralysis upon challenge with dosages of MEF1 sufficient to cause paralysis in unprotected mice would be confirmation of protective immunity.

Transgenic Mice Bearing the Human Poliovirus Receptor

As an alternative to using wild-type mice, transgenic mice expressing the human poliovirus receptor can be used (PVR-Tg21 mice, Central Laboratories for Experimental Animals, Kanagawa, Japan), using the methods described above. Briefly, transgenic PVR-Tg21 mice at 8-10 weeks of age are administered the deoptimized virus (such as a sequence that includes SEQ ID NO: 5 or 58), wild-type virus, other polio virus, or buffer alone. Administration can be by any mode, such as injection into the muscle as described above, intranasal, intraspinal or intracerebral inoculation. However, injection into muscle in some examples requires a higher dose of virus than intraspinal or intracerebral inoculation. Intraspinal injection can be performed as described in Horie et al. (*Appl. Envir. Microbiology* 68:138-142, 2002). Briefly, the desired virus is serially diluted 10-fold, and 5 μl of each dilution inoculated into the spinal cord of 5-10 mice per dilution. Intracerebral injection can be performed as described in Kew et al. (*Science* 296:356-9, 2002). Briefly, mice are inoculated (30 μl/mouse) intracerebrally for each virus dilution (in 10-fold increments). Intranasal infection can be performed using the method of Nagata et al. (*Virology* 321:87-100, 2004), as transgenic mice are susceptible to polio infection via the intranasal route.

Analysis of Challenge/Protection

After the neurovirulence properties of the codon-deoptimized viruses are determined, challenge studies can be used to demonstrate that the codon-deoptimized viruses protect mice from disease. Briefly, mice are inoculated with a codon-deoptimized virus using conditions that induce neutralizing antibody. Immunized mice are challenged 21 days later with neurovirulent type 2 MEF1 virus at paralytic doses. The absence of paralytic signs when challenged with neurovirulent prototype MEF1 indicates that the transgenic PVR-Tg21 mice are protected by their prior exposure to codon-deoptimized MEF1 virus. The type-specificity of protection is measured by challenge with the neurovirulent type 1 poliovirus, Mahoney and neurovirulent type 3 poliovirus.

Monkey Neurovirulence

As an alternative to using mice, the ability of a deoptimized poliovirus to be used as an immunogen can be determined in rhesus monkeys. Deoptimized polioviruses, such as those disclosed herein, can be administered to monkeys and neurovirulence assayed. Examples of deoptimized viruses include, but are not limited to sequences that include SEQ ID NOS: 5, 8, 58, or 65-70). Briefly, intraspinal inoculation of rhesus monkeys will be performed according to the recommendations of the World Health Organization for Type 2 OPV (WHO Tech. Rep. Ser. 800, 30-65, 1990). Requirements for poliomyelitis vaccine (oral), and the United States Code of Federal Regulations, Title 21, Part 630.16 (1994). For example, 10-14 juvenile rhesus monkeys will be inoculated in the lumbar region of the spinal cord with 0.1-0.2 ml of virus (6-7 $\log_{10}$ $CCID_{50}$/monkey). The ability of the deoptimized virus to stimulate an immune response in the treated monkeys can be determined as described above.

Example 26

Methods of Determining Replicative Fitness

This example describes methods that can be used to measure the replicative fitness of a virus or bacteria. One skilled in the art will appreciate that other methods can also be used.

In one example, the replicative fitness of a deoptimized virus is determined by calculation of plaque size and number. Briefly, RNA transcripts of viral sequences having a deoptimized sequence or a native sequence are transfected into the appropriate cell line. The resulting virus obtained from the primary transfection can be passaged again to increase virus titers. The virus is then used to infect cells (such as confluent HeLa cell monolayers), and incubated at room temperature for 10-60 minutes, such as 30 minutes, prior to the addition of 0.45% SeaKem LE Agarose (Bio-Whittaker Molecular, Rockland, Me.) in culture medium. Plates are incubated for 50-100 hours at 35° C. (or at a temperature most appropriate for the virus strain under study), fixed with 0.4% formaldehyde and stained with 3% crystal violet. Plaque size is the quantified, for example by manual measurement and counting of the plaques, or by scanning plates (for example on a FOTO/Analyst Archiver system, Fotodyne, Hartland, Wis.) and subsequent image analysis (for example using Scion Image for Windows, Scion Corp., Frederick, Md.). A codon-deoptimized virus is considered to have reduced replicative fitness when the size or number of plaques is reduced by at least 50%, for example at least 75%, as compared to the size or number of plaques generated by the native virus.

The replicative fitness of a virus can also be determined using single-step growth experiments. Virus (deoptimized and native) is generated as described above. The appropriate cells (such as HeLa cells) are infected at a multiplicity of infection (MOI) of 1-10 PFU/cell with stirring for 10-60 minutes at 35° C. Cells are then sedimented by low-speed centrifugation and resuspended in culture media. Incubation continued at 35° C. in a water bath with orbital shaking at 300 rpm. Samples are withdrawn at 2-hour intervals from 0 to 14 hours postinfection, and titered by plaque assay as described above.

To determine the replicative fitness of a bacterium or yeast pathogen, a colony-forming assay can be performed. Briefly, bacterial or yeast suspensions can be plated onto agar plates containing solidified medium with the appropriate nutrients, and after incubation (normally at 37° C.), the number of colonies are counted. Alternatively, growth rates can be measured spectrophotometrically by following the increase in optical density of the appropriate liquid medium after inoculation with the bacterial or yeast cultures. Another method to measure growth rates would use quantitative PCR to determine the rate of increase of specific nucleic acid targets as the bacterial or yeast cells are incubated in the appropriate liquid medium.

In view of the many possible embodiments to which the principles of our invention may be applied, it should be recognized that the illustrated examples are only particular examples of the invention and should not be taken as a limitation on the scope of the invention. Rather, the scope of the invention is defined by the following claims. We therefore claim as our invention all that comes within the scope and spirit of these claims.

We claim:

1. A modified respiratory syncytial virus (RSV) comprising:

a fusion (F) or glycoprotein (G) coding sequence of the respiratory syncytial virus wherein at least twenty codons in the coding sequence are deoptimized as compared to its native coding sequence, wherein the at least twenty deoptimized codons are each a synonymous codon less frequently used in the native respiratory syncytial virus, wherein the synonymous codon less frequently used in the native respiratory syncytial virus is a codon that encodes the same amino acid, but the codon is an unpreferred codon by the native RSV for the amino acid.

2. The modified respiratory syncytial virus of claim 1, wherein the deoptimized coding sequence comprises at least 50% of the coding sequence having synonymous codons less frequently used in the native respiratory syncytial virus compared to the native coding sequence.

3. The modified respiratory syncytial virus of claim 1, wherein G+C content in the deoptimized coding sequence is altered by at least 20% compared to the native coding sequence.

4. The modified respiratory syncytial virus of claim 3, wherein the G+C content in the deoptimized coding sequence is increased by at least 40%, is increased by at least 48%, or is decreased by at least 40% compared to the native coding sequence.

5. The modified respiratory syncytial virus of claim 1, wherein the number of CG dinucleotides, TA dinucleotides, or CG dinucleotides and TA nucleotides in the deoptimized coding sequence is altered by at least 20% compared to the native coding sequence.

6. The modified respiratory syncytial virus of claim 5, wherein the number CG dinucleotides or TA dinucleotides in the deoptimized coding sequence is increased by at least 100% compared to the native coding sequence.

7. The modified respiratory syncytial virus of claim 1, wherein the deoptimized coding sequence is a fusion (F) coding sequence and comprises at least 50-500 deoptimized codons compared to the native coding sequence and the deoptimized codons are each synonymous codons less frequently used in the native respiratory syncytial virus.

8. The modified respiratory syncytial virus of claim 1, wherein the deoptimized coding sequence comprises a coding sequence having an increased number of CG dinucleotides, TA dinucleotides, or CG dinucleotides and TA nucleotides in the coding sequence compared to the native coding sequence, wherein the CG or TA dinucleotides fall across codon boundaries.

9. The modified respiratory syncytial virus of claim 1, wherein the deoptimized coding sequence comprises a coding sequence having at least 90% sequence identity to the nucleic acid sequence of SEQ ID NO: 33 or SEQ ID NO: 36.

10. A method of eliciting an immune response against a respiratory syncytial virus in a subject, comprising administering to the subject an immunologically effective amount of the modified respiratory syncytial virus of claim 1, thereby eliciting an immune response in the subject.

11. A method of producing a modified respiratory syncytial virus, comprising:

introducing the modified respiratory syncytial virus of claim 1 into a host cell;

allowing the modified respiratory syncytial virus to replicate; and isolating the replicated modified respiratory syncytial virus.

12. The modified respiratory syncytial virus of claim 1, wherein the deoptimized coding sequence comprises the nucleic acid sequence of SEQ ID NO: 33 or SEQ ID NO: 36.

13. The modified respiratory syncytial virus of claim 1, wherein the deoptimized codons in the coding sequence comprises at least 50 deoptimized codons in a glycoprotein (G) coding sequence as compared to the native coding sequence and each deoptimized codon is a synonymous codon less frequently used in the native respiratory syncytial virus.

14. The modified respiratory syncytial virus of claim 1, wherein the deoptimized codons in the coding sequence comprises at least 100 deoptimized codons in a glycoprotein (G) coding sequence as compared to the native coding sequence and each deoptimized codon is a synonymous codon less frequently used in the native respiratory syncytial virus.

15. The modified respiratory syncytial virus of claim 1, wherein the native coding sequence is an RSV having GenBank Accession No. NC_001781 (SEQ ID NO: 71), U63644 (SEQ ID NO: 72), AY353550 (SEQ ID NO: 73), NC_001803 (SEQ ID NO: 74), AF013254 (SEQ ID NO: 75), or U39661 (SEQ ID NO: 76).

16. The modified respiratory syncytial virus of claim 1, wherein the deoptimized codons in the coding sequence comprises at least 30 deoptimized codons in the coding sequence as compared to the native coding sequence and each deoptimized codon is a synonymous codon less frequently used in the native respiratory syncytial virus.

17. The modified respiratory syncytial virus of claim 1, wherein the deoptimized coding sequence is a glycoprotein (G) coding sequence and comprises at least 50-200 deoptimized codons compared to the native coding sequence and the deoptimized codons are each synonymous codons less frequently used in the native respiratory syncytial virus.

* * * * *

SEQUENCE LISTING

```
<160> NUMBER OF SEQ ID NOS: 76

<210> SEQ ID NO 1
<211> LENGTH: 67
<212> TYPE: DNA
<213> ORGANISM: Artificial
<220> FEATURE:
<223> OTHER INFORMATION: primer

<400> SEQUENCE: 1

cctaagcttt tttttttttt tttttttttt tttttttccc cgaattaaag aaaaatttac      60

ccctaca                                                                 67


<210> SEQ ID NO 2
<211> LENGTH: 48
<212> TYPE: DNA
<213> ORGANISM: Artificial
<220> FEATURE:
<223> OTHER INFORMATION: primer

<400> SEQUENCE: 2

gtagtcgact aatacgactc actataggtt aaaacagctc tggggttg                   48


<210> SEQ ID NO 3
<211> LENGTH: 2745
<212> TYPE: DNA
<213> ORGANISM: Human poliovirus 2
<220> FEATURE:
<221> NAME/KEY: CDS
<222> LOCATION: (109)..(2745)

<400> SEQUENCE: 3

gagtgttgtg tcaggtatac aactgtttgt tggaaccact gtgttagctt tacttctcat      60

ttaaccaatt aatcaaaaac aatacgagga taaaacaaca atactaca atg ggc gcc     117
                                                     Met Gly Ala
                                                     1

caa gtt tca tca cag aaa gtt gga gcc cac gaa aat tca aac aga gcc      165
Gln Val Ser Ser Gln Lys Val Gly Ala His Glu Asn Ser Asn Arg Ala
    5                   10                  15

tat ggc ggg tcc acc atc aat tac act aca atc aat tac tat agg gac      213
Tyr Gly Gly Ser Thr Ile Asn Tyr Thr Thr Ile Asn Tyr Tyr Arg Asp
20                  25                  30                  35

tct gca agc aat gca gca agc aag caa gat ttt gca caa gat ccg tcc      261
Ser Ala Ser Asn Ala Ala Ser Lys Gln Asp Phe Ala Gln Asp Pro Ser
                40                  45                  50

aag ttc acc gaa ccc att aag gac gtc ctt att aag acc gct ccc atg      309
Lys Phe Thr Glu Pro Ile Lys Asp Val Leu Ile Lys Thr Ala Pro Met
            55                  60                  65

cta aac tcc cca aac att gag gcg tgt ggt tat agt gac agg gta atg      357
Leu Asn Ser Pro Asn Ile Glu Ala Cys Gly Tyr Ser Asp Arg Val Met
        70                  75                  80

cag cta act ctg ggc aat tca acg atc acc acc caa gaa gcg gcc aat      405
Gln Leu Thr Leu Gly Asn Ser Thr Ile Thr Thr Gln Glu Ala Ala Asn
    85                  90                  95

tct gtt gtt gcc tac ggt aga tgg cct gaa tac atc aga gat acc gag      453
Ser Val Val Ala Tyr Gly Arg Trp Pro Glu Tyr Ile Arg Asp Thr Glu
```

-continued

```
100                 105                 110                 115

gca aat cct gta gac caa cca acc gag ccc gat gta gcc gcg tgc agg      501
Ala Asn Pro Val Asp Gln Pro Thr Glu Pro Asp Val Ala Ala Cys Arg
                120                 125                 130

ttc tac aca tta gat acc gtc act tgg cgc aag gag tcc aga ggg tgg      549
Phe Tyr Thr Leu Asp Thr Val Thr Trp Arg Lys Glu Ser Arg Gly Trp
            135                 140                 145

tgg tgg aaa cta cca gac gct tta aaa gac atg ggg tta ttt ggt caa      597
Trp Trp Lys Leu Pro Asp Ala Leu Lys Asp Met Gly Leu Phe Gly Gln
        150                 155                 160

aac atg ttt tat cac tat ctt ggg agg gct ggc tac aca gtg cac gta      645
Asn Met Phe Tyr His Tyr Leu Gly Arg Ala Gly Tyr Thr Val His Val
    165                 170                 175

cag tgc aat gct tca aag ttt cat caa gga gct cta ggg gtg ttt gca      693
Gln Cys Asn Ala Ser Lys Phe His Gln Gly Ala Leu Gly Val Phe Ala
180                 185                 190                 195

gtt cca gaa atg tgt tta gct ggt gat agc aca act cac atg ttc aca      741
Val Pro Glu Met Cys Leu Ala Gly Asp Ser Thr Thr His Met Phe Thr
                200                 205                 210

aag tac gag aat gcg aat cca ggc gaa aaa gga ggt gaa ttc aaa ggg      789
Lys Tyr Glu Asn Ala Asn Pro Gly Glu Lys Gly Gly Glu Phe Lys Gly
            215                 220                 225

agt ttc acc ctt gat acc aac gcc act aac cct gca cgg aac ttc tgc      837
Ser Phe Thr Leu Asp Thr Asn Ala Thr Asn Pro Ala Arg Asn Phe Cys
        230                 235                 240

cca gtt gat tac ctc ttc ggg agt gga gtg ctg gta ggg aat gca ttt      885
Pro Val Asp Tyr Leu Phe Gly Ser Gly Val Leu Val Gly Asn Ala Phe
    245                 250                 255

gtt tat cca cat caa ata ata aac ctg cgc act aac aac tgt gct acg      933
Val Tyr Pro His Gln Ile Ile Asn Leu Arg Thr Asn Asn Cys Ala Thr
260                 265                 270                 275

cta gta ttg ccc tat gta aac tca ctc tca ata gat agc atg aca aag      981
Leu Val Leu Pro Tyr Val Asn Ser Leu Ser Ile Asp Ser Met Thr Lys
                280                 285                 290

cac aac aac tgg ggg atc gct atc ctc ccc ctg gcg cca cta gac ttt     1029
His Asn Asn Trp Gly Ile Ala Ile Leu Pro Leu Ala Pro Leu Asp Phe
            295                 300                 305

gcc act gaa tct tcc act gag ata ccc att aca ctg acc att gct ccc     1077
Ala Thr Glu Ser Ser Thr Glu Ile Pro Ile Thr Leu Thr Ile Ala Pro
        310                 315                 320

atg tgc tgc gaa ttc aat ggt tta cgc aac atc act gtg cca aga acc     1125
Met Cys Cys Glu Phe Asn Gly Leu Arg Asn Ile Thr Val Pro Arg Thr
    325                 330                 335

caa gga tta cca gtc ctg aac act cca ggg agt aac cag tac ctg acc     1173
Gln Gly Leu Pro Val Leu Asn Thr Pro Gly Ser Asn Gln Tyr Leu Thr
340                 345                 350                 355

gca gac aat tac cag tct ccg tgt gcg ata cct gag ttt gat gtc act     1221
Ala Asp Asn Tyr Gln Ser Pro Cys Ala Ile Pro Glu Phe Asp Val Thr
                360                 365                 370

cca ccc ata gac ata cca ggg gag gtg cgc aac atg atg gaa ttg gcg     1269
Pro Pro Ile Asp Ile Pro Gly Glu Val Arg Asn Met Met Glu Leu Ala
            375                 380                 385

gaa ata gac acc atg ata ccc ctc aac ttg aca agt caa cgc aag aac     1317
Glu Ile Asp Thr Met Ile Pro Leu Asn Leu Thr Ser Gln Arg Lys Asn
        390                 395                 400

aca atg gac atg tat aga gtc gag ttg agc gac acg gct cac tct gac     1365
Thr Met Asp Met Tyr Arg Val Glu Leu Ser Asp Thr Ala His Ser Asp
    405                 410                 415

acg ccg atc ttg tgt ctc tcg ttg tcc ccc gct tca gac ccc aga ttg     1413
```

-continued

```
Thr Pro Ile Leu Cys Leu Ser Leu Ser Pro Ala Ser Asp Pro Arg Leu
420                 425                 430                 435

gca cac act atg ttg ggt gag ata tta aat tac tac aca cac tgg gca      1461
Ala His Thr Met Leu Gly Glu Ile Leu Asn Tyr Tyr Thr His Trp Ala
                440                 445                 450

ggg tcc ttg aaa ttt acc ttt ctc ttt tgc ggc tca atg atg gcc acc      1509
Gly Ser Leu Lys Phe Thr Phe Leu Phe Cys Gly Ser Met Met Ala Thr
            455                 460                 465

gga aag tta ttg gtt tct tac gca cca ccc gga gca gag gcc ccc aag      1557
Gly Lys Leu Leu Val Ser Tyr Ala Pro Pro Gly Ala Glu Ala Pro Lys
        470                 475                 480

agt cgc aaa gaa gca atg ctt ggg aca cat gtg ata tgg gac att ggg      1605
Ser Arg Lys Glu Ala Met Leu Gly Thr His Val Ile Trp Asp Ile Gly
    485                 490                 495

ttg cag tct tca tgc act atg gtg gta cct tgg atc agt aat acc aca      1653
Leu Gln Ser Ser Cys Thr Met Val Val Pro Trp Ile Ser Asn Thr Thr
500                 505                 510                 515

tac aga caa acc atc aac gat agt ttc aca gaa ggt ggc tac att agc      1701
Tyr Arg Gln Thr Ile Asn Asp Ser Phe Thr Glu Gly Gly Tyr Ile Ser
                520                 525                 530

atg ttc tat caa act agg gtt gtt gtc ccg ttg tcc aca ccc aga aag      1749
Met Phe Tyr Gln Thr Arg Val Val Val Pro Leu Ser Thr Pro Arg Lys
            535                 540                 545

atg gac atc ctg ggt ttt gtg tca gct tgc aat gac ttc agt gtg cgc      1797
Met Asp Ile Leu Gly Phe Val Ser Ala Cys Asn Asp Phe Ser Val Arg
        550                 555                 560

tta ctg cga gat aca aca cac att agt caa gag gct atg cca caa gga      1845
Leu Leu Arg Asp Thr Thr His Ile Ser Gln Glu Ala Met Pro Gln Gly
    565                 570                 575

att ggt gac atg att gag ggg gcc gtt gaa ggg att act aaa aat gca      1893
Ile Gly Asp Met Ile Glu Gly Ala Val Glu Gly Ile Thr Lys Asn Ala
580                 585                 590                 595

ttg gtt ccc ccg act tcc acc aat agc ctg cct gac aca aag ccg agc      1941
Leu Val Pro Pro Thr Ser Thr Asn Ser Leu Pro Asp Thr Lys Pro Ser
                600                 605                 610

ggt cca gcc cac tcc aag gag ata cct gca ttg aca gcc gtg gag aca      1989
Gly Pro Ala His Ser Lys Glu Ile Pro Ala Leu Thr Ala Val Glu Thr
            615                 620                 625

ggg gct acc aat ccg ttg gtg cct tcg gac acc gtg caa acg cgc cat      2037
Gly Ala Thr Asn Pro Leu Val Pro Ser Asp Thr Val Gln Thr Arg His
        630                 635                 640

gtc atc cag aga cga acg cga tca gag tcc acg gtt gag tca ttc ttt      2085
Val Ile Gln Arg Arg Thr Arg Ser Glu Ser Thr Val Glu Ser Phe Phe
    645                 650                 655

gca aga ggg gct tgc gtg gct atc att gag gtg gac aat gat gca ccg      2133
Ala Arg Gly Ala Cys Val Ala Ile Ile Glu Val Asp Asn Asp Ala Pro
660                 665                 670                 675

aca aag cgc gcc agc aga ttg ttt tcg gtt tgg aaa ata act tac aaa      2181
Thr Lys Arg Ala Ser Arg Leu Phe Ser Val Trp Lys Ile Thr Tyr Lys
                680                 685                 690

gat act gtt caa ctg aga cgc aaa ctg gaa ttt ttc aca tat tcg aga      2229
Asp Thr Val Gln Leu Arg Arg Lys Leu Glu Phe Phe Thr Tyr Ser Arg
            695                 700                 705

ttt gac atg gag ttc act ttt gtg gtc acc tca aac tac att gat gca      2277
Phe Asp Met Glu Phe Thr Phe Val Val Thr Ser Asn Tyr Ile Asp Ala
        710                 715                 720

aat aac gga cat gca ttg aac caa gtt tat cag ata atg tat ata cca      2325
Asn Asn Gly His Ala Leu Asn Gln Val Tyr Gln Ile Met Tyr Ile Pro
    725                 730                 735
```

```
ccc gga gca cct atc cct ggt aaa tgg aat gac tat acg tgg cag acg     2373
Pro Gly Ala Pro Ile Pro Gly Lys Trp Asn Asp Tyr Thr Trp Gln Thr
740                 745                 750                 755

tcc tct aac ccg tcg gtg ttt tac acc tat ggg gcg ccc cca gca aga     2421
Ser Ser Asn Pro Ser Val Phe Tyr Thr Tyr Gly Ala Pro Pro Ala Arg
                760                 765                 770

ata tca gtg ccc tac gtg gga att gct aat gcg tat tcc cac ttt tat     2469
Ile Ser Val Pro Tyr Val Gly Ile Ala Asn Ala Tyr Ser His Phe Tyr
            775                 780                 785

gat ggg ttt gca aaa gta cca cta gcg ggt caa gcc tca act gaa ggc     2517
Asp Gly Phe Ala Lys Val Pro Leu Ala Gly Gln Ala Ser Thr Glu Gly
        790                 795                 800

gat tcg ttg tac ggt gct gcc tca ctg aat gat ttt gga tca ctg gct     2565
Asp Ser Leu Tyr Gly Ala Ala Ser Leu Asn Asp Phe Gly Ser Leu Ala
    805                 810                 815

gtt cgc gtg gta aat gat cac aac ccc acg cgg ctc acc tcc aag atc     2613
Val Arg Val Val Asn Asp His Asn Pro Thr Arg Leu Thr Ser Lys Ile
820                 825                 830                 835

aga gtg tac atg aag cca aag cat gtc aga gtc tgg tgc cca cga cct     2661
Arg Val Tyr Met Lys Pro Lys His Val Arg Val Trp Cys Pro Arg Pro
                840                 845                 850

cca cga gca gtc cca tac ttc gga cca ggt gtt gat tat aaa gat ggg     2709
Pro Arg Ala Val Pro Tyr Phe Gly Pro Gly Val Asp Tyr Lys Asp Gly
            855                 860                 865

ctc acc cca cta cca gaa aag gga tta acg act tat                     2745
Leu Thr Pro Leu Pro Glu Lys Gly Leu Thr Thr Tyr
        870                 875


<210> SEQ ID NO 4
<211> LENGTH: 879
<212> TYPE: PRT
<213> ORGANISM: Human poliovirus 2

<400> SEQUENCE: 4

Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
            20                  25                  30

Tyr Arg Asp Ser Ala Ser Asn Ala Ala Ser Lys Gln Asp Phe Ala Gln
        35                  40                  45

Asp Pro Ser Lys Phe Thr Glu Pro Ile Lys Asp Val Leu Ile Lys Thr
    50                  55                  60

Ala Pro Met Leu Asn Ser Pro Asn Ile Glu Ala Cys Gly Tyr Ser Asp
65                  70                  75                  80

Arg Val Met Gln Leu Thr Leu Gly Asn Ser Thr Ile Thr Thr Gln Glu
                85                  90                  95

Ala Ala Asn Ser Val Val Ala Tyr Gly Arg Trp Pro Glu Tyr Ile Arg
            100                 105                 110

Asp Thr Glu Ala Asn Pro Val Asp Gln Pro Thr Glu Pro Asp Val Ala
        115                 120                 125

Ala Cys Arg Phe Tyr Thr Leu Asp Thr Val Thr Trp Arg Lys Glu Ser
    130                 135                 140

Arg Gly Trp Trp Trp Lys Leu Pro Asp Ala Leu Lys Asp Met Gly Leu
145                 150                 155                 160

Phe Gly Gln Asn Met Phe Tyr His Tyr Leu Gly Arg Ala Gly Tyr Thr
                165                 170                 175

Val His Val Gln Cys Asn Ala Ser Lys Phe His Gln Gly Ala Leu Gly
            180                 185                 190
```

-continued

```
Val Phe Ala Val Pro Glu Met Cys Leu Ala Gly Asp Ser Thr Thr His
        195                 200                 205

Met Phe Thr Lys Tyr Glu Asn Ala Asn Pro Gly Glu Lys Gly Gly Glu
    210                 215                 220

Phe Lys Gly Ser Phe Thr Leu Asp Thr Asn Ala Thr Asn Pro Ala Arg
225                 230                 235                 240

Asn Phe Cys Pro Val Asp Tyr Leu Phe Gly Ser Gly Val Leu Val Gly
                245                 250                 255

Asn Ala Phe Val Tyr Pro His Gln Ile Ile Asn Leu Arg Thr Asn Asn
            260                 265                 270

Cys Ala Thr Leu Val Leu Pro Tyr Val Asn Ser Leu Ser Ile Asp Ser
        275                 280                 285

Met Thr Lys His Asn Asn Trp Gly Ile Ala Ile Leu Pro Leu Ala Pro
    290                 295                 300

Leu Asp Phe Ala Thr Glu Ser Ser Thr Glu Ile Pro Ile Thr Leu Thr
305                 310                 315                 320

Ile Ala Pro Met Cys Cys Glu Phe Asn Gly Leu Arg Asn Ile Thr Val
                325                 330                 335

Pro Arg Thr Gln Gly Leu Pro Val Leu Asn Thr Pro Gly Ser Asn Gln
            340                 345                 350

Tyr Leu Thr Ala Asp Asn Tyr Gln Ser Pro Cys Ala Ile Pro Glu Phe
        355                 360                 365

Asp Val Thr Pro Pro Ile Asp Ile Pro Gly Glu Val Arg Asn Met Met
    370                 375                 380

Glu Leu Ala Glu Ile Asp Thr Met Ile Pro Leu Asn Leu Thr Ser Gln
385                 390                 395                 400

Arg Lys Asn Thr Met Asp Met Tyr Arg Val Glu Leu Ser Asp Thr Ala
                405                 410                 415

His Ser Asp Thr Pro Ile Leu Cys Leu Ser Leu Ser Pro Ala Ser Asp
            420                 425                 430

Pro Arg Leu Ala His Thr Met Leu Gly Glu Ile Leu Asn Tyr Tyr Thr
        435                 440                 445

His Trp Ala Gly Ser Leu Lys Phe Thr Phe Leu Phe Cys Gly Ser Met
    450                 455                 460

Met Ala Thr Gly Lys Leu Leu Val Ser Tyr Ala Pro Pro Gly Ala Glu
465                 470                 475                 480

Ala Pro Lys Ser Arg Lys Glu Ala Met Leu Gly Thr His Val Ile Trp
                485                 490                 495

Asp Ile Gly Leu Gln Ser Ser Cys Thr Met Val Val Pro Trp Ile Ser
            500                 505                 510

Asn Thr Thr Tyr Arg Gln Thr Ile Asn Asp Ser Phe Thr Glu Gly Gly
        515                 520                 525

Tyr Ile Ser Met Phe Tyr Gln Thr Arg Val Val Val Pro Leu Ser Thr
    530                 535                 540

Pro Arg Lys Met Asp Ile Leu Gly Phe Val Ser Ala Cys Asn Asp Phe
545                 550                 555                 560

Ser Val Arg Leu Leu Arg Asp Thr Thr His Ile Ser Gln Glu Ala Met
                565                 570                 575

Pro Gln Gly Ile Gly Asp Met Ile Glu Gly Ala Val Glu Gly Ile Thr
            580                 585                 590

Lys Asn Ala Leu Val Pro Pro Thr Ser Thr Asn Ser Leu Pro Asp Thr
        595                 600                 605
```

-continued

```
Lys Pro Ser Gly Pro Ala His Ser Lys Glu Ile Pro Ala Leu Thr Ala
    610                 615                 620

Val Glu Thr Gly Ala Thr Asn Pro Leu Val Pro Ser Asp Thr Val Gln
625                 630                 635                 640

Thr Arg His Val Ile Gln Arg Arg Thr Arg Ser Glu Ser Thr Val Glu
                645                 650                 655

Ser Phe Phe Ala Arg Gly Ala Cys Val Ala Ile Ile Glu Val Asp Asn
            660                 665                 670

Asp Ala Pro Thr Lys Arg Ala Ser Arg Leu Phe Ser Val Trp Lys Ile
        675                 680                 685

Thr Tyr Lys Asp Thr Val Gln Leu Arg Arg Lys Leu Glu Phe Phe Thr
    690                 695                 700

Tyr Ser Arg Phe Asp Met Glu Phe Thr Phe Val Val Thr Ser Asn Tyr
705                 710                 715                 720

Ile Asp Ala Asn Asn Gly His Ala Leu Asn Gln Val Tyr Gln Ile Met
                725                 730                 735

Tyr Ile Pro Pro Gly Ala Pro Ile Pro Gly Lys Trp Asn Asp Tyr Thr
            740                 745                 750

Trp Gln Thr Ser Ser Asn Pro Ser Val Phe Tyr Thr Tyr Gly Ala Pro
        755                 760                 765

Pro Ala Arg Ile Ser Val Pro Tyr Val Gly Ile Ala Asn Ala Tyr Ser
    770                 775                 780

His Phe Tyr Asp Gly Phe Ala Lys Val Pro Leu Ala Gly Gln Ala Ser
785                 790                 795                 800

Thr Glu Gly Asp Ser Leu Tyr Gly Ala Ala Ser Leu Asn Asp Phe Gly
                805                 810                 815

Ser Leu Ala Val Arg Val Val Asn Asp His Asn Pro Thr Arg Leu Thr
            820                 825                 830

Ser Lys Ile Arg Val Tyr Met Lys Pro Lys His Val Arg Val Trp Cys
        835                 840                 845

Pro Arg Pro Pro Arg Ala Val Pro Tyr Phe Gly Pro Gly Val Asp Tyr
    850                 855                 860

Lys Asp Gly Leu Thr Pro Leu Pro Glu Lys Gly Leu Thr Thr Tyr
865                 870                 875
```

<210> SEQ ID NO 5
<211> LENGTH: 2745
<212> TYPE: DNA
<213> ORGANISM: Artificial
<220> FEATURE:
<223> OTHER INFORMATION: deoptimized Sabin 2 sequence

<400> SEQUENCE: 5

```
gagtgttgtg tcaggtatac aactgtttgt tggaaccact gtgttagctt tacttctcat      60

ttaaccaatt aatcaaaaac aatacgagga taaaacaaca atactacaat gggtgcgcaa     120

gtcagcagcc agaaagtcgg tgcgcacgaa aatagcaacc gggcgtatgg tggtagcacg     180

atcaattaca cgacgatcaa ttactatcgg gacagcgcga gcaatgcggc gagcaagcaa     240

gattttgcgc aagatccgag caagttcacg gaaccgatca aggacgtcct tatcaagacg     300

gcgccgatgc ttaacagccc gaacatcgag gcgtgtggtt atagtgaccg ggtcatgcag     360

cttacgcttg gtaatagcac gatcacgacg caagaagcgg cgaatagcgt cgtcgcgtac     420

ggtcggtggc cggaatacat ccgggatacg gaggcgaatc cggtcgacca accgacggag     480

ccggatgtcg cggcgtgccg gttctacacg cttgatacgg tcacgtggcg gaaggagagc     540
```

-continued

```
cggggttggt ggtggaaact tccggacgcg cttaaagaca tgggtctttt tggtcaaaac    600
atgttttatc actatcttgg tcgggcgggt tacacggtcc acgtccagtg caatgcgagc    660
aagtttcatc aaggtgccct tggtgtcttt gcggtcccgg aaatgtgtct tgcgggtgat    720
agcacgacgc acatgttcac gaagtacgag aatgcgaatc cgggtgaaaa aggtggtgaa    780
ttcaaaggta gcttcacgct tgatacgaac gcgacgaacc cggcgcggaa cttctgcccg    840
gtcgattacc ttttcggtag cggtgtcctt gtcggtaatg cgtttgtcta tccgcatcaa    900
atcatcaacc ttcggacgaa caactgtgcg acgcttgtct tgccgtatgt caacagccty    960
agcatcgata gcatgacgaa gcacaacaac tggggtatcg cgatccttcc gcttgcgccg   1020
cttgactttg cgacggaaag cagcacggag atcccgatca cgcttacgat cgcgccgatg   1080
tgctgcgaat tcaatggtct tcggaacatc acggtcccgc ggacgcaagg tcttccggtc   1140
cttaacacgc cgggtagcaa ccagtacctt acggcggaca attaccagag cccgtgtgcg   1200
atcccggagt ttgatgtcac gccgccgatc gacatcccgg gtgaggtccg gaacatgatg   1260
gaacttgcgg aaatcgacac gatgatcccg cttaacctta cgagccaacg gaagaacacg   1320
atggacatgt atcgggtcga gcttagcgac acggcgcaca gcgacacgcc gatcctttgt   1380
cttagcttga gcccggcgag cgacccgcgg cttgcgcaca cgatgcttgg tgagatcctt   1440
aattactaca cgcactgggc gggtagcttg aaatttacgt ttctttttg cggtagcatg    1500
atggcgacgg gtaagcttct tgtcagctac gcgccgccgg gtgcggaggc gccgaagagc   1560
cggaaagaag cgatgcttgg tacgcatgtc atctgggaca tcggtcttca gagcagctgc   1620
acgatggtcg tcccgtggat cagcaatacg acgtaccggc aaacgatcaa cgatagcttc   1680
acggaaggtg gttacatcag catgttctat caaacgcggg tcgtcgtccc gcttagcacg   1740
ccgcggaaga tggacatcct tggttttgtc agcgcgtgca atgacttcag cgtccggctt   1800
cttcgggata cgacgcacat cagccaagag gcgatgccgc aaggtatcgg tgacatgatc   1860
gagggtgcgg tcgaaggtat cacgaaaaat gcgcttgtcc cgccgacgag cacgaatagc   1920
cttccggaca cgaagccgag cggtccggcg cacagcaagg agatcccggc gcttacggcg   1980
gtcgagacgg gtgcgacgaa tccgcttgtc ccgagcgaca cggtccaaac gcggcatgtc   2040
atccagcggc ggacgcggag cgagagcacg gtcgagagct tctttgcgcg gggtgcgtgc   2100
gtcgcgatca tcgaggtcga caatgatgcg ccgacgaagc gggcgagccg gctttttagc   2160
gtctggaaaa tcacgtacaa agatacggtc caacttcggc ggaaacttga atttttcacg   2220
tatagccggt ttgacatgga gttcacgttt gtcgtcacga gcaactacat cgatgcgaat   2280
aacggtcatg cgcttaacca agtctatcag atcatgtata tcccgccggg tgcgccgatc   2340
ccgggtaaat ggaatgacta tacgtggcag acgagcagca acccgagcgt cttttacacg   2400
tatggtgcgc cgccggcgcg gatcagcgtc ccgtacgtcg gtatcgcgaa tgcgtatagc   2460
cacttttatg atggttttgc gaaagtcccg cttgcgggtc aagcgagcac ggaaggtgat   2520
agcctttacg gtgcggcgag ccttaatgat tttggtagcc ttgcggtccg ggtcgtcaat   2580
gatcacaacc cgacgcggct tacgagcaag atccgggtct acatgaagcc gaagcatgtc   2640
cgggtctggt gcccgcggcc tcctcgagcg gtcccgtact tcggtccggg tgtcgattat   2700
aaagatgggc tcaccccact accagaaaag ggattaacga cttat                   2745
```

<210> SEQ ID NO 6
<211> LENGTH: 6621
<212> TYPE: DNA
<213> ORGANISM: Human poliovirus 2

```
<220> FEATURE:
<221> NAME/KEY: CDS
<222> LOCATION: (1)..(6621)

<400> SEQUENCE: 6

atg ggc gcc caa gtc tca tca cag aaa gtt gga gcc cat gag aat tca       48
Met Gly Ala Gln Val Ser Ser Gln Lys Val Gly Ala His Glu Asn Ser
1               5                   10                  15

aac aga gct tat ggc gga tcc acc att aat tac act act att aat tat       96
Asn Arg Ala Tyr Gly Gly Ser Thr Ile Asn Tyr Thr Thr Ile Asn Tyr
            20                  25                  30

tac agg gat tct gcg agc aat gcc gct agt aag cag gac ttt gca caa      144
Tyr Arg Asp Ser Ala Ser Asn Ala Ala Ser Lys Gln Asp Phe Ala Gln
        35                  40                  45

gac cca tcc aag ttc act gaa cct att aaa gat gtt ctc att aag acc      192
Asp Pro Ser Lys Phe Thr Glu Pro Ile Lys Asp Val Leu Ile Lys Thr
    50                  55                  60

gct ccc acg cta aac tct cct aat atc gag gcg tgt ggg tat agc gac      240
Ala Pro Thr Leu Asn Ser Pro Asn Ile Glu Ala Cys Gly Tyr Ser Asp
65                  70                  75                  80

aga gtg atg caa cta acc cta ggc aat tcc acc att acc aca cag gag      288
Arg Val Met Gln Leu Thr Leu Gly Asn Ser Thr Ile Thr Thr Gln Glu
                85                  90                  95

gcg gcc aat tct gtc gtt gca tac ggc cgg tgg ccc gag tac atc aag      336
Ala Ala Asn Ser Val Val Ala Tyr Gly Arg Trp Pro Glu Tyr Ile Lys
            100                 105                 110

gac tca gaa gca aat cct gtg gac cag cca act gaa ccg gac gtt gcc      384
Asp Ser Glu Ala Asn Pro Val Asp Gln Pro Thr Glu Pro Asp Val Ala
        115                 120                 125

gcg tgc agg ttt tac aca cta gac act gtt act tgg cgc aag gag tcc      432
Ala Cys Arg Phe Tyr Thr Leu Asp Thr Val Thr Trp Arg Lys Glu Ser
    130                 135                 140

aga ggg tgg tgg tgg aaa ctg cct gat gca cta aag gac atg gga tta      480
Arg Gly Trp Trp Trp Lys Leu Pro Asp Ala Leu Lys Asp Met Gly Leu
145                 150                 155                 160

ttc ggc cag aac atg ttc tac cac tac ctc ggg agg gct ggc tat act      528
Phe Gly Gln Asn Met Phe Tyr His Tyr Leu Gly Arg Ala Gly Tyr Thr
                165                 170                 175

gtg cac gta cag tgt aat gct tca aag ttt cac cag ggc gcc ctc ggg      576
Val His Val Gln Cys Asn Ala Ser Lys Phe His Gln Gly Ala Leu Gly
            180                 185                 190

gta ttc gca gtt cca gaa atg tgc ctg gca ggc gac agc aca acc cac      624
Val Phe Ala Val Pro Glu Met Cys Leu Ala Gly Asp Ser Thr Thr His
        195                 200                 205

atg ttt aca aaa tat gag aat gca aat ccg ggt gag aaa ggg ggt gaa      672
Met Phe Thr Lys Tyr Glu Asn Ala Asn Pro Gly Glu Lys Gly Gly Glu
    210                 215                 220

ttc aaa ggg agt ttt act ctg gat act aac gct acc aac cct gca cgc      720
Phe Lys Gly Ser Phe Thr Leu Asp Thr Asn Ala Thr Asn Pro Ala Arg
225                 230                 235                 240

aac ttt tgt ccc gtt gat tat ctc ttc ggg agc gga gta ctg gcg gga      768
Asn Phe Cys Pro Val Asp Tyr Leu Phe Gly Ser Gly Val Leu Ala Gly
                245                 250                 255

aat gcg ttt gtt tac cca cat cag ata att aat ctg cgc acc aac aac      816
Asn Ala Phe Val Tyr Pro His Gln Ile Ile Asn Leu Arg Thr Asn Asn
            260                 265                 270

tgt gcc acg ttg gtg ctg cca tac gtt aat tca ctt tcc ata gac agc      864
Cys Ala Thr Leu Val Leu Pro Tyr Val Asn Ser Leu Ser Ile Asp Ser
        275                 280                 285

atg aca aaa cac aac aat tgg gga att gct atc ctt ccg ctg gca cca      912
```

-continued

```
Met Thr Lys His Asn Asn Trp Gly Ile Ala Ile Leu Pro Leu Ala Pro
    290                 295                 300

ctt gac ttt gcc acc gag tcc tcc act gag ata ccc att act cta act      960
Leu Asp Phe Ala Thr Glu Ser Ser Thr Glu Ile Pro Ile Thr Leu Thr
305                 310                 315                 320

att gcc cct atg tgt tgt gaa ttc aat ggg ttg cgc aac atc act gta     1008
Ile Ala Pro Met Cys Cys Glu Phe Asn Gly Leu Arg Asn Ile Thr Val
                325                 330                 335

ccc aga act caa ggg ttg cca gtc tta aac act cca gga agc aac cag     1056
Pro Arg Thr Gln Gly Leu Pro Val Leu Asn Thr Pro Gly Ser Asn Gln
            340                 345                 350

tac tta aca gca gac aac tat caa tcc cca tgt gcg ata ccc gag ttt     1104
Tyr Leu Thr Ala Asp Asn Tyr Gln Ser Pro Cys Ala Ile Pro Glu Phe
        355                 360                 365

gat gta aca cca ccc ata gac atc ccg ggg gaa gtg cgc aac atg atg     1152
Asp Val Thr Pro Pro Ile Asp Ile Pro Gly Glu Val Arg Asn Met Met
    370                 375                 380

gaa ttg gca gag ata gac acc atg ata cct ctc aat ctg acg aac cag     1200
Glu Leu Ala Glu Ile Asp Thr Met Ile Pro Leu Asn Leu Thr Asn Gln
385                 390                 395                 400

cgc aag aac acc atg gat atg tac aga gtc gaa ctg aat gat gcg gct     1248
Arg Lys Asn Thr Met Asp Met Tyr Arg Val Glu Leu Asn Asp Ala Ala
                405                 410                 415

cac tct gac aca cca ata ttg tgt ctc tca ctg tct cca gca tca gat     1296
His Ser Asp Thr Pro Ile Leu Cys Leu Ser Leu Ser Pro Ala Ser Asp
            420                 425                 430

cct agg cta gca cac act atg cta ggt gaa ata ctg aac tac tac aca     1344
Pro Arg Leu Ala His Thr Met Leu Gly Glu Ile Leu Asn Tyr Tyr Thr
        435                 440                 445

cac tgg gca ggg tca ttg aag ttc aca ttt ctc ttc tgc ggc tca atg     1392
His Trp Ala Gly Ser Leu Lys Phe Thr Phe Leu Phe Cys Gly Ser Met
    450                 455                 460

atg gcc act ggt aaa ttg cta gtg tcc tat gca cct cct ggt gcg gaa     1440
Met Ala Thr Gly Lys Leu Leu Val Ser Tyr Ala Pro Pro Gly Ala Glu
465                 470                 475                 480

gcc cct aaa agc cgc aaa gaa gcg atg ctc ggc acc cac gtg atc tgg     1488
Ala Pro Lys Ser Arg Lys Glu Ala Met Leu Gly Thr His Val Ile Trp
                485                 490                 495

gac atc gga tta cag tca tca tgc act atg gtg gta cct tgg att agc     1536
Asp Ile Gly Leu Gln Ser Ser Cys Thr Met Val Val Pro Trp Ile Ser
            500                 505                 510

aac acc aca tac aga caa acc atc aac gat agc ttc aca gaa gga ggg     1584
Asn Thr Thr Tyr Arg Gln Thr Ile Asn Asp Ser Phe Thr Glu Gly Gly
        515                 520                 525

tac atc agt atg ttt tac caa act aga gtt gtt gtg cca ttg tcc acc     1632
Tyr Ile Ser Met Phe Tyr Gln Thr Arg Val Val Val Pro Leu Ser Thr
    530                 535                 540

cct aga aag atg gac ata ttg ggc ttt gtg tca gcc tgc aat gac ttc     1680
Pro Arg Lys Met Asp Ile Leu Gly Phe Val Ser Ala Cys Asn Asp Phe
545                 550                 555                 560

agt gtg cgc ctg ttg cgt gac acg acg cac ata agc caa gag gct atg     1728
Ser Val Arg Leu Leu Arg Asp Thr Thr His Ile Ser Gln Glu Ala Met
                565                 570                 575

cca caa gga ttg ggt gat tta att gaa ggg gtt gtt gag gga gtc acg     1776
Pro Gln Gly Leu Gly Asp Leu Ile Glu Gly Val Val Glu Gly Val Thr
            580                 585                 590

aga aat gcc ttg aca cca ctg aca cct gcc aac aac ttg cct gat aca     1824
Arg Asn Ala Leu Thr Pro Leu Thr Pro Ala Asn Asn Leu Pro Asp Thr
        595                 600                 605
```

-continued

```
caa tct agc ggc cca gcc cac tct aag gaa aca cca gcg cta aca gcc      1872
Gln Ser Ser Gly Pro Ala His Ser Lys Glu Thr Pro Ala Leu Thr Ala
    610                 615                 620

gta gag aca ggg gcc acc aac cca ttg gtg cct tca gac acg gta caa      1920
Val Glu Thr Gly Ala Thr Asn Pro Leu Val Pro Ser Asp Thr Val Gln
625                 630                 635                 640

act cgt cac gtc atc caa aag cgg acg cgg tcg gag tct acg gtt gag      1968
Thr Arg His Val Ile Gln Lys Arg Thr Arg Ser Glu Ser Thr Val Glu
                645                 650                 655

tct ttc ttc gca aga gga gct tgt gtg gcc att att gaa gtg gat aat      2016
Ser Phe Phe Ala Arg Gly Ala Cys Val Ala Ile Ile Glu Val Asp Asn
            660                 665                 670

gat gct cca aca aag cgt gcc agt aaa tta ttt tca gtc tgg aag ata      2064
Asp Ala Pro Thr Lys Arg Ala Ser Lys Leu Phe Ser Val Trp Lys Ile
        675                 680                 685

act tac aaa gac acc gtt cag tta aga cgt aag ttg gag ttc ttt aca      2112
Thr Tyr Lys Asp Thr Val Gln Leu Arg Arg Lys Leu Glu Phe Phe Thr
    690                 695                 700

tat tca agg ttt gac atg gag ttc acc ttt gtg gtt aca tcc aat tat      2160
Tyr Ser Arg Phe Asp Met Glu Phe Thr Phe Val Val Thr Ser Asn Tyr
705                 710                 715                 720

acc gat gca aac aat ggg cac gca cta aat caa gtt tac cag ata atg      2208
Thr Asp Ala Asn Asn Gly His Ala Leu Asn Gln Val Tyr Gln Ile Met
                725                 730                 735

tac ata cca cct ggg gca ccg atc cct ggc aag tgg aat gat tac aca      2256
Tyr Ile Pro Pro Gly Ala Pro Ile Pro Gly Lys Trp Asn Asp Tyr Thr
            740                 745                 750

tgg caa acg tca tct aac cca tca gtg ttt tac act tac ggg gca cct      2304
Trp Gln Thr Ser Ser Asn Pro Ser Val Phe Tyr Thr Tyr Gly Ala Pro
        755                 760                 765

cca gct aga ata tca gtg ccc tac gtg ggc att gcc aat gca tat tct      2352
Pro Ala Arg Ile Ser Val Pro Tyr Val Gly Ile Ala Asn Ala Tyr Ser
    770                 775                 780

cat ttt tac gat ggg ttt gcc aaa gta cca cta gca ggc caa gcc tca      2400
His Phe Tyr Asp Gly Phe Ala Lys Val Pro Leu Ala Gly Gln Ala Ser
785                 790                 795                 800

aca gag ggt gac tcg ctg tat gga gcg gct tca ttg aat gac ttc gga      2448
Thr Glu Gly Asp Ser Leu Tyr Gly Ala Ala Ser Leu Asn Asp Phe Gly
                805                 810                 815

tca ctg gct gtt cga gtg gtg aat gac cac aac cct acg aaa ctc act      2496
Ser Leu Ala Val Arg Val Val Asn Asp His Asn Pro Thr Lys Leu Thr
            820                 825                 830

tca aaa atc aga gtg tac atg aaa cca aag cac gtc aga gtg tgg tgt      2544
Ser Lys Ile Arg Val Tyr Met Lys Pro Lys His Val Arg Val Trp Cys
        835                 840                 845

ccg cga ccc cct cga gca gtc cca tac tac gga cca ggg gtt gac tac      2592
Pro Arg Pro Pro Arg Ala Val Pro Tyr Tyr Gly Pro Gly Val Asp Tyr
    850                 855                 860

aag gat gga cta gcc cca ctg cca gag aaa ggc ttg aca acc tat ggt      2640
Lys Asp Gly Leu Ala Pro Leu Pro Glu Lys Gly Leu Thr Thr Tyr Gly
865                 870                 875                 880

ttt ggc cac caa aat aag gca gtg tac acg gca ggt tac aaa att tgc      2688
Phe Gly His Gln Asn Lys Ala Val Tyr Thr Ala Gly Tyr Lys Ile Cys
                885                 890                 895

aat tac cac ctc gcc acc cag gaa gac tta caa aat gcg gta aac att      2736
Asn Tyr His Leu Ala Thr Gln Glu Asp Leu Gln Asn Ala Val Asn Ile
            900                 905                 910

atg tgg att aga gac ctt tta gta gtg gaa tcc aaa gcc caa ggc ata      2784
Met Trp Ile Arg Asp Leu Leu Val Val Glu Ser Lys Ala Gln Gly Ile
        915                 920                 925
```

-continued

```
gac tca att gct aga tgt aac tgc cac act gga gtg tac tac tgt gaa      2832
Asp Ser Ile Ala Arg Cys Asn Cys His Thr Gly Val Tyr Tyr Cys Glu
    930                 935                 940

tcc agg agg aag tac tac ccg gtc tct ttt act ggc ccc acc ttt cag      2880
Ser Arg Arg Lys Tyr Tyr Pro Val Ser Phe Thr Gly Pro Thr Phe Gln
945                 950                 955                 960

tac atg gaa gca aat gag tac tat cca gcc cga tac caa tcc cac atg      2928
Tyr Met Glu Ala Asn Glu Tyr Tyr Pro Ala Arg Tyr Gln Ser His Met
                965                 970                 975

tta att ggc cat ggt ttt gca tct cca ggg gac tgt ggt ggg att ctc      2976
Leu Ile Gly His Gly Phe Ala Ser Pro Gly Asp Cys Gly Gly Ile Leu
            980                 985                 990

agg tgc caa cat gga gta att gga  atc att aca gct gga  gga gaa ggc   3024
Arg Cys Gln His Gly Val Ile Gly  Ile Ile Thr Ala Gly  Gly Glu Gly
        995                 1000                 1005

cta gtc  gct ttc tcg gac atc  aga gat ctg tac gca  tac gag gag      3069
Leu Val  Ala Phe Ser Asp Ile  Arg Asp Leu Tyr Ala  Tyr Glu Glu
    1010                 1015                 1020

gag gct  atg gag cag gga gtc  tcc aac tat att gag  tcc ctt ggg      3114
Glu Ala  Met Glu Gln Gly Val  Ser Asn Tyr Ile Glu  Ser Leu Gly
    1025                 1030                 1035

gct gca  ttt ggg agt gga ttc  acc cag caa ata gga  aac aaa att      3159
Ala Ala  Phe Gly Ser Gly Phe  Thr Gln Gln Ile Gly  Asn Lys Ile
    1040                 1045                 1050

tca gaa  ctc act agc atg gtc  acc agc act ata act  gag aaa cta      3204
Ser Glu  Leu Thr Ser Met Val  Thr Ser Thr Ile Thr  Glu Lys Leu
    1055                 1060                 1065

cta aag  aat ctc att aaa ata  att tca tcc ctt gtt  atc atc acc      3249
Leu Lys  Asn Leu Ile Lys Ile  Ile Ser Ser Leu Val  Ile Ile Thr
    1070                 1075                 1080

aga aac  tat gaa gac acg acc  aca gtg ctg gct acc  ctt gct ctc      3294
Arg Asn  Tyr Glu Asp Thr Thr  Thr Val Leu Ala Thr  Leu Ala Leu
    1085                 1090                 1095

ctc ggt  tgt gat gcg tcc cca  tgg caa tgg cta aag  aag aaa gcc      3339
Leu Gly  Cys Asp Ala Ser Pro  Trp Gln Trp Leu Lys  Lys Lys Ala
    1100                 1105                 1110

tgt gac  atc ttg gaa atc ccc  tac atc atg cga cag  ggc gat agc      3384
Cys Asp  Ile Leu Glu Ile Pro  Tyr Ile Met Arg Gln  Gly Asp Ser
    1115                 1120                 1125

tgg ttg  aag aag ttt aca gag  gca tgc aat gca gcc  aag gga ttg      3429
Trp Leu  Lys Lys Phe Thr Glu  Ala Cys Asn Ala Ala  Lys Gly Leu
    1130                 1135                 1140

gaa tgg  gtg tct aat aaa ata  tcc aaa ttt att gac  tgg ctc aaa      3474
Glu Trp  Val Ser Asn Lys Ile  Ser Lys Phe Ile Asp  Trp Leu Lys
    1145                 1150                 1155

gag aag  atc att cca cag gct  aga gac aag cta gag  ttt gtt acc      3519
Glu Lys  Ile Ile Pro Gln Ala  Arg Asp Lys Leu Glu  Phe Val Thr
    1160                 1165                 1170

aaa ctg  aag caa cta gaa atg  ttg gag aac caa att  gca acc att      3564
Lys Leu  Lys Gln Leu Glu Met  Leu Glu Asn Gln Ile  Ala Thr Ile
    1175                 1180                 1185

cat caa  tcg tgc cca agt cag  gag cat caa gaa atc  ctg ttc aat      3609
His Gln  Ser Cys Pro Ser Gln  Glu His Gln Glu Ile  Leu Phe Asn
    1190                 1195                 1200

aac gtg  aga tgg tta tcc ata  cag tca aag aga ttt  gcc ccg ctc      3654
Asn Val  Arg Trp Leu Ser Ile  Gln Ser Lys Arg Phe  Ala Pro Leu
    1205                 1210                 1215

tat gcg  gtt gag gct aag aga  ata caa aag tta gag  cac acg att      3699
Tyr Ala  Val Glu Ala Lys Arg  Ile Gln Lys Leu Glu  His Thr Ile
```

```
    1220                1225                1230

aac aac  tac gta cag ttc aag  agc aaa cac cgt att  gaa cca gta      3744
Asn Asn  Tyr Val Gln Phe Lys  Ser Lys His Arg Ile  Glu Pro Val
    1235                1240                1245

tgt ttg  ttg gtg cac ggt agc  cca ggc acg ggc aag  tca gtt gcc      3789
Cys Leu  Leu Val His Gly Ser  Pro Gly Thr Gly Lys  Ser Val Ala
    1250                1255                1260

acc aat  tta att gcc aga gca  ata gca gag aag gag  aac acc tcc      3834
Thr Asn  Leu Ile Ala Arg Ala  Ile Ala Glu Lys Glu  Asn Thr Ser
    1265                1270                1275

aca tac  tca cta cca cca gat  ccc tcc cat ttc gat  ggg tac aag      3879
Thr Tyr  Ser Leu Pro Pro Asp  Pro Ser His Phe Asp  Gly Tyr Lys
    1280                1285                1290

caa caa  ggt gtg gtg atc atg  gat gat ttg aat cag  aac cca gac      3924
Gln Gln  Gly Val Val Ile Met  Asp Asp Leu Asn Gln  Asn Pro Asp
    1295                1300                1305

gga gca  gac atg aag ctg ttt  tgt cag atg gtc tcc  act gta gaa      3969
Gly Ala  Asp Met Lys Leu Phe  Cys Gln Met Val Ser  Thr Val Glu
    1310                1315                1320

ttc ata  cca cca atg gct tcg  cta gaa gaa aag ggt  att ttg ttc      4014
Phe Ile  Pro Pro Met Ala Ser  Leu Glu Glu Lys Gly  Ile Leu Phe
    1325                1330                1335

aca tct  aat tac gtt ttg gcc  tca acc aat tcc agt  cgc atc acc      4059
Thr Ser  Asn Tyr Val Leu Ala  Ser Thr Asn Ser Ser  Arg Ile Thr
    1340                1345                1350

cca cca  act gtt gcg cac agc  gat gcc cta gcc agg  cgc ttt gca      4104
Pro Pro  Thr Val Ala His Ser  Asp Ala Leu Ala Arg  Arg Phe Ala
    1355                1360                1365

ttt gac  atg gac ata caa atc  atg agc gag tat tct  aga gat gga      4149
Phe Asp  Met Asp Ile Gln Ile  Met Ser Glu Tyr Ser  Arg Asp Gly
    1370                1375                1380

aaa ttg  aac atg gcg atg gca  act gaa atg tgt aag  aac tgt cat      4194
Lys Leu  Asn Met Ala Met Ala  Thr Glu Met Cys Lys  Asn Cys His
    1385                1390                1395

caa cca  gca aac ttc aag aga  tgt tgc cca ttg gtg  tgt ggc aaa      4239
Gln Pro  Ala Asn Phe Lys Arg  Cys Cys Pro Leu Val  Cys Gly Lys
    1400                1405                1410

gcc atc  cag ctg atg gac aaa  tct tcc aga gtc aga  tat agt ata      4284
Ala Ile  Gln Leu Met Asp Lys  Ser Ser Arg Val Arg  Tyr Ser Ile
    1415                1420                1425

gat cag  att act acc atg att  att aat gag agg aac  aga aga tca      4329
Asp Gln  Ile Thr Thr Met Ile  Ile Asn Glu Arg Asn  Arg Arg Ser
    1430                1435                1440

agt atc  ggt aat tgc atg gag  gca ctt ttc caa ggt  cct ctt caa      4374
Ser Ile  Gly Asn Cys Met Glu  Ala Leu Phe Gln Gly  Pro Leu Gln
    1445                1450                1455

tac aaa  gac ctg aaa ata gac  att aag acc aca cct  cct cct gag      4419
Tyr Lys  Asp Leu Lys Ile Asp  Ile Lys Thr Thr Pro  Pro Pro Glu
    1460                1465                1470

tgc atc  aat gat ttg ctc caa  gca gtt gat tct caa  gag gta aga      4464
Cys Ile  Asn Asp Leu Leu Gln  Ala Val Asp Ser Gln  Glu Val Arg
    1475                1480                1485

gac tac  tgt gag aag aag ggt  tgg ata gta gac atc  act agt cag      4509
Asp Tyr  Cys Glu Lys Lys Gly  Trp Ile Val Asp Ile  Thr Ser Gln
    1490                1495                1500

gtg caa  acc gaa aga aac atc  aat aga gca atg act  att ctt cag      4554
Val Gln  Thr Glu Arg Asn Ile  Asn Arg Ala Met Thr  Ile Leu Gln
    1505                1510                1515

gcg gtc  acc aca ttt gcc gca  gtt gct gga gtg gtg  tat gtg atg      4599
```

-continued

```
Ala Val  Thr Thr Phe Ala Ala  Val Ala Gly Val Val  Tyr Val Met
    1520                 1525                 1530

tac aaa  ctc ttt gca ggg cat  caa gga gcg tat aca  ggg ctt ccc      4644
Tyr Lys  Leu Phe Ala Gly His  Gln Gly Ala Tyr Thr  Gly Leu Pro
    1535                 1540                 1545

aat aag  aga ccc aat gtc ccc  acc atc agg act gcc  aag gtt cag      4689
Asn Lys  Arg Pro Asn Val Pro  Thr Ile Arg Thr Ala  Lys Val Gln
    1550                 1555                 1560

ggc cca  gga ttt gac tac gca  gtg gca atg gcc aaa  aga aac att      4734
Gly Pro  Gly Phe Asp Tyr Ala  Val Ala Met Ala Lys  Arg Asn Ile
    1565                 1570                 1575

ctt acg  gca act acc att aag  gga gag ttc aca atg  ctc gga gtg      4779
Leu Thr  Ala Thr Thr Ile Lys  Gly Glu Phe Thr Met  Leu Gly Val
    1580                 1585                 1590

cat gat  aat gtg gcc att cta  cca acc cac gca tca  ccg ggt gaa      4824
His Asp  Asn Val Ala Ile Leu  Pro Thr His Ala Ser  Pro Gly Glu
    1595                 1600                 1605

aca ata  gtc att gat ggc aag  gaa gta gag gta ctg  gat gct aaa      4869
Thr Ile  Val Ile Asp Gly Lys  Glu Val Glu Val Leu  Asp Ala Lys
    1610                 1615                 1620

gcc ctg  gag gac cag gcc ggg  acc aac cta gaa atc  acc att gtc      4914
Ala Leu  Glu Asp Gln Ala Gly  Thr Asn Leu Glu Ile  Thr Ile Val
    1625                 1630                 1635

act ctt  aag aga aat gag aag  ttc agg gac atc aga  cca cac atc      4959
Thr Leu  Lys Arg Asn Glu Lys  Phe Arg Asp Ile Arg  Pro His Ile
    1640                 1645                 1650

ccc act  caa atc act gag aca  aat gat gga gtt tta  att gtg aac      5004
Pro Thr  Gln Ile Thr Glu Thr  Asn Asp Gly Val Leu  Ile Val Asn
    1655                 1660                 1665

act agt  aag tac ccc aac atg  tat gtt cct gtc ggt  gct gtg act      5049
Thr Ser  Lys Tyr Pro Asn Met  Tyr Val Pro Val Gly  Ala Val Thr
    1670                 1675                 1680

gaa cag  ggg tat ctc aat ctc  ggt gga cgc caa act  gct cgt act      5094
Glu Gln  Gly Tyr Leu Asn Leu  Gly Gly Arg Gln Thr  Ala Arg Thr
    1685                 1690                 1695

tta atg  tac aac ttt cca acg  aga gca ggt caa tgt  ggt gga gtt      5139
Leu Met  Tyr Asn Phe Pro Thr  Arg Ala Gly Gln Cys  Gly Gly Val
    1700                 1705                 1710

atc acc  tgc act ggc aag gtc  atc ggg atg cat gtt  ggt ggg aac      5184
Ile Thr  Cys Thr Gly Lys Val  Ile Gly Met His Val  Gly Gly Asn
    1715                 1720                 1725

ggt tca  cat ggg ttc gca gca  gcc ctg aag cga tcc  tat ttc act      5229
Gly Ser  His Gly Phe Ala Ala  Ala Leu Lys Arg Ser  Tyr Phe Thr
    1730                 1735                 1740

cag agt  caa ggt gaa atc cag  tgg atg aga cca tca  aaa gaa gtg      5274
Gln Ser  Gln Gly Glu Ile Gln  Trp Met Arg Pro Ser  Lys Glu Val
    1745                 1750                 1755

ggc tac  ccc gtt att aat gct  cca tct aaa act aaa  ctg gaa ccc      5319
Gly Tyr  Pro Val Ile Asn Ala  Pro Ser Lys Thr Lys  Leu Glu Pro
    1760                 1765                 1770

agt gca  ttc cat tat gtg ttt  gaa ggt gtc aag gaa  cca gct gtg      5364
Ser Ala  Phe His Tyr Val Phe  Glu Gly Val Lys Glu  Pro Ala Val
    1775                 1780                 1785

ctc acc  aaa agt gac ccc aga  ttg aag aca gat ttt  gaa gag gct      5409
Leu Thr  Lys Ser Asp Pro Arg  Leu Lys Thr Asp Phe  Glu Glu Ala
    1790                 1795                 1800

atc ttt  tcc aag tat gtg gga  aat aag att act gaa  gtg gat gag      5454
Ile Phe  Ser Lys Tyr Val Gly  Asn Lys Ile Thr Glu  Val Asp Glu
    1805                 1810                 1815
```

-continued

```
tac atg  aaa gaa gct gtc gat  cat tac gca ggc cag  ctc atg tca      5499
Tyr Met  Lys Glu Ala Val Asp  His Tyr Ala Gly Gln  Leu Met Ser
    1820                 1825                 1830

cta gac  atc aac aca gaa caa  atg tgc ctt gag gat  gca atg tat      5544
Leu Asp  Ile Asn Thr Glu Gln  Met Cys Leu Glu Asp  Ala Met Tyr
    1835                 1840                 1845

ggc act  gac ggt ctc gaa gct  cta gac ctc agt acc  agt gct ggg      5589
Gly Thr  Asp Gly Leu Glu Ala  Leu Asp Leu Ser Thr  Ser Ala Gly
    1850                 1855                 1860

tat ccc  tat gtg gca atg ggg  aaa aag aaa aga gac  att ttg aat      5634
Tyr Pro  Tyr Val Ala Met Gly  Lys Lys Lys Arg Asp  Ile Leu Asn
    1865                 1870                 1875

aag caa  acc aga gac aca aag  gaa atg caa agg ctt  ctg gac acc      5679
Lys Gln  Thr Arg Asp Thr Lys  Glu Met Gln Arg Leu  Leu Asp Thr
    1880                 1885                 1890

tat ggt  att aat tta cct tta  gtc acc tat gtg aaa  gat gag ctt      5724
Tyr Gly  Ile Asn Leu Pro Leu  Val Thr Tyr Val Lys  Asp Glu Leu
    1895                 1900                 1905

aga tcc  aag acc aaa gtg gaa  cag ggc aag tcc agg  cta att gag      5769
Arg Ser  Lys Thr Lys Val Glu  Gln Gly Lys Ser Arg  Leu Ile Glu
    1910                 1915                 1920

gcc tca  agt ctc aat gac tct  gtc gcc atg agg atg  gct ttt ggc      5814
Ala Ser  Ser Leu Asn Asp Ser  Val Ala Met Arg Met  Ala Phe Gly
    1925                 1930                 1935

aac ttg  tac gca gca ttc cac  aag aac cca ggt gta  gtg aca gga      5859
Asn Leu  Tyr Ala Ala Phe His  Lys Asn Pro Gly Val  Val Thr Gly
    1940                 1945                 1950

tcg gct  gtt ggc tgt gac cca  gat ttg ttt tgg agt  aaa ata cca      5904
Ser Ala  Val Gly Cys Asp Pro  Asp Leu Phe Trp Ser  Lys Ile Pro
    1955                 1960                 1965

gtc ctc  atg gag gaa aaa ctc  ttt gca ttt gat tac  acg ggt tat      5949
Val Leu  Met Glu Glu Lys Leu  Phe Ala Phe Asp Tyr  Thr Gly Tyr
    1970                 1975                 1980

gat gct  tca cta agc ccc gcc  tgg ttt gag gct ctc  aag atg gtt      5994
Asp Ala  Ser Leu Ser Pro Ala  Trp Phe Glu Ala Leu  Lys Met Val
    1985                 1990                 1995

cta gag  aaa att ggg ttt ggt  gac aga gtg gat tac  att gat tat      6039
Leu Glu  Lys Ile Gly Phe Gly  Asp Arg Val Asp Tyr  Ile Asp Tyr
    2000                 2005                 2010

ctg aat  cac tcg cac cat cta  tat aaa aat aag aca  tat tgt gtt      6084
Leu Asn  His Ser His His Leu  Tyr Lys Asn Lys Thr  Tyr Cys Val
    2015                 2020                 2025

aag ggc  ggc atg cca tct ggc  tgc tct ggc acc tca  att ttt aat      6129
Lys Gly  Gly Met Pro Ser Gly  Cys Ser Gly Thr Ser  Ile Phe Asn
    2030                 2035                 2040

tca atg  att aat aat cta ata  atc agg act ctc tta  ctg aaa acc      6174
Ser Met  Ile Asn Asn Leu Ile  Ile Arg Thr Leu Leu  Leu Lys Thr
    2045                 2050                 2055

tac aag  ggc ata gat tta gac  cac ctg aag atg ata  gcc tat ggt      6219
Tyr Lys  Gly Ile Asp Leu Asp  His Leu Lys Met Ile  Ala Tyr Gly
    2060                 2065                 2070

gat gat  gta att gct tcc tac  ccc cat gag gtt gat  gct agt ctc      6264
Asp Asp  Val Ile Ala Ser Tyr  Pro His Glu Val Asp  Ala Ser Leu
    2075                 2080                 2085

cta gcc  caa tca gga aaa gac  tat gga cta acc atg  aca cca gct      6309
Leu Ala  Gln Ser Gly Lys Asp  Tyr Gly Leu Thr Met  Thr Pro Ala
    2090                 2095                 2100

gac aaa  tca gcc acc ttt gaa  aca gtc aca tgg gag  aat gta aca      6354
Asp Lys  Ser Ala Thr Phe Glu  Thr Val Thr Trp Glu  Asn Val Thr
    2105                 2110                 2115
```

```
ttc ttg  aaa aga ttc ttt aga  gca gat gaa aag tat  ccc ttt ctg      6399
Phe Leu  Lys Arg Phe Phe Arg  Ala Asp Glu Lys Tyr  Pro Phe Leu
    2120                 2125                 2130

gta cat  cca gtg atg cca atg  aaa gaa att cac gaa  tca att aga      6444
Val His  Pro Val Met Pro Met  Lys Glu Ile His Glu  Ser Ile Arg
    2135                 2140                 2145

tgg act  aaa gat ccc aga aac  act cag gat cat gtt  cgc tca ctg      6489
Trp Thr  Lys Asp Pro Arg Asn  Thr Gln Asp His Val  Arg Ser Leu
    2150                 2155                 2160

tgc tta  ttg gct tgg cac aat  ggc gag gaa gag tac  aat aaa ttt      6534
Cys Leu  Leu Ala Trp His Asn  Gly Glu Glu Glu Tyr  Asn Lys Phe
    2165                 2170                 2175

tta gct  aag att aga agt gtg  cca atc gga aga gca  tta ctg ctc      6579
Leu Ala  Lys Ile Arg Ser Val  Pro Ile Gly Arg Ala  Leu Leu Leu
    2180                 2185                 2190

cct gag  tac tcc aca ttg tac  cgc cgt tgg ctc gac  tca ttt          6621
Pro Glu  Tyr Ser Thr Leu Tyr  Arg Arg Trp Leu Asp  Ser Phe
    2195                 2200                 2205


<210> SEQ ID NO 7
<211> LENGTH: 2207
<212> TYPE: PRT
<213> ORGANISM: Human poliovirus 2

<400> SEQUENCE: 7

Met Gly Ala Gln Val Ser Ser Gln Lys Val Gly Ala His Glu Asn Ser
1               5                   10                  15

Asn Arg Ala Tyr Gly Gly Ser Thr Ile Asn Tyr Thr Thr Ile Asn Tyr
            20                  25                  30

Tyr Arg Asp Ser Ala Ser Asn Ala Ala Ser Lys Gln Asp Phe Ala Gln
        35                  40                  45

Asp Pro Ser Lys Phe Thr Glu Pro Ile Lys Asp Val Leu Ile Lys Thr
    50                  55                  60

Ala Pro Thr Leu Asn Ser Pro Asn Ile Glu Ala Cys Gly Tyr Ser Asp
65                  70                  75                  80

Arg Val Met Gln Leu Thr Leu Gly Asn Ser Thr Ile Thr Thr Gln Glu
                85                  90                  95

Ala Ala Asn Ser Val Val Ala Tyr Gly Arg Trp Pro Glu Tyr Ile Lys
            100                 105                 110

Asp Ser Glu Ala Asn Pro Val Asp Gln Pro Thr Glu Pro Asp Val Ala
        115                 120                 125

Ala Cys Arg Phe Tyr Thr Leu Asp Thr Val Thr Trp Arg Lys Glu Ser
    130                 135                 140

Arg Gly Trp Trp Trp Lys Leu Pro Asp Ala Leu Lys Asp Met Gly Leu
145                 150                 155                 160

Phe Gly Gln Asn Met Phe Tyr His Tyr Leu Gly Arg Ala Gly Tyr Thr
                165                 170                 175

Val His Val Gln Cys Asn Ala Ser Lys Phe His Gln Gly Ala Leu Gly
            180                 185                 190

Val Phe Ala Val Pro Glu Met Cys Leu Ala Gly Asp Ser Thr Thr His
        195                 200                 205

Met Phe Thr Lys Tyr Glu Asn Ala Asn Pro Gly Glu Lys Gly Gly Glu
    210                 215                 220

Phe Lys Gly Ser Phe Thr Leu Asp Thr Asn Ala Thr Asn Pro Ala Arg
225                 230                 235                 240

Asn Phe Cys Pro Val Asp Tyr Leu Phe Gly Ser Gly Val Leu Ala Gly
```

-continued

```
                245                 250                 255

Asn Ala Phe Val Tyr Pro His Gln Ile Ile Asn Leu Arg Thr Asn Asn
            260                 265                 270

Cys Ala Thr Leu Val Leu Pro Tyr Val Asn Ser Leu Ser Ile Asp Ser
        275                 280                 285

Met Thr Lys His Asn Asn Trp Gly Ile Ala Ile Leu Pro Leu Ala Pro
    290                 295                 300

Leu Asp Phe Ala Thr Glu Ser Ser Thr Glu Ile Pro Ile Thr Leu Thr
305                 310                 315                 320

Ile Ala Pro Met Cys Cys Glu Phe Asn Gly Leu Arg Asn Ile Thr Val
                325                 330                 335

Pro Arg Thr Gln Gly Leu Pro Val Leu Asn Thr Pro Gly Ser Asn Gln
            340                 345                 350

Tyr Leu Thr Ala Asp Asn Tyr Gln Ser Pro Cys Ala Ile Pro Glu Phe
        355                 360                 365

Asp Val Thr Pro Pro Ile Asp Ile Pro Gly Glu Val Arg Asn Met Met
    370                 375                 380

Glu Leu Ala Glu Ile Asp Thr Met Ile Pro Leu Asn Leu Thr Asn Gln
385                 390                 395                 400

Arg Lys Asn Thr Met Asp Met Tyr Arg Val Glu Leu Asn Asp Ala Ala
                405                 410                 415

His Ser Asp Thr Pro Ile Leu Cys Leu Ser Leu Ser Pro Ala Ser Asp
            420                 425                 430

Pro Arg Leu Ala His Thr Met Leu Gly Glu Ile Leu Asn Tyr Tyr Thr
        435                 440                 445

His Trp Ala Gly Ser Leu Lys Phe Thr Phe Leu Phe Cys Gly Ser Met
    450                 455                 460

Met Ala Thr Gly Lys Leu Leu Val Ser Tyr Ala Pro Pro Gly Ala Glu
465                 470                 475                 480

Ala Pro Lys Ser Arg Lys Glu Ala Met Leu Gly Thr His Val Ile Trp
                485                 490                 495

Asp Ile Gly Leu Gln Ser Ser Cys Thr Met Val Val Pro Trp Ile Ser
            500                 505                 510

Asn Thr Thr Tyr Arg Gln Thr Ile Asn Asp Ser Phe Thr Glu Gly Gly
        515                 520                 525

Tyr Ile Ser Met Phe Tyr Gln Thr Arg Val Val Val Pro Leu Ser Thr
    530                 535                 540

Pro Arg Lys Met Asp Ile Leu Gly Phe Val Ser Ala Cys Asn Asp Phe
545                 550                 555                 560

Ser Val Arg Leu Leu Arg Asp Thr Thr His Ile Ser Gln Glu Ala Met
                565                 570                 575

Pro Gln Gly Leu Gly Asp Leu Ile Glu Gly Val Val Glu Gly Val Thr
            580                 585                 590

Arg Asn Ala Leu Thr Pro Leu Thr Pro Ala Asn Asn Leu Pro Asp Thr
        595                 600                 605

Gln Ser Ser Gly Pro Ala His Ser Lys Glu Thr Pro Ala Leu Thr Ala
    610                 615                 620

Val Glu Thr Gly Ala Thr Asn Pro Leu Val Pro Ser Asp Thr Val Gln
625                 630                 635                 640

Thr Arg His Val Ile Gln Lys Arg Thr Arg Ser Glu Ser Thr Val Glu
                645                 650                 655

Ser Phe Phe Ala Arg Gly Ala Cys Val Ala Ile Ile Glu Val Asp Asn
            660                 665                 670
```

```
Asp Ala Pro Thr Lys Arg Ala Ser Lys Leu Phe Ser Val Trp Lys Ile
        675                 680                 685

Thr Tyr Lys Asp Thr Val Gln Leu Arg Arg Lys Leu Glu Phe Phe Thr
    690                 695                 700

Tyr Ser Arg Phe Asp Met Glu Phe Thr Phe Val Val Thr Ser Asn Tyr
705                 710                 715                 720

Thr Asp Ala Asn Asn Gly His Ala Leu Asn Gln Val Tyr Gln Ile Met
                725                 730                 735

Tyr Ile Pro Pro Gly Ala Pro Ile Pro Gly Lys Trp Asn Asp Tyr Thr
            740                 745                 750

Trp Gln Thr Ser Ser Asn Pro Ser Val Phe Tyr Thr Tyr Gly Ala Pro
        755                 760                 765

Pro Ala Arg Ile Ser Val Pro Tyr Val Gly Ile Ala Asn Ala Tyr Ser
    770                 775                 780

His Phe Tyr Asp Gly Phe Ala Lys Val Pro Leu Ala Gly Gln Ala Ser
785                 790                 795                 800

Thr Glu Gly Asp Ser Leu Tyr Gly Ala Ala Ser Leu Asn Asp Phe Gly
                805                 810                 815

Ser Leu Ala Val Arg Val Val Asn Asp His Asn Pro Thr Lys Leu Thr
            820                 825                 830

Ser Lys Ile Arg Val Tyr Met Lys Pro Lys His Val Arg Val Trp Cys
        835                 840                 845

Pro Arg Pro Pro Arg Ala Val Pro Tyr Tyr Gly Pro Gly Val Asp Tyr
    850                 855                 860

Lys Asp Gly Leu Ala Pro Leu Pro Glu Lys Gly Leu Thr Thr Tyr Gly
865                 870                 875                 880

Phe Gly His Gln Asn Lys Ala Val Tyr Thr Ala Gly Tyr Lys Ile Cys
                885                 890                 895

Asn Tyr His Leu Ala Thr Gln Glu Asp Leu Gln Asn Ala Val Asn Ile
            900                 905                 910

Met Trp Ile Arg Asp Leu Leu Val Val Glu Ser Lys Ala Gln Gly Ile
        915                 920                 925

Asp Ser Ile Ala Arg Cys Asn Cys His Thr Gly Val Tyr Tyr Cys Glu
    930                 935                 940

Ser Arg Arg Lys Tyr Tyr Pro Val Ser Phe Thr Gly Pro Thr Phe Gln
945                 950                 955                 960

Tyr Met Glu Ala Asn Glu Tyr Tyr Pro Ala Arg Tyr Gln Ser His Met
                965                 970                 975

Leu Ile Gly His Gly Phe Ala Ser Pro Gly Asp Cys Gly Gly Ile Leu
            980                 985                 990

Arg Cys Gln His Gly Val Ile Gly  Ile Ile Thr Ala Gly  Gly Glu Gly
        995                 1000                1005

Leu Val  Ala Phe Ser Asp Ile  Arg Asp Leu Tyr Ala  Tyr Glu Glu
    1010                1015                1020

Glu Ala  Met Glu Gln Gly Val  Ser Asn Tyr Ile Glu  Ser Leu Gly
    1025                1030                1035

Ala Ala  Phe Gly Ser Gly Phe  Thr Gln Gln Ile Gly  Asn Lys Ile
    1040                1045                1050

Ser Glu  Leu Thr Ser Met Val  Thr Ser Thr Ile Thr  Glu Lys Leu
    1055                1060                1065

Leu Lys  Asn Leu Ile Lys Ile  Ile Ser Ser Leu Val  Ile Ile Thr
    1070                1075                1080
```

```
Arg Asn  Tyr Glu Asp Thr Thr  Thr Val Leu Ala Thr  Leu Ala Leu
    1085                 1090                 1095

Leu Gly  Cys Asp Ala Ser Pro  Trp Gln Trp Leu Lys  Lys Lys Ala
    1100                 1105                 1110

Cys Asp  Ile Leu Glu Ile Pro  Tyr Ile Met Arg Gln  Gly Asp Ser
    1115                 1120                 1125

Trp Leu  Lys Lys Phe Thr Glu  Ala Cys Asn Ala Ala  Lys Gly Leu
    1130                 1135                 1140

Glu Trp  Val Ser Asn Lys Ile  Ser Lys Phe Ile Asp  Trp Leu Lys
    1145                 1150                 1155

Glu Lys  Ile Ile Pro Gln Ala  Arg Asp Lys Leu Glu  Phe Val Thr
    1160                 1165                 1170

Lys Leu  Lys Gln Leu Glu Met  Leu Glu Asn Gln Ile  Ala Thr Ile
    1175                 1180                 1185

His Gln  Ser Cys Pro Ser Gln  Glu His Gln Glu Ile  Leu Phe Asn
    1190                 1195                 1200

Asn Val  Arg Trp Leu Ser Ile  Gln Ser Lys Arg Phe  Ala Pro Leu
    1205                 1210                 1215

Tyr Ala  Val Glu Ala Lys Arg  Ile Gln Lys Leu Glu  His Thr Ile
    1220                 1225                 1230

Asn Asn  Tyr Val Gln Phe Lys  Ser Lys His Arg Ile  Glu Pro Val
    1235                 1240                 1245

Cys Leu  Leu Val His Gly Ser  Pro Gly Thr Gly Lys  Ser Val Ala
    1250                 1255                 1260

Thr Asn  Leu Ile Ala Arg Ala  Ile Ala Glu Lys Glu  Asn Thr Ser
    1265                 1270                 1275

Thr Tyr  Ser Leu Pro Pro Asp  Pro Ser His Phe Asp  Gly Tyr Lys
    1280                 1285                 1290

Gln Gln  Gly Val Val Ile Met  Asp Asp Leu Asn Gln  Asn Pro Asp
    1295                 1300                 1305

Gly Ala  Asp Met Lys Leu Phe  Cys Gln Met Val Ser  Thr Val Glu
    1310                 1315                 1320

Phe Ile  Pro Pro Met Ala Ser  Leu Glu Glu Lys Gly  Ile Leu Phe
    1325                 1330                 1335

Thr Ser  Asn Tyr Val Leu Ala  Ser Thr Asn Ser Ser  Arg Ile Thr
    1340                 1345                 1350

Pro Pro  Thr Val Ala His Ser  Asp Ala Leu Ala Arg  Arg Phe Ala
    1355                 1360                 1365

Phe Asp  Met Asp Ile Gln Ile  Met Ser Glu Tyr Ser  Arg Asp Gly
    1370                 1375                 1380

Lys Leu  Asn Met Ala Met Ala  Thr Glu Met Cys Lys  Asn Cys His
    1385                 1390                 1395

Gln Pro  Ala Asn Phe Lys Arg  Cys Cys Pro Leu Val  Cys Gly Lys
    1400                 1405                 1410

Ala Ile  Gln Leu Met Asp Lys  Ser Ser Arg Val Arg  Tyr Ser Ile
    1415                 1420                 1425

Asp Gln  Ile Thr Thr Met Ile  Ile Asn Glu Arg Asn  Arg Arg Ser
    1430                 1435                 1440

Ser Ile  Gly Asn Cys Met Glu  Ala Leu Phe Gln Gly  Pro Leu Gln
    1445                 1450                 1455

Tyr Lys  Asp Leu Lys Ile Asp  Ile Lys Thr Thr Pro  Pro Pro Glu
    1460                 1465                 1470

Cys Ile  Asn Asp Leu Leu Gln  Ala Val Asp Ser Gln  Glu Val Arg
```

```
    1475                1480                1485

Asp Tyr  Cys Glu Lys Lys Gly  Trp Ile Val Asp Ile  Thr Ser Gln
    1490                1495                1500

Val Gln  Thr Glu Arg Asn Ile  Asn Arg Ala Met Thr  Ile Leu Gln
    1505                1510                1515

Ala Val  Thr Thr Phe Ala Ala  Val Ala Gly Val Val  Tyr Val Met
    1520                1525                1530

Tyr Lys  Leu Phe Ala Gly His  Gln Gly Ala Tyr Thr  Gly Leu Pro
    1535                1540                1545

Asn Lys  Arg Pro Asn Val Pro  Thr Ile Arg Thr Ala  Lys Val Gln
    1550                1555                1560

Gly Pro  Gly Phe Asp Tyr Ala  Val Ala Met Ala Lys  Arg Asn Ile
    1565                1570                1575

Leu Thr  Ala Thr Thr Ile Lys  Gly Glu Phe Thr Met  Leu Gly Val
    1580                1585                1590

His Asp  Asn Val Ala Ile Leu  Pro Thr His Ala Ser  Pro Gly Glu
    1595                1600                1605

Thr Ile  Val Ile Asp Gly Lys  Glu Val Glu Val Leu  Asp Ala Lys
    1610                1615                1620

Ala Leu  Glu Asp Gln Ala Gly  Thr Asn Leu Glu Ile  Thr Ile Val
    1625                1630                1635

Thr Leu  Lys Arg Asn Glu Lys  Phe Arg Asp Ile Arg  Pro His Ile
    1640                1645                1650

Pro Thr  Gln Ile Thr Glu Thr  Asn Asp Gly Val Leu  Ile Val Asn
    1655                1660                1665

Thr Ser  Lys Tyr Pro Asn Met  Tyr Val Pro Val Gly  Ala Val Thr
    1670                1675                1680

Glu Gln  Gly Tyr Leu Asn Leu  Gly Gly Arg Gln Thr  Ala Arg Thr
    1685                1690                1695

Leu Met  Tyr Asn Phe Pro Thr  Arg Ala Gly Gln Cys  Gly Gly Val
    1700                1705                1710

Ile Thr  Cys Thr Gly Lys Val  Ile Gly Met His Val  Gly Gly Asn
    1715                1720                1725

Gly Ser  His Gly Phe Ala Ala  Ala Leu Lys Arg Ser  Tyr Phe Thr
    1730                1735                1740

Gln Ser  Gln Gly Glu Ile Gln  Trp Met Arg Pro Ser  Lys Glu Val
    1745                1750                1755

Gly Tyr  Pro Val Ile Asn Ala  Pro Ser Lys Thr Lys  Leu Glu Pro
    1760                1765                1770

Ser Ala  Phe His Tyr Val Phe  Glu Gly Val Lys Glu  Pro Ala Val
    1775                1780                1785

Leu Thr  Lys Ser Asp Pro Arg  Leu Lys Thr Asp Phe  Glu Glu Ala
    1790                1795                1800

Ile Phe  Ser Lys Tyr Val Gly  Asn Lys Ile Thr Glu  Val Asp Glu
    1805                1810                1815

Tyr Met  Lys Glu Ala Val Asp  His Tyr Ala Gly Gln  Leu Met Ser
    1820                1825                1830

Leu Asp  Ile Asn Thr Glu Gln  Met Cys Leu Glu Asp  Ala Met Tyr
    1835                1840                1845

Gly Thr  Asp Gly Leu Glu Ala  Leu Asp Leu Ser Thr  Ser Ala Gly
    1850                1855                1860

Tyr Pro  Tyr Val Ala Met Gly  Lys Lys Lys Arg Asp  Ile Leu Asn
    1865                1870                1875
```

Lys Gln Thr Arg Asp Thr Lys Glu Met Gln Arg Leu Leu Asp Thr
1880 1885 1890

Tyr Gly Ile Asn Leu Pro Leu Val Thr Tyr Val Lys Asp Glu Leu
1895 1900 1905

Arg Ser Lys Thr Lys Val Glu Gln Gly Lys Ser Arg Leu Ile Glu
1910 1915 1920

Ala Ser Ser Leu Asn Asp Ser Val Ala Met Arg Met Ala Phe Gly
1925 1930 1935

Asn Leu Tyr Ala Ala Phe His Lys Asn Pro Gly Val Val Thr Gly
1940 1945 1950

Ser Ala Val Gly Cys Asp Pro Asp Leu Phe Trp Ser Lys Ile Pro
1955 1960 1965

Val Leu Met Glu Glu Lys Leu Phe Ala Phe Asp Tyr Thr Gly Tyr
1970 1975 1980

Asp Ala Ser Leu Ser Pro Ala Trp Phe Glu Ala Leu Lys Met Val
1985 1990 1995

Leu Glu Lys Ile Gly Phe Gly Asp Arg Val Asp Tyr Ile Asp Tyr
2000 2005 2010

Leu Asn His Ser His His Leu Tyr Lys Asn Lys Thr Tyr Cys Val
2015 2020 2025

Lys Gly Gly Met Pro Ser Gly Cys Ser Gly Thr Ser Ile Phe Asn
2030 2035 2040

Ser Met Ile Asn Asn Leu Ile Ile Arg Thr Leu Leu Leu Lys Thr
2045 2050 2055

Tyr Lys Gly Ile Asp Leu Asp His Leu Lys Met Ile Ala Tyr Gly
2060 2065 2070

Asp Asp Val Ile Ala Ser Tyr Pro His Glu Val Asp Ala Ser Leu
2075 2080 2085

Leu Ala Gln Ser Gly Lys Asp Tyr Gly Leu Thr Met Thr Pro Ala
2090 2095 2100

Asp Lys Ser Ala Thr Phe Glu Thr Val Thr Trp Glu Asn Val Thr
2105 2110 2115

Phe Leu Lys Arg Phe Phe Arg Ala Asp Glu Lys Tyr Pro Phe Leu
2120 2125 2130

Val His Pro Val Met Pro Met Lys Glu Ile His Glu Ser Ile Arg
2135 2140 2145

Trp Thr Lys Asp Pro Arg Asn Thr Gln Asp His Val Arg Ser Leu
2150 2155 2160

Cys Leu Leu Ala Trp His Asn Gly Glu Glu Glu Tyr Asn Lys Phe
2165 2170 2175

Leu Ala Lys Ile Arg Ser Val Pro Ile Gly Arg Ala Leu Leu Leu
2180 2185 2190

Pro Glu Tyr Ser Thr Leu Tyr Arg Arg Trp Leu Asp Ser Phe
2195 2200 2205

<210> SEQ ID NO 8
<211> LENGTH: 6621
<212> TYPE: DNA
<213> ORGANISM: Artificial
<220> FEATURE:
<223> OTHER INFORMATION: deoptimized MEF1 sequence

<400> SEQUENCE: 8
atgggcgccc aagtctcatc acagaaagtt ggagcccatg agaattcaaa ccgggcttat 60

-continued

```
ggcggatcca ccattaatta cactactatt aattattacc gggattctgc gagcaatgcc    120
gctagtaagc aggactttgc acaagaccca tccaagttca ctgaacctat taaagatgtt    180
ctcattaaga ccgctcccac gctaaactct cctaatatcg aggcgtgtgg gtatagcgac    240
cgggtgatgc aactaaccct aggcaattcc accattacca cacaggaggc ggccaattct    300
gtcgttgcat acggccggtg gcccgagtac atcaaggact cagaagcaaa tcctgtggac    360
cagccaactg aaccggacgt tgccgcgtgc cggttttaca cactagacac tgttacttgg    420
cggaaggagt cccgggggtg gtggtggaaa ctgcctgatg cactaaagga catgggatta    480
ttcggccaga acatgttcta ccactacctc gggcgggctg gctatactgt gcacgtacag    540
tgtaatgctt caaagtttca ccagggcgcc ctcggggtat tcgcagttcc agaaatgtgc    600
ctggcaggcg acagcacaac ccacatgttt acaaaatatg agaatgcaaa tccgggtgag    660
aaagggggtg aattcaaagg gagttttact ctggatacta acgctaccaa ccctgcacgg    720
aacttttgtc ccgttgatta tctcttcggg agcggagtac tggcgggaaa tgcgtttgtt    780
tacccacatc agataattaa tctgcggacc aacaactgtg ccacgttggt gctgccatac    840
gttaattcac tttccataga cagcatgaca aaacacaaca attggggaat tgctatcctt    900
ccgctggcac cacttgactt tgccaccgag tcctccactg agatacccat tactctaact    960
attgccccta tgtgttgtga attcaatggg ttgcggaaca tcactgtacc ccggactcaa   1020
gggttgccag tcttaaacac tccaggaagc aaccagtact taacagcaga caactatcaa   1080
tccccatgtg cgatacccga gtttgatgta acaccaccca tagacatccc gggggaagtg   1140
cggaacatga tggaattggc agagatagac accatgatac ctctcaatct gacgaaccag   1200
cggaagaaca ccatggatat gtaccgggtc gaactgaatg atgcggctca ctctgacaca   1260
ccaatattgt gtctctcact gtctccagca tcagatcctc ggctagcaca cactatgcta   1320
ggtgaaatac tgaactacta cacacactgg gcagggtcat tgaagttcac atttctcttc   1380
tgcggctcaa tgatggccac tggtaaattg ctagtgtcct atgcacctcc tggtgcggaa   1440
gcccctaaaa gccggaaaga agcgatgctc ggcacccacg tgatctggga catcggatta   1500
cagtcatcat gcactatggt ggtaccttgg attagcaaca ccacataccg gcaaaccatc   1560
aacgatagct tcacagaagg agggtacatc agtatgtttt accaaactcg ggttgttgtg   1620
ccattgtcca cccctcggaa gatggacata ttgggctttg tgtcagcctg caatgacttc   1680
agtgtgcggc tgttgcggga cacgacgcac ataagccaag aggctatgcc acaaggattg   1740
ggtgatttaa ttgaaggggt tgttgaggga gtcacgcgga atgccttgac accactgaca   1800
cctgccaaca acttgcctga tacacaatct agcggcccag cccactctaa ggaaacacca   1860
gcgctaacag ccgtagagac aggggccacc aacccattgg tgccttcaga cacggtacaa   1920
actcggcacg tcatccaaaa gcggacgcgg tcggagtcta cggttgagtc tttcttcgca   1980
cggggagctt gtgtggccat tattgaagtg gataatgatg ctccaacaaa gcgggccagt   2040
aaattatttt cagtctggaa gataacttac aaagacaccg ttcagttacg gcggaagttg   2100
gagttcttta catattcacg gtttgacatg gagttcacct ttgtggttac atccaattat   2160
accgatgcaa acaatgggca cgcactaaat caagtttacc agataatgta cataccacct   2220
ggggcaccga tccctggcaa gtggaatgat tacacatggc aaacgtcatc taacccatca   2280
gtgttttaca cttacggggc acctccagct cggatatcag tgccctacgt gggcattgcc   2340
aatgcatatt ctcattttta cgatgggttt gccaaagtac cactagcagg ccaagcctca   2400
acagagggtg actcgctgta tggagcggct tcattgaatg acttcggatc actggctgtt   2460
```

-continued

```
cgggtggtga atgaccacaa ccctacgaaa ctcacttcaa aaatccgggt gtacatgaaa   2520
ccaaagcacg tccgggtgtg gtgtccgcgg ccccctcggg cagtcccata ctacggacca   2580
ggggttgact acaaggatgg actagcccca ctgccagaga aaggcttgac aacctatggt   2640
tttggccacc aaaataaggc agtgtacacg gcaggttaca aaatttgcaa ttaccacctc   2700
gccacccagg aagacttaca aaatgcggta aacattatgt ggattcggga ccttttagta   2760
gtggaatcca aagcccaagg catagactca attgctcggt gtaactgcca cactggagtg   2820
tactactgtg aatcccggcg gaagtactac ccggtctctt ttactggccc cacctttcag   2880
tacatggaag caaatgagta ctatccagcc cggtaccaat cccacatgtt aattggccat   2940
ggttttgcat ctccagggga ctgtggtggg attctccggt gccaacatgg agtaattgga   3000
atcattacag ctggaggaga aggcctagtc gctttctcgg acatccggga tctgtacgca   3060
tacgaggagg aggctatgga gcagggagtc tccaactata ttgagtccct tggggctgca   3120
tttgggagtg gattcaccca gcaaatagga aacaaaattt cagaactcac tagcatggtc   3180
accagcacta taactgagaa actactaaag aatctcatta aaataatttc atcccttgtt   3240
atcatcaccc ggaactatga agacacgacc acagtgctgg ctacccttgc tctcctcggt   3300
tgtgatgcgt ccccatggca atggctaaag aagaaagcct gtgacatctt ggaaatcccc   3360
tacatcatgc ggcagggcga tagctggttg aagaagttta cagaggcatg caatgcagcc   3420
aagggattgg aatgggtgtc taataaaata tccaaattta ttgactggct caaagagaag   3480
atcattccac aggctcggga caagctagag tttgttacca aactgaagca actagaaatg   3540
ttggagaacc aaattgcaac cattcatcaa tcgtgcccaa gtcaggagca tcaagaaatc   3600
ctgttcaata acgtgcggtg gttatccata cagtcaaagc ggtttgcccc gctctatgcg   3660
gttgaggcta agcggataca aaagttagag cacacgatta acaactacgt acagttcaag   3720
agcaaacacc ggattgaacc agtatgtttg ttggtgcacg gtagcccagg cacgggcaag   3780
tcagttgcca ccaatttaat tgcccgggca atagcagaga aggagaacac ctccacatac   3840
tcactaccac cagatccctc ccatttcgat gggtacaagc aacaaggtgt ggtgatcatg   3900
gatgatttga atcagaaccc agacggagca gacatgaagc tgttttgtca gatggtctcc   3960
actgtagaat tcataccacc aatggcttcg ctagaagaaa agggtatttt gttcacatct   4020
aattacgttt tggcctcaac caattccagt cggatcaccc caccaactgt tgcgcacagc   4080
gatgccctag cccggcggtt tgcatttgac atggacatac aaatcatgag cgagtattct   4140
cgggatggaa aattgaacat ggcgatggca actgaaatgt gtaagaactg tcatcaacca   4200
gcaaacttca agcggtgttg cccattggtg tgtggcaaag ccatccagct gatggacaaa   4260
tcttcccggg tccggtatag tatagatcag attactacca tgattattaa tgagcggaac   4320
cggcggtcaa gtatcggtaa ttgcatggag gcacttttcc aaggtcctct tcaatacaaa   4380
gacctgaaaa tagacattaa gaccacacct cctcctgagt gcatcaatga tttgctccaa   4440
gcagttgatt ctcaagaggt acgggactac tgtgagaaga agggttggat agtagacatc   4500
actagtcagg tgcaaaccga acggaacatc aatcgggcaa tgactattct tcaggcggtc   4560
accacatttg ccgcagttgc tggagtggtg tatgtgatgt acaaactctt tgcagggcat   4620
caaggagcgt atacagggct tcccaataag cggcccaatg tccccaccat ccggactgcc   4680
aaggttcagg gcccaggatt tgactacgca gtggcaatgg ccaaacggaa cattcttacg   4740
gcaactacca ttaagggaga gttcacaatg ctcggagtgc atgataatgt ggccattcta   4800
```

```
ccaacccacg catcaccggg tgaaacaata gtcattgatg gcaaggaagt agaggtactg   4860

gatgctaaag ccctggagga ccaggccggg accaacctag aaatcaccat tgtcactctt   4920

aagcggaatg agaagttccg ggacatccgg ccacacatcc ccactcaaat cactgagaca   4980

aatgatggag ttttaattgt gaacactagt aagtacccca acatgtatgt tcctgtcggt   5040

gctgtgactg aacaggggta tctcaatctc ggtggacggc aaactgctcg gactttaatg   5100

tacaactttc caacgcgggc aggtcaatgt ggtggagtta tcacctgcac tggcaaggtc   5160

atcgggatgc atgttggtgg gaacggttca catgggttcg cagcagccct gaagcggtcc   5220

tatttcactc agagtcaagg tgaaatccag tggatgcggc catcaaaaga agtgggctac   5280

cccgttatta atgctccatc taaaactaaa ctggaaccca gtgcattcca ttatgtgttt   5340

gaaggtgtca aggaaccagc tgtgctcacc aaaagtgacc cccggttgaa gacagatttt   5400

gaagaggcta tcttttccaa gtatgtggga aataagatta ctgaagtgga tgagtacatg   5460

aaagaagctg tcgatcatta cgcaggccag ctcatgtcac tagacatcaa cacagaacaa   5520

atgtgccttg aggatgcaat gtatggcact gacggtctcg aagctctaga cctcagtacc   5580

agtgctgggt atccctatgt ggcaatgggg aaaaagaaac gggacatttt gaataagcaa   5640

acccgggaca caaaggaaat gcaacggctt ctggacacct atggtattaa tttaccttta   5700

gtcacctatg tgaaagatga gcttcggtcc aagaccaaag tggaacaggg caagtcccgg   5760

ctaattgagg cctcaagtct caatgactct gtcgccatgc ggatggcttt tggcaacttg   5820

tacgcagcat tccacaagaa cccaggtgta gtgacaggat cggctgttgg ctgtgaccca   5880

gatttgtttt ggagtaaaat accagtcctc atggaggaaa aactctttgc atttgattac   5940

acgggttatg atgcttcact aagccccgcc tggtttgagg ctctcaagat ggttctagag   6000

aaaattgggt ttggtgaccg ggtggattac attgattatc tgaatcactc gcaccatcta   6060

tataaaaata agacatattg tgttaagggc ggcatgccat ctggctgctc tggcacctca   6120

atttttaatt caatgattaa taatctaata atccggactc tcttactgaa aacctacaag   6180

ggcatagatt tagaccacct gaagatgata gcctatggtg atgatgtaat tgcttcctac   6240

ccccatgagg ttgatgctag tctcctagcc caatcaggaa aagactatgg actaaccatg   6300

acaccagctg acaaatcagc cacctttgaa acagtcacat gggagaatgt aacattcttg   6360

aaacggttct ttcgggcaga tgaaaagtat ccctttctgg tacatccagt gatgccaatg   6420

aaagaaattc acgaatcaat tcggtggact aaagatcccc ggaacactca ggatcatgtt   6480

cggtcactgt gcttattggc ttggcacaat ggcgaggaag agtacaataa atttttagct   6540

aagattcgga gtgtgccaat cggacgggca ttactgctcc ctgagtactc cacattgtac   6600

cggcggtggc tcgactcatt t                                             6621
```

<210> SEQ ID NO 9
<211> LENGTH: 2202
<212> TYPE: DNA
<213> ORGANISM: Foot-and-mouth disease virus - type O
<220> FEATURE:
<221> NAME/KEY: CDS
<222> LOCATION: (1)..(2202)

<400> SEQUENCE: 9

```
ggc gcc ggg caa tcc agc ccg gcg act ggg tca cag aac cag tca ggc      48
Gly Ala Gly Gln Ser Ser Pro Ala Thr Gly Ser Gln Asn Gln Ser Gly
1               5                   10                  15

aac act gga agc att atc aac aat tac tac atg cag cag tac cag aac      96
Asn Thr Gly Ser Ile Ile Asn Asn Tyr Tyr Met Gln Gln Tyr Gln Asn
```

-continued

```
            20                  25                  30

tcc atg gac acg cag ctt ggt gac aac gct att agc gga ggc tcc aac      144
Ser Met Asp Thr Gln Leu Gly Asp Asn Ala Ile Ser Gly Gly Ser Asn
        35                  40                  45

gag ggg tcc acg gac acc acc tcc act cac aca acc aac act cag aac      192
Glu Gly Ser Thr Asp Thr Thr Ser Thr His Thr Thr Asn Thr Gln Asn
    50                  55                  60

aat gac tgg ttt tca aag ctg gcc agt tcc gct ttt agc ggt ctt ttc      240
Asn Asp Trp Phe Ser Lys Leu Ala Ser Ser Ala Phe Ser Gly Leu Phe
65                  70                  75                  80

ggc gct ctt ctt gct gac aag aaa acc gag gag acc act ctt ctc gag      288
Gly Ala Leu Leu Ala Asp Lys Lys Thr Glu Glu Thr Thr Leu Leu Glu
                85                  90                  95

gac cgc atc ctc act acc cgc aac gga cac acg acc tcg aca acc cag      336
Asp Arg Ile Leu Thr Thr Arg Asn Gly His Thr Thr Ser Thr Thr Gln
            100                 105                 110

tcg agc gtt gga gtc act tac ggg tac gca aca gct gag gac ttt gtg      384
Ser Ser Val Gly Val Thr Tyr Gly Tyr Ala Thr Ala Glu Asp Phe Val
        115                 120                 125

agc gga cca aac aca tct ggg ctt gag acc agg gtt gtg cag gca gag      432
Ser Gly Pro Asn Thr Ser Gly Leu Glu Thr Arg Val Val Gln Ala Glu
    130                 135                 140

cgg ttc ttc aaa acc cac ttg ttc gac tgg gtc acc agt gac ccg ttt      480
Arg Phe Phe Lys Thr His Leu Phe Asp Trp Val Thr Ser Asp Pro Phe
145                 150                 155                 160

gga cgg tgc tat ctg ctg gaa ctc cca act gac cac aaa ggt gtc tac      528
Gly Arg Cys Tyr Leu Leu Glu Leu Pro Thr Asp His Lys Gly Val Tyr
                165                 170                 175

ggc agc ctg acc gac tct tat gct tac atg aga aac ggt tgg gat gtt      576
Gly Ser Leu Thr Asp Ser Tyr Ala Tyr Met Arg Asn Gly Trp Asp Val
            180                 185                 190

gag gtc acc gca gtg gga aat cag ttc aac gga gga tgt ctg ttg gtg      624
Glu Val Thr Ala Val Gly Asn Gln Phe Asn Gly Gly Cys Leu Leu Val
        195                 200                 205

gcc atg gtg cca gaa ctt tgc tct att gac aag aga gag ctg tac cag      672
Ala Met Val Pro Glu Leu Cys Ser Ile Asp Lys Arg Glu Leu Tyr Gln
    210                 215                 220

ctc acg ctc ttt ccc cac cag ttc atc aac ccc cgg acg aac atg acg      720
Leu Thr Leu Phe Pro His Gln Phe Ile Asn Pro Arg Thr Asn Met Thr
225                 230                 235                 240

gcg cac atc act gtg ccc ttt gtt ggc gtc aac cgc tac gac cag tac      768
Ala His Ile Thr Val Pro Phe Val Gly Val Asn Arg Tyr Asp Gln Tyr
                245                 250                 255

aag gta cac aaa cct tgg acc ctc gtg gtt atg gtt gtg gcc ccg ctg      816
Lys Val His Lys Pro Trp Thr Leu Val Val Met Val Val Ala Pro Leu
            260                 265                 270

act gtc aac acc gaa ggt gcc cca cag atc aag gtc tat gcc aac atc      864
Thr Val Asn Thr Glu Gly Ala Pro Gln Ile Lys Val Tyr Ala Asn Ile
        275                 280                 285

gcc cct acc aac gtg cac gtt gcg ggt gag ttc cct tct aag gaa ggg      912
Ala Pro Thr Asn Val His Val Ala Gly Glu Phe Pro Ser Lys Glu Gly
    290                 295                 300

atc ttc ccc gtg gca tgt agc gac ggt tac ggt ggt ctg gtg acc act      960
Ile Phe Pro Val Ala Cys Ser Asp Gly Tyr Gly Gly Leu Val Thr Thr
305                 310                 315                 320

gac cca aag acg gct gac ccc gcc tac ggg aaa gtg ttc aat cca cct     1008
Asp Pro Lys Thr Ala Asp Pro Ala Tyr Gly Lys Val Phe Asn Pro Pro
                325                 330                 335

cgc aac atg ttg ccg ggg cgg ttc acc aac ttc ctt gat gtg gct gag     1056
```

-continued

```
Arg Asn Met Leu Pro Gly Arg Phe Thr Asn Phe Leu Asp Val Ala Glu
            340                 345                 350

gcg tgc cct acg ttt ctg cac ttt gag ggt ggc gtg ccg tac gtg acc      1104
Ala Cys Pro Thr Phe Leu His Phe Glu Gly Gly Val Pro Tyr Val Thr
        355                 360                 365

aca aag acg gac tca gac agg gtg ctc gcc cag ttc gac ttg tct ctg      1152
Thr Lys Thr Asp Ser Asp Arg Val Leu Ala Gln Phe Asp Leu Ser Leu
    370                 375                 380

gca gca aag cac atg tca aac acc ttc ctg gca ggt ctc gcc cag tac      1200
Ala Ala Lys His Met Ser Asn Thr Phe Leu Ala Gly Leu Ala Gln Tyr
385                 390                 395                 400

tac aca cag tac agc ggc acc atc aac ctg cac ttc atg ttc aca gga      1248
Tyr Thr Gln Tyr Ser Gly Thr Ile Asn Leu His Phe Met Phe Thr Gly
                405                 410                 415

ccc act gac gcg aaa gcg cgt tac atg att gca tac gcc ccc cct ggt      1296
Pro Thr Asp Ala Lys Ala Arg Tyr Met Ile Ala Tyr Ala Pro Pro Gly
            420                 425                 430

atg gag ccg ccc aaa aca cct gag gcg gcc gcc cac tgc att cat gcg      1344
Met Glu Pro Pro Lys Thr Pro Glu Ala Ala Ala His Cys Ile His Ala
        435                 440                 445

gag tgg gac aca ggg ttg aat tca aaa ttc aca ttt tca atc cct tac      1392
Glu Trp Asp Thr Gly Leu Asn Ser Lys Phe Thr Phe Ser Ile Pro Tyr
    450                 455                 460

ctt tcg gcg gct gat tac gcg tac acc gcg tct gac gct gcg gag acc      1440
Leu Ser Ala Ala Asp Tyr Ala Tyr Thr Ala Ser Asp Ala Ala Glu Thr
465                 470                 475                 480

aca aat gta cag gga tgg gtt tgc ctg ttt caa att aca cac ggg aag      1488
Thr Asn Val Gln Gly Trp Val Cys Leu Phe Gln Ile Thr His Gly Lys
                485                 490                 495

gct gac ggc gac gca ctg gtc gtt cta gct agc gcc ggt aag gac ttt      1536
Ala Asp Gly Asp Ala Leu Val Val Leu Ala Ser Ala Gly Lys Asp Phe
            500                 505                 510

gag ctg cgt ctg cca gtt gac gct cgc acg cag acc acc tcc gca ggt      1584
Glu Leu Arg Leu Pro Val Asp Ala Arg Thr Gln Thr Thr Ser Ala Gly
        515                 520                 525

gag tcg gct gac ccc gtg act gcc act gtt gag aac tac ggt ggt gag      1632
Glu Ser Ala Asp Pro Val Thr Ala Thr Val Glu Asn Tyr Gly Gly Glu
    530                 535                 540

aca cag gtc cag aga cgc caa cac acg gat gtc tcg ttc ata tta gac      1680
Thr Gln Val Gln Arg Arg Gln His Thr Asp Val Ser Phe Ile Leu Asp
545                 550                 555                 560

aga ttt gtg aaa gta aca cca aaa gac caa att aat gtg ttg gac ctg      1728
Arg Phe Val Lys Val Thr Pro Lys Asp Gln Ile Asn Val Leu Asp Leu
                565                 570                 575

atg caa acc cct gca cac act ttg gta ggc gcg ctc ctc cgt act gcc      1776
Met Gln Thr Pro Ala His Thr Leu Val Gly Ala Leu Leu Arg Thr Ala
            580                 585                 590

acc tac tac ttc gca gat cta gaa gtg gca gtg aaa cac gag ggg aac      1824
Thr Tyr Tyr Phe Ala Asp Leu Glu Val Ala Val Lys His Glu Gly Asn
        595                 600                 605

ctt acc tgg gtc ccg aat ggg gcg ccc gag aca gcg ttg gac aac acc      1872
Leu Thr Trp Val Pro Asn Gly Ala Pro Glu Thr Ala Leu Asp Asn Thr
    610                 615                 620

acc aat cca acg gct tac cac aag gca ccg ctc acc cgg ctt gca ctg      1920
Thr Asn Pro Thr Ala Tyr His Lys Ala Pro Leu Thr Arg Leu Ala Leu
625                 630                 635                 640

cct tac acg gca ccg cac cgt gtc ttg gct act gtt tac aac ggg aac      1968
Pro Tyr Thr Ala Pro His Arg Val Leu Ala Thr Val Tyr Asn Gly Asn
                645                 650                 655
```

```
tgc aag tat ggc gag agc ccc gtg acc aat gtg aga ggt gac ctg caa      2016
Cys Lys Tyr Gly Glu Ser Pro Val Thr Asn Val Arg Gly Asp Leu Gln
            660                 665                 670

gta ttg gcc caa aag gcg gca aga acg ctg cct acc tcc ttc aat tac      2064
Val Leu Ala Gln Lys Ala Ala Arg Thr Leu Pro Thr Ser Phe Asn Tyr
        675                 680                 685

ggt gcc atc aaa gcc act cgg gtg act gaa ctg ctt tac cgc atg aag      2112
Gly Ala Ile Lys Ala Thr Arg Val Thr Glu Leu Leu Tyr Arg Met Lys
    690                 695                 700

agg gcc gaa aca tac tgc ccc cgg cct ctt ttg gct att cac cca agc      2160
Arg Ala Glu Thr Tyr Cys Pro Arg Pro Leu Leu Ala Ile His Pro Ser
705                 710                 715                 720

gaa gct aga cac aaa caa aag att gtt gcg cct gtg aaa cag              2202
Glu Ala Arg His Lys Gln Lys Ile Val Ala Pro Val Lys Gln
                725                 730
```

<210> SEQ ID NO 10
<211> LENGTH: 734
<212> TYPE: PRT
<213> ORGANISM: Foot-and-mouth disease virus - type O

<400> SEQUENCE: 10

```
Gly Ala Gly Gln Ser Ser Pro Ala Thr Gly Ser Gln Asn Gln Ser Gly
1               5                   10                  15

Asn Thr Gly Ser Ile Ile Asn Asn Tyr Tyr Met Gln Gln Tyr Gln Asn
            20                  25                  30

Ser Met Asp Thr Gln Leu Gly Asp Asn Ala Ile Ser Gly Gly Ser Asn
        35                  40                  45

Glu Gly Ser Thr Asp Thr Thr Ser Thr His Thr Thr Asn Thr Gln Asn
    50                  55                  60

Asn Asp Trp Phe Ser Lys Leu Ala Ser Ser Ala Phe Ser Gly Leu Phe
65                  70                  75                  80

Gly Ala Leu Leu Ala Asp Lys Lys Thr Glu Glu Thr Thr Leu Leu Glu
                85                  90                  95

Asp Arg Ile Leu Thr Thr Arg Asn Gly His Thr Thr Ser Thr Thr Gln
            100                 105                 110

Ser Ser Val Gly Val Thr Tyr Gly Tyr Ala Thr Ala Glu Asp Phe Val
        115                 120                 125

Ser Gly Pro Asn Thr Ser Gly Leu Glu Thr Arg Val Val Gln Ala Glu
    130                 135                 140

Arg Phe Phe Lys Thr His Leu Phe Asp Trp Val Thr Ser Asp Pro Phe
145                 150                 155                 160

Gly Arg Cys Tyr Leu Leu Glu Leu Pro Thr Asp His Lys Gly Val Tyr
                165                 170                 175

Gly Ser Leu Thr Asp Ser Tyr Ala Tyr Met Arg Asn Gly Trp Asp Val
            180                 185                 190

Glu Val Thr Ala Val Gly Asn Gln Phe Asn Gly Gly Cys Leu Leu Val
        195                 200                 205

Ala Met Val Pro Glu Leu Cys Ser Ile Asp Lys Arg Glu Leu Tyr Gln
    210                 215                 220

Leu Thr Leu Phe Pro His Gln Phe Ile Asn Pro Arg Thr Asn Met Thr
225                 230                 235                 240

Ala His Ile Thr Val Pro Phe Val Gly Val Asn Arg Tyr Asp Gln Tyr
                245                 250                 255

Lys Val His Lys Pro Trp Thr Leu Val Val Met Val Val Ala Pro Leu
            260                 265                 270
```

-continued

```
Thr Val Asn Thr Glu Gly Ala Pro Gln Ile Lys Val Tyr Ala Asn Ile
        275                 280                 285

Ala Pro Thr Asn Val His Val Ala Gly Glu Phe Pro Ser Lys Glu Gly
    290                 295                 300

Ile Phe Pro Val Ala Cys Ser Asp Gly Tyr Gly Gly Leu Val Thr Thr
305                 310                 315                 320

Asp Pro Lys Thr Ala Asp Pro Ala Tyr Gly Lys Val Phe Asn Pro Pro
                325                 330                 335

Arg Asn Met Leu Pro Gly Arg Phe Thr Asn Phe Leu Asp Val Ala Glu
            340                 345                 350

Ala Cys Pro Thr Phe Leu His Phe Glu Gly Gly Val Pro Tyr Val Thr
        355                 360                 365

Thr Lys Thr Asp Ser Asp Arg Val Leu Ala Gln Phe Asp Leu Ser Leu
    370                 375                 380

Ala Ala Lys His Met Ser Asn Thr Phe Leu Ala Gly Leu Ala Gln Tyr
385                 390                 395                 400

Tyr Thr Gln Tyr Ser Gly Thr Ile Asn Leu His Phe Met Phe Thr Gly
                405                 410                 415

Pro Thr Asp Ala Lys Ala Arg Tyr Met Ile Ala Tyr Ala Pro Pro Gly
            420                 425                 430

Met Glu Pro Pro Lys Thr Pro Glu Ala Ala Ala His Cys Ile His Ala
        435                 440                 445

Glu Trp Asp Thr Gly Leu Asn Ser Lys Phe Thr Phe Ser Ile Pro Tyr
    450                 455                 460

Leu Ser Ala Ala Asp Tyr Ala Tyr Thr Ala Ser Asp Ala Ala Glu Thr
465                 470                 475                 480

Thr Asn Val Gln Gly Trp Val Cys Leu Phe Gln Ile Thr His Gly Lys
                485                 490                 495

Ala Asp Gly Asp Ala Leu Val Val Leu Ala Ser Ala Gly Lys Asp Phe
            500                 505                 510

Glu Leu Arg Leu Pro Val Asp Ala Arg Thr Gln Thr Thr Ser Ala Gly
        515                 520                 525

Glu Ser Ala Asp Pro Val Thr Ala Thr Val Glu Asn Tyr Gly Gly Glu
    530                 535                 540

Thr Gln Val Gln Arg Arg Gln His Thr Asp Val Ser Phe Ile Leu Asp
545                 550                 555                 560

Arg Phe Val Lys Val Thr Pro Lys Asp Gln Ile Asn Val Leu Asp Leu
                565                 570                 575

Met Gln Thr Pro Ala His Thr Leu Val Gly Ala Leu Leu Arg Thr Ala
            580                 585                 590

Thr Tyr Tyr Phe Ala Asp Leu Glu Val Ala Val Lys His Glu Gly Asn
        595                 600                 605

Leu Thr Trp Val Pro Asn Gly Ala Pro Glu Thr Ala Leu Asp Asn Thr
    610                 615                 620

Thr Asn Pro Thr Ala Tyr His Lys Ala Pro Leu Thr Arg Leu Ala Leu
625                 630                 635                 640

Pro Tyr Thr Ala Pro His Arg Val Leu Ala Thr Val Tyr Asn Gly Asn
                645                 650                 655

Cys Lys Tyr Gly Glu Ser Pro Val Thr Asn Val Arg Gly Asp Leu Gln
            660                 665                 670

Val Leu Ala Gln Lys Ala Ala Arg Thr Leu Pro Thr Ser Phe Asn Tyr
        675                 680                 685

Gly Ala Ile Lys Ala Thr Arg Val Thr Glu Leu Leu Tyr Arg Met Lys
```

-continued

```
    690                 695                 700

Arg Ala Glu Thr Tyr Cys Pro Arg Pro Leu Leu Ala Ile His Pro Ser
705                 710                 715                 720

Glu Ala Arg His Lys Gln Lys Ile Val Ala Pro Val Lys Gln
                725                 730


<210> SEQ ID NO 11
<211> LENGTH: 2202
<212> TYPE: DNA
<213> ORGANISM: Artificial
<220> FEATURE:
<223> OTHER INFORMATION: deoptimized FMVD capsid sequence

<400> SEQUENCE: 11

ggggcggggc aatcgagccc ggcgacgggg tcgcagaacc agtcggggaa cacggggagc      60

ataataaaca attactacat gcagcagtac cagaactcga tggacacgca gctaggggac     120

aacgcgataa gcggggggtc gaacgagggg tcgacggaca cgacgtcgac gcacacgacg     180

aacacgcaga acaatgactg gttttcgaag ctagcgtcgt cggcgtttag cgggctattc     240

ggggcgctac tagcggacaa gaaaacggag gagacgacgc tactagagga ccgaatacta     300

acgacgcgaa acgggcacac gacgtcgacg acgcagtcga gcgtaggggt aacgtacggg     360

tacgcgacgg cggaggactt tgtaagcggg ccgaacacgt cggggctaga gacgcgagta     420

gtacaggcgg agcgattctt caaaacgcac ctattcgact gggtaacgtc ggacccgttt     480

gggcgatgct atctactaga actaccgacg gaccacaaag ggtatacggg gagcctaacg     540

gactcgtatg cgtacatgcg aaacgggtgg gatgtagagg taacggcggt agggaatcag     600

ttcaacgggg ggtgtctact agtagcgatg gtaccggaac tatgctcgat agacaagcga     660

gagctatacc agctaacgct atttccgcac cagttcataa acccgcgaac gaacatgacg     720

gcgcacataa cggtaccgtt tgtaggggta aaccgatacg accagtacaa ggtacacaaa     780

ccgtggacgc tagtagtaat ggtagtagcg ccgctaacgg taaacacgga aggggcgccg     840

cagataaagg tatatgcgaa catagcgccg acgaacgtac acgtagcggg ggagttcccg     900

tcgaaggaag ggatattccc ggtagcgtgt agcgacgggt acgggggggct agtaacgacg     960

gacccgaaga cggcggaccc ggcgtacggg aaagtattca atccgccgcg aaacatgcta    1020

ccggggcgat tcacgaactt cctagatgta gcggaggcgt gcccgacgtt tctacacttt    1080

gaggggggggg taccgtacgt aacgacgaag acggactcgg accgagtact agcgcagttc    1140

gacctatcgc tagcggcgaa gcacatgtcg aacacgttcc tagcggggct agcgcagtac    1200

tacacgcagt acagcgggac gataaaccta cacttcatgt tcacggggcc gacggacgcg    1260

aaagcgcgat acatgatagc gtacgcgccg ccggggatgg agccgccgaa aacgccggag    1320

gcggcggcgc actgcataca tgcggagtgg gacacggggc taaattcgaa attcacgttt    1380

tcgataccgt acctatcggc ggcggattac gcgtacacgg cgtcggacgc ggcggagacg    1440

acgaatgtac aggggtgggt atgcctattt caaataacgc acgggaaggc ggacggggac    1500

gcgctagtag tactagcgag cgcggggaag gactttgagc tacgactacc ggtagacgcg    1560

cgaacgcaga cgacgtcggc gggggagtcg gcggacccgg taacggcgac ggtagagaac    1620

tacggggggg agacgcaggt acagcgacga caacacacgg atgtatcgtt catactagac    1680

cgatttgtaa aagtaacgcc gaaagaccaa ataaatgtac tagacctaat gcaaacgccg    1740

gcgcacacgc tagtaggggc gctactacga acggcgacgt actacttcgc ggatctagaa    1800

gtagcggtaa aacacgaggg gaacctaacg tgggtaccga atggggcgcc ggagacggcg    1860
```

```
ctagacaaca cgacgaatcc gacggcgtac cacaaggcgc cgctaacgcg actagcgcta   1920

ccgtacacgg cgccgcaccg agtactagcg acggtataca acgggaactg caagtatggg   1980

gagagcccgg taacgaatgt acgaggggac ctacaagtac tagcgcaaaa ggcggcgcga   2040

acgctaccga cgtcgttcaa ttacggggcg ataaaagcga cgcgagtaac ggaactacta   2100

taccgaatga agcgagcgga aacgtactgc ccgcgaccgc tactagcgat acacccgagc   2160

gaagcgcgac acaaacaaaa gatagtagcg ccggtaaaac ag                      2202


<210> SEQ ID NO 12
<211> LENGTH: 3768
<212> TYPE: DNA
<213> ORGANISM: SARS coronavirus Urbani
<220> FEATURE:
<221> NAME/KEY: CDS
<222> LOCATION: (1)..(3768)

<400> SEQUENCE: 12

atg ttt att ttc tta tta ttt ctt act ctc act agt ggt agt gac ctt       48
Met Phe Ile Phe Leu Leu Phe Leu Thr Leu Thr Ser Gly Ser Asp Leu
1               5                   10                  15

gac cgg tgc acc act ttt gat gat gtt caa gct cct aat tac act caa       96
Asp Arg Cys Thr Thr Phe Asp Asp Val Gln Ala Pro Asn Tyr Thr Gln
            20                  25                  30

cat act tca tct atg agg ggg gtt tac tat cct gat gaa att ttt aga      144
His Thr Ser Ser Met Arg Gly Val Tyr Tyr Pro Asp Glu Ile Phe Arg
        35                  40                  45

tca gac act ctt tat tta act cag gat tta ttt ctt cca ttt tat tct      192
Ser Asp Thr Leu Tyr Leu Thr Gln Asp Leu Phe Leu Pro Phe Tyr Ser
    50                  55                  60

aat gtt aca ggg ttt cat act att aat cat acg ttt ggc aac cct gtc      240
Asn Val Thr Gly Phe His Thr Ile Asn His Thr Phe Gly Asn Pro Val
65                  70                  75                  80

ata cct ttt aag gat ggt att tat ttt gct gcc aca gag aaa tca aat      288
Ile Pro Phe Lys Asp Gly Ile Tyr Phe Ala Ala Thr Glu Lys Ser Asn
                85                  90                  95

gtt gtc cgt ggt tgg gtt ttt ggt tct acc atg aac aac aag tca cag      336
Val Val Arg Gly Trp Val Phe Gly Ser Thr Met Asn Asn Lys Ser Gln
            100                 105                 110

tcg gtg att att att aac aat tct act aat gtt gtt ata cga gca tgt      384
Ser Val Ile Ile Ile Asn Asn Ser Thr Asn Val Val Ile Arg Ala Cys
        115                 120                 125

aac ttt gaa ttg tgt gac aac cct ttc ttt gct gtt tct aaa ccc atg      432
Asn Phe Glu Leu Cys Asp Asn Pro Phe Phe Ala Val Ser Lys Pro Met
    130                 135                 140

ggt aca cag aca cat act atg ata ttc gat aat gca ttt aat tgc act      480
Gly Thr Gln Thr His Thr Met Ile Phe Asp Asn Ala Phe Asn Cys Thr
145                 150                 155                 160

ttc gag tac ata tct gat gcc ttt tcg ctt gat gtt tca gaa aag tca      528
Phe Glu Tyr Ile Ser Asp Ala Phe Ser Leu Asp Val Ser Glu Lys Ser
                165                 170                 175

ggt aat ttt aaa cac tta cga gag ttt gtg ttt aaa aat aaa gat ggg      576
Gly Asn Phe Lys His Leu Arg Glu Phe Val Phe Lys Asn Lys Asp Gly
            180                 185                 190

ttt ctc tat gtt tat aag ggc tat caa cct ata gat gta gtt cgt gat      624
Phe Leu Tyr Val Tyr Lys Gly Tyr Gln Pro Ile Asp Val Val Arg Asp
        195                 200                 205

cta cct tct ggt ttt aac act ttg aaa cct att ttt aag ttg cct ctt      672
Leu Pro Ser Gly Phe Asn Thr Leu Lys Pro Ile Phe Lys Leu Pro Leu
    210                 215                 220
```

```
ggt att aac att aca aat ttt aga gcc att ctt aca gcc ttt tca cct      720
Gly Ile Asn Ile Thr Asn Phe Arg Ala Ile Leu Thr Ala Phe Ser Pro
225                 230                 235                 240

gct caa gac att tgg ggc acg tca gct gca gcc tat ttt gtt ggc tat      768
Ala Gln Asp Ile Trp Gly Thr Ser Ala Ala Ala Tyr Phe Val Gly Tyr
                245                 250                 255

tta aag cca act aca ttt atg ctc aag tat gat gaa aat ggt aca atc      816
Leu Lys Pro Thr Thr Phe Met Leu Lys Tyr Asp Glu Asn Gly Thr Ile
            260                 265                 270

aca gat gct gtt gat tgt tct caa aat cca ctt gct gaa ctc aaa tgc      864
Thr Asp Ala Val Asp Cys Ser Gln Asn Pro Leu Ala Glu Leu Lys Cys
        275                 280                 285

tct gtt aag agc ttt gag att gac aaa gga att tac cag acc tct aat      912
Ser Val Lys Ser Phe Glu Ile Asp Lys Gly Ile Tyr Gln Thr Ser Asn
    290                 295                 300

ttc agg gtt gtt ccc tca gga gat gtt gtg aga ttc cct aat att aca      960
Phe Arg Val Val Pro Ser Gly Asp Val Val Arg Phe Pro Asn Ile Thr
305                 310                 315                 320

aac ttg tgt cct ttt gga gag gtt ttt aat gct act aaa ttc cct tct     1008
Asn Leu Cys Pro Phe Gly Glu Val Phe Asn Ala Thr Lys Phe Pro Ser
                325                 330                 335

gtc tat gca tgg gag aga aaa aaa att tct aat tgt gtt gct gat tac     1056
Val Tyr Ala Trp Glu Arg Lys Lys Ile Ser Asn Cys Val Ala Asp Tyr
            340                 345                 350

tct gtg ctc tac aac tca aca ttt ttt tca acc ttt aag tgc tat ggc     1104
Ser Val Leu Tyr Asn Ser Thr Phe Phe Ser Thr Phe Lys Cys Tyr Gly
        355                 360                 365

gtt tct gcc act aag ttg aat gat ctt tgc ttc tcc aat gtc tat gca     1152
Val Ser Ala Thr Lys Leu Asn Asp Leu Cys Phe Ser Asn Val Tyr Ala
    370                 375                 380

gat tct ttt gta gtc aag gga gat gat gta aga caa ata gcg cca gga     1200
Asp Ser Phe Val Val Lys Gly Asp Asp Val Arg Gln Ile Ala Pro Gly
385                 390                 395                 400

caa act ggt gtt att gct gat tat aat tat aaa ttg cca gat gat ttc     1248
Gln Thr Gly Val Ile Ala Asp Tyr Asn Tyr Lys Leu Pro Asp Asp Phe
                405                 410                 415

atg ggt tgt gtc ctt gct tgg aat act agg aac att gat gct act tca     1296
Met Gly Cys Val Leu Ala Trp Asn Thr Arg Asn Ile Asp Ala Thr Ser
            420                 425                 430

act ggt aat tat aat tat aaa tat agg tat ctt aga cat ggc aag ctt     1344
Thr Gly Asn Tyr Asn Tyr Lys Tyr Arg Tyr Leu Arg His Gly Lys Leu
        435                 440                 445

agg ccc ttt gag aga gac ata tct aat gtg cct ttc tcc cct gat ggc     1392
Arg Pro Phe Glu Arg Asp Ile Ser Asn Val Pro Phe Ser Pro Asp Gly
    450                 455                 460

aaa cct tgc acc cca cct gct ctt aat tgt tat tgg cca tta aat gat     1440
Lys Pro Cys Thr Pro Pro Ala Leu Asn Cys Tyr Trp Pro Leu Asn Asp
465                 470                 475                 480

tat ggt ttt tac acc act act ggc att ggc tac caa cct tac aga gtt     1488
Tyr Gly Phe Tyr Thr Thr Thr Gly Ile Gly Tyr Gln Pro Tyr Arg Val
                485                 490                 495

gta gta ctt tct ttt gaa ctt tta aat gca ccg gcc acg gtt tgt gga     1536
Val Val Leu Ser Phe Glu Leu Leu Asn Ala Pro Ala Thr Val Cys Gly
            500                 505                 510

cca aaa tta tcc act gac ctt att aag aac cag tgt gtc aat ttt aat     1584
Pro Lys Leu Ser Thr Asp Leu Ile Lys Asn Gln Cys Val Asn Phe Asn
        515                 520                 525

ttt aat gga ctc act ggt act ggt gtg tta act cct tct tca aag aga     1632
Phe Asn Gly Leu Thr Gly Thr Gly Val Leu Thr Pro Ser Ser Lys Arg
```

```
    530                 535                 540

ttt caa cca ttt caa caa ttt ggc cgt gat gtt tct gat ttc act gat      1680
Phe Gln Pro Phe Gln Gln Phe Gly Arg Asp Val Ser Asp Phe Thr Asp
545                 550                 555                 560

tcc gtt cga gat cct aaa aca tct gaa ata tta gac att tca cct tgc      1728
Ser Val Arg Asp Pro Lys Thr Ser Glu Ile Leu Asp Ile Ser Pro Cys
                565                 570                 575

tct ttt ggg ggt gta agt gta att aca cct gga aca aat gct tca tct      1776
Ser Phe Gly Gly Val Ser Val Ile Thr Pro Gly Thr Asn Ala Ser Ser
            580                 585                 590

gaa gtt gct gtt cta tat caa gat gtt aac tgc act gat gtt tct aca      1824
Glu Val Ala Val Leu Tyr Gln Asp Val Asn Cys Thr Asp Val Ser Thr
        595                 600                 605

gca att cat gca gat caa ctc aca cca gct tgg cgc ata tat tct act      1872
Ala Ile His Ala Asp Gln Leu Thr Pro Ala Trp Arg Ile Tyr Ser Thr
    610                 615                 620

gga aac aat gta ttc cag act caa gca ggc tgt ctt ata gga gct gag      1920
Gly Asn Asn Val Phe Gln Thr Gln Ala Gly Cys Leu Ile Gly Ala Glu
625                 630                 635                 640

cat gtc gac act tct tat gag tgc gac att cct att gga gct ggc att      1968
His Val Asp Thr Ser Tyr Glu Cys Asp Ile Pro Ile Gly Ala Gly Ile
                645                 650                 655

tgt gct agt tac cat aca gtt tct tta tta cgt agt act agc caa aaa      2016
Cys Ala Ser Tyr His Thr Val Ser Leu Leu Arg Ser Thr Ser Gln Lys
            660                 665                 670

tct att gtg gct tat act atg tct tta ggt gct gat agt tca att gct      2064
Ser Ile Val Ala Tyr Thr Met Ser Leu Gly Ala Asp Ser Ser Ile Ala
        675                 680                 685

tac tct aat aac acc att gct ata cct act aac ttt tca att agc att      2112
Tyr Ser Asn Asn Thr Ile Ala Ile Pro Thr Asn Phe Ser Ile Ser Ile
    690                 695                 700

act aca gaa gta atg cct gtt tct atg gct aaa acc tcc gta gat tgt      2160
Thr Thr Glu Val Met Pro Val Ser Met Ala Lys Thr Ser Val Asp Cys
705                 710                 715                 720

aat atg tac atc tgc gga gat tct act gaa tgt gct aat ttg ctt ctc      2208
Asn Met Tyr Ile Cys Gly Asp Ser Thr Glu Cys Ala Asn Leu Leu Leu
                725                 730                 735

caa tat ggt agc ttt tgc aca caa cta aat cgt gca ctc tca ggt att      2256
Gln Tyr Gly Ser Phe Cys Thr Gln Leu Asn Arg Ala Leu Ser Gly Ile
            740                 745                 750

gct gct gaa cag gat cgc aac aca cgt gaa gtg ttc gct caa gtc aaa      2304
Ala Ala Glu Gln Asp Arg Asn Thr Arg Glu Val Phe Ala Gln Val Lys
        755                 760                 765

caa atg tac aaa acc cca act ttg aaa tat ttt ggt ggt ttt aat ttt      2352
Gln Met Tyr Lys Thr Pro Thr Leu Lys Tyr Phe Gly Gly Phe Asn Phe
    770                 775                 780

tca caa ata tta cct gac cct cta aag cca act aag agg tct ttt att      2400
Ser Gln Ile Leu Pro Asp Pro Leu Lys Pro Thr Lys Arg Ser Phe Ile
785                 790                 795                 800

gag gac ttg ctc ttt aat aag gtg aca ctc gct gat gct ggc ttc atg      2448
Glu Asp Leu Leu Phe Asn Lys Val Thr Leu Ala Asp Ala Gly Phe Met
                805                 810                 815

aag caa tat ggc gaa tgc cta ggt gat att aat gct aga gat ctc att      2496
Lys Gln Tyr Gly Glu Cys Leu Gly Asp Ile Asn Ala Arg Asp Leu Ile
            820                 825                 830

tgt gcg cag aag ttc aat gga ctt aca gtg ttg cca cct ctg ctc act      2544
Cys Ala Gln Lys Phe Asn Gly Leu Thr Val Leu Pro Pro Leu Leu Thr
        835                 840                 845

gat gat atg att gct gcc tac act gct gct cta gtt agt ggt act gcc      2592
```

```
Asp Asp Met Ile Ala Ala Tyr Thr Ala Ala Leu Val Ser Gly Thr Ala
    850                 855                 860

act gct gga tgg aca ttt ggt gct ggc gct gct ctt caa ata cct ttt     2640
Thr Ala Gly Trp Thr Phe Gly Ala Gly Ala Ala Leu Gln Ile Pro Phe
865                 870                 875                 880

gct atg caa atg gca tat agg ttc aat ggc att gga gtt acc caa aat     2688
Ala Met Gln Met Ala Tyr Arg Phe Asn Gly Ile Gly Val Thr Gln Asn
                885                 890                 895

gtt ctc tat gag aac caa aaa caa atc gcc aac caa ttt aac aag gcg     2736
Val Leu Tyr Glu Asn Gln Lys Gln Ile Ala Asn Gln Phe Asn Lys Ala
            900                 905                 910

att agt caa att caa gaa tca ctt aca aca aca tca act gca ttg ggc     2784
Ile Ser Gln Ile Gln Glu Ser Leu Thr Thr Thr Ser Thr Ala Leu Gly
        915                 920                 925

aag ctg caa gac gtt gtt aac cag aat gct caa gca tta aac aca ctt     2832
Lys Leu Gln Asp Val Val Asn Gln Asn Ala Gln Ala Leu Asn Thr Leu
    930                 935                 940

gtt aaa caa ctt agc tct aat ttt ggt gca att tca agt gtg cta aat     2880
Val Lys Gln Leu Ser Ser Asn Phe Gly Ala Ile Ser Ser Val Leu Asn
945                 950                 955                 960

gat atc ctt tcg cga ctt gat aaa gtc gag gcg gag gta caa att gac     2928
Asp Ile Leu Ser Arg Leu Asp Lys Val Glu Ala Glu Val Gln Ile Asp
                965                 970                 975

agg tta att aca ggc aga ctt caa agc ctt caa acc tat gta aca caa     2976
Arg Leu Ile Thr Gly Arg Leu Gln Ser Leu Gln Thr Tyr Val Thr Gln
            980                 985                 990

caa cta atc agg gct gct gaa atc  agg gct tct gct aat  ctt gct gct   3024
Gln Leu Ile Arg Ala Ala Glu Ile  Arg Ala Ser Ala Asn  Leu Ala Ala
        995                 1000                1005

act aaa  atg tct gag tgt gtt  ctt gga caa tca aaa  aga gtt gac      3069
Thr Lys  Met Ser Glu Cys Val  Leu Gly Gln Ser Lys  Arg Val Asp
    1010                 1015                 1020

ttt tgt  gga aag ggc tac cac  ctt atg tcc ttc cca  caa gca gcc      3114
Phe Cys  Gly Lys Gly Tyr His  Leu Met Ser Phe Pro  Gln Ala Ala
    1025                 1030                 1035

ccg cat  ggt gtt gtc ttc cta  cat gtc acg tat gtg  cca tcc cag      3159
Pro His  Gly Val Val Phe Leu  His Val Thr Tyr Val  Pro Ser Gln
    1040                 1045                 1050

gag agg  aac ttc acc aca gcg  cca gca att tgt cat  gaa ggc aaa      3204
Glu Arg  Asn Phe Thr Thr Ala  Pro Ala Ile Cys His  Glu Gly Lys
    1055                 1060                 1065

gca tac  ttc cct cgt gaa ggt  gtt ttt gtg ttt aat  ggc act tct      3249
Ala Tyr  Phe Pro Arg Glu Gly  Val Phe Val Phe Asn  Gly Thr Ser
    1070                 1075                 1080

tgg ttt  att aca cag agg aac  ttc ttt tct cca caa  ata att act      3294
Trp Phe  Ile Thr Gln Arg Asn  Phe Phe Ser Pro Gln  Ile Ile Thr
    1085                 1090                 1095

aca gac  aat aca ttt gtc tca  gga aat tgt gat gtc  gtt att ggc      3339
Thr Asp  Asn Thr Phe Val Ser  Gly Asn Cys Asp Val  Val Ile Gly
    1100                 1105                 1110

atc att  aac aac aca gtt tat  gat cct ctg caa cct  gag ctc gac      3384
Ile Ile  Asn Asn Thr Val Tyr  Asp Pro Leu Gln Pro  Glu Leu Asp
    1115                 1120                 1125

tca ttc  aaa gaa gag ctg gac  aag tac ttc aaa aat  cat aca tca      3429
Ser Phe  Lys Glu Glu Leu Asp  Lys Tyr Phe Lys Asn  His Thr Ser
    1130                 1135                 1140

cca gat  gtt gat ctt ggc gac  att tca ggc att aac  gct tct gtc      3474
Pro Asp  Val Asp Leu Gly Asp  Ile Ser Gly Ile Asn  Ala Ser Val
    1145                 1150                 1155
```

-continued

```
gtc aac  att caa aaa gaa att  gac cgc ctc aat gag  gtc gct aaa      3519
Val Asn  Ile Gln Lys Glu Ile  Asp Arg Leu Asn Glu  Val Ala Lys
    1160                 1165                 1170

aat tta  aat gaa tca ctc att  gac ctt caa gaa ttg  gga aaa tat      3564
Asn Leu  Asn Glu Ser Leu Ile  Asp Leu Gln Glu Leu  Gly Lys Tyr
    1175                 1180                 1185

gag caa  tat att aaa tgg cct  tgg tat gtt tgg ctc  ggc ttc att      3609
Glu Gln  Tyr Ile Lys Trp Pro  Trp Tyr Val Trp Leu  Gly Phe Ile
    1190                 1195                 1200

gct gga  cta att gcc atc gtc  atg gtt aca atc ttg  ctt tgt tgc      3654
Ala Gly  Leu Ile Ala Ile Val  Met Val Thr Ile Leu  Leu Cys Cys
    1205                 1210                 1215

atg act  agt tgt tgc agt tgc  ctc aag ggt gca tgc  tct tgt ggt      3699
Met Thr  Ser Cys Cys Ser Cys  Leu Lys Gly Ala Cys  Ser Cys Gly
    1220                 1225                 1230

tct tgc  tgc aag ttt gat gag  gat gac tct gag cca  gtt ctc aag      3744
Ser Cys  Cys Lys Phe Asp Glu  Asp Asp Ser Glu Pro  Val Leu Lys
    1235                 1240                 1245

ggt gtc  aaa tta cat tac aca  taa                                   3768
Gly Val  Lys Leu His Tyr Thr
    1250                 1255
```

<210> SEQ ID NO 13
<211> LENGTH: 1255
<212> TYPE: PRT
<213> ORGANISM: SARS coronavirus Urbani

<400> SEQUENCE: 13

```
Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
            20                  25                  30

His Thr Ser Ser Met Arg Gly Val Tyr Tyr Pro Asp Glu Ile Phe Arg
        35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
            100                 105                 110

Ser Val Ile Ile Ile Asn Asn Ser Thr Asn Val Val Ile Arg Ala Cys
        115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
            180                 185                 190

Phe Leu Tyr Val Tyr Lys Gly Tyr Gln Pro Ile Asp Val Val Arg Asp
        195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
```

-continued

```
225                 230                 235                 240

Ala Gln Asp Ile Trp Gly Thr Ser Ala Ala Ala Tyr Phe Val Gly Tyr
                245                 250                 255

Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
        275                 280                 285

Ser Val Lys Ser Phe Glu Ile Asp Lys Gly Ile Tyr Gln Thr Ser Asn
    290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Ala Thr Lys Phe Pro Ser
                325                 330                 335

Val Tyr Ala Trp Glu Arg Lys Lys Ile Ser Asn Cys Val Ala Asp Tyr
            340                 345                 350

Ser Val Leu Tyr Asn Ser Thr Phe Phe Ser Thr Phe Lys Cys Tyr Gly
        355                 360                 365

Val Ser Ala Thr Lys Leu Asn Asp Leu Cys Phe Ser Asn Val Tyr Ala
    370                 375                 380

Asp Ser Phe Val Val Lys Gly Asp Asp Val Arg Gln Ile Ala Pro Gly
385                 390                 395                 400

Gln Thr Gly Val Ile Ala Asp Tyr Asn Tyr Lys Leu Pro Asp Asp Phe
                405                 410                 415

Met Gly Cys Val Leu Ala Trp Asn Thr Arg Asn Ile Asp Ala Thr Ser
            420                 425                 430

Thr Gly Asn Tyr Asn Tyr Lys Tyr Arg Tyr Leu Arg His Gly Lys Leu
        435                 440                 445

Arg Pro Phe Glu Arg Asp Ile Ser Asn Val Pro Phe Ser Pro Asp Gly
    450                 455                 460

Lys Pro Cys Thr Pro Pro Ala Leu Asn Cys Tyr Trp Pro Leu Asn Asp
465                 470                 475                 480

Tyr Gly Phe Tyr Thr Thr Thr Gly Ile Gly Tyr Gln Pro Tyr Arg Val
                485                 490                 495

Val Val Leu Ser Phe Glu Leu Leu Asn Ala Pro Ala Thr Val Cys Gly
            500                 505                 510

Pro Lys Leu Ser Thr Asp Leu Ile Lys Asn Gln Cys Val Asn Phe Asn
        515                 520                 525

Phe Asn Gly Leu Thr Gly Thr Gly Val Leu Thr Pro Ser Ser Lys Arg
    530                 535                 540

Phe Gln Pro Phe Gln Gln Phe Gly Arg Asp Val Ser Asp Phe Thr Asp
545                 550                 555                 560

Ser Val Arg Asp Pro Lys Thr Ser Glu Ile Leu Asp Ile Ser Pro Cys
                565                 570                 575

Ser Phe Gly Gly Val Ser Val Ile Thr Pro Gly Thr Asn Ala Ser Ser
            580                 585                 590

Glu Val Ala Val Leu Tyr Gln Asp Val Asn Cys Thr Asp Val Ser Thr
        595                 600                 605

Ala Ile His Ala Asp Gln Leu Thr Pro Ala Trp Arg Ile Tyr Ser Thr
    610                 615                 620

Gly Asn Asn Val Phe Gln Thr Gln Ala Gly Cys Leu Ile Gly Ala Glu
625                 630                 635                 640

His Val Asp Thr Ser Tyr Glu Cys Asp Ile Pro Ile Gly Ala Gly Ile
                645                 650                 655
```

```
Cys Ala Ser Tyr His Thr Val Ser Leu Leu Arg Ser Thr Ser Gln Lys
            660                 665                 670

Ser Ile Val Ala Tyr Thr Met Ser Leu Gly Ala Asp Ser Ser Ile Ala
        675                 680                 685

Tyr Ser Asn Asn Thr Ile Ala Ile Pro Thr Asn Phe Ser Ile Ser Ile
    690                 695                 700

Thr Thr Glu Val Met Pro Val Ser Met Ala Lys Thr Ser Val Asp Cys
705                 710                 715                 720

Asn Met Tyr Ile Cys Gly Asp Ser Thr Glu Cys Ala Asn Leu Leu Leu
                725                 730                 735

Gln Tyr Gly Ser Phe Cys Thr Gln Leu Asn Arg Ala Leu Ser Gly Ile
            740                 745                 750

Ala Ala Glu Gln Asp Arg Asn Thr Arg Glu Val Phe Ala Gln Val Lys
        755                 760                 765

Gln Met Tyr Lys Thr Pro Thr Leu Lys Tyr Phe Gly Gly Phe Asn Phe
    770                 775                 780

Ser Gln Ile Leu Pro Asp Pro Leu Lys Pro Thr Lys Arg Ser Phe Ile
785                 790                 795                 800

Glu Asp Leu Leu Phe Asn Lys Val Thr Leu Ala Asp Ala Gly Phe Met
                805                 810                 815

Lys Gln Tyr Gly Glu Cys Leu Gly Asp Ile Asn Ala Arg Asp Leu Ile
            820                 825                 830

Cys Ala Gln Lys Phe Asn Gly Leu Thr Val Leu Pro Pro Leu Leu Thr
        835                 840                 845

Asp Asp Met Ile Ala Ala Tyr Thr Ala Ala Leu Val Ser Gly Thr Ala
    850                 855                 860

Thr Ala Gly Trp Thr Phe Gly Ala Gly Ala Ala Leu Gln Ile Pro Phe
865                 870                 875                 880

Ala Met Gln Met Ala Tyr Arg Phe Asn Gly Ile Gly Val Thr Gln Asn
                885                 890                 895

Val Leu Tyr Glu Asn Gln Lys Gln Ile Ala Asn Gln Phe Asn Lys Ala
            900                 905                 910

Ile Ser Gln Ile Gln Glu Ser Leu Thr Thr Thr Ser Thr Ala Leu Gly
        915                 920                 925

Lys Leu Gln Asp Val Val Asn Gln Asn Ala Gln Ala Leu Asn Thr Leu
    930                 935                 940

Val Lys Gln Leu Ser Ser Asn Phe Gly Ala Ile Ser Ser Val Leu Asn
945                 950                 955                 960

Asp Ile Leu Ser Arg Leu Asp Lys Val Glu Ala Glu Val Gln Ile Asp
                965                 970                 975

Arg Leu Ile Thr Gly Arg Leu Gln Ser Leu Gln Thr Tyr Val Thr Gln
            980                 985                 990

Gln Leu Ile Arg Ala Ala Glu Ile  Arg Ala Ser Ala Asn  Leu Ala Ala
        995                 1000                1005

Thr Lys  Met Ser Glu Cys Val  Leu Gly Gln Ser Lys  Arg Val Asp
    1010                1015                1020

Phe Cys  Gly Lys Gly Tyr His  Leu Met Ser Phe Pro  Gln Ala Ala
    1025                1030                1035

Pro His  Gly Val Val Phe Leu  His Val Thr Tyr Val  Pro Ser Gln
    1040                1045                1050

Glu Arg  Asn Phe Thr Thr Ala  Pro Ala Ile Cys His  Glu Gly Lys
    1055                1060                1065
```

```
Ala Tyr  Phe Pro Arg Glu Gly  Val Phe Val Phe Asn  Gly Thr Ser
    1070                 1075                 1080

Trp Phe  Ile Thr Gln Arg Asn  Phe Phe Ser Pro Gln  Ile Ile Thr
    1085                 1090                 1095

Thr Asp  Asn Thr Phe Val Ser  Gly Asn Cys Asp Val  Val Ile Gly
    1100                 1105                 1110

Ile Ile  Asn Asn Thr Val Tyr  Asp Pro Leu Gln Pro  Glu Leu Asp
    1115                 1120                 1125

Ser Phe  Lys Glu Glu Leu Asp  Lys Tyr Phe Lys Asn  His Thr Ser
    1130                 1135                 1140

Pro Asp  Val Asp Leu Gly Asp  Ile Ser Gly Ile Asn  Ala Ser Val
    1145                 1150                 1155

Val Asn  Ile Gln Lys Glu Ile  Asp Arg Leu Asn Glu  Val Ala Lys
    1160                 1165                 1170

Asn Leu  Asn Glu Ser Leu Ile  Asp Leu Gln Glu Leu  Gly Lys Tyr
    1175                 1180                 1185

Glu Gln  Tyr Ile Lys Trp Pro  Trp Tyr Val Trp Leu  Gly Phe Ile
    1190                 1195                 1200

Ala Gly  Leu Ile Ala Ile Val  Met Val Thr Ile Leu  Leu Cys Cys
    1205                 1210                 1215

Met Thr  Ser Cys Cys Ser Cys  Leu Lys Gly Ala Cys  Ser Cys Gly
    1220                 1225                 1230

Ser Cys  Cys Lys Phe Asp Glu  Asp Asp Ser Glu Pro  Val Leu Lys
    1235                 1240                 1245

Gly Val  Lys Leu His Tyr Thr
    1250                 1255
```

<210> SEQ ID NO 14
<211> LENGTH: 3768
<212> TYPE: DNA
<213> ORGANISM: Artificial
<220> FEATURE:
<223> OTHER INFORMATION: deoptimized SARS spike glycoprotein nucleic acid sequence

<400> SEQUENCE: 14

```
atgtttatct tcctgctgtt tctgacgctg acgtcggggt cggacctgga ccggtgcacg     60

acgtttgatg atgtccaagc gccgaattac acgcaacata cgtcgtcgat gcggggggtc    120

tactatccgg atgaaatctt tcggtcggac acgctgtatc tgacgcagga tctgtttctg    180

ccgttttatt cgaatgtcac ggggtttcat acgatcaatc atacgtttgg gaacccggtc    240

atcccgttta aggatgggat ctattttgcg gcgacggaga aatcgaatgt cgtccggggg    300

tgggtctttg ggtcgacgat gaacaacaag tcgcagtcgg tcatcatcat caacaattcg    360

acgaatgtcg tcatccgggc gtgtaacttt gaactgtgtg acaacccgtt ctttgcggtc    420

tcgaaaccga tggggacgca gacgcatacg atgatcttcg ataatgcgtt taattgcacg    480

ttcgagtaca tctcggatgc gttttcgctg gatgtctcgg aaaagtcggg gaattttaaa    540

cacctgcggg agtttgtctt taaaaataaa gatgggtttc tgtatgtcta taaggggtat    600

caaccgatcg atgtcgtccg ggatctgccg tcggggttta acacgctgaa accgatcttt    660

aagctgccgc tggggatcaa catcacgaat tttcgggcga tcctgacggc gttttcgccg    720

gcgcaagaca tctgggggac gtcggcggcg gcgtattttg tcgggtatct gaagccgacg    780

acgtttatgc tgaagtatga tgaaaatggg acgatcacgg atgcggtcga ttgttcgcaa    840

aatccgctgg cggaactgaa atgctcggtc aagtcgtttg agatcgacaa agggatctac    900
```

-continued

```
cagacgtcga atttccgggt cgtcccgtcg ggggatgtcg tccggttccc gaatatcacg    960
aacctgtgtc cgtttgggga ggtctttaat gcgacgaaat tcccgtcggt ctatgcgtgg   1020
gagcggaaaa aaatctcgaa ttgtgtcgcg gattactcgg tcctgtacaa ctcgacgttt   1080
ttttcgacgt ttaagtgcta tggggtctcg gcgacgaagc tgaatgatct gtgcttctcg   1140
aatgtctatg cggattcgtt tgtcgtcaag ggggatgatg tccggcaaat cgcgccgggg   1200
caaacggggg tcatcgcgga ttataattat aaactgccgg atgatttcat ggggtgtgtc   1260
ctggcgtgga atacgcggaa catcgatgcg acgtcgacgg ggaattataa ttataaatat   1320
cggtatctgc ggcatgggaa gctgcggccg tttgagcggg acatctcgaa tgtcccgttc   1380
tcgccggatg ggaaaccgtg cacgccgccg gcgctgaatt gttattggcc gctgaatgat   1440
tatgggtttt acacgacgac ggggatcggg taccaaccgt accgggtcgt cgtcctgtcg   1500
tttgaactgc tgaatgcgcc ggcgacggtc tgtgggccga aactgtcgac ggacctgatc   1560
aagaaccagt gtgtcaattt taattttaat gggctgacgg ggacgggggt cctgacgccg   1620
tcgtcgaagc ggtttcaacc gtttcaacaa tttgggcggg atgtctcgga tttcacggat   1680
tcggtccggg atccgaaaac gtcggaaatc ctggacatct cgccgtgctc gtttgggggg   1740
gtctcggtca tcacgccggg gacgaatgcg tcgtcggaag tcgcggtcct gtatcaagat   1800
gtcaactgca cggatgtctc gacggcgatc catgcggatc aactgacgcc ggcgtggcgg   1860
atctattcga cggggaacaa tgtcttccag acgcaagcgg ggtgtctgat cggggcggag   1920
catgtcgaca cgtcgtatga gtgcgacatc ccgatcgggg cggggatctg tgcgtcgtac   1980
catacggtct cgctgctgcg gtcgacgtcg caaaaatcga tcgtcgcgta tacgatgtcg   2040
ctgggggcgg attcgtcgat cgcgtactcg aataacacga tcgcgatccc gacgaacttt   2100
tcgatctcga tcacgacgga agtcatgccg gtctcgatgg cgaaaacgtc ggtcgattgt   2160
aatatgtaca tctgcgggga ttcgacggaa tgtgcgaatc tgctgctgca atatgggtcg   2220
ttttgcacgc aactgaatcg ggcgctgtcg gggatcgcgg cggaacagga tcggaacacg   2280
cgggaagtct tcgcgcaagt caaacaaatg tacaaaacgc cgacgctgaa atattttggg   2340
gggtttaatt tttcgcaaat cctgccggac ccgctgaagc cgacgaagcg gtcgtttatc   2400
gaggacctgc tgtttaataa ggtcacgctg gcggatgcgg ggttcatgaa gcaatatggg   2460
gaatgcctgg gggatatcaa tgcgcgggat ctgatctgtg cgcagaagtt caatgggctg   2520
acggtcctgc cgccgctgct gacggatgat atgatcgcgg cgtacacggc ggcgctggtc   2580
tcggggacgg cgacggcggg gtggacgttt ggggcggggg cggcgctgca aatcccgttt   2640
gcgatgcaaa tggcgtatcg gttcaatggg atcggggtca cgcaaaatgt cctgtatgag   2700
aaccaaaaac aaatcgcgaa ccaatttaac aaggcgatct cgcaaatcca agaatcgctg   2760
acgacgacgt cgacggcgct ggggaagctg caagacgtcg tcaaccagaa tgcgcaagcg   2820
ctgaacacgc tggtcaaaca actgtcgtcg aattttgggg cgatctcgtc ggtcctgaat   2880
gatatcctgt cgcggctgga taaagtcgag gcggaggtcc aaatcgaccg gctgatcacg   2940
gggcggctgc aatcgctgca aacgtatgtc acgcaacaac tgatccgggc ggcggaaatc   3000
cgggcgtcgg cgaatctggc ggcgacgaaa atgtcggagt gtgtcctggg gcaatcgaaa   3060
cgggtcgact tttgtgggaa ggggtaccac ctgatgtcgt tcccgcaagc ggcgccgcat   3120
ggggtcgtct tcctgcatgt cacgtatgtc ccgtcgcagg agcggaactt cacgacggcg   3180
ccggcgatct gtcatgaagg gaaagcgtac ttcccgcggg aaggggtctt tgtctttaat   3240
```

```
gggacgtcgt ggtttatcac gcagcggaac ttcttttcgc cgcaaatcat cacgacggac   3300

aatacgtttg tctcggggaa ttgtgatgtc gtcatcggga tcatcaacaa cacggtctat   3360

gatccgctgc aaccggagct ggactcgttc aaagaagagc tggacaagta cttcaaaaat   3420

catacgtcgc cggatgtcga tctgggggac atctcgggga tcaacgcgtc ggtcgtcaac   3480

atccaaaaag aaatcgaccg gctgaatgag gtcgcgaaaa atctgaatga atcgctgatc   3540

gacctgcaag aactggggaa atatgagcaa tatatcaaat ggccgtggta tgtctggctg   3600

gggttcatcg cggggctgat cgcgatcgtc atggtcacga tcctgctgtg ttgcatgacg   3660

tcgtgttgct cgtgcctgaa gggggcgtgc tcgtgtgggt cgtgctgcaa gtttgatgag   3720

gatgactcgg agccggtcct gaagggggtc aaactgcatt acacgtaa               3768
```

```
<210> SEQ ID NO 15
<211> LENGTH: 9762
<212> TYPE: DNA
<213> ORGANISM: Rubella virus
<220> FEATURE:
<221> NAME/KEY: CDS
<222> LOCATION: (41)..(6391)
<220> FEATURE:
<221> NAME/KEY: CDS
<222> LOCATION: (6512)..(9703)

<400> SEQUENCE: 15

caatgggagc tatcggacct cgcttaggac tcctattccc atg gag aga ctc cta       55
                                          Met Glu Arg Leu Leu
                                          1               5

gat gag gtt ctt gcc ccc ggt ggg cct tat aac tta acc gtc ggc agt      103
Asp Glu Val Leu Ala Pro Gly Gly Pro Tyr Asn Leu Thr Val Gly Ser
                10                  15                  20

tgg gta aga gac cac gtc cgc tca att gtc gag ggc gcg tgg gaa gtg      151
Trp Val Arg Asp His Val Arg Ser Ile Val Glu Gly Ala Trp Glu Val
            25                  30                  35

cgc gat gtt gtt tcc gct gcc caa aag cgg gcc atc gta gcc gtg ata      199
Arg Asp Val Val Ser Ala Ala Gln Lys Arg Ala Ile Val Ala Val Ile
        40                  45                  50

ccc aga cct gtg ttc acg cag atg cag gtc agt gat cac cca gca ctc      247
Pro Arg Pro Val Phe Thr Gln Met Gln Val Ser Asp His Pro Ala Leu
    55                  60                  65

cac gca att tcg cgg tat acc cgc cgc cat tgg atc gag tgg ggc cct      295
His Ala Ile Ser Arg Tyr Thr Arg Arg His Trp Ile Glu Trp Gly Pro
70                  75                  80                  85

aaa gaa gcc cta cac gtc ctc atc gac cca agc ccg ggc ctg ctc cgc      343
Lys Glu Ala Leu His Val Leu Ile Asp Pro Ser Pro Gly Leu Leu Arg
                90                  95                  100

gag gtc gct cgc gtt gag cgc cgc tgg gtc gca ctg tgc ctc cac agg      391
Glu Val Ala Arg Val Glu Arg Arg Trp Val Ala Leu Cys Leu His Arg
            105                 110                 115

acg gca cgc aaa ctc gcc acc gcc ctg gcc gag acg gcc agc gag gcg      439
Thr Ala Arg Lys Leu Ala Thr Ala Leu Ala Glu Thr Ala Ser Glu Ala
        120                 125                 130

tgg cac gct gac tac gtg tgc gcg ctg cgt ggc gca ccg agc ggc ccc      487
Trp His Ala Asp Tyr Val Cys Ala Leu Arg Gly Ala Pro Ser Gly Pro
    135                 140                 145

ttc tac gtc cac cct gag gac gtc ccg cac ggc ggt cgc gcc gtg gcg      535
Phe Tyr Val His Pro Glu Asp Val Pro His Gly Gly Arg Ala Val Ala
150                 155                 160                 165

gac aga tgc ttg ctc tac tac aca ccc atg cag atg tgc gag ctg atg      583
Asp Arg Cys Leu Leu Tyr Tyr Thr Pro Met Gln Met Cys Glu Leu Met
                170                 175                 180
```

-continued

```
cgt acc att gac gcc acc ctg ctc gtg gcg gtc gac ttg tgg ccg gtc      631
Arg Thr Ile Asp Ala Thr Leu Leu Val Ala Val Asp Leu Trp Pro Val
            185                 190                 195

gcc ctt gcg gcc cac gtc ggc gac gac tgg gac gac ctg ggc att gcc      679
Ala Leu Ala Ala His Val Gly Asp Asp Trp Asp Asp Leu Gly Ile Ala
        200                 205                 210

tgg cat ctc gac cat gac ggc ggt tgc ccc gcc gat tgc cgc gga gcc      727
Trp His Leu Asp His Asp Gly Gly Cys Pro Ala Asp Cys Arg Gly Ala
    215                 220                 225

ggc gct ggg ccc acg ccc ggc tac acc cgc ccc tgc acc aca cgc atc      775
Gly Ala Gly Pro Thr Pro Gly Tyr Thr Arg Pro Cys Thr Thr Arg Ile
230                 235                 240                 245

tac caa gtc ctg ccg gac acc gcc cac ccc ggg cgc ctc tac cgg tgc      823
Tyr Gln Val Leu Pro Asp Thr Ala His Pro Gly Arg Leu Tyr Arg Cys
                250                 255                 260

ggg ccc cgc ctg tgg acg cgc gat tgc gcc gtg gcc gaa ctc tca tgg      871
Gly Pro Arg Leu Trp Thr Arg Asp Cys Ala Val Ala Glu Leu Ser Trp
            265                 270                 275

gag gtt gcc caa cac tgc ggg cac cag gcg cgc gtg cgc gcc gtg cgg      919
Glu Val Ala Gln His Cys Gly His Gln Ala Arg Val Arg Ala Val Arg
        280                 285                 290

tgc acc ctc cct atc cgc cac gtg cgc agc ctc caa ccc agc gcg cgg      967
Cys Thr Leu Pro Ile Arg His Val Arg Ser Leu Gln Pro Ser Ala Arg
    295                 300                 305

gtc cga ctc ccg gac ctc gtc cat ctc gcc gag gtg ggc cgg tgg cgg     1015
Val Arg Leu Pro Asp Leu Val His Leu Ala Glu Val Gly Arg Trp Arg
310                 315                 320                 325

tgg ttc agc ctc ccc cgc ccc gtg ttc cag cgc atg ctg tcc tac tgc     1063
Trp Phe Ser Leu Pro Arg Pro Val Phe Gln Arg Met Leu Ser Tyr Cys
                330                 335                 340

aag acc ctg agc ccc gac gcg tac tac agc gag cgc gtg ttc aag ttc     1111
Lys Thr Leu Ser Pro Asp Ala Tyr Tyr Ser Glu Arg Val Phe Lys Phe
            345                 350                 355

aag aac gcc ctg agc cac agc atc acg ctc gcg ggc aat gtg ctg caa     1159
Lys Asn Ala Leu Ser His Ser Ile Thr Leu Ala Gly Asn Val Leu Gln
        360                 365                 370

gag ggg tgg aag ggc acg tgc gcc gag gaa gac gcg ctg tgc gca tac     1207
Glu Gly Trp Lys Gly Thr Cys Ala Glu Glu Asp Ala Leu Cys Ala Tyr
    375                 380                 385

gta gcc ttc cgc gcg tgg cag tct aac gcc agg ttg gcg ggg att atg     1255
Val Ala Phe Arg Ala Trp Gln Ser Asn Ala Arg Leu Ala Gly Ile Met
390                 395                 400                 405

aaa agc gcg aag cgc tgc gcc gcc gac tct ttg agc gtg gcc ggc tgg     1303
Lys Ser Ala Lys Arg Cys Ala Ala Asp Ser Leu Ser Val Ala Gly Trp
                410                 415                 420

ctg gac acc att tgg ggc gcc att aag cgg ttc ttc ggc agc gtg ccc     1351
Leu Asp Thr Ile Trp Gly Ala Ile Lys Arg Phe Phe Gly Ser Val Pro
            425                 430                 435

ctc gcc gag cgc atg gag gag tgg gaa cag gac gcc gcg gtc gcc gcc     1399
Leu Ala Glu Arg Met Glu Glu Trp Glu Gln Asp Ala Ala Val Ala Ala
        440                 445                 450

ttc gac cgc ggc ccc ctc gag gac ggc ggg cgc cac ttg gac acc gtg     1447
Phe Asp Arg Gly Pro Leu Glu Asp Gly Gly Arg His Leu Asp Thr Val
    455                 460                 465

caa ccc cca aaa tcg ccg ccc cgc cct gag atc gcc gcg acc tgg atc     1495
Gln Pro Pro Lys Ser Pro Pro Arg Pro Glu Ile Ala Ala Thr Trp Ile
470                 475                 480                 485

gtc cac gca gcc agc gca gac cgc cat tgt gcg tgc gct ccc cgc tgc     1543
Val His Ala Ala Ser Ala Asp Arg His Cys Ala Cys Ala Pro Arg Cys
```

```
                490                 495                 500

gac gtc ccg cgc gaa cgt cct tcc gcg ccc gcc ggc ccg ccg gat gac      1591
Asp Val Pro Arg Glu Arg Pro Ser Ala Pro Ala Gly Pro Pro Asp Asp
            505                 510                 515

gag gcg ctc atc ccg ccg tgg ctg ttc gcc gag cac cgt gcc ctc cgc      1639
Glu Ala Leu Ile Pro Pro Trp Leu Phe Ala Glu His Arg Ala Leu Arg
        520                 525                 530

tgc cgc gag tgg gat ttc gag gtt ctc cgc gcg cgc gcc gat acg gcg      1687
Cys Arg Glu Trp Asp Phe Glu Val Leu Arg Ala Arg Ala Asp Thr Ala
    535                 540                 545

gcc gcg ccc gcc ccg ctg gct cca cgc cct gcg cgg tac ccc acc gtg      1735
Ala Ala Pro Ala Pro Leu Ala Pro Arg Pro Ala Arg Tyr Pro Thr Val
550                 555                 560                 565

ctc tac cgc cac ccc gcc cac cac ggt ccg tgg ctc acc ctt gac gag      1783
Leu Tyr Arg His Pro Ala His His Gly Pro Trp Leu Thr Leu Asp Glu
                570                 575                 580

ccg ggc gag gct gac gcg gcc ctg gtc cta tgc gac cca ctt ggc cag      1831
Pro Gly Glu Ala Asp Ala Ala Leu Val Leu Cys Asp Pro Leu Gly Gln
            585                 590                 595

ccg ctc cgg ggc cct gaa cgc cac ttc gcc gcc ggc gcg cat atg tgc      1879
Pro Leu Arg Gly Pro Glu Arg His Phe Ala Ala Gly Ala His Met Cys
        600                 605                 610

gcg cag gcg cgg ggg ctc cag gct ttt gtc cgt gtc gtg cct cca ccc      1927
Ala Gln Ala Arg Gly Leu Gln Ala Phe Val Arg Val Val Pro Pro Pro
    615                 620                 625

gag cgc ccc tgg gcc gac ggg ggc gcc aga gcg tgg gcg aag ttc ttc      1975
Glu Arg Pro Trp Ala Asp Gly Gly Ala Arg Ala Trp Ala Lys Phe Phe
630                 635                 640                 645

cgc ggc tgc gcc tgg gcg cag cgc ttg ctc ggc gag cca gca gtt atg      2023
Arg Gly Cys Ala Trp Ala Gln Arg Leu Leu Gly Glu Pro Ala Val Met
                650                 655                 660

cac ctc cca tac acc gat ggc gac gtg cca cag ctg atc gca ctg gct      2071
His Leu Pro Tyr Thr Asp Gly Asp Val Pro Gln Leu Ile Ala Leu Ala
            665                 670                 675

ttg cgc acg ctg gcc caa cag ggg gcc gcc ttg gca ctc tcg gtg cgt      2119
Leu Arg Thr Leu Ala Gln Gln Gly Ala Ala Leu Ala Leu Ser Val Arg
        680                 685                 690

gac ctg ccc ggg ggt gca gcg ttc gac gca aac gcg gtc acc gcc gcc      2167
Asp Leu Pro Gly Gly Ala Ala Phe Asp Ala Asn Ala Val Thr Ala Ala
    695                 700                 705

gtg cgc gct ggc ccc ggc cag tcc gcg gcc acg tca tcg cca ccc ggc      2215
Val Arg Ala Gly Pro Gly Gln Ser Ala Ala Thr Ser Ser Pro Pro Gly
710                 715                 720                 725

gac ccc ccg ccg ccg cgc tgc gca cgg cga tcg caa cgg cac tcg gac      2263
Asp Pro Pro Pro Pro Arg Cys Ala Arg Arg Ser Gln Arg His Ser Asp
                730                 735                 740

gcc cgc ggc act ccg ccc ccc gcg cct gcg cgc gac ccg ccg ccg ccc      2311
Ala Arg Gly Thr Pro Pro Pro Ala Pro Ala Arg Asp Pro Pro Pro Pro
            745                 750                 755

gcc ccc agc ccg ccc gcg cca ccc cgc gcg ggt gac ccg gtc cct ccc      2359
Ala Pro Ser Pro Pro Ala Pro Pro Arg Ala Gly Asp Pro Val Pro Pro
        760                 765                 770

act tcc gcg ggg ccg gcg gat cgc gcg cgt gac gcc gag ctg gag gtc      2407
Thr Ser Ala Gly Pro Ala Asp Arg Ala Arg Asp Ala Glu Leu Glu Val
    775                 780                 785

gcc tac gaa ccg agc ggc ccc ccc acg tca acc aag gca gac cca gac      2455
Ala Tyr Glu Pro Ser Gly Pro Pro Thr Ser Thr Lys Ala Asp Pro Asp
790                 795                 800                 805

agc gac atc gtt gaa agt tac gcc cgc gcc gcc gga ccc gtg cac ctc      2503
```

-continued

```
Ser Asp Ile Val Glu Ser Tyr Ala Arg Ala Ala Gly Pro Val His Leu
                810                 815                 820

cga gtc cgc gac atc atg gac cca ccg ccc ggc tgc aag gtc gtg gtc      2551
Arg Val Arg Asp Ile Met Asp Pro Pro Pro Gly Cys Lys Val Val Val
            825                 830                 835

aac gcc gcc aac gag ggg ctg ctg gcc ggc tct ggc gtg tgc ggt gcc      2599
Asn Ala Ala Asn Glu Gly Leu Leu Ala Gly Ser Gly Val Cys Gly Ala
        840                 845                 850

atc ttt gcc aac gcc acg gcg gcc ctc gct gca gac tgc cgg cgc ctc      2647
Ile Phe Ala Asn Ala Thr Ala Ala Leu Ala Ala Asp Cys Arg Arg Leu
    855                 860                 865

gcc cca tgc ccc acc ggc gag gca gtg gcg aca ccc ggc cac ggc tgc      2695
Ala Pro Cys Pro Thr Gly Glu Ala Val Ala Thr Pro Gly His Gly Cys
870                 875                 880                 885

ggg tac acc cac atc atc cac gcc gtc gcg ccg cgg cgt cct cgg gac      2743
Gly Tyr Thr His Ile Ile His Ala Val Ala Pro Arg Arg Pro Arg Asp
                890                 895                 900

ccc gcc gcc ctc gag gag ggc gaa gcg ctg ctc gag cgc gcc tac cgc      2791
Pro Ala Ala Leu Glu Glu Gly Glu Ala Leu Leu Glu Arg Ala Tyr Arg
            905                 910                 915

agc atc gtc gcg cta gcc gcc gcg cgt cgg tgg gcg cgt gtc gcg tgc      2839
Ser Ile Val Ala Leu Ala Ala Ala Arg Arg Trp Ala Arg Val Ala Cys
        920                 925                 930

ccc ctc ctc ggc gct ggc gtc tac ggc tgg tct gct gcg gag tcc ctc      2887
Pro Leu Leu Gly Ala Gly Val Tyr Gly Trp Ser Ala Ala Glu Ser Leu
    935                 940                 945

cga gcc gcg ctc gcg gct acg cgc acc gag ccc gcc gag cgc gtg agc      2935
Arg Ala Ala Leu Ala Ala Thr Arg Thr Glu Pro Ala Glu Arg Val Ser
950                 955                 960                 965

ctg cac atc tgc cat ccc gac cgc gcc acg ctg acg cac gcc tcc gtg      2983
Leu His Ile Cys His Pro Asp Arg Ala Thr Leu Thr His Ala Ser Val
                970                 975                 980

ctc gtc ggc gcg ggg ctc gct gcc agg cgc gtc agt cct cct ccg acc      3031
Leu Val Gly Ala Gly Leu Ala Ala Arg Arg Val Ser Pro Pro Pro Thr
            985                 990                 995

gag ccc ctc  gca tct tgc ccc gcc  ggt gac ccg ggc cga  ccg gct      3076
Glu Pro Leu  Ala Ser Cys Pro Ala  Gly Asp Pro Gly Arg  Pro Ala
        1000                 1005                 1010

cag cgc agc  gcg tcg ccc cca gcg  acc ccc ctt ggg gat  gcc acc      3121
Gln Arg Ser  Ala Ser Pro Pro Ala  Thr Pro Leu Gly Asp  Ala Thr
        1015                 1020                 1025

gcg ccc gag  ccc cgc gga tgc cag  ggg tgc gaa ctc tgc  cgg tac      3166
Ala Pro Glu  Pro Arg Gly Cys Gln  Gly Cys Glu Leu Cys  Arg Tyr
        1030                 1035                 1040

acg cgc gtc  acc aat gac cgc gcc  tat gtc aac ctg tgg  ctc gag      3211
Thr Arg Val  Thr Asn Asp Arg Ala  Tyr Val Asn Leu Trp  Leu Glu
        1045                 1050                 1055

cgc gac cgc  ggc gcc acc agc tgg  gcc atg cgc att ccc  gag gtg      3256
Arg Asp Arg  Gly Ala Thr Ser Trp  Ala Met Arg Ile Pro  Glu Val
        1060                 1065                 1070

gtt gtc tac  ggg ccg gag cac ctc  gcc acg cat ttt cca  tta aac      3301
Val Val Tyr  Gly Pro Glu His Leu  Ala Thr His Phe Pro  Leu Asn
        1075                 1080                 1085

cac tac agt  gtg ctc aag ccc gcg  gag gtc agg ccc ccg  cga ggc      3346
His Tyr Ser  Val Leu Lys Pro Ala  Glu Val Arg Pro Pro  Arg Gly
        1090                 1095                 1100

atg tgc ggg  agt gac atg tgg cgc  tgc cgc ggc tgg cag  ggc gtg      3391
Met Cys Gly  Ser Asp Met Trp Arg  Cys Arg Gly Trp Gln  Gly Val
        1105                 1110                 1115
```

-continued

```
ccg cag gtg  cgg tgc acc ccc tcc  aac gct cac gcc gcc  ctg tgc      3436
Pro Gln Val  Arg Cys Thr Pro Ser  Asn Ala His Ala Ala  Leu Cys
        1120                 1125                 1130

cgc aca ggc  gtg ccc cct cgg gtg  agc acg cga ggc ggc  gag cta      3481
Arg Thr Gly  Val Pro Pro Arg Val  Ser Thr Arg Gly Gly  Glu Leu
        1135                 1140                 1145

gac cca aac  acc tgc tgg ctc cgc  gcc gcc gcc aac gtt  gcg cag      3526
Asp Pro Asn  Thr Cys Trp Leu Arg  Ala Ala Ala Asn Val  Ala Gln
        1150                 1155                 1160

gct gcg cgc  gcc tgc ggc gcc tac  acg agt gcc ggg tgc  ccc agg      3571
Ala Ala Arg  Ala Cys Gly Ala Tyr  Thr Ser Ala Gly Cys  Pro Arg
        1165                 1170                 1175

tgc gcc tac  ggc cgc gcc ctg agc  gaa gcc cgc act cat  aag gac      3616
Cys Ala Tyr  Gly Arg Ala Leu Ser  Glu Ala Arg Thr His  Lys Asp
        1180                 1185                 1190

ttc gcc gcg  ctg agc cag cgg tgg  agc gcg agc cac gcc  gat gcc      3661
Phe Ala Ala  Leu Ser Gln Arg Trp  Ser Ala Ser His Ala  Asp Ala
        1195                 1200                 1205

tcc tct gac  ggc acc gga gat ccc  ctc gac ccc ctg atg  gag acc      3706
Ser Ser Asp  Gly Thr Gly Asp Pro  Leu Asp Pro Leu Met  Glu Thr
        1210                 1215                 1220

gtg gga tgc  gcc tgt tcg cgc gtg  tgg gtc ggc tcc gag  cac gag      3751
Val Gly Cys  Ala Cys Ser Arg Val  Trp Val Gly Ser Glu  His Glu
        1225                 1230                 1235

gcc ccg ccc  gac cac ctc ctg gtg  tcc ctc cac cgt gcc  cca aat      3796
Ala Pro Pro  Asp His Leu Leu Val  Ser Leu His Arg Ala  Pro Asn
        1240                 1245                 1250

ggt ccg tgg  ggc gta gtg ctc gag  gtg cgt gcg cgc ccc  gag ggg      3841
Gly Pro Trp  Gly Val Val Leu Glu  Val Arg Ala Arg Pro  Glu Gly
        1255                 1260                 1265

ggc aac ccc  acc ggc cac ttc gtc  tgc gcg gtc ggc ggc  ggc cca      3886
Gly Asn Pro  Thr Gly His Phe Val  Cys Ala Val Gly Gly  Gly Pro
        1270                 1275                 1280

cgc cgc gtc  tcg gac cgc ccc cac  ctt tgg ctc gcg gtc  ccc ctg      3931
Arg Arg Val  Ser Asp Arg Pro His  Leu Trp Leu Ala Val  Pro Leu
        1285                 1290                 1295

tct cgg ggc  ggt ggc acc tgt gcc  gcg acc gac gag ggg  ctg gcc      3976
Ser Arg Gly  Gly Gly Thr Cys Ala  Ala Thr Asp Glu Gly  Leu Ala
        1300                 1305                 1310

cag gcg tac  tac gac gac ctc gag  gtg cgc cgc ctc ggg  gat gac      4021
Gln Ala Tyr  Tyr Asp Asp Leu Glu  Val Arg Arg Leu Gly  Asp Asp
        1315                 1320                 1325

gcc atg gcc  cgg gcg gcc ctc gca  tca gtc caa cgc cct  cgc aaa      4066
Ala Met Ala  Arg Ala Ala Leu Ala  Ser Val Gln Arg Pro  Arg Lys
        1330                 1335                 1340

ggc cct tac  aat atc agg gta tgg  aac atg gcc gca ggc  gct ggc      4111
Gly Pro Tyr  Asn Ile Arg Val Trp  Asn Met Ala Ala Gly  Ala Gly
        1345                 1350                 1355

aag acc acc  cgc atc ctc gct gcc  ttc acg cgc gaa gac  ctt tac      4156
Lys Thr Thr  Arg Ile Leu Ala Ala  Phe Thr Arg Glu Asp  Leu Tyr
        1360                 1365                 1370

gtc tgc ccc  acc aat gcg ctc ctg  cac gag atc cag gcc  aaa ctc      4201
Val Cys Pro  Thr Asn Ala Leu Leu  His Glu Ile Gln Ala  Lys Leu
        1375                 1380                 1385

cgc gcg cgc  gat atc gag atc aag  aac gcc gcc acc tac  gag cgc      4246
Arg Ala Arg  Asp Ile Glu Ile Lys  Asn Ala Ala Thr Tyr  Glu Arg
        1390                 1395                 1400

gcg ctg acg  aaa ccg ctc gcc gcc  tac cgc cgc atc tac  atc gat      4291
Ala Leu Thr  Lys Pro Leu Ala Ala  Tyr Arg Arg Ile Tyr  Ile Asp
        1405                 1410                 1415
```

-continued

```
gag gcg ttc  act ctc ggc ggc gag  tac tgc gcg ttc gtt  gcc agc      4336
Glu Ala Phe  Thr Leu Gly Gly Glu  Tyr Cys Ala Phe Val  Ala Ser
        1420                 1425                 1430

caa acc acc  gcg gag gtg atc tgc  gtc ggt gat cgg gac  cag tgc      4381
Gln Thr Thr  Ala Glu Val Ile Cys  Val Gly Asp Arg Asp  Gln Cys
        1435                 1440                 1445

ggc cca cac  tac gcc aat aac tgc  cgc acc ccc gtc cct  gac cgc      4426
Gly Pro His  Tyr Ala Asn Asn Cys  Arg Thr Pro Val Pro  Asp Arg
        1450                 1455                 1460

tgg cct acc  gag cgc tcg cgc cac  act tgg cgc ttc ccc  gac tgc      4471
Trp Pro Thr  Glu Arg Ser Arg His  Thr Trp Arg Phe Pro  Asp Cys
        1465                 1470                 1475

tgg gcg gcc  cgc ctg cgc gcg ggg  ctc gat tat gac atc  gag ggc      4516
Trp Ala Ala  Arg Leu Arg Ala Gly  Leu Asp Tyr Asp Ile  Glu Gly
        1480                 1485                 1490

gag cgc acc  ggc acc ttc gcc tgc  aac ctt tgg gac ggc  cgc cag      4561
Glu Arg Thr  Gly Thr Phe Ala Cys  Asn Leu Trp Asp Gly  Arg Gln
        1495                 1500                 1505

gtc gac ctt  cac ctc gcc ttc tcg  cgc gaa acc gtg cgc  cgc ctt      4606
Val Asp Leu  His Leu Ala Phe Ser  Arg Glu Thr Val Arg  Arg Leu
        1510                 1515                 1520

cac gag gct  ggc ata cgc gca tac  acc gtg cgc gag gcc  cag ggt      4651
His Glu Ala  Gly Ile Arg Ala Tyr  Thr Val Arg Glu Ala  Gln Gly
        1525                 1530                 1535

atg agc gtc  ggc acc gcc tgc atc  cat gta ggc aga gac  ggc acc      4696
Met Ser Val  Gly Thr Ala Cys Ile  His Val Gly Arg Asp  Gly Thr
        1540                 1545                 1550

gac gtt gcc  ctg gcg ctg aca cgc  gac ctc gcc atc gtc  agc ctg      4741
Asp Val Ala  Leu Ala Leu Thr Arg  Asp Leu Ala Ile Val  Ser Leu
        1555                 1560                 1565

acc cgg gcc  tcc gac gca ctc tac  ctc cac gag ctc gag  gac ggc      4786
Thr Arg Ala  Ser Asp Ala Leu Tyr  Leu His Glu Leu Glu  Asp Gly
        1570                 1575                 1580

tca ctg cgc  gct gcg ggg ctc agc  gcg ttc ctc gac gcc  ggg gca      4831
Ser Leu Arg  Ala Ala Gly Leu Ser  Ala Phe Leu Asp Ala  Gly Ala
        1585                 1590                 1595

ctg gcg gag  ctc aag gag gtt ccc  gct ggc att gac cgc  gtt gtc      4876
Leu Ala Glu  Leu Lys Glu Val Pro  Ala Gly Ile Asp Arg  Val Val
        1600                 1605                 1610

gcc gtc gag  cag gca cca cca ccg  ttg ccg ccc gcc gac  ggc atc      4921
Ala Val Glu  Gln Ala Pro Pro Pro  Leu Pro Pro Ala Asp  Gly Ile
        1615                 1620                 1625

ccc gag gcc  caa gac gtg ccg ccc  ttc tgc ccc cgc act  ctg gag      4966
Pro Glu Ala  Gln Asp Val Pro Pro  Phe Cys Pro Arg Thr  Leu Glu
        1630                 1635                 1640

gag ctc gtc  ttc ggc cgt gcc ggc  cac ccc cat tac gcg  gac ctc      5011
Glu Leu Val  Phe Gly Arg Ala Gly  His Pro His Tyr Ala  Asp Leu
        1645                 1650                 1655

aac cgc gtg  act gag ggc gaa cga  gaa gtg cgg tat atg  cgc atc      5056
Asn Arg Val  Thr Glu Gly Glu Arg  Glu Val Arg Tyr Met  Arg Ile
        1660                 1665                 1670

tcg cgt cac  ctg ctc aac aag aat  cac acc gag atg ccc  gga acg      5101
Ser Arg His  Leu Leu Asn Lys Asn  His Thr Glu Met Pro  Gly Thr
        1675                 1680                 1685

gaa cgc gtt  ctc agt gcc gtt tgc  gcc gtg cgg cgc tac  cgc gcg      5146
Glu Arg Val  Leu Ser Ala Val Cys  Ala Val Arg Arg Tyr  Arg Ala
        1690                 1695                 1700

ggc gag gat  ggg tcg acc ctc cgc  act gct gtg gcc cgc  cag cac      5191
Gly Glu Asp  Gly Ser Thr Leu Arg  Thr Ala Val Ala Arg  Gln His
```

-continued

```
        1705                1710                1715

ccg cgc cct  ttt cgc cag atc cca  ccc ccg cgc gtc act  gct ggg      5236
Pro Arg Pro  Phe Arg Gln Ile Pro  Pro Pro Arg Val Thr  Ala Gly
        1720                1725                1730

gtc gcc cag  gag tgg cgc atg acg  tac ttg cgg gaa cgg  atc gac      5281
Val Ala Gln  Glu Trp Arg Met Thr  Tyr Leu Arg Glu Arg  Ile Asp
        1735                1740                1745

ctc act gac  gtc tac acg cag atg  ggc gtg gcc gcg cgg  gag ctc      5326
Leu Thr Asp  Val Tyr Thr Gln Met  Gly Val Ala Ala Arg  Glu Leu
        1750                1755                1760

acc gac cgc  tac gcg cgc cgc tat  cct gag atc ttc gcc  ggc atg      5371
Thr Asp Arg  Tyr Ala Arg Arg Tyr  Pro Glu Ile Phe Ala  Gly Met
        1765                1770                1775

tgt acc gcc  cag agc ctg agc gtc  ccc gcc ttc ctc aaa  gcc acc      5416
Cys Thr Ala  Gln Ser Leu Ser Val  Pro Ala Phe Leu Lys  Ala Thr
        1780                1785                1790

ttg aag tgc  gta gac gcc gcc ctc  ggc ccc agg gac acc  gag gac      5461
Leu Lys Cys  Val Asp Ala Ala Leu  Gly Pro Arg Asp Thr  Glu Asp
        1795                1800                1805

tgc cac gcc  gct cag ggg aaa gcc  ggc ctt gag atc cgt  gcg tgg      5506
Cys His Ala  Ala Gln Gly Lys Ala  Gly Leu Glu Ile Arg  Ala Trp
        1810                1815                1820

gcc aag gag  tgg gtt cag gtt atg  tcc ccg cat ttc cgc  gcg atc      5551
Ala Lys Glu  Trp Val Gln Val Met  Ser Pro His Phe Arg  Ala Ile
        1825                1830                1835

cag aag atc  atc atg cgc gcc ttg  cgc ccg caa ttc ctt  gtg gcc      5596
Gln Lys Ile  Ile Met Arg Ala Leu  Arg Pro Gln Phe Leu  Val Ala
        1840                1845                1850

gct ggc cat  acg gag ccc gag gtc  gat gcg tgg tgg cag  gct cat      5641
Ala Gly His  Thr Glu Pro Glu Val  Asp Ala Trp Trp Gln  Ala His
        1855                1860                1865

tac acc acc  aac gcc atc gag gtc  gac ttc act gag ttc  gac atg      5686
Tyr Thr Thr  Asn Ala Ile Glu Val  Asp Phe Thr Glu Phe  Asp Met
        1870                1875                1880

aac cag acc  ctc gct act cgg gac  gtc gag ctc gag att  agc gcc      5731
Asn Gln Thr  Leu Ala Thr Arg Asp  Val Glu Leu Glu Ile  Ser Ala
        1885                1890                1895

gct ctc ttg  ggc ctc cct tgc gcc  gaa gac tac cgc gcg  ctc cgc      5776
Ala Leu Leu  Gly Leu Pro Cys Ala  Glu Asp Tyr Arg Ala  Leu Arg
        1900                1905                1910

gcc ggc agc  tac tgc acc ctg cgc  gaa ctg ggc tcc act  gag acc      5821
Ala Gly Ser  Tyr Cys Thr Leu Arg  Glu Leu Gly Ser Thr  Glu Thr
        1915                1920                1925

ggc tgc gag  cgc aca agc ggc gag  ccc gcc acg ctg ctg  cac aac      5866
Gly Cys Glu  Arg Thr Ser Gly Glu  Pro Ala Thr Leu Leu  His Asn
        1930                1935                1940

acc acc gtg  gcc atg tgc atg gcc  atg cgc atg gtc ccc  aaa ggc      5911
Thr Thr Val  Ala Met Cys Met Ala  Met Arg Met Val Pro  Lys Gly
        1945                1950                1955

gtg cgc tgg  gct ggg att ttc cag  ggt gac gat atg gtc  atc ttc      5956
Val Arg Trp  Ala Gly Ile Phe Gln  Gly Asp Asp Met Val  Ile Phe
        1960                1965                1970

ctc ccc gag  ggc gcg cgc agt gcg  gca ctc aag tgg acc  ccc gcc      6001
Leu Pro Glu  Gly Ala Arg Ser Ala  Ala Leu Lys Trp Thr  Pro Ala
        1975                1980                1985

gag gtg ggc  ttg ttc ggc ttc cac  atc ccg gtg aag cat  gtg agc      6046
Glu Val Gly  Leu Phe Gly Phe His  Ile Pro Val Lys His  Val Ser
        1990                1995                2000

acc cct acc  ccc agc ttc tgc ggg  cac gtc ggc acc gcg  gcc ggc      6091
```

```
Thr Pro Thr  Pro Ser Phe Cys Gly  His Val Gly Thr Ala  Ala Gly
        2005                 2010                 2015

ctc ttc cat  gat gtc atg cac cag  gcg atc aag gtg ctt  tgc cgc      6136
Leu Phe His  Asp Val Met His Gln  Ala Ile Lys Val Leu  Cys Arg
        2020                 2025                 2030

cgt ttc gac  cca gac gtg ctt gaa  gaa cag cag gtg gcc  ctc ctc      6181
Arg Phe Asp  Pro Asp Val Leu Glu  Glu Gln Gln Val Ala  Leu Leu
        2035                 2040                 2045

gac cgc ctc  cgg ggg gtc tac gcg  gct ctg cct gac acc  gtt gcc      6226
Asp Arg Leu  Arg Gly Val Tyr Ala  Ala Leu Pro Asp Thr  Val Ala
        2050                 2055                 2060

gcc aat gct  gcg tac tac gac tac  agc gcg gag cgc gtc  ctc gct      6271
Ala Asn Ala  Ala Tyr Tyr Asp Tyr  Ser Ala Glu Arg Val  Leu Ala
        2065                 2070                 2075

atc gtg cgc  gaa ctt acc gcg tac  gcg cgg ggg cgc ggc  ctc gac      6316
Ile Val Arg  Glu Leu Thr Ala Tyr  Ala Arg Gly Arg Gly  Leu Asp
        2080                 2085                 2090

cac ccg gcc  acc atc ggc gcg ctc  gag gag att cag acc  ccc tac      6361
His Pro Ala  Thr Ile Gly Ala Leu  Glu Glu Ile Gln Thr  Pro Tyr
        2095                 2100                 2105

gcg cgc gcc  aat ctc cac gac gct  gac taa cgcccctgta cgtggggcct     6411
Ala Arg Ala  Asn Leu His Asp Ala  Asp
        2110                 2115

ttaatcttac ctactctaac caggtcatca cccaccgttg tttcgccgca tctggtgggt   6471

acccaacttt tgccattcgg gagagcccca gggtgcccga atg gct tct act  acc    6526
                                            Met Ala Ser Thr  Thr
                                                        2120

ccc atc acc atg  gag gac ctc cag aag  gcc ctc gag aca caa  tcc      6571
Pro Ile Thr Met  Glu Asp Leu Gln Lys  Ala Leu Glu Thr Gln  Ser
            2125                 2130                 2135

cgc gcc ctg cgc  gcg gaa ctc gcc gcc  ggc gcc tcg cag tcg  cgc      6616
Arg Ala Leu Arg  Ala Glu Leu Ala Ala  Gly Ala Ser Gln Ser  Arg
            2140                 2145                 2150

cgg ccg cgg ccg  ccg cga cag cgc gac  tcc agc acc acc gga  gat      6661
Arg Pro Arg Pro  Pro Arg Gln Arg Asp  Ser Ser Thr Thr Gly  Asp
            2155                 2160                 2165

gac tcc ggc cgt  gac tcc gga ggg ccc  cgc cgc cgc cgc ggc  aac      6706
Asp Ser Gly Arg  Asp Ser Gly Gly Pro  Arg Arg Arg Arg Gly  Asn
            2170                 2175                 2180

cgg ggc cgt ggc  cag cgc agg gac tgg  tcc agg gcc ccg ccc  ccc      6751
Arg Gly Arg Gly  Gln Arg Arg Asp Trp  Ser Arg Ala Pro Pro  Pro
            2185                 2190                 2195

ccg gag gag cgg  caa gaa act cgc tcc  cag act ccg gcc ccg  aag      6796
Pro Glu Glu Arg  Gln Glu Thr Arg Ser  Gln Thr Pro Ala Pro  Lys
            2200                 2205                 2210

cca tcg cgg gcg  ccg cca caa cag cct  caa ccc ccg cgt atg  caa      6841
Pro Ser Arg Ala  Pro Pro Gln Gln Pro  Gln Pro Pro Arg Met  Gln
            2215                 2220                 2225

acc ggg cgt ggg  ggc tct gcc ccg cgc  ccc gag ctg ggg cca  ccg      6886
Thr Gly Arg Gly  Gly Ser Ala Pro Arg  Pro Glu Leu Gly Pro  Pro
            2230                 2235                 2240

acc aac ccg ttc  caa gca gcc gtg gcg  cgt ggc ctg cgc ccg  cct      6931
Thr Asn Pro Phe  Gln Ala Ala Val Ala  Arg Gly Leu Arg Pro  Pro
            2245                 2250                 2255

ctc cac gac cct  gac acc gag gca ccc  acc gag gcc tgc gtg  acc      6976
Leu His Asp Pro  Asp Thr Glu Ala Pro  Thr Glu Ala Cys Val  Thr
            2260                 2265                 2270

tca tgg ctt tgg  agc gag ggc gaa ggc  gcg gtc ttt tac cgc  gtc      7021
Ser Trp Leu Trp  Ser Glu Gly Glu Gly  Ala Val Phe Tyr Arg  Val
```

```
            2275                2280                2285

gac ctg cat ttc  acc aac ctg ggc acc  ccc cca ctc gac gag  gac      7066
Asp Leu His Phe  Thr Asn Leu Gly Thr  Pro Pro Leu Asp Glu  Asp
            2290                2295                2300

ggc cgc tgg gac  cct gcg ctc atg tac  aac cct tgc ggg ccc  gag      7111
Gly Arg Trp Asp  Pro Ala Leu Met Tyr  Asn Pro Cys Gly Pro  Glu
            2305                2310                2315

ccg ccc gct cac  gtc gtc cgc gcg tac  aat caa cct gcc ggc  gac      7156
Pro Pro Ala His  Val Val Arg Ala Tyr  Asn Gln Pro Ala Gly  Asp
            2320                2325                2330

gtc agg ggc gtt  tgg ggt aaa ggt gag  cgc acc tac gcc gag  cag      7201
Val Arg Gly Val  Trp Gly Lys Gly Glu  Arg Thr Tyr Ala Glu  Gln
            2335                2340                2345

gat ttc cgc gtc  ggc ggc acg cgc tgg  cac cga ctg ctg cgc  atg      7246
Asp Phe Arg Val  Gly Gly Thr Arg Trp  His Arg Leu Leu Arg  Met
            2350                2355                2360

cca gtg cgc ggc  ctc gac ggc gac agc  gcc ccg ctt ccc ccc  cac      7291
Pro Val Arg Gly  Leu Asp Gly Asp Ser  Ala Pro Leu Pro Pro  His
            2365                2370                2375

acc acc gag cgc  att gag acc cgc tcg  gcg cgc cat cct tgg  cgc      7336
Thr Thr Glu Arg  Ile Glu Thr Arg Ser  Ala Arg His Pro Trp  Arg
            2380                2385                2390

atc cgc ttc ggt  gcc ccc cag gcc ttc  ctt gcc ggg ctc ttg  ctc      7381
Ile Arg Phe Gly  Ala Pro Gln Ala Phe  Leu Ala Gly Leu Leu  Leu
            2395                2400                2405

gcc gcg gtc gcc  gtt ggc acc gcg cgc  gcc ggg ctc cag ccc  cgc      7426
Ala Ala Val Ala  Val Gly Thr Ala Arg  Ala Gly Leu Gln Pro  Arg
            2410                2415                2420

gct gat atg gcg  gca cct cct acg ctg  ccg cag ccc ccc cgt  gcg      7471
Ala Asp Met Ala  Ala Pro Pro Thr Leu  Pro Gln Pro Pro Arg  Ala
            2425                2430                2435

cac ggg cag cat  tac ggc cac cac cac  cat cag ctg ccg ttc  ctc      7516
His Gly Gln His  Tyr Gly His His His  His Gln Leu Pro Phe  Leu
            2440                2445                2450

ggg cac gac ggc  cat cat ggc ggc acc  ttg cgc gtc ggc cag  cat      7561
Gly His Asp Gly  His His Gly Gly Thr  Leu Arg Val Gly Gln  His
            2455                2460                2465

cac cga aac gcc  agc gac gtg ctg ccc  ggc cac tgg ctc caa  ggc      7606
His Arg Asn Ala  Ser Asp Val Leu Pro  Gly His Trp Leu Gln  Gly
            2470                2475                2480

ggc tgg ggt tgc  tac aac ctg agc gac  tgg cac cag ggc act  cat      7651
Gly Trp Gly Cys  Tyr Asn Leu Ser Asp  Trp His Gln Gly Thr  His
            2485                2490                2495

gtc tgt cac acc  aag cac atg gac ttt  tgg tgt gtg gag cac  gac      7696
Val Cys His Thr  Lys His Met Asp Phe  Trp Cys Val Glu His  Asp
            2500                2505                2510

cga ccg ccg ccc  gcg acc ccg acg cct  ctc acc acc gcg gcg  aac      7741
Arg Pro Pro Pro  Ala Thr Pro Thr Pro  Leu Thr Thr Ala Ala  Asn
            2515                2520                2525

tcc acg acc gcc  gcc acc ccc gcc act  gcg ccg gcc ccc tgc  cac      7786
Ser Thr Thr Ala  Ala Thr Pro Ala Thr  Ala Pro Ala Pro Cys  His
            2530                2535                2540

gcc ggc ctc aat  gac agc tgc ggc ggc  ttc ttg tct ggg tgc  ggg      7831
Ala Gly Leu Asn  Asp Ser Cys Gly Gly  Phe Leu Ser Gly Cys  Gly
            2545                2550                2555

ccg atg cgc ctg  cgc cac ggc gct gac  acc cgg tgc ggt cgg  ttg      7876
Pro Met Arg Leu  Arg His Gly Ala Asp  Thr Arg Cys Gly Arg  Leu
            2560                2565                2570

atc tgc ggg ctg  tct acc acc gcc cag  tac ccg cct acc cgg  ttt      7921
```

-continued

```
Ile Cys Gly Leu  Ser Thr Thr Ala Gln  Tyr Pro Pro Thr Arg  Phe
            2575                 2580                 2585

ggc tgc gct atg  cgg tgg ggc ctt ccc  ccc tgg gaa ctg gtc  gtc      7966
Gly Cys Ala Met  Arg Trp Gly Leu Pro  Pro Trp Glu Leu Val  Val
            2590                 2595                 2600

ctt acc gcc cgc  ccc gaa gac ggc tgg  act tgc cgc ggc gtg  ccc      8011
Leu Thr Ala Arg  Pro Glu Asp Gly Trp  Thr Cys Arg Gly Val  Pro
            2605                 2610                 2615

gcc cac cca ggc  acc cgc tgc ccc gaa  ctg gtg agc ccc atg  gga      8056
Ala His Pro Gly  Thr Arg Cys Pro Glu  Leu Val Ser Pro Met  Gly
            2620                 2625                 2630

cgc gcg act tgc  tcc cca gcc tcg gcc  ctc tgg ctc gcc aca  gcg      8101
Arg Ala Thr Cys  Ser Pro Ala Ser Ala  Leu Trp Leu Ala Thr  Ala
            2635                 2640                 2645

aac gcg ctg tct  ctt gat cac gcc ctc  gcg gcc ttc gtc ctg  ctg      8146
Asn Ala Leu Ser  Leu Asp His Ala Leu  Ala Ala Phe Val Leu  Leu
            2650                 2655                 2660

gtc ccg tgg gtc  ctg ata ttc atg gtg  tgc cgc cgc acc tgt  cgc      8191
Val Pro Trp Val  Leu Ile Phe Met Val  Cys Arg Arg Thr Cys  Arg
            2665                 2670                 2675

cgc cgc ggc gcc  gcc gcc gcc ctc acc  gcg gtc gtc ctg cag  ggg      8236
Arg Arg Gly Ala  Ala Ala Ala Leu Thr  Ala Val Val Leu Gln  Gly
            2680                 2685                 2690

tac aac ccc ccc  gcc tat ggc gag gag  gct ttc acc tac ctc  tgc      8281
Tyr Asn Pro Pro  Ala Tyr Gly Glu Glu  Ala Phe Thr Tyr Leu  Cys
            2695                 2700                 2705

act gca ccg ggg  tgc gcc act caa gca  cct gtc ccc gtg cgc  ctc      8326
Thr Ala Pro Gly  Cys Ala Thr Gln Ala  Pro Val Pro Val Arg  Leu
            2710                 2715                 2720

gct ggc gtc cgc  ttt gag tcc aag att  gtg gac ggc ggc tgc  ttt      8371
Ala Gly Val Arg  Phe Glu Ser Lys Ile  Val Asp Gly Gly Cys  Phe
            2725                 2730                 2735

gcc cca tgg gac  ctc gag gcc act gga  gcc tgc att tgc gag  atc      8416
Ala Pro Trp Asp  Leu Glu Ala Thr Gly  Ala Cys Ile Cys Glu  Ile
            2740                 2745                 2750

ccc act gat gtc  tcg tgc gag ggc ttg  ggg gcc tgg gta ccc  aca      8461
Pro Thr Asp Val  Ser Cys Glu Gly Leu  Gly Ala Trp Val Pro  Thr
            2755                 2760                 2765

gcc cct tgc gcg  cgc atc tgg aat ggc  aca cag cgc gcg tgc  acc      8506
Ala Pro Cys Ala  Arg Ile Trp Asn Gly  Thr Gln Arg Ala Cys  Thr
            2770                 2775                 2780

ttc tgg gct gtc  aac gcc tac tcc tct  ggc ggg tac gcg cag  ctg      8551
Phe Trp Ala Val  Asn Ala Tyr Ser Ser  Gly Gly Tyr Ala Gln  Leu
            2785                 2790                 2795

gcc tct tac ttc  aac cct ggc ggc agc  tac tac aag cag tac  cac      8596
Ala Ser Tyr Phe  Asn Pro Gly Gly Ser  Tyr Tyr Lys Gln Tyr  His
            2800                 2805                 2810

cct acc gcg tgc  gag gtt gaa cct gcc  ttc gga cac agc gac  gcg      8641
Pro Thr Ala Cys  Glu Val Glu Pro Ala  Phe Gly His Ser Asp  Ala
            2815                 2820                 2825

gcc tgc tgg ggc  ttc ccc acc gac acc  gtg atg agc gtg ttc  gcc      8686
Ala Cys Trp Gly  Phe Pro Thr Asp Thr  Val Met Ser Val Phe  Ala
            2830                 2835                 2840

ctt gct agc tac  gtc cag cac cct cac  aag acc gtc cgg gtc  aag      8731
Leu Ala Ser Tyr  Val Gln His Pro His  Lys Thr Val Arg Val  Lys
            2845                 2850                 2855

ttc cat aca gag  acc agg acc gtc tgg  caa ctc tcc gtt gct  ggc      8776
Phe His Thr Glu  Thr Arg Thr Val Trp  Gln Leu Ser Val Ala  Gly
            2860                 2865                 2870
```

-continued

```
gtg tcg tgc aac  gtc acc act gaa cac  ccg ttc tgc aac acg  ccg      8821
Val Ser Cys Asn  Val Thr Thr Glu His  Pro Phe Cys Asn Thr  Pro
            2875                 2880                 2885

cac gga caa ctc  gag gtc cag gtc ccg  ccc gac ccc ggg gac  ctg      8866
His Gly Gln Leu  Glu Val Gln Val Pro  Pro Asp Pro Gly Asp  Leu
            2890                 2895                 2900

gtt gag tac att  atg aac cac acc ggc  aat cag cag tcc cgg  tgg      8911
Val Glu Tyr Ile  Met Asn His Thr Gly  Asn Gln Gln Ser Arg  Trp
            2905                 2910                 2915

ggc ctc ggg agc  ccg aat tgc cat ggc  ccc gat tgg gcc tcc  ccg      8956
Gly Leu Gly Ser  Pro Asn Cys His Gly  Pro Asp Trp Ala Ser  Pro
            2920                 2925                 2930

gtt tgc caa cgc  cat tcc cct gac tgc  tcg cgg ctt gtg ggg  gct      9001
Val Cys Gln Arg  His Ser Pro Asp Cys  Ser Arg Leu Val Gly  Ala
            2935                 2940                 2945

acg cca gag cgt  ccc cgg ctg cgc ctg  gtc gac gcc gac gac  ccc      9046
Thr Pro Glu Arg  Pro Arg Leu Arg Leu  Val Asp Ala Asp Asp  Pro
            2950                 2955                 2960

ctg ctg cgc act  gcc cct ggg ccc ggc  gag gtg tgg gtc acg  cct      9091
Leu Leu Arg Thr  Ala Pro Gly Pro Gly  Glu Val Trp Val Thr  Pro
            2965                 2970                 2975

gtc ata ggc tct  cag gcg cgc aag tgc  gga ctc cac ata cgc  gct      9136
Val Ile Gly Ser  Gln Ala Arg Lys Cys  Gly Leu His Ile Arg  Ala
            2980                 2985                 2990

gga ccg tac ggc  cat gct acc gtc gaa  atg ccc gag tgg atc  cac      9181
Gly Pro Tyr Gly  His Ala Thr Val Glu  Met Pro Glu Trp Ile  His
            2995                 3000                 3005

gcc cac acc acc  agc gac ccc tgg cac  cca ccg ggc ccc ttg  ggg      9226
Ala His Thr Thr  Ser Asp Pro Trp His  Pro Pro Gly Pro Leu  Gly
            3010                 3015                 3020

ctg aag ttc aag  aca gtt cgc ccg gtg  gcc ctg cca cgc acg  tta      9271
Leu Lys Phe Lys  Thr Val Arg Pro Val  Ala Leu Pro Arg Thr  Leu
            3025                 3030                 3035

gcg cca ccc cgc  aat gtg cgt gtg acc  ggg tgc tac cag tgc  ggt      9316
Ala Pro Pro Arg  Asn Val Arg Val Thr  Gly Cys Tyr Gln Cys  Gly
            3040                 3045                 3050

acc ccc gcg ctg  gtg gaa ggc ctt gcc  ccc ggg gga ggg aat  tgc      9361
Thr Pro Ala Leu  Val Glu Gly Leu Ala  Pro Gly Gly Gly Asn  Cys
            3055                 3060                 3065

cat ctc acc gtc  aat ggc gag gat ctc  ggc gcc ttc ccc cct  ggg      9406
His Leu Thr Val  Asn Gly Glu Asp Leu  Gly Ala Phe Pro Pro  Gly
            3070                 3075                 3080

aag ttc gtc acc  gcc gcc ctc ctc aac  acc ccc ccg ccc tac  caa      9451
Lys Phe Val Thr  Ala Ala Leu Leu Asn  Thr Pro Pro Pro Tyr  Gln
            3085                 3090                 3095

gtc agc tgc ggg  ggc gag agc gat cgc  gcg agc gcg cgg gtc  att      9496
Val Ser Cys Gly  Gly Glu Ser Asp Arg  Ala Ser Ala Arg Val  Ile
            3100                 3105                 3110

gac ccc gcc gcg  caa tcg ttt acc ggc  gtg gtg tat ggc aca  cac      9541
Asp Pro Ala Ala  Gln Ser Phe Thr Gly  Val Val Tyr Gly Thr  His
            3115                 3120                 3125

acc act gct gtg  tcg gag acc cgg cag  acc tgg gcg gag tgg  gct      9586
Thr Thr Ala Val  Ser Glu Thr Arg Gln  Thr Trp Ala Glu Trp  Ala
            3130                 3135                 3140

gct gcc cat tgg  tgg cag ctc act ctg  ggc gcc att tgc gcc  ctc      9631
Ala Ala His Trp  Trp Gln Leu Thr Leu  Gly Ala Ile Cys Ala  Leu
            3145                 3150                 3155

cta ctc gct ggc  tta ctc gct tgc tgt  gcc aaa tgc ttg tac  tac      9676
Leu Leu Ala Gly  Leu Leu Ala Cys Cys  Ala Lys Cys Leu Tyr  Tyr
            3160                 3165                 3170
```

```
ttg cgc ggc gct  ata gcg ccg cgc tag tgggcccccg cgcgaaaccc         9723
Leu Arg Gly Ala  Ile Ala Pro Arg
            3175

gcactagccc actagattcc cgcacctgtt gctgcatag                         9762


<210> SEQ ID NO 16
<211> LENGTH: 2116
<212> TYPE: PRT
<213> ORGANISM: Rubella virus

<400> SEQUENCE: 16

Met Glu Arg Leu Leu Asp Glu Val Leu Ala Pro Gly Gly Pro Tyr Asn
1               5                   10                  15

Leu Thr Val Gly Ser Trp Val Arg Asp His Val Arg Ser Ile Val Glu
            20                  25                  30

Gly Ala Trp Glu Val Arg Asp Val Val Ser Ala Ala Gln Lys Arg Ala
        35                  40                  45

Ile Val Ala Val Ile Pro Arg Pro Val Phe Thr Gln Met Gln Val Ser
    50                  55                  60

Asp His Pro Ala Leu His Ala Ile Ser Arg Tyr Thr Arg Arg His Trp
65                  70                  75                  80

Ile Glu Trp Gly Pro Lys Glu Ala Leu His Val Leu Ile Asp Pro Ser
                85                  90                  95

Pro Gly Leu Leu Arg Glu Val Ala Arg Val Glu Arg Arg Trp Val Ala
            100                 105                 110

Leu Cys Leu His Arg Thr Ala Arg Lys Leu Ala Thr Ala Leu Ala Glu
        115                 120                 125

Thr Ala Ser Glu Ala Trp His Ala Asp Tyr Val Cys Ala Leu Arg Gly
    130                 135                 140

Ala Pro Ser Gly Pro Phe Tyr Val His Pro Glu Asp Val Pro His Gly
145                 150                 155                 160

Gly Arg Ala Val Ala Asp Arg Cys Leu Leu Tyr Tyr Thr Pro Met Gln
                165                 170                 175

Met Cys Glu Leu Met Arg Thr Ile Asp Ala Thr Leu Leu Val Ala Val
            180                 185                 190

Asp Leu Trp Pro Val Ala Leu Ala Ala His Val Gly Asp Asp Trp Asp
        195                 200                 205

Asp Leu Gly Ile Ala Trp His Leu Asp His Asp Gly Gly Cys Pro Ala
    210                 215                 220

Asp Cys Arg Gly Ala Gly Ala Gly Pro Thr Pro Gly Tyr Thr Arg Pro
225                 230                 235                 240

Cys Thr Thr Arg Ile Tyr Gln Val Leu Pro Asp Thr Ala His Pro Gly
                245                 250                 255

Arg Leu Tyr Arg Cys Gly Pro Arg Leu Trp Thr Arg Asp Cys Ala Val
            260                 265                 270

Ala Glu Leu Ser Trp Glu Val Ala Gln His Cys Gly His Gln Ala Arg
        275                 280                 285

Val Arg Ala Val Arg Cys Thr Leu Pro Ile Arg His Val Arg Ser Leu
    290                 295                 300

Gln Pro Ser Ala Arg Val Arg Leu Pro Asp Leu Val His Leu Ala Glu
305                 310                 315                 320

Val Gly Arg Trp Arg Trp Phe Ser Leu Pro Arg Pro Val Phe Gln Arg
                325                 330                 335

Met Leu Ser Tyr Cys Lys Thr Leu Ser Pro Asp Ala Tyr Tyr Ser Glu
```

-continued

```
            340                 345                 350

Arg Val Phe Lys Phe Lys Asn Ala Leu Ser His Ser Ile Thr Leu Ala
        355                 360                 365

Gly Asn Val Leu Gln Glu Gly Trp Lys Gly Thr Cys Ala Glu Glu Asp
    370                 375                 380

Ala Leu Cys Ala Tyr Val Ala Phe Arg Ala Trp Gln Ser Asn Ala Arg
385                 390                 395                 400

Leu Ala Gly Ile Met Lys Ser Ala Lys Arg Cys Ala Ala Asp Ser Leu
                405                 410                 415

Ser Val Ala Gly Trp Leu Asp Thr Ile Trp Gly Ala Ile Lys Arg Phe
            420                 425                 430

Phe Gly Ser Val Pro Leu Ala Glu Arg Met Glu Glu Trp Glu Gln Asp
        435                 440                 445

Ala Ala Val Ala Ala Phe Asp Arg Gly Pro Leu Glu Asp Gly Gly Arg
    450                 455                 460

His Leu Asp Thr Val Gln Pro Pro Lys Ser Pro Pro Arg Pro Glu Ile
465                 470                 475                 480

Ala Ala Thr Trp Ile Val His Ala Ala Ser Ala Asp Arg His Cys Ala
                485                 490                 495

Cys Ala Pro Arg Cys Asp Val Pro Arg Glu Arg Pro Ser Ala Pro Ala
            500                 505                 510

Gly Pro Pro Asp Asp Glu Ala Leu Ile Pro Pro Trp Leu Phe Ala Glu
        515                 520                 525

His Arg Ala Leu Arg Cys Arg Glu Trp Asp Phe Glu Val Leu Arg Ala
    530                 535                 540

Arg Ala Asp Thr Ala Ala Ala Pro Ala Pro Leu Ala Pro Arg Pro Ala
545                 550                 555                 560

Arg Tyr Pro Thr Val Leu Tyr Arg His Pro Ala His His Gly Pro Trp
                565                 570                 575

Leu Thr Leu Asp Glu Pro Gly Glu Ala Asp Ala Ala Leu Val Leu Cys
            580                 585                 590

Asp Pro Leu Gly Gln Pro Leu Arg Gly Pro Glu Arg His Phe Ala Ala
        595                 600                 605

Gly Ala His Met Cys Ala Gln Ala Arg Gly Leu Gln Ala Phe Val Arg
    610                 615                 620

Val Val Pro Pro Pro Glu Arg Pro Trp Ala Asp Gly Gly Ala Arg Ala
625                 630                 635                 640

Trp Ala Lys Phe Phe Arg Gly Cys Ala Trp Ala Gln Arg Leu Leu Gly
                645                 650                 655

Glu Pro Ala Val Met His Leu Pro Tyr Thr Asp Gly Asp Val Pro Gln
            660                 665                 670

Leu Ile Ala Leu Ala Leu Arg Thr Leu Ala Gln Gln Gly Ala Ala Leu
        675                 680                 685

Ala Leu Ser Val Arg Asp Leu Pro Gly Gly Ala Ala Phe Asp Ala Asn
    690                 695                 700

Ala Val Thr Ala Ala Val Arg Ala Gly Pro Gly Gln Ser Ala Ala Thr
705                 710                 715                 720

Ser Ser Pro Pro Gly Asp Pro Pro Pro Pro Arg Cys Ala Arg Arg Ser
                725                 730                 735

Gln Arg His Ser Asp Ala Arg Gly Thr Pro Pro Pro Ala Pro Ala Arg
            740                 745                 750

Asp Pro Pro Pro Pro Ala Pro Ser Pro Pro Ala Pro Pro Arg Ala Gly
        755                 760                 765
```

-continued

```
Asp Pro Val Pro Pro Thr Ser Ala Gly Pro Ala Asp Arg Ala Arg Asp
    770                 775                 780

Ala Glu Leu Glu Val Ala Tyr Glu Pro Ser Gly Pro Pro Thr Ser Thr
785                 790                 795                 800

Lys Ala Asp Pro Asp Ser Asp Ile Val Glu Ser Tyr Ala Arg Ala Ala
                805                 810                 815

Gly Pro Val His Leu Arg Val Arg Asp Ile Met Asp Pro Pro Pro Gly
            820                 825                 830

Cys Lys Val Val Val Asn Ala Ala Asn Glu Gly Leu Leu Ala Gly Ser
        835                 840                 845

Gly Val Cys Gly Ala Ile Phe Ala Asn Ala Thr Ala Ala Leu Ala Ala
    850                 855                 860

Asp Cys Arg Arg Leu Ala Pro Cys Pro Thr Gly Glu Ala Val Ala Thr
865                 870                 875                 880

Pro Gly His Gly Cys Gly Tyr Thr His Ile Ile His Ala Val Ala Pro
                885                 890                 895

Arg Arg Pro Arg Asp Pro Ala Ala Leu Glu Glu Gly Glu Ala Leu Leu
            900                 905                 910

Glu Arg Ala Tyr Arg Ser Ile Val Ala Leu Ala Ala Ala Arg Arg Trp
        915                 920                 925

Ala Arg Val Ala Cys Pro Leu Leu Gly Ala Gly Val Tyr Gly Trp Ser
    930                 935                 940

Ala Ala Glu Ser Leu Arg Ala Ala Leu Ala Ala Thr Arg Thr Glu Pro
945                 950                 955                 960

Ala Glu Arg Val Ser Leu His Ile Cys His Pro Asp Arg Ala Thr Leu
                965                 970                 975

Thr His Ala Ser Val Leu Val Gly Ala Gly Leu Ala Ala Arg Arg Val
            980                 985                 990

Ser Pro Pro Pro Thr Glu Pro Leu  Ala Ser Cys Pro Ala  Gly Asp Pro
        995                 1000                1005

Gly Arg  Pro Ala Gln Arg Ser  Ala Ser Pro Pro Ala  Thr Pro Leu
    1010                1015                1020

Gly Asp  Ala Thr Ala Pro Glu  Pro Arg Gly Cys Gln  Gly Cys Glu
    1025                1030                1035

Leu Cys  Arg Tyr Thr Arg Val  Thr Asn Asp Arg Ala  Tyr Val Asn
    1040                1045                1050

Leu Trp  Leu Glu Arg Asp Arg  Gly Ala Thr Ser Trp  Ala Met Arg
    1055                1060                1065

Ile Pro  Glu Val Val Val Tyr  Gly Pro Glu His Leu  Ala Thr His
    1070                1075                1080

Phe Pro  Leu Asn His Tyr Ser  Val Leu Lys Pro Ala  Glu Val Arg
    1085                1090                1095

Pro Pro  Arg Gly Met Cys Gly  Ser Asp Met Trp Arg  Cys Arg Gly
    1100                1105                1110

Trp Gln  Gly Val Pro Gln Val  Arg Cys Thr Pro Ser  Asn Ala His
    1115                1120                1125

Ala Ala  Leu Cys Arg Thr Gly  Val Pro Pro Arg Val  Ser Thr Arg
    1130                1135                1140

Gly Gly  Glu Leu Asp Pro Asn  Thr Cys Trp Leu Arg  Ala Ala Ala
    1145                1150                1155

Asn Val  Ala Gln Ala Ala Arg  Ala Cys Gly Ala Tyr  Thr Ser Ala
    1160                1165                1170
```

-continued

```
Gly Cys  Pro Arg Cys Ala Tyr  Gly Arg Ala Leu Ser  Glu Ala Arg
    1175                 1180                 1185

Thr His  Lys Asp Phe Ala Ala  Leu Ser Gln Arg Trp  Ser Ala Ser
    1190                 1195                 1200

His Ala  Asp Ala Ser Ser Asp  Gly Thr Gly Asp Pro  Leu Asp Pro
    1205                 1210                 1215

Leu Met  Glu Thr Val Gly Cys  Ala Cys Ser Arg Val  Trp Val Gly
    1220                 1225                 1230

Ser Glu  His Glu Ala Pro Pro  Asp His Leu Leu Val  Ser Leu His
    1235                 1240                 1245

Arg Ala  Pro Asn Gly Pro Trp  Gly Val Val Leu Glu  Val Arg Ala
    1250                 1255                 1260

Arg Pro  Glu Gly Gly Asn Pro  Thr Gly His Phe Val  Cys Ala Val
    1265                 1270                 1275

Gly Gly  Gly Pro Arg Arg Val  Ser Asp Arg Pro His  Leu Trp Leu
    1280                 1285                 1290

Ala Val  Pro Leu Ser Arg Gly  Gly Gly Thr Cys Ala  Ala Thr Asp
    1295                 1300                 1305

Glu Gly  Leu Ala Gln Ala Tyr  Tyr Asp Asp Leu Glu  Val Arg Arg
    1310                 1315                 1320

Leu Gly  Asp Asp Ala Met Ala  Arg Ala Ala Leu Ala  Ser Val Gln
    1325                 1330                 1335

Arg Pro  Arg Lys Gly Pro Tyr  Asn Ile Arg Val Trp  Asn Met Ala
    1340                 1345                 1350

Ala Gly  Ala Gly Lys Thr Thr  Arg Ile Leu Ala Ala  Phe Thr Arg
    1355                 1360                 1365

Glu Asp  Leu Tyr Val Cys Pro  Thr Asn Ala Leu Leu  His Glu Ile
    1370                 1375                 1380

Gln Ala  Lys Leu Arg Ala Arg  Asp Ile Glu Ile Lys  Asn Ala Ala
    1385                 1390                 1395

Thr Tyr  Glu Arg Ala Leu Thr  Lys Pro Leu Ala Ala  Tyr Arg Arg
    1400                 1405                 1410

Ile Tyr  Ile Asp Glu Ala Phe  Thr Leu Gly Gly Glu  Tyr Cys Ala
    1415                 1420                 1425

Phe Val  Ala Ser Gln Thr Thr  Ala Glu Val Ile Cys  Val Gly Asp
    1430                 1435                 1440

Arg Asp  Gln Cys Gly Pro His  Tyr Ala Asn Asn Cys  Arg Thr Pro
    1445                 1450                 1455

Val Pro  Asp Arg Trp Pro Thr  Glu Arg Ser Arg His  Thr Trp Arg
    1460                 1465                 1470

Phe Pro  Asp Cys Trp Ala Ala  Arg Leu Arg Ala Gly  Leu Asp Tyr
    1475                 1480                 1485

Asp Ile  Glu Gly Glu Arg Thr  Gly Thr Phe Ala Cys  Asn Leu Trp
    1490                 1495                 1500

Asp Gly  Arg Gln Val Asp Leu  His Leu Ala Phe Ser  Arg Glu Thr
    1505                 1510                 1515

Val Arg  Arg Leu His Glu Ala  Gly Ile Arg Ala Tyr  Thr Val Arg
    1520                 1525                 1530

Glu Ala  Gln Gly Met Ser Val  Gly Thr Ala Cys Ile  His Val Gly
    1535                 1540                 1545

Arg Asp  Gly Thr Asp Val Ala  Leu Ala Leu Thr Arg  Asp Leu Ala
    1550                 1555                 1560

Ile Val  Ser Leu Thr Arg Ala  Ser Asp Ala Leu Tyr  Leu His Glu
```

```
    1565                1570                1575

Leu Glu  Asp Gly Ser Leu Arg  Ala Ala Gly Leu Ser  Ala Phe Leu
    1580                1585                1590

Asp Ala  Gly Ala Leu Ala Glu  Leu Lys Glu Val Pro  Ala Gly Ile
    1595                1600                1605

Asp Arg  Val Val Ala Val Glu  Gln Ala Pro Pro Pro  Leu Pro Pro
    1610                1615                1620

Ala Asp  Gly Ile Pro Glu Ala  Gln Asp Val Pro Pro  Phe Cys Pro
    1625                1630                1635

Arg Thr  Leu Glu Glu Leu Val  Phe Gly Arg Ala Gly  His Pro His
    1640                1645                1650

Tyr Ala  Asp Leu Asn Arg Val  Thr Glu Gly Glu Arg  Glu Val Arg
    1655                1660                1665

Tyr Met  Arg Ile Ser Arg His  Leu Leu Asn Lys Asn  His Thr Glu
    1670                1675                1680

Met Pro  Gly Thr Glu Arg Val  Leu Ser Ala Val Cys  Ala Val Arg
    1685                1690                1695

Arg Tyr  Arg Ala Gly Glu Asp  Gly Ser Thr Leu Arg  Thr Ala Val
    1700                1705                1710

Ala Arg  Gln His Pro Arg Pro  Phe Arg Gln Ile Pro  Pro Pro Arg
    1715                1720                1725

Val Thr  Ala Gly Val Ala Gln  Glu Trp Arg Met Thr  Tyr Leu Arg
    1730                1735                1740

Glu Arg  Ile Asp Leu Thr Asp  Val Tyr Thr Gln Met  Gly Val Ala
    1745                1750                1755

Ala Arg  Glu Leu Thr Asp Arg  Tyr Ala Arg Arg Tyr  Pro Glu Ile
    1760                1765                1770

Phe Ala  Gly Met Cys Thr Ala  Gln Ser Leu Ser Val  Pro Ala Phe
    1775                1780                1785

Leu Lys  Ala Thr Leu Lys Cys  Val Asp Ala Ala Leu  Gly Pro Arg
    1790                1795                1800

Asp Thr  Glu Asp Cys His Ala  Ala Gln Gly Lys Ala  Gly Leu Glu
    1805                1810                1815

Ile Arg  Ala Trp Ala Lys Glu  Trp Val Gln Val Met  Ser Pro His
    1820                1825                1830

Phe Arg  Ala Ile Gln Lys Ile  Ile Met Arg Ala Leu  Arg Pro Gln
    1835                1840                1845

Phe Leu  Val Ala Ala Gly His  Thr Glu Pro Glu Val  Asp Ala Trp
    1850                1855                1860

Trp Gln  Ala His Tyr Thr Thr  Asn Ala Ile Glu Val  Asp Phe Thr
    1865                1870                1875

Glu Phe  Asp Met Asn Gln Thr  Leu Ala Thr Arg Asp  Val Glu Leu
    1880                1885                1890

Glu Ile  Ser Ala Ala Leu Leu  Gly Leu Pro Cys Ala  Glu Asp Tyr
    1895                1900                1905

Arg Ala  Leu Arg Ala Gly Ser  Tyr Cys Thr Leu Arg  Glu Leu Gly
    1910                1915                1920

Ser Thr  Glu Thr Gly Cys Glu  Arg Thr Ser Gly Glu  Pro Ala Thr
    1925                1930                1935

Leu Leu  His Asn Thr Thr Val  Ala Met Cys Met Ala  Met Arg Met
    1940                1945                1950

Val Pro  Lys Gly Val Arg Trp  Ala Gly Ile Phe Gln  Gly Asp Asp
    1955                1960                1965
```

```
Met Val  Ile Phe Leu Pro Glu  Gly Ala Arg Ser Ala  Ala Leu Lys
    1970                 1975                 1980

Trp Thr  Pro Ala Glu Val Gly  Leu Phe Gly Phe His  Ile Pro Val
    1985                 1990                 1995

Lys His  Val Ser Thr Pro Thr  Pro Ser Phe Cys Gly  His Val Gly
    2000                 2005                 2010

Thr Ala  Ala Gly Leu Phe His  Asp Val Met His Gln  Ala Ile Lys
    2015                 2020                 2025

Val Leu  Cys Arg Arg Phe Asp  Pro Asp Val Leu Glu  Glu Gln Gln
    2030                 2035                 2040

Val Ala  Leu Leu Asp Arg Leu  Arg Gly Val Tyr Ala  Ala Leu Pro
    2045                 2050                 2055

Asp Thr  Val Ala Ala Asn Ala  Ala Tyr Tyr Asp Tyr  Ser Ala Glu
    2060                 2065                 2070

Arg Val  Leu Ala Ile Val Arg  Glu Leu Thr Ala Tyr  Ala Arg Gly
    2075                 2080                 2085

Arg Gly  Leu Asp His Pro Ala  Thr Ile Gly Ala Leu  Glu Glu Ile
    2090                 2095                 2100

Gln Thr  Pro Tyr Ala Arg Ala  Asn Leu His Asp Ala  Asp
    2105                 2110                 2115


<210> SEQ ID NO 17
<211> LENGTH: 1063
<212> TYPE: PRT
<213> ORGANISM: Rubella virus

<400> SEQUENCE: 17

Met Ala Ser Thr Thr Pro Ile Thr Met Glu Asp Leu Gln Lys Ala Leu
1               5                   10                  15

Glu Thr Gln Ser Arg Ala Leu Arg Ala Glu Leu Ala Ala Gly Ala Ser
            20                  25                  30

Gln Ser Arg Arg Pro Arg Pro Pro Arg Gln Arg Asp Ser Ser Thr Thr
        35                  40                  45

Gly Asp Asp Ser Gly Arg Asp Ser Gly Gly Pro Arg Arg Arg Arg Gly
    50                  55                  60

Asn Arg Gly Arg Gly Gln Arg Arg Asp Trp Ser Arg Ala Pro Pro Pro
65                  70                  75                  80

Pro Glu Glu Arg Gln Glu Thr Arg Ser Gln Thr Pro Ala Pro Lys Pro
                85                  90                  95

Ser Arg Ala Pro Pro Gln Gln Pro Gln Pro Pro Arg Met Gln Thr Gly
            100                 105                 110

Arg Gly Gly Ser Ala Pro Arg Pro Glu Leu Gly Pro Pro Thr Asn Pro
        115                 120                 125

Phe Gln Ala Ala Val Ala Arg Gly Leu Arg Pro Pro Leu His Asp Pro
    130                 135                 140

Asp Thr Glu Ala Pro Thr Glu Ala Cys Val Thr Ser Trp Leu Trp Ser
145                 150                 155                 160

Glu Gly Glu Gly Ala Val Phe Tyr Arg Val Asp Leu His Phe Thr Asn
                165                 170                 175

Leu Gly Thr Pro Pro Leu Asp Glu Asp Gly Arg Trp Asp Pro Ala Leu
            180                 185                 190

Met Tyr Asn Pro Cys Gly Pro Glu Pro Pro Ala His Val Val Arg Ala
        195                 200                 205

Tyr Asn Gln Pro Ala Gly Asp Val Arg Gly Val Trp Gly Lys Gly Glu
```

-continued

```
    210                 215                 220

Arg Thr Tyr Ala Glu Gln Asp Phe Arg Val Gly Gly Thr Arg Trp His
225                 230                 235                 240

Arg Leu Leu Arg Met Pro Val Arg Gly Leu Asp Gly Asp Ser Ala Pro
                245                 250                 255

Leu Pro Pro His Thr Thr Glu Arg Ile Glu Thr Arg Ser Ala Arg His
            260                 265                 270

Pro Trp Arg Ile Arg Phe Gly Ala Pro Gln Ala Phe Leu Ala Gly Leu
        275                 280                 285

Leu Leu Ala Ala Val Ala Val Gly Thr Ala Arg Ala Gly Leu Gln Pro
    290                 295                 300

Arg Ala Asp Met Ala Ala Pro Pro Thr Leu Pro Gln Pro Pro Arg Ala
305                 310                 315                 320

His Gly Gln His Tyr Gly His His His His Gln Leu Pro Phe Leu Gly
                325                 330                 335

His Asp Gly His His Gly Gly Thr Leu Arg Val Gly Gln His His Arg
            340                 345                 350

Asn Ala Ser Asp Val Leu Pro Gly His Trp Leu Gln Gly Gly Trp Gly
        355                 360                 365

Cys Tyr Asn Leu Ser Asp Trp His Gln Gly Thr His Val Cys His Thr
    370                 375                 380

Lys His Met Asp Phe Trp Cys Val Glu His Asp Arg Pro Pro Pro Ala
385                 390                 395                 400

Thr Pro Thr Pro Leu Thr Thr Ala Ala Asn Ser Thr Thr Ala Ala Thr
                405                 410                 415

Pro Ala Thr Ala Pro Ala Pro Cys His Ala Gly Leu Asn Asp Ser Cys
            420                 425                 430

Gly Gly Phe Leu Ser Gly Cys Gly Pro Met Arg Leu Arg His Gly Ala
        435                 440                 445

Asp Thr Arg Cys Gly Arg Leu Ile Cys Gly Leu Ser Thr Thr Ala Gln
    450                 455                 460

Tyr Pro Pro Thr Arg Phe Gly Cys Ala Met Arg Trp Gly Leu Pro Pro
465                 470                 475                 480

Trp Glu Leu Val Val Leu Thr Ala Arg Pro Glu Asp Gly Trp Thr Cys
                485                 490                 495

Arg Gly Val Pro Ala His Pro Gly Thr Arg Cys Pro Glu Leu Val Ser
            500                 505                 510

Pro Met Gly Arg Ala Thr Cys Ser Pro Ala Ser Ala Leu Trp Leu Ala
        515                 520                 525

Thr Ala Asn Ala Leu Ser Leu Asp His Ala Leu Ala Ala Phe Val Leu
    530                 535                 540

Leu Val Pro Trp Val Leu Ile Phe Met Val Cys Arg Arg Thr Cys Arg
545                 550                 555                 560

Arg Arg Gly Ala Ala Ala Ala Leu Thr Ala Val Val Leu Gln Gly Tyr
                565                 570                 575

Asn Pro Pro Ala Tyr Gly Glu Glu Ala Phe Thr Tyr Leu Cys Thr Ala
            580                 585                 590

Pro Gly Cys Ala Thr Gln Ala Pro Val Pro Val Arg Leu Ala Gly Val
        595                 600                 605

Arg Phe Glu Ser Lys Ile Val Asp Gly Gly Cys Phe Ala Pro Trp Asp
    610                 615                 620

Leu Glu Ala Thr Gly Ala Cys Ile Cys Glu Ile Pro Thr Asp Val Ser
625                 630                 635                 640
```

```
Cys Glu Gly Leu Gly Ala Trp Val Pro Thr Ala Pro Cys Ala Arg Ile
                645                 650                 655

Trp Asn Gly Thr Gln Arg Ala Cys Thr Phe Trp Ala Val Asn Ala Tyr
            660                 665                 670

Ser Ser Gly Gly Tyr Ala Gln Leu Ala Ser Tyr Phe Asn Pro Gly Gly
        675                 680                 685

Ser Tyr Tyr Lys Gln Tyr His Pro Thr Ala Cys Glu Val Glu Pro Ala
    690                 695                 700

Phe Gly His Ser Asp Ala Ala Cys Trp Gly Phe Pro Thr Asp Thr Val
705                 710                 715                 720

Met Ser Val Phe Ala Leu Ala Ser Tyr Val Gln His Pro His Lys Thr
                725                 730                 735

Val Arg Val Lys Phe His Thr Glu Thr Arg Thr Val Trp Gln Leu Ser
            740                 745                 750

Val Ala Gly Val Ser Cys Asn Val Thr Thr Glu His Pro Phe Cys Asn
        755                 760                 765

Thr Pro His Gly Gln Leu Glu Val Gln Val Pro Pro Asp Pro Gly Asp
    770                 775                 780

Leu Val Glu Tyr Ile Met Asn His Thr Gly Asn Gln Gln Ser Arg Trp
785                 790                 795                 800

Gly Leu Gly Ser Pro Asn Cys His Gly Pro Asp Trp Ala Ser Pro Val
                805                 810                 815

Cys Gln Arg His Ser Pro Asp Cys Ser Arg Leu Val Gly Ala Thr Pro
            820                 825                 830

Glu Arg Pro Arg Leu Arg Leu Val Asp Ala Asp Asp Pro Leu Leu Arg
        835                 840                 845

Thr Ala Pro Gly Pro Gly Glu Val Trp Val Thr Pro Val Ile Gly Ser
    850                 855                 860

Gln Ala Arg Lys Cys Gly Leu His Ile Arg Ala Gly Pro Tyr Gly His
865                 870                 875                 880

Ala Thr Val Glu Met Pro Glu Trp Ile His Ala His Thr Thr Ser Asp
                885                 890                 895

Pro Trp His Pro Pro Gly Pro Leu Gly Leu Lys Phe Lys Thr Val Arg
            900                 905                 910

Pro Val Ala Leu Pro Arg Thr Leu Ala Pro Pro Arg Asn Val Arg Val
        915                 920                 925

Thr Gly Cys Tyr Gln Cys Gly Thr Pro Ala Leu Val Glu Gly Leu Ala
    930                 935                 940

Pro Gly Gly Gly Asn Cys His Leu Thr Val Asn Gly Glu Asp Leu Gly
945                 950                 955                 960

Ala Phe Pro Pro Gly Lys Phe Val Thr Ala Ala Leu Leu Asn Thr Pro
                965                 970                 975

Pro Pro Tyr Gln Val Ser Cys Gly Gly Glu Ser Asp Arg Ala Ser Ala
            980                 985                 990

Arg Val Ile Asp Pro Ala Ala Gln  Ser Phe Thr Gly Val  Val Tyr Gly
        995                 1000                1005

Thr His  Thr Thr Ala Val Ser  Glu Thr Arg Gln Thr  Trp Ala Glu
    1010                1015                1020

Trp Ala  Ala Ala His Trp Trp  Gln Leu Thr Leu Gly  Ala Ile Cys
    1025                1030                1035

Ala Leu  Leu Leu Ala Gly Leu  Leu Ala Cys Cys Ala  Lys Cys Leu
    1040                1045                1050
```

```
Tyr Tyr  Leu Arg Gly Ala Ile  Ala Pro Arg
    1055                 1060


<210> SEQ ID NO 18
<211> LENGTH: 9762
<212> TYPE: DNA
<213> ORGANISM: Artificial
<220> FEATURE:
<223> OTHER INFORMATION: deoptimized rubella sequence

<400> SEQUENCE: 18

caatgggagc tatcggacct cgcttaggac tcctattccc atggagagat tattagatga     60

ggtattagca ccaggaggac catataactt aacagtagga tcatgggtaa gagaccacgt    120

aagatcaatt gtagagggag catgggaagt aagagatgta gtatcagcag cacaaaagag    180

agcaatcgta gcagtaatac caagaccagt attcacgcag atgcaggtat cagatcaccc    240

agcattacac gcaatttcaa gatatacaag aagacattgg atcgagtggg gaccaaaaga    300

agcattacac gtattaatcg acccatcacc aggattatta agagaggtag caagagtaga    360

gagaagatgg gtagcattat gtttacacag aagagcaaga aaattagcaa cagcattagc    420

agagagagca tcagaggcat ggcacgcaga ctatgtatgt gcattaagag gagcaccatc    480

aggaccattc tatgtacacc cagaggacgt accacacgga ggaagagcag tagcagacag    540

atgtttatta tattatacac caatgcagat gtgtgagtta atgagaacaa ttgacgcaac    600

attattagta gcagtagact tatggccagt agcattagca gcacacgtag gagacgactg    660

ggacgactta ggaattgcat ggcatttaga ccatgacgga ggatgtccag cagattgtag    720

aggagcagga gcaggaccaa gaccaggata tacaagacca tgtacaacaa gaatctatca    780

agtattacca gacacagcac acccaggaag attatataga tgtggaccaa gattatggag    840

aagagattgt gcagtagcag aattatcatg ggaggtagca caacactgtg gacaccaggc    900

aagagtaaga gcagtaagat gtacattacc aatcagacac gtaagatcat tacaaccatc    960

agcaagagta agattaccag acttagtaca tttagcagag gtaggaagat ggagatggtt   1020

ctcattacca agaccagtat tccagagaat gttatcatat tgtaagacat tatcaccaga   1080

cgcatattat tcagagagag tattcaagtt caagaacgca ttatcacact caatcagatt   1140

agcaggaaat gtattacaag agggatggaa gggaagatgt gcagaggaag acgcattatg   1200

tgcatatgta gcattcagag catggcagtc aaacgcaaga ttagcaggaa ttatgaaatc   1260

agcaaagaga tgtgcagcag actcattatc agtagcagga tggttagaca caatttgggg   1320

agcaattaag agattcttcg gatcagtacc attagcagag agaatggagg agtgggaaca   1380

ggacgcagca gtagcagcat tcgacagagg accattagag gacggaggaa gacacttaga   1440

cacagtacaa ccaccaaaat caccaccaag accagagatc gcagcaacat ggatcgtaca   1500

cgcagcatca gcagacagac attgtgcatg tgcaccaaga tgtgacgtac caagagaaag   1560

accatcagca ccagcaggac caccagatga cgaggcatta atcccaccat ggttattcgc   1620

agagcacaga gcattaagat gtagagagtg ggatttcgag gtattaagag caagagcaga   1680

tagagcagca gcaccagcac cattagcacc aagaccagca agatatccaa cagtattata   1740

tagacaccca gcacaccacg gaccatggtt aacattagac gagccaggag aggcagacgc   1800

agcattagta ttatgtgacc cattaggaca gccattaaga ggaccagaaa gacacttcgc   1860

agcaggagca catatgtgtg cacaggcaag aggattacag gcatttgtaa gagtagtacc   1920

accaccagag agaccatggg cagacggagg agcaagagca tgggcaaagt tcttcagagg   1980
```

-continued

```
atgtgcatgg gcacagagat tattaggaga gccagcagta atgcacttac catatacaga   2040
tggagacgta ccacagttaa tcgcattagc attaagaaga ttagcacaac agggagcagc   2100
attagcatta tcagtaagag acttaccagg aggagcagca ttcgacgcaa acgcagtaac   2160
agcagcagta agagcaggac caggacagtc agcagcaaga tcatcaccac caggagaccc   2220
accaccacca agatgtgcaa gaagatcaca aagacactca gacgcaagag gaacaccacc   2280
accagcacca gcaagagacc caccaccacc agcaccatca ccaccagcac caccaagagc   2340
aggagaccca gtaccaccaa catcagcagg accagcagat agagcaagag acgcagagtt   2400
agaggtagca tatgaaccat caggaccacc aagatcaaca aaggcagacc cagactcaga   2460
catcgtagaa tcatatgcaa gagcagcagg accagtacac ttaagagtaa gagacatcat   2520
ggacccacca ccaggatgta aggtagtagt aaacgcagca aacgagggat tattagcagg   2580
atcaggagta tgtggagcaa tctttgcaaa cgcaagagca gcattagcag cagactgtag   2640
aagattagca ccatgtccaa caggagaggc agtagcaaca ccaggacacg gatgtggata   2700
tacacacatc atccacgcag tagcaccaag aagaccaaga gacccagcag cattagagga   2760
gggagaagca ttattagaga gagcatatag atcaatcgta gcattagcag cagcaagaag   2820
atgggcaaga gtagcatgtc cattattagg agcaggagta tatggatggt cagcagcaga   2880
gtcattaaga gcagcattag cagcaagaag aacagagcca gcagagagag tatcattaca   2940
catctgtcat ccagacagag caagattaag acacgcatca gtattagtag gagcaggatt   3000
agcagcaaga agagtatcac caccaccaac agagccatta gcatcatgtc cagcaggaga   3060
cccaggaaga ccagcacaga gatcagcatc accaccagca acaccattag gagatgcaac   3120
agcaccagag ccaagaggat gtcagggatg tgaattatgt agatatagaa gagtaacaaa   3180
tgacagagca tatgtaaact tatggttaga gagagacaga ggagcaacat catgggcaat   3240
gagaattcca gaggtagtag tatatggacc agagcactta gcaagacatt ttccattaaa   3300
ccactattca gtattaaagc cagcagaggt aagaccacca agaggaatgt gtggatcaga   3360
catgtggaga tgtagaggat ggcagggagt accacaggta agatgtacac catcaaacgc   3420
acacgcagca ttatgtagaa caggagtacc accaagagta tcaagaagag gaggagagtt   3480
agacccaaac acatgttggt taagagcagc agcaaacgta gcacaggcag caagagcatg   3540
tggagcatat agatcagcag gatgtccaag atgtgcatat ggaagagcat tatcagaagc   3600
aagaacacat aaggacttcg cagcattatc acagagatgg tcagcatcac acgcagatgc   3660
atcatcagac ggaacaggag atccattaga cccattaatg gagacagtag gatgtgcatg   3720
ttcaagagta tgggtaggat cagagcacga ggcaccacca gaccacttat tagtatcatt   3780
acacagagca ccaaatggac catggggagt agtattagag gtaagagcaa gaccagaggg   3840
aggaaaccca acaggacact tcgtatgtgc agtaggagga ggaccaagaa gagtatcaga   3900
cagaccacac ttatggttag cagtaccatt atcaagagga ggaggaacat gtgcagcaac   3960
agacgaggga ttagcacagg catattatga cgacttagag gtaagaagat taggagatga   4020
cgcaatggca agagcagcat tagcatcagt acaaagacca agaaaaggac catataatat   4080
cagagtatgg aacatggcag caggagcagg aaagacaaca agaatcttag cagcattcag   4140
aagagaagac ttatatgtat gtccaacaaa tgcattatta cacgagatcc aggcaaaatt   4200
aagagcaaga gatatcgaga tcaagaacgc agcaacatat gagagagcat taagaaaacc   4260
attagcagca tatagaagaa tctatatcga tgaggcattc acattaggag gagagtattg   4320
tgcattcgta gcatcacaaa caacagcaga ggtaatctgt gtaggagata gagaccagtg   4380
```

-continued

```
tggaccacac tatgcaaata actgtagaac accagtacca gacagatggc caacagagag   4440
atcaagacac acatggagat tcccagactg ttgggcagca agattaagag caggattaga   4500
ttatgacatc gagggagaga gaacaggaac attcgcatgt aacttatggg acggaagaca   4560
ggtagactta cacttagcat tctcaagaga aacagtaaga agattacacg aggcaggaat   4620
aagagcatat acagtaagag aggcacaggg aatgtcagta ggaacagcat gtatccatgt   4680
aggaagagac ggaacagacg tagcattagc attaacaaga gacttagcaa tcgtatcatt   4740
aacaagagca tcagacgcat tatatttaca cgagttagag gacggatcat taagagcagc   4800
aggattatca gcattcttag acgcaggagc attagcagag ttaaaggagg taccagcagg   4860
aattgacaga gtagtagcag tagagcaggc accaccacca ttaccaccag cagacggaat   4920
cccagaggca caagacgtac caccattctg tccaagaaca ttagaggagt tagtattcgg   4980
aagagcagga cacccacatt atgcagactt aaacagagta acagagggag aaagagaagt   5040
aagatatatg agaatctcaa gacacttatt aaacaagaat cacacagaga tgccaggaag   5100
agaaagagta ttatcagcag tatgtgcagt aagaagatat agagcaggag aggatggatc   5160
aacattaaga acagcagtag caagacagca cccaagacca tttagacaga tcccaccacc   5220
aagagtaaca gcaggagtag cacaggagtg gagaatgaga tatttaagag aaagaatcga   5280
cttaacagac gtatatagac agatgggagt agcagcaaga gagttaacag acagatatgc   5340
aagaagatat ccagagatct tcgcaggaat gtgtacagca cagtcattat cagtaccagc   5400
attcttaaaa gcaacattaa agtgtgtaga cgcagcatta ggaccaagag acacagagga   5460
ctgtcacgca gcacagggaa aagcaggatt agagatcaga gcatgggcaa aggagtgggt   5520
acaggtaatg tcaccacatt tcagagcaat ccagaagatc atcatgagag cattaagacc   5580
acaattctta gtagcagcag gacatagaga gccagaggta gatgcatggt ggcaggcaca   5640
ttatacaaca aacgcaatcg aggtagactt cacagagttc gacatgaacc agacattagc   5700
aacaagagac gtagagttag agatttcagc agcattatta ggattaccat gtgcagaaga   5760
ctatagagca ttaagagcag gatcatattg tacattaaga gaattaggat caacagagac   5820
aggatgtgag agaacatcag gagagccagc aagattatta cacaacacaa cagtagcaat   5880
gtgtatggca atgagaatgg taccaaaagg agtaagatgg gcaggaattt tccagggaga   5940
cgatatggta atcttcttac cagagggagc aagatcagca gcattaaagt ggacaccagc   6000
agaggtagga ttattcggat tccacatccc agtaaagcat gtatcaacac caacaccatc   6060
attctgtgga cacgtaggaa cagcagcagg attattccat gatgtaatgc accaggcaat   6120
caaggtatta tgtagaagat tcgacccaga cgtattagaa gaacagcagg tagcattatt   6180
agacagatta agaggagtat atgcagcatt accagacaca gtagcagcaa atgcagcata   6240
ttatgactat tcagcagaga gagtattagc aatcgtaaga gaattaacag catatgcaag   6300
aggaagagga ttagaccacc cagcaacaat cggagcatta gaggagattc agacaccata   6360
tgcaagagca aatttacacg acgcagacta acgcccctgt acgtggggcc tttaatctta   6420
cctactctaa ccaggtcatc acccaccgtt gtttcgccgc atctggtggg tacccaactt   6480
ttgccattcg ggagagcccc agggtgcccg aatggcatca acaacaccaa tcacaatgga   6540
ggacttacag aaggcattag agacacaatc aagagcatta agagcagaat tagcagcagg   6600
agcatcacag tcaagaagac caagaccacc aagacagaga gactcatcaa caacaggaga   6660
tgactcagga agagactcag gaggaccaag aagaagaaga ggaaacagag gaagaggaca   6720
```

```
gagaagagac tggtcaagag caccaccacc accagaggag agacaagaaa caagatcaca   6780
gacaccagca ccaaagccat caagagcacc accacaacag ccacaaccac caagaatgca   6840
aacaggaaga ggaggatcag caccaagacc agagttagga ccaccaacaa acccattcca   6900
agcagcagta gcaagaggat taagaccacc attacacgac ccagacacag aggcaccaac   6960
agaggcatgt gtaacatcat ggttatggtc agagggagaa ggagcagtat tttatagagt   7020
agacttacat ttcacaaact taggaacacc accattagac gaggacggaa gatgggaccc   7080
agcattaatg tataacccat gtggaccaga gccaccagca cacgtagtaa gagcatataa   7140
tcaaccagca ggagacgtaa gaggagtatg ggaaaaagga gagagaacat atgcagagca   7200
ggatttcaga gtaggaggaa gaagatggca cagattatta agaatgccag taagaggatt   7260
agacggagac tcagcaccat taccaccaca cacaacagag agaattgaga caagatcagc   7320
aagacatcca tggagaatca gattcggagc accacaggca ttcttagcag gattattatt   7380
agcagcagta gcagtaggaa cagcaagagc aggattacag ccaagagcag atatggcagc   7440
accaccaaga ttaccacagc caccaagagc acacggacag cattatggac accaccacca   7500
tcagttacca ttcttaggac acgacggaca tcatggagga acattaagag taggacagca   7560
tcacagaaac gcatcagacg tattaccagg acactggtta caaggaggat ggggatgtta   7620
taacttatca gactggcacc agggaacaca tgtatgtcac acaaagcaca tggacttttg   7680
gtgtgtagag cacgacagac caccaccagc aacaccaaga ccattaacaa cagcagcaaa   7740
ctcaagaaca gcagcaacac cagcaacagc accagcacca tgtcacgcag gattaaatga   7800
ctcatgtgga ggattcttat caggatgtgg accaatgaga ttaagacacg gagcagacac   7860
aagatgtgga agattaatct gtggattatc aacaacagca cagtatccac caacaagatt   7920
tggatgtgca atgagatggg gattaccacc atgggaatta gtagtattaa cagcaagacc   7980
agaagacgga tggacatgta gaggagtacc agcacaccca ggaacaagat gtccagaatt   8040
agtatcacca atgggaagag caacatgttc accagcatca gcattatggt tagcaacagc   8100
aaacgcatta tcattagatc acgcattagc agcattcgta ttattagtac catgggtatt   8160
aatattcatg gtatgtagaa gaacatgtag aagaagagga gcagcagcag cattaacagc   8220
agtagtatta cagggatata acccaccagc atatggagag gaggcattca catatttatg   8280
tacagcacca ggatgtgcaa cacaagcacc agtaccagta agattagcag gagtaagatt   8340
tgagtcaaag attgtagacg gaggatgttt tgcaccatgg gacttagagg caacaggagc   8400
atgtatttgt gagatcccaa cagatgtatc atgtgaggga ttaggagcat gggtaccaac   8460
agcaccatgt gcaagaatct ggaatggaac acagagagca tgtacattct gggcagtaaa   8520
cgcatattca tcaggaggat atgcacagtt agcatcatat ttcaacccag gaggatcata   8580
ttataagcag tatcacccaa cagcatgtga ggtagaacca gcattcggac actcagacgc   8640
agcatgttgg ggattcccaa cagacacagt aatgtcagta ttcgcattag catcatatgt   8700
acagcaccca cacaagacag taagagtaaa gttccataca gagacaagaa cagtatggca   8760
attatcagta gcaggagtat catgtaacgt aacaacagaa cacccattct gtaacagacc   8820
acacggacaa ttagaggtac aggtaccacc agacccagga gacttagtag agtatattat   8880
gaaccacaca ggaaatcagc agtcaagatg gggattagga tcaccaaatt gtcatggacc   8940
agattgggca tcaccagtat gtcaaagaca ttcaccagac tgttcaagat tagtaggagc   9000
aagaccagag agaccaagat taagattagt agacgcagac gacccattat taagaacagc   9060
accaggacca ggagaggtat gggtaagacc agtaatagga tcacaggcaa gaaagtgtgg   9120
```

```
attacacata agagcaggac catatggaca tgcaacagta gaaatgccag agtggatcca   9180

cgcacacaca acatcagacc catggcaccc accaggacca ttaggattaa agttcaagac   9240

agtaagacca gtagcattac caagaagatt agcaccacca agaaatgtaa gagtaacagg   9300

atgttatcag tgtggaacac cagcattagt agaaggatta gcaccaggag gaggaaattg   9360

tcatttaaca gtaaatggag aggatttagg agcattccca ccaggaaagt tcgtaacagc   9420

agcattatta aacacaccac caccatatca agtatcatgt ggaggagagt cagatagagc   9480

atcagcaaga gtaattgacc cagcagcaca atcatttaca ggagtagtat atggaacaca   9540

cacaacagca gtatcagaga caagacagac atgggcagag tgggcagcag cacattggtg   9600

gcagttaact ttaggagcaa tttgtgcatt attattagca ggattattag catgttgtgc   9660

aaaatgttta tattatttaa gaggagcaat agcaccaaga tagtgggccc ccgcgcgaaa   9720

cccgcactag cccactagat tcccgcacct gttgctgcat ag                      9762


<210> SEQ ID NO 19
<211> LENGTH: 2526
<212> TYPE: DNA
<213> ORGANISM: Varicella zoster
<220> FEATURE:
<221> NAME/KEY: CDS
<222> LOCATION: (1)..(2526)

<400> SEQUENCE: 19

atg ttt gcg cta gtt tta gcg gtg gta att ctt cct ctt tgg acc acg       48
Met Phe Ala Leu Val Leu Ala Val Val Ile Leu Pro Leu Trp Thr Thr
1               5                   10                  15

gct aat aaa tct tac gta aca cca acc cct gcg act cgc tct atc gga       96
Ala Asn Lys Ser Tyr Val Thr Pro Thr Pro Ala Thr Arg Ser Ile Gly
            20                  25                  30

cat atg tct gct ctt cta cga gaa tat tcc gac cgt aat atg tct ctg      144
His Met Ser Ala Leu Leu Arg Glu Tyr Ser Asp Arg Asn Met Ser Leu
        35                  40                  45

aaa tta gaa gcc ttt tat cct act ggt ttc gat gaa gaa ctc att aaa      192
Lys Leu Glu Ala Phe Tyr Pro Thr Gly Phe Asp Glu Glu Leu Ile Lys
    50                  55                  60

tca ctt cac tgg gga aat gat aga aaa cac gtt ttc ttg gtt att gtt      240
Ser Leu His Trp Gly Asn Asp Arg Lys His Val Phe Leu Val Ile Val
65                  70                  75                  80

aag gtt aac cct aca aca cac gaa gga gac gtc ggg ctg gtt ata ttt      288
Lys Val Asn Pro Thr Thr His Glu Gly Asp Val Gly Leu Val Ile Phe
                85                  90                  95

cca aaa tac ttg tta tcg cca tac cat ttc aaa gca gaa cat cga gca      336
Pro Lys Tyr Leu Leu Ser Pro Tyr His Phe Lys Ala Glu His Arg Ala
            100                 105                 110

ccg ttt cct gct gga cgt ttt gga ttt ctt agt cac cct gtg aca ccc      384
Pro Phe Pro Ala Gly Arg Phe Gly Phe Leu Ser His Pro Val Thr Pro
        115                 120                 125

gac gtg agc ttc ttt gac agt tcg ttt gcg ccg tat tta act acg caa      432
Asp Val Ser Phe Phe Asp Ser Ser Phe Ala Pro Tyr Leu Thr Thr Gln
    130                 135                 140

cat ctt gtt gcg ttt act acg ttc cca cca aac ccc ctt gta tgg cat      480
His Leu Val Ala Phe Thr Thr Phe Pro Pro Asn Pro Leu Val Trp His
145                 150                 155                 160

ttg gaa aga gct gag acc gca gca act gca gaa agg ccg ttt ggg gta      528
Leu Glu Arg Ala Glu Thr Ala Ala Thr Ala Glu Arg Pro Phe Gly Val
                165                 170                 175

agt ctt tta ccc gct cgc cca aca gtc ccc aag aat act att ctt gaa      576
```

-continued

```
Ser Leu Leu Pro Ala Arg Pro Thr Val Pro Lys Asn Thr Ile Leu Glu
            180                 185                 190

cat aaa gcg cat ttt gct aca tgg gat gcc ctt gcc cga cat act ttt      624
His Lys Ala His Phe Ala Thr Trp Asp Ala Leu Ala Arg His Thr Phe
        195                 200                 205

ttt tct gcc gaa gca att atc acc aac tca acg ttg aga ata cac gtt      672
Phe Ser Ala Glu Ala Ile Ile Thr Asn Ser Thr Leu Arg Ile His Val
    210                 215                 220

ccc ctt ttt ggg tcg gta tgg cca att cga tac tgg gcc acc ggt tcg      720
Pro Leu Phe Gly Ser Val Trp Pro Ile Arg Tyr Trp Ala Thr Gly Ser
225                 230                 235                 240

gtg ctt ctc aca agc gac tcg ggt cgt gtg gaa gta aat att ggt gta      768
Val Leu Leu Thr Ser Asp Ser Gly Arg Val Glu Val Asn Ile Gly Val
                245                 250                 255

gga ttt atg agc tcg ctc att tct tta tcc tct gga cta ccg ata gaa      816
Gly Phe Met Ser Ser Leu Ile Ser Leu Ser Ser Gly Leu Pro Ile Glu
            260                 265                 270

tta att gtt gta cca cat aca gta aaa ctg aac gcg gtt aca agc gac      864
Leu Ile Val Val Pro His Thr Val Lys Leu Asn Ala Val Thr Ser Asp
        275                 280                 285

acc aca tgg ttc cag cta aat cca ccg ggt ccg gat ccg ggg cca tct      912
Thr Thr Trp Phe Gln Leu Asn Pro Pro Gly Pro Asp Pro Gly Pro Ser
    290                 295                 300

tat cga gtt tat tta ctt gga cgt ggg ttg gat atg aat ttt tca aag      960
Tyr Arg Val Tyr Leu Leu Gly Arg Gly Leu Asp Met Asn Phe Ser Lys
305                 310                 315                 320

cat gct acg gtc gat ata tgc gca tat ccc gaa gag agt ttg gat tac     1008
His Ala Thr Val Asp Ile Cys Ala Tyr Pro Glu Glu Ser Leu Asp Tyr
                325                 330                 335

cgc tat cat tta tcc atg gcc cac acg gag gct ctg cgg atg aca acg     1056
Arg Tyr His Leu Ser Met Ala His Thr Glu Ala Leu Arg Met Thr Thr
            340                 345                 350

aag gcg gat caa cat gac ata aac gag gaa agc tat tac cat atc gcc     1104
Lys Ala Asp Gln His Asp Ile Asn Glu Glu Ser Tyr Tyr His Ile Ala
        355                 360                 365

gca aga ata gcc aca tca att ttt gcg ttg tcg gaa atg ggc cgt acc     1152
Ala Arg Ile Ala Thr Ser Ile Phe Ala Leu Ser Glu Met Gly Arg Thr
    370                 375                 380

aca gaa tat ttt ctg tta gat gag atc gta gat gtt cag tat caa tta     1200
Thr Glu Tyr Phe Leu Leu Asp Glu Ile Val Asp Val Gln Tyr Gln Leu
385                 390                 395                 400

aaa ttc ctt aat tac att tta atg cgg ata gga gca gga gct cat ccc     1248
Lys Phe Leu Asn Tyr Ile Leu Met Arg Ile Gly Ala Gly Ala His Pro
                405                 410                 415

aac act ata tcc gga acc tcg gat ctg atc ttt gcc gat cca tcg cag     1296
Asn Thr Ile Ser Gly Thr Ser Asp Leu Ile Phe Ala Asp Pro Ser Gln
            420                 425                 430

ctt cat gac gaa ctt tca ctt ctt ttt ggt cag gta aaa ccc gca aat     1344
Leu His Asp Glu Leu Ser Leu Leu Phe Gly Gln Val Lys Pro Ala Asn
        435                 440                 445

gtc gat tat ttt att tca tat gat gaa gcc cgt gat caa cta aag acc     1392
Val Asp Tyr Phe Ile Ser Tyr Asp Glu Ala Arg Asp Gln Leu Lys Thr
    450                 455                 460

gca tac gcg ctt tcc cgt ggt caa gac cat gtg aat gca ctt tct ctc     1440
Ala Tyr Ala Leu Ser Arg Gly Gln Asp His Val Asn Ala Leu Ser Leu
465                 470                 475                 480

gcc agg cgt gtt ata atg agc ata tac aag ggg ctg ctt gtg aag caa     1488
Ala Arg Arg Val Ile Met Ser Ile Tyr Lys Gly Leu Leu Val Lys Gln
                485                 490                 495
```

-continued

```
aat tta aat gct aca gag agg cag gct tta ttt ttt gcc tca atg att      1536
Asn Leu Asn Ala Thr Glu Arg Gln Ala Leu Phe Phe Ala Ser Met Ile
            500                 505                 510

tta tta aat ttc cgc gaa gga cta gaa aat tca tct cgg gta tta gac      1584
Leu Leu Asn Phe Arg Glu Gly Leu Glu Asn Ser Ser Arg Val Leu Asp
        515                 520                 525

ggt cgc aca act ttg ctt tta atg aca tcc atg tgt acg gca gct cac      1632
Gly Arg Thr Thr Leu Leu Leu Met Thr Ser Met Cys Thr Ala Ala His
    530                 535                 540

gcc acg caa gca gca ctt aac ata caa gaa ggc ctg gca tac tta aat      1680
Ala Thr Gln Ala Ala Leu Asn Ile Gln Glu Gly Leu Ala Tyr Leu Asn
545                 550                 555                 560

cct tca aaa cac atg ttt aca ata cca aac gta tac agt cct tgt atg      1728
Pro Ser Lys His Met Phe Thr Ile Pro Asn Val Tyr Ser Pro Cys Met
                565                 570                 575

ggt tcc ctt cgt aca gac ctc acg gaa gag att cat gtt atg aat ctc      1776
Gly Ser Leu Arg Thr Asp Leu Thr Glu Glu Ile His Val Met Asn Leu
            580                 585                 590

ctg tcg gca ata cca aca cgc cca gga ctt aac gag gta ttg cat acc      1824
Leu Ser Ala Ile Pro Thr Arg Pro Gly Leu Asn Glu Val Leu His Thr
        595                 600                 605

caa cta gac gaa tct gaa ata ttc gac gcg gca ttt aaa acc atg atg      1872
Gln Leu Asp Glu Ser Glu Ile Phe Asp Ala Ala Phe Lys Thr Met Met
    610                 615                 620

att ttt acc aca tgg act gcc aaa gat ttg cat ata ctc cac acc cat      1920
Ile Phe Thr Thr Trp Thr Ala Lys Asp Leu His Ile Leu His Thr His
625                 630                 635                 640

gta cca gaa gta ttt acg tgt caa gat gca gcc gcg cgt aac gga gaa      1968
Val Pro Glu Val Phe Thr Cys Gln Asp Ala Ala Ala Arg Asn Gly Glu
                645                 650                 655

tat gtg ctc att ctt cca gct gtc cag gga cac agt tat gtg att aca      2016
Tyr Val Leu Ile Leu Pro Ala Val Gln Gly His Ser Tyr Val Ile Thr
            660                 665                 670

cga aac aaa cct caa agg ggt ttg gta tat tcc ctg gca gat gtg gat      2064
Arg Asn Lys Pro Gln Arg Gly Leu Val Tyr Ser Leu Ala Asp Val Asp
        675                 680                 685

gta tat aac ccc ata tcc gtt gtt tat tta agc aag gat act tgc gtg      2112
Val Tyr Asn Pro Ile Ser Val Val Tyr Leu Ser Lys Asp Thr Cys Val
    690                 695                 700

tct gaa cat ggt gtc ata gag acg gtc gca ctg ccc cat ccg gac aat      2160
Ser Glu His Gly Val Ile Glu Thr Val Ala Leu Pro His Pro Asp Asn
705                 710                 715                 720

tta aaa gaa tgt ttg tat tgc gga agt gtt ttt ctt agg tat cta acc      2208
Leu Lys Glu Cys Leu Tyr Cys Gly Ser Val Phe Leu Arg Tyr Leu Thr
                725                 730                 735

acg ggg gcg att atg gat ata att att att gac agc aaa gat aca gaa      2256
Thr Gly Ala Ile Met Asp Ile Ile Ile Ile Asp Ser Lys Asp Thr Glu
            740                 745                 750

cga caa cta gcc gct atg gga aac tcc aca att cca ccc ttc aat cca      2304
Arg Gln Leu Ala Ala Met Gly Asn Ser Thr Ile Pro Pro Phe Asn Pro
        755                 760                 765

gac atg cac ggg gat gac tct aag gct gtg ttg ttg ttt cca aac gga      2352
Asp Met His Gly Asp Asp Ser Lys Ala Val Leu Leu Phe Pro Asn Gly
    770                 775                 780

act gtg gta acg ctt cta gga ttc gaa cga cga caa gcc ata cga atg      2400
Thr Val Val Thr Leu Leu Gly Phe Glu Arg Arg Gln Ala Ile Arg Met
785                 790                 795                 800

tcg gga caa tac ctt ggg gcc tct tta gga ggg gcg ttt ctg gcg gta      2448
Ser Gly Gln Tyr Leu Gly Ala Ser Leu Gly Gly Ala Phe Leu Ala Val
                805                 810                 815
```

```
gtg ggg ttt ggt att atc gga tgg atg tta tgt gga aat tcc cgc ctt      2496
Val Gly Phe Gly Ile Ile Gly Trp Met Leu Cys Gly Asn Ser Arg Leu
            820                 825                 830

cga gaa tat aat aaa ata cct ctg aca taa                              2526
Arg Glu Tyr Asn Lys Ile Pro Leu Thr
        835                 840


<210> SEQ ID NO 20
<211> LENGTH: 841
<212> TYPE: PRT
<213> ORGANISM: Varicella zoster

<400> SEQUENCE: 20

Met Phe Ala Leu Val Leu Ala Val Val Ile Leu Pro Leu Trp Thr Thr
1               5                   10                  15

Ala Asn Lys Ser Tyr Val Thr Pro Thr Pro Ala Thr Arg Ser Ile Gly
            20                  25                  30

His Met Ser Ala Leu Leu Arg Glu Tyr Ser Asp Arg Asn Met Ser Leu
        35                  40                  45

Lys Leu Glu Ala Phe Tyr Pro Thr Gly Phe Asp Glu Glu Leu Ile Lys
    50                  55                  60

Ser Leu His Trp Gly Asn Asp Arg Lys His Val Phe Leu Val Ile Val
65                  70                  75                  80

Lys Val Asn Pro Thr Thr His Glu Gly Asp Val Gly Leu Val Ile Phe
                85                  90                  95

Pro Lys Tyr Leu Leu Ser Pro Tyr His Phe Lys Ala Glu His Arg Ala
            100                 105                 110

Pro Phe Pro Ala Gly Arg Phe Gly Phe Leu Ser His Pro Val Thr Pro
        115                 120                 125

Asp Val Ser Phe Phe Asp Ser Ser Phe Ala Pro Tyr Leu Thr Thr Gln
    130                 135                 140

His Leu Val Ala Phe Thr Thr Phe Pro Pro Asn Pro Leu Val Trp His
145                 150                 155                 160

Leu Glu Arg Ala Glu Thr Ala Ala Thr Ala Glu Arg Pro Phe Gly Val
                165                 170                 175

Ser Leu Leu Pro Ala Arg Pro Thr Val Pro Lys Asn Thr Ile Leu Glu
            180                 185                 190

His Lys Ala His Phe Ala Thr Trp Asp Ala Leu Ala Arg His Thr Phe
        195                 200                 205

Phe Ser Ala Glu Ala Ile Ile Thr Asn Ser Thr Leu Arg Ile His Val
    210                 215                 220

Pro Leu Phe Gly Ser Val Trp Pro Ile Arg Tyr Trp Ala Thr Gly Ser
225                 230                 235                 240

Val Leu Leu Thr Ser Asp Ser Gly Arg Val Glu Val Asn Ile Gly Val
                245                 250                 255

Gly Phe Met Ser Ser Leu Ile Ser Leu Ser Ser Gly Leu Pro Ile Glu
            260                 265                 270

Leu Ile Val Val Pro His Thr Val Lys Leu Asn Ala Val Thr Ser Asp
        275                 280                 285

Thr Thr Trp Phe Gln Leu Asn Pro Pro Gly Pro Asp Pro Gly Pro Ser
    290                 295                 300

Tyr Arg Val Tyr Leu Leu Gly Arg Gly Leu Asp Met Asn Phe Ser Lys
305                 310                 315                 320

His Ala Thr Val Asp Ile Cys Ala Tyr Pro Glu Glu Ser Leu Asp Tyr
                325                 330                 335
```

```
Arg Tyr His Leu Ser Met Ala His Thr Glu Ala Leu Arg Met Thr Thr
            340                 345                 350

Lys Ala Asp Gln His Asp Ile Asn Glu Glu Ser Tyr Tyr His Ile Ala
        355                 360                 365

Ala Arg Ile Ala Thr Ser Ile Phe Ala Leu Ser Glu Met Gly Arg Thr
    370                 375                 380

Thr Glu Tyr Phe Leu Leu Asp Glu Ile Val Asp Val Gln Tyr Gln Leu
385                 390                 395                 400

Lys Phe Leu Asn Tyr Ile Leu Met Arg Ile Gly Ala Gly Ala His Pro
                405                 410                 415

Asn Thr Ile Ser Gly Thr Ser Asp Leu Ile Phe Ala Asp Pro Ser Gln
            420                 425                 430

Leu His Asp Glu Leu Ser Leu Leu Phe Gly Gln Val Lys Pro Ala Asn
        435                 440                 445

Val Asp Tyr Phe Ile Ser Tyr Asp Glu Ala Arg Asp Gln Leu Lys Thr
    450                 455                 460

Ala Tyr Ala Leu Ser Arg Gly Gln Asp His Val Asn Ala Leu Ser Leu
465                 470                 475                 480

Ala Arg Arg Val Ile Met Ser Ile Tyr Lys Gly Leu Leu Val Lys Gln
                485                 490                 495

Asn Leu Asn Ala Thr Glu Arg Gln Ala Leu Phe Phe Ala Ser Met Ile
            500                 505                 510

Leu Leu Asn Phe Arg Glu Gly Leu Glu Asn Ser Ser Arg Val Leu Asp
        515                 520                 525

Gly Arg Thr Thr Leu Leu Leu Met Thr Ser Met Cys Thr Ala Ala His
    530                 535                 540

Ala Thr Gln Ala Ala Leu Asn Ile Gln Glu Gly Leu Ala Tyr Leu Asn
545                 550                 555                 560

Pro Ser Lys His Met Phe Thr Ile Pro Asn Val Tyr Ser Pro Cys Met
                565                 570                 575

Gly Ser Leu Arg Thr Asp Leu Thr Glu Glu Ile His Val Met Asn Leu
            580                 585                 590

Leu Ser Ala Ile Pro Thr Arg Pro Gly Leu Asn Glu Val Leu His Thr
        595                 600                 605

Gln Leu Asp Glu Ser Glu Ile Phe Asp Ala Ala Phe Lys Thr Met Met
    610                 615                 620

Ile Phe Thr Thr Trp Thr Ala Lys Asp Leu His Ile Leu His Thr His
625                 630                 635                 640

Val Pro Glu Val Phe Thr Cys Gln Asp Ala Ala Ala Arg Asn Gly Glu
                645                 650                 655

Tyr Val Leu Ile Leu Pro Ala Val Gln Gly His Ser Tyr Val Ile Thr
            660                 665                 670

Arg Asn Lys Pro Gln Arg Gly Leu Val Tyr Ser Leu Ala Asp Val Asp
        675                 680                 685

Val Tyr Asn Pro Ile Ser Val Val Tyr Leu Ser Lys Asp Thr Cys Val
    690                 695                 700

Ser Glu His Gly Val Ile Glu Thr Val Ala Leu Pro His Pro Asp Asn
705                 710                 715                 720

Leu Lys Glu Cys Leu Tyr Cys Gly Ser Val Phe Leu Arg Tyr Leu Thr
                725                 730                 735

Thr Gly Ala Ile Met Asp Ile Ile Ile Ile Asp Ser Lys Asp Thr Glu
            740                 745                 750
```

-continued

```
Arg Gln Leu Ala Ala Met Gly Asn Ser Thr Ile Pro Pro Phe Asn Pro
        755                 760                 765

Asp Met His Gly Asp Asp Ser Lys Ala Val Leu Leu Phe Pro Asn Gly
    770                 775                 780

Thr Val Val Thr Leu Leu Gly Phe Glu Arg Arg Gln Ala Ile Arg Met
785                 790                 795                 800

Ser Gly Gln Tyr Leu Gly Ala Ser Leu Gly Gly Ala Phe Leu Ala Val
                805                 810                 815

Val Gly Phe Gly Ile Ile Gly Trp Met Leu Cys Gly Asn Ser Arg Leu
            820                 825                 830

Arg Glu Tyr Asn Lys Ile Pro Leu Thr
        835                 840
```

<210> SEQ ID NO 21
<211> LENGTH: 2526
<212> TYPE: DNA
<213> ORGANISM: Artificial
<220> FEATURE:
<223> OTHER INFORMATION: deoptimized VZV gH sequence

<400> SEQUENCE: 21

```
atgtttgctc tagtcctagc tgtcgtcatc ctacctctat ggactactgc taataaaagt     60

tacgtcactc ctactcctgc tactaggagt atcggccata tgagtgctct actaagggaa    120

tatagtgaca ggaatatgag tctaaaacta gaagcttttt atcctactgg cttcgatgaa    180

gaactaatca aaagtctaca ctggggcaat gataggaaac acgtcttcct agtcatcgtc    240

aaggtcaacc ctactactca cgaaggcgac gtcggcctag tcatctttcc taaataccta    300

ctaagtcctt accatttcaa agctgaacat agggctcctt ttcctgctgg caggtttggc    360

tttctaagtc accctgtcac tcctgacgtc agtttctttg acagtagttt tgctccttat    420

ctaactactc aacatctagt cgcttttact actttccctc ctaaccctct agtctggcat    480

ctagaaaggg ctgagactgc tgctactgct gaaaggcctt ttggcgtcag tctactacct    540

gctaggccta ctgtccctaa gaatactatc ctagaacata aagctcattt tgctacttgg    600

gatgctctag ctaggcatac ttttttttagt gctgaagcta tcatcactaa cagtactcta    660

aggatccacg tccctctatt tggcagtgtc tggcctatca ggtactgggc tactggcagt    720

gtcctactaa ctagtgacag tggcagggtc gaagtcaata tcggcgtcgg ctttatgagt    780

agtctaatca gtctaagtag tggcctacct atcgaactaa tcgtcgtccc tcatactgtc    840

aaactaaacg ctgtcactag tgacactact tggttccagc taaatcctcc tggccctgat    900

cctggcccta gttatagggt ctatctacta ggcaggggcc tagatatgaa ttttagtaag    960

catgctactg tcgatatctg cgcttatcct gaagagagtc tagattacag gtatcatcta   1020

agtatggctc acactgaggc tctaaggatg actactaagg ctgatcaaca tgacatcaac   1080

gaggaaagtt attaccatat cgctgctagg atcgctacta gtatctttgc tctaagtgaa   1140

atgggcagga ctactgaata ttttctacta gatgagatcg tcgatgtcca gtatcaacta   1200

aaattcctaa attacatcct aatgaggatc ggcgctggcg ctcatcctaa cactatcagt   1260

ggcactagtg atctaatctt tgctgatcct agtcagctac atgacgaact aagtctacta   1320

tttggccagg tcaaacctgc taatgtcgat tattttatca gttatgatga agctagggat   1380

caactaaaga ctgcttacgc tctaagtagg ggccaagacc atgtcaatgc tctaagtcta   1440

gctaggaggg tcatcatgag tatctacaag ggcctactag tcaagcaaaa tctaaatgct   1500

actgagaggc aggctctatt ttttgctagt atgatcctac taaatttcag ggaaggccta   1560
```

```
gaaaatagta gtagggtcct agacggcagg actactctac tactaatgac tagtatgtgt   1620

actgctgctc acgctactca agctgctcta aacatccaag aaggcctagc ttacctaaat   1680

cctagtaaac acatgtttac tatccctaac gtctacagtc cttgtatggg cagtctaagg   1740

actgacctaa ctgaagagat ccatgtcatg aatctactaa gtgctatccc tactaggcct   1800

ggcctaaacg aggtcctaca tactcaacta gacgaaagtg aaatcttcga cgctgctttt   1860

aaaactatga tgatctttac tacttggact gctaaagatc tacatatcct acacactcat   1920

gtccctgaag tctttacttg tcaagatgct gctgctagga acggcgaata tgtcctaatc   1980

ctacctgctg tccagggcca cagttatgtc atcactagga acaaacctca aaggggccta   2040

gtctatagtc tagctgatgt cgatgtctat aaccctatca gtgtcgtcta tctaagtaag   2100

gatacttgcg tcagtgaaca tggcgtcatc gagactgtcg ctctacctca tcctgacaat   2160

ctaaaagaat gtctatattg cggcagtgtc tttctaaggt atctaactac tggcgctatc   2220

atggatatca tcatcatcga cagtaaagat actgaaaggc aactagctgc tatgggcaac   2280

agtactatcc ctcctttcaa tcctgacatg cacggcgatg acagtaaggc tgtcctacta   2340

tttcctaacg gcactgtcgt cactctacta ggcttcgaaa ggaggcaagc tatcaggatg   2400

agtggccaat acctaggcgc tagtctaggc ggcgcttttc tagctgtcgt cggctttggc   2460

atcatcggct ggatgctatg tggcaatagt aggctaaggg aatataataa aatccctcta   2520

acttaa                                                              2526
```

<210> SEQ ID NO 22
<211> LENGTH: 1872
<212> TYPE: DNA
<213> ORGANISM: Varicella zoster
<220> FEATURE:
<221> NAME/KEY: CDS
<222> LOCATION: (1)..(1872)

<400> SEQUENCE: 22

```
atg ggg aca gtt aat aaa cct gtg gtg ggg gta ttg atg ggg ttc gga       48
Met Gly Thr Val Asn Lys Pro Val Val Gly Val Leu Met Gly Phe Gly
1               5                   10                  15

att atc acg gga acg ttg cgt ata acg aat ccg gtc aga gca tcc gtc       96
Ile Ile Thr Gly Thr Leu Arg Ile Thr Asn Pro Val Arg Ala Ser Val
            20                  25                  30

ttg cga tac gat gat ttt cac atc gat gaa gac aaa ctg gat aca aac      144
Leu Arg Tyr Asp Asp Phe His Ile Asp Glu Asp Lys Leu Asp Thr Asn
        35                  40                  45

tcc gta tat gag cct tac tac cat tca gat cat gcg gag tct tca tgg      192
Ser Val Tyr Glu Pro Tyr Tyr His Ser Asp His Ala Glu Ser Ser Trp
    50                  55                  60

gta aat cgg gga gag tct tcg cga aaa gcg tac gat cat aac tca cct      240
Val Asn Arg Gly Glu Ser Ser Arg Lys Ala Tyr Asp His Asn Ser Pro
65                  70                  75                  80

tat ata tgg cca cgt aat gat tat gat gga ttt tta gag aac gca cac      288
Tyr Ile Trp Pro Arg Asn Asp Tyr Asp Gly Phe Leu Glu Asn Ala His
                85                  90                  95

gaa cac cat ggg gtg tat aat cag ggc cgt ggt atc gat agc ggg gaa      336
Glu His His Gly Val Tyr Asn Gln Gly Arg Gly Ile Asp Ser Gly Glu
            100                 105                 110

cgg tta atg caa ccc aca caa atg tct gca cag gag gat ctt ggg gac      384
Arg Leu Met Gln Pro Thr Gln Met Ser Ala Gln Glu Asp Leu Gly Asp
        115                 120                 125

gat acg ggc atc cac gtt atc cct acg tta aac ggc gat gac aga cat      432
```

-continued

```
Asp Thr Gly Ile His Val Ile Pro Thr Leu Asn Gly Asp Asp Arg His
    130                 135                 140

aaa att gta aat gtg gac caa cgt caa tac ggt gac gtg ttt aaa gga      480
Lys Ile Val Asn Val Asp Gln Arg Gln Tyr Gly Asp Val Phe Lys Gly
145                 150                 155                 160

gat ctt aat cca aaa ccc caa ggc caa aga ctc att gag gtg tca gtg      528
Asp Leu Asn Pro Lys Pro Gln Gly Gln Arg Leu Ile Glu Val Ser Val
                165                 170                 175

gaa gaa aat cac ccg ttt act tta cgc gca ccg att cag cgg att tat      576
Glu Glu Asn His Pro Phe Thr Leu Arg Ala Pro Ile Gln Arg Ile Tyr
            180                 185                 190

gga gtc cgg tac acc gag act tgg agc ttt ttg ccg tca tta acc tgt      624
Gly Val Arg Tyr Thr Glu Thr Trp Ser Phe Leu Pro Ser Leu Thr Cys
        195                 200                 205

acg gga gac gca gcg ccc gcc atc cag cat ata tgt tta aaa cat aca      672
Thr Gly Asp Ala Ala Pro Ala Ile Gln His Ile Cys Leu Lys His Thr
    210                 215                 220

aca tgc ttt caa gac gtg gtg gtg gat gtg gat tgc gcg gaa aat act      720
Thr Cys Phe Gln Asp Val Val Val Asp Val Asp Cys Ala Glu Asn Thr
225                 230                 235                 240

aaa gag gat cag ttg gcc gaa atc agt tac cgt ttt caa ggt aag aag      768
Lys Glu Asp Gln Leu Ala Glu Ile Ser Tyr Arg Phe Gln Gly Lys Lys
                245                 250                 255

gaa gcg gac caa ccg tgg att gtt gta aac acg agc aca ctg ttt gat      816
Glu Ala Asp Gln Pro Trp Ile Val Val Asn Thr Ser Thr Leu Phe Asp
            260                 265                 270

gaa ctc gaa tta gac ccc ccc gag att gaa ccg ggt gtc ttg aaa gta      864
Glu Leu Glu Leu Asp Pro Pro Glu Ile Glu Pro Gly Val Leu Lys Val
        275                 280                 285

ctt cgg aca gaa aaa caa tac ttg ggt gtg tac att tgg aac atg cgc      912
Leu Arg Thr Glu Lys Gln Tyr Leu Gly Val Tyr Ile Trp Asn Met Arg
    290                 295                 300

ggc tcc gat ggt acg tct acc tac gcc acg ttt ttg gtc acc tgg aaa      960
Gly Ser Asp Gly Thr Ser Thr Tyr Ala Thr Phe Leu Val Thr Trp Lys
305                 310                 315                 320

ggg gat gaa aaa aca aga aac cct acg ccc gca gta act cct caa cca     1008
Gly Asp Glu Lys Thr Arg Asn Pro Thr Pro Ala Val Thr Pro Gln Pro
                325                 330                 335

aga ggg gct gag ttt cat atg tgg aat tac cac tcg cat gta ttt tca     1056
Arg Gly Ala Glu Phe His Met Trp Asn Tyr His Ser His Val Phe Ser
            340                 345                 350

gtt ggt gat acg ttt agc ttg gca atg cat ctt cag tat aag ata cat     1104
Val Gly Asp Thr Phe Ser Leu Ala Met His Leu Gln Tyr Lys Ile His
        355                 360                 365

gaa gcg cca ttt gat ttg ctg tta gag tgg ttg tat gtc ccc atc gat     1152
Glu Ala Pro Phe Asp Leu Leu Leu Glu Trp Leu Tyr Val Pro Ile Asp
    370                 375                 380

cct aca tgt caa cca atg cgg tta tat tct acg tgt ttg tat cat ccc     1200
Pro Thr Cys Gln Pro Met Arg Leu Tyr Ser Thr Cys Leu Tyr His Pro
385                 390                 395                 400

aac gca ccc caa tgc ctc tct cat atg aat tcc ggt tgt aca ttt acc     1248
Asn Ala Pro Gln Cys Leu Ser His Met Asn Ser Gly Cys Thr Phe Thr
                405                 410                 415

tcg cca cat tta gcc cag cgt gtt gca agc aca gtg tat caa aat tgt     1296
Ser Pro His Leu Ala Gln Arg Val Ala Ser Thr Val Tyr Gln Asn Cys
            420                 425                 430

gaa cat gca gat aac tac acc gca tat tgt ctg gga ata tct cat atg     1344
Glu His Ala Asp Asn Tyr Thr Ala Tyr Cys Leu Gly Ile Ser His Met
        435                 440                 445
```

-continued

```
gag cct agc ttt ggt cta atc tta cac gac ggg ggc acc acg tta aag      1392
Glu Pro Ser Phe Gly Leu Ile Leu His Asp Gly Gly Thr Thr Leu Lys
    450                 455                 460

ttt gta gat aca ccc gag agt ttg tcg gga tta tac gtt ttt gtg gtg      1440
Phe Val Asp Thr Pro Glu Ser Leu Ser Gly Leu Tyr Val Phe Val Val
465                 470                 475                 480

tat ttt aac ggg cat gtt gaa gcc gta gca tac act gtt gta tcc aca      1488
Tyr Phe Asn Gly His Val Glu Ala Val Ala Tyr Thr Val Val Ser Thr
                485                 490                 495

gta gat cat ttt gta aac gca att gaa gag cgt gga ttt ccg cca acg      1536
Val Asp His Phe Val Asn Ala Ile Glu Glu Arg Gly Phe Pro Pro Thr
            500                 505                 510

gcc ggt cag cca ccg gcg act act aaa ccc aag gaa att acc ccc gta      1584
Ala Gly Gln Pro Pro Ala Thr Thr Lys Pro Lys Glu Ile Thr Pro Val
        515                 520                 525

aac ccc gga acg tca cca ctt cta cga tat gcc gca tgg acc gga ggg      1632
Asn Pro Gly Thr Ser Pro Leu Leu Arg Tyr Ala Ala Trp Thr Gly Gly
    530                 535                 540

ctt gca gca gta gta ctt tta tgt ctc gta ata ttt tta atc tgt acg      1680
Leu Ala Ala Val Val Leu Leu Cys Leu Val Ile Phe Leu Ile Cys Thr
545                 550                 555                 560

gct aaa cga atg agg gtt aaa gcc tat agg gta gac aag tcc ccg tat      1728
Ala Lys Arg Met Arg Val Lys Ala Tyr Arg Val Asp Lys Ser Pro Tyr
                565                 570                 575

aac caa agc atg tat tac gct ggc ctt cca gtg gac gat ttc gag gac      1776
Asn Gln Ser Met Tyr Tyr Ala Gly Leu Pro Val Asp Asp Phe Glu Asp
            580                 585                 590

tcg gaa tct acg gat acg gaa gaa gag ttt ggt aac gcg att gga ggg      1824
Ser Glu Ser Thr Asp Thr Glu Glu Glu Phe Gly Asn Ala Ile Gly Gly
        595                 600                 605

agt cac ggg ggt tcg agt tac acg gtg tat ata gat aag acc cgg tga      1872
Ser His Gly Gly Ser Ser Tyr Thr Val Tyr Ile Asp Lys Thr Arg
    610                 615                 620


<210> SEQ ID NO 23
<211> LENGTH: 623
<212> TYPE: PRT
<213> ORGANISM: Varicella zoster

<400> SEQUENCE: 23

Met Gly Thr Val Asn Lys Pro Val Val Gly Val Leu Met Gly Phe Gly
1               5                   10                  15

Ile Ile Thr Gly Thr Leu Arg Ile Thr Asn Pro Val Arg Ala Ser Val
            20                  25                  30

Leu Arg Tyr Asp Asp Phe His Ile Asp Glu Asp Lys Leu Asp Thr Asn
        35                  40                  45

Ser Val Tyr Glu Pro Tyr Tyr His Ser Asp His Ala Glu Ser Ser Trp
    50                  55                  60

Val Asn Arg Gly Glu Ser Ser Arg Lys Ala Tyr Asp His Asn Ser Pro
65                  70                  75                  80

Tyr Ile Trp Pro Arg Asn Asp Tyr Asp Gly Phe Leu Glu Asn Ala His
                85                  90                  95

Glu His His Gly Val Tyr Asn Gln Gly Arg Gly Ile Asp Ser Gly Glu
            100                 105                 110

Arg Leu Met Gln Pro Thr Gln Met Ser Ala Gln Glu Asp Leu Gly Asp
        115                 120                 125

Asp Thr Gly Ile His Val Ile Pro Thr Leu Asn Gly Asp Asp Arg His
    130                 135                 140
```

-continued

```
Lys Ile Val Asn Val Asp Gln Arg Gln Tyr Gly Asp Val Phe Lys Gly
145                 150                 155                 160

Asp Leu Asn Pro Lys Pro Gln Gly Gln Arg Leu Ile Glu Val Ser Val
                165                 170                 175

Glu Glu Asn His Pro Phe Thr Leu Arg Ala Pro Ile Gln Arg Ile Tyr
            180                 185                 190

Gly Val Arg Tyr Thr Glu Thr Trp Ser Phe Leu Pro Ser Leu Thr Cys
        195                 200                 205

Thr Gly Asp Ala Ala Pro Ala Ile Gln His Ile Cys Leu Lys His Thr
    210                 215                 220

Thr Cys Phe Gln Asp Val Val Val Asp Val Asp Cys Ala Glu Asn Thr
225                 230                 235                 240

Lys Glu Asp Gln Leu Ala Glu Ile Ser Tyr Arg Phe Gln Gly Lys Lys
                245                 250                 255

Glu Ala Asp Gln Pro Trp Ile Val Val Asn Thr Ser Thr Leu Phe Asp
            260                 265                 270

Glu Leu Glu Leu Asp Pro Pro Glu Ile Glu Pro Gly Val Leu Lys Val
        275                 280                 285

Leu Arg Thr Glu Lys Gln Tyr Leu Gly Val Tyr Ile Trp Asn Met Arg
    290                 295                 300

Gly Ser Asp Gly Thr Ser Thr Tyr Ala Thr Phe Leu Val Thr Trp Lys
305                 310                 315                 320

Gly Asp Glu Lys Thr Arg Asn Pro Thr Pro Ala Val Thr Pro Gln Pro
                325                 330                 335

Arg Gly Ala Glu Phe His Met Trp Asn Tyr His Ser His Val Phe Ser
            340                 345                 350

Val Gly Asp Thr Phe Ser Leu Ala Met His Leu Gln Tyr Lys Ile His
        355                 360                 365

Glu Ala Pro Phe Asp Leu Leu Leu Glu Trp Leu Tyr Val Pro Ile Asp
    370                 375                 380

Pro Thr Cys Gln Pro Met Arg Leu Tyr Ser Thr Cys Leu Tyr His Pro
385                 390                 395                 400

Asn Ala Pro Gln Cys Leu Ser His Met Asn Ser Gly Cys Thr Phe Thr
                405                 410                 415

Ser Pro His Leu Ala Gln Arg Val Ala Ser Thr Val Tyr Gln Asn Cys
            420                 425                 430

Glu His Ala Asp Asn Tyr Thr Ala Tyr Cys Leu Gly Ile Ser His Met
        435                 440                 445

Glu Pro Ser Phe Gly Leu Ile Leu His Asp Gly Gly Thr Thr Leu Lys
    450                 455                 460

Phe Val Asp Thr Pro Glu Ser Leu Ser Gly Leu Tyr Val Phe Val Val
465                 470                 475                 480

Tyr Phe Asn Gly His Val Glu Ala Val Ala Tyr Thr Val Val Ser Thr
                485                 490                 495

Val Asp His Phe Val Asn Ala Ile Glu Glu Arg Gly Phe Pro Pro Thr
            500                 505                 510

Ala Gly Gln Pro Pro Ala Thr Thr Lys Pro Lys Glu Ile Thr Pro Val
        515                 520                 525

Asn Pro Gly Thr Ser Pro Leu Leu Arg Tyr Ala Ala Trp Thr Gly Gly
    530                 535                 540

Leu Ala Ala Val Val Leu Leu Cys Leu Val Ile Phe Leu Ile Cys Thr
545                 550                 555                 560

Ala Lys Arg Met Arg Val Lys Ala Tyr Arg Val Asp Lys Ser Pro Tyr
```

-continued

```
                565                 570                 575

Asn Gln Ser Met Tyr Tyr Ala Gly Leu Pro Val Asp Asp Phe Glu Asp
            580                 585                 590

Ser Glu Ser Thr Asp Thr Glu Glu Glu Phe Gly Asn Ala Ile Gly Gly
        595                 600                 605

Ser His Gly Gly Ser Ser Tyr Thr Val Tyr Ile Asp Lys Thr Arg
    610                 615                 620


<210> SEQ ID NO 24
<211> LENGTH: 1872
<212> TYPE: DNA
<213> ORGANISM: Artificial
<220> FEATURE:
<223> OTHER INFORMATION: deoptimized VZV gE sequence

<400> SEQUENCE: 24

atgggcactg tcaataaacc tgtcgtcggc gtcctaatgg gcttcggcat catcactggc     60

actctaagga tcactaatcc tgtcagggct agtgtcctaa ggtacgatga ttttcacatc    120

gatgaagaca aactagatac taacagtgtc tatgagcctt actaccatag tgatcatgct    180

gagagtagtt gggtcaatag gggcgagagt agtaggaaag cttacgatca taacagtcct    240

tatatctggc ctaggaatga ttatgatggc tttctagaga acgctcacga acaccatggc    300

gtctataatc agggcagggg catcgatagt ggcgaaaggc taatgcaacc tactcaaatg    360

agtgctcagg aggatctagg cgacgatact ggcatccacg tcatccctac tctaaacggc    420

gatgacaggc ataaaatcgt caatgtcgac caaaggcaat acggcgacgt ctttaaaggc    480

gatctaaatc ctaaacctca aggccaaagg ctaatcgagg tcagtgtcga agaaaatcac    540

ccttttactc taagggctcc tatccagagg atctatggcg tcaggtacac tgagacttgg    600

agttttctac ctagtctaac ttgtactggc gacgctgctc ctgctatcca gcatatctgt    660

ctaaaacata ctacttgctt tcaagacgtc gtcgtcgatg tcgattgcgc tgaaaatact    720

aaagaggatc agctagctga aatcagttac aggtttcaag gcaagaagga agctgaccaa    780

ccttggatcg tcgtcaacac tagtactcta tttgatgaac tagaactaga ccctcctgag    840

atcgaacctg gcgtcctaaa agtcctaagg actgaaaaac aatacctagg cgtctacatc    900

tggaacatga ggggcagtga tggcactagt acttacgcta cttttctagt cacttggaaa    960

ggcgatgaaa aaactaggaa ccctactcct gctgtcactc ctcaacctag ggggcgctgag  1020

tttcatatgt ggaattacca cagtcatgtc tttagtgtcg gcgatacttt tagtctagct   1080

atgcatctac agtataagat ccatgaagct ccttttgatc tactactaga gtggctatat   1140

gtccctatcg atcctacttg tcaacctatg aggctatata gtacttgtct atatcatcct   1200

aacgctcctc aatgcctaag tcatatgaat agtggctgta cttttactag tcctcatcta   1260

gctcagaggg tcgctagtac tgtctatcaa aattgtgaac atgctgataa ctacactgct   1320

tattgtctag gcatcagtca tatggagcct agttttggcc taatcctaca cgacggcggc   1380

actactctaa agtttgtcga tactcctgag agtctaagtg gcctatacgt ctttgtcgtc   1440

tattttaacg gccatgtcga agctgtcgct tacactgtcg tcagtactgt cgatcatttt   1500

gtcaacgcta tcgaagagag gggctttcct cctactgctg gccagcctcc tgctactact   1560

aaacctaagg aaatcactcc tgtcaaccct ggcactagtc ctctactaag gtatgctgct   1620

tggactggcg gcctagctgc tgtcgtccta ctatgtctag tcatctttct aatctgtact   1680

gctaaaagga tgagggtcaa agcttatagg gtcgacaaga gtccttataa ccaaagtatg   1740
```

```
tattacgctg gcctacctgt cgacgatttc gaggacagtg aaagtactga tactgaagaa   1800

gagtttggca acgctatcgg cggcagtcac ggcggcagta gttacactgt ctatatcgat   1860

aagactaggt ga                                                       1872


<210> SEQ ID NO 25
<211> LENGTH: 2373
<212> TYPE: DNA
<213> ORGANISM: Measles virus strain Moraten
<220> FEATURE:
<221> NAME/KEY: CDS
<222> LOCATION: (575)..(2236)

<400> SEQUENCE: 25

agggccaagg aacatacaca cccaacagaa cccagacccc ggcccacggc gccgcgcccc     60

caacccccga caaccagagg gagcccccaa ccaatcccgc cggctccccc ggtgcccaca    120

ggcagggaca ccaacccccg aacagaccca gcacccaacc atcgacaatc caagacgggg    180

gggccccccc aaaaaaaggc ccccaggggc cgacagccag caccgcgagg aagcccaccc    240

accccacaca cgaccacggc aaccaaacca gaacccagac caccctgggc caccagctcc    300

cagactcggc catcaccccg cagaaaggaa aggccacaac ccgcgcaccc cagccccgat    360

ccggcgggga gccacccaac ccgaaccagc acccaagagc gatccccgaa ggacccccga    420

accgcaaagg acatcagtat cccacagcct ctccaagtcc cccggtctcc tcctcttctc    480

gaagggacca aaagatcaat ccaccacacc cgacgacact caactcccca cccctaaagg    540

agacaccggg aatcccagaa tcaagactca tcca atg tcc atc atg ggt ctc aag    595
                                      Met Ser Ile Met Gly Leu Lys
                                      1               5

gtg aac gtc tct gcc ata ttc atg gca gta ctg tta act ctc caa aca      643
Val Asn Val Ser Ala Ile Phe Met Ala Val Leu Leu Thr Leu Gln Thr
        10                  15                  20

ccc acc ggt caa atc cat tgg ggc aat ctc tct aag ata ggg gtg gta      691
Pro Thr Gly Gln Ile His Trp Gly Asn Leu Ser Lys Ile Gly Val Val
    25                  30                  35

gga ata gga agt gca agc tac aaa gtt atg act cgt tcc agc cat caa      739
Gly Ile Gly Ser Ala Ser Tyr Lys Val Met Thr Arg Ser Ser His Gln
40                  45                  50                  55

tca tta gtc ata aaa tta atg ccc aat ata act ctc ctc aat aac tgc      787
Ser Leu Val Ile Lys Leu Met Pro Asn Ile Thr Leu Leu Asn Asn Cys
                60                  65                  70

acg agg gta gag att gca gaa tac agg aga cta ctg aga aca gtt ttg      835
Thr Arg Val Glu Ile Ala Glu Tyr Arg Arg Leu Leu Arg Thr Val Leu
            75                  80                  85

gaa cca att aga gat gca ctt aat gca atg acc cag aat ata aga ccg      883
Glu Pro Ile Arg Asp Ala Leu Asn Ala Met Thr Gln Asn Ile Arg Pro
        90                  95                  100

gtt cag agt gta gct tca agt agg aga cac aag aga ttt gcg gga gta      931
Val Gln Ser Val Ala Ser Ser Arg Arg His Lys Arg Phe Ala Gly Val
    105                 110                 115

gtc ctg gca ggt gcg gcc cta ggc gtt gcc aca gct gct cag ata aca      979
Val Leu Ala Gly Ala Ala Leu Gly Val Ala Thr Ala Ala Gln Ile Thr
120                 125                 130                 135

gcc ggc att gca ctt cac cag tcc atg ctg aac tct caa gcc atc gac     1027
Ala Gly Ile Ala Leu His Gln Ser Met Leu Asn Ser Gln Ala Ile Asp
                140                 145                 150

aat ctg aga gcg agc ctg gaa act act aat cag gca att gag aca atc     1075
Asn Leu Arg Ala Ser Leu Glu Thr Thr Asn Gln Ala Ile Glu Thr Ile
            155                 160                 165
```

-continued

```
aga caa gca ggg cag gag atg ata ttg gct gtt cag ggt gtc caa gac      1123
Arg Gln Ala Gly Gln Glu Met Ile Leu Ala Val Gln Gly Val Gln Asp
        170                 175                 180

tac atc aat aat gag ctg ata ccg tct atg aac caa cta tct tgt gat      1171
Tyr Ile Asn Asn Glu Leu Ile Pro Ser Met Asn Gln Leu Ser Cys Asp
    185                 190                 195

tta atc ggc cag aag ctc ggg ctc aaa ttg ctc aga tac tat aca gaa      1219
Leu Ile Gly Gln Lys Leu Gly Leu Lys Leu Leu Arg Tyr Tyr Thr Glu
200                 205                 210                 215

atc ctg tca tta ttt ggc ccc agt tta cgg gac ccc ata tct gcg gag      1267
Ile Leu Ser Leu Phe Gly Pro Ser Leu Arg Asp Pro Ile Ser Ala Glu
                220                 225                 230

ata tct atc cag gct ttg agc tat gcg ctt gga gga gac atc aat aag      1315
Ile Ser Ile Gln Ala Leu Ser Tyr Ala Leu Gly Gly Asp Ile Asn Lys
            235                 240                 245

gtg tta gaa aag ctc gga tac agt gga ggt gat tta ctg ggc atc tta      1363
Val Leu Glu Lys Leu Gly Tyr Ser Gly Gly Asp Leu Leu Gly Ile Leu
        250                 255                 260

gag agc gga gga ata aag gcc cgg ata act cac gtc gac aca gag tcc      1411
Glu Ser Gly Gly Ile Lys Ala Arg Ile Thr His Val Asp Thr Glu Ser
    265                 270                 275

tac ttc att gtc ctc agt ata gcc tat ccg acg ctg tcc gag att aag      1459
Tyr Phe Ile Val Leu Ser Ile Ala Tyr Pro Thr Leu Ser Glu Ile Lys
280                 285                 290                 295

ggg gtg att gtc cac cgg cta gag ggg gtc tcg tac aac ata ggc tct      1507
Gly Val Ile Val His Arg Leu Glu Gly Val Ser Tyr Asn Ile Gly Ser
                300                 305                 310

caa gag tgg tat acc act gtg ccc aag tat gtt gca acc caa ggg tac      1555
Gln Glu Trp Tyr Thr Thr Val Pro Lys Tyr Val Ala Thr Gln Gly Tyr
            315                 320                 325

ctt atc tcg aat ttt gat gag tca tcg tgt act ttc atg cca gag ggg      1603
Leu Ile Ser Asn Phe Asp Glu Ser Ser Cys Thr Phe Met Pro Glu Gly
        330                 335                 340

act gtg tgc agc caa aat gcc ttg tac ccg atg agt cct ctg ctc caa      1651
Thr Val Cys Ser Gln Asn Ala Leu Tyr Pro Met Ser Pro Leu Leu Gln
    345                 350                 355

gaa tgc ctc cgg ggg tac acc aag tcc tgt gct cgt aca ctc gta tcc      1699
Glu Cys Leu Arg Gly Tyr Thr Lys Ser Cys Ala Arg Thr Leu Val Ser
360                 365                 370                 375

ggg tct ttt ggg aac cgg ttc att tta tca caa ggg aac cta ata gcc      1747
Gly Ser Phe Gly Asn Arg Phe Ile Leu Ser Gln Gly Asn Leu Ile Ala
                380                 385                 390

aat tgt gca tca atc ctt tgc aag tgt tac aca aca gga acg atc att      1795
Asn Cys Ala Ser Ile Leu Cys Lys Cys Tyr Thr Thr Gly Thr Ile Ile
            395                 400                 405

aat caa gac cct gac aag atc cta aca tac att gct gcc gat cac tgc      1843
Asn Gln Asp Pro Asp Lys Ile Leu Thr Tyr Ile Ala Ala Asp His Cys
        410                 415                 420

ccg gta gtc gag gtg aac ggc gtg acc atc caa gtc ggg agc agg agg      1891
Pro Val Val Glu Val Asn Gly Val Thr Ile Gln Val Gly Ser Arg Arg
    425                 430                 435

tat cca gac gct gtg tac ttg cac aga att gac ctc ggt cct ccc ata      1939
Tyr Pro Asp Ala Val Tyr Leu His Arg Ile Asp Leu Gly Pro Pro Ile
440                 445                 450                 455

tca ttg gag agg ttg gac gta ggg aca aat ctg ggg aat gca att gct      1987
Ser Leu Glu Arg Leu Asp Val Gly Thr Asn Leu Gly Asn Ala Ile Ala
                460                 465                 470

aag ttg gag gat gcc aag gaa ttg ttg gag tca tcg gac cag ata ttg      2035
Lys Leu Glu Asp Ala Lys Glu Leu Leu Glu Ser Ser Asp Gln Ile Leu
            475                 480                 485
```

```
agg agt atg aaa ggt tta tcg agc act agc ata gtc tac atc ctg att      2083
Arg Ser Met Lys Gly Leu Ser Ser Thr Ser Ile Val Tyr Ile Leu Ile
        490                 495                 500

gca gtg tgt ctt gga ggg ttg ata ggg atc ccc gct tta ata tgt tgc      2131
Ala Val Cys Leu Gly Gly Leu Ile Gly Ile Pro Ala Leu Ile Cys Cys
    505                 510                 515

tgc agg ggg cgt tgt aac aaa aag gga gaa caa gtt ggt atg tca aga      2179
Cys Arg Gly Arg Cys Asn Lys Lys Gly Glu Gln Val Gly Met Ser Arg
520                 525                 530                 535

cca ggc cta aag cct gat ctt acg gga aca tca aaa tcc tat gta agg      2227
Pro Gly Leu Lys Pro Asp Leu Thr Gly Thr Ser Lys Ser Tyr Val Arg
                540                 545                 550

tcg ctc tga tcctctacaa ctcttgaaac acaaatgtcc cacaagtctc             2276
Ser Leu

ctcttcgtca tcaagcaacc accgcaccca gcatcaagcc cacctgaaat tatctccggc   2336

ttccctctgg ccgaacaata tcggtagtta atcaaaa                            2373


<210> SEQ ID NO 26
<211> LENGTH: 553
<212> TYPE: PRT
<213> ORGANISM: Measles virus strain Moraten

<400> SEQUENCE: 26

Met Ser Ile Met Gly Leu Lys Val Asn Val Ser Ala Ile Phe Met Ala
1               5                   10                  15

Val Leu Leu Thr Leu Gln Thr Pro Thr Gly Gln Ile His Trp Gly Asn
            20                  25                  30

Leu Ser Lys Ile Gly Val Val Gly Ile Gly Ser Ala Ser Tyr Lys Val
        35                  40                  45

Met Thr Arg Ser Ser His Gln Ser Leu Val Ile Lys Leu Met Pro Asn
    50                  55                  60

Ile Thr Leu Leu Asn Asn Cys Thr Arg Val Glu Ile Ala Glu Tyr Arg
65                  70                  75                  80

Arg Leu Leu Arg Thr Val Leu Glu Pro Ile Arg Asp Ala Leu Asn Ala
                85                  90                  95

Met Thr Gln Asn Ile Arg Pro Val Gln Ser Val Ala Ser Ser Arg Arg
            100                 105                 110

His Lys Arg Phe Ala Gly Val Val Leu Ala Gly Ala Ala Leu Gly Val
        115                 120                 125

Ala Thr Ala Ala Gln Ile Thr Ala Gly Ile Ala Leu His Gln Ser Met
    130                 135                 140

Leu Asn Ser Gln Ala Ile Asp Asn Leu Arg Ala Ser Leu Glu Thr Thr
145                 150                 155                 160

Asn Gln Ala Ile Glu Thr Ile Arg Gln Ala Gly Gln Glu Met Ile Leu
                165                 170                 175

Ala Val Gln Gly Val Gln Asp Tyr Ile Asn Asn Glu Leu Ile Pro Ser
            180                 185                 190

Met Asn Gln Leu Ser Cys Asp Leu Ile Gly Gln Lys Leu Gly Leu Lys
        195                 200                 205

Leu Leu Arg Tyr Tyr Thr Glu Ile Leu Ser Leu Phe Gly Pro Ser Leu
    210                 215                 220

Arg Asp Pro Ile Ser Ala Glu Ile Ser Ile Gln Ala Leu Ser Tyr Ala
225                 230                 235                 240

Leu Gly Gly Asp Ile Asn Lys Val Leu Glu Lys Leu Gly Tyr Ser Gly
                245                 250                 255
```

```
Gly Asp Leu Leu Gly Ile Leu Glu Ser Gly Gly Ile Lys Ala Arg Ile
            260                 265                 270

Thr His Val Asp Thr Glu Ser Tyr Phe Ile Val Leu Ser Ile Ala Tyr
        275                 280                 285

Pro Thr Leu Ser Glu Ile Lys Gly Val Ile Val His Arg Leu Glu Gly
    290                 295                 300

Val Ser Tyr Asn Ile Gly Ser Gln Glu Trp Tyr Thr Thr Val Pro Lys
305                 310                 315                 320

Tyr Val Ala Thr Gln Gly Tyr Leu Ile Ser Asn Phe Asp Glu Ser Ser
                325                 330                 335

Cys Thr Phe Met Pro Glu Gly Thr Val Cys Ser Gln Asn Ala Leu Tyr
            340                 345                 350

Pro Met Ser Pro Leu Leu Gln Glu Cys Leu Arg Gly Tyr Thr Lys Ser
        355                 360                 365

Cys Ala Arg Thr Leu Val Ser Gly Ser Phe Gly Asn Arg Phe Ile Leu
    370                 375                 380

Ser Gln Gly Asn Leu Ile Ala Asn Cys Ala Ser Ile Leu Cys Lys Cys
385                 390                 395                 400

Tyr Thr Thr Gly Thr Ile Ile Asn Gln Asp Pro Asp Lys Ile Leu Thr
                405                 410                 415

Tyr Ile Ala Ala Asp His Cys Pro Val Val Glu Val Asn Gly Val Thr
            420                 425                 430

Ile Gln Val Gly Ser Arg Arg Tyr Pro Asp Ala Val Tyr Leu His Arg
        435                 440                 445

Ile Asp Leu Gly Pro Pro Ile Ser Leu Glu Arg Leu Asp Val Gly Thr
    450                 455                 460

Asn Leu Gly Asn Ala Ile Ala Lys Leu Glu Asp Ala Lys Glu Leu Leu
465                 470                 475                 480

Glu Ser Ser Asp Gln Ile Leu Arg Ser Met Lys Gly Leu Ser Ser Thr
                485                 490                 495

Ser Ile Val Tyr Ile Leu Ile Ala Val Cys Leu Gly Gly Leu Ile Gly
            500                 505                 510

Ile Pro Ala Leu Ile Cys Cys Cys Arg Gly Arg Cys Asn Lys Lys Gly
        515                 520                 525

Glu Gln Val Gly Met Ser Arg Pro Gly Leu Lys Pro Asp Leu Thr Gly
    530                 535                 540

Thr Ser Lys Ser Tyr Val Arg Ser Leu
545                 550
```

<210> SEQ ID NO 27
<211> LENGTH: 2373
<212> TYPE: DNA
<213> ORGANISM: Artificial
<220> FEATURE:
<223> OTHER INFORMATION: deoptimized measles F sequence

<400> SEQUENCE: 27

```
agggccaagg aacatacaca cccaacagaa cccagacccc ggcccacggc gccgcgcccc      60

caaccccga caaccagagg gagcccccaa ccaatcccgc cggctccccc ggtgcccaca     120

ggcagggaca ccaacccccg aacagaccca gcacccaacc atcgacaatc caagacgggg     180

gggccccccc aaaaaaaggc ccccaggggc cgacagccag caccgcgagg aagcccaccc     240

accccacaca cgaccacggc aaccaaacca gaacccagac caccctgggc caccagctcc     300

cagactcggc catcaccccg cagaaaggaa aggccacaac ccgcgcaccc cagccccgat     360
```

```
ccggcgggga gccacccaac ccgaaccagc acccaagagc gatccccgaa ggacccccga    420
accgcaaagg acatcagtat cccacagcct ctccaagtcc cccggtctcc tcctcttctc    480
gaagggacca aaagatcaat ccaccacacc cgacgacact caactcccca cccctaaagg    540
agacaccggg aatcccagaa tcaagactca tccaatgtcg atcatgggcc ttaaggtaaa    600
cgtatcggcg atattcatgg cggtacttct tacgcttcaa acgccgacgg gccaaatcca    660
ttggggcaat ctttcgaaga taggcgtagt aggcataggc tcggcgtcgt acaaagtaat    720
gacgcgctcg tcgcatcaat cgcttgtaat aaaacttatg ccgaatataa cgcttcttaa    780
taactgcacg cgcgtagaga ttgcggaata ccgccgcctt cttcgcacgg tacttgaacc    840
gattcgcgat gcgcttaatg cgatgacgca gaatatacgc ccggtacagt cggtagcgtc    900
gtcgcgccgc cacaagcgct ttgcgggcgt agtacttgcg ggcgcggcgc ttggcgtagc    960
gacggcggcg cagataacgg cgggcattgc gcttcaccag tcgatgctta actcgcaagc   1020
gatcgacaat cttcgcgcgt cgcttgaaac gacgaatcag gcgattgaga cgatccgcca   1080
agcgggccag gagatgatac ttgcggtaca gggcgtacaa gactacatca ataatgagct   1140
tataccgtcg atgaaccaac tttcgtgtga tcttatcggc cagaagcttg gccttaaact   1200
tcttcgctac tatacggaaa tcctttcgct ttttggcccg tcgcttcggg acccgatatc   1260
ggcggagata tcgatccagg cgctttcgta tgcgcttggc ggcgacatca ataaggtact   1320
tgaaaagctt ggctactcgg gcggcgatct tcttggcatc cttgagtcgg gcggcataaa   1380
ggcgcgcata acgcacgtag acacggagtc gtacttcatt gtactttcga tagcgtatcc   1440
gacgctttcg gagattaagg gcgtaattgt acaccgcctt gagggcgtat cgtacaacat   1500
aggctcgcaa gagtggtata cgacggtacc gaagtatgta gcgacgcaag gctaccttat   1560
ctcgaatttt gatgagtcgt cgtgtacgtt catgccggag ggcacggtat gctcgcaaaa   1620
tgcgctttac ccgatgtcgc cgcttcttca agaatgcctt cgcggctaca cgaagtcgtg   1680
tgcgcgcacg cttgtatcgg gctcgtttgg caaccgcttc attctttcgc aaggcaacct   1740
tatagcgaat tgtgcgtcga tcctttgcaa gtgttacacg acgggcacga tcattaatca   1800
agacccggac aagatcctta cgtacattgc ggcggatcac tgcccggtag tagaggtaaa   1860
cggcgtaacg atccaagtag gctcgcgccg ctatccggac gcggtatacc ttcaccgcat   1920
tgaccttggc ccgccgatat cgcttgagcg ccttgacgta ggcacgaatc ttggcaatgc   1980
gattgcgaag cttgaggatg cgaaggaact tcttgagtcg tcggaccaga tacttcgctc   2040
gatgaaaggc ctttcgtcga cgtcgatagt atacatcctt attgcggtat gtcttggcgg   2100
ccttataggc atcccggcgc ttatatgttg ctgccgcggc cgctgtaaca aaaagggcga   2160
acaagtaggc atgtcgcgcc cgggccttaa gccggatctt acgggcacgt cgaaatcgta   2220
tgtacgctcg ctttgatcct ctacaactct tgaaacacaa atgtcccaca agtctcctct   2280
tcgtcatcaa gcaaccaccg cacccagcat caagcccacc tgaaattatc tccggcttcc   2340
ctctggccga acaatatcgg tagttaatca aaa                                2373
```

<210> SEQ ID NO 28
<211> LENGTH: 1958
<212> TYPE: DNA
<213> ORGANISM: Measles virus strain Moraten
<220> FEATURE:
<221> NAME/KEY: CDS
<222> LOCATION: (21)..(1874)

<400> SEQUENCE: 28

-continued

```
agggtgcaag atcatccaca atg tca cca caa cga gac cgg ata aat gcc ttc      53
                     Met Ser Pro Gln Arg Asp Arg Ile Asn Ala Phe
                     1               5                   10

tac aaa gat aac ccc cat ccc aag gga agt agg ata gtc att aac aga       101
Tyr Lys Asp Asn Pro His Pro Lys Gly Ser Arg Ile Val Ile Asn Arg
            15                  20                  25

gaa cat ctt atg att gat aga cct tat gtt ttg ctg gct gtt ctg ttt       149
Glu His Leu Met Ile Asp Arg Pro Tyr Val Leu Leu Ala Val Leu Phe
        30                  35                  40

gtc atg ttt ctg agc ttg atc ggg ttg cta gcc att gca ggc att aga       197
Val Met Phe Leu Ser Leu Ile Gly Leu Leu Ala Ile Ala Gly Ile Arg
    45                  50                  55

ctt cat cgg gca gcc atc tac acc gca gag atc cat aaa agc ctc agc       245
Leu His Arg Ala Ala Ile Tyr Thr Ala Glu Ile His Lys Ser Leu Ser
60                  65                  70                  75

acc aat cta gat gta act aac tca atc gag cat cag gtc aag gac gtg       293
Thr Asn Leu Asp Val Thr Asn Ser Ile Glu His Gln Val Lys Asp Val
                80                  85                  90

ctg aca cca ctc ttc aaa atc atc ggt gat gaa gtg ggc ctg agg aca       341
Leu Thr Pro Leu Phe Lys Ile Ile Gly Asp Glu Val Gly Leu Arg Thr
            95                  100                 105

cct cag aga ttc act gac cta gtg aaa tta atc tct gac aag att aaa       389
Pro Gln Arg Phe Thr Asp Leu Val Lys Leu Ile Ser Asp Lys Ile Lys
        110                 115                 120

ttc ctt aat ccg gat agg gag tac gac ttc aga gat ctc act tgg tgt       437
Phe Leu Asn Pro Asp Arg Glu Tyr Asp Phe Arg Asp Leu Thr Trp Cys
    125                 130                 135

atc aac ccg cca gag aga atc aaa ttg gat tat gat caa tac tgt gca       485
Ile Asn Pro Pro Glu Arg Ile Lys Leu Asp Tyr Asp Gln Tyr Cys Ala
140                 145                 150                 155

gat gtg gct gct gaa gag ctc atg aat gca ttg gtg aac tca act cta       533
Asp Val Ala Ala Glu Glu Leu Met Asn Ala Leu Val Asn Ser Thr Leu
                160                 165                 170

ctg gag acc aga aca acc aat cag ttc cta gct gtc tca aag gga aac       581
Leu Glu Thr Arg Thr Thr Asn Gln Phe Leu Ala Val Ser Lys Gly Asn
            175                 180                 185

tgc tca ggg ccc act aca atc aga ggt caa ttc tca aac atg tcg ctg       629
Cys Ser Gly Pro Thr Thr Ile Arg Gly Gln Phe Ser Asn Met Ser Leu
        190                 195                 200

tcc ctg tta gac ttg tat tta ggt cga ggt tac aat gtg tca tct ata       677
Ser Leu Leu Asp Leu Tyr Leu Gly Arg Gly Tyr Asn Val Ser Ser Ile
    205                 210                 215

gtc act atg aca tcc cag gga atg tat ggg gga act tac cta gtg gaa       725
Val Thr Met Thr Ser Gln Gly Met Tyr Gly Gly Thr Tyr Leu Val Glu
220                 225                 230                 235

aag cct aat ctg agc agc aaa agg tca gag ttg tca caa ctg agc atg       773
Lys Pro Asn Leu Ser Ser Lys Arg Ser Glu Leu Ser Gln Leu Ser Met
                240                 245                 250

tac cga gtg ttt gaa gta ggt gtt atc aga aat ccg ggt ttg ggg gct       821
Tyr Arg Val Phe Glu Val Gly Val Ile Arg Asn Pro Gly Leu Gly Ala
            255                 260                 265

ccg gtg ttc cat atg aca aac tat ctt gag caa cca gtc agt aat gat       869
Pro Val Phe His Met Thr Asn Tyr Leu Glu Gln Pro Val Ser Asn Asp
        270                 275                 280

ctc agc aac tgt atg gtg gct ttg ggg gag ctc aaa ctc gca gcc ctt       917
Leu Ser Asn Cys Met Val Ala Leu Gly Glu Leu Lys Leu Ala Ala Leu
    285                 290                 295

tgt cac ggg gaa gat tct atc aca att ccc tat cag gga tca ggg aaa       965
Cys His Gly Glu Asp Ser Ile Thr Ile Pro Tyr Gln Gly Ser Gly Lys
```

-continued

```
300                 305                 310                 315

ggt gtc agc ttc cag ctc gtc aag cta ggt gtc tgg aaa tcc cca acc      1013
Gly Val Ser Phe Gln Leu Val Lys Leu Gly Val Trp Lys Ser Pro Thr
                320                 325                 330

gac atg caa tcc tgg gtc ccc tta tca acg gat gat cca gtg ata gac      1061
Asp Met Gln Ser Trp Val Pro Leu Ser Thr Asp Asp Pro Val Ile Asp
            335                 340                 345

agg ctt tac ctc tca tct cac aga ggt gtt atc gct gac aat caa gca      1109
Arg Leu Tyr Leu Ser Ser His Arg Gly Val Ile Ala Asp Asn Gln Ala
        350                 355                 360

aaa tgg gct gtc ccg aca aca cga aca gat gac aag ttg cga atg gag      1157
Lys Trp Ala Val Pro Thr Thr Arg Thr Asp Asp Lys Leu Arg Met Glu
    365                 370                 375

aca tgc ttc caa cag gcg tgt aag ggt aaa atc caa gca ctc tgc gag      1205
Thr Cys Phe Gln Gln Ala Cys Lys Gly Lys Ile Gln Ala Leu Cys Glu
380                 385                 390                 395

aat ccc gag tgg gca cca ttg aag gat aac agg att cct tca tac ggg      1253
Asn Pro Glu Trp Ala Pro Leu Lys Asp Asn Arg Ile Pro Ser Tyr Gly
                400                 405                 410

gtc ttg tct gtt gat ctg agt ctg aca gtt gag ctt aaa atc aaa att      1301
Val Leu Ser Val Asp Leu Ser Leu Thr Val Glu Leu Lys Ile Lys Ile
            415                 420                 425

gct tcg gga ttc ggg cca ttg atc aca cac ggt tca ggg atg gac cta      1349
Ala Ser Gly Phe Gly Pro Leu Ile Thr His Gly Ser Gly Met Asp Leu
        430                 435                 440

tac aaa tcc aac cac aac aat gtg tat tgg ctg act atc ccg cca atg      1397
Tyr Lys Ser Asn His Asn Asn Val Tyr Trp Leu Thr Ile Pro Pro Met
    445                 450                 455

aag aac cta gcc tta ggt gta atc aac aca ttg gag tgg ata ccg aga      1445
Lys Asn Leu Ala Leu Gly Val Ile Asn Thr Leu Glu Trp Ile Pro Arg
460                 465                 470                 475

ttc aag gtt agt ccc tac ctc ttc act gtc cca att aag gaa gca ggc      1493
Phe Lys Val Ser Pro Tyr Leu Phe Thr Val Pro Ile Lys Glu Ala Gly
                480                 485                 490

gaa gac tgc cat gcc cca aca tac cta cct gcg gag gtg gat ggt gat      1541
Glu Asp Cys His Ala Pro Thr Tyr Leu Pro Ala Glu Val Asp Gly Asp
            495                 500                 505

gtc aaa ctc agt tcc aat ctg gtg att cta cct ggt caa gat ctc caa      1589
Val Lys Leu Ser Ser Asn Leu Val Ile Leu Pro Gly Gln Asp Leu Gln
        510                 515                 520

tat gtt ttg gca acc tac gat act tcc agg gtt gaa cat gct gtg gtt      1637
Tyr Val Leu Ala Thr Tyr Asp Thr Ser Arg Val Glu His Ala Val Val
    525                 530                 535

tat tac gtt tac agc cca agc cgc tca ttt tct tac ttt tat cct ttt      1685
Tyr Tyr Val Tyr Ser Pro Ser Arg Ser Phe Ser Tyr Phe Tyr Pro Phe
540                 545                 550                 555

agg ttg cct ata aag ggg gtc ccc atc gaa tta caa gtg gaa tgc ttc      1733
Arg Leu Pro Ile Lys Gly Val Pro Ile Glu Leu Gln Val Glu Cys Phe
                560                 565                 570

aca tgg gac caa aaa ctc tgg tgc cgt cac ttc tgt gtg ctt gcg gac      1781
Thr Trp Asp Gln Lys Leu Trp Cys Arg His Phe Cys Val Leu Ala Asp
            575                 580                 585

tca gaa tct ggt gga cat atc act cac tct ggg atg gtg ggc atg gga      1829
Ser Glu Ser Gly Gly His Ile Thr His Ser Gly Met Val Gly Met Gly
        590                 595                 600

gtc agc tgc aca gtc acc cgg gaa gat gga acc aat cgc aga tag          1874
Val Ser Cys Thr Val Thr Arg Glu Asp Gly Thr Asn Arg Arg
    605                 610                 615

ggctgctagt gaaccaatca catgatgtca cccagacatc aggcataccc actagtgtga   1934
```

```
aatagacatc agaattaaga aaaa                                          1958


<210> SEQ ID NO 29
<211> LENGTH: 617
<212> TYPE: PRT
<213> ORGANISM: Measles virus strain Moraten

<400> SEQUENCE: 29

Met Ser Pro Gln Arg Asp Arg Ile Asn Ala Phe Tyr Lys Asp Asn Pro
1               5                   10                  15

His Pro Lys Gly Ser Arg Ile Val Ile Asn Arg Glu His Leu Met Ile
            20                  25                  30

Asp Arg Pro Tyr Val Leu Leu Ala Val Leu Phe Val Met Phe Leu Ser
        35                  40                  45

Leu Ile Gly Leu Leu Ala Ile Ala Gly Ile Arg Leu His Arg Ala Ala
    50                  55                  60

Ile Tyr Thr Ala Glu Ile His Lys Ser Leu Ser Thr Asn Leu Asp Val
65                  70                  75                  80

Thr Asn Ser Ile Glu His Gln Val Lys Asp Val Leu Thr Pro Leu Phe
                85                  90                  95

Lys Ile Ile Gly Asp Glu Val Gly Leu Arg Thr Pro Gln Arg Phe Thr
            100                 105                 110

Asp Leu Val Lys Leu Ile Ser Asp Lys Ile Lys Phe Leu Asn Pro Asp
        115                 120                 125

Arg Glu Tyr Asp Phe Arg Asp Leu Thr Trp Cys Ile Asn Pro Pro Glu
    130                 135                 140

Arg Ile Lys Leu Asp Tyr Asp Gln Tyr Cys Ala Asp Val Ala Ala Glu
145                 150                 155                 160

Glu Leu Met Asn Ala Leu Val Asn Ser Thr Leu Leu Glu Thr Arg Thr
                165                 170                 175

Thr Asn Gln Phe Leu Ala Val Ser Lys Gly Asn Cys Ser Gly Pro Thr
            180                 185                 190

Thr Ile Arg Gly Gln Phe Ser Asn Met Ser Leu Ser Leu Leu Asp Leu
        195                 200                 205

Tyr Leu Gly Arg Gly Tyr Asn Val Ser Ser Ile Val Thr Met Thr Ser
    210                 215                 220

Gln Gly Met Tyr Gly Gly Thr Tyr Leu Val Glu Lys Pro Asn Leu Ser
225                 230                 235                 240

Ser Lys Arg Ser Glu Leu Ser Gln Leu Ser Met Tyr Arg Val Phe Glu
                245                 250                 255

Val Gly Val Ile Arg Asn Pro Gly Leu Gly Ala Pro Val Phe His Met
            260                 265                 270

Thr Asn Tyr Leu Glu Gln Pro Val Ser Asn Asp Leu Ser Asn Cys Met
        275                 280                 285

Val Ala Leu Gly Glu Leu Lys Leu Ala Ala Leu Cys His Gly Glu Asp
    290                 295                 300

Ser Ile Thr Ile Pro Tyr Gln Gly Ser Gly Lys Gly Val Ser Phe Gln
305                 310                 315                 320

Leu Val Lys Leu Gly Val Trp Lys Ser Pro Thr Asp Met Gln Ser Trp
                325                 330                 335

Val Pro Leu Ser Thr Asp Asp Pro Val Ile Asp Arg Leu Tyr Leu Ser
            340                 345                 350

Ser His Arg Gly Val Ile Ala Asp Asn Gln Ala Lys Trp Ala Val Pro
        355                 360                 365
```

```
Thr Thr Arg Thr Asp Asp Lys Leu Arg Met Glu Thr Cys Phe Gln Gln
    370                 375                 380

Ala Cys Lys Gly Lys Ile Gln Ala Leu Cys Glu Asn Pro Glu Trp Ala
385                 390                 395                 400

Pro Leu Lys Asp Asn Arg Ile Pro Ser Tyr Gly Val Leu Ser Val Asp
                405                 410                 415

Leu Ser Leu Thr Val Glu Leu Lys Ile Lys Ile Ala Ser Gly Phe Gly
            420                 425                 430

Pro Leu Ile Thr His Gly Ser Gly Met Asp Leu Tyr Lys Ser Asn His
        435                 440                 445

Asn Asn Val Tyr Trp Leu Thr Ile Pro Pro Met Lys Asn Leu Ala Leu
    450                 455                 460

Gly Val Ile Asn Thr Leu Glu Trp Ile Pro Arg Phe Lys Val Ser Pro
465                 470                 475                 480

Tyr Leu Phe Thr Val Pro Ile Lys Glu Ala Gly Glu Asp Cys His Ala
                485                 490                 495

Pro Thr Tyr Leu Pro Ala Glu Val Asp Gly Asp Val Lys Leu Ser Ser
            500                 505                 510

Asn Leu Val Ile Leu Pro Gly Gln Asp Leu Gln Tyr Val Leu Ala Thr
        515                 520                 525

Tyr Asp Thr Ser Arg Val Glu His Ala Val Val Tyr Tyr Val Tyr Ser
    530                 535                 540

Pro Ser Arg Ser Phe Ser Tyr Phe Tyr Pro Phe Arg Leu Pro Ile Lys
545                 550                 555                 560

Gly Val Pro Ile Glu Leu Gln Val Glu Cys Phe Thr Trp Asp Gln Lys
                565                 570                 575

Leu Trp Cys Arg His Phe Cys Val Leu Ala Asp Ser Glu Ser Gly Gly
            580                 585                 590

His Ile Thr His Ser Gly Met Val Gly Met Gly Val Ser Cys Thr Val
        595                 600                 605

Thr Arg Glu Asp Gly Thr Asn Arg Arg
    610                 615
```

<210> SEQ ID NO 30
<211> LENGTH: 1958
<212> TYPE: DNA
<213> ORGANISM: Artificial
<220> FEATURE:
<223> OTHER INFORMATION: deoptimized measles H sequence.

<400> SEQUENCE: 30

```
agggtgcaag atcatccaca atgtcgccgc aacgcgaccg cataaatgcg ttctacaaag     60

ataacccgca tccgaagggc tcgcgcatag taattaaccg cgaacatctt atgattgatc    120

gcccgtatgt acttcttgcg gtactttttg taatgtttct ttcgcttatc ggccttcttg    180

cgattgcggg cattcgcctt catcgcgcgg cgatctacac cgcggagatc cataaatcgc    240

tctcgacgaa tcttgatgta acgaactcga tcgagcatca ggtaaaggac gtacttacgc    300

cgcttttcaa aatcatcggc gatgaagtag gccttcgcac gccgcagcgc ttcacggacc    360

ttgtaaaact tatctcggac aagattaaat tccttaatcc ggatcgcgag tacgacttcc    420

gcgatcttac gtggtgtatc aacccgccgg agcgcatcaa acttgattat gatcaatact    480

gtgcggatgt agcggcggaa gagcttatga atgcgcttgt aaactcgacg cttcttgaga    540

cgcgcacgac gaatcagttc cttgcggtat cgaagggcaa ctgctcgggc ccgacgacga    600
```

```
tccgcggcca attctcgaac atgtcgcttt cgcttcttga cctttatctt ggccgcggct    660

acaatgtatc gtcgatagta acgatgacgt cccagggcat gtatggcggc acgtaccttg    720

tagaaaagcc gaatctttcg tcgaaacgct cggagctttc gcaactttcg atgtaccgcg    780

tatttgaagt aggcgtaatc cgcaatccgg gccttggcgc gccggtattc catatgacga    840

actatcttga gcaaccggta tcgaatgatc tttcgaactg tatggtagcg cttggcgagc    900

ttaaacttgc ggcgctttgt cacggcgaag attcgatcac gattccgtat cagggctcgg    960

gcaaaggcgt atcgttccag cttgtaaagc ttggcgtatg gaaatcgccg acggacatgc   1020

aatcgtgggt accgctttcg acggatgatc cggtaataga ccgcctttac ctttcgtcgc   1080

accgcggcgt aatcgcggac aatcaagcga aatgggcggt accgacgacg cgcacggatg   1140

acaagcttcg catggagacg tgcttccaac aggcgtgtaa gggcaaaatc caagcgcttt   1200

gcgagaatcc ggagtgggcg ccgcttaagg ataaccgcat tccgtcgtac ggcgtacttt   1260

cggtagatct ttcgcttacg gtagagctta aaatcaaaat tgcgtcgggc ttcggcccgc   1320

ttatcacgca cggctcgggc atggaccttt acaaatcgaa ccacaacaat gtatattggc   1380

ttacgatccc gccgatgaag aaccttgcgc ttggcgtaat caacacgctt gagtggatac   1440

cgcgcttcaa ggtatcgccg taccttttca cggtaccgat taaggaagcg ggcgaagact   1500

gccatgcgcc gacgtacctt ccggcggagg tagatggcga tgtaaaactt tcgtcgaatc   1560

ttgtaattct tccgggccaa gatcttcaat atgtacttgc gacgtacgat acgtcgcgcg   1620

tagaacatgc ggtagtatat tacgtatact cgccgtcgcg ctcgttttcg tacttttatc   1680

cgtttcgcct tccgataaag ggcgtaccga tcgaacttca agtagaatgc ttcacgtggg   1740

accaaaaact ttggtgccgc cacttctgtg tacttgcgga ctcggaatcg ggcggccata   1800

tcacgcactc gggcatggta ggcatgggcg tatcgtgcac ggtaacgcgc gaagatggca   1860

cgaatcgccg ctagggctgc tagtgaacca atcacatgat gtcacccaga catcaggcat   1920

acccactagt gtgaaataga catcagaatt aagaaaaa                           1958
```

<210> SEQ ID NO 31
<211> LENGTH: 1903
<212> TYPE: DNA
<213> ORGANISM: Human respiratory syncytial virus
<220> FEATURE:
<221> NAME/KEY: CDS
<222> LOCATION: (14)..(1738)

<400> SEQUENCE: 31

```
ggggcaaata aca atg gag ttg cta atc ctc aaa gca aat gca att acc        49
               Met Glu Leu Leu Ile Leu Lys Ala Asn Ala Ile Thr
               1               5                   10

aca atc ctc act gca gtc aca ttt tgt ttt gct tct ggt caa aac atc       97
Thr Ile Leu Thr Ala Val Thr Phe Cys Phe Ala Ser Gly Gln Asn Ile
        15                  20                  25

act gaa gaa ttt tat caa tca aca tgc agt gca gtt agc aaa ggc tat      145
Thr Glu Glu Phe Tyr Gln Ser Thr Cys Ser Ala Val Ser Lys Gly Tyr
    30                  35                  40

ctt agt gct ctg aga act ggt tgg tat acc agt gtt ata act ata gaa      193
Leu Ser Ala Leu Arg Thr Gly Trp Tyr Thr Ser Val Ile Thr Ile Glu
45                  50                  55                  60

tta agt aat atc aag gaa aat aag tgt aat gga aca gat gct aag gta      241
Leu Ser Asn Ile Lys Glu Asn Lys Cys Asn Gly Thr Asp Ala Lys Val
                65                  70                  75

aaa ttg ata aaa caa gaa tta gat aaa tat aaa aat gct gta aca gaa      289
Lys Leu Ile Lys Gln Glu Leu Asp Lys Tyr Lys Asn Ala Val Thr Glu
```

```
            80                  85                  90

ttg cag ttg ctc atg caa agc aca cca gca aca aac aat cga gcc aga      337
Leu Gln Leu Leu Met Gln Ser Thr Pro Ala Thr Asn Asn Arg Ala Arg
        95                  100                 105

aga gaa cta cca agg ttt atg aat tat aca ctc aac aat gcc aaa aaa      385
Arg Glu Leu Pro Arg Phe Met Asn Tyr Thr Leu Asn Asn Ala Lys Lys
    110                 115                 120

acc aat gta aca tta agc aag aaa agg aaa aga aga ttt ctt ggt ttt      433
Thr Asn Val Thr Leu Ser Lys Lys Arg Lys Arg Arg Phe Leu Gly Phe
125                 130                 135                 140

ttg tta ggt gtt gga tct gca atc gcc agt ggc gtt gct gta tct aag      481
Leu Leu Gly Val Gly Ser Ala Ile Ala Ser Gly Val Ala Val Ser Lys
                145                 150                 155

gtc ctg cac cta gaa ggg gaa gtg aac aag atc aaa agt gct cta cta      529
Val Leu His Leu Glu Gly Glu Val Asn Lys Ile Lys Ser Ala Leu Leu
            160                 165                 170

tcc aca aac aag gct gta gtc agc tta tca aat gga gtt agt gtc tta      577
Ser Thr Asn Lys Ala Val Val Ser Leu Ser Asn Gly Val Ser Val Leu
        175                 180                 185

acc agc aaa gtg tta gac ctc aaa aac tat ata gat aaa caa ttg tta      625
Thr Ser Lys Val Leu Asp Leu Lys Asn Tyr Ile Asp Lys Gln Leu Leu
    190                 195                 200

cct att gtg aac aag caa agc tgc agc ata tca aat ata gca act gtg      673
Pro Ile Val Asn Lys Gln Ser Cys Ser Ile Ser Asn Ile Ala Thr Val
205                 210                 215                 220

ata gag ttc caa caa aag aac aac aga cta cta gag att acc agg gaa      721
Ile Glu Phe Gln Gln Lys Asn Asn Arg Leu Leu Glu Ile Thr Arg Glu
                225                 230                 235

ttt agt gtt aat gca ggt gta act aca cct gta agc act tac atg tta      769
Phe Ser Val Asn Ala Gly Val Thr Thr Pro Val Ser Thr Tyr Met Leu
            240                 245                 250

act aat agt gaa tta ttg tca tta atc aat gat atg cct ata aca aat      817
Thr Asn Ser Glu Leu Leu Ser Leu Ile Asn Asp Met Pro Ile Thr Asn
        255                 260                 265

gat cag aaa aag tta atg tcc aac aat gtt caa ata gtt aga cag caa      865
Asp Gln Lys Lys Leu Met Ser Asn Asn Val Gln Ile Val Arg Gln Gln
    270                 275                 280

agt tac tct atc atg tcc ata ata aaa gag gaa gtc tta gca tat gta      913
Ser Tyr Ser Ile Met Ser Ile Ile Lys Glu Glu Val Leu Ala Tyr Val
285                 290                 295                 300

gta caa tta cca cta tat ggt gtt ata gat aca ccc tgt tgg aaa cta      961
Val Gln Leu Pro Leu Tyr Gly Val Ile Asp Thr Pro Cys Trp Lys Leu
                305                 310                 315

cac aca tcc cct cta tgt aca acc aac aca aaa gaa ggg tcc aac atc     1009
His Thr Ser Pro Leu Cys Thr Thr Asn Thr Lys Glu Gly Ser Asn Ile
            320                 325                 330

tgt tta aca aga act gac aga gga tgg tac tgt gac aat gca gga tca     1057
Cys Leu Thr Arg Thr Asp Arg Gly Trp Tyr Cys Asp Asn Ala Gly Ser
        335                 340                 345

gta tct ttc ttc cca caa gct gaa aca tgt aaa gtt caa tca aat cga     1105
Val Ser Phe Phe Pro Gln Ala Glu Thr Cys Lys Val Gln Ser Asn Arg
    350                 355                 360

gta ttt tgt gac aca atg aac agt tta aca tta cca agt gaa gta aat     1153
Val Phe Cys Asp Thr Met Asn Ser Leu Thr Leu Pro Ser Glu Val Asn
365                 370                 375                 380

ctc tgc aat gtt gac ata ttc aac ccc aaa tat gat tgt aaa att atg     1201
Leu Cys Asn Val Asp Ile Phe Asn Pro Lys Tyr Asp Cys Lys Ile Met
                385                 390                 395

act tca aaa aca gat gta agc agc tcc gtt atc aca tct cta gga gcc     1249
```

```
Thr Ser Lys Thr Asp Val Ser Ser Ser Val Ile Thr Ser Leu Gly Ala
            400                 405                 410

att gtg tca tgc tat ggc aaa act aaa tgt aca gca tcc aat aaa aat     1297
Ile Val Ser Cys Tyr Gly Lys Thr Lys Cys Thr Ala Ser Asn Lys Asn
        415                 420                 425

cgt gga atc ata aag aca ttt tct aac ggg tgc gat tat gta tca aat     1345
Arg Gly Ile Ile Lys Thr Phe Ser Asn Gly Cys Asp Tyr Val Ser Asn
    430                 435                 440

aaa ggg gtg gac act gtg tct gta ggt aac aca tta tat tat gta aat     1393
Lys Gly Val Asp Thr Val Ser Val Gly Asn Thr Leu Tyr Tyr Val Asn
445                 450                 455                 460

aag caa gaa ggt aaa agt ctc tat gta aaa ggt gaa cca ata ata aat     1441
Lys Gln Glu Gly Lys Ser Leu Tyr Val Lys Gly Glu Pro Ile Ile Asn
                465                 470                 475

ttc tat gac cca tta gta ttc ccc tct gat gaa ttt gat gca tca ata     1489
Phe Tyr Asp Pro Leu Val Phe Pro Ser Asp Glu Phe Asp Ala Ser Ile
            480                 485                 490

tct caa gtc aac gag aag att aac cag agc cta gca ttt att cgt aaa     1537
Ser Gln Val Asn Glu Lys Ile Asn Gln Ser Leu Ala Phe Ile Arg Lys
        495                 500                 505

tcc gat gaa tta tta cat aat gta aat gct ggt aaa tcc acc ata aat     1585
Ser Asp Glu Leu Leu His Asn Val Asn Ala Gly Lys Ser Thr Ile Asn
    510                 515                 520

atc atg ata act act ata att ata gtg att ata gta ata ttg tta tca     1633
Ile Met Ile Thr Thr Ile Ile Ile Val Ile Ile Val Ile Leu Leu Ser
525                 530                 535                 540

tta att gct gtt gga ctg ctc tta tac tgt aag gcc aga agc aca cca     1681
Leu Ile Ala Val Gly Leu Leu Leu Tyr Cys Lys Ala Arg Ser Thr Pro
                545                 550                 555

gtc aca cta agc aaa gat caa ctg agt ggt ata aat aat att gca ttt     1729
Val Thr Leu Ser Lys Asp Gln Leu Ser Gly Ile Asn Asn Ile Ala Phe
            560                 565                 570

agt aac taa ataaaaatag cacctaatca tgttcttaca atggtttact             1778
Ser Asn

atctgctcat agacaaccca tctgtcattg gattttctta aaatctgaac ttcatcgaaa   1838

ctctcatcta taaaccatct cacttacact atttaagtag attcctagtt tatagttata   1898

taaaa                                                               1903


<210> SEQ ID NO 32
<211> LENGTH: 574
<212> TYPE: PRT
<213> ORGANISM: Human respiratory syncytial virus

<400> SEQUENCE: 32

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
```

```
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Ala Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Ile Asn Ile Met Ile Thr
        515                 520                 525
```

```
Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

<210> SEQ ID NO 33
<211> LENGTH: 1903
<212> TYPE: DNA
<213> ORGANISM: Artificial
<220> FEATURE:
<223> OTHER INFORMATION: deoptimized RSV F sequence

<400> SEQUENCE: 33

```
ggggcaaata acaatggagc tgctgatcct gaaagcgaat gcgattacca cgatcctgac     60
ggcggtcacg ttttgttttg cgtcggggca aaacatcacg gaggagtttt atcaatcgac    120
gtgctcggcg gtttcgaaag ggtatctgtc ggcgctgcgg acggggtggt atacctcggt    180
tataacgata gagctgtcga atatcaagga gaataagtgt aatgggacgg atgcgaaggt    240
aaaactgata aaacaagagc tggataaata taaaaatgcg gtaacggagc tgcagctgct    300
gatgcaatcg acgccggcga cgaacaatcg ggcgcggcgg gagctgccga ggtttatgaa    360
ttatacgctg aacaatgcga aaaaaacgaa tgtaacgctg tcgaagaaaa ggaaacggcg    420
gtttctgggg tttctgctgg gggttgggtc ggcgatcgcg tcgggggttg cggtatcgaa    480
ggtcctgcac ctggaggggg aggtgaacaa gatcaaatcg gcgctgctgt ccacgaacaa    540
ggcggtagtc tcgctgtcga atggggtttc ggtcctgacg tcgaaagtgc tggacctgaa    600
aaactatata gataaacaac tgctgccgat tgtgaacaag caatcgtgct cgatatcgaa    660
tatagcgacg gtgatagagt tccaacaaaa gaacaaccgg ctgctggaga ttacgcggga    720
gttttcggtt aatgcggggg taacgacgcc ggtatcgacg tacatgctga cgaattcgga    780
gctgctgtcg ctgatcaatg atatgccgat aacgaatgat cagaaaaagc tgatgtcgaa    840
caatgttcaa atagttcggc agcaatcgta ctcgatcatg tcgataataa aagaggaggt    900
cctggcgtat gtagtacaac tgccgctgta tggggttata gatacgccgt gttggaaact    960
gcacacgtcg ccgctgtgta cgacgaacac gaaagagggg tcgaacatct gtctgacgcg   1020
gacggaccgg gggtggtact gtgacaatgc ggggtcggta tcgttcttcc cgcaagcgga   1080
gacgtgtaaa gttcaatcga atcgggtatt ttgtgacacg atgaactcgc tgacgctgcc   1140
gtcggaggta aatctgtgca atgttgacat attcaacccg aaatatgatt gtaaaattat   1200
gacgtcgaaa acggatgtat cgtcgtcggt tatcacgtcg ctgggggcga ttgtgtcgtg   1260
ctatgggaaa acgaaatgta cggcgtcgaa taaaaatcgg gggatcataa agacgttttc   1320
gaacgggtgc gattatgtat cgaataaagg ggtggacacg gtgtcggtag ggaacacgct   1380
gtattatgta aataagcaag aggggaaatc gctgtatgta aaaggggagc cgataataaa   1440
tttctatgac ccgctggtat tcccgtcgga tgagtttgat gcgtcgatat cgcaagtcaa   1500
cgagaagatt aaccagtcgc tggcgtttat tcggaaatcg gatgagctgc tgcataatgt   1560
aaatgcgggg aaatcgacga taaatatcat gataacgacg ataattatag tgattatagt   1620
aatactgctg tcgctgattg cggttgggct gctgctgtac tgtaaggccc ggtcgacgcc   1680
ggtcacgctg tcgaaagatc aactgtcggg gataaataat attgcgtttt cgaactaaat   1740
aaaaatagcg cctaatcatg ttctgacgat ggtttactat ctgctgatag acaacccatc   1800
```

```
ggtcattgga ttttcttaaa atctgaactt catcgaaact ctcatctata aaccatctca   1860

cttacactat ttaagtagat tcctagttta tagttatata aaa                     1903


<210> SEQ ID NO 34
<211> LENGTH: 1903
<212> TYPE: DNA
<213> ORGANISM: Human respiratory syncytial virus
<220> FEATURE:
<221> NAME/KEY: CDS
<222> LOCATION: (14)..(1735)

<400> SEQUENCE: 34

ggggcaaata aca atg gag ctg ctg atc ctg aaa gcg aat gcg att acc        49
               Met Glu Leu Leu Ile Leu Lys Ala Asn Ala Ile Thr
               1               5                   10

acg atc ctg acg gcg gtc acg ttt tgt ttt gcg tcg ggg caa aac atc       97
Thr Ile Leu Thr Ala Val Thr Phe Cys Phe Ala Ser Gly Gln Asn Ile
        15                  20                  25

acg gag gag ttt tat caa tcg acg tgc tcg gcg gtt tcg aaa ggg tat      145
Thr Glu Glu Phe Tyr Gln Ser Thr Cys Ser Ala Val Ser Lys Gly Tyr
    30                  35                  40

ctg tcg gcg ctg cgg acg ggg tgg tat acc tcg gtt ata acg ata gag      193
Leu Ser Ala Leu Arg Thr Gly Trp Tyr Thr Ser Val Ile Thr Ile Glu
45                  50                  55                  60

ctg tcg aat atc aag gag aat aag tgt aat ggg acg gat gcg aag gta      241
Leu Ser Asn Ile Lys Glu Asn Lys Cys Asn Gly Thr Asp Ala Lys Val
                65                  70                  75

aaa ctg ata aaa caa gag ctg gat aaa tat aaa aat gcg gta acg gag      289
Lys Leu Ile Lys Gln Glu Leu Asp Lys Tyr Lys Asn Ala Val Thr Glu
            80                  85                  90

ctg cag ctg ctg atg caa tcg acg ccg gcg acg aac aat cgg gcg cgg      337
Leu Gln Leu Leu Met Gln Ser Thr Pro Ala Thr Asn Asn Arg Ala Arg
        95                  100                 105

cgg gag ctg ccg agg ttt atg aat tat acg ctg aac aat gcg aaa aaa      385
Arg Glu Leu Pro Arg Phe Met Asn Tyr Thr Leu Asn Asn Ala Lys Lys
    110                 115                 120

acg aat gta acg ctg tcg aag aaa agg aaa cgg cgg ttt ctg ggg ttt      433
Thr Asn Val Thr Leu Ser Lys Lys Arg Lys Arg Arg Phe Leu Gly Phe
125                 130                 135                 140

ctg ctg ggg gtt ggg tcg gcg atc gcg tcg ggg gtt gcg gta tcg aag      481
Leu Leu Gly Val Gly Ser Ala Ile Ala Ser Gly Val Ala Val Ser Lys
                145                 150                 155

gtc ctg cac ctg gag ggg gag gtg aac aag atc aaa tcg gcg ctg ctg      529
Val Leu His Leu Glu Gly Glu Val Asn Lys Ile Lys Ser Ala Leu Leu
            160                 165                 170

tcc acg aac aag gcg gta gtc tcg ctg tcg aat ggg gtt tcg gtc ctg      577
Ser Thr Asn Lys Ala Val Val Ser Leu Ser Asn Gly Val Ser Val Leu
        175                 180                 185

acg tcg aaa gtg ctg gac ctg aaa aac tat ata gat aaa caa ctg ctg      625
Thr Ser Lys Val Leu Asp Leu Lys Asn Tyr Ile Asp Lys Gln Leu Leu
    190                 195                 200

ccg att gtg aac aag caa tcg tgc tcg ata tcg aat ata gcg acg gtg      673
Pro Ile Val Asn Lys Gln Ser Cys Ser Ile Ser Asn Ile Ala Thr Val
205                 210                 215                 220

ata gag ttc caa caa aag aac aac cgg ctg ctg gag att acg cgg gag      721
Ile Glu Phe Gln Gln Lys Asn Asn Arg Leu Leu Glu Ile Thr Arg Glu
                225                 230                 235

ttt tcg gtt aat gcg ggg gta acg acg ccg gta tcg acg tac atg ctg      769
Phe Ser Val Asn Ala Gly Val Thr Thr Pro Val Ser Thr Tyr Met Leu
            240                 245                 250
```

-continued

```
acg aat tcg gag ctg ctg tcg ctg atc aat gat atg ccg ata acg aat      817
Thr Asn Ser Glu Leu Leu Ser Leu Ile Asn Asp Met Pro Ile Thr Asn
        255                 260                 265

gat cag aaa aag ctg atg tcg aac aat gtt caa ata gtt cgg cag caa      865
Asp Gln Lys Lys Leu Met Ser Asn Asn Val Gln Ile Val Arg Gln Gln
    270                 275                 280

tcg tac tcg atc atg tcg ata ata aaa gag gag gtc ctg gcg tat gta      913
Ser Tyr Ser Ile Met Ser Ile Ile Lys Glu Glu Val Leu Ala Tyr Val
285                 290                 295                 300

gta caa ctg ccg ctg tat ggg gtt ata gat acg ccg tgt tgg aaa ctg      961
Val Gln Leu Pro Leu Tyr Gly Val Ile Asp Thr Pro Cys Trp Lys Leu
                305                 310                 315

cac acg tcg ccg ctg tgt acg acg aac acg aaa gag ggg tcg aac atc     1009
His Thr Ser Pro Leu Cys Thr Thr Asn Thr Lys Glu Gly Ser Asn Ile
            320                 325                 330

tgt ctg acg cgg acg gac cgg ggg tgg tac tgt gac aat gcg ggg tcg     1057
Cys Leu Thr Arg Thr Asp Arg Gly Trp Tyr Cys Asp Asn Ala Gly Ser
        335                 340                 345

gta tcg ttc ttc ccg caa gcg gag acg tgt aaa gtt caa tcg aat cgg     1105
Val Ser Phe Phe Pro Gln Ala Glu Thr Cys Lys Val Gln Ser Asn Arg
    350                 355                 360

gta ttt tgt gac acg atg aac tcg ctg acg ctg ccg tcg gag gta aat     1153
Val Phe Cys Asp Thr Met Asn Ser Leu Thr Leu Pro Ser Glu Val Asn
365                 370                 375                 380

ctg tgc aat gtt gac ata ttc aac ccg aaa tat gat tgt aaa att atg     1201
Leu Cys Asn Val Asp Ile Phe Asn Pro Lys Tyr Asp Cys Lys Ile Met
                385                 390                 395

acg tcg aaa acg gat gta tcg tcg tcg gtt atc acg tcg ctg ggg gcg     1249
Thr Ser Lys Thr Asp Val Ser Ser Ser Val Ile Thr Ser Leu Gly Ala
            400                 405                 410

att gtg tcg tgc tat ggg aaa acg aaa tgt acg gcg tcg aat aaa aat     1297
Ile Val Ser Cys Tyr Gly Lys Thr Lys Cys Thr Ala Ser Asn Lys Asn
        415                 420                 425

cgg ggg atc ata aag acg ttt tcg aac ggg tgc gat tat gta tcg aat     1345
Arg Gly Ile Ile Lys Thr Phe Ser Asn Gly Cys Asp Tyr Val Ser Asn
    430                 435                 440

aaa ggg gtg gac acg gtg tcg gta ggg aac acg ctg tat tat gta aat     1393
Lys Gly Val Asp Thr Val Ser Val Gly Asn Thr Leu Tyr Tyr Val Asn
445                 450                 455                 460

aag caa gag ggg aaa tcg ctg tat gta aaa ggg gag ccg ata ata aat     1441
Lys Gln Glu Gly Lys Ser Leu Tyr Val Lys Gly Glu Pro Ile Ile Asn
                465                 470                 475

ttc tat gac ccg ctg gta ttc ccg tcg gat gag ttt gat gcg tcg ata     1489
Phe Tyr Asp Pro Leu Val Phe Pro Ser Asp Glu Phe Asp Ala Ser Ile
            480                 485                 490

tcg caa gtc aac gag aag att aac cag tcg ctg gcg ttt att cgg aaa     1537
Ser Gln Val Asn Glu Lys Ile Asn Gln Ser Leu Ala Phe Ile Arg Lys
        495                 500                 505

tcg gat gag ctg ctg cat aat gta aat gcg ggg aaa tcg acg ata aat     1585
Ser Asp Glu Leu Leu His Asn Val Asn Ala Gly Lys Ser Thr Ile Asn
    510                 515                 520

atc atg ata acg acg ata att ata gtg att ata gta ata ctg ctg tcg     1633
Ile Met Ile Thr Thr Ile Ile Ile Val Ile Ile Val Ile Leu Leu Ser
525                 530                 535                 540

ctg att gcg gtt ggg ctg ctg ctg tac tgt aag gcc cgg tcg acg ccg     1681
Leu Ile Ala Val Gly Leu Leu Leu Tyr Cys Lys Ala Arg Ser Thr Pro
                545                 550                 555

gtc acg ctg tcg aaa gat caa ctg tcg ggg ata aat aat att gcg ttt     1729
Val Thr Leu Ser Lys Asp Gln Leu Ser Gly Ile Asn Asn Ile Ala Phe
```

-continued

```
            560                 565                 570

tcg aac taaataaaaa tagcgcctaa tcatgttctg acgatggttt actatctgct      1785
Ser Asn

gatagacaac ccatcggtca ttggattttc ttaaaatctg aacttcatcg aaactctcat   1845

ctataaacca tctcacttac actatttaag tagattccta gtttatagtt atataaaa     1903


<210> SEQ ID NO 35
<211> LENGTH: 574
<212> TYPE: PRT
<213> ORGANISM: Human respiratory syncytial virus

<400> SEQUENCE: 35

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Glu Asn Lys Cys Asn Gly Thr Asp Ala Lys Val Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Ala Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320

Leu Cys Thr Thr Asn Thr Lys Glu Gly Ser Asn Ile Cys Leu Thr Arg
                325                 330                 335
```

```
Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
    370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
                405                 410                 415

Tyr Gly Lys Thr Lys Cys Thr Ala Ser Asn Lys Asn Arg Gly Ile Ile
            420                 425                 430

Lys Thr Phe Ser Asn Gly Cys Asp Tyr Val Ser Asn Lys Gly Val Asp
        435                 440                 445

Thr Val Ser Val Gly Asn Thr Leu Tyr Tyr Val Asn Lys Gln Glu Gly
    450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
                485                 490                 495

Glu Lys Ile Asn Gln Ser Leu Ala Phe Ile Arg Lys Ser Asp Glu Leu
            500                 505                 510

Leu His Asn Val Asn Ala Gly Lys Ser Thr Ile Asn Ile Met Ile Thr
        515                 520                 525

Thr Ile Ile Ile Val Ile Ile Val Ile Leu Leu Ser Leu Ile Ala Val
    530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
                565                 570
```

```
<210> SEQ ID NO 36
<211> LENGTH: 923
<212> TYPE: DNA
<213> ORGANISM: Artificial
<220> FEATURE:
<223> OTHER INFORMATION: deoptimized RSV G sequence

<400> SEQUENCE: 36

ggggcgaatg cgaacatgtc gaaaaacaag gaccaacgga cggcgaagac gctggagcgg      60

acgtgggaca cgctgaatca tctgctgttc atatcgtcgt gcctgtataa gctgaatctg     120

aaatcggtag cgcaaatcac gctgtcgatt ctggcgatga taatctcgac gtcgctgata     180

attgcggcga tcatattcat agcgtcggcg aaccacaaag tcacgccgac gacggcgatc     240

atacaagatg cgacgtcgca gatcaagaac acgacgccga cgtacctgac gcagaatccg     300

cagctgggga tctcgccgtc gaatccgtcg gagattacgt cgcaaatcac gacgatactg     360

gcgtcgacga cgccgggggt caagtcgacg ctgcaatcga cgacggtcaa gacgaaaaac     420

acgacgacga cgcaaacgca accgtcgaag ccgacgacga aacaacggca aaacaaaccg     480

ccgtcgaaac cgaataatga ttttcacttt gaggtgttca actttgtacc gtgctcgata     540

tgctcgaaca atccgacgtg ctgggcgatc tgcaaacgga taccgaacaa aaaaccgggg     600

aagaaaacga cgacgaagcc gacgaaaaaa ccgacgctga agacgacgaa aaaagatccg     660

aaaccgcaaa cgacgaaatc gaaggaggta ccgacgacga agccgacgga ggagccgacg     720
```

```
atcaacacga cgaaaacgaa catcataacg acgctgctga cgtcgaacac gacggggaat    780

ccggagctga cgtcgcaaat ggagacgttc cactcgacgt cgtcggaggg gaatccgtcg    840

ccgtcgcaag tctcgacgac gtcggagtac ccgtcgcaac cgtcgtcgcc gccgaacacg    900

ccgcggcagt agctgctgaa aaa                                            923


<210> SEQ ID NO 37
<211> LENGTH: 1042
<212> TYPE: DNA
<213> ORGANISM: Influenza A virus
<220> FEATURE:
<221> NAME/KEY: CDS
<222> LOCATION: (1)..(1041)

<400> SEQUENCE: 37

caa aaa ctt ccc gga aat gac aac agc acg gca acg ctg tgc ctt ggg       48
Gln Lys Leu Pro Gly Asn Asp Asn Ser Thr Ala Thr Leu Cys Leu Gly
1               5                   10                  15

cac cat gca gta cca aac gga acg att gtg aaa aca atc acg aat gac       96
His His Ala Val Pro Asn Gly Thr Ile Val Lys Thr Ile Thr Asn Asp
            20                  25                  30

caa att gaa gtt act aat gct act gag ctg gtt cag agt tcc tca aca      144
Gln Ile Glu Val Thr Asn Ala Thr Glu Leu Val Gln Ser Ser Ser Thr
        35                  40                  45

ggt gga ata tgc gac agt cct cat cag atc ctt gat gga gaa aac tgc      192
Gly Gly Ile Cys Asp Ser Pro His Gln Ile Leu Asp Gly Glu Asn Cys
    50                  55                  60

aca cta ata gat gct cta ttg gga gac cct cag tgt gat ggc ttc caa      240
Thr Leu Ile Asp Ala Leu Leu Gly Asp Pro Gln Cys Asp Gly Phe Gln
65                  70                  75                  80

aat aag aaa tgg gac ctt ttt gtt gaa cgc agc aaa gcc tac agc aac      288
Asn Lys Lys Trp Asp Leu Phe Val Glu Arg Ser Lys Ala Tyr Ser Asn
                85                  90                  95

tgt tac cct tat gat gtg ccg gat tat gcc tcc ctt agg tca cta gtt      336
Cys Tyr Pro Tyr Asp Val Pro Asp Tyr Ala Ser Leu Arg Ser Leu Val
            100                 105                 110

gcc tca tcc ggc aca ctg gag ttt aac aat gaa agc ttc aat tgg act      384
Ala Ser Ser Gly Thr Leu Glu Phe Asn Asn Glu Ser Phe Asn Trp Thr
        115                 120                 125

gga gtc act cag aat gga aca agc tct gct tgc aaa agg aga tct aat      432
Gly Val Thr Gln Asn Gly Thr Ser Ser Ala Cys Lys Arg Arg Ser Asn
    130                 135                 140

aaa agt ttc ttt agt aga ttg aat tgg ttg acc cat tta aaa tac aaa      480
Lys Ser Phe Phe Ser Arg Leu Asn Trp Leu Thr His Leu Lys Tyr Lys
145                 150                 155                 160

tac cca gca ttg aac gtg act atg cca aac aat gaa aaa ttt gac aaa      528
Tyr Pro Ala Leu Asn Val Thr Met Pro Asn Asn Glu Lys Phe Asp Lys
                165                 170                 175

ttg tac att tgg ggg gtt cac cac ccg ggt acg gac agt gac caa atc      576
Leu Tyr Ile Trp Gly Val His His Pro Gly Thr Asp Ser Asp Gln Ile
            180                 185                 190

agc cta tat gct caa gca tca gga aga atc aca gtc tct acc aaa aga      624
Ser Leu Tyr Ala Gln Ala Ser Gly Arg Ile Thr Val Ser Thr Lys Arg
        195                 200                 205

agc caa caa act gta atc ccg aat atc gga tct aga ccc agg gta agg      672
Ser Gln Gln Thr Val Ile Pro Asn Ile Gly Ser Arg Pro Arg Val Arg
    210                 215                 220

gat gtc tcc agc aga ata agc atc tat tgg aca ata gta aaa ccg gga      720
Asp Val Ser Ser Arg Ile Ser Ile Tyr Trp Thr Ile Val Lys Pro Gly
225                 230                 235                 240
```

```
gac ata ctt ttg att aac agc aca ggg aat cta att gct cct agg ggt      768
Asp Ile Leu Leu Ile Asn Ser Thr Gly Asn Leu Ile Ala Pro Arg Gly
                245                 250                 255

tac ttc aaa ata cga agt ggg aaa agc tca ata atg aga tca gat gca      816
Tyr Phe Lys Ile Arg Ser Gly Lys Ser Ser Ile Met Arg Ser Asp Ala
            260                 265                 270

ccc att ggc aaa tgc aat tct gaa tgc atc act cca aat gga agc att      864
Pro Ile Gly Lys Cys Asn Ser Glu Cys Ile Thr Pro Asn Gly Ser Ile
        275                 280                 285

ccc aat gac aaa cca ttt caa aat gta aac agg atc aca tat ggg gcc      912
Pro Asn Asp Lys Pro Phe Gln Asn Val Asn Arg Ile Thr Tyr Gly Ala
    290                 295                 300

tgt ccc aga tat gtt aag caa aac act ctg aaa ttg gca aca ggg atg      960
Cys Pro Arg Tyr Val Lys Gln Asn Thr Leu Lys Leu Ala Thr Gly Met
305                 310                 315                 320

cga aat gta cca gag aaa caa act aga ggc ata ttt ggc gca atc gcg     1008
Arg Asn Val Pro Glu Lys Gln Thr Arg Gly Ile Phe Gly Ala Ile Ala
                325                 330                 335

ggt ttc ata gaa aat ggt tgg gag gga atg gtg g                       1042
Gly Phe Ile Glu Asn Gly Trp Glu Gly Met Val
            340                 345


<210> SEQ ID NO 38
<211> LENGTH: 347
<212> TYPE: PRT
<213> ORGANISM: Influenza A virus

<400> SEQUENCE: 38

Gln Lys Leu Pro Gly Asn Asp Asn Ser Thr Ala Thr Leu Cys Leu Gly
1               5                   10                  15

His His Ala Val Pro Asn Gly Thr Ile Val Lys Thr Ile Thr Asn Asp
            20                  25                  30

Gln Ile Glu Val Thr Asn Ala Thr Glu Leu Val Gln Ser Ser Ser Thr
        35                  40                  45

Gly Gly Ile Cys Asp Ser Pro His Gln Ile Leu Asp Gly Glu Asn Cys
    50                  55                  60

Thr Leu Ile Asp Ala Leu Leu Gly Asp Pro Gln Cys Asp Gly Phe Gln
65                  70                  75                  80

Asn Lys Lys Trp Asp Leu Phe Val Glu Arg Ser Lys Ala Tyr Ser Asn
                85                  90                  95

Cys Tyr Pro Tyr Asp Val Pro Asp Tyr Ala Ser Leu Arg Ser Leu Val
            100                 105                 110

Ala Ser Ser Gly Thr Leu Glu Phe Asn Asn Glu Ser Phe Asn Trp Thr
        115                 120                 125

Gly Val Thr Gln Asn Gly Thr Ser Ser Ala Cys Lys Arg Arg Ser Asn
    130                 135                 140

Lys Ser Phe Phe Ser Arg Leu Asn Trp Leu Thr His Leu Lys Tyr Lys
145                 150                 155                 160

Tyr Pro Ala Leu Asn Val Thr Met Pro Asn Asn Glu Lys Phe Asp Lys
                165                 170                 175

Leu Tyr Ile Trp Gly Val His His Pro Gly Thr Asp Ser Asp Gln Ile
            180                 185                 190

Ser Leu Tyr Ala Gln Ala Ser Gly Arg Ile Thr Val Ser Thr Lys Arg
        195                 200                 205

Ser Gln Gln Thr Val Ile Pro Asn Ile Gly Ser Arg Pro Arg Val Arg
    210                 215                 220
```

```
Asp Val Ser Ser Arg Ile Ser Ile Tyr Trp Thr Ile Val Lys Pro Gly
225                 230                 235                 240

Asp Ile Leu Leu Ile Asn Ser Thr Gly Asn Leu Ile Ala Pro Arg Gly
                245                 250                 255

Tyr Phe Lys Ile Arg Ser Gly Lys Ser Ser Ile Met Arg Ser Asp Ala
            260                 265                 270

Pro Ile Gly Lys Cys Asn Ser Glu Cys Ile Thr Pro Asn Gly Ser Ile
        275                 280                 285

Pro Asn Asp Lys Pro Phe Gln Asn Val Asn Arg Ile Thr Tyr Gly Ala
    290                 295                 300

Cys Pro Arg Tyr Val Lys Gln Asn Thr Leu Lys Leu Ala Thr Gly Met
305                 310                 315                 320

Arg Asn Val Pro Glu Lys Gln Thr Arg Gly Ile Phe Gly Ala Ile Ala
                325                 330                 335

Gly Phe Ile Glu Asn Gly Trp Glu Gly Met Val
            340                 345
```

<210> SEQ ID NO 39
<211> LENGTH: 1042
<212> TYPE: DNA
<213> ORGANISM: Artificial
<220> FEATURE:
<223> OTHER INFORMATION: deoptimized influenza HA sequence

<400> SEQUENCE: 39

```
caaaaattac cgggcaatga caactcgacg gcgacgttat gcttaggcca ccatgcggta     60

ccgaacggca cgatcgtgaa aacgatcacg aatgaccaaa tcgaagttac gaatgctacg    120

gagttagttc agtcgtcgtc gacgggcggc atctgcgact cgccgcatca gatcttagat    180

ggcgaaaact gcacgttaat cgatgcttta ttaggcgacc cgcagtgtga tggcttccaa    240

aataagaaat gggacttatt tgttgaacgc tcgaaagcgt actcgaactg ttacccgtat    300

gatgtgccgg attatgcgtc gttacgctcg ttagttgcgt cgtcgggcac gttagagttt    360

aacaatgaat cgttcaattg gacgggcgtc acgcagaatg gcacgtcgtc ggcttgcaaa    420

cgccgctcga ataaatcgtt cttttcgcgc ttaaattggt taacgcattt aaaatacaaa    480

tacccggcgt taaacgtgac gatgccgaac aatgaaaaat ttgacaaatt atacatctgg    540

ggcgttcacc acccgggcac ggactcggac caaatctcgt tatatgctca agcgtcgggc    600

cgcatcacgg tctcgacgaa acgctcgcaa caaacggtaa tcccgaatat cggctcgcgc    660

ccgcgcgtac gcgatgtctc gtcgcgcatc tcgatctatt ggacgatcgt aaaaccgggc    720

gacatcttat taatcaactc gacgggcaat ttaatcgctc cgcgcggcta cttcaaaatc    780

cgctcgggca aatcgtcgat catgcgctcg gatgcgccga tcggcaaatg caattcggaa    840

tgcatcacgc cgaatggctc gatcccgaat gacaaaccgt ttcaaaatgt aaaccgcatc    900

acgtatggcg cgtgtccgcg ctatgttaag caaaacacgt taaaattagc gacgggcatg    960

cgcaatgtac cggagaaaca aacgcgcggc atctttggcg cgatcgcggg cttcatcgaa   1020

aatggctggg agggcatggt gg                                            1042
```

<210> SEQ ID NO 40
<211> LENGTH: 1459
<212> TYPE: DNA
<213> ORGANISM: Influenza virus
<220> FEATURE:
<221> NAME/KEY: CDS
<222> LOCATION: (1)..(1425)
<220> FEATURE:

```
<221> NAME/KEY: misc_feature
<222> LOCATION: (15)..(15)
<223> OTHER INFORMATION: n is a, c, g, or t

<400> SEQUENCE: 40

aaa gca gga gtg aan atg aat cca aat caa aag ata ata acg att ggc       48
Lys Ala Gly Val Xaa Met Asn Pro Asn Gln Lys Ile Ile Thr Ile Gly
1               5                   10                  15

tct gtt tct ctc acc att tcc aca ata tgc ttc ttc atg caa att gcc       96
Ser Val Ser Leu Thr Ile Ser Thr Ile Cys Phe Phe Met Gln Ile Ala
            20                  25                  30

atc ctg ata act act gta aca ttg cat ttc aag caa tat gaa ttc aac      144
Ile Leu Ile Thr Thr Val Thr Leu His Phe Lys Gln Tyr Glu Phe Asn
        35                  40                  45

tcc ccc cca aac aac caa gtg atg ctg tgt gaa cca aca ata ata gaa      192
Ser Pro Pro Asn Asn Gln Val Met Leu Cys Glu Pro Thr Ile Ile Glu
    50                  55                  60

aga aac ata aca gag ata gtg tat ctg acc aac acc acc ata gag aag      240
Arg Asn Ile Thr Glu Ile Val Tyr Leu Thr Asn Thr Thr Ile Glu Lys
65                  70                  75                  80

gaa ata tgc ccc aaa cta gca gaa tac aga aat tgg tca aag ccg caa      288
Glu Ile Cys Pro Lys Leu Ala Glu Tyr Arg Asn Trp Ser Lys Pro Gln
                85                  90                  95

tgt aac att aca gga ttt gca cct ttt tct aag gac aat tcg att cgg      336
Cys Asn Ile Thr Gly Phe Ala Pro Phe Ser Lys Asp Asn Ser Ile Arg
            100                 105                 110

ctt tcc gct ggt ggg gac atc tgg gtg aca aga gaa cct tat gtg tca      384
Leu Ser Ala Gly Gly Asp Ile Trp Val Thr Arg Glu Pro Tyr Val Ser
        115                 120                 125

tgc gat cct gac aag tgt tat caa ttt gcc ctt gga cag gga aca aca      432
Cys Asp Pro Asp Lys Cys Tyr Gln Phe Ala Leu Gly Gln Gly Thr Thr
    130                 135                 140

cta aac aac gtg cat tca aat gac aca gta cat gat agg acc cct tat      480
Leu Asn Asn Val His Ser Asn Asp Thr Val His Asp Arg Thr Pro Tyr
145                 150                 155                 160

cgg acc cta ttg atg aat gag ttg ggt gtt cca ttt cat ctg ggg acc      528
Arg Thr Leu Leu Met Asn Glu Leu Gly Val Pro Phe His Leu Gly Thr
                165                 170                 175

aag caa gtg tgc ata gca tgg tcc agc tca agt tgt cac gat gga aag      576
Lys Gln Val Cys Ile Ala Trp Ser Ser Ser Ser Cys His Asp Gly Lys
            180                 185                 190

gca tgg ctg cat gtt tgt gta acg ggg gat gat gaa aat gca act gct      624
Ala Trp Leu His Val Cys Val Thr Gly Asp Asp Glu Asn Ala Thr Ala
        195                 200                 205

agc ttc att tac aat ggg agg ctt gta gat agt att gtt tca tgg tcc      672
Ser Phe Ile Tyr Asn Gly Arg Leu Val Asp Ser Ile Val Ser Trp Ser
    210                 215                 220

aaa aaa atc ctc agg acc cag gag tca gaa tgc gtt tgt atc aat gga      720
Lys Lys Ile Leu Arg Thr Gln Glu Ser Glu Cys Val Cys Ile Asn Gly
225                 230                 235                 240

act tgt aca gta gta atg act gat ggg agt gct tca gga aaa gct gat      768
Thr Cys Thr Val Val Met Thr Asp Gly Ser Ala Ser Gly Lys Ala Asp
                245                 250                 255

act aaa ata cta ttc att gag gag ggg aaa atc gtt cat act agc aca      816
Thr Lys Ile Leu Phe Ile Glu Glu Gly Lys Ile Val His Thr Ser Thr
            260                 265                 270

ttg tca gga agt gct cag cat gtc gag gag tgc tcc tgt tat cct cga      864
Leu Ser Gly Ser Ala Gln His Val Glu Glu Cys Ser Cys Tyr Pro Arg
        275                 280                 285

tat cct ggt gtc aga tgt gtc tgc aga gac aac tgg aaa ggc tcc aat      912
```

```
Tyr Pro Gly Val Arg Cys Val Cys Arg Asp Asn Trp Lys Gly Ser Asn
    290                 295                 300

agg ccc atc gta gat ata aac ata aag gat tat agc att gtt tcc agt      960
Arg Pro Ile Val Asp Ile Asn Ile Lys Asp Tyr Ser Ile Val Ser Ser
305                 310                 315                 320

tat gtg tgc tca gga ctt gtt gga gac aca ccc aga aaa aac gac agc     1008
Tyr Val Cys Ser Gly Leu Val Gly Asp Thr Pro Arg Lys Asn Asp Ser
                325                 330                 335

tcc agc agt agc cat tgc ttg gat cca aac aat gag gaa ggt ggt cat     1056
Ser Ser Ser Ser His Cys Leu Asp Pro Asn Asn Glu Glu Gly Gly His
            340                 345                 350

gga gtg aaa ggc tgg gcc ttt gat gat gga aat gac gtg tgg atg gga     1104
Gly Val Lys Gly Trp Ala Phe Asp Asp Gly Asn Asp Val Trp Met Gly
        355                 360                 365

aga acg atc agc gag aag tta cgc tca gga tat gaa acc ttc aaa gtc     1152
Arg Thr Ile Ser Glu Lys Leu Arg Ser Gly Tyr Glu Thr Phe Lys Val
    370                 375                 380

att gaa ggc tgg tcc aac cct aac tcc aaa ttg cag ata aat agg caa     1200
Ile Glu Gly Trp Ser Asn Pro Asn Ser Lys Leu Gln Ile Asn Arg Gln
385                 390                 395                 400

gtc ata gtt gac aga ggt aat agg tcc ggt tat tct ggt att ttc tct     1248
Val Ile Val Asp Arg Gly Asn Arg Ser Gly Tyr Ser Gly Ile Phe Ser
                405                 410                 415

gtt gaa ggc aaa agc tgc atc aat cgg tgc ttt tat gtg gag ttg ata     1296
Val Glu Gly Lys Ser Cys Ile Asn Arg Cys Phe Tyr Val Glu Leu Ile
            420                 425                 430

agg gga aga aaa caa gaa act gaa gtc ttg tgg acc tca aac agt att     1344
Arg Gly Arg Lys Gln Glu Thr Glu Val Leu Trp Thr Ser Asn Ser Ile
        435                 440                 445

gtt gtg ttt tgt ggc acc tca ggt aca tat gga aca ggc tca tgg cct     1392
Val Val Phe Cys Gly Thr Ser Gly Thr Tyr Gly Thr Gly Ser Trp Pro
    450                 455                 460

gat ggg gcg gac atc aat ctc atg cct ata taa gctttcgcaa ttttagaaaa   1445
Asp Gly Ala Asp Ile Asn Leu Met Pro Ile
465                 470

aactccttgt ttcc                                                      1459


<210> SEQ ID NO 41
<211> LENGTH: 474
<212> TYPE: PRT
<213> ORGANISM: Influenza virus
<220> FEATURE:
<221> NAME/KEY: misc_feature
<222> LOCATION: (5)..(5)
<223> OTHER INFORMATION: The 'Xaa' at location 5 stands for Lys, or Asn.

<400> SEQUENCE: 41

Lys Ala Gly Val Xaa Met Asn Pro Asn Gln Lys Ile Ile Thr Ile Gly
1               5                   10                  15

Ser Val Ser Leu Thr Ile Ser Thr Ile Cys Phe Phe Met Gln Ile Ala
            20                  25                  30

Ile Leu Ile Thr Thr Val Thr Leu His Phe Lys Gln Tyr Glu Phe Asn
        35                  40                  45

Ser Pro Pro Asn Asn Gln Val Met Leu Cys Glu Pro Thr Ile Ile Glu
    50                  55                  60

Arg Asn Ile Thr Glu Ile Val Tyr Leu Thr Asn Thr Thr Ile Glu Lys
65                  70                  75                  80

Glu Ile Cys Pro Lys Leu Ala Glu Tyr Arg Asn Trp Ser Lys Pro Gln
                85                  90                  95
```

-continued

```
Cys Asn Ile Thr Gly Phe Ala Pro Phe Ser Lys Asp Asn Ser Ile Arg
            100                 105                 110

Leu Ser Ala Gly Gly Asp Ile Trp Val Thr Arg Glu Pro Tyr Val Ser
        115                 120                 125

Cys Asp Pro Asp Lys Cys Tyr Gln Phe Ala Leu Gly Gln Gly Thr Thr
    130                 135                 140

Leu Asn Asn Val His Ser Asn Asp Thr Val His Asp Arg Thr Pro Tyr
145                 150                 155                 160

Arg Thr Leu Leu Met Asn Glu Leu Gly Val Pro Phe His Leu Gly Thr
                165                 170                 175

Lys Gln Val Cys Ile Ala Trp Ser Ser Ser Ser Cys His Asp Gly Lys
            180                 185                 190

Ala Trp Leu His Val Cys Val Thr Gly Asp Asp Glu Asn Ala Thr Ala
        195                 200                 205

Ser Phe Ile Tyr Asn Gly Arg Leu Val Asp Ser Ile Val Ser Trp Ser
    210                 215                 220

Lys Lys Ile Leu Arg Thr Gln Glu Ser Glu Cys Val Cys Ile Asn Gly
225                 230                 235                 240

Thr Cys Thr Val Val Met Thr Asp Gly Ser Ala Ser Gly Lys Ala Asp
                245                 250                 255

Thr Lys Ile Leu Phe Ile Glu Glu Gly Lys Ile Val His Thr Ser Thr
            260                 265                 270

Leu Ser Gly Ser Ala Gln His Val Glu Glu Cys Ser Cys Tyr Pro Arg
        275                 280                 285

Tyr Pro Gly Val Arg Cys Val Cys Arg Asp Asn Trp Lys Gly Ser Asn
    290                 295                 300

Arg Pro Ile Val Asp Ile Asn Ile Lys Asp Tyr Ser Ile Val Ser Ser
305                 310                 315                 320

Tyr Val Cys Ser Gly Leu Val Gly Asp Thr Pro Arg Lys Asn Asp Ser
                325                 330                 335

Ser Ser Ser Ser His Cys Leu Asp Pro Asn Asn Glu Glu Gly Gly His
            340                 345                 350

Gly Val Lys Gly Trp Ala Phe Asp Asp Gly Asn Asp Val Trp Met Gly
        355                 360                 365

Arg Thr Ile Ser Glu Lys Leu Arg Ser Gly Tyr Glu Thr Phe Lys Val
    370                 375                 380

Ile Glu Gly Trp Ser Asn Pro Asn Ser Lys Leu Gln Ile Asn Arg Gln
385                 390                 395                 400

Val Ile Val Asp Arg Gly Asn Arg Ser Gly Tyr Ser Gly Ile Phe Ser
                405                 410                 415

Val Glu Gly Lys Ser Cys Ile Asn Arg Cys Phe Tyr Val Glu Leu Ile
            420                 425                 430

Arg Gly Arg Lys Gln Glu Thr Glu Val Leu Trp Thr Ser Asn Ser Ile
        435                 440                 445

Val Val Phe Cys Gly Thr Ser Gly Thr Tyr Gly Thr Gly Ser Trp Pro
    450                 455                 460

Asp Gly Ala Asp Ile Asn Leu Met Pro Ile
465                 470
```

<210> SEQ ID NO 42
<211> LENGTH: 1459
<212> TYPE: DNA
<213> ORGANISM: Artificial
<220> FEATURE:
<223> OTHER INFORMATION: deoptimized influena NA sequence
<220> FEATURE:
<221> NAME/KEY: misc_feature
<222> LOCATION: (15)..(15)
<223> OTHER INFORMATION: n is a, c, g, or t

<400> SEQUENCE: 42

```
aaagcgggcg tgaanatgaa tccgaatcaa aagatcatca cgatcggctc ggtttcgtta      60

acgatctcga cgatctgctt cttcatgcaa atcgcgatct taatcacgac ggtaacgtta     120

catttcaagc aatatgaatt caactcgccg ccgaacaacc aagtgatgtt atgtgaaccg     180

acgatcatcg aacgcaacat cacggagatc gtgtatttaa cgaacacgac gatcgagaag     240

gaaatctgcc cgaaattagc ggaataccgc aattggtcga agccgcaatg taacatcacg     300

ggctttgcgc cgttttcgaa ggacaattcg atccgcttat cggcgggcgg cgacatctgg     360

gtgacgcgcg aaccgtatgt gtcgtgcgat ccggacaagt gttatcaatt tgcgttaggc     420

cagggcacga cgttaaacaa cgtgcattcg aatgacacgg tacatgatcg cacgccgtat     480

cgcacgttat taatgaatga gttaggcgtt ccgtttcatt taggcacgaa gcaagtgtgc     540

atcgcgtggt cgtcgtcgtc gtgtcacgat ggcaaggcgt ggttacatgt ttgtgtaacg     600

ggcgatgatg aaaatgcgac ggcgtcgttc atctacaatg gccgcttagt agattcgatc     660

gtttcgtggt cgaaaaaaat cttacgcacg caggagtcgg aatgcgtttg tatcaatggc     720

acgtgtacgg tagtaatgac ggatggctcg gcgtcgggca aagcggatac gaaaatctta     780

ttcatcgagg agggcaaaat cgttcatacg tcgacgttat cgggctcggc gcagcatgtc     840

gaggagtgct cgtgttatcc gcgctatccg ggcgtccgct gtgtctgccg cgacaactgg     900

aaaggctcga atcgcccgat cgtagatatc aacatcaagg attattcgat cgtttcgtcg     960

tatgtgtgct cgggcttagt tggcgacacg ccgcgcaaaa acgactcgtc gtcgtcgtcg    1020

cattgcttag atccgaacaa tgaggaaggc ggccatggcg tgaaaggctg ggcgtttgat    1080

gatggcaatg acgtgtggat gggccgcacg atctcggaga agttacgctc gggctatgaa    1140

acgttcaaag tcatcgaagg ctggtcgaac ccgaactcga aattacagat caatcgccaa    1200

gtcatcgttg accgcggcaa tcgctcgggc tattcgggca tcttctcggt tgaaggcaaa    1260

tcgtgcatca atcgctgctt ttatgtggag ttaatccgcg gccgcaaaca agaaacggaa    1320

gtcttatgga cgtcgaactc gatcgttgtg ttttgtggca cgtcgggcac gtatggcacg    1380

ggctcgtggc cggatggcgc ggacatcaat ttaatgccga tctaagcgtt cgcgatctta    1440

gaaaaaacgc cgtgtttcc                                                 1459
```

<210> SEQ ID NO 43
<211> LENGTH: 2550
<212> TYPE: DNA
<213> ORGANISM: Human immunodeficiency virus type 1
<220> FEATURE:
<221> NAME/KEY: CDS
<222> LOCATION: (1)..(2550)

<400> SEQUENCE: 43

```
atg aga gtg atg ggg ata ttg aag aat tat cag caa tgg tgg atg tgg       48
Met Arg Val Met Gly Ile Leu Lys Asn Tyr Gln Gln Trp Trp Met Trp
1               5                   10                  15

ggc atc tta ggc ttt tgg atg tta ata att agt agt gtg gta gga aac       96
Gly Ile Leu Gly Phe Trp Met Leu Ile Ile Ser Ser Val Val Gly Asn
            20                  25                  30

ttg tgg gtc aca gtc tat tat ggg gta cct gtg tgg aaa gaa gca aaa      144
Leu Trp Val Thr Val Tyr Tyr Gly Val Pro Val Trp Lys Glu Ala Lys
        35                  40                  45
```

-continued

```
act act cta ttc tgt aca tca gat gct aaa gca tat gag aca gag gtg      192
Thr Thr Leu Phe Cys Thr Ser Asp Ala Lys Ala Tyr Glu Thr Glu Val
    50                  55                  60

cat aat gtc tgg gct aca cat gcc tgt gta ccc aca gac ccc aac cca      240
His Asn Val Trp Ala Thr His Ala Cys Val Pro Thr Asp Pro Asn Pro
65                  70                  75                  80

caa gaa ata gtt ttg gaa aat gta aca gaa aat ttt aac atg tgg aaa      288
Gln Glu Ile Val Leu Glu Asn Val Thr Glu Asn Phe Asn Met Trp Lys
                85                  90                  95

aat gac atg gtg gat cag atg cat gag gat ata atc agt tta tgg gac      336
Asn Asp Met Val Asp Gln Met His Glu Asp Ile Ile Ser Leu Trp Asp
            100                 105                 110

caa agc cta aag cca tgt gta aag ttg acc cca ctc tgt gtc act tta      384
Gln Ser Leu Lys Pro Cys Val Lys Leu Thr Pro Leu Cys Val Thr Leu
        115                 120                 125

aaa tgt aga aat gtt aat gct acc aac aat att aat agc atg att gat      432
Lys Cys Arg Asn Val Asn Ala Thr Asn Asn Ile Asn Ser Met Ile Asp
    130                 135                 140

aac agt aat aag gga gaa atg aaa aat tgc tct ttc aat gta acc aca      480
Asn Ser Asn Lys Gly Glu Met Lys Asn Cys Ser Phe Asn Val Thr Thr
145                 150                 155                 160

gaa cta aga gat agg aaa cag gaa gta cat gca ctt ttt tat aga ctt      528
Glu Leu Arg Asp Arg Lys Gln Glu Val His Ala Leu Phe Tyr Arg Leu
                165                 170                 175

gat gta gta cca ctt cag ggc aac aac tct aat gag tat aga tta ata      576
Asp Val Val Pro Leu Gln Gly Asn Asn Ser Asn Glu Tyr Arg Leu Ile
            180                 185                 190

aat tgt aat acg tca gcc ata aca caa gcc tgt cca aag gtc tct ttt      624
Asn Cys Asn Thr Ser Ala Ile Thr Gln Ala Cys Pro Lys Val Ser Phe
        195                 200                 205

gat cca att cct ata cat tat tgt act cca gct ggt tat gcg att cta      672
Asp Pro Ile Pro Ile His Tyr Cys Thr Pro Ala Gly Tyr Ala Ile Leu
    210                 215                 220

aag tgt aat aat cag aca ttc aat ggg aca gga cca tgc aat aat gtc      720
Lys Cys Asn Asn Gln Thr Phe Asn Gly Thr Gly Pro Cys Asn Asn Val
225                 230                 235                 240

agc tca gta caa tgt gca cat gga att aag cca gtg gta tca act cag      768
Ser Ser Val Gln Cys Ala His Gly Ile Lys Pro Val Val Ser Thr Gln
                245                 250                 255

cta ctg tta aat ggt agc gta gca aaa gga gag ata ata att aga tct      816
Leu Leu Leu Asn Gly Ser Val Ala Lys Gly Glu Ile Ile Ile Arg Ser
            260                 265                 270

gaa aat ctg aca aac aat gcc aaa ata ata ata gta caa ctt aat aaa      864
Glu Asn Leu Thr Asn Asn Ala Lys Ile Ile Ile Val Gln Leu Asn Lys
        275                 280                 285

cct gta aaa att gtg tgt gta agg cct aac aat aat aca aga aaa agt      912
Pro Val Lys Ile Val Cys Val Arg Pro Asn Asn Asn Thr Arg Lys Ser
    290                 295                 300

gta agg ata gga cca gga caa aca ttc tat gca aca gga gaa ata ata      960
Val Arg Ile Gly Pro Gly Gln Thr Phe Tyr Ala Thr Gly Glu Ile Ile
305                 310                 315                 320

gga gac ata aga caa gca tat tgt atc att aat aaa act gaa tgg aat     1008
Gly Asp Ile Arg Gln Ala Tyr Cys Ile Ile Asn Lys Thr Glu Trp Asn
                325                 330                 335

agc act tta caa ggg gta agt aaa aaa tta gaa gaa cac ttc tct aaa     1056
Ser Thr Leu Gln Gly Val Ser Lys Lys Leu Glu Glu His Phe Ser Lys
            340                 345                 350

aaa gca ata aaa tgt gaa ccg tca tca gga ggg gac cta gaa att aca     1104
Lys Ala Ile Lys Cys Glu Pro Ser Ser Gly Gly Asp Leu Glu Ile Thr
```

-continued

```
        355                 360                 365

aca cat agc ttt aat tgt aga gga gaa ttt ttc tat tgc gac aca tca     1152
Thr His Ser Phe Asn Cys Arg Gly Glu Phe Phe Tyr Cys Asp Thr Ser
    370                 375                 380

caa ctg ttt aat agt aca tac agt ccc agt ttt aat ggt aca gaa aat     1200
Gln Leu Phe Asn Ser Thr Tyr Ser Pro Ser Phe Asn Gly Thr Glu Asn
385                 390                 395                 400

aaa tta aac ggg acc atc aca atc aca tgt aga ata aaa caa att ata     1248
Lys Leu Asn Gly Thr Ile Thr Ile Thr Cys Arg Ile Lys Gln Ile Ile
                405                 410                 415

aac atg tgg caa aag gta gga aga gca atg tat gcc cct ccc att gca     1296
Asn Met Trp Gln Lys Val Gly Arg Ala Met Tyr Ala Pro Pro Ile Ala
            420                 425                 430

gga aac cta aca tgt gaa tca gat atc aca gga tta cta ttg aca cgt     1344
Gly Asn Leu Thr Cys Glu Ser Asp Ile Thr Gly Leu Leu Leu Thr Arg
        435                 440                 445

gat gga gga aaa aca ggt cca aat gac aca gag ata ttc aga cct gga     1392
Asp Gly Gly Lys Thr Gly Pro Asn Asp Thr Glu Ile Phe Arg Pro Gly
    450                 455                 460

gga ggg gat atg agg gac aac tgg aga aat gaa tta tat aaa tat aaa     1440
Gly Gly Asp Met Arg Asp Asn Trp Arg Asn Glu Leu Tyr Lys Tyr Lys
465                 470                 475                 480

gta gta gaa att aag cca ttg gga gta gca ccc act gag gca aaa agg     1488
Val Val Glu Ile Lys Pro Leu Gly Val Ala Pro Thr Glu Ala Lys Arg
                485                 490                 495

aga gtg gtg gag aga gaa aaa aga gca gtg gga ata gga gct gtg tgc     1536
Arg Val Val Glu Arg Glu Lys Arg Ala Val Gly Ile Gly Ala Val Cys
            500                 505                 510

ctt ggg ttc ttg gga gca gct gga agc act atg ggc gcg gcg tca ata     1584
Leu Gly Phe Leu Gly Ala Ala Gly Ser Thr Met Gly Ala Ala Ser Ile
        515                 520                 525

acg ctg acg gta cag gcc aga cta ttg ttg tct ggt ata gtg cag cag     1632
Thr Leu Thr Val Gln Ala Arg Leu Leu Leu Ser Gly Ile Val Gln Gln
    530                 535                 540

caa aac aat ctg ctg agg gct ata gag gcg caa cag cat ctg ttg caa     1680
Gln Asn Asn Leu Leu Arg Ala Ile Glu Ala Gln Gln His Leu Leu Gln
545                 550                 555                 560

ctc aca gtc tgg ggc att aag cag ctc cag aca aga atc ttg gct gta     1728
Leu Thr Val Trp Gly Ile Lys Gln Leu Gln Thr Arg Ile Leu Ala Val
                565                 570                 575

gaa aga tac cta aag gat caa cag ctc cta ggg att tgg ggc tgc tct     1776
Glu Arg Tyr Leu Lys Asp Gln Gln Leu Leu Gly Ile Trp Gly Cys Ser
            580                 585                 590

gga aaa ctc atc tgc acc act gct gtg cct tgg aac tcc agt tgg agt     1824
Gly Lys Leu Ile Cys Thr Thr Ala Val Pro Trp Asn Ser Ser Trp Ser
        595                 600                 605

aat aga tct cat gat gag att tgg gat aac atg acc tgg atg cag tgg     1872
Asn Arg Ser His Asp Glu Ile Trp Asp Asn Met Thr Trp Met Gln Trp
    610                 615                 620

gat aga gaa att aat aat tac aca gac aca ata tac agg ttg ctt gaa     1920
Asp Arg Glu Ile Asn Asn Tyr Thr Asp Thr Ile Tyr Arg Leu Leu Glu
625                 630                 635                 640

gaa tca caa aac cag cag gag aaa aat gaa aag gat tta tta gca ttg     1968
Glu Ser Gln Asn Gln Gln Glu Lys Asn Glu Lys Asp Leu Leu Ala Leu
                645                 650                 655

gac agt tgg caa aat ctg tgg aat tgg ttt agc ata aca aat tgg ctg     2016
Asp Ser Trp Gln Asn Leu Trp Asn Trp Phe Ser Ile Thr Asn Trp Leu
            660                 665                 670

tgg tat ata aaa ata ttc ata atg ata gta gga ggc ttg ata ggt tta     2064
```

```
Trp Tyr Ile Lys Ile Phe Ile Met Ile Val Gly Gly Leu Ile Gly Leu
        675                 680                 685

aga ata att ttt gct gtg ctt tct ata gtg aat aga gtt agg cag gga      2112
Arg Ile Ile Phe Ala Val Leu Ser Ile Val Asn Arg Val Arg Gln Gly
    690                 695                 700

tac tca cct ctg ccg ttt cag acc ctt acc ccg aac cca agg gaa ccc      2160
Tyr Ser Pro Leu Pro Phe Gln Thr Leu Thr Pro Asn Pro Arg Glu Pro
705                 710                 715                 720

gac agg ctc gga aga atc gaa gaa gaa ggt gga gag caa gac aga ggc      2208
Asp Arg Leu Gly Arg Ile Glu Glu Glu Gly Gly Glu Gln Asp Arg Gly
                725                 730                 735

aga tcc att cgc tta gtg agc gga ttc tta gcg ctt gcc tgg gac gac      2256
Arg Ser Ile Arg Leu Val Ser Gly Phe Leu Ala Leu Ala Trp Asp Asp
            740                 745                 750

ctg cgg agc ctg tgc ctt ttc agc tac cac cga ttg aga gac ttc ata      2304
Leu Arg Ser Leu Cys Leu Phe Ser Tyr His Arg Leu Arg Asp Phe Ile
        755                 760                 765

ttg att gca gca aga gtg ttg gaa ctt ctg gga cag agg ggg tgg gaa      2352
Leu Ile Ala Ala Arg Val Leu Glu Leu Leu Gly Gln Arg Gly Trp Glu
    770                 775                 780

gcc ctt aaa tat ctg gga agc ctt gtg cag tat tgg ggt cta gag cta      2400
Ala Leu Lys Tyr Leu Gly Ser Leu Val Gln Tyr Trp Gly Leu Glu Leu
785                 790                 795                 800

aaa aag agt gct att agt ctg ctt gat acc ata gca ata gca gta gct      2448
Lys Lys Ser Ala Ile Ser Leu Leu Asp Thr Ile Ala Ile Ala Val Ala
                805                 810                 815

gaa gga aca gat agg att ata gaa ttc ata caa aga att tgt aga gct      2496
Glu Gly Thr Asp Arg Ile Ile Glu Phe Ile Gln Arg Ile Cys Arg Ala
            820                 825                 830

att cgc aac ata cct aga aga ata aga cag ggc ttt gaa gca gct ttg      2544
Ile Arg Asn Ile Pro Arg Arg Ile Arg Gln Gly Phe Glu Ala Ala Leu
        835                 840                 845

caa taa                                                              2550
Gln
```

<210> SEQ ID NO 44
<211> LENGTH: 849
<212> TYPE: PRT
<213> ORGANISM: Human immunodeficiency virus type 1

<400> SEQUENCE: 44

```
Met Arg Val Met Gly Ile Leu Lys Asn Tyr Gln Gln Trp Trp Met Trp
1               5                   10                  15

Gly Ile Leu Gly Phe Trp Met Leu Ile Ile Ser Ser Val Val Gly Asn
            20                  25                  30

Leu Trp Val Thr Val Tyr Tyr Gly Val Pro Val Trp Lys Glu Ala Lys
        35                  40                  45

Thr Thr Leu Phe Cys Thr Ser Asp Ala Lys Ala Tyr Glu Thr Glu Val
    50                  55                  60

His Asn Val Trp Ala Thr His Ala Cys Val Pro Thr Asp Pro Asn Pro
65                  70                  75                  80

Gln Glu Ile Val Leu Glu Asn Val Thr Glu Asn Phe Asn Met Trp Lys
                85                  90                  95

Asn Asp Met Val Asp Gln Met His Glu Asp Ile Ile Ser Leu Trp Asp
            100                 105                 110

Gln Ser Leu Lys Pro Cys Val Lys Leu Thr Pro Leu Cys Val Thr Leu
        115                 120                 125

Lys Cys Arg Asn Val Asn Ala Thr Asn Asn Ile Asn Ser Met Ile Asp
```

```
    130                 135                 140

Asn Ser Asn Lys Gly Glu Met Lys Asn Cys Ser Phe Asn Val Thr Thr
145                 150                 155                 160

Glu Leu Arg Asp Arg Lys Gln Glu Val His Ala Leu Phe Tyr Arg Leu
                165                 170                 175

Asp Val Val Pro Leu Gln Gly Asn Asn Ser Asn Glu Tyr Arg Leu Ile
            180                 185                 190

Asn Cys Asn Thr Ser Ala Ile Thr Gln Ala Cys Pro Lys Val Ser Phe
        195                 200                 205

Asp Pro Ile Pro Ile His Tyr Cys Thr Pro Ala Gly Tyr Ala Ile Leu
    210                 215                 220

Lys Cys Asn Asn Gln Thr Phe Asn Gly Thr Gly Pro Cys Asn Asn Val
225                 230                 235                 240

Ser Ser Val Gln Cys Ala His Gly Ile Lys Pro Val Val Ser Thr Gln
                245                 250                 255

Leu Leu Leu Asn Gly Ser Val Ala Lys Gly Glu Ile Ile Ile Arg Ser
            260                 265                 270

Glu Asn Leu Thr Asn Asn Ala Lys Ile Ile Ile Val Gln Leu Asn Lys
        275                 280                 285

Pro Val Lys Ile Val Cys Val Arg Pro Asn Asn Asn Thr Arg Lys Ser
    290                 295                 300

Val Arg Ile Gly Pro Gly Gln Thr Phe Tyr Ala Thr Gly Glu Ile Ile
305                 310                 315                 320

Gly Asp Ile Arg Gln Ala Tyr Cys Ile Ile Asn Lys Thr Glu Trp Asn
                325                 330                 335

Ser Thr Leu Gln Gly Val Ser Lys Lys Leu Glu Glu His Phe Ser Lys
            340                 345                 350

Lys Ala Ile Lys Cys Glu Pro Ser Ser Gly Gly Asp Leu Glu Ile Thr
        355                 360                 365

Thr His Ser Phe Asn Cys Arg Gly Glu Phe Phe Tyr Cys Asp Thr Ser
    370                 375                 380

Gln Leu Phe Asn Ser Thr Tyr Ser Pro Ser Phe Asn Gly Thr Glu Asn
385                 390                 395                 400

Lys Leu Asn Gly Thr Ile Thr Ile Thr Cys Arg Ile Lys Gln Ile Ile
                405                 410                 415

Asn Met Trp Gln Lys Val Gly Arg Ala Met Tyr Ala Pro Pro Ile Ala
            420                 425                 430

Gly Asn Leu Thr Cys Glu Ser Asp Ile Thr Gly Leu Leu Leu Thr Arg
        435                 440                 445

Asp Gly Gly Lys Thr Gly Pro Asn Asp Thr Glu Ile Phe Arg Pro Gly
    450                 455                 460

Gly Gly Asp Met Arg Asp Asn Trp Arg Asn Glu Leu Tyr Lys Tyr Lys
465                 470                 475                 480

Val Val Glu Ile Lys Pro Leu Gly Val Ala Pro Thr Glu Ala Lys Arg
                485                 490                 495

Arg Val Val Glu Arg Glu Lys Arg Ala Val Gly Ile Gly Ala Val Cys
            500                 505                 510

Leu Gly Phe Leu Gly Ala Ala Gly Ser Thr Met Gly Ala Ala Ser Ile
        515                 520                 525

Thr Leu Thr Val Gln Ala Arg Leu Leu Leu Ser Gly Ile Val Gln Gln
    530                 535                 540

Gln Asn Asn Leu Leu Arg Ala Ile Glu Ala Gln Gln His Leu Leu Gln
545                 550                 555                 560
```

```
Leu Thr Val Trp Gly Ile Lys Gln Leu Gln Thr Arg Ile Leu Ala Val
                565                 570                 575

Glu Arg Tyr Leu Lys Asp Gln Gln Leu Leu Gly Ile Trp Gly Cys Ser
            580                 585                 590

Gly Lys Leu Ile Cys Thr Thr Ala Val Pro Trp Asn Ser Ser Trp Ser
        595                 600                 605

Asn Arg Ser His Asp Glu Ile Trp Asp Asn Met Thr Trp Met Gln Trp
    610                 615                 620

Asp Arg Glu Ile Asn Asn Tyr Thr Asp Thr Ile Tyr Arg Leu Leu Glu
625                 630                 635                 640

Glu Ser Gln Asn Gln Gln Glu Lys Asn Glu Lys Asp Leu Leu Ala Leu
                645                 650                 655

Asp Ser Trp Gln Asn Leu Trp Asn Trp Phe Ser Ile Thr Asn Trp Leu
            660                 665                 670

Trp Tyr Ile Lys Ile Phe Ile Met Ile Val Gly Gly Leu Ile Gly Leu
        675                 680                 685

Arg Ile Ile Phe Ala Val Leu Ser Ile Val Asn Arg Val Arg Gln Gly
    690                 695                 700

Tyr Ser Pro Leu Pro Phe Gln Thr Leu Thr Pro Asn Pro Arg Glu Pro
705                 710                 715                 720

Asp Arg Leu Gly Arg Ile Glu Glu Glu Gly Gly Glu Gln Asp Arg Gly
                725                 730                 735

Arg Ser Ile Arg Leu Val Ser Gly Phe Leu Ala Leu Ala Trp Asp Asp
            740                 745                 750

Leu Arg Ser Leu Cys Leu Phe Ser Tyr His Arg Leu Arg Asp Phe Ile
        755                 760                 765

Leu Ile Ala Ala Arg Val Leu Glu Leu Leu Gly Gln Arg Gly Trp Glu
    770                 775                 780

Ala Leu Lys Tyr Leu Gly Ser Leu Val Gln Tyr Trp Gly Leu Glu Leu
785                 790                 795                 800

Lys Lys Ser Ala Ile Ser Leu Leu Asp Thr Ile Ala Ile Ala Val Ala
                805                 810                 815

Glu Gly Thr Asp Arg Ile Ile Glu Phe Ile Gln Arg Ile Cys Arg Ala
            820                 825                 830

Ile Arg Asn Ile Pro Arg Arg Ile Arg Gln Gly Phe Glu Ala Ala Leu
        835                 840                 845

Gln


<210> SEQ ID NO 45
<211> LENGTH: 2550
<212> TYPE: DNA
<213> ORGANISM: Artificial
<220> FEATURE:
<223> OTHER INFORMATION: deoptimized HIV-1 ENV sequence

<400> SEQUENCE: 45

atgcgtgtca tgggtatact caagaattat cagcaatggt ggatgtgggg tatcctcggt      60

ttttggatgc tcataatttc gtcggtcgtc ggtaacctct gggtcacggt ctattatggt     120

gtcccggtct ggaaagaagc gaaaacgacg ctcttctgta cgtcggatgc gaaagcgtat     180

gagacggagg tccataatgt ctgggcgacg catgcgtgtg tcccgacgga cccgaacccg     240

caagaaatag tcctcgaaaa tgtcacggaa aattttaaca tgtggaaaaa tgacatggtc     300

gatcagatgc atgaggatat aatctcgctc tgggaccaat cgctcaagcc gtgtgtcaag     360
```

```
ctcacgccgc tctgtgtcac gctcaaatgt cgtaatgtca atgcgacgaa caatattaat    420
tcgatgattg ataactcgaa taagggtgaa atgaaaaatt gctcgttcaa tgtcacgacg    480
gaactccgtg atcgtaaaca ggaagtccat gcgctctttt atcgtctcga tgtcgtcccg    540
ctccagggta acaactcgaa tgagtatcgt ctcataaatt gtaatacgtc ggcgataacg    600
caagcgtgtc cgaaggtctc gtttgatccg attccgatac attattgtac gccggcgggt    660
tatgcgattc tcaagtgtaa taatcagacg ttcaatggta cgggtccgtg caataatgtc    720
tcgtcggtcc aatgtgcgca tggtattaag ccggtcgtct cgacgcagct cctcctcaat    780
ggttcggtcg cgaaaggtga gataataatt cgttcggaaa atctcacgaa caatgcgaaa    840
ataataatag tccaactcaa taaaccggtc aaaattgtct gtgtccgtcc gaacaataat    900
acgcgtaaat cggtccgtat aggtccgggt caaacgttct atgcgacggg tgaaataata    960
ggtgacatac gtcaagcgta ttgtatcatt aataaaacgg aatggaattc gacgctccaa   1020
ggtgtctcga aaaaactcga agaacacttc tcgaaaaaag cgataaaatg tgaaccgtcg   1080
tcgggtggtg acctcgaaat tacgacgcat tcgtttaatt gtcgtggtga atttttctat   1140
tgcgacacgt ctcaactctt taattcgacg tactcgccgt cgtttaatgg tacggaaaat   1200
aaactcaacg gtacgatcac gatcacgtgt cgtataaaac aaattataaa catgtggcaa   1260
aaggtcggtc gtgcgatgta tgcgccgccg attgcgggta acctcacgtg tgaatcggat   1320
atcacgggtc tcctcctcac gcgtgatggt ggtaaaacgg gtccgaatga cacggagata   1380
ttccgtccgg gtggtggtga tatgcgtgac aactggcgta atgaactcta taaatataaa   1440
gtcgtcgaaa ttaagccgct cggtgtcgcg ccgacggagg cgaaacgtcg tgtcgtcgag   1500
cgtgaaaaac gtgcggtcgg tataggtgcg gtctgcctcg gtttcctcgg tgcggcgggt   1560
tcgacgatgg gtgcggcgtc gataacgctc acggtccagg cgcgtctcct cctctcgggt   1620
atagtccagc agcaaaacaa tctcctccgt gcgatagagg cgcaacagca tctcctccaa   1680
ctcacggtct ggggtattaa gcagctccag acgcgtatcc tcgcggtcga acgttacctc   1740
aaggatcaac agctcctcgg tatttggggt tgctcgggta aactcatctg cacgacggcg   1800
gtcccgtgga actcgtcgtg gtcgaatcgt tcgcatgatg agatttggga taacatgacg   1860
tggatgcagt gggatcgtga aattaataat tacacggaca cgatataccg tctcctcgaa   1920
gaatcgcaaa accagcagga gaaaaatgaa aaggatctcc tcgcgctcga ctcgtggcaa   1980
aatctctgga attggttttc gataacgaat tggctctggt atataaaaat attcataatg   2040
atagtcggtg gtctcatagg tctccgtata atttttgcgg tcctctcgat agtcaatcgt   2100
gtccgtcagg gttactcgcc gctcccgttt cagacgctca cgccgaaccc gcgtgaaccg   2160
gaccgtctcg gtcgtatcga agaagaaggt ggtgagcaag accgtggtag ttcgattcgt   2220
ctcgtctcgg gtttcctcgc gctcgcgtgg gacgacctcc gttcgctctg cctcttctcg   2280
taccaccgtc tccgtgactt catactcatt gcggcgcgtg tcctcgaact cctcggtcag   2340
cgtggttggg aagcgctcaa atatctcggt tcgctcgtcc agtattgggg tctcgagctc   2400
aaaaagtcgg cgatttcgct cctcgatacg atagcgatag cggtcgcgga aggtacggat   2460
cgtattatag aattcataca acgtatttgt cgtgcgattc gtaacatacc gcgtcgtata   2520
cgtcagggtt ttgaagcggc gctccaataa                                    2550
```

<210> SEQ ID NO 46
<211> LENGTH: 1734
<212> TYPE: DNA
<213> ORGANISM: Escherichia coli

<220> FEATURE:
<221> NAME/KEY: CDS
<222> LOCATION: (1)..(1734)

<400> SEQUENCE: 46

```
gtg aat att cag gct ctt ctc tca gaa aaa gtc cgt cag gcc atg att       48
Val Asn Ile Gln Ala Leu Leu Ser Glu Lys Val Arg Gln Ala Met Ile
1               5                   10                  15

gcg gca ggc gcg cct gcg gat tgc gaa ccg cag gtt cgt cag tca gca       96
Ala Ala Gly Ala Pro Ala Asp Cys Glu Pro Gln Val Arg Gln Ser Ala
            20                  25                  30

aaa gtt cag ttc ggc gac tat cag gct aac ggc atg atg gca gtt gct      144
Lys Val Gln Phe Gly Asp Tyr Gln Ala Asn Gly Met Met Ala Val Ala
        35                  40                  45

aaa aaa ctg ggt atg gca ccg cga caa tta gca gag cag gtg ctg act      192
Lys Lys Leu Gly Met Ala Pro Arg Gln Leu Ala Glu Gln Val Leu Thr
    50                  55                  60

cat ctg gat ctt aac ggt atc gcc agc aaa gtt gag atc gcc ggt cca      240
His Leu Asp Leu Asn Gly Ile Ala Ser Lys Val Glu Ile Ala Gly Pro
65                  70                  75                  80

ggc ttt atc aac att ttc ctt gat ccg gca ttc ctg gct gaa cat gtt      288
Gly Phe Ile Asn Ile Phe Leu Asp Pro Ala Phe Leu Ala Glu His Val
                85                  90                  95

cag cag gcg ctg gcg tcc gat cgt ctc ggt gtt gct acg cca gaa aaa      336
Gln Gln Ala Leu Ala Ser Asp Arg Leu Gly Val Ala Thr Pro Glu Lys
            100                 105                 110

cag acc att gtg gtt gac tac tct gcg cca aac gtg gcg aaa gag atg      384
Gln Thr Ile Val Val Asp Tyr Ser Ala Pro Asn Val Ala Lys Glu Met
        115                 120                 125

cat gtc ggt cac ctg cgc tct acc att att ggt gac gca gca gtg cgt      432
His Val Gly His Leu Arg Ser Thr Ile Ile Gly Asp Ala Ala Val Arg
    130                 135                 140

act ctg gag ttc ctc ggt cac aaa gtg att cgc gca aac cac gtc ggc      480
Thr Leu Glu Phe Leu Gly His Lys Val Ile Arg Ala Asn His Val Gly
145                 150                 155                 160

gac tgg ggc act cag ttc ggt atg ctg att gca tgg ctg gaa aag cag      528
Asp Trp Gly Thr Gln Phe Gly Met Leu Ile Ala Trp Leu Glu Lys Gln
                165                 170                 175

cag cag gaa aac gcc ggt gaa atg gag ctg gct gac ctt gaa ggt ttc      576
Gln Gln Glu Asn Ala Gly Glu Met Glu Leu Ala Asp Leu Glu Gly Phe
            180                 185                 190

tac cgc gat gcg aaa aag cat tac gat gaa gat gaa gag ttc gcc gag      624
Tyr Arg Asp Ala Lys Lys His Tyr Asp Glu Asp Glu Glu Phe Ala Glu
        195                 200                 205

cgc gca cgt aac tac gtg gta aaa ctg caa agc ggt gac gaa tat ttc      672
Arg Ala Arg Asn Tyr Val Val Lys Leu Gln Ser Gly Asp Glu Tyr Phe
    210                 215                 220

cgc gag atg tgg cgc aaa ctg gtc gac atc acc atg acg cag aac cag      720
Arg Glu Met Trp Arg Lys Leu Val Asp Ile Thr Met Thr Gln Asn Gln
225                 230                 235                 240

atc acc tac gat cgt ctc aac gtg acg ctg acc cgt gat gac gtg atg      768
Ile Thr Tyr Asp Arg Leu Asn Val Thr Leu Thr Arg Asp Asp Val Met
                245                 250                 255

ggc gaa agc ctc tac aac ccg atg ctg cca gga att gtg gcg gat ctc      816
Gly Glu Ser Leu Tyr Asn Pro Met Leu Pro Gly Ile Val Ala Asp Leu
            260                 265                 270

aaa gcc aaa ggt ctg gca gta gaa agc gaa ggg gcg acc gtc gta ttc      864
Lys Ala Lys Gly Leu Ala Val Glu Ser Glu Gly Ala Thr Val Val Phe
        275                 280                 285

ctt gat gag ttt aaa aac aag gaa ggc gaa ccg atg ggc gtg atc att      912
```

-continued

```
Leu Asp Glu Phe Lys Asn Lys Glu Gly Glu Pro Met Gly Val Ile Ile
    290                 295                 300

cag aag aaa gat ggc ggc tat ctc tac acc acc act gat atc gcc tgt      960
Gln Lys Lys Asp Gly Gly Tyr Leu Tyr Thr Thr Thr Asp Ile Ala Cys
305                 310                 315                 320

gcg aaa tat cgt tat gaa aca ctg cat gcc gat cgc gtg ctg tat tac     1008
Ala Lys Tyr Arg Tyr Glu Thr Leu His Ala Asp Arg Val Leu Tyr Tyr
                325                 330                 335

atc gac tcc cgt cag cat caa cac ctg atg cag gca tgg gcg atc gtc     1056
Ile Asp Ser Arg Gln His Gln His Leu Met Gln Ala Trp Ala Ile Val
            340                 345                 350

cgt aaa gca ggc tat gta ccg gaa tcc gta ccg ctg gaa cac cac atg     1104
Arg Lys Ala Gly Tyr Val Pro Glu Ser Val Pro Leu Glu His His Met
        355                 360                 365

ttc ggc atg atg ctg ggt aaa gac ggc aaa ccg ttc aaa acc cgc gcg     1152
Phe Gly Met Met Leu Gly Lys Asp Gly Lys Pro Phe Lys Thr Arg Ala
    370                 375                 380

ggt ggt aca gtg aaa ctg gcc gat ctg ctg gat gaa gcc ctg gaa cgt     1200
Gly Gly Thr Val Lys Leu Ala Asp Leu Leu Asp Glu Ala Leu Glu Arg
385                 390                 395                 400

gca cgc cgt ctg gtg gca gaa aag aac ccg gat atg cca gcc gac gag     1248
Ala Arg Arg Leu Val Ala Glu Lys Asn Pro Asp Met Pro Ala Asp Glu
                405                 410                 415

ctg gaa aaa ctg gct aac gcg gtt ggt att ggt gcg gtg aaa tat gcg     1296
Leu Glu Lys Leu Ala Asn Ala Val Gly Ile Gly Ala Val Lys Tyr Ala
            420                 425                 430

gat ctc tcc aaa aac cgc acc acg gac tac atc ttc gac tgg gac aac     1344
Asp Leu Ser Lys Asn Arg Thr Thr Asp Tyr Ile Phe Asp Trp Asp Asn
        435                 440                 445

atg ctg gcg ttt gag ggt aat acc gcg cca tac atg cag tat gca tac     1392
Met Leu Ala Phe Glu Gly Asn Thr Ala Pro Tyr Met Gln Tyr Ala Tyr
    450                 455                 460

acg cgt gta ttg tcc gtg ttc cgt aaa gca gaa att gac gaa gag caa     1440
Thr Arg Val Leu Ser Val Phe Arg Lys Ala Glu Ile Asp Glu Glu Gln
465                 470                 475                 480

ctg gct gca gct ccg gtt atc atc cgt gaa gat cgt gaa gcg caa ctg     1488
Leu Ala Ala Ala Pro Val Ile Ile Arg Glu Asp Arg Glu Ala Gln Leu
                485                 490                 495

gca gct cgc ctg ctg cag ttt gaa gaa acc ctc acc gtg gtt gcc cgt     1536
Ala Ala Arg Leu Leu Gln Phe Glu Glu Thr Leu Thr Val Val Ala Arg
            500                 505                 510

gaa ggc acg ccg cat gta atg tgt gct tac ctg tac gat ctg gcc ggt     1584
Glu Gly Thr Pro His Val Met Cys Ala Tyr Leu Tyr Asp Leu Ala Gly
        515                 520                 525

ctg ttc tct ggc ttc tac gag cac tgc ccg atc ctc agc gca gaa aac     1632
Leu Phe Ser Gly Phe Tyr Glu His Cys Pro Ile Leu Ser Ala Glu Asn
    530                 535                 540

gaa gaa gtg cgt aac agc cgt cta aaa ctg gca caa ctg acg gcg aag     1680
Glu Glu Val Arg Asn Ser Arg Leu Lys Leu Ala Gln Leu Thr Ala Lys
545                 550                 555                 560

acg ctg aag ctg ggt ctg gat acg ctg ggt att gag act gta gag cgt     1728
Thr Leu Lys Leu Gly Leu Asp Thr Leu Gly Ile Glu Thr Val Glu Arg
                565                 570                 575

atg taa                                                             1734
Met

<210> SEQ ID NO 47
<211> LENGTH: 577
<212> TYPE: PRT
<213> ORGANISM: Escherichia coli
```

<400> SEQUENCE: 47

Val Asn Ile Gln Ala Leu Leu Ser Glu Lys Val Arg Gln Ala Met Ile
1 5 10 15

Ala Ala Gly Ala Pro Ala Asp Cys Glu Pro Gln Val Arg Gln Ser Ala
20 25 30

Lys Val Gln Phe Gly Asp Tyr Gln Ala Asn Gly Met Met Ala Val Ala
35 40 45

Lys Lys Leu Gly Met Ala Pro Arg Gln Leu Ala Glu Gln Val Leu Thr
50 55 60

His Leu Asp Leu Asn Gly Ile Ala Ser Lys Val Glu Ile Ala Gly Pro
65 70 75 80

Gly Phe Ile Asn Ile Phe Leu Asp Pro Ala Phe Leu Ala Glu His Val
85 90 95

Gln Gln Ala Leu Ala Ser Asp Arg Leu Gly Val Ala Thr Pro Glu Lys
100 105 110

Gln Thr Ile Val Val Asp Tyr Ser Ala Pro Asn Val Ala Lys Glu Met
115 120 125

His Val Gly His Leu Arg Ser Thr Ile Ile Gly Asp Ala Ala Val Arg
130 135 140

Thr Leu Glu Phe Leu Gly His Lys Val Ile Arg Ala Asn His Val Gly
145 150 155 160

Asp Trp Gly Thr Gln Phe Gly Met Leu Ile Ala Trp Leu Glu Lys Gln
165 170 175

Gln Gln Glu Asn Ala Gly Glu Met Glu Leu Ala Asp Leu Glu Gly Phe
180 185 190

Tyr Arg Asp Ala Lys Lys His Tyr Asp Glu Asp Glu Glu Phe Ala Glu
195 200 205

Arg Ala Arg Asn Tyr Val Val Lys Leu Gln Ser Gly Asp Glu Tyr Phe
210 215 220

Arg Glu Met Trp Arg Lys Leu Val Asp Ile Thr Met Thr Gln Asn Gln
225 230 235 240

Ile Thr Tyr Asp Arg Leu Asn Val Thr Leu Thr Arg Asp Asp Val Met
245 250 255

Gly Glu Ser Leu Tyr Asn Pro Met Leu Pro Gly Ile Val Ala Asp Leu
260 265 270

Lys Ala Lys Gly Leu Ala Val Glu Ser Glu Gly Ala Thr Val Val Phe
275 280 285

Leu Asp Glu Phe Lys Asn Lys Glu Gly Glu Pro Met Gly Val Ile Ile
290 295 300

Gln Lys Lys Asp Gly Gly Tyr Leu Tyr Thr Thr Thr Asp Ile Ala Cys
305 310 315 320

Ala Lys Tyr Arg Tyr Glu Thr Leu His Ala Asp Arg Val Leu Tyr Tyr
325 330 335

Ile Asp Ser Arg Gln His Gln His Leu Met Gln Ala Trp Ala Ile Val
340 345 350

Arg Lys Ala Gly Tyr Val Pro Glu Ser Val Pro Leu Glu His His Met
355 360 365

Phe Gly Met Met Leu Gly Lys Asp Gly Lys Pro Phe Lys Thr Arg Ala
370 375 380

Gly Gly Thr Val Lys Leu Ala Asp Leu Leu Asp Glu Ala Leu Glu Arg
385 390 395 400

Ala Arg Arg Leu Val Ala Glu Lys Asn Pro Asp Met Pro Ala Asp Glu

-continued

```
                405                 410                 415

Leu Glu Lys Leu Ala Asn Ala Val Gly Ile Gly Ala Val Lys Tyr Ala
            420                 425                 430

Asp Leu Ser Lys Asn Arg Thr Thr Asp Tyr Ile Phe Asp Trp Asp Asn
        435                 440                 445

Met Leu Ala Phe Glu Gly Asn Thr Ala Pro Tyr Met Gln Tyr Ala Tyr
    450                 455                 460

Thr Arg Val Leu Ser Val Phe Arg Lys Ala Glu Ile Asp Glu Glu Gln
465                 470                 475                 480

Leu Ala Ala Ala Pro Val Ile Ile Arg Glu Asp Arg Glu Ala Gln Leu
                485                 490                 495

Ala Ala Arg Leu Leu Gln Phe Glu Glu Thr Leu Thr Val Val Ala Arg
            500                 505                 510

Glu Gly Thr Pro His Val Met Cys Ala Tyr Leu Tyr Asp Leu Ala Gly
        515                 520                 525

Leu Phe Ser Gly Phe Tyr Glu His Cys Pro Ile Leu Ser Ala Glu Asn
    530                 535                 540

Glu Glu Val Arg Asn Ser Arg Leu Lys Leu Ala Gln Leu Thr Ala Lys
545                 550                 555                 560

Thr Leu Lys Leu Gly Leu Asp Thr Leu Gly Ile Glu Thr Val Glu Arg
                565                 570                 575

Met
```

<210> SEQ ID NO 48
<211> LENGTH: 1734
<212> TYPE: DNA
<213> ORGANISM: Artificial
<220> FEATURE:
<223> OTHER INFORMATION: deoptimized E. coli ArgS sequence.

<400> SEQUENCE: 48

```
gtgaatattc aggctcttct ctcagaaaaa gtcaggcagg ccatgattgc ggcaggcgcg     60

cctgcggatt gcgaaccgca ggttaggcag tcagcaaaag ttcagttcgg cgactatcag    120

gctaacggca tgatggcagt tgctaaaaaa ctgggtatgg caccgaggca attagcagag    180

caggtgctga ctcatctgga tcttaacggt atcgccagca aagttgagat cgccggtcca    240

ggctttatca acattttcct tgatccggca ttcctggctg aacatgttca gcaggcgctg    300

gcgtccgata ggctcggtgt tgctacgcca gaaaaacaga ccattgtggt tgactactct    360

gaggcaaacg tggcgaaaga gatgcatgtc ggtcacctgc gctctaccat tattggtgac    420

gcagcagtga ggactctgga gttcctcggt cacaaagtga ttagggcaaa ccacgtcggc    480

gactggggca ctcagttcgg tatgctgatt gcatggctgg aaaagcagca gcaggaaaac    540

gccggtgaaa tggagctggc tgaccttgaa ggtttctaca gggatgcgaa aaagcattac    600

gatgaagatg aagagttcgc cgagagggca aggaactacg tggtaaaact gcaaagcggt    660

gacgaatatt tcagggagat gtggaggaaa ctggtcgaca tcaccatgac gcagaaccag    720

atcacctacg ataggctcaa cgtgacgctg accagggatg acgtgatggg cgaaagcctc    780

tacaacccga tgctgccagg aattgtggcg gatctcaaag ccaaaggtct ggcagtagaa    840

agcgaagggg cgaccgtcgt attccttgat gagtttaaaa acaaggaagg cgaaccgatg    900

ggcgtgatca ttcagaagaa agatggcggc tatctctaca ccaccactga tatcgcctgt    960

gcgaaatata ggtatgaaac actgcatgcc gatagggtgc tgtattacat cgactccagg   1020

cagcatcaac acctgatgca ggcatgggcg atcgtcagga aagcaggcta tgtaccggaa   1080
```

```
tccgtaccgc tggaacacca catgttcggc atgatgctgg gtaaagacgg caaaccgttc   1140

aaaaccaggg cgggtggtac agtgaaactg gccgatctgc tggatgaagc cctggaaagg   1200

gcaaggaggc tggtggcaga aaagaacccg gatatgccag ccgacgagct ggaaaaactg   1260

gctaacgcgg ttggtattgg tgcggtgaaa tatgcggatc tctccaaaaa caggaccacg   1320

gactacatct tcgactggga caacatgctg gcgtttgagg gtaataccgc gccatacatg   1380

cagtatgcat acacgagggt attgtccgtg ttcaggaaag cagaaattga cgaagagcaa   1440

ctggctgcag ctccggttat catcagggaa gatagggaag cgcaactggc agctaggctg   1500

ctgcagtttg aagaaaccct caccgtggtt gccagggaag gcacgccgca tgtaatgtgt   1560

gcttacctgt acgatctggc cggtctgttc tctggcttct acgagcactg cccgatcctc   1620

agcgcagaaa acgaagaagt gaggaacagc aggctaaaac tggcacaact gacggcgaag   1680

acgctgaagc tgggtctgga tacgctgggt attgagactg tagagaggat gtaa         1734
```

<210> SEQ ID NO 49
<211> LENGTH: 1185
<212> TYPE: DNA
<213> ORGANISM: Escherichia coli
<220> FEATURE:
<221> NAME/KEY: CDS
<222> LOCATION: (1)..(1185)

<400> SEQUENCE: 49

```
gtg tct aaa gaa aaa ttt gaa cgt aca aaa ccg cac gtt aac gtt ggt       48
Val Ser Lys Glu Lys Phe Glu Arg Thr Lys Pro His Val Asn Val Gly
1               5                   10                  15

act atc ggc cac gtt gac cac ggt aaa act act ctg acc gct gca atc       96
Thr Ile Gly His Val Asp His Gly Lys Thr Thr Leu Thr Ala Ala Ile
            20                  25                  30

acc acc gta ctg gct aaa acc tac ggc ggt gct gct cgt gca ttc gac      144
Thr Thr Val Leu Ala Lys Thr Tyr Gly Gly Ala Ala Arg Ala Phe Asp
        35                  40                  45

cag atc gat aac gcg ccg gaa gaa aaa gct cgt ggt atc acc atc aac      192
Gln Ile Asp Asn Ala Pro Glu Glu Lys Ala Arg Gly Ile Thr Ile Asn
    50                  55                  60

act tct cac gtt gaa tac gac acc ccg acc cgt cac tac gca cac gta      240
Thr Ser His Val Glu Tyr Asp Thr Pro Thr Arg His Tyr Ala His Val
65                  70                  75                  80

gac tgc ccg ggg cac gcc gac tat gtt aaa aac atg atc acc ggt gct      288
Asp Cys Pro Gly His Ala Asp Tyr Val Lys Asn Met Ile Thr Gly Ala
                85                  90                  95

gct cag atg gac ggc gcg atc ctg gta gtt gct gcg act gac ggc ccg      336
Ala Gln Met Asp Gly Ala Ile Leu Val Val Ala Ala Thr Asp Gly Pro
            100                 105                 110

atg ccg cag act cgt gag cac atc ctg ctg ggt cgt cag gta ggc gtt      384
Met Pro Gln Thr Arg Glu His Ile Leu Leu Gly Arg Gln Val Gly Val
        115                 120                 125

ccg tac atc atc gtg ttc ctg aac aaa tgc gac atg gtt gat gac gaa      432
Pro Tyr Ile Ile Val Phe Leu Asn Lys Cys Asp Met Val Asp Asp Glu
    130                 135                 140

gag ctg ctg gaa ctg gtt gaa atg gaa gtt cgt gaa ctt ctg tct cag      480
Glu Leu Leu Glu Leu Val Glu Met Glu Val Arg Glu Leu Leu Ser Gln
145                 150                 155                 160

tac gac ttc ccg ggc gac gac act ccg atc gtt cgt ggt tct gct ctg      528
Tyr Asp Phe Pro Gly Asp Asp Thr Pro Ile Val Arg Gly Ser Ala Leu
                165                 170                 175

aaa gcg ctg gaa ggc gac gca gag tgg gaa gcg aaa atc ctg gaa ctg      576
```

```
Lys Ala Leu Glu Gly Asp Ala Glu Trp Glu Ala Lys Ile Leu Glu Leu
            180                 185                 190

gct ggc ttc ctg gat tct tat att ccg gaa cca gag cgt gcg att gac      624
Ala Gly Phe Leu Asp Ser Tyr Ile Pro Glu Pro Glu Arg Ala Ile Asp
        195                 200                 205

aag ccg ttc ctg ctg ccg atc gaa gac gta ttc tcc atc tcc ggt cgt      672
Lys Pro Phe Leu Leu Pro Ile Glu Asp Val Phe Ser Ile Ser Gly Arg
    210                 215                 220

ggt acc gtt gtt acc ggt cgt gta gaa cgc ggt atc atc aaa gtt ggt      720
Gly Thr Val Val Thr Gly Arg Val Glu Arg Gly Ile Ile Lys Val Gly
225                 230                 235                 240

gaa gaa gtt gaa atc gtt ggt atc aaa gag act cag aag tct acc tgt      768
Glu Glu Val Glu Ile Val Gly Ile Lys Glu Thr Gln Lys Ser Thr Cys
                245                 250                 255

act ggc gtt gaa atg ttc cgc aaa ctg ctg gac gaa ggc cgt gct ggt      816
Thr Gly Val Glu Met Phe Arg Lys Leu Leu Asp Glu Gly Arg Ala Gly
            260                 265                 270

gag aac gta ggt gtt ctg ctg cgt ggt atc aaa cgt gaa gaa atc gaa      864
Glu Asn Val Gly Val Leu Leu Arg Gly Ile Lys Arg Glu Glu Ile Glu
        275                 280                 285

cgt ggt cag gta ctg gct aag ccg ggc acc atc aag ccg cac acc aag      912
Arg Gly Gln Val Leu Ala Lys Pro Gly Thr Ile Lys Pro His Thr Lys
    290                 295                 300

ttc gaa tct gaa gtg tac att ctg tcc aaa gat gaa ggc ggc cgt cat      960
Phe Glu Ser Glu Val Tyr Ile Leu Ser Lys Asp Glu Gly Gly Arg His
305                 310                 315                 320

act ccg ttc ttc aaa ggc tac cgt ccg cag ttc tac ttc cgt act act     1008
Thr Pro Phe Phe Lys Gly Tyr Arg Pro Gln Phe Tyr Phe Arg Thr Thr
                325                 330                 335

gac gtg act ggt acc atc gaa ctg ccg gaa ggc gta gag atg gta atg     1056
Asp Val Thr Gly Thr Ile Glu Leu Pro Glu Gly Val Glu Met Val Met
            340                 345                 350

ccg ggc gac aac atc aaa atg gtt gtt acc ctg atc cac ccg atc gcg     1104
Pro Gly Asp Asn Ile Lys Met Val Val Thr Leu Ile His Pro Ile Ala
        355                 360                 365

atg gac gac ggt ctg cgt ttc gca atc cgt gaa ggc ggc cgt acc gtt     1152
Met Asp Asp Gly Leu Arg Phe Ala Ile Arg Glu Gly Gly Arg Thr Val
    370                 375                 380

ggc gcg ggc gtt gtt gct aaa gtt ctg ggc taa                         1185
Gly Ala Gly Val Val Ala Lys Val Leu Gly
385                 390


<210> SEQ ID NO 50
<211> LENGTH: 394
<212> TYPE: PRT
<213> ORGANISM: Escherichia coli

<400> SEQUENCE: 50

Val Ser Lys Glu Lys Phe Glu Arg Thr Lys Pro His Val Asn Val Gly
1               5                   10                  15

Thr Ile Gly His Val Asp His Gly Lys Thr Thr Leu Thr Ala Ala Ile
            20                  25                  30

Thr Thr Val Leu Ala Lys Thr Tyr Gly Gly Ala Ala Arg Ala Phe Asp
        35                  40                  45

Gln Ile Asp Asn Ala Pro Glu Glu Lys Ala Arg Gly Ile Thr Ile Asn
    50                  55                  60

Thr Ser His Val Glu Tyr Asp Thr Pro Thr Arg His Tyr Ala His Val
65                  70                  75                  80

Asp Cys Pro Gly His Ala Asp Tyr Val Lys Asn Met Ile Thr Gly Ala
```

```
                85                  90                  95

Ala Gln Met Asp Gly Ala Ile Leu Val Val Ala Ala Thr Asp Gly Pro
            100                 105                 110

Met Pro Gln Thr Arg Glu His Ile Leu Leu Gly Arg Gln Val Gly Val
        115                 120                 125

Pro Tyr Ile Ile Val Phe Leu Asn Lys Cys Asp Met Val Asp Asp Glu
    130                 135                 140

Glu Leu Leu Glu Leu Val Glu Met Glu Val Arg Glu Leu Leu Ser Gln
145                 150                 155                 160

Tyr Asp Phe Pro Gly Asp Asp Thr Pro Ile Val Arg Gly Ser Ala Leu
                165                 170                 175

Lys Ala Leu Glu Gly Asp Ala Glu Trp Glu Ala Lys Ile Leu Glu Leu
            180                 185                 190

Ala Gly Phe Leu Asp Ser Tyr Ile Pro Glu Pro Glu Arg Ala Ile Asp
        195                 200                 205

Lys Pro Phe Leu Leu Pro Ile Glu Asp Val Phe Ser Ile Ser Gly Arg
    210                 215                 220

Gly Thr Val Val Thr Gly Arg Val Glu Arg Gly Ile Ile Lys Val Gly
225                 230                 235                 240

Glu Glu Val Glu Ile Val Gly Ile Lys Glu Thr Gln Lys Ser Thr Cys
                245                 250                 255

Thr Gly Val Glu Met Phe Arg Lys Leu Leu Asp Glu Gly Arg Ala Gly
            260                 265                 270

Glu Asn Val Gly Val Leu Leu Arg Gly Ile Lys Arg Glu Glu Ile Glu
        275                 280                 285

Arg Gly Gln Val Leu Ala Lys Pro Gly Thr Ile Lys Pro His Thr Lys
    290                 295                 300

Phe Glu Ser Glu Val Tyr Ile Leu Ser Lys Asp Glu Gly Gly Arg His
305                 310                 315                 320

Thr Pro Phe Phe Lys Gly Tyr Arg Pro Gln Phe Tyr Phe Arg Thr Thr
                325                 330                 335

Asp Val Thr Gly Thr Ile Glu Leu Pro Glu Gly Val Glu Met Val Met
            340                 345                 350

Pro Gly Asp Asn Ile Lys Met Val Val Thr Leu Ile His Pro Ile Ala
        355                 360                 365

Met Asp Asp Gly Leu Arg Phe Ala Ile Arg Glu Gly Gly Arg Thr Val
    370                 375                 380

Gly Ala Gly Val Val Ala Lys Val Leu Gly
385                 390
```

<210> SEQ ID NO 51
<211> LENGTH: 1185
<212> TYPE: DNA
<213> ORGANISM: Artificial
<220> FEATURE:
<223> OTHER INFORMATION: deoptimized E. coli TufA sequence.

<400> SEQUENCE: 51

```
gtgtctaaag aaaaatttga aaggacaaaa ccgcacgtta acgttggtac tatcggccac      60

gttgaccacg gtaaaactac tctgaccgct gcaatcacca ccgtactggc taaaacctac     120

ggcggtgctg ctagggcatt cgaccagatc gataacgcgc cggaagaaaa agctaggggt     180

atcaccatca acacttctca cgttgaatac gacaccccga ccaggcacta cgcacacgta     240

gactgcccgg ggcacgccga ctatgttaaa aacatgatca ccggtgctgc tcagatggac     300
```

```
ggcgcgatcc tggtagttgc tgcgactgac ggcccgatgc cgcagactag ggagcacatc    360

ctgctgggta ggcaggtagg cgttccgtac atcatcgtgt tcctgaacaa atgcgacatg    420

gttgatgacg aagagctgct ggaactggtt gaaatggaag ttagggaact tctgtctcag    480

tacgacttcc cgggcgacga cactccgatc gttaggggtt ctgctctgaa agcgctggaa    540

ggcgacgcag agtgggaagc gaaaatcctg gaactggctg gcttcctgga ttcttatatt    600

ccggaaccag agagggcgat tgacaagccg ttcctgctgc cgatcgaaga cgtattctcc    660

atctccggta ggggtaccgt tgttaccggt agggtagaaa ggggtatcat caaagttggt    720

gaagaagttg aaatcgttgg tatcaaagag actcagaagt ctacctgtac tggcgttgaa    780

atgttcacga aactgctgga cgaaggcagg gctggtgaga acgtaggtgt tctgctgagg    840

ggtatcaaaa gggaagaaat cgaaaggggt caggtactgg ctaagccggg caccatcaag    900

ccgcacacca agttcgaatc tgaagtgtac attctgtcca aagatgaagg cggcaggcat    960

actccgttct tcaaaggcta caggccgcag ttctacttca ggactactga cgtgactggt   1020

accatcgaac tgccggaagg cgtagagatg gtaatgccgg gcgacaacat caaaatggtt   1080

gttaccctga tccacccgat cgcgatggac gacggtctga ggttcgcaat cagggaaggc   1140

ggcaggaccg ttggcgcggg cgttgttgct aaagttctgg gctaa                   1185
```

<210> SEQ ID NO 52
<211> LENGTH: 7439
<212> TYPE: DNA
<213> ORGANISM: Human poliovirus 2

<400> SEQUENCE: 52

```
ttaaaacagc tctggggttg ttcccacccc agaggcccac gtggcggcca gtacactggt     60

attgcggtac ctttgtacgc ctgttttata ctcccttccc ccgtaactta gaagcacaat    120

gtccaagttc aataggaggg ggtacaaacc agtaccacca cgaacaagca cttctgttcc    180

cccggtgagg ctgtataggc tgtttccacg gctaaaagcg gctgatccgt tatccgctca    240

tgtacttcga gaagcctagt atcaccttgg aatcttcgat gcgttgcgct caacactcaa    300

ccccagagtg tagcttaggt cgatgagtct ggacgttcct caccggcgac ggtggtccag    360

gctgcgttgg cggcctacct gtggcccaaa gccacaggac gctagttgtg aacaaggtgt    420

gaagagccta ttgagctacc tgagagtcct ccggcccctg aatgcggcta atcctaacca    480

cggagcaggc agtggcaatc cagcgaccag cctgtcgtaa cgcgcaagtt cgtggcggaa    540

ccgactactt tgggtgtccg tgtttccttt tatttttaca atggctgctt atggtgacaa    600

tcattgattg ttatcataaa gcaaattgga ttggccatcc ggtgagaatt tgattattaa    660

attactctct tgttgggatt gctcctttga aatcctgtgc actcacacct attggaatta    720

cctcattgtt aagatatcat caccactatg ggcgcccaag tctcatcaca gaaagttgga    780

gcccatgaga attcaaacag agcttatggc ggatccacca ttaattacac tactattaat    840

tattacaggg attctgcgag caatgccgct agtaagcagg actttgcaca agacccatcc    900

aagttcactg aacctattaa agatgttctc attaagaccg ctcccacgct aaactctcct    960

aatatcgagg cgtgtgggta tagcgacaga gtgatgcaac taaccctagg caattccacc   1020

attaccacac aggaggcggc caattctgtc gttgcatacg gccggtggcc cgagtacatc   1080

aaggactcag aagcaaatcc tgtggaccag ccaactgaac cggacgttgc cgcgtgcagg   1140

ttttacacac tagacactgt tacttggcgc aaggagtcca gagggtggtg gtggaaactg   1200

cctgatgcac taaaggacat gggattattc ggccagaaca tgttctacca ctacctcggg   1260
```

```
agggctggct atactgtgca cgtacagtgt aatgcttcaa agtttcacca gggcgccctc   1320
ggggtattcg cagttccaga aatgtgcctg gcaggcgaca gcacaaccca catgtttaca   1380
aaatatgaga atgcaaatcc gggtgagaaa gggggtgaat tcaaagggag ttttactctg   1440
gatactaacg ctaccaaccc tgcacgcaac ttttgtcccg ttgattatct cttcgggagc   1500
ggagtactgg cgggaaatgc gtttgtttac ccacatcaga taattaatct gcgcaccaac   1560
aactgtgcca cgttggtgct gccatacgtt aattcacttt ccatagacag catgacaaaa   1620
cacaacaatt ggggaattgc tatccttccg ctggcaccac ttgactttgc caccgagtcc   1680
tccactgaga tacccattac tctaactatt gcccctatgt gttgtgaatt caatgggttg   1740
cgcaacatca ctgtacccag aactcaaggg ttgccagtct taaacactcc aggaagcaac   1800
cagtacttaa cagcagacaa ctatcaatcc ccatgtgcga tacccgagtt tgatgtaaca   1860
ccacccatag acatcccggg ggaagtgcgc aacatgatgg aattggcaga gatagacacc   1920
atgatacctc tcaatctgac gaaccagcgc aagaacacca tggatatgta cagagtcgaa   1980
ctgaatgatg cggctcactc tgacacacca atattgtgtc tctcactgtc tccagcatca   2040
gatcctaggc tagcacacac tatgctaggt gaaatactga actactacac acactgggca   2100
gggtcattga agttcacatt tctcttctgc ggctcaatga tggccactgg taaattgcta   2160
gtgtcctatg cacctcctgg tgcggaagcc cctaaaagcc gcaaagaagc gatgctcggc   2220
acccacgtga tctgggacat cggattacag tcatcatgca ctatggtggt accttggatt   2280
agcaacacca catacagaca aaccatcaac gatagcttca cagaaggagg gtacatcagt   2340
atgttttacc aaactagagt tgttgtgcca ttgtccaccc ctagaaagat ggacatattg   2400
ggctttgtgt cagcctgcaa tgacttcagt gtgcgcctgt tgcgtgacac gacgcacata   2460
agccaagagg ctatgccaca aggattgggt gatttaattg aaggggttgt tgagggagtc   2520
acgagaaatg ccttgacacc actgacacct gccaacaact tgcctgatac acaatctagc   2580
ggcccagccc actctaagga aacaccagcg ctaacagccg tagagacagg ggccaccaac   2640
ccattggtgc cttcagacac ggtacaaact cgtcacgtca tccaaaagcg gacgcggtcg   2700
gagtctacgg ttgagtcttt cttcgcaaga ggagcttgtg tggccattat tgaagtggat   2760
aatgatgctc caacaaagcg tgccagtaaa ttattttcag tctggaagat aacttacaaa   2820
gacaccgttc agttaagacg taagttggag ttctttacat attcaaggtt tgacatggag   2880
ttcacctttg tggttacatc caattatacc gatgcaaaca atgggcacgc actaaatcaa   2940
gtttaccaga taatgtacat accacctggg gcaccgatcc ctggcaagtg gaatgattac   3000
acatggcaaa cgtcatctaa cccatcagtg ttttacactt acggggcacc tccagctaga   3060
atatcagtgc cctacgtggg cattgccaat gcatattctc atttttacga tgggtttgcc   3120
aaagtaccac tagcaggcca agcctcaaca gagggtgact cgctgtatgg agcggcttca   3180
ttgaatgact tcggatcact ggctgttcga gtggtgaatg accacaaccc tacgaaactc   3240
acttcaaaaa tcagagtgta catgaaacca aagcacgtca gagtgtggtg tccgcgaccc   3300
cctcgagcag tcccatacta cggaccaggg gttgactaca aggatggact agccccactg   3360
ccagagaaag gcttgacaac ctatggtttt ggccaccaaa ataaggcagt gtacacggca   3420
ggttacaaaa tttgcaatta ccacctcgcc acccaggaag acttacaaaa tgcggtaaac   3480
attatgtgga ttagagacct tttagtagtg gaatccaaag cccaaggcat agactcaatt   3540
gctagatgta actgccacac tggagtgtac tactgtgaat ccaggaggaa gtactacccg   3600
```

-continued

```
gtctctttta ctggccccac ctttcagtac atggaagcaa atgagtacta tccagcccga   3660
taccaatccc acatgttaat tggccatggt tttgcatctc caggggactg tggtgggatt   3720
ctcaggtgcc aacatggagt aattggaatc attacagctg gaggagaagg cctagtcgct   3780
ttctcggaca tcagagatct gtacgcatac gaggaggagg ctatggagca gggagtctcc   3840
aactatattg agtcccttgg ggctgcattt gggagtggat tcacccagca aataggaaac   3900
aaaatttcag aactcactag catggtcacc agcactataa ctgagaaact actaaagaat   3960
ctcattaaaa taatttcatc ccttgttatc atcaccagaa actatgaaga cacgaccaca   4020
gtgctggcta cccttgctct cctcggttgt gatgcgtccc catggcaatg gctaaagaag   4080
aaagcctgtg acatcttgga aatcccctac atcatgcgac agggcgatag ctggttgaag   4140
aagtttacag aggcatgcaa tgcagccaag ggattggaat gggtgtctaa taaaatatcc   4200
aaatttattg actggctcaa agagaagatc attccacagg ctagagacaa gctagagttt   4260
gttaccaaac tgaagcaact agaaatgttg gagaaccaaa ttgcaaccat tcatcaatcg   4320
tgcccaagtc aggagcatca agaaatcctg ttcaataacg tgagatggtt atccatacag   4380
tcaaagagat ttgccccgct ctatgcggtt gaggctaaga gaatacaaaa gttagagcac   4440
acgattaaca actacgtaca gttcaagagc aaacaccgta ttgaaccagt atgtttgttg   4500
gtgcacggta gcccaggcac gggcaagtca gttgccacca atttaattgc cagagcaata   4560
gcagagaagg agaacacctc cacatactca ctaccaccag atccctccca tttcgatggg   4620
tacaagcaac aaggtgtggt gatcatggat gatttgaatc agaacccaga cggagcagac   4680
atgaagctgt tttgtcagat ggtctccact gtagaattca taccaccaat ggcttcgcta   4740
gaagaaaagg gtattttgtt cacatctaat tacgttttgg cctcaaccaa ttccagtcgc   4800
atcaccccac caactgttgc gcacagcgat gccctagcca ggcgctttgc atttgacatg   4860
gacatacaaa tcatgagcga gtattctaga gatggaaaat tgaacatggc gatggcaact   4920
gaaatgtgta agaactgtca tcaaccagca aacttcaaga gatgttgccc attggtgtgt   4980
ggcaaagcca tccagctgat ggacaaatct tccagagtca gatatagtat agatcagatt   5040
actaccatga ttattaatga gaggaacaga agatcaagta tcggtaattg catggaggca   5100
cttttccaag gtcctcttca atacaaagac ctgaaaatag acattaagac cacacctcct   5160
cctgagtgca tcaatgattt gctccaagca gttgattctc aagaggtaag agactactgt   5220
gagaagaagg gttggatagt agacatcact agtcaggtgc aaaccgaaag aaacatcaat   5280
agagcaatga ctattcttca ggcggtcacc acatttgccg cagttgctgg agtggtgtat   5340
gtgatgtaca aactctttgc agggcatcaa ggagcgtata cagggcttcc caataagaga   5400
cccaatgtcc ccaccatcag gactgccaag gttcagggcc caggatttga ctacgcagtg   5460
gcaatggcca aaagaaacat tcttacggca actaccatta agggagagtt cacaatgctc   5520
ggagtgcatg ataatgtggc cattctacca acccacgcat caccgggtga aacaatagtc   5580
attgatggca aggaagtaga ggtactggat gctaaagccc tggaggacca ggccgggacc   5640
aacctagaaa tcaccattgt cactcttaag agaaatgaga agttcaggga catcagacca   5700
cacatcccca ctcaaatcac tgagacaaat gatggagttt taattgtgaa cactagtaag   5760
taccccaaca tgtatgttcc tgtcggtgct gtgactgaac aggggtatct caatctcggt   5820
ggacgccaaa ctgctcgtac tttaatgtac aactttccaa cgagagcagg tcaatgtggt   5880
ggagttatca cctgcactgg caaggtcatc gggatgcatg ttggtgggaa cggttcacat   5940
gggttcgcag cagccctgaa gcgatcctat ttcactcaga gtcaaggtga aatccagtgg   6000
```

atgagaccat caaaagaagt gggctacccc gttattaatg ctccatctaa aactaaactg 6060
gaacccagtg cattccatta tgtgtttgaa ggtgtcaagg aaccagctgt gctcaccaaa 6120
agtgacccca gattgaagac agattttgaa gaggctatct tttccaagta tgtgggaaat 6180
aagattactg aagtggatga gtacatgaaa gaagctgtcg atcattacgc aggccagctc 6240
atgtcactag acatcaacac agaacaaatg tgccttgagg atgcaatgta tggcactgac 6300
ggtctcgaag ctctagacct cagtaccagt gctgggtatc cctatgtggc aatggggaaa 6360
aagaaaagag acattttgaa taagcaaacc agagacacaa aggaaatgca aaggcttctg 6420
gacacctatg gtattaattt acctttagtc acctatgtga aagatgagct tagatccaag 6480
accaaagtgg aacagggcaa gtccaggcta attgaggcct caagtctcaa tgactctgtc 6540
gccatgagga tggcttttgg caacttgtac gcagcattcc acaagaaccc aggtgtagtg 6600
acaggatcgg ctgttggctg tgacccagat ttgttttgga gtaaaatacc agtcctcatg 6660
gaggaaaaac tctttgcatt tgattacacg ggttatgatg cttcactaag ccccgcctgg 6720
tttgaggctc tcaagatggt tctagagaaa attgggtttg gtgacagagt ggattacatt 6780
gattatctga atcactcgca ccatctatat aaaaataaga catattgtgt taagggcggc 6840
atgccatctg gctgctctgg cacctcaatt tttaattcaa tgattaataa tctaataatc 6900
aggactctct tactgaaaac ctacaagggc atagatttag accacctgaa gatgatagcc 6960
tatggtgatg atgtaattgc ttcctacccc catgaggttg atgctagtct cctagcccaa 7020
tcaggaaaag actatggact aaccatgaca ccagctgaca aatcagccac ctttgaaaca 7080
gtcacatggg agaatgtaac attcttgaaa agattcttta gagcagatga aaagtatccc 7140
tttctggtac atccagtgat gccaatgaaa gaaattcacg aatcaattag atggactaaa 7200
gatcccagaa acactcagga tcatgttcgc tcactgtgct tattggcttg gcacaatggc 7260
gaggaagagt acaataaatt tttagctaag attagaagtg tgccaatcgg aagagcatta 7320
ctgctccctg agtactccac attgtaccgc cgttggctcg actcatttta gtaaccctac 7380
ctcagtcgaa ttggattggg tcatactgtt gtaggggtaa atttttcttt aattcggag 7439

<210> SEQ ID NO 53
<211> LENGTH: 7439
<212> TYPE: DNA
<213> ORGANISM: Human poliovirus 2

<400> SEQUENCE: 53
ttaaaacagc tctggggttg ttcccacccc agaggcccac gtggcggcca gtacactggt 60
attgcggtac ctttgtacgc ctgttttata ctcccttccc ccgtaactta gaagcacaat 120
gtccaagttc aataggaggg ggtacaaacc agtaccacca cgaacaagca cttctgttcc 180
cccggtgagg ctgtataggc tgtttccacg gctaaaagcg gctgatccgt tatccgctca 240
tgtacttcga gaagcctagt atcaccttgg aatcttcgat gcgttgcgct caacactcaa 300
ccccagagtg tagcttaggt cgatgagtct ggacgttcct caccggcgac ggtggtccag 360
gctgcgttgg cggcctacct gtggcccaaa gccacaggac gctagttgtg aacaaggtgt 420
gaagagccta ttgagctacc tgagagtcct ccggcccctg aatgcggcta atcctaacca 480
cggagcaggc agtggcaatc cagcgaccag cctgtcgtaa cgcgcaagtt cgtggcggaa 540
ccgactactt tgggtgtccg tgtttccttt tatttttaca atggctgctt atggtgacaa 600
tcattgattg ttatcataaa gcaaattgga ttggccatcc ggtgagaatt tgattattaa 660

-continued

```
attactctct tgttgggatt gctcctttga aatcctgtgc actcacacct attggaatta    720
cctcattgtt aagatatcat caccactatg ggcgcccaag tctcatcaca gaaagttgga    780
gcccatgaga attcaaacag agcttatggc ggatccacca ttaattacac tactattaat    840
tattacaggg attctgcgag caatgccgct agtaagcagg actttgcaca agacccatcc    900
aagttcactg aacctattaa agatgttctc attaagaccg ctcccacgct aaactctcct    960
aatatcgagg cgtgtgggta tagcgacaga gtgatgcaac taaccctagg caattccacc   1020
attaccacac aggaggcggc caattctgtc gttgcatacg gccggtggcc cgagtacatc   1080
aaggactcag aagcaaatcc tgtggaccag ccaactgaac cggacgttgc cgcgtgcagg   1140
ttttacacac tagacactgt tacttggcgc aaggagtcca gagggtggtg gtggaaactg   1200
cctgatgcac taaaggacat gggattattc ggccagaaca tgttctacca ctacctcggg   1260
agggctggct atactgtgca cgtacagtgt aatgcttcaa agtttcacca gggcgccctc   1320
ggggtattcg cagttccaga aatgtgcctg gcaggcgaca gcacaaccca catgtttaca   1380
aaatatgaga atgcaaatcc gggtgagaaa gggggtgaat tcaaagggag ttttactctg   1440
gatactaacg ctaccaaccc tgcacgcaac ttttgtcccg ttgattatct cttcgggagc   1500
ggagtactgg cgggaaatgc gtttgtttac ccacatcaga taattaatct gcgcaccaac   1560
aactgtgcca cgttggtgct gccatacgtt aattcacttt ccatagacag catgacaaaa   1620
cacaacaatt ggggaattgc tatccttccg ctggcaccac ttgactttgc caccgagtcc   1680
tccactgaga tacccattac tctaactatt gcccctatgt gttgtgaatt caatgggttg   1740
cgcaacatca ctgtacccag aactcaaggg ttaccggtct taaacactcc aggaagcaac   1800
cagtacttaa cagcagacaa ctatcaatcc ccatgtgcga tacccgagtt tgatgtaaca   1860
ccacccatag acatcccggg ggaagtgcgc aacatgatgg aattggcaga gatagacacc   1920
atgatacctc tcaatctgac gaaccagcgc aagaacacca tggatatgta cagagtcgaa   1980
ctgaatgatg cggctcactc tgacacacca atattgtgtc tctcactgtc tccagcatca   2040
gatcctaggc tagcacacac tatgctaggt gaaatactga actactacac acactgggca   2100
gggtcattga agttcacatt tctcttctgc ggctcaatga tggccactgg taaattgcta   2160
gtgtcctatg cacctcctgg tgcggaagcc cctaaaagcc gcaaagaagc gatgctcggc   2220
acccacgtga tctgggacat cggattacag tcatcatgca ctatggtggt accttggatt   2280
agcaacacca catacagaca aaccatcaac gatagcttca cagaaggagg gtacatcagt   2340
atgttttacc aaactagagt tgttgtgcca ttgtccaccc ctagaaagat ggacatattg   2400
ggctttgtgt cagcctgcaa tgacttcagt gtgcgcctgt tgcgtgacac gacgcacata   2460
agccaagagg ctatgccaca aggattgggt gatttaattg aaggggttgt tgagggagtc   2520
acgagaaatg ccttgacacc actgacacct gccaacaact tgcctgatac acaatctagc   2580
ggcccagccc actctaagga aacaccagcg ctaacagccg tagagacagg ggccaccaac   2640
ccattggtgc cttcagacac ggtacaaact cgtcacgtca tccaaaagcg gacgcggtcg   2700
gagtctacgg ttgagtcttt cttcgcaaga ggagcttgtg tggccattat tgaagtggat   2760
aatgatgctc caacaaagcg tgccagtaaa ttattttcag tctggaagat aacttacaaa   2820
gacaccgttc agttaagacg taagttggag ttctttacat attcaaggtt tgacatggag   2880
ttcacctttg tggttacatc caattatacc gatgcaaaca atgggcacgc actaaatcaa   2940
gtttaccaga taatgtacat accacctggg gcaccgatcc ctggcaagtg gaatgattac   3000
acatggcaaa cgtcatctaa cccatcagtg ttttacactt acggggcacc tccagctaga   3060
```

-continued

```
atatcagtgc cctacgtggg cattgccaat gcatattctc atttttacga tgggtttgcc   3120
aaagtaccac tagcaggcca agcctcaaca gagggtgact cgctgtatgg agcggcttca   3180
ttgaatgact tcggatcact ggctgttcga gtggtgaatg accacaaccc tacgaaactc   3240
acttcaaaaa tcagagtgta catgaaacca aagcacgtca gagtgtggtg tccgcgaccc   3300
cctcgagcag tcccatacta cggaccaggg gttgactaca aggatggact agccccactg   3360
ccagagaaag gcttgacaac ctatggtttt ggccaccaaa ataaggcagt gtacacggca   3420
ggttacaaaa tttgcaatta ccacctcgcc acccaggaag acttacaaaa tgcggtaaac   3480
attatgtgga ttagagacct tttagtagtg gaatccaaag cccaaggcat agactcaatt   3540
gctagatgta actgccacac tggagtgtac tactgtgaat ccaggaggaa gtactacccg   3600
gtctctttta ctggccccac ctttcagtac atggaagcaa atgagtacta tccagcccga   3660
taccaatccc acatgttaat tggccatggt tttgcatctc caggggactg tggtgggatt   3720
ctcaggtgcc aacatggagt aattggaatc attacagctg gaggagaagg cctagtcgct   3780
ttctcggaca tcagagatct gtacgcatac gaggaggagg ctatggagca gggagtctcc   3840
aactatattg agtcccttgg ggctgcattt gggagtggat tcacccagca aataggaaac   3900
aaaatttcag aactcactag catggtcacc agcactataa ctgagaaact actaaagaat   3960
ctcattaaaa taatttcatc ccttgttatc atcaccagaa actatgaaga cacgaccaca   4020
gtgctggcta cccttgctct cctcggttgt gatgcgtccc catggcaatg gctaaagaag   4080
aaagcctgtg acatcttgga aatcccctac atcatgcgac agggcgatag ctggttgaag   4140
aagtttacag aggcatgcaa tgcagccaag ggattggaat gggtgtctaa taaaatatcc   4200
aaatttattg actggctcaa agagaagatc attccacagg ctagagacaa gctagagttt   4260
gttaccaaac tgaagcaact agaaatgttg gagaaccaaa ttgcaaccat tcatcaatcg   4320
tgcccaagtc aggagcatca agaaatcctg ttcaataacg tgagatggtt atccatacag   4380
tcaaagagat ttgccccgct ctatgcggtt gaggctaaga gaatacaaaa gttagagcac   4440
acgattaaca actacgtaca gttcaagagc aaacaccgta ttgaaccagt atgtttgttg   4500
gtgcacggta gcccaggcac gggcaagtca gttgccacca atttaattgc cagagcaata   4560
gcagagaagg agaacacctc cacatactca ctaccaccag atccctccca tttcgatggg   4620
tacaagcaac aaggtgtggt gatcatggat gatttgaatc agaacccaga cggagcagac   4680
atgaagctgt tttgtcagat ggtctccact gtagaattca taccaccaat ggcttcgcta   4740
gaagaaaagg gtattttgtt cacatctaat tacgttttgg cctcaaccaa ttccagtcgc   4800
atcaccccac caactgttgc gcacagcgat gccctagcca ggcgctttgc atttgacatg   4860
gacatacaaa tcatgagcga gtattctaga gatggaaaat tgaacatggc gatggcaact   4920
gaaatgtgta agaactgtca tcaaccagca aacttcaaga gatgttgccc attggtgtgt   4980
ggcaaagcca tccagctgat ggacaaatct tccagagtca gatatagtat agatcagatt   5040
actaccatga ttattaatga gaggaacaga agatcaagta tcggtaattg catggaggca   5100
cttttccaag gtcctcttca atacaaagac ctgaaaatag acattaagac cacacctcct   5160
cctgagtgca tcaatgattt gctccaagca gttgattctc aagaggtaag agactactgt   5220
gagaagaagg gttggatagt agacatcact agtcaggtgc aaaccgaaag aaacatcaat   5280
agagcaatga ctattcttca ggcggtcacc acatttgccg cagttgctgg agtggtgtat   5340
gtgatgtaca aactctttgc agggcatcaa ggagcgtata cagggcttcc caataagaga   5400
```

cccaatgtcc ccaccatcag gactgccaag gttcagggcc caggatttga ctacgcagtg 5460
gcaatggcca aaagaaacat tcttacggca actaccatta agggagagtt cacaatgctc 5520
ggagtgcatg ataatgtggc cattctacca acccacgcat caccgggtga aacaatagtc 5580
attgatggca aggaagtaga ggtactggat gctaaagccc tggaggacca ggccgggacc 5640
aacctagaaa tcaccattgt cactcttaag agaaatgaga agttcaggga catcagacca 5700
cacatcccca ctcaaatcac tgagacaaat gatggagttt taattgtgaa cactagtaag 5760
taccccaaca tgtatgttcc tgtcggtgct gtgactgaac aggggtatct caatctcggt 5820
ggacgccaaa ctgctcgtac tttaatgtac aactttccaa cgagagcagg tcaatgtggt 5880
ggagttatca cctgcactgg caaggtcatc gggatgcatg ttggtgggaa cggttcacat 5940
gggttcgcag cagccctgaa gcgatcctat ttcactcaga gtcaaggtga aatccagtgg 6000
atgagaccat caaaagaagt gggctacccc gttattaatg ctccatctaa aactaaactg 6060
gaacccagtg cattccatta tgtgtttgaa ggtgtcaagg aaccagctgt gctcaccaaa 6120
agtgacccca gattgaagac agattttgaa gaggctatct tttccaagta tgtgggaaat 6180
aagattactg aagtggatga gtacatgaaa gaagctgtcg atcattacgc aggccagctc 6240
atgtcactag acatcaacac agaacaaatg tgccttgagg atgcaatgta tggcactgac 6300
ggtctcgaag ctctagacct cagtaccagt gctgggtatc cctatgtggc aatggggaaa 6360
aagaaaagag acattttgaa taagcaaacc agagacacaa aggaaatgca aaggcttctg 6420
gacacctatg gtattaattt acctttagtc acctatgtga aagatgagct tagatccaag 6480
accaaagtgg aacagggcaa gtccaggcta attgaggcct caagtctcaa tgactctgtc 6540
gccatgagga tggcttttgg caacttgtac gcagcattcc acaagaaccc aggtgtagtg 6600
acaggatcgg ctgttggctg tgacccagat ttgttttgga gtaaaatacc agtcctcatg 6660
gaggaaaaac tctttgcatt tgattacacg ggttatgatg cttcactaag ccccgcctgg 6720
tttgaggctc tcaagatggt tctagagaaa attgggtttg gtgacagagt ggattacatt 6780
gattatctga atcactcgca ccatctatat aaaaataaga catattgtgt taagggcggc 6840
atgccatctg gctgctctgg cacctcaatt tttaattcaa tgattaataa tctaataatc 6900
aggactctct tactgaaaac ctacaagggc atagatttag accacctgaa gatgatagcc 6960
tatggtgatg atgtaattgc ttcctacccc catgaggttg atgctagtct cctagcccaa 7020
tcaggaaaag actatggact aaccatgaca ccagctgaca aatcagccac ctttgaaaca 7080
gtcacatggg agaatgtaac attcttgaaa agattcttta gagcagatga aaagtatccc 7140
tttctggtac atccagtgat gccaatgaaa gaaattcacg aatcaattag atggactaaa 7200
gatcccagaa acactcagga tcatgttcgc tcactgtgct tattggcttg gcacaatggc 7260
gaggaagagt acaataaatt tttagctaag attagaagtg tgccaatcgg aagagcatta 7320
ctgctccctg agtactccac attgtaccgc cgttggctcg actcatttta gtaaccctac 7380
ctcagtcgaa ttggattggg tcatactgtt gtaggggtaa atttttcttt aattcggag 7439

<210> SEQ ID NO 54
<211> LENGTH: 7439
<212> TYPE: DNA
<213> ORGANISM: Artificial
<220> FEATURE:
<223> OTHER INFORMATION: deoptimized MEF1 poliovirus

<400> SEQUENCE: 54
ttaaaacagc tctggggttg ttcccacccc agaggcccac gtggcggcca gtacactggt 60

```
attgcggtac ctttgtacgc ctgttttata ctcccttccc ccgtaactta gaagcacaat    120
gtccaagttc aataggaggg ggtacaaacc agtaccacca cgaacaagca cttctgttcc    180
cccggtgagg ctgtataggc tgtttccacg gctaaaagcg gctgatccgt tatccgctca    240
tgtacttcga gaagcctagt atcaccttgg aatcttcgat gcgttgcgct caacactcaa    300
ccccagagtg tagcttaggt cgatgagtct ggacgttcct caccggcgac ggtggtccag    360
gctgcgttgg cggcctacct gtggcccaaa gccacaggac gctagttgtg aacaaggtgt    420
gaagagccta ttgagctacc tgagagtcct ccggcccctg aatgcggcta atcctaacca    480
cggagcaggc agtggcaatc cagcgaccag cctgtcgtaa cgcgcaagtt cgtggcggaa    540
ccgactactt tgggtgtccg tgtttccttt tatttttaca atggctgctt atggtgacaa    600
tcattgattg ttatcataaa gcaaattgga ttggccatcc ggtgagaatt tgattattaa    660
attactctct tgttgggatt gctcctttga aatcctgtgc actcacacct attggaatta    720
cctcattgtt aagatatcat caccactatg ggcgcccaag tctcatcaca gaaagttgga    780
gcccatgaga attcaaacag agcttatggc ggatccacca ttaattacac tactattaat    840
tattacaggg attctgcgag caatgccgct agtaagcagg actttgcaca agacccatcc    900
aagttcactg aacctattaa agatgttctc attaagaccg ctcccacgct aaactctcct    960
aatatcgagg cgtgtgggta tagcgacaga gtgatgcaac taaccctagg caattccacc   1020
attaccacac aggaggcggc caattctgtc gttgcatacg gccggtggcc cgagtacatc   1080
aaggactcag aagcaaatcc tgtggaccag ccaactgaac cggacgttgc cgcgtgcagg   1140
ttttacacac tagacactgt tacttggcgc aaggagtcca gagggtggtg gtggaaactg   1200
cctgatgcac taaaggacat gggattattc ggccagaaca tgttctacca ctacctcggg   1260
agggctggct atactgtgca cgtacagtgt aatgcttcaa agtttcacca gggcgccctc   1320
ggggtattcg cagttccaga aatgtgcctg gcaggcgaca gcacaaccca catgtttaca   1380
aaatatgaga atgcaaatcc gggtgagaaa gggggtgaat tcaaagggag ttttactctg   1440
gatactaacg ctaccaaccc tgcacgcaac ttttgtcccg ttgattatct cttcgggagc   1500
ggagtactgg cgggaaatgc gtttgtttac ccacatcaga taattaatct gcgcaccaac   1560
aactgtgcca cgttggtgct gccatacgtt aattcacttt ccatagacag catgacaaaa   1620
cacaacaatt ggggaattgc tatccttccg ctggcaccac ttgactttgc caccgagtcc   1680
tccactgaga tacccattac tctaactatt gcccctatgt gttgtgaatt caatgggttg   1740
cgcaacatca ctgtacccag aactcaaggg ttaccggtct taaacactcc aggaagcaac   1800
cagtacttaa cagcagacaa ctatcaatcc ccatgtgcga tacccgagtt tgatgtaaca   1860
ccacccatag acatcccggg ggaagtgcgc aacatgatgg aattggcaga gatagacacc   1920
atgatacctc tcaatctgac gaaccagcgc aagaacacca tggatatgta cagagtcgaa   1980
ctgaatgatg cggctcactc tgacacacca atattgtgtc tctcactgtc tccagcatca   2040
gatcctaggc tagcacacac tatgctaggt gaaatactga actactacac acactgggca   2100
gggtcattga agttcacatt tctcttctgc ggctcaatga tggccactgg taaattgcta   2160
gtgtcctatg cacctcctgg tgcggaagcc cctaaaagcc gcaaagaagc gatgctcggc   2220
acccacgtga tctgggacat cggattacag tcatcatgca ctatggtggt accttggatt   2280
agcaacacca catacagaca aaccatcaac gatagcttca cagaaggagg gtacatcagt   2340
atgttttacc aaactagagt tgttgtgcca ttgtccaccc ctagaaagat ggacatattg   2400
```

-continued

```
ggctttgtgt cagcctgcaa tgacttcagt gtgcgcctgt tgcgtgacac gacgcacata   2460
agccaagagg ctatgccaca aggattgggt gatttaattg aaggggttgt tgagggagtc   2520
acgagaaatg ccttgacacc actgacacct gccaacaact tgcctgatac acaatctagc   2580
ggcccagccc actctaagga aacaccagcg cttacggcgg tcgagacggg tgcgacgaac   2640
ccgcttgtcc cgagcgacac ggtccaaacg cggcacgtca tccaaaagcg gacgcggagc   2700
gagagcacgg tcgagagctt cttcgcgcgg ggtgcgtgtg tcgcgatcat cgaagtcgat   2760
aatgatgcgc cgacgaagcg ggcgagcaaa ctttttagcg tctggaagat cacgtacaaa   2820
gacacggtcc agcttcggcg gaagctggag ttctttacgt atagccggtt tgacatggag   2880
ttcacgtttg tcgtcacgag caattatacg gatgcgaaca atggtcacgc gcttaatcaa   2940
gtctaccaga tcatgtacat cccgccgggt gcgccgatcc cgggtaagtg gaatgattac   3000
acgtggcaaa cgagcagcaa cccgagcgtc ttttacacgt acggtgcgcc gccggcgcgg   3060
atcagcgtcc cgtacgtcgg tatcgcgaat gcgtatagcc atttttacga tggttttgcg   3120
aaagtcccgc ttgcgggtca agcgagcacg gagggtgaca gcctttatgg tgcggcgagc   3180
cttaatgact tcggtagcct tgcggtccgg gtcgtcaatg accacaaccc gacgaaactt   3240
acgagcaaaa tccgggtcta catgaaaccg aagcacgtcc gggtctggtg tccgcggccc   3300
cctcgagcag tcccatacta cggaccaggg gttgactaca aggatggact agccccactg   3360
ccagagaaag gcttgacaac ctatggtttt ggccaccaaa ataaggcagt gtacacggca   3420
ggttacaaaa tttgcaatta ccacctcgcc acccaggaag acttacaaaa tgcggtaaac   3480
attatgtgga ttagagacct tttagtagtg gaatccaaag cccaaggcat agactcaatt   3540
gctagatgta actgccacac tggagtgtac tactgtgaat ccaggaggaa gtactacccg   3600
gtctctttta ctggccccac ctttcagtac atggaagcaa atgagtacta tccagcccga   3660
taccaatccc acatgttaat tggccatggt tttgcatctc caggggactg tggtgggatt   3720
ctcaggtgcc aacatggagt aattggaatc attacagctg gaggagaagg cctagtcgct   3780
ttctcggaca tcagagatct gtacgcatac gaggaggagg ctatggagca gggagtctcc   3840
aactatattg agtcccttgg ggctgcattt gggagtggat tcacccagca aataggaaac   3900
aaaatttcag aactcactag catggtcacc agcactataa ctgagaaact actaaagaat   3960
ctcattaaaa taatttcatc ccttgttatc atcaccagaa actatgaaga cacgaccaca   4020
gtgctggcta cccttgctct cctcggttgt gatgcgtccc catggcaatg gctaaagaag   4080
aaagcctgtg acatcttgga aatcccctac atcatgcgac agggcgatag ctggttgaag   4140
aagtttacag aggcatgcaa tgcagccaag ggattggaat gggtgtctaa taaaatatcc   4200
aaatttattg actggctcaa agagaagatc attccacagg ctagagacaa gctagagttt   4260
gttaccaaac tgaagcaact agaaatgttg gagaaccaaa ttgcaaccat tcatcaatcg   4320
tgcccaagtc aggagcatca agaaatcctg ttcaataacg tgagatggtt atccatacag   4380
tcaaagagat ttgccccgct ctatgcggtt gaggctaaga gaatacaaaa gttagagcac   4440
acgattaaca actacgtaca gttcaagagc aaacaccgta ttgaaccagt atgtttgttg   4500
gtgcacggta gcccaggcac gggcaagtca gttgccacca atttaattgc cagagcaata   4560
gcagagaagg agaacacctc cacatactca ctaccaccag atccctccca tttcgatggg   4620
tacaagcaac aaggtgtggt gatcatggat gatttgaatc agaacccaga cggagcagac   4680
atgaagctgt tttgtcagat ggtctccact gtagaattca taccaccaat ggcttcgcta   4740
gaagaaaagg gtattttgtt cacatctaat tacgttttgg cctcaaccaa ttccagtcgc   4800
```

-continued

```
atcaccccac caactgttgc gcacagcgat gccctagcca ggcgctttgc atttgacatg   4860
gacatacaaa tcatgagcga gtattctaga gatggaaaat tgaacatggc gatggcaact   4920
gaaatgtgta agaactgtca tcaaccagca aacttcaaga gatgttgccc attggtgtgt   4980
ggcaaagcca tccagctgat ggacaaatct tccagagtca gatatagtat agatcagatt   5040
actaccatga ttattaatga gaggaacaga agatcaagta tcggtaattg catggaggca   5100
cttttccaag gtcctcttca atacaaagac ctgaaaatag acattaagac cacacctcct   5160
cctgagtgca tcaatgattt gctccaagca gttgattctc aagaggtaag agactactgt   5220
gagaagaagg gttggatagt agacatcact agtcaggtgc aaaccgaaag aaacatcaat   5280
agagcaatga ctattcttca ggcggtcacc acatttgccg cagttgctgg agtggtgtat   5340
gtgatgtaca aactctttgc agggcatcaa ggagcgtata cagggcttcc caataagaga   5400
cccaatgtcc ccaccatcag gactgccaag gttcagggcc caggatttga ctacgcagtg   5460
gcaatggcca aaagaaacat tcttacggca actaccatta agggagagtt cacaatgctc   5520
ggagtgcatg ataatgtggc cattctacca acccacgcat caccgggtga aacaatagtc   5580
attgatggca aggaagtaga ggtactggat gctaaagccc tggaggacca ggccgggacc   5640
aacctagaaa tcaccattgt cactcttaag agaaatgaga agttcaggga catcagacca   5700
cacatcccca ctcaaatcac tgagacaaat gatggagttt taattgtgaa cactagtaag   5760
taccccaaca tgtatgttcc tgtcggtgct gtgactgaac aggggtatct caatctcggt   5820
ggacgccaaa ctgctcgtac tttaatgtac aactttccaa cgagagcagg tcaatgtggt   5880
ggagttatca cctgcactgg caaggtcatc gggatgcatg ttggtgggaa cggttcacat   5940
gggttcgcag cagccctgaa gcgatcctat ttcactcaga gtcaaggtga aatccagtgg   6000
atgagaccat caaaagaagt gggctacccc gttattaatg ctccatctaa aactaaactg   6060
gaacccagtg cattccatta tgtgtttgaa ggtgtcaagg aaccagctgt gctcaccaaa   6120
agtgacccca gattgaagac agattttgaa gaggctatct tttccaagta tgtgggaaat   6180
aagattactg aagtggatga gtacatgaaa gaagctgtcg atcattacgc aggccagctc   6240
atgtcactag acatcaacac agaacaaatg tgccttgagg atgcaatgta tggcactgac   6300
ggtctcgaag ctctagacct cagtaccagt gctgggtatc cctatgtggc aatggggaaa   6360
aagaaaagag acattttgaa taagcaaacc agagacacaa aggaaatgca aaggcttctg   6420
gacacctatg gtattaattt acctttagtc acctatgtga aagatgagct tagatccaag   6480
accaaagtgg aacagggcaa gtccaggcta attgaggcct caagtctcaa tgactctgtc   6540
gccatgagga tggcttttgg caacttgtac gcagcattcc acaagaaccc aggtgtagtg   6600
acaggatcgg ctgttggctg tgacccagat ttgttttgga gtaaaatacc agtcctcatg   6660
gaggaaaaac tctttgcatt tgattacacg ggttatgatg cttcactaag ccccgcctgg   6720
tttgaggctc tcaagatggt tctagagaaa attgggtttg gtgacagagt ggattacatt   6780
gattatctga atcactcgca ccatctatat aaaaataaga catattgtgt taagggcggc   6840
atgccatctg gctgctctgg cacctcaatt tttaattcaa tgattaataa tctaataatc   6900
aggactctct tactgaaaac ctacaagggc atagatttag accacctgaa gatgatagcc   6960
tatggtgatg atgtaattgc ttcctacccc catgaggttg atgctagtct cctagcccaa   7020
tcaggaaaag actatggact aaccatgaca ccagctgaca aatcagccac ctttgaaaca   7080
gtcacatggg agaatgtaac attcttgaaa agattcttta gagcagatga aaagtatccc   7140
```

-continued

```
tttctggtac atccagtgat gccaatgaaa gaaattcacg aatcaattag atggactaaa   7200

gatcccagaa acactcagga tcatgttcgc tcactgtgct tattggcttg gcacaatggc   7260

gaggaagagt acaataaatt tttagctaag attagaagtg tgccaatcgg aagagcatta   7320

ctgctccctg agtactccac attgtaccgc cgttggctcg actcatttta gtaaccctac   7380

ctcagtcgaa ttggattggg tcatactgtt gtaggggtaa atttttcttt aattcggag    7439
```

<210> SEQ ID NO 55
<211> LENGTH: 7439
<212> TYPE: DNA
<213> ORGANISM: Artificial
<220> FEATURE:
<223> OTHER INFORMATION: deoptimized MEF1 poliovirus

<400> SEQUENCE: 55

```
ttaaaacagc tctggggttg ttcccacccc agaggcccac gtggcggcca gtacactggt     60

attgcggtac ctttgtacgc ctgttttata ctcccttccc ccgtaactta gaagcacaat    120

gtccaagttc aataggaggg ggtacaaacc agtaccacca cgaacaagca cttctgttcc    180

cccggtgagg ctgtataggc tgtttccacg gctaaaagcg gctgatccgt tatccgctca    240

tgtacttcga gaagcctagt atcaccttgg aatcttcgat gcgttgcgct caacactcaa    300

ccccagagtg tagcttaggt cgatgagtct ggacgttcct caccggcgac ggtggtccag    360

gctgcgttgg cggcctacct gtggcccaaa gccacaggac gctagttgtg aacaaggtgt    420

gaagagccta ttgagctacc tgagagtcct ccggcccctg aatgcggcta atcctaacca    480

cggagcaggc agtggcaatc cagcgaccag cctgtcgtaa cgcgcaagtt cgtggcggaa    540

ccgactactt tgggtgtccg tgtttccttt tatttttaca atggctgctt atggtgacaa    600

tcattgattg ttatcataaa gcaaattgga ttggccatcc ggtgagaatt tgattattaa    660

attactctct tgttgggatt gctcctttga aatcctgtgc actcacacct attggaatta    720

cctcattgtt aagatatcat caccactatg ggtgcgcaag tcagcagcca gaaagtcggt    780

gcgcatgaga atagcaaccg ggcgtatggt ggtagcacga tcaattacac gacgatcaat    840

tattaccggg atagcgcgag caatgcggcg agcaagcagg actttgcgca agacccgagc    900

aagttcacgg aaccgatcaa agatgtcctt atcaagacgg cgccgacgct taacagcccg    960

aatatcgagg cgtgtggtta tagcgaccgg gtcatgcaac ttacgcttgg taatagcacg   1020

atcacgacgc aggaggcggc gaatagcgtc gtcgcgtacg gccggtggcc ggagtacatc   1080

aaggacagcg aagcgaatcc ggtggaccag ccgacggaac cggacgtcgc ggcgtgccgg   1140

ttttacacgc ttgacacggt cacgtggcgg aaggagagcc ggggttggtg gtggaaactt   1200

ccggatgcgc ttaaggacat gggtcttttc ggtcagaaca tgttctacca ctaccttggt   1260

cgggcgggtt atacggtcca cgtccagtgt aatgcgagca agtttcacca gggtgcgctt   1320

ggtgtcttcg cggtcccgga aatgtgcctt gcgggtgaca gcacgacgca catgtttacg   1380

aaatatgaga atgcgaatcc gggtgagaaa ggtggtgaat tcaaaggtag ctttacgctt   1440

gatacgaacg cgacgaaccc ggcgcggaac ttttgtccgg tcgattatct tttcggtagc   1500

ggtgtccttg cgggtaatgc gtttgtctac ccgcatcaga tcatcaatct tcggacgaac   1560

aactgtgcga cgcttgtcct tccgtacgtc aatagcctta gcatcgacag catgacgaaa   1620

cacaacaatt ggggtatcgc gatccttccg cttgcgccgc ttgactttgc gacggagagc   1680

agcacggaga tcccgatcac gcttacgatc gcgccgatgt gttgtgaatt caatggtctt   1740

cggaacatca cggtcccgcg gacgcaaggt ctaccggtct taaacactcc aggaagcaac   1800
```

-continued

```
cagtacttaa cagcagacaa ctatcaatcc ccatgtgcga tacccgagtt tgatgtaaca   1860
ccacccatag acatcccggg ggaagtgcgc aacatgatgg aattggcaga gatagacacc   1920
atgatacctc tcaatctgac gaaccagcgc aagaacacca tggatatgta cagagtcgaa   1980
ctgaatgatg cggctcactc tgacacacca atattgtgtc tctcactgtc tccagcatca   2040
gatcctaggc tagcacacac tatgctaggt gaaatactga actactacac acactgggca   2100
gggtcattga agttcacatt tctcttctgc ggctcaatga tggccactgg taaattgcta   2160
gtgtcctatg cacctcctgg tgcggaagcc cctaaaagcc gcaaagaagc gatgctcggc   2220
acccacgtga tctgggacat cggattacag tcatcatgca ctatggtggt accttggatt   2280
agcaacacca catacagaca aaccatcaac gatagcttca cagaaggagg gtacatcagt   2340
atgttttacc aaactagagt tgttgtgcca ttgtccaccc ctagaaagat ggacatattg   2400
ggctttgtgt cagcctgcaa tgacttcagt gtgcgcctgt tgcgtgacac gacgcacata   2460
agccaagagg ctatgccaca aggattgggt gatttaattg aaggggttgt tgagggagtc   2520
acgagaaatg ccttgacacc actgacacct gccaacaact tgcctgatac acaatctagc   2580
ggcccagccc actctaagga aacaccagcg ctaacagccg tagagacagg ggccaccaac   2640
ccattggtgc cttcagacac ggtacaaact cgtcacgtca tccaaaagcg gacgcggtcg   2700
gagtctacgg ttgagtcttt cttcgcaaga ggagcttgtg tggccattat tgaagtggat   2760
aatgatgctc caacaaagcg tgccagtaaa ttattttcag tctggaagat aacttacaaa   2820
gacaccgttc agttaagacg taagttggag ttctttacat attcaaggtt tgacatggag   2880
ttcacctttg tggttacatc caattatacc gatgcaaaca atgggcacgc actaaatcaa   2940
gtttaccaga taatgtacat accacctggg gcaccgatcc ctggcaagtg gaatgattac   3000
acatggcaaa cgtcatctaa cccatcagtg ttttacactt acggggcacc tccagctaga   3060
atatcagtgc cctacgtggg cattgccaat gcatattctc atttttacga tgggtttgcc   3120
aaagtaccac tagcaggcca agcctcaaca gagggtgact cgctgtatgg agcggcttca   3180
ttgaatgact tcggatcact ggctgttcga gtggtgaatg accacaaccc tacgaaactc   3240
acttcaaaaa tcagagtgta catgaaacca aagcacgtca gagtgtggtg tccgcgaccc   3300
cctcgagcag tcccatacta cggaccaggg gttgactaca aggatggact agccccactg   3360
ccagagaaag gcttgacaac ctatggtttt ggccaccaaa ataaggcagt gtacacggca   3420
ggttacaaaa tttgcaatta ccacctcgcc acccaggaag acttacaaaa tgcggtaaac   3480
attatgtgga ttagagacct tttagtagtg gaatccaaag cccaaggcat agactcaatt   3540
gctagatgta actgccacac tggagtgtac tactgtgaat ccaggaggaa gtactacccg   3600
gtctctttta ctggccccac ctttcagtac atggaagcaa atgagtacta tccagcccga   3660
taccaatccc acatgttaat tggccatggt tttgcatctc caggggactg tggtgggatt   3720
ctcaggtgcc aacatggagt aattggaatc attacagctg gaggagaagg cctagtcgct   3780
ttctcggaca tcagagatct gtacgcatac gaggaggagg ctatggagca gggagtctcc   3840
aactatattg agtcccttgg ggctgcattt gggagtggat tcacccagca aataggaaac   3900
aaaatttcag aactcactag catggtcacc agcactataa ctgagaaact actaaagaat   3960
ctcattaaaa taatttcatc ccttgttatc atcaccagaa actatgaaga cacgaccaca   4020
gtgctggcta cccttgctct cctcggttgt gatgcgtccc catggcaatg gctaaagaag   4080
aaagcctgtg acatcttgga aatcccctac atcatgcgac agggcgatag ctggttgaag   4140
```

-continued

```
aagtttacag aggcatgcaa tgcagccaag ggattggaat gggtgtctaa taaaatatcc   4200
aaatttattg actggctcaa agagaagatc attccacagg ctagagacaa gctagagttt   4260
gttaccaaac tgaagcaact agaaatgttg gagaaccaaa ttgcaaccat tcatcaatcg   4320
tgcccaagtc aggagcatca agaaatcctg ttcaataacg tgagatggtt atccatacag   4380
tcaaagagat ttgccccgct ctatgcggtt gaggctaaga gaatacaaaa gttagagcac   4440
acgattaaca actacgtaca gttcaagagc aaacaccgta ttgaaccagt atgtttgttg   4500
gtgcacggta gcccaggcac gggcaagtca gttgccacca atttaattgc cagagcaata   4560
gcagagaagg agaacacctc cacatactca ctaccaccag atccctccca tttcgatggg   4620
tacaagcaac aaggtgtggt gatcatggat gatttgaatc agaacccaga cggagcagac   4680
atgaagctgt tttgtcagat ggtctccact gtagaattca taccaccaat ggcttcgcta   4740
gaagaaaagg gtattttgtt cacatctaat tacgttttgg cctcaaccaa ttccagtcgc   4800
atcaccccac caactgttgc gcacagcgat gccctagcca ggcgctttgc atttgacatg   4860
gacatacaaa tcatgagcga gtattctaga gatggaaaat tgaacatggc gatggcaact   4920
gaaatgtgta agaactgtca tcaaccagca aacttcaaga gatgttgccc attggtgtgt   4980
ggcaaagcca tccagctgat ggacaaatct tccagagtca gatatagtat agatcagatt   5040
actaccatga ttattaatga gaggaacaga agatcaagta tcggtaattg catggaggca   5100
cttttccaag gtcctcttca atacaaagac ctgaaaatag acattaagac cacacctcct   5160
cctgagtgca tcaatgattt gctccaagca gttgattctc aagaggtaag agactactgt   5220
gagaagaagg gttggatagt agacatcact agtcaggtgc aaaccgaaag aaacatcaat   5280
agagcaatga ctattcttca ggcggtcacc acatttgccg cagttgctgg agtggtgtat   5340
gtgatgtaca aactctttgc agggcatcaa ggagcgtata cagggcttcc caataagaga   5400
cccaatgtcc ccaccatcag gactgccaag gttcagggcc caggatttga ctacgcagtg   5460
gcaatggcca aaagaaacat tcttacggca actaccatta agggagagtt cacaatgctc   5520
ggagtgcatg ataatgtggc cattctacca acccacgcat caccgggtga aacaatagtc   5580
attgatggca aggaagtaga ggtactggat gctaaagccc tggaggacca ggccgggacc   5640
aacctagaaa tcaccattgt cactcttaag agaaatgaga agttcaggga catcagacca   5700
cacatcccca ctcaaatcac tgagacaaat gatggagttt taattgtgaa cactagtaag   5760
taccccaaca tgtatgttcc tgtcggtgct gtgactgaac aggggtatct caatctcggt   5820
ggacgccaaa ctgctcgtac tttaatgtac aactttccaa cgagagcagg tcaatgtggt   5880
ggagttatca cctgcactgg caaggtcatc gggatgcatg ttggtgggaa cggttcacat   5940
gggttcgcag cagccctgaa gcgatcctat ttcactcaga gtcaaggtga aatccagtgg   6000
atgagaccat caaaagaagt gggctacccc gttattaatg ctccatctaa aactaaactg   6060
gaacccagtg cattccatta tgtgtttgaa ggtgtcaagg aaccagctgt gctcaccaaa   6120
agtgacccca gattgaagac agattttgaa gaggctatct tttccaagta tgtgggaaat   6180
aagattactg aagtggatga gtacatgaaa gaagctgtcg atcattacgc aggccagctc   6240
atgtcactag acatcaacac agaacaaatg tgccttgagg atgcaatgta tggcactgac   6300
ggtctcgaag ctctagacct cagtaccagt gctgggtatc cctatgtggc aatggggaaa   6360
aagaaaagag acattttgaa taagcaaacc agagacacaa aggaaatgca aaggcttctg   6420
gacacctatg gtattaattt acctttagtc acctatgtga aagatgagct tagatccaag   6480
accaaagtgg aacagggcaa gtccaggcta attgaggcct caagtctcaa tgactctgtc   6540
```

gccatgagga tggcttttgg caacttgtac gcagcattcc acaagaaccc aggtgtagtg 6600
acaggatcgg ctgttggctg tgacccagat ttgttttgga gtaaaatacc agtcctcatg 6660
gaggaaaaac tctttgcatt tgattacacg ggttatgatg cttcactaag ccccgcctgg 6720
tttgaggctc tcaagatggt tctagagaaa attgggtttg gtgacagagt ggattacatt 6780
gattatctga atcactcgca ccatctatat aaaaataaga catattgtgt taagggcggc 6840
atgccatctg gctgctctgg cacctcaatt tttaattcaa tgattaataa tctaataatc 6900
aggactctct tactgaaaac ctacaagggc atagatttag accacctgaa gatgatagcc 6960
tatggtgatg atgtaattgc ttcctacccc catgaggttg atgctagtct cctagcccaa 7020
tcaggaaaag actatggact aaccatgaca ccagctgaca aatcagccac ctttgaaaca 7080
gtcacatggg agaatgtaac attcttgaaa agattcttta gagcagatga aaagtatccc 7140
tttctggtac atccagtgat gccaatgaaa gaaattcacg aatcaattag atggactaaa 7200
gatcccagaa acactcagga tcatgttcgc tcactgtgct tattggcttg gcacaatggc 7260
gaggaagagt acaataaatt tttagctaag attagaagtg tgccaatcgg aagagcatta 7320
ctgctccctg agtactccac attgtaccgc cgttggctcg actcatttta gtaaccctac 7380
ctcagtcgaa ttggattggg tcatactgtt gtaggggtaa atttttcttt aattcggag 7439

<210> SEQ ID NO 56
<211> LENGTH: 7439
<212> TYPE: DNA
<213> ORGANISM: Artificial
<220> FEATURE:
<223> OTHER INFORMATION: deoptimized MEF1 poliovirus

<400> SEQUENCE: 56
ttaaaacagc tctggggttg ttcccacccc agaggcccac gtggcggcca gtacactggt 60
attgcggtac ctttgtacgc ctgttttata ctcccttccc ccgtaactta gaagcacaat 120
gtccaagttc aataggaggg ggtacaaacc agtaccacca cgaacaagca cttctgttcc 180
cccggtgagg ctgtataggc tgtttccacg gctaaaagcg gctgatccgt tatccgctca 240
tgtacttcga gaagcctagt atcaccttgg aatcttcgat gcgttgcgct caacactcaa 300
ccccagagtg tagcttaggt cgatgagtct ggacgttcct caccggcgac ggtggtccag 360
gctgcgttgg cggcctacct gtggcccaaa gccacaggac gctagttgtg aacaaggtgt 420
gaagagccta ttgagctacc tgagagtcct ccggcccctg aatgcggcta atcctaacca 480
cggagcaggc agtggcaatc cagcgaccag cctgtcgtaa cgcgcaagtt cgtggcggaa 540
ccgactactt tgggtgtccg tgtttccttt tatttttaca atggctgctt atggtgacaa 600
tcattgattg ttatcataaa gcaaattgga ttggccatcc ggtgagaatt tgattattaa 660
attactctct tgttgggatt gctcctttga aatcctgtgc actcacacct attggaatta 720
cctcattgtt aagatatcat caccactatg ggcgcccaag tctcatcaca gaaagttgga 780
gcccatgaga attcaaacag agcttatggc ggatccacca ttaattacac tactattaat 840
tattacaggg attctgcgag caatgccgct agtaagcagg actttgcaca agacccatcc 900
aagttcactg aacctattaa agatgttctc attaagaccg ctcccacgct aaactctcct 960
aatatcgagg cgtgtgggta tagcgacaga gtgatgcaac taaccctagg caattccacc 1020
attaccacac aggaggcggc caattctgtc gttgcatacg gccggtggcc cgagtacatc 1080
aaggactcag aagcaaatcc tgtggaccag ccaactgaac cggacgttgc cgcgtgcagg 1140

-continued

```
ttttacacac tagacactgt tacttggcgc aaggagtcca gagggtggtg gtggaaactg   1200
cctgatgcac taaaggacat gggattattc ggccagaaca tgttctacca ctacctcggg   1260
agggctggct atactgtgca cgtacagtgt aatgcttcaa agtttcacca gggcgccctc   1320
ggggtattcg cagttccaga aatgtgcctg gcaggcgaca gcacaaccca catgtttaca   1380
aaatatgaga atgcaaatcc gggtgagaaa gggggtgaat tcaaagggag ttttactctg   1440
gatactaacg ctaccaaccc tgcacgcaac ttttgtcccg ttgattatct cttcgggagc   1500
ggagtactgg cgggaaatgc gtttgtttac ccacatcaga taattaatct gcgcaccaac   1560
aactgtgcca cgttggtgct gccatacgtt aattcacttt ccatagacag catgacaaaa   1620
cacaacaatt ggggaattgc tatccttccg ctggcaccac ttgactttgc caccgagtcc   1680
tccactgaga tacccattac tctaactatt gcccctatgt gttgtgaatt caatgggttg   1740
cgcaacatca ctgtacccag aactcaaggg ttaccggtcc ttaacacgcc gggtagcaac   1800
cagtacctta cggcggacaa ctatcaaagc ccgtgtgcga tcccggagtt tgatgtcacg   1860
ccgccgatcg acatcccggg tgaagtccgg aacatgatgg aacttgcgga gatcgacacg   1920
atgatcccgc ttaatcttac gaaccagcgg aagaacacga tggatatgta ccgggtcgaa   1980
cttaatgatg cggcgcacag cgacacgccg atcctttgtc ttagccttag cccggcgagc   2040
gatccgcggc tagcgcacac gatgcttggt gaaatcctta actactacac gcactgggcg   2100
ggtagcctta agttcacgtt tctttctgc ggtagcatga tggcgacggg taaacttctt   2160
gtcagctatg cgccgccggg tgcggaagcg ccgaaaagcc ggaaagaagc gatgcttggt   2220
acgcacgtca tctgggacat cggtcttcag agcagctgca cgatggtcgt cccgtggatc   2280
agcaacacga cgtaccggca aacgatcaac gatagcttca cggaaggtgg ttacatcagc   2340
atgttttacc aaacgcgggt cgtcgtcccg cttagcacgc cgcggaagat ggacatcctt   2400
ggttttgtca gcgcgtgcaa tgacttcagc gtccggcttc ttcgggacac gacgcacatc   2460
agccaagagg cgatgccgca aggtcttggt gatcttatcg aaggtgtcgt cgagggtgtc   2520
acgcggaatg cgcttacgcc gcttacgccg gcgaacaacc ttccggatac gcaaagcagc   2580
ggtccggcgc acagcaagga aacgccagcg ctaacagccg tagagacagg ggccaccaac   2640
ccattggtgc cttcagacac ggtacaaact cgtcacgtca tccaaaagcg gacgcggtcg   2700
gagtctacgg ttgagtcttt cttcgcaaga ggagcttgtg tggccattat tgaagtggat   2760
aatgatgctc caacaaagcg tgccagtaaa ttattttcag tctggaagat aacttacaaa   2820
gacaccgttc agttaagacg taagttggag ttctttacat attcaaggtt tgacatggag   2880
ttcacctttg tggttacatc caattatacc gatgcaaaca atgggcacgc actaaatcaa   2940
gtttaccaga taatgtacat accacctggg gcaccgatcc ctggcaagtg gaatgattac   3000
acatggcaaa cgtcatctaa cccatcagtg ttttacactt acggggcacc tccagctaga   3060
atatcagtgc cctacgtggg cattgccaat gcatattctc atttttacga tgggtttgcc   3120
aaagtaccac tagcaggcca agcctcaaca gagggtgact cgctgtatgg agcggcttca   3180
ttgaatgact tcggatcact ggctgttcga gtggtgaatg accacaaccc tacgaaactc   3240
acttcaaaaa tcagagtgta catgaaacca aagcacgtca gagtgtggtg tccgcgaccc   3300
cctcgagcag tcccatacta cggaccaggg gttgactaca aggatggact agccccactg   3360
ccagagaaag gcttgacaac ctatggtttt ggccaccaaa ataaggcagt gtacacggca   3420
ggttacaaaa tttgcaatta ccacctcgcc acccaggaag acttacaaaa tgcggtaaac   3480
attatgtgga ttagagacct tttagtagtg gaatccaaag cccaaggcat agactcaatt   3540
```

-continued gctagatgta actgccacac tggagtgtac tactgtgaat ccaggaggaa gtactacccg 3600
gtctctttta ctggccccac ctttcagtac atggaagcaa atgagtacta tccagcccga 3660
taccaatccc acatgttaat tggccatggt tttgcatctc caggggactg tggtgggatt 3720
ctcaggtgcc aacatggagt aattggaatc attacagctg gaggagaagg cctagtcgct 3780
ttctcggaca tcagagatct gtacgcatac gaggaggagg ctatggagca gggagtctcc 3840
aactatattg agtcccttgg ggctgcattt gggagtggat tcacccagca aataggaaac 3900
aaaatttcag aactcactag catggtcacc agcactataa ctgagaaact actaaagaat 3960
ctcattaaaa taatttcatc ccttgttatc atcaccagaa actatgaaga cacgaccaca 4020
gtgctggcta cccttgctct cctcggttgt gatgcgtccc catggcaatg gctaaagaag 4080
aaagcctgtg acatcttgga aatcccctac atcatgcgac agggcgatag ctggttgaag 4140
aagtttacag aggcatgcaa tgcagccaag ggattggaat gggtgtctaa taaaatatcc 4200
aaatttattg actggctcaa agagaagatc attccacagg ctagagacaa gctagagttt 4260
gttaccaaac tgaagcaact agaaatgttg gagaaccaaa ttgcaaccat tcatcaatcg 4320
tgcccaagtc aggagcatca agaaatcctg ttcaataacg tgagatggtt atccatacag 4380
tcaaagagat ttgccccgct ctatgcggtt gaggctaaga gaatacaaaa gttagagcac 4440
acgattaaca actacgtaca gttcaagagc aaacaccgta ttgaaccagt atgtttgttg 4500
gtgcacggta gcccaggcac gggcaagtca gttgccacca atttaattgc cagagcaata 4560
gcagagaagg agaacacctc cacatactca ctaccaccag atccctccca tttcgatggg 4620
tacaagcaac aaggtgtggt gatcatggat gatttgaatc agaacccaga cggagcagac 4680
atgaagctgt tttgtcagat ggtctccact gtagaattca taccaccaat ggcttcgcta 4740
gaagaaaagg gtattttgtt cacatctaat tacgttttgg cctcaaccaa ttccagtcgc 4800
atcaccccac caactgttgc gcacagcgat gccctagcca ggcgctttgc atttgacatg 4860
gacatacaaa tcatgagcga gtattctaga gatggaaaat tgaacatggc gatggcaact 4920
gaaatgtgta agaactgtca tcaaccagca aacttcaaga gatgttgccc attggtgtgt 4980
ggcaaagcca tccagctgat ggacaaatct tccagagtca gatatagtat agatcagatt 5040
actaccatga ttattaatga gaggaacaga agatcaagta tcggtaattg catggaggca 5100
cttttccaag gtcctcttca atacaaagac ctgaaaatag acattaagac cacacctcct 5160
cctgagtgca tcaatgattt gctccaagca gttgattctc aagaggtaag agactactgt 5220
gagaagaagg gttggatagt agacatcact agtcaggtgc aaaccgaaag aaacatcaat 5280
agagcaatga ctattcttca ggcggtcacc acatttgccg cagttgctgg agtggtgtat 5340
gtgatgtaca aactctttgc agggcatcaa ggagcgtata cagggcttcc caataagaga 5400
cccaatgtcc ccaccatcag gactgccaag gttcagggcc caggatttga ctacgcagtg 5460
gcaatggcca aaagaaacat tcttacggca actaccatta agggagagtt cacaatgctc 5520
ggagtgcatg ataatgtggc cattctacca acccacgcat caccgggtga aacaatagtc 5580
attgatggca aggaagtaga ggtactggat gctaaagccc tggaggacca ggccgggacc 5640
aacctagaaa tcaccattgt cactcttaag agaaatgaga agttcaggga catcagacca 5700
cacatcccca ctcaaatcac tgagacaaat gatggagttt taattgtgaa cactagtaag 5760
taccccaaca tgtatgttcc tgtcggtgct gtgactgaac aggggtatct caatctcggt 5820
ggacgccaaa ctgctcgtac tttaatgtac aactttccaa cgagagcagg tcaatgtggt 5880

-continued ggagttatca cctgcactgg caaggtcatc gggatgcatg ttggtgggaa cggttcacat 5940
gggttcgcag cagccctgaa gcgatcctat ttcactcaga gtcaaggtga aatccagtgg 6000
atgagaccat caaaagaagt gggctacccc gttattaatg ctccatctaa aactaaactg 6060
gaacccagtg cattccatta tgtgtttgaa ggtgtcaagg aaccagctgt gctcaccaaa 6120
agtgacccca gattgaagac agattttgaa gaggctatct tttccaagta tgtgggaaat 6180
aagattactg aagtggatga gtacatgaaa gaagctgtcg atcattacgc aggccagctc 6240
atgtcactag acatcaacac agaacaaatg tgccttgagg atgcaatgta tggcactgac 6300
ggtctcgaag ctctagacct cagtaccagt gctgggtatc cctatgtggc aatggggaaa 6360
aagaaaagag acattttgaa taagcaaacc agagacacaa aggaaatgca aaggcttctg 6420
gacacctatg gtattaattt acctttagtc acctatgtga aagatgagct tagatccaag 6480
accaaagtgg aacagggcaa gtccaggcta attgaggcct caagtctcaa tgactctgtc 6540
gccatgagga tggcttttgg caacttgtac gcagcattcc acaagaaccc aggtgtagtg 6600
acaggatcgg ctgttggctg tgacccagat ttgttttgga gtaaaatacc agtcctcatg 6660
gaggaaaaac tctttgcatt tgattacacg ggttatgatg cttcactaag ccccgcctgg 6720
tttgaggctc tcaagatggt tctagagaaa attgggtttg gtgacagagt ggattacatt 6780
gattatctga atcactcgca ccatctatat aaaaataaga catattgtgt taagggcggc 6840
atgccatctg gctgctctgg cacctcaatt tttaattcaa tgattaataa tctaataatc 6900
aggactctct tactgaaaac ctacaagggc atagatttag accacctgaa gatgatagcc 6960
tatggtgatg atgtaattgc ttcctacccc catgaggttg atgctagtct cctagcccaa 7020
tcaggaaaag actatggact aaccatgaca ccagctgaca aatcagccac ctttgaaaca 7080
gtcacatggg agaatgtaac attcttgaaa agattcttta gagcagatga aaagtatccc 7140
tttctggtac atccagtgat gccaatgaaa gaaattcacg aatcaattag atggactaaa 7200
gatcccagaa acactcagga tcatgttcgc tcactgtgct tattggcttg gcacaatggc 7260
gaggaagagt acaataaatt tttagctaag attagaagtg tgccaatcgg aagagcatta 7320
ctgctccctg agtactccac attgtaccgc cgttggctcg actcatttta gtaaccctac 7380
ctcagtcgaa ttggattggg tcatactgtt gtaggggtaa atttttcttt aattcggag 7439

<210> SEQ ID NO 57
<211> LENGTH: 7439
<212> TYPE: DNA
<213> ORGANISM: Artificial
<220> FEATURE:
<223> OTHER INFORMATION: deoptimized MEF1 poliovirus

<400> SEQUENCE: 57
ttaaaacagc tctggggttg ttcccacccc agaggcccac gtggcggcca gtacactggt 60
attgcggtac ctttgtacgc ctgttttata ctcccttccc ccgtaactta gaagcacaat 120
gtccaagttc aataggaggg ggtacaaacc agtaccacca cgaacaagca cttctgttcc 180
cccggtgagg ctgtataggc tgtttccacg gctaaaagcg gctgatccgt tatccgctca 240
tgtacttcga gaagcctagt atcaccttgg aatcttcgat gcgttgcgct caacactcaa 300
ccccagagtg tagcttaggt cgatgagtct ggacgttcct caccggcgac ggtggtccag 360
gctgcgttgg cggcctacct gtggcccaaa gccacaggac gctagttgtg aacaaggtgt 420
gaagagccta ttgagctacc tgagagtcct ccggcccctg aatgcggcta atcctaacca 480
cggagcaggc agtggcaatc cagcgaccag cctgtcgtaa cgcgcaagtt cgtggcggaa 540

-continued

```
ccgactactt tgggtgtccg tgtttccttt tatttttaca atggctgctt atggtgacaa    600
tcattgattg ttatcataaa gcaaattgga ttggccatcc ggtgagaatt tgattattaa    660
attactctct tgttgggatt gctcctttga aatcctgtgc actcacacct attggaatta    720
cctcattgtt aagatatcat caccactatg ggtgcgcaag tcagcagcca gaaagtcggt    780
gcgcatgaga atagcaaccg ggcgtatggt ggtagcacga tcaattacac gacgatcaat    840
tattaccggg atagcgcgag caatgcggcg agcaagcagg actttgcgca agacccgagc    900
aagttcacgg aaccgatcaa agatgtcctt atcaagacgg cgccgacgct taacagcccg    960
aatatcgagg cgtgtggtta tagcgaccgg gtcatgcaac ttacgcttgg taatagcacg   1020
atcacgacgc aggaggcggc gaatagcgtc gtcgcgtacg gccggtggcc ggagtacatc   1080
aaggacagcg aagcgaatcc ggtggaccag ccgacggaac cggacgtcgc ggcgtgccgg   1140
ttttacacgc ttgacacggt cacgtggcgg aaggagagcc ggggttggtg gtggaaactt   1200
ccggatgcgc ttaaggacat gggtcttttc ggtcagaaca tgttctacca ctaccttggt   1260
cgggcgggtt atacggtcca cgtccagtgt aatgcgagca agtttcacca gggtgcgctt   1320
ggtgtcttcg cggtcccgga aatgtgcctt gcgggtgaca gcacgacgca catgtttacg   1380
aaatatgaga atgcgaatcc gggtgagaaa ggtggtgaat tcaaaggtag ctttacgctt   1440
gatacgaacg cgacgaaccc ggcgcggaac ttttgtccgg tcgattatct tttcggtagc   1500
ggtgtccttg cgggtaatgc gtttgtctac ccgcatcaga tcatcaatct tcggacgaac   1560
aactgtgcga cgcttgtcct tccgtacgtc aatagcctta gcatcgacag catgacgaaa   1620
cacaacaatt ggggtatcgc gatccttccg cttgcgccgc ttgactttgc gacggagagc   1680
agcacggaga tcccgatcac gcttacgatc gcgccgatgt gttgtgaatt caatggtctt   1740
cggaacatca cggtcccgcg gacgcaaggt ctaccggtcc ttaacacgcc gggtagcaac   1800
cagtacctta cggcggacaa ctatcaaagc ccgtgtgcga tcccggagtt tgatgtcacg   1860
ccgccgatcg acatcccggg tgaagtccgg aacatgatgg aacttgcgga gatcgacacg   1920
atgatcccgc ttaatcttac gaaccagcgg aagaacacga tggatatgta ccgggtcgaa   1980
cttaatgatg cggcgcacag cgacacgccg atcctttgtc ttagccttag cccggcgagc   2040
gatccgcggc tagcgcacac gatgcttggt gaaatcctta actactacac gcactgggcg   2100
ggtagcctta agttcacgtt tcttttctgc ggtagcatga tggcgacggg taaacttctt   2160
gtcagctatg cgccgccggg tgcggaagcg ccgaaaagcc ggaaagaagc gatgcttggt   2220
acgcacgtca tctgggacat cggtcttcag agcagctgca cgatggtcgt cccgtggatc   2280
agcaacacga cgtaccggca aacgatcaac gatagcttca cggaaggtgg ttacatcagc   2340
atgttttacc aaacgcgggt cgtcgtcccg cttagcacgc cgcggaagat ggacatcctt   2400
ggttttgtca gcgcgtgcaa tgacttcagc gtccggcttc ttcgggacac gacgcacatc   2460
agccaagagg cgatgccgca aggtcttggt gatcttatcg aaggtgtcgt cgagggtgtc   2520
acgcggaatg cgcttacgcc gcttacgccg gcgaacaacc ttccggatac gcaaagcagc   2580
ggtccggcgc acagcaagga aacgccagcg ctaacagccg tagagacagg ggccaccaac   2640
ccattggtgc cttcagacac ggtacaaact cgtcacgtca tccaaaagcg gacgcggtcg   2700
gagtctacgg ttgagtcttt cttcgcaaga ggagcttgtg tggccattat tgaagtggat   2760
aatgatgctc caacaaagcg tgccagtaaa ttattttcag tctggaagat aacttacaaa   2820
gacaccgttc agttaagacg taagttggag ttctttacat attcaaggtt tgacatggag   2880
```

-continued

```
ttcacctttg tggttacatc caattatacc gatgcaaaca atgggcacgc actaaatcaa   2940
gtttaccaga taatgtacat accacctggg gcaccgatcc ctggcaagtg gaatgattac   3000
acatggcaaa cgtcatctaa cccatcagtg ttttacactt acggggcacc tccagctaga   3060
atatcagtgc cctacgtggg cattgccaat gcatattctc atttttacga tgggtttgcc   3120
aaagtaccac tagcaggcca agcctcaaca gagggtgact cgctgtatgg agcggcttca   3180
ttgaatgact tcggatcact ggctgttcga gtggtgaatg accacaaccc tacgaaactc   3240
acttcaaaaa tcagagtgta catgaaacca aagcacgtca gagtgtggtg tccgcgaccc   3300
cctcgagcag tcccatacta cggaccaggg gttgactaca aggatggact agccccactg   3360
ccagagaaag gcttgacaac ctatggtttt ggccaccaaa ataaggcagt gtacacggca   3420
ggttacaaaa tttgcaatta ccacctcgcc acccaggaag acttacaaaa tgcggtaaac   3480
attatgtgga ttagagacct tttagtagtg gaatccaaag cccaaggcat agactcaatt   3540
gctagatgta actgccacac tggagtgtac tactgtgaat ccaggaggaa gtactacccg   3600
gtctctttta ctggccccac ctttcagtac atggaagcaa atgagtacta tccagcccga   3660
taccaatccc acatgttaat tggccatggt tttgcatctc caggggactg tggtgggatt   3720
ctcaggtgcc aacatggagt aattggaatc attacagctg gaggagaagg cctagtcgct   3780
ttctcggaca tcagagatct gtacgcatac gaggaggagg ctatggagca gggagtctcc   3840
aactatattg agtcccttgg ggctgcattt gggagtggat tcacccagca aataggaaac   3900
aaaatttcag aactcactag catggtcacc agcactataa ctgagaaact actaaagaat   3960
ctcattaaaa taatttcatc ccttgttatc atcaccagaa actatgaaga cacgaccaca   4020
gtgctggcta cccttgctct cctcggttgt gatgcgtccc catggcaatg gctaaagaag   4080
aaagcctgtg acatcttgga aatcccctac atcatgcgac agggcgatag ctggttgaag   4140
aagtttacag aggcatgcaa tgcagccaag ggattggaat gggtgtctaa taaaatatcc   4200
aaatttattg actggctcaa agagaagatc attccacagg ctagagacaa gctagagttt   4260
gttaccaaac tgaagcaact agaaatgttg gagaaccaaa ttgcaaccat tcatcaatcg   4320
tgcccaagtc aggagcatca agaaatcctg ttcaataacg tgagatggtt atccatacag   4380
tcaaagagat ttgccccgct ctatgcggtt gaggctaaga gaatacaaaa gttagagcac   4440
acgattaaca actacgtaca gttcaagagc aaacaccgta ttgaaccagt atgtttgttg   4500
gtgcacggta gcccaggcac gggcaagtca gttgccacca atttaattgc cagagcaata   4560
gcagagaagg agaacacctc cacatactca ctaccaccag atccctccca tttcgatggg   4620
tacaagcaac aaggtgtggt gatcatggat gatttgaatc agaacccaga cggagcagac   4680
atgaagctgt tttgtcagat ggtctccact gtagaattca taccaccaat ggcttcgcta   4740
gaagaaaagg gtattttgtt cacatctaat tacgttttgg cctcaaccaa ttccagtcgc   4800
atcaccccac caactgttgc gcacagcgat gccctagcca ggcgctttgc atttgacatg   4860
gacatacaaa tcatgagcga gtattctaga gatggaaaat tgaacatggc gatggcaact   4920
gaaatgtgta agaactgtca tcaaccagca aacttcaaga gatgttgccc attggtgtgt   4980
ggcaaagcca tccagctgat ggacaaatct tccagagtca gatatagtat agatcagatt   5040
actaccatga ttattaatga gaggaacaga agatcaagta tcggtaattg catggaggca   5100
cttttccaag gtcctcttca atacaaagac ctgaaaatag acattaagac cacacctcct   5160
cctgagtgca tcaatgattt gctccaagca gttgattctc aagaggtaag agactactgt   5220
gagaagaagg gttggatagt agacatcact agtcaggtgc aaaccgaaag aaacatcaat   5280
```

agagcaatga ctattcttca ggcggtcacc acatttgccg cagttgctgg agtggtgtat 5340
gtgatgtaca aactctttgc agggcatcaa ggagcgtata cagggcttcc caataagaga 5400
cccaatgtcc ccaccatcag gactgccaag gttcagggcc caggatttga ctacgcagtg 5460
gcaatggcca aaagaaacat tcttacggca actaccatta agggagagtt cacaatgctc 5520
ggagtgcatg ataatgtggc cattctacca acccacgcat caccgggtga aacaatagtc 5580
attgatggca aggaagtaga ggtactggat gctaaagccc tggaggacca ggccgggacc 5640
aacctagaaa tcaccattgt cactcttaag agaaatgaga agttcaggga catcagacca 5700
cacatcccca ctcaaatcac tgagacaaat gatggagttt taattgtgaa cactagtaag 5760
taccccaaca tgtatgttcc tgtcggtgct gtgactgaac aggggtatct caatctcggt 5820
ggacgccaaa ctgctcgtac tttaatgtac aactttccaa cgagagcagg tcaatgtggt 5880
ggagttatca cctgcactgg caaggtcatc gggatgcatg ttggtgggaa cggttcacat 5940
gggttcgcag cagccctgaa gcgatcctat ttcactcaga gtcaaggtga aatccagtgg 6000
atgagaccat caaaagaagt gggctacccc gttattaatg ctccatctaa aactaaactg 6060
gaacccagtg cattccatta tgtgtttgaa ggtgtcaagg aaccagctgt gctcaccaaa 6120
agtgacccca gattgaagac agattttgaa gaggctatct tttccaagta tgtgggaaat 6180
aagattactg aagtggatga gtacatgaaa gaagctgtcg atcattacgc aggccagctc 6240
atgtcactag acatcaacac agaacaaatg tgccttgagg atgcaatgta tggcactgac 6300
ggtctcgaag ctctagacct cagtaccagt gctgggtatc cctatgtggc aatggggaaa 6360
aagaaaagag acattttgaa taagcaaacc agagacacaa aggaaatgca aaggcttctg 6420
gacacctatg gtattaattt acctttagtc acctatgtga aagatgagct tagatccaag 6480
accaaagtgg aacagggcaa gtccaggcta attgaggcct caagtctcaa tgactctgtc 6540
gccatgagga tggcttttgg caacttgtac gcagcattcc acaagaaccc aggtgtagtg 6600
acaggatcgg ctgttggctg tgacccagat ttgttttgga gtaaaatacc agtcctcatg 6660
gaggaaaaac tctttgcatt tgattacacg ggttatgatg cttcactaag ccccgcctgg 6720
tttgaggctc tcaagatggt tctagagaaa attgggtttg gtgacagagt ggattacatt 6780
gattatctga atcactcgca ccatctatat aaaaataaga catattgtgt taagggcggc 6840
atgccatctg gctgctctgg cacctcaatt tttaattcaa tgattaataa tctaataatc 6900
aggactctct tactgaaaac ctacaagggc atagatttag accacctgaa gatgatagcc 6960
tatggtgatg atgtaattgc ttcctacccc catgaggttg atgctagtct cctagcccaa 7020
tcaggaaaag actatggact aaccatgaca ccagctgaca aatcagccac ctttgaaaca 7080
gtcacatggg agaatgtaac attcttgaaa agattcttta gagcagatga aaagtatccc 7140
tttctggtac atccagtgat gccaatgaaa gaaattcacg aatcaattag atggactaaa 7200
gatcccagaa acactcagga tcatgttcgc tcactgtgct tattggcttg gcacaatggc 7260
gaggaagagt acaataaatt tttagctaag attagaagtg tgccaatcgg aagagcatta 7320
ctgctccctg agtactccac attgtaccgc cgttggctcg actcatttta gtaaccctac 7380
ctcagtcgaa ttggattggg tcatactgtt gtaggggtaa atttttcttt aattcggag 7439

<210> SEQ ID NO 58
<211> LENGTH: 7439
<212> TYPE: DNA
<213> ORGANISM: Artificial
<220> FEATURE:

<223> OTHER INFORMATION: deoptimized MEF1 poliovirus

<400> SEQUENCE: 58

```
ttaaaacagc tctggggttg ttcccacccc agaggcccac gtggcggcca gtacactggt     60
attgcggtac ctttgtacgc ctgttttata ctcccttccc ccgtaactta gaagcacaat    120
gtccaagttc aataggaggg ggtacaaacc agtaccacca cgaacaagca cttctgttcc    180
cccggtgagg ctgtataggc tgtttccacg gctaaaagcg gctgatccgt tatccgctca    240
tgtacttcga gaagcctagt atcaccttgg aatcttcgat gcgttgcgct caacactcaa    300
ccccagagtg tagcttaggt cgatgagtct ggacgttcct caccggcgac ggtggtccag    360
gctgcgttgg cggcctacct gtggcccaaa gccacaggac gctagttgtg aacaaggtgt    420
gaagagccta ttgagctacc tgagagtcct ccggcccctg aatgcggcta atcctaacca    480
cggagcaggc agtggcaatc cagcgaccag cctgtcgtaa cgcgcaagtt cgtggcggaa    540
ccgactactt tgggtgtccg tgtttccttt tatttttaca atggctgctt atggtgacaa    600
tcattgattg ttatcataaa gcaaattgga ttggccatcc ggtgagaatt tgattattaa    660
attactctct tgttgggatt gctcctttga aatcctgtgc actcacacct attggaatta    720
cctcattgtt aagatatcat caccactatg ggtgcgcaag tcagcagcca gaaagtcggt    780
gcgcatgaga atagcaaccg ggcgtatggt ggtagcacga tcaattacac gacgatcaat    840
tattaccggg atagcgcgag caatgcggcg agcaagcagg actttgcgca agacccgagc    900
aagttcacgg aaccgatcaa agatgtcctt atcaagacgg cgccgacgct taacagcccg    960
aatatcgagg cgtgtggtta tagcgaccgg gtcatgcaac ttacgcttgg taatagcacg   1020
atcacgacgc aggaggcggc gaatagcgtc gtcgcgtacg gccggtggcc ggagtacatc   1080
aaggacagcg aagcgaatcc ggtggaccag ccgacggaac cggacgtcgc ggcgtgccgg   1140
ttttacacgc ttgacacggt cacgtggcgg aaggagagcc ggggttggtg gtggaaactt   1200
ccggatgcgc ttaaggacat gggtcttttc ggtcagaaca tgttctacca ctaccttggt   1260
cgggcgggtt atacggtcca cgtccagtgt aatgcgagca agtttcacca gggtgcgctt   1320
ggtgtcttcg cggtcccgga aatgtgcctt gcgggtgaca gcacgacgca catgtttacg   1380
aaatatgaga atgcgaatcc gggtgagaaa ggtggtgaat tcaaaggtag ctttacgctt   1440
gatacgaacg cgacgaaccc ggcgcggaac ttttgtccgg tcgattatct tttcggtagc   1500
ggtgtccttg cgggtaatgc gtttgtctac ccgcatcaga tcatcaatct tcggacgaac   1560
aactgtgcga cgcttgtcct tccgtacgtc aatagcctta gcatcgacag catgacgaaa   1620
cacaacaatt ggggtatcgc gatccttccg cttgcgccgc ttgactttgc gacggagagc   1680
agcacggaga tcccgatcac gcttacgatc gcgccgatgt gttgtgaatt caatggtctt   1740
cggaacatca cggtcccgcg gacgcaaggt ctaccggtcc ttaacacgcc gggtagcaac   1800
cagtacctta cggcggacaa ctatcaaagc ccgtgtgcga tcccggagtt tgatgtcacg   1860
ccgccgatcg acatcccggg tgaagtccgg aacatgatgg aacttgcgga gatcgacacg   1920
atgatcccgc ttaatcttac gaaccagcgg aagaacacga tggatatgta ccgggtcgaa   1980
cttaatgatg cggcgcacag cgacacgccg atcctttgtc ttagccttag cccggcgagc   2040
gatccgcggc tagcgcacac gatgcttggt gaaatcctta actactacac gcactgggcg   2100
ggtagcctta agttcacgtt tcttttctgc ggtagcatga tggcgacggg taaacttctt   2160
gtcagctatg cgccgccggg tgcggaagcg ccgaaaagcc ggaaagaagc gatgcttggt   2220
acgcacgtca tctgggacat cggtcttcag agcagctgca cgatggtcgt cccgtggatc   2280
```

```
agcaacacga cgtaccggca aacgatcaac gatagcttca cggaaggtgg ttacatcagc   2340
atgttttacc aaacgcgggt cgtcgtcccg cttagcacgc cgcggaagat ggacatcctt   2400
ggttttgtca gcgcgtgcaa tgacttcagc gtccggcttc ttcgggacac gacgcacatc   2460
agccaagagg cgatgccgca aggtcttggt gatcttatcg aaggtgtcgt cgagggtgtc   2520
acgcggaatg cgcttacgcc gcttacgccg gcgaacaacc ttccggatac gcaaagcagc   2580
ggtccggcgc acagcaagga aacgccagcg cttacggcgg tcgagacggg tgcgacgaac   2640
ccgcttgtcc cgagcgacac ggtccaaacg cggcacgtca tccaaaagcg gacgcggagc   2700
gagagcacgg tcgagagctt cttcgcgcgg ggtgcgtgtg tcgcgatcat cgaagtcgat   2760
aatgatgcgc cgacgaagcg ggcgagcaaa ctttttagcg tctggaagat cacgtacaaa   2820
gacacggtcc agcttcggcg gaagctggag ttctttacgt atagccggtt tgacatggag   2880
ttcacgtttg tcgtcacgag caattatacg gatgcgaaca atggtcacgc gcttaatcaa   2940
gtctaccaga tcatgtacat cccgccgggt gcgccgatcc cgggtaagtg gaatgattac   3000
acgtggcaaa cgagcagcaa cccgagcgtc ttttacacgt acggtgcgcc gccggcgcgg   3060
atcagcgtcc cgtacgtcgg tatcgcgaat gcgtatagcc atttttacga tggttttgcg   3120
aaagtcccgc ttgcgggtca agcgagcacg gagggtgaca gcctttatgg tgcggcgagc   3180
cttaatgact tcggtagcct tgcggtccgg gtcgtcaatg accacaaccc gacgaaactt   3240
acgagcaaaa tccgggtcta catgaaaccg aagcacgtcc gggtctggtg tccgcggccc   3300
cctcgagcag tcccatacta cggaccaggg gttgactaca aggatggact agccccactg   3360
ccagagaaag gcttgacaac ctatggtttt ggccaccaaa ataaggcagt gtacacggca   3420
ggttacaaaa tttgcaatta ccacctcgcc acccaggaag acttacaaaa tgcggtaaac   3480
attatgtgga ttagagacct tttagtagtg gaatccaaag cccaaggcat agactcaatt   3540
gctagatgta actgccacac tggagtgtac tactgtgaat ccaggaggaa gtactacccg   3600
gtctctttta ctggccccac ctttcagtac atggaagcaa atgagtacta tccagcccga   3660
taccaatccc acatgttaat tggccatggt tttgcatctc caggggactg tggtgggatt   3720
ctcaggtgcc aacatggagt aattggaatc attacagctg gaggagaagg cctagtcgct   3780
ttctcggaca tcagagatct gtacgcatac gaggaggagg ctatggagca gggagtctcc   3840
aactatattg agtcccttgg ggctgcattt gggagtggat tcacccagca aataggaaac   3900
aaaatttcag aactcactag catggtcacc agcactataa ctgagaaact actaaagaat   3960
ctcattaaaa taatttcatc ccttgttatc atcaccagaa actatgaaga cacgaccaca   4020
gtgctggcta cccttgctct cctcggttgt gatgcgtccc catggcaatg gctaaagaag   4080
aaagcctgtg acatcttgga aatcccctac atcatgcgac agggcgatag ctggttgaag   4140
aagtttacag aggcatgcaa tgcagccaag ggattggaat gggtgtctaa taaaatatcc   4200
aaatttattg actggctcaa agagaagatc attccacagg ctagagacaa gctagagttt   4260
gttaccaaac tgaagcaact agaaatgttg gagaaccaaa ttgcaaccat tcatcaatcg   4320
tgcccaagtc aggagcatca agaaatcctg ttcaataacg tgagatggtt atccatacag   4380
tcaaagagat ttgccccgct ctatgcggtt gaggctaaga gaatacaaaa gttagagcac   4440
acgattaaca actacgtaca gttcaagagc aaacaccgta ttgaaccagt atgtttgttg   4500
gtgcacggta gcccaggcac gggcaagtca gttgccacca atttaattgc cagagcaata   4560
gcagagaagg agaacacctc cacatactca ctaccaccag atccctccca tttcgatggg   4620
```

-continued

```
tacaagcaac aaggtgtggt gatcatggat gatttgaatc agaacccaga cggagcagac   4680
atgaagctgt tttgtcagat ggtctccact gtagaattca taccaccaat ggcttcgcta   4740
gaagaaaagg gtattttgtt cacatctaat tacgttttgg cctcaaccaa ttccagtcgc   4800
atcaccccac caactgttgc gcacagcgat gccctagcca ggcgctttgc atttgacatg   4860
gacatacaaa tcatgagcga gtattctaga gatggaaaat tgaacatggc gatggcaact   4920
gaaatgtgta agaactgtca tcaaccagca aacttcaaga gatgttgccc attggtgtgt   4980
ggcaaagcca tccagctgat ggacaaatct tccagagtca gatatagtat agatcagatt   5040
actaccatga ttattaatga gaggaacaga agatcaagta tcggtaattg catggaggca   5100
cttttccaag gtcctcttca atacaaagac ctgaaaatag acattaagac cacacctcct   5160
cctgagtgca tcaatgattt gctccaagca gttgattctc aagaggtaag agactactgt   5220
gagaagaagg gttggatagt agacatcact agtcaggtgc aaaccgaaag aaacatcaat   5280
agagcaatga ctattcttca ggcggtcacc acatttgccg cagttgctgg agtggtgtat   5340
gtgatgtaca aactctttgc agggcatcaa ggagcgtata cagggcttcc caataagaga   5400
cccaatgtcc ccaccatcag gactgccaag gttcagggcc caggatttga ctacgcagtg   5460
gcaatggcca aaagaaacat tcttacggca actaccatta agggagagtt cacaatgctc   5520
ggagtgcatg ataatgtggc cattctacca acccacgcat caccgggtga aacaatagtc   5580
attgatggca aggaagtaga ggtactggat gctaaagccc tggaggacca ggccgggacc   5640
aacctagaaa tcaccattgt cactcttaag agaaatgaga agttcaggga catcagacca   5700
cacatcccca ctcaaatcac tgagacaaat gatggagttt taattgtgaa cactagtaag   5760
taccccaaca tgtatgttcc tgtcggtgct gtgactgaac aggggtatct caatctcggt   5820
ggacgccaaa ctgctcgtac tttaatgtac aactttccaa cgagagcagg tcaatgtggt   5880
ggagttatca cctgcactgg caaggtcatc gggatgcatg ttggtgggaa cggttcacat   5940
gggttcgcag cagccctgaa gcgatcctat ttcactcaga gtcaaggtga aatccagtgg   6000
atgagaccat caaaagaagt gggctacccc gttattaatg ctccatctaa aactaaactg   6060
gaacccagtg cattccatta tgtgtttgaa ggtgtcaagg aaccagctgt gctcaccaaa   6120
agtgacccca gattgaagac agattttgaa gaggctatct tttccaagta tgtgggaaat   6180
aagattactg aagtggatga gtacatgaaa gaagctgtcg atcattacgc aggccagctc   6240
atgtcactag acatcaacac agaacaaatg tgccttgagg atgcaatgta tggcactgac   6300
ggtctcgaag ctctagacct cagtaccagt gctgggtatc cctatgtggc aatggggaaa   6360
aagaaaagag acattttgaa taagcaaacc agagacacaa aggaaatgca aaggcttctg   6420
gacacctatg gtattaattt acctttagtc acctatgtga aagatgagct tagatccaag   6480
accaaagtgg aacagggcaa gtccaggcta attgaggcct caagtctcaa tgactctgtc   6540
gccatgagga tggcttttgg caacttgtac gcagcattcc acaagaaccc aggtgtagtg   6600
acaggatcgg ctgttggctg tgacccagat ttgttttgga gtaaaatacc agtcctcatg   6660
gaggaaaaac tctttgcatt tgattacacg ggttatgatg cttcactaag ccccgcctgg   6720
tttgaggctc tcaagatggt tctagagaaa attgggtttg gtgacagagt ggattacatt   6780
gattatctga atcactcgca ccatctatat aaaaataaga catattgtgt taagggcggc   6840
atgccatctg gctgctctgg cacctcaatt tttaattcaa tgattaataa tctaataatc   6900
aggactctct tactgaaaac ctacaagggc atagatttag accacctgaa gatgatagcc   6960
tatggtgatg atgtaattgc ttcctacccc catgaggttg atgctagtct cctagcccaa   7020
```

tcaggaaaag actatggact aaccatgaca ccagctgaca aatcagccac ctttgaaaca 7080
gtcacatggg agaatgtaac attcttgaaa agattcttta gagcagatga aaagtatccc 7140
tttctggtac atccagtgat gccaatgaaa gaaattcacg aatcaattag atggactaaa 7200
gatcccagaa acactcagga tcatgttcgc tcactgtgct tattggcttg gcacaatggc 7260
gaggaagagt acaataaatt tttagctaag attagaagtg tgccaatcgg aagagcatta 7320
ctgctccctg agtactccac attgtaccgc cgttggctcg actcatttta gtaaccctac 7380
ctcagtcgaa ttggattggg tcatactgtt gtaggggtaa atttttcttt aattcggag 7439

<210> SEQ ID NO 59
<211> LENGTH: 23
<212> TYPE: DNA
<213> ORGANISM: Artificial
<220> FEATURE:
<223> OTHER INFORMATION: primer

<400> SEQUENCE: 59
attggcacac tcctgatttt agc 23

<210> SEQ ID NO 60
<211> LENGTH: 22
<212> TYPE: DNA
<213> ORGANISM: Artificial
<220> FEATURE:
<223> OTHER INFORMATION: primer

<400> SEQUENCE: 60
caaaggatcc cagaaacaca ca 22

<210> SEQ ID NO 61
<211> LENGTH: 23
<212> TYPE: DNA
<213> ORGANISM: Artificial
<220> FEATURE:
<223> OTHER INFORMATION: TaqMan probe

<400> SEQUENCE: 61
ttcttcttcg ccgttgtgcc agg 23

<210> SEQ ID NO 62
<211> LENGTH: 22
<212> TYPE: DNA
<213> ORGANISM: Artificial
<220> FEATURE:
<223> OTHER INFORMATION: primer

<400> SEQUENCE: 62
ctaaagatcc cagaaacact ca 22

<210> SEQ ID NO 63
<211> LENGTH: 23
<212> TYPE: DNA
<213> ORGANISM: Artificial
<220> FEATURE:
<223> OTHER INFORMATION: primer

<400> SEQUENCE: 63
attggcacac ttctaatctt agc 23

<210> SEQ ID NO 64
<211> LENGTH: 23
<212> TYPE: DNA

<213> ORGANISM: Artificial
<220> FEATURE:
<223> OTHER INFORMATION: probe

<400> SEQUENCE: 64
ctcttcctcg ccattgtgcc aag 23

<210> SEQ ID NO 65
<211> LENGTH: 690
<212> TYPE: DNA
<213> ORGANISM: Artificial
<220> FEATURE:
<223> OTHER INFORMATION: Sabin 2 sequence with decreased number of CG dinucleotides

<400> SEQUENCE: 65
acggccgtgg agacaggggc taccaatcca ttggtgcctt cagacactgt gcaaactaga 60
catgtcatcc agagaagaac tagatcagag tccactgttg agtcattctt tgcaagaggg 120
gcttgtgtgg ctatcattga ggtggacaat gatgcaccaa caaagagagc cagcagattg 180
ttttcagttt ggaaaataac ttacaaagat actgttcaac tgagaagaaa actggaattt 240
ttcacatatt caagatttga catggagttc acttttgtgg tcacctcaaa ctacattgat 300
gcaaataatg gacatgcatt gaaccaagtt tatcagataa tgtatatacc accaggagca 360
cctatccctg gtaaatggaa tgactatact tggcagactt cctctaaccc atcagtgttt 420
tacacctatg gggcaccccc agcaagaata tcagtgccct atgtgggaat tgctaatgca 480
tattcccact tttatgatgg gtttgcaaaa gtaccactag caggtcaagc ctcaactgaa 540
ggtgattcat tgtatggtgc tgcctcactg aatgattttg gatcactggc tgttagagtg 600
gtaaatgatc acaaccccac taggctcacc tccaagatca gagtgtacat gaagccaaag 660
catgtcagag tctggtgccc aagacctcct 690

<210> SEQ ID NO 66
<211> LENGTH: 690
<212> TYPE: DNA
<213> ORGANISM: Artificial
<220> FEATURE:
<223> OTHER INFORMATION: Sabin 2 sequence with reduced number of CG and TA dinucleotides

<400> SEQUENCE: 66
acggccgtgg agacaggggc aaccaatcca ttggtgcctt cagacactgt gcaaacaaga 60
catgtcatcc agagaagaac aagatcagag tccactgttg agtcattctt tgcaagaggg 120
gcttgtgtgg caatcattga ggtggacaat gatgcaccaa caaagagagc cagcagattg 180
ttttcagttt ggaaaatcac ttacaaagac actgttcaac tgagaagaaa actggaattt 240
ttcacatatt caagatttga catggagttc acttttgtgg tcacctcaaa ctacattgat 300
gcaaacaatg gacatgcatt gaaccaagtt tatcagatca tgtacattcc accaggagca 360
ccaatccctg gaaaatggaa tgactacact tggcagactt cctcaaaccc atcagtgttt 420
tacacctatg gggcaccccc agcaagaatt tcagtgccct atgtgggaat tgcaaatgca 480
tattcccact tttatgatgg gtttgcaaaa gtgccactgg caggtcaagc ctcaactgaa 540
ggtgattcat tgtatggtgc tgcctcactg aatgattttg gatcactggc tgtgagagtg 600
gtgaatgatc acaaccccac aaggctcacc tccaagatca gagtgtacat gaagccaaag 660
catgtcagag tctggtgccc aagacctcct 690

<210> SEQ ID NO 67
<211> LENGTH: 690
<212> TYPE: DNA
<213> ORGANISM: Artificial
<220> FEATURE:
<223> OTHER INFORMATION: Sabin 2 sequence with increased CG dinucleotide content

<400> SEQUENCE: 67

```
acggccgtcg agacgggcgc gacgaatccg ctcgtgccgt cggacaccgt gcaaacgcgc     60

cacgtcatcc agcgacgaac gcgatcggag tcgacggtcg agtcgttctt cgcgcgcggc    120

gcgtgcgtcg cgatcatcga ggtcgacaac gacgcgccga cgaagcgcgc gtcgcgattg    180

ttttcggttt ggaaaataac gtacaaagat acggttcaac tgcgacgcaa actcgaattt    240

ttcacgtatt cgcgattcga catggagttc acgttcgtcg tcacgtcgaa ctacatcgac    300

gcgaataacg gacacgcgtt gaaccaagtt tatcagataa tgtatatacc gcccggcgcg    360

ccgatcccgg gtaaatggaa cgactatacg tggcagacgt cgtcgaaccc gtcggtgttt    420

tacacgtacg gcgcgccgcc ggcgcgaata tcggtgccgt acgtcggaat cgcgaacgcg    480

tattcgcact tttacgacgg gttcgcgaaa gtaccgctcg cgggtcaagc gtcgacggaa    540

ggcgattcgt tgtacggcgc ggcgtcgctg aacgatttcg gatcgctcgc ggttcgcgtc    600

gtaaacgatc acaacccgac gcggctcacg tcgaagatcc gcgtgtacat gaagccgaag    660

cacgtccgcg tctggtgccc gcgaccgcct                                     690
```

<210> SEQ ID NO 68
<211> LENGTH: 690
<212> TYPE: DNA
<213> ORGANISM: Artificial
<220> FEATURE:
<223> OTHER INFORMATION: Sabin 2 sequence with increased numbers of CG and TA dinucleotides

<400> SEQUENCE: 68

```
acggccgtcg agacgggcgc gacgaatccg ctcgtaccgt cggataccgt acaaacgcgc     60

cacgtaatac agcgacgtac gcgtagcgag tcgacggtcg agtcgttctt cgcgcgcggc    120

gcgtgcgtcg cgattatcga ggtcgataac gacgcgccga cgaagcgcgc gtcgcgatta    180

ttttcggtat ggaaaataac gtataaagat acggtacaac tacgacgtaa actcgaattt    240

tttacgtatt cgcgattcga tatggagttt acgttcgtcg ttacgtcgaa ctatatcgac    300

gcgaataacg gacacgcgtt aaaccaagta tatcagataa tgtatatacc gcccggcgcg    360

ccgatcccgg gtaaatggaa cgactatacg tggcagacgt cgtcgaaccc gtcggtattt    420

tatacgtacg gcgcgccgcc ggcgcgtata tcggtaccgt acgtcggtat cgcgaacgcg    480

tattcgcact tttacgacgg gttcgcgaaa gtaccgctcg cgggtcaagc gtcgacggaa    540

ggcgattcgt tatacggcgc ggcgtcgctt aacgatttcg gatcgctcgc ggtacgcgtc    600

gtaaacgatc ataacccgac gcggcttacg tcgaagatac gcgtatatat gaagccgaag    660

cacgtacgcg tatggtgccc gcgaccgcct                                     690
```

<210> SEQ ID NO 69
<211> LENGTH: 690
<212> TYPE: DNA
<213> ORGANISM: Artificial
<220> FEATURE:
<223> OTHER INFORMATION: exemplary deoptimized Sabin 2 sequence

<400> SEQUENCE: 69
acggccgtcg agacgggtgc gacgaatccg cttgtcccgt cggacacggt ccaaacgcgg 60
catgtcatac agcggcggac gcggtcggag tcgacggtcg agtcgttctt tgcgcggggt 120
gcgtgcgtcg cgataataga ggtggacaat gatgcgccga cgaaacgggc gtcgcggctt 180
ttttcggtct ggaaaataac gtacaaagat acggtccaac ttcggcggaa acttgaattt 240
ttcacgtatt cgcggtttga catggagttc acgtttgtcg tcacgtcgaa ctacatagat 300
gcgaataacg gtcatgcgct gaaccaagtc tatcagataa tgtatatacc gccgggtgcg 360
ccgataccgg gtaaatggaa tgactatacg tggcagacgt cgtcgaaccc gtcggtcttt 420
tacacgtatg gtgcgccgcc ggcgcggatc tcggtcccgt acgtcggtat cgcgaatgcg 480
tattcgcatt tttatgatgg ttttgcgaaa gtcccgcttg cgggtcaagc gtcgacggaa 540
ggtgattcgc tttacggtgc ggcgtcgctt aatgattttg gttcgcttgc ggtccgggtc 600
gtcaatgatc ataacccgac gcggcttacg tcgaaaatac gggtctacat gaagccgaaa 660
catgtccggg tctggtgccc gcggcctcct 690

<210> SEQ ID NO 70
<211> LENGTH: 690
<212> TYPE: DNA
<213> ORGANISM: Artificial
<220> FEATURE:
<223> OTHER INFORMATION: Sabin 2 sequence that include MEF1 codons

<400> SEQUENCE: 70
acggccgtag agacaggggc caccaaccca ttggtgcctt cagacacggt acaaactcgt 60
cacgtcatcc aaagacggac gcggtcggag tctacggttg agtctttctt cgcaagagga 120
gcttgtgtgg ccattattga agtggataat gatgctccaa caaagcgtgc cagtagatta 180
ttttcagtct ggaagataac ttacaaagac accgttcagt taagacgtaa gttggagttc 240
tttacatatt caaggtttga catggagttc acctttgtgg ttacatccaa ttatattgat 300
gcaaacaatg ggcacgcact aaatcaagtt taccagataa tgtacatacc acctggggca 360
ccgatccctg gcaagtggaa tgattacaca tggcaaacgt catctaaccc atcagtgttt 420
tacacttacg gggcacctcc agctagaata tcagtgccct acgtgggcat tgccaatgca 480
tattctcatt tttacgatgg gtttgccaaa gtaccactag caggccaagc ctcaacagag 540
ggtgactcgc tgtatggagc ggcttcattg aatgacttcg gatcactggc tgttcgagtg 600
gtgaatgacc acaaccctac gcggctcact tcaaaaatca gagtgtacat gaaaccaaag 660
cacgtcagag tgtggtgtcc gcgacccccct 690

<210> SEQ ID NO 71
<211> LENGTH: 15225
<212> TYPE: DNA
<213> ORGANISM: respiratory syncytial virus

<400> SEQUENCE: 71
acgcgaaaaa atgcgtacta caaacttgca cattcggaaa aaatggggca aataagaatt 60
tgataagtgc tatttaagtc taacctttc aatcagaaat ggggtgcaat tcactgagca 120
tgataaaggt tagattacaa aatttatttg acaatgacga agtagcattg ttaaaaataa 180
catgttatac tgacaaatta attcttctga ccaatgcatt agccaaagca gcaatacata 240
caattaaatt aaacggtata gtttttatac atgttataac aagcagtgaa gtgtgccctg 300
ataacaacat tgtagtaaaa tctaacttta caacaatgcc aatattacaa aacggaggat 360
acatatggga attgattgag ttgacacact gctctcaatt aaacggtcta atggatgata 420

```
attgtgaaat caaattttct aaaagactaa gtgactcagt aatgactaat tatatgaatc    480
aaatatctga tttacttggg cttgatctca attcatgaat tatgtttagt ctaactcaat    540
agacatgtgt ttattaccat tttagttaat ataaaaactc atcaaaggga aatggggcaa    600
ataaactcac ctaatcaatc aaactatgag cactacaaat gacaacacta ctatgcaaag    660
attaatgatc acggacatga gacccctgtc gatggattca ataataacat ctctcaccaa    720
agaaatcatc acacacaaat tcatatactt gataaacaat gaatgtattg taagaaaact    780
tgatgaaaga caagctacat ttacattctt agtcaattat gagatgaagc tactgcacaa    840
agtagggagt accaaataca agaaatacac tgaatataat acaaaatatg gcactttccc    900
catgcctata tttatcaatc atggcgggtt tctagaatgt attggcatta agcctacaaa    960
acacactcct ataatataca aatatgacct caacccgtaa attccaacaa aaaaaaccaa   1020
cccaaccaaa ccaagctatt cctcaaacaa caatgctcaa tagttaagaa ggagctaatc   1080
cgttttagta attaaaaata aaagtaaagc caataacata aattggggca aatacaaaga   1140
tggctcttag caaagtcaag ttaaatgata cattaaataa ggatcagctg ctgtcatcca   1200
gcaaatacac tattcaacgt agtacaggag ataatattga cactcccaat tatgatgtgc   1260
aaaaacacct aaacaaacta tgtggtatgc tattaatcac tgaagatgca aatcataaat   1320
tcacaggatt aataggtatg ttatatgcta tgtccaggtt aggaagggaa gacactataa   1380
agatacttaa agatgctgga tatcatgtta aagctaatgg agtagatata acaacatatc   1440
gtcaagatat aaatggaaag gaaatgaaat tcgaagtatt aacattatca agcttgacat   1500
cagaaataca agtcaatatt gagatagaat ctagaaaatc ctacaaaaaa atgctaaaag   1560
agatgggaga agtggctcca gaatataggc atgattctcc agactgtggg atgataatac   1620
tgtgtatagc agcacttgta ataaccaaat tagcagcagg agacagatca ggtcttacag   1680
cagtaattag gagggcaaac aatgtcttaa aaaatgaaat aaaacgctac aagggtctca   1740
taccaaagga tatagctaac agtttttatg aagtgtttga aaaacaccct catcttatag   1800
atgtttttgt gcactttggc attgcacaat catcaacaag agggggtagt agagttgaag   1860
gaatctttgc aggattgttt atgaatgcct atggttcagg gcaagtaatg ctaagatggg   1920
gagttttagc caaatctgta aaaaatatca tgctaggtca tgctagtgtc caggcagaaa   1980
tggagcaagt tgtggaagtc tatgagtatg cacagaagtt gggaggagaa gctggattct   2040
accatatatt gaacaatcca aaagcatcat tgctgtcatt aactcaattt cctaacttct   2100
caagtgtggt cctaggcaat gcagcaggtc taggcataat gggagagtat agaggtacgc   2160
caagaaacca ggatctttat gatgcagcca aagcatatgc agagcaactc aaagaaaatg   2220
gagtaataaa ctacagtgta ttagacttaa cagcagaaga attggaagcc ataaagaatc   2280
aactcaaccc taaagaagat gatgtagagc tttaagttaa caaaaaatac ggggcaaata   2340
agtcaacatg gagaagtttg cacctgaatt tcatggagaa gatgcaaata acaaagctac   2400
caaattccta gaatcaataa agggcaagtt cgcatcatcc aaagatccta agaagaaaga   2460
tagcataata tctgttaact caatagatat agaagtaacc aaagagagcc cgataacatc   2520
tggcaccaac atcatcaatc caacaagtga agccgacagt accccagaaa ccaaagccaa   2580
ctacccaaga aaacccctag taagcttcaa agaagatctc accccaagtg acaacccttt   2640
ttctaagttg tacaaagaaa caatagaaac atttgataac aatgaagaag aatctagcta   2700
ctcatatgaa gagataaatg atcaaacaaa tgacaacatt acagcaagac tagatagaat   2760
```

```
tgatgaaaaa ttaagtgaaa tattaggaat gctccataca ttagtagttg caagtgcagg   2820
acccacttca gctcgcgatg gaataagaga tgctatggtt ggtctgagag aagaaatgat   2880
agaaaaaata agagcggaag cattaatgac caatgatagg ttagaggcta tggcaagact   2940
taggaatgag gaaagcgaaa aaatggcaaa agacacctca gatgaagtgc ctcttaatcc   3000
aacttccaaa aaattgagtg acttgttgga agacaacgat agtgacaatg atctgtcact   3060
tgatgatttt tgatcagtga tcaactcact cagcaatcaa caacatcaat aaaacagaca   3120
tcaatccatt gaatcaactg ccagaccgaa caaacaaatg tccgtcagcg gaaccaccaa   3180
ccaatcaatc aaccaactga tccatcagca acctgacgaa attaacaata tagtaacaaa   3240
aaaagaacaa gatggggcaa atatggaaac atacgtgaac aagcttcacg aaggctccac   3300
atacacagca gctgttcagt acaatgttct agaaaaagat gatgatcctg catcactaac   3360
aatatgggtg cctatgttcc agtcatctgt accagcagac ttgctcataa aagaacttgc   3420
aagcatcaac atactagtga agcagatctc tacgcccaaa ggaccttcac tacgagtcac   3480
gattaactca agaagtgctg tgctggctca aatgcctagt aatttcatca taagcgcaaa   3540
tgtatcatta gatgaaagaa gcaaattagc atatgatgta actacacctt gtgaaatcaa   3600
agcatgcagt ctaacatgct taaaagtgaa aagtatgtta actacagtca aagatcttac   3660
catgaagaca ttcaacccca ctcatgagat cattgctcta tgtgaatttg aaaatattat   3720
gacatcaaaa agagtaataa taccaaccta tctaagacca attagtgtca aaaacaagga   3780
tctgaactca ctagaaaaca tagcaaccac cgaattcaaa aatgctatca ccaatgcgaa   3840
aattattccc tatgctggat tagtattagt tatcacagtt actgacaata aaggagcatt   3900
caaatatatc aagccacaga gtcaatttat agtagatctt ggtgcctacc tagaaaaaga   3960
gagcatatat tatgtgacta ctaattggaa gcatacagct acacgttttt caatcaaacc   4020
actagaggat taaatttaat tatcaacact gaatgacagg tccacatata tcctcaaact   4080
acacactata tccaaacatc atgaacatct acactacaca cttcatcaca caaaccaatc   4140
ccactcaaaa tccaaaatca ctaccagcca ctatctgcta gacctagagt gcgaataggt   4200
aaataaaacc aaaatatggg gtaaatagac attagttaga gttcaatcaa tctcaacaac   4260
catttatacc gccaattcaa tacatatact ataaatctta aaatgggaaa tacatccatc   4320
acaatagaat tcacaagcaa attttggccc tattttacac taatacatat gatcttaact   4380
ctaatctctt tactaattat aatcactatt atgattgcaa tactaaataa gctaagtgaa   4440
cataaaacat tctgtaacaa tactcttgaa ctaggacaga tgcatcaaat caacacatag   4500
tgctctacca tcatgctgtg tcaaattata atcctgtata tataaacaaa caaatccaat   4560
cttctcacag agtcatggtg tcgcaaaacc acgccaacta tcatggtagc atagagtagt   4620
tatttaaaaa ttaacataat gatgaattat tagtatggga tcaaaaacaa cattggggca   4680
aatgcaacca tgtccaaaca caagaatcaa cgcactgcca ggactctaga aaagacctgg   4740
gatactctca atcatctaat tgtaatatcc tcttgtttat acagattaaa tttaaaatct   4800
atagcacaaa tagcactatc agttctggca atgataatct caacctctct cataattgca   4860
gccataatat tcatcatctc tgccaatcac aaagttacac taacaacggt cacagttcaa   4920
acaataaaaa accacactga aaaaaacatc accacctacc ttactcaagt cccaccagaa   4980
agggttagct catccaaaca acctacaacc acatcaccaa tccacacaaa ttcagccaca   5040
acatcaccca acacaaagtc agaaacacac cacacaacag cacaaaccaa aggcagaacc   5100
accacctcaa cacagaccaa caagccgagc acaaaaccac gcctaaaaaa tccaccaaaa   5160
```

```
aaaccaaaag atgattacca ttttgaagtg ttcaacttcg ttccctgtag tatatgtggc   5220
aacaatcaac tttgcaaatc catctgtaaa acaataccaa gcaacaaacc aaagaagaaa   5280
ccaaccatca aacccacaaa caaaccaacc accaaaacca caaacaaaag agacccaaaa   5340
acaccagcca aaacgacgaa aaaagaaact accaccaacc caacaaaaaa accaaccctc   5400
acgaccacag aaagagacac cagcacctca caatccactg tgctcgacac aaccacatta   5460
gaacacacaa tccaacagca atccctccac tcaaccaccc ccgaaaacac acccaactcc   5520
acacaaacac ccacagcatc cgagccctct acatcaaatt ccacccaaaa tacccaatca   5580
catgcttagt tattcaaaaa ctacatctta gcagaaaacc gtgacctatc aagcaagaac   5640
gaaattaaac ctggggcaaa taaccatgga gctgctgatc cacaggttaa gtgcaatctt   5700
cctaactctt gctattaatg cattgtacct cacctcaagt cagaacataa ctgaggagtt   5760
ttaccaatcg acatgtagtg cagttagcag aggttatttt agtgctttaa gaacaggttg   5820
gtataccagt gtcataacaa tagaattaag taatataaaa gaaaccaaat gcaatggaac   5880
tgacactaaa gtaaaactta taaaacaaga attagataag tataagaatg cagtgacaga   5940
attacagcta cttatgcaaa acacaccagc tgccaacaac cgggccagaa gagaagcacc   6000
acagtatatg aactatacaa tcaataccac taaaaaccta aatgtatcaa taagcaagaa   6060
gaggaaacga agatttctgg gcttcttgtt aggtgtagga tctgcaatag caagtggtat   6120
agctgtatcc aaagttctac accttgaagg agaagtgaac aagatcaaaa atgctttgtt   6180
atctacaaac aaagctgtag tcagtctatc aaatggggtc agtgttttaa ccagcaaagt   6240
gttagatctc aagaattaca taaataacca attattaccc atagtaaatc aacagagctg   6300
tcgcatctcc aacattgaaa cagttataga attccagcag aagaacagca gattgttgga   6360
aatcaacaga gaattcagtg tcaatgcagg tgtaacaaca cctttaagca cttacatgtt   6420
aacaaacagt gagttactat cattgatcaa tgatatgcct ataacaaatg atcagaaaaa   6480
attaatgtca agcaatgttc agatagtaag gcaacaaagt tattctatca tgtctataat   6540
aaaggaagaa gtccttgcat atgttgtaca gctacctatc tatggtgtaa tagatacacc   6600
ttgctggaaa ttacacacat cacctctatg caccaccaac atcaaagaag gatcaaatat   6660
ttgtttaaca aggactgata gaggatggta ttgtgataat gcaggatcag tatccttctt   6720
tccacaggct gacacttgta aagtacagtc caatcgagta ttttgtgaca ctatgaacag   6780
tttgacatta ccaagtgaag tcagcctttg taacactgac atattcaatt ccaagtatga   6840
ctgcaaaatt atgacatcaa aaacagacat aagcagctca gtaattactt ctcttggagc   6900
tatagtgtca tgctatggta aaactaaatg cactgcatcc aacaaaaatc gtgggattat   6960
aaagacattt tctaatggtt gtgactatgt gtcaaacaaa ggagtagata ctgtgtcagt   7020
gggcaacact ttatactatg taaacaagct ggaaggcaag aacctttatg taaaagggga   7080
acctataata aattactatg accctctagt gtttccttct gatgagtttg atgcatcaat   7140
atctcaagtc aatgaaaaaa tcaatcaaag tttagctttt attcgtagat ctgatgaatt   7200
actacataat gtaaatactg gcaaatctac tacaaatatt atgataacta caattattat   7260
agtaatcatt gtagtattgt tatcattaat agctattggt ttgctgttgt attgcaaagc   7320
caaaaacaca ccagttacac taagcaaaga ccaactaagt ggaatcaata atattgcatt   7380
cagcaaatag acaaaaaacc acctgatcat gtttcaacaa cagtctgctg atcaccaatc   7440
ccaaatcaac ccataacaaa cacttcaaca tcacagtaca ggctgaatca tttcttcaca   7500
```

-continued

```
tcatgctacc cacacaacta agctagatcc ttaactcata gttacataaa aacctcaagt   7560
atcacaatca aacactaaat caacacatca ttcacaaaat taacagctgg ggcaaatatg   7620
tcgcgaagaa atccttgtaa atttgagatt agaggtcatt gcttgaatgg tagaagatgt   7680
cactacagtc ataattactt tgaatggcct cctcatgcct tactagtgag gcaaaacttc   7740
atgttaaaca agatactcaa gtcaatggac aaaagcatag acactttgtc tgaaataagt   7800
ggagctgctg aactggacag aacagaagaa tatgctcttg gtatagttgg agtgctagag   7860
agttacatag gatctataaa caacataaca aaacaatcag catgtgttgc tatgagtaaa   7920
cttcttattg agatcaatag tgatgacatt aaaaagctga gagataatga agaacccaat   7980
tcacctaaga taagagtgta caatactgtt atatcataca ttgagagcaa tagaaaaaac   8040
aacaagcaaa caatccatct gctcaaaaga ctaccagcag acgtgctgaa gaagacaata   8100
aaaaacacat tagatatcca caaaagcata atcataagca acccaaaaga gtcaaccgtg   8160
aatgatcaaa atgaccaaac caaaaataat gatattaccg gataaatatc cttgtagtat   8220
atcatccata ttgatttcaa gtgaaagcat gattgctaca ttcaatcata aaaacatatt   8280
acaatttaac cataaccatt tggataacca ccagcgttta ttaaataata tatttgatga   8340
aattcattgg acacctaaaa acttattaga tgccactcaa caatttctcc aacatcttaa   8400
catccctgaa gatatatata caatatatat attagtgtca taatgcttgg ccataacgat   8460
tctatatcat ccaaccataa aactatctta ataaggttat gggacaaaat ggatcccatt   8520
attaatggaa actctgctaa tgtgtatcta actgatagtt atttaaaagg tgttatctct   8580
ttttcagaat gtaatgcttt agggagttac ctttttaacg gcccttatct caaaaatgat   8640
tacaccaact taattagtag acaaagtcca ctactagagc atatgaatct taaaaaacta   8700
actataacac agtcattaat atctagatat cataaaggtg aactgaaatt agaagaacca   8760
acttatttcc agtcattact tatgacatat aaaagcatgt cctcgtctga acaaattgct   8820
acaactaact tacttaaaaa aataatacga agagctatag aaataagtga tgtaaaggtg   8880
tacgccatct tgaataaact aggactaaag gaaaaggaca gagttaagcc caacaataat   8940
tcaggtgatg aaaactcagt acttacaact ataattaaag atgatatact ttcggctgtg   9000
gaaagcaatc aatcatatac aaattcagac aaaaatcact cagtaaatca aaatatcact   9060
atcaaaacaa cactcttgaa aaaattgatg tgttcaatgc aacatcctcc atcatggtta   9120
atacactggt tcaatttata tacaaaatta aataacatat taacacaata tcgatcaaat   9180
gaggtaaaaa gtcatgggtt tatattaata gataatcaaa ctttaagtgg ttttcagttt   9240
attttaaatc aatatggttg tatcgtttat cataaaggac tcaaaaaaat cacaactact   9300
acttacaatc aatttttaac atggaaagac atcagcctta gcagattaaa tgtttgctta   9360
attacttgga taagtaattg tttgaataca ttaaataaaa gcttagggct gagatgtgga   9420
ttcaataatg ttgtgttatc acaattattt ctttatggag attgtatact gaaattattt   9480
cataatgaag gcttctacat aataaaagaa gtagagggat ttattatgtc tttaattcta   9540
aacataacag aagaagatca atttaggaaa cgattttata atagcatgct aaataacatc   9600
acagatgcag ctattaaggc tcaaaagaac ctactatcaa gggtatgtca cactttatta   9660
gacaagacag tgtctgataa tatcataaat ggtaaatgga taatcctatt aagtaaattt   9720
cttaaattga ttaagcttgc aggtgataat aatctcaata atttgagtga gctatatttt   9780
ctcttcagaa tctttggaca tccaatggtt gatgaaagac aagcaatgga tgctgtaaga   9840
attaactgta atgaaactaa gttctactta ttaagtagtc taagtacgtt aagaggtgct   9900
```

ttcatttata gaatcataaa agggtttgta aatacctaca acagatggcc cactttaagg 9960
aatgctattg tcctacctct aagatggtta aactattata aacttaatac ttatccatct 10020
ctacttgaaa tcacagaaaa tgatttgatt attttatcag gattgcggtt ctatcgtgaa 10080
tttcatctgc ctaaaaaagt ggatcttgaa atgataataa atgacaaagc catttcacct 10140
ccaaaagatc taatatggac tagttttcct agaaattaca tgccatcaca tatacaaaat 10200
tatatagaac atgaaaagtt gaagttctct gaaagcgaca gatcaagaag agtactagag 10260
tattacttga gagataataa attcaatgaa tgcgatctat acaattgtgt agtcaatcaa 10320
agctatctca acaactctaa tcacgtggta tcactaactg gtaaagaaag agagctcagt 10380
gtaggtagaa tgtttgctat gcaaccaggt atgtttaggc aaatccaaat cttagcagag 10440
aaaatgatag ccgaaaatat tttacaattc ttccctgaga gtttgacaag atatggtgat 10500
ctagagcttc aaaagatatt agaattaaaa gcaggaataa gcaacaagtc aaatcgttat 10560
aatgataact acaacaatta tatcagtaaa tgttctatca ttacagatct tagcaaattc 10620
aatcaagcat ttagatatga aacatcatgt atctgcagtg atgtattaga tgaactgcat 10680
ggagtacaat ctctgttctc ttggttgcat ttaacaatac ctcttgtcac aataatatgt 10740
acatatagac atgcacctcc tttcataaag gatcatgttg ttaatcttaa tgaagttgat 10800
gaacaaagtg gattatacag atatcatatg ggtggtattg agggctggtg tcaaaaactg 10860
tggaccattg aagctatatc attattagat ctaatatctc tcaaagggaa attctctatc 10920
acagctctga taaatggtga taatcagtca attgatataa gtaaaccagt tagacttata 10980
gagggtcaga cccatgctca agcagattat ttgttagcat taaatagcct taaattgcta 11040
tataaagagt atgcaggtat aggccataag cttaagggaa cagagaccta tatatcccga 11100
gatatgcagt tcatgagcaa aacaatccag cacaatggag tgtactatcc agccagtatc 11160
aaaaaagtcc tgagagtagg tccatggata aatacaatac ttgatgattt taaagttagt 11220
ttagaatcta taggtagctt aacacaggag ttagaataca gaggggaaag cttattatgc 11280
agtttaatat ttaggaacat ttggttatac aatcaaattg ctttgcaact ccgaaatcat 11340
gcattatgta acaataagct atatttagat atattgaaag tattaaaaca cttaaaaact 11400
ttttttaatc ttgatagtat cgatatggcg ttatcattgt atatgaattt gcctatgctg 11460
tttggtggtg gtgatcctaa tttgttatat cgaagctttt ataggagaac tccagacttc 11520
cttacagaag ctatagtaca ttcagtgttt gtgttgagct attatactgg tcacgattta 11580
caagataagc tccaggatct tccagatgat agactgaaca aattcttgac atgtgtcatc 11640
acattcgata aaaatcccaa tgccgagttt gtaacattga tgagggatcc acaggcgtta 11700
gggtctgaaa ggcaagctaa aattactagt gagattaata gattagcagt aacagaagtc 11760
ttaagtatag ctccaaacaa aatattttct aaaagtgcac aacattatac taccactgag 11820
attgatctaa atgacattat gcaaaatata gaaccaactt accctcatgg attaagagtt 11880
gtttatgaaa gtctaccttt ttataaagca gaaaaaatag ttaatcttat atcaggaaca 11940
aaatccataa ctaatatact tgaaaaaaca tcagcaatag atacaactga tattaatagg 12000
gctactgata tgatgaggaa aaatataact ttacttataa ggatacttcc actagattgt 12060
aacaaagaca aaagagagtt attaagttta gaaaatctta gtataactga attaagcaag 12120
tatgtaagag aaagatcttg gtcattatcc aatatagtag gagtaacatc gccaagtatt 12180
atgttcacaa tggacattaa atatacaact agcactatag ccagtggtat aattatagaa 12240
aaatataatg ttaatagttt aactcgtggt gaaagaggac ctactaagcc atgggtaggt 12300
tcatctacgc aggagaaaaa aacaatgcca gtgtacaata gacaagtttt aaccaaaaag 12360
caaagagacc aaatagattt attagcaaaa ttagactggg tatatgcatc catagacaac 12420
aaagatgaat tcatggaaga actgagtact ggaacacttg gactgtcata tgaaaaagcc 12480
aaaaagttgt ttccacaata tctaagtgtc aattatttac accgtttaac agtcagtagt 12540
agaccatgtg aattccctgc atcaatacca gcttatagaa caacaaatta tcatttcgat 12600
actagtccta tcaatcatgt attaacagaa aagtatggag atgaagatat cgacattgtg 12660
tttcaaaatt gcataagttt tggtcttagc ctgatgtcgg ttgtggaaca attcacaaac 12720
atatgtccta atagaattat tctcataccg aagctgaatg agatacattt gatgaaacct 12780
cctatattta caggagatgt tgatatcatc aagttgaagc aagtgataca aaaacagcat 12840
atgttcctac cagataaaat aagtttaacc caatatgtag aattattcct aagtaacaaa 12900
gcacttaaat ctggatctaa catcaattct aatttaatat tagtacataa aatgtctgat 12960
tattttcata atgcttatat tttaagtact aatttagctg gacattggat tctaattatt 13020
caacttatga aagattcaaa aggtattttt gaaaaagatt ggggagaggg gtacataact 13080
gatcatatgt tcattaattt gaatgttttc tttaatgctt ataagactta tttgctatgt 13140
tttcataaag gttatggtaa agcaaaatta gaatgtgata tgaacacttc agatcttctt 13200
tgtgttttgg agttaataga cagtagctac tggaaatcta tgtctaaagt tttcctagaa 13260
caaaaagtca taaaatacat agtcaatcaa gacacaagtt tgcatagaat aaaaggctgt 13320
cacagtttta agttgtggtt tttaaaacgc cttaataatg ctaaatttac cgtatgccct 13380
tgggttgtta acatagatta tcacccaaca catatgaaag ctatattatc ttacatagat 13440
ttagttagaa tggggttaat aaatgtagat aaattaacca ttaaaaataa aaacaaattc 13500
aatgatgaat tttacacatc aaatctcttt tacattagtt ataacttttc agacaacact 13560
catttgctaa caaaacaaat aagaattgct aattcagaat tagaagataa ttataacaaa 13620
ctatatcacc caaccccaga aactttagaa aatatatcat taattcctgt taaaagtaat 13680
aatagtaaca aacctaaatt ttgtataagt ggaaataccg aatctataat gatgtcaaca 13740
ttctctaata aaatgcatat taaatcttcc actgttacca caagattcaa ttatagcaaa 13800
caagacttgt acaatttatt tccaaatgtt gtgatagaca ggattataga tcattcaggt 13860
aatacagcaa aatctaacca actttacatc accacttcac atcagacatc tttagtaagg 13920
aatagtgcat cactttattg catgcttcct tggcatcatg tcaatagatt taactttgta 13980
tttagttcca caggatgcaa gatcagtata gagtatattt taaaagatct taagattaag 14040
gaccccagtt gtatagcatt cataggtgaa ggagctggta acttattatt acgtacggta 14100
gtagaacttc atccagacat aagatacatt tacagaagtt taaaagattg caatgatcat 14160
agtttaccta ttgaatttct aagattatac aacgggcata taaacataga ttatggtgag 14220
aatttaacca ttcctgctac agatgcaact aataacattc attggtctta tttacatata 14280
aaatttgcag aacctattag catctttgtc tgcgatgctg aattacctgt tacagccaat 14340
tggagtaaaa ttataattga atggagtaag catgtaagaa agtgcaagta ctgttcttct 14400
gtaaatagat gcattttaat cgcaaaatat catgctcaag atgatattga tttcaaatta 14460
gataacatta ctatattaaa aacttacgtg tgcctaggta gcaagttaaa aggatctgaa 14520
gtttacttag tccttacaat aggccctgca aatatacttc ctgtttttga tgttgtgcaa 14580
aatgctaaat tgattttttc aagaactaaa aatttcatta tgcctaaaaa aactgacaag 14640
gaatctatcg atgcaaatat taaaagctta atacctttcc tttgttaccc tataacaaaa 14700
aaaggaatta agacttcatt gtcaaaattg aagagtgtag ttaatgggga tatattatca 14760
tattctatag ctggacgtaa tgaagtattc agcaacaagc ttataaacca caagcatatg 14820
aatatcctaa aatggctaga tcatgtttta aattttagat cagctgaact taattacaat 14880
catttataca tgatagagtc cacatatcct tacttaagtg aattgttaaa tagtttaaca 14940
accaatgagc tcaagaaact gattaaaata acaggtagtg tactatacaa ccttcccaac 15000
gaacagtaac ttaaaatatc attaacaagt ttggtcaaat ttagatgcta acacatcatt 15060
atattatagt tattaaaaaa tatgcaaact tttcaataat ttagcttact gattccaaaa 15120
ttatcatttt atttttaagg ggttgaataa aagtctaaaa ctaacaatga tacatgtgca 15180
tttacaacac aacgagacat tagtttttga cacttttttt ctcgt 15225

<210> SEQ ID NO 72
<211> LENGTH: 15222
<212> TYPE: DNA
<213> ORGANISM: respiratory syncytial virus

<400> SEQUENCE: 72
acgcgaaaaa atgcgtacaa caaacttgca taaaccaaaa aaatggggca aataagaatt 60
tgataagtac cacttaaatt taactccctt ggttagagat gggcagcaat tcattgagta 120
tgataaaagt tagattacaa aatttgtttg acaatgatga agtagcattg ttaaaaataa 180
catgctatac tgataaatta atacatttaa ctaatgcttt ggctaaggca gtgatacata 240
caatcaaatt gaatggcatt gtgtttgtgc atgttattac aagtagtgat atttgcccta 300
ataataatat tgtagtaaaa tccaatttca caacaatgcc agtactacaa aatggaggtt 360
atatatggga aatgatggaa ttaacacatt gctctcaacc taatggtcta ctagatgaca 420
attgtgaaat taaattctcc aaaaaactaa gtgattcaac aatgaccaat tatatgaatc 480
aattatctga attacttgga tttgatctta atccataaat tataattaat atcaactagc 540
aaatcaatgt cactaacacc attagttaat ataaaactta acagaagaca aaaatggggc 600
aaataaatca attcagccaa cccaaccatg gacacaaccc acaatgataa tacaccacaa 660
agactgatga tcacagacat gagaccgttg tcacttgaga ccataataac atcactaacc 720
agagacatca taacacacaa atttatatac ttgataaatc atgaatgcat agtgagaaaa 780
cttgatgaaa gacaggccac atttacattc ctggtcaact atgaaatgaa actattacac 840
aaagtaggaa gcactaaata taaaaaatat actgaataca acacaaaata tggcactttc 900
cctatgccaa tattcatcaa tcatgatggg ttcttagaat gcattggcat taagcctaca 960
aagcatactc ccataatata caagtatgat ctcaatccat aaatttcaac acaatattca 1020
cacaatctaa aacaacaact ctatgcataa ctatactcca tagtccagat ggagcctgaa 1080
aattatagta atttaaaatt aaggagagat ataagataga agatggggca aatacaaaga 1140
tggctcttag caaagtcaag ttgaatgata cactcaacaa agatcaactt ctgtcatcca 1200
gcaaatacac catccaacgg agcacaggag atagtattga tactcctaat tatgatgtgc 1260
agaaacacat caataagtta tgtggcatgt tattaatcac agaagatgct aatcataaat 1320
tcactgggtt aataggtatg ttatatgcga tgtctaggtt aggaagagaa gacaccataa 1380
aaatactcag agatgcggga tatcatgtaa aagcaaatgg agtagatgta acaacacatc 1440
gtcaagacat taatggaaaa gaaatgaaat ttgaagtgtt aacattggca agcttaacaa 1500

-continued

```
ctgaaattca aatcaacatt gagatagaat ctagaaaatc ctacaaaaaa atgctaaaag   1560

aaatgggaga ggtagctcca gaatacaggc atgactctcc tgattgtggg atgataatat   1620

tatgtatagc agcattagta ataactaaat tagcagcagg ggacagatct ggtcttacag   1680

ccgtgattag gagagctaat aatgtcctaa aaaatgaaat gaaacgttac aaaggcttac   1740

tacccaagga catagccaac agcttctatg aagtgtttga aaaacatccc cactttatag   1800

atgtttttgt tcattttggt atagcacaat cttctaccag aggtggcagt agagttgaag   1860

ggatttttgc aggattgttt atgaatgcct atggtgcagg gcaagtgatg ttacggtggg   1920

gagtcttagc aaaatcaatt aaaaatatta tgttaggaca tgctagtgtg caagcagaaa   1980

tggaacaagt tgttgaggtt tatgaatatg cccaaaaatt gggtggtgaa gcaggattct   2040

accatatatt gaacaaccca aaagcatcat tattatcttt gactcaattt cctcacttct   2100

ccagtgtagt attaggcaat gctgctggcc taggcataat gggagagtac agaggtacac   2160

cgaggaatca agatctatat gatgcagcaa aggcatatgc tgaacaactc aaagaaaatg   2220

gtgtgattaa ctacagtgta ctagacttga cagcagaaga actagaggct atcaaacatc   2280

agcttaatcc aaaagataat gatgtagagc tttgagttaa taaaaaatgg ggcaaataaa   2340

tcatcatgga aaagtttgct cctgaattcc atggagaaga tgcaaacaac agggctacta   2400

aattcctaga atcaataaag ggcaaattca catcacccaa agatcccaag aaaaaagata   2460

gtatcatatc tgtcaactca atagatatag aagtaaccaa agaaagccct ataacatcaa   2520

attcaactat tatcaaccca acaaatgaga cagatgatac tgcagggaac aagcccaatt   2580

atcaaagaaa acctctagta agtttcaaag aagaccctac accaagtgat aatccctttt   2640

ctaaactata caaagaaacc atagaaacat ttgataacaa tgaagaagaa tccagctatt   2700

catacgaaga aataaatgat cagacaaacg ataatataac agcaagatta gataggattg   2760

atgaaaaatt aagtgaaata ctaggaatgc ttcacacatt agtagtggca agtgcaggac   2820

ctacatctgc tcgggatggt ataagagatg ccatggttgg tttaagagaa gaaatgatag   2880

aaaaaatcag aactgaagca ttaatgacca atgacagatt agaagctatg gcaagactca   2940

ggaatgagga aagtgaaaag atggcaaaag acacatcaga tgaagtgtct ctcaatccaa   3000

catcagagaa attgaacaac ctattggaag ggaatgatag tgacaatgat ctatcacttg   3060

aagatttctg attagttacc aatcttcaca tcaacacaca ataccaacag aagaccaaca   3120

aactaaccaa cccaatcatc caaccaaaca tccatccgcc aatcagccaa acagccaaca   3180

aaacaaccag ccaatccaaa actaaccacc cggaaaaaat ctataatata gttacaaaaa   3240

aaggaaaggg tggggcaaat atggaaacat acgtgaacaa gcttcacgaa ggctccacat   3300

acacagctgc tgttcaatac aatgtcttag aaaaagacga tgaccctgca tcacttacaa   3360

tatgggtgcc catgttccaa tcatctatgc cagcagattt acttataaaa gaactagcta   3420

atgtcaacat actagtgaaa caaatatcca cacccaaggg accttcacta agagtcatga   3480

taaactcaag aagtgcagtg ctagcacaaa tgcccagcaa atttaccata tgcgctaatg   3540

tgtccttgga tgaaagaagc aaactagcat atgatgtaac cacaccctgt gaaatcaagg   3600

catgtagtct aacatgccta aaatcaaaaa atatgttgac tacagttaaa gatctcacta   3660

tgaagacact caaccctaca catgatatta ttgctttatg tgaatttgaa aacatagtaa   3720

catcaaaaaa agtcataata ccaacatacc taagatccat cagtgtcaga aataaagatc   3780

tgaacacact tgaaaatata acaaccactg aattcaaaaa tgctatcaca aatgcaaaaa   3840

tcatccctta ctcaggatta ctattagtca tcacagtgac tgacaacaaa ggagcattca   3900
```

aatacataaa gccacaaagt caattcatag tagatcttgg agcttaccta gaaaaagaaa 3960
gtatatatta tgttaccaca aattggaagc acacagctac acgatttgca atcaaaccca 4020
tggaagatta accttttttcc tctacatcag tgtgttaatt catacaaact ttctacctac 4080
attcttcact tcaccatcac aatcacaaac actctgtggt tcaaccaatc aaacaaaact 4140
tatctgaagt cccagatcat cccaagtcat tgtttatcag atctagtact caaataagtt 4200
aataaaaaat atacacatgg ggcaaataat cattggagga aatccaacta atcacaatat 4260
ctgttaacat agacaagtcc acacaccata cagaatcaac caatggaaaa tacatccata 4320
acaatagaat tctcaagcaa attctggcct tactttacac taatacacat gatcacaaca 4380
ataatctctt tgctaatcat aatctccatc atgattgcaa tactaaacaa actttgtgaa 4440
tataacgtat tccataacaa aacctttgag ttaccaagag ctcgagtcaa cacatagcat 4500
tcatcaatcc aacagcccaa aacagtaacc ttgcatttaa aaatgaacaa cccctacctc 4560
tttacaacac ctcattaaca tcccaccatg caaaccacta tccatactat aaagtagtta 4620
attaaaaata gtcataacaa tgaactagga tatcaagact aacaataaca ttggggcaaa 4680
tgcaaacatg tccaaaaaca aggaccaacg caccgctaag acattagaaa ggacctggga 4740
cactctcaat catttattat tcatatcatc gtgcttatat aagttaaatc ttaaatctgt 4800
agcacaaatc acattatcca ttctggcaat gataatctca acttcactta taattgcagc 4860
catcatattc atagcctcgg caaaccacaa agtcacacca acaactgcaa tcatacaaga 4920
tgcaacaagc cagatcaaga acacaacccc aacatacctc acccagaatc ctcagcttgg 4980
aatcagtccc tctaatccgt ctgaaattac atcacaaatc accaccatac tagcttcaac 5040
aacaccagga gtcaagtcaa ccctgcaatc cacaacagtc aagaccaaaa acacaacaac 5100
aactcaaaca caacccagca agcccaccac aaaacaacgc caaaacaaac caccaagcaa 5160
acccaataat gattttcact ttgaagtgtt caactttgta ccctgcagca tatgcagcaa 5220
caatccaacc tgctgggcta tctgcaaaag aataccaaac aaaaaaccag gaaagaaaac 5280
cactaccaag cccacaaaaa aaccaaccct caagacaacc aaaaaagatc ccaaacctca 5340
aaccactaaa tcaaaggaag tacccaccac caagcccaca gaagagccaa ccatcaacac 5400
caccaaaaca aacatcataa ctacactact cacctccaac accacaggaa atccagaact 5460
cacaagtcaa atggaaacct tccactcaac ttcctccgaa ggcaatccaa gcccttctca 5520
agtctctaca acatccgagt acccatcaca accttcatct ccacccaaca caccacgcca 5580
gtagttactt aaaaacatat tatcacaaaa agccatgacc aacttaaaca gaatcaaaat 5640
aaactctggg gcaaataaca atggagttgc taatcctcaa agcaaatgca attaccacaa 5700
tcctcactgc agtcacattt tgttttgctt ctggtcaaaa catcactgaa gaattttatc 5760
aatcaacatg cagtgcagtt agcaaaggct atcttagtgc tctgagaact ggttggtata 5820
ccagtgttat aactatagaa ttaagtaata tcaaggaaaa taagtgtaat ggaacagatg 5880
ctaaggtaaa attgataaaa caagaattag ataaatataa aaatgctgta acagaattgc 5940
agttgctcat gcaaagcaca ccagcaacaa acaatcgagc cagaagagaa ctaccaaggt 6000
ttatgaatta tacactcaac aatgccaaaa aaaccaatgt aacattaagc aagaaaagga 6060
aaagaagatt tcttggtttt ttgttaggtg ttggatctgc aatcgccagt ggcgttgctg 6120
tatctaaggt cctgcaccta gaaggggaag tgaacaagat caaaagtgct ctactatcca 6180
caaacaaggc tgtagtcagc ttatcaaatg gagttagtgt cttaaccagc aaagtgttag 6240

-continued

```
acctcaaaaa ctatatagat aaacaattgt tacctattgt gaacaagcaa agctgcagca   6300
tatcaaatat agcaactgtg atagagttcc aacaaaagaa caacagacta ctagagatta   6360
ccagggaatt tagtgttaat gcaggtgtaa ctacacctgt aagcacttac atgttaacta   6420
atagtgaatt attgtcatta atcaatgata tgcctataac aaatgatcag aaaaagttaa   6480
tgtccaacaa tgttcaaata gttagacagc aaagttactc tatcatgtcc ataataaaag   6540
aggaagtctt agcatatgta gtacaattac cactatatgg tgttatagat acaccctgtt   6600
ggaaactaca cacatcccct ctatgtacaa ccaacacaaa agaagggtcc aacatctgtt   6660
taacaagaac tgacagagga tggtactgtg acaatgcagg atcagtatct ttcttcccac   6720
aagctgaaac atgtaaagtt caatcaaatc gagtattttg tgacacaatg aacagtttaa   6780
cattaccaag tgaagtaaat ctctgcaatg ttgacatatt caaccccaaa tatgattgta   6840
aaattatgac ttcaaaaaca gatgtaagca gctccgttat cacatctcta ggagccattg   6900
tgtcatgcta tggcaaaact aaatgtacag catccaataa aaatcgtgga atcataaaga   6960
cattttctaa cgggtgcgat tatgtatcaa ataaaggggt ggacactgtg tctgtaggta   7020
acacattata ttatgtaaat aagcaagaag gtaaaagtct ctatgtaaaa ggtgaaccaa   7080
taataaattt ctatgaccca ttagtattcc cctctgatga atttgatgca tcaatatctc   7140
aagtcaacga gaagattaac cagagcctag catttattcg taaatccgat gaattattac   7200
ataatgtaaa tgctggtaaa tccaccataa atatcatgat aactactata attatagtga   7260
ttatagtaat attgttatca ttaattgctg ttggactgct cttatactgt aaggccagaa   7320
gcacaccagt cacactaagc aaagatcaac tgagtggtat aaataatatt gcatttagta   7380
actaaataaa aatagcacct aatcatgttc ttacaatggt ttactatctg ctcatagaca   7440
acccatctgt cattggattt tcttaaaatc tgaacttcat cgaaactctc atctataaac   7500
catctcactt acactattta agtagattcc tagtttatag ttatataaaa cacaattgaa   7560
tgccagatta acttaccatc tgtaaaaatg aaaactgggg caaacatgtc acgaaggaat   7620
ccttgcaaat ttgaaattcg aggtcattgc ttaaatggta agaggtgtca ttttagtcat   7680
aattattttg aatggccacc ccatgcactg cttgtaagac aaaactttat gttaaacaga   7740
atacttaagt ctatggataa aagtatagat accttatcag aaataagtgg agctgcagag   7800
ttggacagaa cagaagagta tgctcttggt gtagttggag tgctagagag ttatatagga   7860
tcaataaaca atataactaa acaatcagca tgtgttgcca tgagcaaact cctcactgaa   7920
ctcaatagtg atgatatcaa aaagctgagg gacaatgaag agctaaattc acccaagata   7980
agagtgtaca atactgtcat atcatatatt gaaagcaaca ggaaaaacaa taaacaaact   8040
atccatctgt taaaaagatt gccagcagac gtattgaaga aaaccatcaa aaacacattg   8100
gatatccata agagcataac catcaacaac ccaaaagaat caactgttag tgatacaaat   8160
gaccatgcca aaaataatga tactacctga caaatatcct tgtagtataa cttccatact   8220
aataacaagt agatgtagag ttactatgta taatcaaaag aacacactat atttcaatca   8280
aaacaaccca aataaccata tgtactcacc gaatcaaaca ttcaatgaaa tccattggac   8340
ctctcaagaa ttgattgaca caattcaaaa ttttctacaa catctaggta ttattgagga   8400
tatatataca atatatatat tagtgtcata acactcaatt ctaacactca ccacatcgtt   8460
acattattaa ttcaaacaat tcaagttgtg ggacaaaatg gatcccatta ttaatggaaa   8520
ttctgctaat gtttatctaa ccgatagtta tttaaaaggt gttatctctt tctcagagtg   8580
taatgcttta ggaagttaca tattcaatgg tccttatctc aaaaatgatt ataccaactt   8640
```

-continued

```
aattagtaga caaaatccat taatagaaca catgaatcta aagaaactaa atataacaca   8700
gtccttaata tctaagtatc ataaaggtga aataaaatta gaagaaccta cttattttca   8760
gtcattactt atgacataca agagtatgac ctcgtcagaa cagattgcta ccactaattt   8820
acttaaaaag ataataagaa gagctataga aataagtgat gtcaaagtct atgctatatt   8880
gaataaacta gggcttaaag aaaaggacaa gattaaatcc aacaatggac aagatgaaga   8940
caactcagtt attacgacca taatcaaaga tgatatactt tcagctgtta aagataatca   9000
atctcatctt aaagcagaca aaaatcactc tacaaaacaa aaagacacaa tcaaaacaac   9060
actcttgaag aaattgatgt gttcaatgca acatcctcca tcatggttaa tacattggtt   9120
taacttatac acaaaattaa acaacatatt aacacagtat cgatcaaatg aggtaaaaaa   9180
ccatgggttt acattgatag ataatcaaac tcttagtgga tttcaattta ttttgaacca   9240
atatggttgt atagtttatc ataaggaact caaaagaatt actgtgacaa cctataatca   9300
attcttgaca tggaaagata ttagccttag tagattaaat gtttgtttaa ttacatggat   9360
tagtaactgc ttgaacacat taaataaaag cttaggctta agatgcggat tcaataatgt   9420
tatcttgaca caactattcc tttatggaga ttatatacta aagctatttc acaatgaggg   9480
gttctacata ataaaagagg tagagggatt tattatgtct ctaattttaa atataacaga   9540
agaagatcaa ttcagaaaac gattttataa tagtatgctc aacaacatca cagatgctgc   9600
taataaagct cagaaaaatc tgctatcaag agtatgtcat acattattag ataagacagt   9660
gtccgataat ataataaatg gcagatggat aattctatta agtaagttcc ttaaattaat   9720
taagcttgca ggtgacaata accttaacaa tctgagtgaa ctatattttt tgttcagaat   9780
atttggacac ccaatggtag atgaaagaca agccatggat gctgttaaaa ttaattgcaa   9840
tgagaccaaa ttttacttgt taagcagtct gagtatgtta agaggtgcct ttatatatag   9900
aattataaaa gggtttgtaa ataattacaa cagatggcct actttaagaa atgctattgt   9960
tttaccctta agatggttaa cttactataa actaaacact tatccttctt tgttggaact  10020
tacagaaaga gatttgattg tgttatcagg actacgtttc tatcgtgagt ttcggttgcc  10080
taaaaaagtg gatcttgaaa tgattataaa tgataaagct atatcacctc ctaaaaattt  10140
gatatggact agtttcccta gaaattacat gccatcacac atacaaaact atatagaaca  10200
tgaaaaatta aaattttccg agagtgataa atcaagaaga gtattagagt attatttaag  10260
agataacaaa ttcaatgaat gtgatttata caactgtgta gttaatcaaa gttatctcaa  10320
caaccctaat catgtggtat cattgacagg caaagaaaga gaactcagtg taggtagaat  10380
gtttgcaatg caaccgggaa tgttcagaca ggttcaaata ttggcagaga aaatgatagc  10440
tgaaaacatt ttacaattct ttcctgaaag tcttacaaga tatggtgatc tagaactaca  10500
aaaaatatta gaattgaaag caggaataag taacaaatca aatcgctaca atgataatta  10560
caacaattac attagtaagt gctctatcat cacagatctc agcaaattca atcaagcatt  10620
tcgatatgaa acgtcatgta tttgtagtga tgtgctggat gaactgcatg gtgtacaatc  10680
tctattttcc tggttacatt taactattcc tcatgtcaca ataaatatgca catataggca  10740
tgcacccccc tatataggag atcatattgt agatcttaac aatgtagatg aacaaagtgg  10800
attatataga tatcacatgg gtggcatcga agggtggtgt caaaaactat ggaccataga  10860
agctatatca ctattggatc taatatctct caaagggaaa ttctcaatta ctgctttaat  10920
taatggtgac aatcaatcaa tagatataag caaaccaatc agactcatgg aaggtcaaac  10980
```

-continued

```
tcatgctcta gcagattatt tgctagcatt aaatagcctt aaattactgt ataaagagta  11040
tgcaggcata ggccacaaat taaaaggaac tgagacttat atatcacgag atatgcaatt  11100
tatgagtaaa acaattcaac ataacggtgt atattaccca gctagtataa agaaagtcct  11160
aagagtggga ccgtggataa acactatact tgatgatttc aaagtgagtc tagaatctat  11220
aggtagtttg acacaagaat tagaatatag aggtgaaagt ctattatgca gtttaatatt  11280
tagaaatgta tggttatata atcagattgc tctacaatta aaaaatcatg cattatgtaa  11340
caataaacta tatttggaca tattaaaggt tctgaaacac ttaaaaacct tttttaatct  11400
tgataatatt gatacagcat taacattgta tatgaattta cccatgttat ttggtggtgg  11460
tgatcccaac ttgttatatc gaagtttcta tagaagaact cctgacttcc tcacagaggc  11520
tatagttcac tctgtgttca tacttagtta ttatacaaac catgacttaa aagataaact  11580
tcaagatctg tcagatgata gattgaataa gttcttaaca tgcataatca cgtttgacaa  11640
aaaccctaat gctgaattcg taacattgat gagagatcct caagctttag ggtctgagag  11700
acaagctaaa attactagcg aaatcaatag actggcagtt acagaggttt tgagtacagc  11760
tccaaacaaa atattctcca aaagtgcaca acattatact actacagaga tagatctaaa  11820
tgatattatg caaaatatag aacctacata tcctcatggg ctaagagttg tttatgaaag  11880
tttacccttt tataaagcag agaaaatagt aaatcttata tcaggtacaa aatctataac  11940
taacatactg gaaaaaactt ctgccataga cttaacagat attgatagag ccactgagat  12000
gatgaggaaa aacataactt tgcttataag gatacttcca ttggaatgta acagagataa  12060
aagagagata ttgagtatgg aaaacctaag tattactgaa ttaagcaaat atgttaggga  12120
aagatcttgg tctttatcca atatagttgg tgttacatca cccagtatca tgtatacaat  12180
ggacatcaaa tatactacaa gcactatatc tagtggcata attatagaga aatataatgt  12240
taacagttta acacgtggtg agagaggacc cactaaacca tgggttggtt catctacaca  12300
agagaaaaaa acaatgccag tttataatag acaagtctta accaaaaaac agagagatca  12360
aatagatcta ttagcaaaat tggattgggt gtatgcatct atagataaca aggatgaatt  12420
catggaagaa ctcagcatag gaacccttgg gttaacatat gaaaaggcca agaaattatt  12480
tccacaatat ttaagtgtca attatttgca tcgccttaca gtcagtagta gaccatgtga  12540
attccctgca tcaataccag cttatagaac aacaaattat cactttgaca ctagccctat  12600
taatcgcata ttaacagaaa agtatggtga tgaagatatt gacatagtat tccaaaactg  12660
tataagcttt ggccttagtt taatgtcagt agtagaacaa tttactaatg tatgtcctaa  12720
cagaattatt ctcataccta agcttaatga gatacatttg atgaaacctc ccatattcac  12780
aggtgatgtt gatattcaca agttaaaaca agtgatacaa aaacagcata tgtttttacc  12840
agacaaaata agtttgactc aatatgtgga attattctta agtaataaaa cactcaaatc  12900
tggatctcat gttaattcta atttaatatt ggcacataaa atatctgact attttcataa  12960
tacttacatt ttaagtacta atttagctgg acattggatt ctgattatac aacttatgaa  13020
agattctaaa ggtatttttg aaaaagattg gggagaggga tatataactg atcatatgtt  13080
tattaatttg aaagttttct tcaatgctta taagacctat ctcttgtgtt ttcataaagg  13140
ttatggcaaa gcaaagctgg agtgtgatat gaacacttca gatcttctat gtgtattgga  13200
attaatagac agtagttatt ggaagtctat gtctaaggta tttttagaac aaaaagttat  13260
caaatacatt cttagccaag atgcaagttt acatagagta aaaggatgtc atagcttcaa  13320
attatggttt cttaaacgtc ttaatgtagc agaattcaca gtttgccctt gggttgttaa  13380
```

```
catagattat catccaacac atatgaaagc aatattaact tatatagatc ttgttagaat  13440
gggattgata aatatagata gaatacacat taaaaataaa cacaaattca atgatgaatt  13500
ttatacttct aatctcttct acattaatta taacttctca gataatactc atctattaac  13560
taaatatata aggattgcta attctgaatt agaaaataat tacaacaaat tatatcatcc  13620
tacaccagaa accctagaga atatactagc caatccgatt aaaagtaatg acaaaaagac  13680
actgaatgac tattgtatag gtaaaaatgt tgactcaata atgttaccat tgttatctaa  13740
taagaagctt attaaatcgt ctgcaatgat tagaaccaat tacagcaaac aagatttgta  13800
taatttattc cctatggttg tgattgatag aattatagat cattcaggca atacagccaa  13860
atccaaccaa ctttacacta ctacttccca ccaaatatct ttagtgcaca atagcacatc  13920
actttactgc atgcttcctt ggcatcatat taatagattc aattttgtat ttagttctac  13980
aggttgtaaa attagtatag agtatatttt aaaagatctt aaaattaaag atcccaattg  14040
tatagcattc ataggtgaag gagcagggaa tttattattg cgtacagtag tggaacttca  14100
tcctgacata agatatattt acagaagtct gaaagattgc aatgatcata gtttacctat  14160
tgagttttta aggctgtaca atggacatat caacattgat tatggtgaaa atttgaccat  14220
tcctgctaca gatgcaacca acaacattca ttggtcttat ttacatataa agtttgctga  14280
acctatcagt ctttttgtct gtgatgccga attgtctgta acagtcaact ggagtaaaat  14340
tataatagaa tggagcaagc atgtaagaaa gtgcaagtac tgttcctcag ttaataaatg  14400
tatgttaata gtaaaatatc atgctcaaga tgatattgat ttcaaattag acaatataac  14460
tatattaaaa acttatgtat gcttaggcag taagttaaag ggatcggagg tttacttagt  14520
ccttacaata ggtcctgcga atatattccc agtatttaat gtagtacaaa atgctaaatt  14580
gatactatca agaaccaaaa atttcatcat gcctaagaaa gctgataaag agtctattga  14640
tgcaaatatt aaaagtttga taccctttct ttgttaccct ataacaaaaa aaggaattaa  14700
tactgcattg tcaaaactaa agagtgttgt tagtggagat atactatcat attctatagc  14760
tggacgtaat gaagttttca gcaataaact tataaatcat aagcatatga acatcttaaa  14820
atggttcaat catgttttaa atttcagatc aacagaacta aactataacc atttatatat  14880
ggtagaatct acatatcctt acctaagtga attgttaaac agcttgacaa ccaatgaact  14940
taaaaaactg attaaaatca caggtagtct gttatacaac tttcataatg aataatgaat  15000
aaagatctta taataaaaat tcccatagct atacactaac actgtattca attatagtta  15060
ttaaaaatta aaaatcatat aatttttaa ataactttta gtgaactaat cctaaagtta  15120
tcattttaat cttggaggaa taaatttaaa ccctaatcta attggtttat atgtgtatta  15180
actaaattac gagatattag tttttgacac tttttttctc gt                     15222
```

<210> SEQ ID NO 73
<211> LENGTH: 15225
<212> TYPE: DNA
<213> ORGANISM: respiratory syncytial virus

<400> SEQUENCE: 73

```
acgcgaaaaa atgcgtacta caaacttgca cattcgaaaa aaatggggca aataagaatt     60
tgataagtgt tatttaagtc taaccttttc aatcagaaat ggggtgcaat tcattgagca    120
tgataaaggt tagattacaa aatttatttg acaatgacga agtagcattg ttaaaaataa    180
catgttatac tgacaaatta attcttctga ccaatgcatt agccaaagca gcaatacata    240
```

-continued

```
caattaaatt aaacggcata gtttttatac atgttataac aagcagtgaa gtgtgccctg    300
ataacaatat tgtagtgaaa tctaacttta caacaatgcc aatattacaa aacggaggat    360
acatatggga attgattgag ttgacacact gctctcaatt aaatggtcta atggatgata    420
attgtgaaat caaattttct aaaagactaa gtgactcagt aatgactgat tatatgaatc    480
aaatatctga tttacttggg cttgatctca attcatgaat tgtgtttagt ctaattcaat    540
agacatgtgt ttattaccat tttagttaat ataaaaactc atcaaagaga aatggggcaa    600
ataaactcac ctaatcagtc aaatcatgag cactacaaat aacaacacta ctatgcaaag    660
attgatgatc acagacatga gacccctgtc gatggaatca ataataacat ctctcaccaa    720
agaaatcata acacacaaat tcatatactt gataaacaat gaatgtattg taagaaaact    780
tgatgaaaga caagctacat tcacattcct agtcaattat gagatgaagc tactacacaa    840
agtagggagt accaaatata agaaatacac tgaatataat acaaaatatg gcactttccc    900
tatgcctata tttatcaatc atggcgggtt tctagaatgt attggcatta agcctacaaa    960
acacactcct ataatataca aatatgacct caacccgtaa attccaacaa aaaactaacc   1020
catccaaact aagctattcc ttaaataaca gtgctcaaca gttaagaagg ggctaatcca   1080
ttttagtaat taaaaataaa ggtaaagcca ataacataaa ttggggcaaa tacaaagatg   1140
gctcttagca aagtcaagtt aaatgataca ttaaataagg atcagctgct gtcatctagc   1200
aaatacacta ttcaacgtag tacaggagat aatattgaca ctcccaatta tgatgtgcaa   1260
aaacacttaa acaaactatg tggtatgcta ttaatcactg aagatgcaaa tcataaattc   1320
acaggattaa taggtatgtt atatgctatg tccaggttag gaagggaaga cactataaag   1380
atacttaaag atgctggata tcatgttaaa gctaatggag tagatataac aacatatcgt   1440
caagatataa atggaaagga aatgaaattc gaagtattaa cattatcaag cttgacatca   1500
gaaatacaag tcaatattga gatagaatct agaaagtcct acaaaaaaat gctaaaagag   1560
atgggagaag tggctccaga atataggcat gattctccag actgtgggat gataatactg   1620
tgtatagctg cacttgtaat aaccaaatta gcagcaggag atagatcagg tcttacagca   1680
gtaattagga gggcaaacaa tgtcttaaaa aacgaaataa aacgctacaa gggcctcata   1740
ccaaaggata tagctaacag tttttatgaa gtgtttgaaa aacaccctca tcttatagat   1800
gtttttgtgc actttggcat tgcacaatca tccacaagag gggtagtag agttgaagga   1860
atctttgcag gattatttat gaatgcctat ggttcagggc aagtaatgct aagatgggga   1920
gttttagcca aatctgtaaa aaatatcatg ctaggacatg ctagtgtcca ggcagaaatg   1980
gagcaagttg tggaagtcta tgagtatgca cagaagttgg gaggagaagc tggattctac   2040
catatattga acaatccaaa agcatcattg ctgtcattaa ctcaatttcc taacttctca   2100
agtgtggtcc taggcaatgc agcaggtcta ggcataatgg gagagtatag aggtacacca   2160
agaaaccagg atctttatga tgcagccaaa gcatatgcag agcaactcaa agaaaatgga   2220
gtaataaact acagtgtatt agacttaaca gcagaagaat tggaggccat aaagcatcaa   2280
ctcaacccca aagaagatga tgtagagctc taagttaaca aaaaatacgg ggcaaataag   2340
tcaacatgga gaagtttgca cctgaatttc atggagaaga tgcaaataac aaagctacca   2400
aattcctaga atcaataaag ggcaagttcg catcatccaa agatcctaag aagaaagata   2460
gcataatatc tgttaactca atagatatag aagtaactaa agagagcccg ataacatctg   2520
gcaccaacat caacaatcca acaagtgaag ctgacagtac cccagaagcc aaaaccaact   2580
acccaagaaa acccctagta agcttcaaag aagatctcac cccaagtgac aaccccttt    2640
```

-continued

```
ctaagttgta caaagaaaca atagaaacat ttgataacaa tgaagaagaa tctagctact   2700
catatgaaga aataaatgat caaacaaatg acaacattac agcaagacta gatagaattg   2760
atgaaaaatt aagtgaaata ttaggaatgc tccatacatt agtagttgca agtgcaggac   2820
ccacttcagc tcgcgatgga ataagagatg ctatggttgg tctaagagaa gaaatgatag   2880
aaaaaataag agcggaagca ttaatgacca atgataggtt agaggctatg gcaagactta   2940
ggaatgagga aagcgaaaaa atggcaaaag acacctcaga tgaagtgtct ctcaatccaa   3000
cttccaaaaa attgagtgac ttgctggaag acaacgatag tgacaatgat ctatcacttg   3060
atgatttttg atcagtgatc aactcactca gcaatcaaca acatcaataa gacagacatc   3120
aatccattga atcaactgcc agaccgaaca aacaaacgtt catcagcaga accaccaacc   3180
aatcaatcaa ccaattgatc aatcagcaac ctaacaaaat taacaatata gtaacaaaaa   3240
aagaacaaga tggggcaaat atggaaacat acgtgaacaa gcttcacgaa ggctccacat   3300
acacagcagc tgttcagtac aatgttctag aaaaagatga tgatcctgca tcactaacaa   3360
tatgggtgcc tatgttccag tcatctgtgc cagcagactt gctcataaaa gaacttgcaa   3420
gcatcaacat actagtgaag cagatctcta cgcccaaagg accttcacta cgagtcacga   3480
tcaactcaag aagcgctgtg ctggcacaaa tgcccagtaa ttttatcata agtgcaaatg   3540
tatcattaga tgaaagaagc aaattagcat atgatgtaac tacaccttgt gaaatcaaag   3600
catgcagtct aacatgctta aaagtaaaaa gtatgctaac tacagtcaaa gatcttacca   3660
tgaaaacatt caaccccact catgagatta ttgctctatg tgaatttgaa aatattatga   3720
catcaaaaag agtaataata ccaacctatc taagatcaat tagtgtcaaa aacaaggacc   3780
tgaactcact agaaaatata gcaaccaccg aattcaaaaa tgctatcacc aatgcgaaaa   3840
ttattcccta tgcaggatta gtattagtta tcacagttac tgacaataaa ggagcattca   3900
aatatatcaa gccacagagt caatttatag tagatcttgg agcctaccta gaaaaagaga   3960
gcatatatta tgtgactaca aattggaagc atacagctac acgtttttca atcaaaccac   4020
tagaggatta aacttaatta tcaacgctaa atgacaggtc cacatatatc ctcaaactac   4080
acactatatc caaacatcat gaacatctac actacacact tcatcacaca aaccaatccc   4140
acttaaaatc caaaatcact tccagccact atctgctaga cctagagtgc gaataggtaa   4200
ataaaaccaa aatatggggt aaatagacat tagttagagt tcaatcaatc tcaacaacca   4260
tttatactgc taattcaata catatactat aaatttcaaa atgggaaata catccatcac   4320
aatagaattc actagcaaat tttggcctta ttttacacta atacatatga tcttaactct   4380
aatctcttta ctaattataa tcactattat gattgcaata ctaaataagc taagtgaaca   4440
taaaacattc tgtaacaaaa ctcttgaact aggacagatg tatcaaatca acacatagtg   4500
ttctaccatc atgctgtgtc aaattataat cctgtatatg taaacaaaca aatccaatct   4560
tctcacagag tcatggtggc gcaaagccac gccaactatc atggtagcat agagtagtta   4620
tttaaaaatt aacataatga tgaattatta gtatgggatc aaaaacaaca ttggggcaaa   4680
tgcaaccatg tccaaacaca agagtcaacg cactgccagg actctagaaa agacctggga   4740
tactcttaat catctaattg taatatcctc ttgtttatac agactaaacc taaaatctat   4800
agcacaaata gcactatcag ttttggcaat gataatctca acctctctca taattgcagc   4860
cataatattc atcatctctg ccaatcacaa agttacacta acaacggtta cagttcaaac   4920
aataaaaaac cacactgaaa aaaacatcac cacctacctt actcaagtct caccagaaag   4980
```

-continued

```
ggttagctca tccatacaac ctacaaccac atcaccaatc cacacaaatt cagctacaat   5040
atcaccaaat acaaaatcag aaacacacca tacaacaaca caagccaaaa gcagaatcac   5100
cacttcaaca cagaccaaca agccaagcac aaaatcacgt tcaaaaaatc caccaaaaaa   5160
accaaaagat gattaccatt ttgaagtgtt caattttgtt ccctgtagta tatgtggcaa   5220
caatcaactt tgcaaatcca tctgcaaaac aataccaagc aacaaaccaa agaaaaaacc   5280
aaccatcaaa cccacaaaca aaccaaccgt caaaaccaca aacaaaagag acccaaaaac   5340
accagccaaa atgatgaaaa aagaaaccac caccaaccca acaaaaaaac caaccctcaa   5400
gaccacagaa ggagacacca gcacctcaca atccactgtg ctcgacacaa ccacatcaaa   5460
acacacaatc caacagcaat ccctccactc aatcacctcc gaaaacacac ccaactccac   5520
acaaataccc acagcaaccg aggcctccac atcaaattct acttaaaaaa cctagtcaca   5580
tgcttagtta ttcaaaaact acatcttagc agagaaccgt gatctatcaa gcaagaatga   5640
aattaaacct ggggcaaata accatggagt tgctgatcca caggtcaagt gcaatcttcc   5700
taactcttgc tattaatgca ttgtacctca cctcaagtca gaacataact gaggagtttt   5760
accaatcgac atgtagtgca gttagcagag gttattttag tgctttaaga acaggttggt   5820
ataccagtgt tataacaata gaattaagta atataaaaga aaccaaatgc aatggaactg   5880
acactaaagt aaaacttata aaacaagaat tagataagta taagaatgca gtaacagaat   5940
tacagctact tacgcaaaac acgccagctg ccaacaaccg ggccagaaga gaagcaccac   6000
agtacatgaa ctacacaatc aataccacta aaaacctaaa cgtatcaata agcaagaaga   6060
ggaaacgaag atttctggga ttcttgttag gtgtaggatc tgcaatagca agtggtatag   6120
ctgtatccaa agttctacac cttgaaggag aagtgaacaa aatcaaaaat gctttgttgt   6180
ctacaaacaa agctgtagtc agtctatcaa atggggtcag tgttttaacc agcaaagtgt   6240
tagatctcaa gagttacata aataaccaat tattacccat agtaaatcaa cagagctgtc   6300
gcatctccaa cattgaaaca gttatagaat tccagcagaa gaacagcaga ttgttggaaa   6360
tcaccagaga atttagtgtc aatgcaggtg taacaacacc tttaagcact tacatgttaa   6420
caaacagtga gttactatca ttgatcaatg atatgcctat aacaaatgat cagaaaaaat   6480
taatgtcaag caatgtccag atagtaaggc aacaaagtta ttctatcatg tctataataa   6540
aggaagaagt ccttgcatat gttgtacagc tacctatcta tggtgtaata gatacacctt   6600
gctggaaatt acacacatca cctctatgca ccaccaacat caaagaagga tcaaatattt   6660
gtttaacaag gactgataga ggatggtatt gtgataatgc aggatcagta tccttcttcc   6720
cacaggctga cacttgcaaa gtgcagtcca atcgagtatt ttgtgacact atgaacagtt   6780
tgacattacc aagtgaagtc agcctttgta acactgacat attcaattcc aagtatgact   6840
gcaaaatcat gacttcaaaa acagacataa gcagctcagt aattacttct cttggagcta   6900
tagtgtcatg ctatggtaaa actaaatgca ctgcatccaa taaaaatcgt gggattataa   6960
agacattttc taatggttgt gactatgtgt caaacaaagg agtagatact gtgtcagtgg   7020
gcaacacttt atactatgta aacaagctgg aaggcaaaaa cctttatgta aaaggggaac   7080
ctataataaa ttactatgat cctctagtgt ttccttctga tgagtttgat gcatcaatat   7140
ctcaagtcaa tgaaaaaatc aatcaaagtt tagcttttat acgtagatct gatgaattac   7200
tacataatgt aaatactggc aaatctacta caaatattat gataaccaca atcattatag   7260
taatcattgt agtattgtta tcattaatag ctattggttt actgttgtat tgcaaagcta   7320
aaaacacacc agttacacta agcaaagacc aactaagtgg aatcaacaat attgcattca   7380
```

```
gcaaatagac aaaaaaccac ttgatcatgt ttcaacaaca atctgctgac caccaatccc   7440
aaatcaactt aacaacaaat atttcaacat catagcacag gctgaatcat ttcctcacat   7500
catgctacct acacaactaa gctagatcct taactcatag ttacataaaa acctcaagta   7560
tcacaatcaa acactaaatc gacacatcat tcacaaaatt aacaactggg gcaaatatgt   7620
cgcgaagaaa tccttgtaaa tttgagatta gaggtcattg cttgaatggt agaagatgtc   7680
actacagtca taattatttt gaatggcctc ctcatgcatt actagtgagg caaaacttca   7740
tgttaaacaa gatacttaag tcaatggaca aaagcataga cactttgtcg gaaataagtg   7800
gagctgctga actggataga acagaagaat atgctcttgg tatagttgga gtgctagaga   7860
gttacatagg atctataaac aacataacaa aacaatcagc atgtgttgct atgagtaaac   7920
ttcttattga gatcaacagt gatgacatta aaaaactgag agataatgaa gaacccaatt   7980
cacctaagat aagagtgtac aatactgtta tatcatacat tgagagcaat agaaaaaaca   8040
acaagcaaac catccatctg ctcaaaagac taccagcaga tgtgctgaag aagacaataa   8100
agaacacatt agatatccac aaaagcataa ccataagcaa cccaaaagag tcaaccgtga   8160
atgatcaaaa tgaccaaacc aaaaataatg atattaccgg ataaatatcc ttgtagtata   8220
tcatccatac tgatttcaag tgaaagcatg gttgccacat tcaatcacaa aaacatatta   8280
caatttaacc ataaccattt ggataaccac cagtgtttat taaatcatat atttgatgaa   8340
attcattgga cacctaaaaa cttattagat accactcaac aatttctcca acatcttaac   8400
atccctgaag atatatatac agtatatata ttagtgtcat aatgcttgac cataacgatc   8460
ttatatcatc caaccataaa actatcataa taaggttatg ggacaaaatg gatcccatta   8520
ttaatggaaa ctctgctaat gtgtatctaa ctgatagtta tctaaaaggt gttatctctt   8580
tttcagaatg taatgcttta gggagttacc tttttaacgg cccttatctt aaaaatgatt   8640
acactaactt aattagtaga caaagcccac tactagagca tatgaatcta aaaaaactaa   8700
ctataacaca gtcattaata tctagatatc ataaaggtga actgaaatta gaagaaccaa   8760
cttatttcca gtcattactt atgacatata aaagtatgtc ctcgtctgaa caaattgcta   8820
caactaactt acttaaaaaa ataatacgaa gagctataga aataagtgat gtaaaggtgt   8880
acgccatctt gaataaacta ggactaaagg aaaaggacag agttaagccc aacaataatt   8940
caggtgatga aaactcagtt cttacaacca taattaaaga tgatatactt tcggctgtgg   9000
aaaacaatca atcatataca aattcagaca aaaatcactc agtgaaccaa aatatcacta   9060
tcaaaacaac actcttgaaa aaattgatgt gttcaatgca acatcctcca tcatggttaa   9120
tacactggtt caatttatat acaaaattaa ataacatatt aacacaatat cgatcaaatg   9180
aggtaaaaag tcatgggttt atattaatag ataatcaaac tttaagtggt tttcagttta   9240
ttttaaatca atatggttgt attgtttatc ataaaggact taaaaaaatc acaactacta   9300
cttacaatca atttttgaca tggaaagaca tcagccttag cagattaaat gtttgcttaa   9360
ttacttggat aagtaattgt ttaaatacat taaataaaag cttagggctg agatgtggat   9420
tcaataatgt tgtgttatca caattatttc tttatggaga ttgtatactg aaattatttc   9480
ataatgaagg cttctacata ataaaagaag tagagggatt tattatgtct ttaattctaa   9540
acataacaga agaagatcaa tttaggacac gattttataa cagcatgcta aataacatca   9600
cagatgcagc tattaaggct caaaaaaacc tactatcaag agtatgtcac actttattgg   9660
acaagacagt gtctgataat atcataaatg gtaaatggat aatcctatta agtaaatttc   9720
```

```
ttaaattgat taagcttgca ggtgataata atctcaataa cttgagtgag ctatattttc   9780
tcttcagaat ctttggacat ccaatggtcg atgaaagaca agcaatggat gctgtaagaa   9840
ttaactgtaa tgaaactaag ttctacttat taagtagtct aagtacgtta agaggtgctt   9900
tcatttatag aatcataaaa gggtttgtaa atacctacaa cagatggccc actttaagga   9960
atgctattgt tctacctcta agatggttga actattataa acttaatact tatccatctc  10020
tacttgaaat cacagaaaat gatttgatta ttttatcagg attgaggttc tatcgtgagt  10080
ttcatctgcc taaaaaagtg gatcttgaaa tgataataaa tgacaaagcc atttcacctc  10140
caaaagatct aatatggact agttttccca gaaattacat gccatcacat atacaaaatt  10200
atatagaaca tgaaaagttg aagttctctg aaagcgacag atcaagaaga gtactagagt  10260
attacttgag agataataaa ttcaatgaat gcgatctata caattgtgtg gtcaatcaaa  10320
gctatctcaa caactctaac cacgtggtat cactaactgg taaagaaaga gagctcagtg  10380
taggtagaat gtttgctatg caaccaggta tgtttaggca aattcaaatc ttagcagaga  10440
aaatgatagc cgaaaatatt ttacaattct tccctgagag tttgacaaga tatggtgatc  10500
tagagcttca aaagatatta gaattaaaag caggaataag caacaaatca aatcgttata  10560
atgataacta caacaattat atcagtaaat gttctatcat tacagacctt agcaaattca  10620
atcaagcatt tagatatgaa acatcatgta tctgcagtga tgtattagat gaactgcatg  10680
gagtacaatc actgttctct tggttgcatt taacaatacc tcttgtcaca ataatatgta  10740
catatagaca tgcacctcct ttcataaagg atcatgttgt taatctgaat gaagttgatg  10800
aacaaagtgg attatacaga tatcatatgg gtggtattga gggctggtgt caaaaactgt  10860
ggaccattga agctatatca ttattagatc taatatccct caaagggaaa ttctctatca  10920
cagctctaat aaatggtgat aatcagtcaa ttgatataag taaaccagtt agacttatag  10980
agggtcagac ccatgctcaa gcagattatt tgttagcatt aaatagcctt aaattgctat  11040
ataaagagta tgcaggcata ggccataagc tcaagggaac agaaacctat atatcccgag  11100
atatgcaatt catgagcaaa acaatccagc acaatggagt gtactatcca gccagtatca  11160
aaaaagtcct gagagtaggt ccatggataa atacaatact tgatgatttt aaagttagtt  11220
tagaatctat aggcagctta acacaggagt tagaatacag aggagaaagc ttattatgca  11280
gtttaatatt tagaaacatt tggttataca atcaaattgc tttgcaactc cgaaatcatg  11340
cattatgtca caataagcta tatttagata tattgaaagt attaaaacac ttaaaaactt  11400
tttttaatct tgatagtatc gatatggcat tatcattgta tatgaatttg cctatgctgt  11460
ttggtggtgg tgatcctaat ttgttatatc gaagctttta tagaagaact ccagacttcc  11520
ttacagaagc tatagtacat tcagtgtttg tgttgagcta ttatactggt cacgatttac  11580
aagataagct ccaggatctt ccagatgata gactgaacaa attcttgaca tgtatcatca  11640
catttgataa aaatcccaat gccgagtttg taacattaat gagggatcca caggctttag  11700
ggtctgaaag gcaagctaaa attactagtg agattaatag attagcagta acggaagtct  11760
taagtatagc tccaaacaaa atattttcta aaagtgcaca acattatact accactgaga  11820
ttgatctaaa tgatattatg caaaatatag aaccaactta ccctcatgga ttaagagttg  11880
tttatgaaag tttacctttt tataaagcag aaaaaatagt taatcttata tcaggaacaa  11940
aatccataac taatatactt gaaaaaacat cagcaataga tacaactgat attaataggg  12000
ctactgatat gatgaggaaa aatataactt tacttataag gatacttcca ctagattgta  12060
acaaagacaa aagagagtta ttaagtttag aaaatcttag tataactgaa ttaagcaagt  12120
```

atgtaagaga aagatcttgg tcgttatcca atatagtagg agtaacatcg ccaagtatta 12180
tgttcacaat ggacattaaa tatacaacta gcactatagc cagtggtata attatagaaa 12240
aatataatgt taatagttta actcgtggtg aaagaggacc tactaagcca tgggtaggtt 12300
catctacgca ggagaaaaaa acaatgccag tgtataatag acaagtttta accaaaaagc 12360
aaagagacca aatagattta ttagcaaaat tagactgggt atatgcatcc atagacaaca 12420
aagatgaatt catggaagaa ctgagtactg gaacacttgg attgtcatat gaaaaagcca 12480
aaaaattgtt tccacaatat ctaagtgtca attatttaca ccgcttaaca gtcagtagta 12540
ggccatgtga attccctgca tcaataccag cttatagaac aacaaattat catttcgata 12600
ctagtcctat caatcatgta ttaacagaaa agtatggaga tgaagatatc gacatagtgt 12660
ttcaaaattg cataagtttt ggtcttagcc taatgtcggt tgtggaacaa ttcacaaaca 12720
tatgtcctaa tagaattatt ctcataccga agctgaatga gatacatttg atgaaacctc 12780
ctatatttac aggagatgtt gatatcatca aattgaagca agtgatacaa aaacagcaca 12840
tgttcctacc agataaaata agtttaaccc aatatgtaga attattccta agtaacaaag 12900
cacttaaatc tggatctcac atcaactcta atttaatatt agtacataaa atgtctgatt 12960
attttcataa tgattatatt ttaagtacta atttagctgg acattggatt ctgattattc 13020
aacttatgaa agattcaaaa ggtatttttg aaaaagattg gggagagggg tatataactg 13080
atcatatgtt cattaatttg aatgttttct ttaatgctta taagacttat ttgctatgtt 13140
ttcataaagg ttatggtaaa gcaaaattag aatgtgatat gaacacttca gatcttcttt 13200
gtgttttgga gttaatagac agtagctact ggaaatctat gtctaaagtt ttcctagaac 13260
agaaagtcat aaaatacata gtcaatcaag acacaagttt gcatagaata aaaggttgtc 13320
atagttttaa gttgtggttt ttaaaacgcc ttaataatgc taaatttacc gtatgccctt 13380
gggttgttaa catagattat cacccaacac acatgaaagc tatattatct tacatagatt 13440
tagttagaat ggggttaata aatgtagata aattaaccat taaaaataaa aacaaattca 13500
atgatgaatt ttacacatca aatctctttt atattagtta taacttttca gacaacactc 13560
atttgctaac aaaacaaata agaattgcta attcagaatt agaaaataat tataacaaac 13620
tatatcaccc aaccccagaa actttagaaa atatgtcatt aattcctgtt aaaagtaaca 13680
atagtaacaa acctaaatct tgtataagtg gaaataccga atctatgatg acgtcaacat 13740
tctccaataa aatgcatatt aaatcttcca ctgttaccac aagattaaac tatagcaaac 13800
aagacttgta caatttattt ccaattgttg tgatagacag gattatagat cattcaggca 13860
atacagcaaa atccaaccaa ctttacacca ccacttcaca tcagacatct ttagtaagga 13920
atagtgcatc actttattgc atgcttcctt ggcatcatgt caatagattt aactttgtat 13980
ttagttccac aggatgcaag atcagtatag agtatatttt aaaagatctt aagattaagg 14040
accccagttg tatagcattc ataggtgaag gagctggtaa cttattatta cgtacggtag 14100
tagaacttca tccagacata agatacattt acagaagttt aaaagattgc aatgatcata 14160
gtttacctat tgaatttcta aggttataca acgggcatat aaacatagat tatggtgaga 14220
atttaaccat tcctgctaca gatgcaacta ataacattca ttggtcttat ttacatataa 14280
aatttgcaga acctattagc atctttgtct gcgatgctga attacctgtt acagccaatt 14340
ggagtaaaat tataattgaa tggagtaagc atgtaagaaa gtgcaagtac tgttcctctg 14400
taaatagatg cattttaatt gcaaaatatc atgctcaaga tgatattgat ttcaaattag 14460

-continued ataacattac tatattaaaa acttatgtgt gcctaggtag caagttaaaa ggatctgaag 14520
tttacttagt ccttacaata ggcccttcaa atatacttcc tgtttttaat gttgtgcaaa 14580
atgctaaatt gattctttca agaactaaaa atttcattat gcctaaaaaa actgacaaag 14640
aatctatcga tgcaaatatt aaaagcttaa tacctttcct ttgttaccct ataacaaaaa 14700
aaggaattaa gacttcattg tcaaaattga agagtgtagt taatggagat atattatcat 14760
attctatagc tggacgtaat gaagtattca gcaacaagct tataaaccac aagcatatga 14820
atatcctaaa atggctagat catgttttaa actttagatc aactgaactt aattacaatc 14880
atttatatat gatagagtcc acatatcctt acttaagtga attgttaaat agtttaacaa 14940
ccaatgagct caaaaagctg attaaaatta caggtagtgt actatacaac cttcccaatg 15000
aacagtaact taaaatatca ttaacaagtt tggtcaaatt tagatgctaa cacatcatta 15060
tattatagtt attaaaaaat atgcaaactt ttcaataatt tagcatattg attccaaaat 15120
tatctatttt ggtcttaagg ggttaaataa aaatctaaaa ctaacaatta tacatgtgca 15180
tttacaacac aacgagacat tagtttttga cacttttttt ctcgt 15225

<210> SEQ ID NO 74
<211> LENGTH: 15191
<212> TYPE: DNA
<213> ORGANISM: respiratory syncytial virus

<400> SEQUENCE: 74
acgcgaaaaa atgcgtacaa caaacttgcg taaaccaaaa aaatggggca aataagaatt 60
tgataagtac cacttaaatt taactccctt ggttagagat gggcagcaat tcattgagta 120
tgataaaagt tagattacaa aatttgtttg acaatgatga agtagcattg ttaaaaataa 180
catgctatac tgacaaatta atacatttaa ctaatgcatt ggctaaggca gtgatacata 240
caatcaaatt gaatggcatt gtatttgtgc atgttattac aagtagtgat atttgcccta 300
ataataatat tgtagtgaaa tccaatttca caacaatgcc agtgttacaa aatggaggtt 360
atatatggga aatgatggaa ttaacacact gctctcaacc taatggccta atagatgaca 420
attgtgaaat taaattctcc aaaaaactaa gtgattcaac aatgaccaat tatatgaatc 480
aattatctga attacttgga tttgatctta atccataaat tataataaat atcaactagc 540
aaatcaatgt cactaacacc attagttaat ataaaacttg acagaagata aaaatggggc 600
aaataaatca attcagccga cccaaccatg gacacaacac acaatgacac cacaccacaa 660
agactgatga tcacagacat gagaccattg tcacttgaga ctataataat atcactaacc 720
agagacatca taacacacag atttatatac ttgataaatc atgaatgtat agtgagaaaa 780
cttgatgaaa gacaggccac atttacattc ctggtcaact atgaaatgaa actattgcac 840
aaagtgggaa gcactaaata caaaaaatat actgaataca acacaaaata tggcactttt 900
cctatgccaa tatttatcaa tcatgatggg ttcttagaat gcattggcat taagcctaca 960
aagcacactc ccataatata caagtatgat ctcaatccat gaatttcaac acaagagtca 1020
cacaatctga aataacaact tcatgcataa ccacactcca tagttcaaat ggagcctgaa 1080
aattatagta atttaaaatt aaggagagac ataagatgaa agatggggca aatacaaaaa 1140
tggctcttag caaagtcaag ttgaatgata cactcaacaa agatcaactt ctgtcatcca 1200
gcaaatacac catccaacgg agcacaggag atagtattga tactcctaat tatgatgtgc 1260
agaaacacat caataagtta tgtggcatgt tattaatcac agaagatgct aatcataaat 1320
tcactgggtt aataggtatg ttatatgcta tgtctagatt aggaagagaa gacaccataa 1380

```
aaatactcag agatgcggga tatcatgtaa aagcaaatgg agtggatgta acaacacatc   1440
gtcaagatat taatgggaaa gaaatgaaat ttgaagtgtt aacattgtca agcttaacaa   1500
ctgaaattca aatcaacatt gagatagaat ctagaaaatc ctacaaaaaa atgctaaaag   1560
aaatgggaga ggtagctcca gaatacaggc atgactctcc tgattgtggg atgataatat   1620
tatgtatagc ggcattagta ataaccaaat tagcagcagg ggatagatct ggtcttacag   1680
ctgtgattag gagggctaat aatgtcctaa aaaatgaaat gaaacgttat aaaggcttac   1740
tacccaagga tatagccaac agcttctatg aagtgtttga aaaatatcct cactttatag   1800
atgtttttgt tcattttggt atagcacaat cttctaccag aggtggcagt agagttgaag   1860
ggatttttgc tggattgttt atgaatgcct atggtgcagg gcaagtgatg ttacggtggg   1920
gggtcttagc aaaatcagtt aaaaatatta tgctaggaca cgctagtgtg caagcagaaa   1980
tggaacaagt tgtggaggtt tatgaatatg cccaaaaatt gggtggagaa gcagggttct   2040
accatatatt gaacaaccca aaagcatcat tattgtcttt gactcaattt cctcacttct   2100
ccagtgtagt attaggcaat gctgctggcc taggcataat gggagaatac agaggtacac   2160
caaggaatca agatctatat gatgctgcaa aagcatatgc tgaacaactc aaagaaaatg   2220
gtgtgattaa ctacagtgta ttagacttga cagcagaaga actagaggct atcaaacatc   2280
agcttaatcc aaaagataat gatgtagagc tttgagttaa taaaaaaaat ggggcaaata   2340
aaacatcatg gaaaagtttg ctcctgaatt ccatggagaa gatgcaaaca acagagctac   2400
caaattccta gaatcaataa agggcaaatt cacatcacct aaagatccca agaaaaaaga   2460
tagtatcata tctgtcaact caatagatat agaagtaacc aaagaaagcc ctataacatc   2520
aaattcaacc attataaacc caacaaatga gacagatgat actgtaggga acaagcccaa   2580
ttatcaaaga aaacctctag taagtttcaa agaagaccct acgccaagtg ataatccctt   2640
ttcaaaacta tacaaagaaa ccatagaaac atttgataac aatgaagaag aatctagcta   2700
ttcatatgaa gaaataaatg atcagacaaa cgataatata acagcaagat tagataggat   2760
tgatgaaaaa ttaagtgaaa tactaggaat gcttcacaca ttagtagtag cgagtgcagg   2820
acctacatct gctcgggatg gtataagaga tgccatggtt ggtttaagag aagacatgat   2880
agaaaaaatc agaactgaag cattaatgac caatgacaga ctagaagcta tggcaagact   2940
caggaatgag gaaagtgaaa agatggcaaa agacacatca gatgaagtgt ctctcaatcc   3000
aacatcagag aaattgaaca acctgttgga agggaatgat agtgacaatg atctatcact   3060
tgatgatttc tgatcagtta ccaatctgta catcaacaca caacaccaac agaagaccaa   3120
caaacaaacc aactcaccca tccaaccaaa catctatacg ccaatcagcc aatccaaaac   3180
tagccacccg gaaaaaatag atactatagt tacaaaaaaa gatggggcaa atatggaaac   3240
atacgtgaac aaacttcacg aaggctccac atacacagct gctgttcaat acaatgtctt   3300
agaaaaagac gatgaccctg catcacttac aatatgggtg cccatgttcc aatcatccat   3360
gccagcagat ttacttataa aagaactagc taatgtcaac atactagtga aacaaatatc   3420
cacacccaat ggaccttcat taagagtcat gataaactca agaagtgcag tgctagcaca   3480
aatgcccagc aaatttacca tatgtgccaa tgtgtccttg gatgaaagaa gcaagctggc   3540
atatgatgta accacaccct gtgaaatcaa ggcatgtagt ctaacatgcc taaaatcaaa   3600
aaatatgtta actacagtta aagatctcac tatgaaaaca ctcaacccaa cacatgacat   3660
cattgcttta tgtgaatttg aaaatatagt aacatcaaaa aaagtcataa taccaacata   3720
```

```
cctaagatcc atcagtgtca gaaataaaga tctgaacaca cttgaaaata taacaaccac   3780
tgaattcaaa aatgccatca caaatgcaaa aatcatccct tactcaggat tactgttagt   3840
catcacagtg actgacaaca aaggagcatt caaatacata aagccacaaa gtcaatttat   3900
agtagatctt ggagcttacc tagaaaaaga aagtatatat tatgttacaa caaattggaa   3960
gcacacagct acacgatttg caatcaaacc catggaagat taaccttttt cttctacatc   4020
agtgagttga ttcatacaaa ctttctacct acattcttca cttcaccatc ataatcacca   4080
accctctgtg gttcaactaa tcaaacaaaa cccatctgga gcctcagatc atcccaagtc   4140
attgttcatc agatctagta ctcaaataag ttaataaaaa tatccacatg ggcaaataa    4200
tcattggagg aaatccaact aatcacaata tctgtcaaca tagacaagtc aacacgccag   4260
gcaaaatcaa ccaatggaaa atacatccat aacaatagaa ttctcaagca aattctggcc   4320
ttactttaca ctaatacaca tgataacaac aataatctct ttgctaatca taatctccat   4380
catgattgca atactgaaca aactctgtga atataacgta ttccataaca aaacctttga   4440
gctaccaaga gctcgagtca atacatagca ttcaccaatc tgatggcaca aaacagtaac   4500
cttgcatttg taagtgaaca accctcacct ctttacaaaa ccacatcaac atctcaccat   4560
gcaagccatc atccatatta taaagtagtt aattaaaaat aatcataaca atgaactaag   4620
atattaagac taacaataac gttggggcaa atgcaaacat gtccaaaaac aaggaccaac   4680
gcaccaccaa gacactagaa aagacctggg acactctcaa tcatctatta ttcatatcat   4740
cgtgcttata caagttaaat cttaaatcta tagcacaaat cacattatcc attctggcaa   4800
tgataatctc aacttcactt ataattgcag ccatcatatt catagcctcg gcaaaccaca   4860
aagtcacact aacaactgca atcatacaag atgcaacaag ccagatcaag aacacaaccc   4920
caacatacct cacccagaat ccccagcttg gaatcagctt ctccaatctg tctgaaacta   4980
catcacaaac caccaccata ctagcttcaa caacaccaag tgtcaagtca accctgcaat   5040
ccacaacagt caagaccaaa aacacaacaa caaccaaaat acaacccagc aagcccacca   5100
caaaacaacg ccaaaacaaa ccaccaaaca aacccaataa tgattttcac tttgaagtgt   5160
tcaactttgt accttgcagc atatgcagca acaatccaac ctgctgggct atctgtaaaa   5220
gaataccaaa caaaaaacct ggaaagaaaa ccaccaccaa gcccacaaaa aaaccaacca   5280
tcaagacaac caaaaaagat ctcaaacctc aaaccacaaa accaaaggaa gtacctacca   5340
ccaagcccac agaaaagcca accatcaaca ccaccaaaac aaacatcaga actacactgc   5400
tcaccaacaa taccacagga aatccagaac acacaagtca aaagggaacc ctccactcaa   5460
cctcctccga tggcaatcca agcccttcac aagtctatac aacatccgag tacctatcac   5520
aacctccatc tccatccaac acaacaaacc agtagtcatt aaaaagcgta ttattgcaaa   5580
aagccatgac caaatcaacc agaatcaaaa tcaactctgg ggcaaataac aatggagttg   5640
ccaatcctca aaacaaatgc aattaccgca atccttgctg cagtcacact ctgttttgct   5700
tccagtcaaa acatcactga agaattttat caaacaacat gcagtgcagt cagcaaaggc   5760
tatcttagtg ctctaagaac tggttggtat actagtgtta taactataga attaagtaat   5820
atcaaggaaa ataagtgtaa tggaacagac gctaaggtaa aattgataaa acaagaatta   5880
gataaatata aaagtgctgt aacagaattg cagttgctca tgcaaagcac accggcaacc   5940
aacaatcgag ccagaagaga actaccaagg tttatgaatt atacactcaa caataccaaa   6000
aataccaatg taacattaag caagaaaagg aaaagaagat ttcttggctt tttgttaggt   6060
gttggatctg caatcgccag tggcattgct gtatctaagg tcctgcacct agaaggggaa   6120
```

```
gtgaacaaaa tcaaaagtgc tctactatcc acaaacaagg ctgtagtcag cttatcaaat   6180
ggagttagtg tcttaaccag caaagtgtta gacctcaaaa actatataga taaacagttg   6240
ttacctattg tgaacaagca aagctgtagc atatcaaaca ttgaaactgt gatagagttc   6300
caacaaaaga acaacagact actagagatt accagggaat ttagtgttaa tgcaggtgta   6360
actacacctg taagcactta tatgttaaca aatagtgaat tattatcatt aatcaatgat   6420
atgcctataa caaatgatca gaaaaagtta atgtccaaca atgttcaaat agttagacag   6480
caaagttact ctatcatgtc cataataaag gaggaagtct tagcatatgt agtacaatta   6540
ccactatatg gtgtaataga tacaccttgt tggaaactgc acacatcccc tctatgtaca   6600
accaacacaa aggaagggtc caacatctgt ttaacaagaa ccgacagagg atggtactgt   6660
gacaatgcag gatcagtatc tttcttccca ctagctgaaa catgtaaagt tcaatcgaat   6720
cgagtatttt gtgacacaat gaacagttta acattaccaa gtgaagtaaa tctctgcaac   6780
attgacatat tcaaccccaa atatgattgc aaaattatga cttcaaaaac agatgtaagc   6840
agctccgtta tcacatctct aggagccatt gtgtcatgct atggcaaaac taaatgtaca   6900
gcatccaata aaaatcgtgg aatcataaag acattttcta acgggtgcga ttatgtatca   6960
aataaggggg ttgacactgt gtctgtaggt aatacattat attatgtaaa taagcaagaa   7020
ggcaaaagtc tctatgtaaa aggtgaacca ataataaatt tctatgaccc attagtgttc   7080
ccctctgatg aatttgatgc atcaatatct caagtcaatg agaagattaa ccagagccta   7140
gcatttattc gtaaatccga tgaattatta cataatgtaa atgctggtaa atccaccata   7200
aatatcatga taactactat aattatagtg attatagtaa tattgttatc attaattgcc   7260
gttggactgc tcctatactg caaggccaga agcacaccag tcacactaag caaggatcaa   7320
ctgagtggta taaataatat tgcatttagt aactaaataa aaatagcacc taatcatgtt   7380
cttacaatgg tttcatatct gctcatagac aacccatcta tcattggatt ttcttaaaat   7440
ctgaacttca tcgaaactct catctataaa ccatctcact tacattattt aagtagattc   7500
ctagtttata gttatataaa acaattgaat accagattaa cttactattt gtaaaaaatg   7560
agaactgggg caaatatgtc acgaaggaat ccttgcaaat ttgaaattcg aggtcattgc   7620
ttgaatggta agaggtgtca ttttagtcat aattattttg aatggccacc ccatgcactg   7680
cttgtaagac aaaactttat gttaaacaga atacttaagt ctatggataa aagcatcgat   7740
actttatcag aaataagtgg agctgcagag ttggacagaa cagaagagta tgccctcggt   7800
gtagttggag tgctagagag ttatatagga tctataaata atataactaa acaatcagca   7860
tgtgttgcca tgagcaaact cctcactgaa ctcaacagtg atgacatcaa aaaactgagg   7920
gacaatgaag agccaaattc acccaagata agagtgtaca atactgtcat atcatatatt   7980
gaaagcaaca ggaaaaacaa taaacaaact atccatctgt taaaaagatt gccagcagac   8040
gtattgaaga aaaccataaa aaccacattg gatatccaca agagcataac catcaataac   8100
ccaaaagaat caactgttag tgatataaac gaccatgcca aaaataatga tactacctga   8160
caaatatcct tgtagtataa attccatact aataacaagt agttgtagag ttactatgta   8220
taatcaaaag aacacactat atttcaatca aaacaaccaa aataaccata tatactcacc   8280
gaatcaacca ttcaatgaaa tccattggac ctctcaagac ttgattgatg caattcaaaa   8340
ttttctacaa catctaggta ttactgatga tatatacaca atatatatat tagtgtcata   8400
acactcaatc ctaatgctta ccacatcatc aaactattaa ctcaaacaat tcaagccatg   8460
```

-continued

```
ggacaaaatg gatcccatta ttaatggaaa ttctgctaat gtgtatctaa ccgatagtta   8520
tttaaaaggt gttatttctt tctcagaatg taatgcttta ggaagttaca tattcaatgg   8580
tccttatctc aaaaatgatt ataccaactt aattagtaga caaaatccat taatagaaca   8640
cataaatcta aagaaactaa atataacaca gtccttaatg tctaagtatc ataaaggtga   8700
aataaaaata gaagaaccta cttattttca gtcattactt atgacataca agagtatgac   8760
ctcgttagaa cagattacta ccactaattt acttaaaaag ataataagaa gagctataga   8820
aattagtgat gtcaaagtct atgctatatt gaataaactg gggcttaaag aaaaagacaa   8880
gattaaatcc aacaatggac aagatgaaga caactcagtt attacaacca taatcaaaga   8940
tgatatactt ttagctgtta aggataatca atctcatctt aaagcagtca aaaatcactc   9000
tacaaaacaa aaagatacaa tcaaaacaac actcttgaag aaattaatgt gttcaatgca   9060
acatcctcca tcatggttaa tacattggtt taatttatac acaaaattaa acaacatatt   9120
aacacagtat cgatcaagtg aggtaaaaaa ccatggtttt atattgatag acaatcatac   9180
tctcaatgga ttccaattta ttttgaatca atatggttgt atagtttatc ataaggaact   9240
caaaagaatt actgtgacaa cctataatca attcttgaca tggaaaaata ttagccttag   9300
tagattaaat gtttgtttaa ttacatggat tagtaactgt ttgaacacat taaataaaag   9360
cttaggctta agatgcggat tcaataatgt tatcttgaca caactattcc tctatggaga   9420
ttgtatacta aaactattcc acaatgaggg gttctacata ataaaagagg tagagggatt   9480
tattatgtct ctaattttaa atataacaga agaagatcaa ttcagaaaac ggttttataa   9540
tagtatgctc aacaacatca cagatgctgc taataaagct cagaaaaatc tgctatcaag   9600
agtatgtcat acattattag ataagacagt atccgataat ataataaatg gcagatggat   9660
aattctatta agtaagttcc ttaaattaat taagcttgca ggtgacaata accttaacaa   9720
tctgagtgaa ttatattttt tgttcagaat atttggacac ccaatggtag atgaaagaca   9780
agccatggat gctgttaaag ttaattgcaa cgagaccaaa ttttacttgt taagcagttt   9840
gagtatgtta agaggtgcct ttatatatag aattataaaa ggatttgtaa ataattacaa   9900
cagatggcct actttaagga atgctattgt tttaccctta agatggttaa cttactataa   9960
actaaacact tatccttcct tgttggaact tacagaaaga gatttgattg ttttatcagg  10020
actacgtttc tatcgtgagt ttcggttgcc taaaaaagtg gatcttgaaa tgatcataaa  10080
tgataaggct atatcacctc ctaaaaattt gatatggact agtttcccta gaaattatat  10140
gccgtcacac atacaaaatt atatagaaca tgaaaaatta aaattttccg agagtgataa  10200
atcaagaaga gtattagagt actatttaag agataacaaa ttcaatgaat gtgatttata  10260
caactgtgta gttaatcaaa gttatcttaa caaccctaat catgtggtat ctttgacagg  10320
caaagaaaga gaactcagtg taggtagaat gtttgcaatg caaccaggaa tgttcagaca  10380
agttcaaata ttagcagaga aaatgatagc tgaaaacatt ttacaattct ttcctgaaag  10440
tcttacaaga tatggtgatc tagaactaca gaaaatatta gaattgaaag caggaataag  10500
taacaaatca aatcgttaca atgataatta caacaattac attagtaagt gctctatcat  10560
cacagatctc agcaaattca atcaagcatt tcgatatgaa acatcatgta tttgtagtga  10620
tgtactggat gaactgcatg gtgtacaatc tctatttttc tggttacatt tagctattcc  10680
tcatgtcaca ataatatgca catataggca tgcacccccc tatataagag atcatattgt  10740
agatcttaac aatgtagatg aacaaagtgg attatataga tatcatatgg gtggtatcga  10800
agggtggtgt caaaaactat ggaccataga agctatatca ctattggatc taatatctct  10860
```

-continued caaagggaaa ttctcaatta ctgctttaat taatggtgac aatcaatcaa tagatataag 10920
taaaccagtc agactcatgg aaggtcaaac tcatgctcaa gcagattatt tgctagcatt 10980
aaatagtctt aaattactgt ataaagagta tgcaggcata ggccacaaat taaaaggaac 11040
tgagacttat atatcaagag atatgcaatt tatgagtaaa acaattcaac ataacggtgt 11100
atattaccca gctagtataa agaaagtcct aagagtggga ccgtggataa acactatact 11160
tgatgatttc aaagtgagtc tagaatctat aggtagtttg acacaagaat tagaatatag 11220
aggagaaagt ctattatgca gtttaatatt tagaaatgta tggttatata atcaaattgc 11280
tttacaacta aaaaatcatg cattatgtaa caataaatta tatttggaca tattaaaggt 11340
tctgaaacac ttaaaaacct tttttaatct tgataatatt gatacagcat taacattgta 11400
tatgaatttg cccatgttat ttggtggtgg tgatcccaac ttgttatatc gaagtttcta 11460
tagaagaact cctgatttcc tcacagaggc tatagttcac tctgtgttca tacttagtta 11520
ttatacaaac catgatttaa aagataaact tcaagatctg tcagatgata gattgaataa 11580
gttcttaaca tgcataatca catttgacaa aaaccctaat gctgaattcg taacattgat 11640
gagagatcct caagctttag ggtctgagag acaagctaaa attactagcg aaatcaatag 11700
actggcagtt actgaggttt tgagcacagc tccaaacaaa atattctcca aaagtgcaca 11760
acactatacc actacagaga tagatctaaa tgatattatg caaaatatag aacctacata 11820
tcctcacggg ctaagagttg tttatgaaag tttacccttt tataaagcag agaaaatagt 11880
aaatcttata tccggtacaa aatctataac taacatactg gaaaagactt ctgccataga 11940
cttaacagat attgatagag ccactgagat gatgaggaaa aacataactt tgcttataag 12000
gatatttcca ttagattgta acagagataa aagggaaata ttgagtatgg aaaacctaag 12060
tattactgaa ttaagcaaat atgttaggga aagatcttgg tctttatcca atatagttgg 12120
tgttacatca cctagtatca tgtatacaat ggacatcaaa tatacaacaa gcactatagc 12180
tagtggcata atcatagaga aatataatgt taacagttta acacgtggtg agagaggacc 12240
cactaaacca tgggttggtt catctacaca agagaaaaaa acaatgccag tttataatag 12300
acaagtttta accaaaaaac agagagatca aatagatcta ttagcaaaat tggattgggt 12360
gtatgcatct atagataaca aggatgaatt catggaagaa cttagcatag gaattcttgg 12420
gttaacatat gagaaagcca aaaaattatt tccacaatat ttaagtgtta actatttgca 12480
tcgccttaca gtcagtagta gaccatgtga attccctgca tcaataccag cttatagaac 12540
tacaaattat cactttgata ctagccctat taatcgcata ttaacagaaa agtatggtga 12600
tgaagatatt gatatagtat tccaaaactg tataagcttt ggccttagct taatgtcagt 12660
agtagaacaa tttactaatg tatgtcctaa cagaattatt cttataccta agcttaatga 12720
gatacattta atgaaacctc ccatattcac aggtgatgtt gatattcaca agttaaaaca 12780
agtgatacaa aaacagcata tgtttttacc agacaaaata agtttgactc aatatgtgga 12840
attattctta agtaataaaa cactcaaatc tggatctcat gttaattcta atttaatatt 12900
ggcgcataag atatctgact attttcataa tacttacatt ttaagtacta atttagctgg 12960
acattggatt ctgattatac aacttatgaa agattctaag ggtatttttg aaaaagattg 13020
gggagaggga tatataactg atcatatgtt cattaatttg aaagttttct tcaatgctta 13080
taagacctat ctcttgtgtt ttcataaagg ttacggcaga gcaaagctgg agtgtgatat 13140
gaatacttca gatctcctat gtgtattgga attaatagac agtagttatt ggaagtctat 13200

-continued

```
gtctaaggta tttttagaac aaaaagttat caaatacatt cttagccagg atgcaagttt  13260
acatagagta aaaggatgtc atagcttcaa actatggttt cttaaacgtc ttaatgtagc  13320
agaattcaca gtttgccctt gggttgttaa catagattat catccaacac atatgaaagc  13380
aatattaact tatatagatc ttgttagaat gggattgata aatatagata aaatatacat  13440
taaaaataaa cacaaattca atgatgaatt ttatacttct aatctctttt acattaatta  13500
taacttctca gataatactc atctattaac taaacatata aggattgcta attctgaatt  13560
agaaaataat tacaacaaat tatatcatcc tacaccagaa accctagaaa atatactaac  13620
caatccggtt aaatgtaatg acaaaaagac actgaatgac tattgtatag gtaaaaatgt  13680
tgactcaata atgttaccat tgttatctaa taagaagctt attaaatcgc ctacaatgat  13740
tagaaccaat tacagcaaac aagatttgta taatttattt cctacggttg tgattgataa  13800
aattatagat cattcaggta atacagccaa atctaaccaa ctttacacta ctacttctca  13860
tcaaatacct ttagtgcaca atagcacatc actttattgc atgcttcctt ggcatcatat  13920
taatagattc aattttgtat ttagttctac aggttgtaaa attagtatag agtatatttt  13980
aaaagacctt ataattaaag atcctaattg tatagcattc ataggtgaag gagcagggaa  14040
tttattattg cgtacagtag tggaacttca tcccgatata agatatattt acagaagtct  14100
gaaggattgc aatgatcata gtttacctat tgagttttta aggctgtaca atggacatat  14160
caacattgat tatggtgaaa atttgaccat tcctgctaca gatgcaacca acaacattca  14220
ttggtcttat ttacatataa agtttgctga acctatcagt ctttttgtct gtgatgctga  14280
attgcctgta acagtcaact ggagtaaaat tataatagag tggagcaagc atgtaagaaa  14340
atgcaagtac tgttcctcag ttaataaatg tacgttaata gtaaaatatc atgctcaaga  14400
tgatatcgat ttcaaattag acaatataac tatattaaaa acttatgtat gcttaggcag  14460
taagttaaag gggtctgaag tttacttagt ccttacaata ggtcctgcaa atgtgttccc  14520
agtatttaat gtagtacaaa atgctaaatt gatactatca agaaccaaaa atttcatcat  14580
gcctaagaag gctgataaag agtctattga tgcaaatatt aaaagtttga taccctttct  14640
ttgttaccct ataacaaaaa aaggaattaa tactgcattg tcaaaactaa agagtgttgt  14700
tagtggagat atactatcat attctatagc aggacgtaat gaagttttca gcaataaact  14760
tataaatcat aagcatatga acatcttaaa atggttcaat catgttttaa atttcagatc  14820
aacagaacta aactataatc atttatatat ggtagaatct acatatcctt atctaagtga  14880
attgttaaac agcttgacaa ctaatgaact taaaaaactg attaaaatca caggtagttt  14940
gttatacaac tttcataatg aataatgaat aaaaatctta tattaaaaat tcccatagct  15000
acacactaac actgtattca attatagtta tttaaaatta aaaattatat aattttttaa  15060
taacttttag tgaactaatc ctaaaattat cattttgatc taggaggaat aaatttaaat  15120
ccaaatctaa ttggtttata tgtatattaa ctaaactacg agatattagt tttgacact  15180 ttttttctcg t                                                       15191
```

<210> SEQ ID NO 75
<211> LENGTH: 15225
<212> TYPE: DNA
<213> ORGANISM: respiratory syncytial virus

<400> SEQUENCE: 75

```
acgcgaaaaa atgcgtacta caaacttgca cattcggaaa aaatggggca aataagaatt     60
tgataagtgc tatttaagtc taaccttttc aatcagaaat ggggtgcaat tcactgagca    120
```

-continued

```
tgataaaggt tagattacaa aatttatttg acaatgacga agtagcattg ttaaaaataa    180
catgttatac tgacaaatta attcttctga ccaatgcatt agccaaagca gcaatacata    240
caattaaatt aaacggtata gtttttatac atgttataac aagcagtgaa gtgtgccctg    300
ataacaacat tgtagtaaaa tctaacttta caacaatgcc aatattacaa aacggaggat    360
acatatggga attgattgag ttgacacact gctctcaatt aaacggtcta atggatgata    420
attgtgaaat caaattttct aaaagactaa gtgactcagt aatgactaat tatatgaatc    480
aaatatctga tttacttggg cttgatctca attcatgaat tatgtttagt ctaactcaat    540
agacatgtgt ttattaccat tttagttaat ataaaaactc atcaaaggga aatggggcaa    600
ataaactcac ctaatcaatc aaactatgag cactacaaat gacaacacta ctatgcaaag    660
attaatgatc acggacatga gacccctgtc gatggattca ataataacat ctctcaccaa    720
agaaatcatc acacacaaat tcatatactt gataaacaat gaatgtattg taagaaaact    780
tgatgaaaga caagctacat ttacattctt agtcaattat gagatgaagc tactgcacaa    840
agtagggagt accaaataca agaaatacac tgaatataat acaaaatatg gcactttccc    900
catgcctata tttatcaatc atggcgggtt tctagaatgt attggcatta agcctacaaa    960
acacactcct ataatataca aatatgacct caacccgtaa attccaacaa aaaaaaccaa   1020
cccaaccaaa ccaagctatt cctcaaacaa caatgctcaa tagttaagaa ggagctaatc   1080
cgttttagta attaaaaata aaagtaaagc caataacata aattggggca aatacaaaga   1140
tggctcttag caaagtcaag ttaaatgata cattaaataa ggatcagctg ctgtcatcca   1200
gcaaatacac tattcaacgt agtacaggag ataatattga cactcccaat tatgatgtgc   1260
aaaaacacct aaacaaacta tgtggtatgc tattaatcac tgaagatgca aatcataaat   1320
tcacaggatt aataggtatg ttatatgcta tgtccaggtt aggaagggaa gacactataa   1380
agatacttaa agatgctgga tatcatgtta aagctaatgg agtagatata acaacatatc   1440
gtcaagatat aaatggaaag gaaatgaaat tcgaagtatt aacattatca agcttgacat   1500
cagaaataca agtcaatatt gagatagaat ctagaaaatc ctacaaaaaa atgctaaaag   1560
agatgggaga agtggctcca gaatataggc atgattctcc agactgtggg atgataatac   1620
tgtgtatagc agcacttgta ataaccaaat tagcagcagg agacagatca ggtcttacag   1680
cagtaattag gagggcaaac aatgtcttaa aaaatgaaat aaaacgctac aagggtctca   1740
taccaaagga tatagctaac agtttttatg aagtgtttga aaaacaccct catcttatag   1800
atgtttttgt gcactttggc attgcacaat catcaacaag agggggtagt agagttgaag   1860
gaatctttgc aggattgttt atgaatgcct atggttcagg gcaagtaatg ctaagatggg   1920
gagttttagc caaatctgta aaaaatatca tgctaggtca tgctagtgtc caggcagaaa   1980
tggagcaagt tgtggaagtc tatgagtatg cacagaagtt gggaggagaa gctggattct   2040
accatatatt gaacaatcca aaagcatcat tgctgtcatt aactcaattt cctaacttct   2100
caagtgtggt cctaggcaat gcagcaggtc taggcataat gggagagtat agaggtacgc   2160
caagaaacca ggatctttat gatgcagcca aagcatatgc agagcaactc aaagaaaatg   2220
gagtaataaa ctacagtgta ttagacttaa cagcagaaga attggaagcc ataaagaatc   2280
aactcaaccc taaagaagat gatgtagagc tttaagttaa caaaaaatac ggggcaaata   2340
agtcaacatg gagaagtttg cacctgaatt tcatggagaa gatgcaaata acaaagctac   2400
caaattccta gaatcaataa agggcaagtt cgcatcatcc aaagatccta agaagaaaga   2460
```

-continued

```
tagcataata tctgttaact caatagatat agaagtaacc aaagagagcc cgataacatc   2520
tggcaccaac atcatcaatc caacaagtga agccgacagt accccagaaa ccaaagccaa   2580
ctacccaaga aaacccctag taagcttcaa agaagatctc accccaagtg acaacccttt   2640
ttctaagttg tacaaagaaa caatagaaac atttgataac aatgaagaag aatctagcta   2700
ctcatatgaa gagataaatg atcaaacaaa tgacaacatt acagcaagac tagatagaat   2760
tgatgaaaaa ttaagtgaaa tattaggaat gctccataca ttagtagttg caagtgcagg   2820
acccacttca gctcgcgatg gaataagaga tgctatggtt ggtctgagag aagaaatgat   2880
agaaaaaata agagcggaag cattaatgac caatgatagg ttagaggcta tggcaagact   2940
taggaatgag gaaagcgaaa aaatggcaaa agacacctca gatgaagtgc ctcttaatcc   3000
aacttccaaa aaattgagtg acttgttgga agacaacgat agtgacaatg atctgtcact   3060
tgatgatttt tgatcagtga tcaactcact cagcaatcaa caacatcaat aaaacagaca   3120
tcaatccatt gaatcaactg ccagaccgaa caaacaaatg tccgtcagcg gaaccaccaa   3180
ccaatcaatc aaccaactga tccatcagca acctgacgaa attaacaata tagtaacaaa   3240
aaaagaacaa gatggggcaa atatggaaac atacgtgaac aagcttcacg aaggctccac   3300
atacacagca gctgttcagt acaatgttct agaaaaagat gatgatcctg catcactaac   3360
aatatgggtg cctatgttcc agtcatctgt accagcagac ttgctcataa aagaacttgc   3420
aagcatcaac atactagtga agcagatctc tacgcccaaa ggaccttcac tacgagtcac   3480
gattaactca agaagtgctg tgctggctca aatgcctagt aatttcatca taagcgcaaa   3540
tgtatcatta gatgaaagaa gcaaattagc atatgatgta actacacctt gtgaaatcaa   3600
agcatgcagt ctaacatgct taaaagtgaa aagtatgtta actacagtca aagatcttac   3660
catgaagaca ttcaacccca ctcatgagat cattgctcta tgtgaatttg aaaatattat   3720
gacatcaaaa agagtaataa taccaaccta tctaagacca attagtgtca aaaacaagga   3780
tctgaactca ctagaaaaca tagcaaccac cgaattcaaa aatgctatca ccaatgcgaa   3840
aattattccc tatgctggat tagtattagt tatcacagtt actgacaata aaggagcatt   3900
caaatatatc aagccacaga gtcaatttat agtagatctt ggtgcctacc tagaaaaaga   3960
gagcatatat tatgtgacta ctaattggaa gcatacagct acacgttttt caatcaaacc   4020
actagaggat taaatttaat tatcaacact gaatgacagg tccacatata tcctcaaact   4080
acacactata tccaaacatc atgaacatct acactacaca cttcatcaca caaaccaatc   4140
ccactcaaaa tccaaaatca ctaccagcca ctatctgcta gacctagagt gcgaataggt   4200
aaataaaacc aaaatatggg gtaaatagac attagttaga gttcaatcaa tctcaacaac   4260
catttatacc gccaattcaa tacatatact ataaatctta aaatgggaaa tacatccatc   4320
acaatagaat tcacaagcaa attttggccc tattttacac taatacatat gatcttaact   4380
ctaatctctt tactaattat aatcactatt atgattgcaa tactaaataa gctaagtgaa   4440
cataaaacat tctgtaacaa tactcttgaa ctaggacaga tgcatcaaat caacacatag   4500
tgctctacca tcatgctgtg tcaaattata atcctgtata tataaacaaa caaatccaat   4560
cttctcacag agtcatggtg tcgcaaaacc acgccaacta tcatggtagc atagagtagt   4620
tatttaaaaa ttaacataat gatgaattat tagtatggga tcaaaaacaa cattggggca   4680
aatgcaacca tgtccaaaca caagaatcaa cgcactgcca ggactctaga aaagacctgg   4740
gatactctca atcatctaat tgtaatatcc tcttgtttat acagattaaa tttaaaatct   4800
atagcacaaa tagcactatc agttctggca atgataatct caacctctct cataattgca   4860
```

gccataatat tcatcatctc tgccaatcac aaagttacac taacaacggt cacagttcaa 4920
acaataaaaa accacactga aaaaaacatc accacctacc ttactcaagt cccaccagaa 4980
agggttagct catccaaaca acctacaacc acatcaccaa tccacacaaa ttcagccaca 5040
acatcaccca acacaaagtc agaaacacac cacacaacag cacaaaccaa aggcagaacc 5100
accacctcaa cacagaccaa caagccgagc acaaaaccac gcctaaaaaa tccaccaaaa 5160
aaaccaaaag atgattacca ttttgaagtg ttcaacttcg ttccctgtag tatatgtggc 5220
aacaatcaac tttgcaaatc catctgtaaa acaataccaa gcaacaaacc aaagaagaaa 5280
ccaaccatca aacccacaaa caaaccaacc accaaaacca caaacaaaag agacccaaaa 5340
acaccagcca aaacgacgaa aaaagaaact accaccaacc caacaaaaaa accaaccctc 5400
acgaccacag aaagagacac cagcacctca caatccactg tgctcgacac aaccacatta 5460
gaacacacaa tccaacagca atccctccac tcaaccaccc ccgaaaacac acccaactcc 5520
acacaaacac ccacagcatc cgagccctct acatcaaatt ccacccaaaa tacccaatca 5580
catgcttagt tattcaaaaa ctacatctta gcagaaaacc gtgacctatc aagcaagaac 5640
gaaattaaac ctggggcaaa taaccatgga gctgctgatc cacaggttaa gtgcaatctt 5700
cctaactctt gctattaatg cattgtacct cacctcaagt cagaacataa ctgaggagtt 5760
ttaccaatcg acatgtagtg cagttagcag aggttatttt agtgctttaa gaacaggttg 5820
gtataccagt gtcataacaa tagaattaag taatataaaa gaaaccaaat gcaatggaac 5880
tgacactaaa gtaaaactta taaaacaaga attagataag tataagaatg cagtgacaga 5940
attacagcta cttatgcaaa acacaccagc tgccaacaac cgggccagaa gagaagcacc 6000
acagtatatg aactatacaa tcaataccac taaaaaccta aatgtatcaa taagcaagaa 6060
gaggaaacga agatttctgg gcttcttgtt aggtgtagga tctgcaatag caagtggtat 6120
agctgtatcc aaagttctac accttgaagg agaagtgaac aagatcaaaa atgctttgtt 6180
atctacaaac aaagctgtag tcagtctatc aaatggggtc agtgttttaa ccagcaaagt 6240
gttagatctc aagaattaca taaataacca attattaccc atagtaaatc aacagagctg 6300
tcgcatctcc aacattgaaa cagttataga attccagcag aagaacagca gattgttgga 6360
aatcaacaga gaattcagtg tcaatgcagg tgtaacaaca cctttaagca cttacatgtt 6420
aacaaacagt gagttactat cattgatcaa tgatatgcct ataacaaatg atcagaaaaa 6480
attaatgtca agcaatgttc agatagtaag gcaacaaagt tattctatca tgtctataat 6540
aaaggaagaa gtccttgcat atgttgtaca gctacctatc tatggtgtaa tagatacacc 6600
ttgctggaaa ttacacacat cacctctatg caccaccaac atcaaagaag gatcaaatat 6660
ttgtttaaca aggactgata gaggatggta ttgtgataat gcaggatcag tatccttctt 6720
tccacaggct gacacttgta aagtacagtc caatcgagta ttttgtgaca ctatgaacag 6780
tttgacatta ccaagtgaag tcagcctttg taacactgac atattcaatt ccaagtatga 6840
ctgcaaaatt atgacatcaa aaacagacat aagcagctca gtaattactt ctcttggagc 6900
tatagtgtca tgctatggta aaactaaatg cactgcatcc aacaaaaatc gtgggattat 6960
aaagacattt tctaatggtt gtgactatgt gtcaaacaaa ggagtagata ctgtgtcagt 7020
gggcaacact ttatactatg taaacaagct ggaaggcaag aacctttatg taaaagggga 7080
acctataata aattactatg accctctagt gtttccttct gatgagtttg atgcatcaat 7140
atctcaagtc aatgaaaaaa tcaatcaaag tttagctttt attcgtagat ctgatgaatt 7200

-continued

```
actacataat gtaaatactg gcaaatctac tacaaatatt atgataacta caattattat   7260
agtaatcatt gtagtattgt tatcattaat agctattggt ttgctgttgt attgcaaagc   7320
caaaaacaca ccagttacac taagcaaaga ccaactaagt ggaatcaata atattgcatt   7380
cagcaaatag acaaaaaacc acctgatcat gtttcaacaa cagtctgctg atcaccaatc   7440
ccaaatcaac ccataacaaa cacttcaaca tcacagtaca ggctgaatca tttcttcaca   7500
tcatgctacc cacacaacta agctagatcc ttaactcata gttacataaa aacctcaagt   7560
atcacaatca aacactaaat caacacatca ttcacaaaat taacagctgg ggcaaatatg   7620
tcgcgaagaa atccttgtaa atttgagatt agaggtcatt gcttgaatgg tagaagatgt   7680
cactacagtc ataattactt tgaatggcct cctcatgcct tactagtgag gcaaaacttc   7740
atgttaaaca agatactcaa gtcaatggac aaaagcatag acactttgtc tgaaataagt   7800
ggagctgctg aactggacag aacagaagaa tatgctcttg gtatagttgg agtgctagag   7860
agttacatag gatctataaa caacataaca aaacaatcag catgtgttgc tatgagtaaa   7920
cttcttattg agatcaatag tgatgacatt aaaaagctga gagataatga agaacccaat   7980
tcacctaaga taagagtgta caatactgtt atatcataca ttgagagcaa tagaaaaaac   8040
aacaagcaaa caatccatct gctcaaaaga ctaccagcag acgtgctgaa gaagacaata   8100
aaaaacacat tagatatcca caaaagcata atcataagca acccaaaaga gtcaaccgtg   8160
aatgatcaaa atgaccaaac caaaaataat gatattaccg gataaatatc cttgtagtat   8220
atcatccata ttgatttcaa gtgaaagcat gattgctaca ttcaatcata aaaacatatt   8280
acaatttaac cataaccatt tggataacca ccagcgttta ttaaataata tatttgatga   8340
aattcattgg acacctaaaa acttattaga tgccactcaa caatttctcc aacatcttaa   8400
catccctgaa gatatatata caatatatat attagtgtca taatgcttgg ccataacgat   8460
tctatatcat ccaaccataa aactatctta ataaggttat gggacaaaat ggatcccatt   8520
attaatggaa actctgctaa tgtgtatcta actgatagtt atttaaaagg tgttatctct   8580
ttttcagaat gtaatgcttt agggagttac ctttttaacg gcccttatct caaaaatgat   8640
tacaccaact taattagtag acaaagtcca ctactagagc atatgaatct taaaaaacta   8700
actataacac agtcattaat atctagatat cataaaggtg aactgaaatt agaagaacca   8760
acttatttcc agtcattact tatgacatat aaaagcatgt cctcgtctga acaaattgct   8820
acaactaact tacttaaaaa aataatacga agagctatag aaataagtga tgtaaaggtg   8880
tacgccatct tgaataaact aggactaaag gaaaaggaca gagttaagcc caacaataat   8940
tcaggtgatg aaaactcagt acttacaact ataattaaag atgatatact ttcggctgtg   9000
gaaagcaatc aatcatatac aaattcagac aaaaatcact cagtaaatca aaatatcact   9060
atcaaaacaa cactcttgaa aaaattgatg tgttcaatgc aacatcctcc atcatggtta   9120
atacactggt tcaatttata tacaaaatta aataacatat taacacaata tcgatcaaat   9180
gaggtaaaaa gtcatgggtt tatattaata gataatcaaa ctttaagtgg ttttcagttt   9240
attttaaatc aatatggttg tatcgtttat cataaaggac tcaaaaaaat cacaactact   9300
acttacaatc aatttttaac atggaaagac atcagcctta gcagattaaa tgtttgctta   9360
attacttgga taagtaattg tttgaataca ttaaataaaa gcttagggct gagatgtgga   9420
ttcaataatg ttgtgttatc acaattattt ctttatggag attgtatact gaaattattt   9480
cataatgaag gcttctacat aataaaagaa gtagagggat ttattatgtc tttaattcta   9540
aacataacag aagaagatca atttaggaaa cgattttata atagcatgct aaataacatc   9600
```

```
acagatgcag ctattaaggc tcaaaagaac ctactatcaa gggtatgtca cactttatta   9660
gacaagacag tgtctgataa tatcataaat ggtaaatgga taatcctatt aagtaaattt   9720
cttaaattga ttaagcttgc aggtgataat aatctcaata atttgagtga gctatatttt   9780
ctcttcagaa tctttggaca tccaatggtt gatgaaagac aagcaatgga tgctgtaaga   9840
attaactgta atgaaactaa gttctactta ttaagtagtc taagtacgtt aagaggtgct   9900
ttcatttata gaatcataaa agggtttgta aatacctaca acagatggcc cactttaagg   9960
aatgctattg tcctacctct aagatggtta aactattata aacttaatac ttatccatct  10020
ctacttgaaa tcacagaaaa tgatttgatt attttatcag gattgcggtt ctatcgtgaa  10080
tttcatctgc ctaaaaaagt ggatcttgaa atgataataa atgacaaagc catttcacct  10140
ccaaaagatc taatatggac tagttttcct agaaattaca tgccatcaca tatacaaaat  10200
tatatagaac atgaaaagtt gaagttctct gaaagcgaca gatcaagaag agtactagag  10260
tattacttga gagataataa attcaatgaa tgcgatctat acaattgtgt agtcaatcaa  10320
agctatctca acaactctaa tcacgtggta tcactaactg gtaaagaaag agagctcagt  10380
gtaggtagaa tgtttgctat gcaaccaggt atgtttaggc aaatccaaat cttagcagag  10440
aaaatgatag ccgaaaatat tttacaattc ttccctgaga gtttgacaag atatggtgat  10500
ctagagcttc aaaagatatt agaattaaaa gcaggaataa gcaacaagtc aaatcgttat  10560
aatgataact acaacaatta tatcagtaaa tgttctatca ttacagatct tagcaaattc  10620
aatcaagcat ttagatatga aacatcatgt atctgcagtg atgtattaga tgaactgcat  10680
ggagtacaat ctctgttctc ttggttgcat ttaacaatac ctcttgtcac aataatatgt  10740
acatatagac atgcacctcc tttcataaag gatcatgttg ttaatcttaa tgaagttgat  10800
gaacaaagtg gattatacag atatcatatg ggtggtattg agggctggtg tcaaaaactg  10860
tggaccattg aagctatatc attattagat ctaatatctc tcaaagggaa attctctatc  10920
acagctctga taaatggtga taatcagtca attgatataa gtaaaccagt tagacttata  10980
gagggtcaga cccatgctca agcagattat ttgttagcat taaatagcct taaattgcta  11040
tataaagagt atgcaggtat aggccataag cttaagggaa cagagaccta tatatcccga  11100
gatatgcagt tcatgagcaa aacaatccag cacaatggag tgtactatcc agccagtatc  11160
aaaaaagtcc tgagagtagg tccatggata aatacaatac ttgatgattt taaagttagt  11220
ttagaatcta taggtagctt aacacaggag ttagaataca gaggggaaag cttattatgc  11280
agtttaatat ttaggaacat ttggttatac aatcaaattg ctttgcaact ccgaaatcat  11340
gcattatgta acaataagct atatttagat atattgaaag tattaaaaca cttaaaaact  11400
ttttttaatc ttgatagtat cgatatggcg ttatcattgt atatgaattt gcctatgctg  11460
tttggtggtg gtgatcctaa tttgttatat cgaagctttt ataggagaac tccagacttc  11520
cttacagaag ctatagtaca ttcagtgttt gtgttgagct attatactgg tcacgattta  11580
caagataagc tccaggatct tccagatgat agactgaaca aattcttgac atgtgtcatc  11640
acattcgata aaaatcccaa tgccgagttt gtaacattga tgagggatcc acaggcgtta  11700
gggtctgaaa ggcaagctaa aattactagt gagattaata gattagcagt aacagaagtc  11760
ttaagtatag ctccaaacaa aatattttct aaaagtgcac aacattatac taccactgag  11820
attgatctaa atgacattat gcaaaatata gaaccaactt accctcatgg attaagagtt  11880
gtttatgaaa gtctaccttt ttataaagca gaaaaaatag ttaatcttat atcaggaaca  11940
```

```
aaatccataa ctaatatact tgaaaaaaca tcagcaatag atacaactga tattaatagg  12000
gctactgata tgatgaggaa aaatataact ttacttataa ggatacttcc actagattgt  12060
aacaaagaca aaagagagtt attaagttta gaaaatctta gtataactga attaagcaag  12120
tatgtaagag aaagatcttg gtcattatcc aatatagtag gagtaacatc gccaagtatt  12180
atgttcacaa tggacattaa atatacaact agcactatag ccagtggtat aattatagaa  12240
aaatataatg ttaatagttt aactcgtggt gaaagaggac ctactaagcc atgggtaggt  12300
tcatctacgc aggagaaaaa aacaatgcca gtgtacaata gacaagtttt aaccaaaaag  12360
caaagagacc aaatagattt attagcaaaa ttagactggg tatatgcatc catagacaac  12420
aaagatgaat tcatggaaga actgagtact ggaacacttg gactgtcata tgaaaaagcc  12480
aaaaagttgt ttccacaata tctaagtgtc aattatttac accgtttaac agtcagtagt  12540
agaccatgtg aattccctgc atcaatacca gcttatagaa caacaaatta tcatttcgat  12600
actagtccta tcaatcatgt attaacagaa aagtatggag atgaagatat cgacattgtg  12660
tttcaaaatt gcataagttt tggtcttagc ctgatgtcgg ttgtggaaca attcacaaac  12720
atatgtccta atagaattat tctcataccg aagctgaatg agatacattt gatgaaacct  12780
cctatattta caggagatgt tgatatcatc aagttgaagc aagtgataca aaaacagcat  12840
atgttcctac cagataaaat aagtttaacc caatatgtag aattattcct aagtaacaaa  12900
gcacttaaat ctggatctaa catcaattct aatttaatat tagtacataa aatgtctgat  12960
tattttcata atgcttatat tttaagtact aatttagctg gacattggat tctaattatt  13020
caacttatga aagattcaaa aggtattttt gaaaaagatt ggggagaggg gtacataact  13080
gatcatatgt tcattaattt gaatgttttc tttaatgctt ataagactta tttgctatgt  13140
tttcataaag gttatggtaa agcaaaatta gaatgtgata tgaacacttc agatcttctt  13200
tgtgttttgg agttaataga cagtagctac tggaaatcta tgtctaaagt tttcctagaa  13260
caaaaagtca taaaatacat agtcaatcaa gacacaagtt tgcatagaat aaaaggctgt  13320
cacagtttta agttgtggtt tttaaaacgc cttaataatg ctaaatttac cgtatgccct  13380
tgggttgtta acatagatta tcacccaaca catatgaaag ctatattatc ttacatagat  13440
ttagttagaa tggggttaat aaatgtagat aaattaacca ttaaaaataa aaacaaattc  13500
aatgatgaat tttacacatc aaatctcttt tacattagtt ataacttttc agacaacact  13560
catttgctaa caaaacaaat aagaattgct aattcagaat tagaagataa ttataacaaa  13620
ctatatcacc caaccccaga aactttagaa aatatatcat taattcctgt taaaagtaat  13680
aatagtaaca aacctaaatt ttgtataagt ggaaataccg aatctataat gatgtcaaca  13740
ttctctaata aaatgcatat taaatcttcc actgttacca caagattcaa ttatagcaaa  13800
caagacttgt acaatttatt tccaaatgtt gtgatagaca ggattataga tcattcaggt  13860
aatacagcaa aatctaacca actttacatc accacttcac atcagacatc tttagtaagg  13920
aatagtgcat cactttattg catgcttcct tggcatcatg tcaatagatt taactttgta  13980
tttagttcca caggatgcaa gatcagtata gagtatattt taaaagatct taagattaag  14040
gaccccagtt gtatagcatt cataggtgaa ggagctggta acttattatt acgtacggta  14100
gtagaacttc atccagacat aagatacatt tacagaagtt taaaagattg caatgatcat  14160
agtttaccta ttgaatttct aagattatac aacgggcata taaacataga ttatggtgag  14220
aatttaacca ttcctgctac agatgcaact aataacattc attggtctta tttacatata  14280
aaatttgcag aacctattag catctttgtc tgcgatgctg aattacctgt tacagccaat  14340
```

tggagtaaaa ttataattga atggagtaag catgtaagaa agtgcaagta ctgttcttct 14400
gtaaatagat gcattttaat cgcaaaatat catgctcaag atgatattga tttcaaatta 14460
gataacatta ctatattaaa aacttacgtg tgcctaggta gcaagttaaa aggatctgaa 14520
gtttacttag tccttacaat aggccctgca aatatacttc ctgtttttga tgttgtgcaa 14580
aatgctaaat tgatttttc aagaactaaa aatttcatta tgcctaaaaa aactgacaag 14640
gaatctatcg atgcaaatat taaaagctta atacctttcc tttgttaccc tataacaaaa 14700
aaaggaatta agacttcatt gtcaaaattg aagagtgtag ttaatgggga tatattatca 14760
tattctatag ctggacgtaa tgaagtattc agcaacaagc ttataaacca caagcatatg 14820
aatatcctaa aatggctaga tcatgtttta aattttagat cagctgaact taattacaat 14880
catttataca tgatagagtc cacatatcct tacttaagtg aattgttaaa tagtttaaca 14940
accaatgagc tcaagaaact gattaaaata acaggtagtg tactatacaa ccttcccaac 15000
gaacagtaac ttaaaatatc attaacaagt ttggtcaaat ttagatgcta acacatcatt 15060
atattatagt tattaaaaaa tatgcaaact tttcaataat ttagcttact gattccaaaa 15120
ttatcatttt atttttaagg ggttgaataa aagtctaaaa ctaacaatga tacatgtgca 15180
tttacaacac aacgagacat tagtttttga cacttttttt ctcgt 15225

<210> SEQ ID NO 76
<211> LENGTH: 15191
<212> TYPE: DNA
<213> ORGANISM: respiratory syncytial virus
<400> SEQUENCE: 76
acgcgaaaaa atgcgtacaa caaacttgcg taaaccaaaa aaatggggca aataagaatt 60
tgataagtac cacttaaatt taactccctt ggttagagat gggcagcaat tcattgagta 120
tgataaaagt tagattacaa aatttgtttg acaatgatga agtagcattg ttaaaaataa 180
catgctatac tgacaaatta atacatttaa ctaatgcatt ggctaaggca gtgatacata 240
caatcaaatt gaatggcatt gtatttgtgc atgttattac aagtagtgat atttgcccta 300
ataataatat tgtagtgaaa tccaatttca caacaatgcc agtgttacaa aatggaggtt 360
atatatggga aatgatggaa ttaacacact gctctcaacc taatggccta atagatgaca 420
attgtgaaat taaattctcc aaaaaactaa gtgattcaac aatgaccaat tatatgaatc 480
aattatctga attacttgga tttgatctta atccataaat tataataaat atcaactagc 540
aaatcaatgt cactaacacc attagttaat ataaaacttg acagaagata aaaatggggc 600
aaataaatca attcagccga cccaaccatg gacacaacac acaatgacac cacaccacaa 660
agactgatga tcacagacat gagaccattg tcacttgaga ctataataat atcactaacc 720
agagacatca taacacacag atttatatac ttgataaatc atgaatgtat agtgagaaaa 780
cttgatgaaa gacaggccac atttacattc ctggtcaact atgaaatgaa actattgcac 840
aaagtgggaa gcactaaata caaaaaatat actgaataca acacaaaata tggcactttt 900
cctatgccaa tatttatcaa tcatgatggg ttcttagaat gcattggcat taagcctaca 960
aagcacactc ccataatata caagtatgat ctcaatccat gaatttcaac acaagagtca 1020
cacaatctga aataacaact tcatgcataa ccacactcca tagttcaaat ggagcctgaa 1080
aattatagta atttaaaatt aaggagagac ataagatgaa agatggggca aatacaaaaa 1140
tggctcttag caaagtcaag ttgaatgata cactcaacaa agatcaactt ctgtcatcca 1200

-continued

```
gcaaatacac catccaacgg agcacaggag atagtattga tactcctaat tatgatgtgc   1260
agaaacacat caataagtta tgtggcatgt tattaatcac agaagatgct aatcataaat   1320
tcactgggtt aataggtatg ttatatgcta tgtctagatt aggaagagaa gacaccataa   1380
aaatactcag agatgcggga tatcatgtaa aagcaaatgg agtggatgta acaacacatc   1440
gtcaagatat taatgggaaa gaaatgaaat ttgaagtgtt aacattgtca agcttaacaa   1500
ctgaaattca aatcaacatt gagatagaat ctagaaaatc ctacaaaaaa atgctaaaag   1560
aaatgggaga ggtagctcca gaatacaggc atgactctcc tgattgtggg atgataatat   1620
tatgtatagc ggcattagta ataaccaaat tagcagcagg ggatagatct ggtcttacag   1680
ctgtgattag gagggctaat aatgtcctaa aaaatgaaat gaaacgttat aaaggcttac   1740
tacccaagga tatagccaac agcttctatg aagtgtttga aaaatatcct cactttatag   1800
atgtttttgt tcattttggt atagcacaat cttctaccag aggtggcagt agagttgaag   1860
ggatttttgc tggattgttt atgaatgcct atggtgcagg gcaagtgatg ttacggtggg   1920
gggtcttagc aaaatcagtt aaaaatatta tgctaggaca cgctagtgtg caagcagaaa   1980
tggaacaagt tgtggaggtt tatgaatatg cccaaaaatt gggtggagaa gcagggttct   2040
accatatatt gaacaaccca aaagcatcat tattgtcttt gactcaattt cctcacttct   2100
ccagtgtagt attaggcaat gctgctggcc taggcataat gggagaatac agaggtacac   2160
caaggaatca agatctatat gatgctgcaa aagcatatgc tgaacaactc aaagaaaatg   2220
gtgtgattaa ctacagtgta ttagacttga cagcagaaga actagaggct atcaaacatc   2280
agcttaatcc aaaagataat gatgtagagc tttgagttaa taaaaaaaat ggggcaaata   2340
aaacatcatg gaaaagtttg ctcctgaatt ccatggagaa gatgcaaaca acagagctac   2400
caaattccta gaatcaataa agggcaaatt cacatcacct aaagatccca agaaaaaaga   2460
tagtatcata tctgtcaact caatagatat agaagtaacc aaagaaagcc ctataacatc   2520
aaattcaacc attataaacc caacaaatga gacagatgat actgtaggga acaagcccaa   2580
ttatcaaaga aaacctctag taagtttcaa agaagaccct acgccaagtg ataatccctt   2640
ttcaaaacta tacaaagaaa ccatagaaac atttgataac aatgaagaag aatctagcta   2700
ttcatatgaa gaaataaatg atcagacaaa cgataatata acagcaagat tagataggat   2760
tgatgaaaaa ttaagtgaaa tactaggaat gcttcacaca ttagtagtag cgagtgcagg   2820
acctacatct gctcgggatg gtataagaga tgccatggtt ggtttaagag aagacatgat   2880
agaaaaaatc agaactgaag cattaatgac caatgacaga ctagaagcta tggcaagact   2940
caggaatgag gaaagtgaaa agatggcaaa agacacatca gatgaagtgt ctctcaatcc   3000
aacatcagag aaattgaaca acctgttgga agggaatgat agtgacaatg atctatcact   3060
tgatgatttc tgatcagtta ccaatctgta catcaacaca caacaccaac agaagaccaa   3120
caaacaaacc aactcaccca tccaaccaaa catctatacg ccaatcagcc aatccaaaac   3180
tagccacccg gaaaaaatag atactatagt tacaaaaaaa gatggggcaa atatggaaac   3240
atacgtgaac aaacttcacg aaggctccac atacacagct gctgttcaat acaatgtctt   3300
agaaaaagac gatgaccctg catcacttac aatatgggtg cccatgttcc aatcatccat   3360
gccagcagat ttacttataa aagaactagc taatgtcaac atactagtga aacaaatatc   3420
cacacccaat ggaccttcat taagagtcat gataaactca agaagtgcag tgctagcaca   3480
aatgcccagc aaatttacca tatgtgccaa tgtgtccttg gatgaaagaa gcaagctggc   3540
atatgatgta accacaccct gtgaaatcaa ggcatgtagt ctaacatgcc taaaatcaaa   3600
```

```
aaatatgtta actacagtta aagatctcac tatgaaaaca ctcaacccaa cacatgacat   3660
cattgcttta tgtgaatttg aaaatatagt aacatcaaaa aaagtcataa taccaacata   3720
cctaagatcc atcagtgtca gaaataaaga tctgaacaca cttgaaaata taacaaccac   3780
tgaattcaaa aatgccatca caaatgcaaa aatcatccct tactcaggat tactgttagt   3840
catcacagtg actgacaaca aaggagcatt caaatacata aagccacaaa gtcaatttat   3900
agtagatctt ggagcttacc tagaaaaaga aagtatatat tatgttacaa caaattggaa   3960
gcacacagct acacgatttg caatcaaacc catggaagat taaccttttt cttctacatc   4020
agtgagttga ttcatacaaa ctttctacct acattcttca cttcaccatc ataatcacca   4080
accctctgtg gttcaactaa tcaaacaaaa cccatctgga gcctcagatc atcccaagtc   4140
attgttcatc agatctagta ctcaaataag ttaataaaaa tatccacatg ggcaaataa    4200
tcattggagg aaatccaact aatcacaata tctgtcaaca tagacaagtc aacacgccag   4260
gcaaaatcaa ccaatggaaa atacatccat aacaatagaa ttctcaagca aattctggcc   4320
ttactttaca ctaatacaca tgataacaac aataatctct ttgctaatca taatctccat   4380
catgattgca atactgaaca aactctgtga atataacgta ttccataaca aaacctttga   4440
gctaccaaga gctcgagtca atacatagca ttcaccaatc tgatggcaca aaacagtaac   4500
cttgcatttg taagtgaaca accctcacct ctttacaaaa ccacatcaac atctcaccat   4560
gcaagccatc atccatatta taaagtagtt aattaaaaat aatcataaca atgaactaag   4620
atattaagac taacaataac gttggggcaa atgcaaacat gtccaaaaac aaggaccaac   4680
gcaccaccaa gacactagaa aagacctggg acactctcaa tcatctatta ttcatatcat   4740
cgtgcttata caagttaaat cttaaatcta tagcacaaat cacattatcc attctggcaa   4800
tgataatctc aacttcactt ataattgcag ccatcatatt catagcctcg gcaaaccaca   4860
aagtcacact aacaactgca atcatacaag atgcaacaag ccagatcaag aacacaaccc   4920
caacatacct cacccagaat ccccagcttg gaatcagctt ctccaatctg tctgaaacta   4980
catcacaaac caccaccata ctagcttcaa caacaccaag tgtcaagtca accctgcaat   5040
ccacaacagt caagaccaaa aacacaacaa caaccaaaat acaacccagc aagcccacca   5100
caaaacaacg ccaaaacaaa ccaccaaaca aacccaataa tgattttcac tttgaagtgt   5160
tcaactttgt accttgcagc atatgcagca acaatccaac ctgctgggct atctgtaaaa   5220
gaataccaaa caaaaaacct ggaaagaaaa ccaccaccaa gcccacaaaa aaaccaacca   5280
tcaagacaac caaaaaagat ctcaaacctc aaaccacaaa accaaaggaa gtacctacca   5340
ccaagcccac agaaaagcca accatcaaca ccaccaaaac aaacatcaga actacactgc   5400
tcaccaacaa taccacagga aatccagaac acacaagtca aaagggaacc ctccactcaa   5460
cctcctccga tggcaatcca agcccttcac aagtctatac aacatccgag tacctatcac   5520
aacctccatc tccatccaac acaacaaacc agtagtcatt aaaaagcgta ttattgcaaa   5580
aagccatgac caaatcaacc agaatcaaaa tcaactctgg ggcaaataac aatggagttg   5640
ccaatcctca aaacaaatgc aattaccgca atccttgctg cagtcacact ctgttttgct   5700
tccagtcaaa acatcactga agaattttat caaacaacat gcagtgcagt cagcaaaggc   5760
tatcttagtg ctctaagaac tggttggtat actagtgtta taactataga attaagtaat   5820
atcaaggaaa ataagtgtaa tggaacagac gctaaggtaa aattgataaa acaagaatta   5880
gataaatata aaagtgctgt aacagaattg cagttgctca tgcaaagcac accggcaacc   5940
```

-continued

```
aacaatcgag ccagaagaga actaccaagg tttatgaatt atacactcaa caataccaaa   6000
aataccaatg taacattaag caagaaaagg aaaagaagat ttcttggctt tttgttaggt   6060
gttggatctg caatcgccag tggcattgct gtatctaagg tcctgcacct agaaggggaa   6120
gtgaacaaaa tcaaaagtgc tctactatcc acaaacaagg ctgtagtcag cttatcaaat   6180
ggagttagtg tcttaaccag caaagtgtta gacctcaaaa actatataga taaacagttg   6240
ttacctattg tgaacaagca aagctgtagc atatcaaaca ttgaaactgt gatagagttc   6300
caacaaaaga acaacagact actagagatt accagggaat ttagtgttaa tgcaggtgta   6360
actacacctg taagcactta tatgttaaca aatagtgaat tattatcatt aatcaatgat   6420
atgcctataa caaatgatca gaaaaagtta atgtccaaca atgttcaaat agttagacag   6480
caaagttact ctatcatgtc cataataaag gaggaagtct tagcatatgt agtacaatta   6540
ccactatatg gtgtaataga tacaccttgt tggaaactgc acacatcccc tctatgtaca   6600
accaacacaa aggaagggtc caacatctgt ttaacaagaa ccgacagagg atggtactgt   6660
gacaatgcag gatcagtatc tttcttccca ctagctgaaa catgtaaagt tcaatcgaat   6720
cgagtatttt gtgacacaat gaacagttta acattaccaa gtgaagtaaa tctctgcaac   6780
attgacatat tcaaccccaa atatgattgc aaaattatga cttcaaaaac agatgtaagc   6840
agctccgtta tcacatctct aggagccatt gtgtcatgct atggcaaaac taaatgtaca   6900
gcatccaata aaaatcgtgg aatcataaag acattttcta acgggtgcga ttatgtatca   6960
aataaggggg ttgacactgt gtctgtaggt aatacattat attatgtaaa taagcaagaa   7020
ggcaaaagtc tctatgtaaa aggtgaacca ataataaatt tctatgaccc attagtgttc   7080
ccctctgatg aatttgatgc atcaatatct caagtcaatg agaagattaa ccagagccta   7140
gcatttattc gtaaatccga tgaattatta cataatgtaa atgctggtaa atccaccata   7200
aatatcatga taactactat aattatagtg attatagtaa tattgttatc attaattgcc   7260
gttggactgc tcctatactg caaggccaga agcacaccag tcacactaag caaggatcaa   7320
ctgagtggta taaataatat tgcatttagt aactaaataa aaatagcacc taatcatgtt   7380
cttacaatgg tttcatatct gctcatagac aacccatcta tcattggatt ttcttaaaat   7440
ctgaacttca tcgaaactct catctataaa ccatctcact tacattattt aagtagattc   7500
ctagtttata gttatataaa acaattgaat accagattaa cttactattt gtaaaaaatg   7560
agaactgggg caaatatgtc acgaaggaat ccttgcaaat ttgaaattcg aggtcattgc   7620
ttgaatggta agaggtgtca ttttagtcat aattattttg aatggccacc ccatgcactg   7680
cttgtaagac aaaactttat gttaaacaga atacttaagt ctatggataa aagcatcgat   7740
actttatcag aaataagtgg agctgcagag ttggacagaa cagaagagta tgccctcggt   7800
gtagttggag tgctagagag ttatatagga tctataaata atataactaa acaatcagca   7860
tgtgttgcca tgagcaaact cctcactgaa ctcaacagtg atgacatcaa aaaactgagg   7920
gacaatgaag agccaaattc acccaagata agagtgtaca atactgtcat atcatatatt   7980
gaaagcaaca ggaaaaacaa taaacaaact atccatctgt taaaaagatt gccagcagac   8040
gtattgaaga aaaccataaa aaccacattg gatatccaca agagcataac catcaataac   8100
ccaaaagaat caactgttag tgatataaac gaccatgcca aaaataatga tactacctga   8160
caaatatcct tgtagtataa attccatact aataacaagt agttgtagag ttactatgta   8220
taatcaaaag aacacactat atttcaatca aaacaaccaa aataaccata tatactcacc   8280
gaatcaacca ttcaatgaaa tccattggac ctctcaagac ttgattgatg caattcaaaa   8340
```

ttttctacaa catctaggta ttactgatga tatatacaca atatatatat tagtgtcata 8400
acactcaatc ctaatgctta ccacatcatc aaactattaa ctcaaacaat tcaagccatg 8460
ggacaaaatg gatcccatta ttaatggaaa ttctgctaat gtgtatctaa ccgatagtta 8520
tttaaaaggt gttatttctt tctcagaatg taatgcttta ggaagttaca tattcaatgg 8580
tccttatctc aaaaatgatt ataccaactt aattagtaga caaaatccat taatagaaca 8640
cataaatcta aagaaactaa atataacaca gtccttaatg tctaagtatc ataaaggtga 8700
aataaaaata gaagaaccta cttattttca gtcattactt atgacataca agagtatgac 8760
ctcgttagaa cagattacta ccactaattt acttaaaaag ataataagaa gagctataga 8820
aattagtgat gtcaaagtct atgctatatt gaataaactg gggcttaaag aaaaagacaa 8880
gattaaatcc aacaatggac aagatgaaga caactcagtt attacaacca taatcaaaga 8940
tgatatactt ttagctgtta aggataatca atctcatctt aaagcagtca aaaatcactc 9000
tacaaaacaa aaagatacaa tcaaaacaac actcttgaag aaattaatgt gttcaatgca 9060
acatcctcca tcatggttaa tacattggtt taatttatac acaaaattaa acaacatatt 9120
aacacagtat cgatcaagtg aggtaaaaaa ccatggtttt atattgatag acaatcatac 9180
tctcaatgga ttccaattta ttttgaatca atatggttgt atagtttatc ataaggaact 9240
caaaagaatt actgtgacaa cctataatca attcttgaca tggaaaaata ttagccttag 9300
tagattaaat gtttgtttaa ttacatggat tagtaactgt ttgaacacat taaataaaag 9360
cttaggctta agatgcggat tcaataatgt tatcttgaca caactattcc tctatggaga 9420
ttgtatacta aaactattcc acaatgaggg gttctacata ataaaagagg tagagggatt 9480
tattatgtct ctaattttaa atataacaga agaagatcaa ttcagaaaac ggttttataa 9540
tagtatgctc aacaacatca cagatgctgc taataaagct cagaaaaatc tgctatcaag 9600
agtatgtcat acattattag ataagacagt atccgataat ataataaatg gcagatggat 9660
aattctatta agtaagttcc ttaaattaat taagcttgca ggtgacaata accttaacaa 9720
tctgagtgaa ttatattttt tgttcagaat atttggacac ccaatggtag atgaaagaca 9780
agccatggat gctgttaaag ttaattgcaa cgagaccaaa ttttacttgt taagcagttt 9840
gagtatgtta agaggtgcct ttatatatag aattataaaa ggatttgtaa ataattacaa 9900
cagatggcct actttaagga atgctattgt tttaccctta agatggttaa cttactataa 9960
actaaacact tatccttcct tgttggaact tacagaaaga gatttgattg ttttatcagg 10020
actacgtttc tatcgtgagt ttcggttgcc taaaaaagtg gatcttgaaa tgatcataaa 10080
tgataaggct atatcacctc ctaaaaattt gatatggact agtttcccta gaaattatat 10140
gccgtcacac atacaaaatt atatagaaca tgaaaaatta aaattttccg agagtgataa 10200
atcaagaaga gtattagagt actatttaag agataacaaa ttcaatgaat gtgatttata 10260
caactgtgta gttaatcaaa gttatcttaa caaccctaat catgtggtat ctttgacagg 10320
caaagaaaga gaactcagtg taggtagaat gtttgcaatg caaccaggaa tgttcagaca 10380
agttcaaata ttagcagaga aaatgatagc tgaaaacatt ttacaattct ttcctgaaag 10440
tcttacaaga tatggtgatc tagaactaca gaaaatatta gaattgaaag caggaataag 10500
taacaaatca aatcgttaca atgataatta caacaattac attagtaagt gctctatcat 10560
cacagatctc agcaaattca atcaagcatt tcgatatgaa acatcatgta tttgtagtga 10620
tgtactggat gaactgcatg gtgtacaatc tctatttttc tggttacatt tagctattcc 10680
tcatgtcaca ataatatgca catataggca tgcaccccc tatataagag atcatattgt 10740
agatcttaac aatgtagatg aacaaagtgg attatataga tatcatatgg gtggtatcga 10800
agggtggtgt caaaaactat ggaccataga agctatatca ctattggatc taatatctct 10860
caaagggaaa ttctcaatta ctgctttaat taatggtgac aatcaatcaa tagatataag 10920
taaaccagtc agactcatgg aaggtcaaac tcatgctcaa gcagattatt tgctagcatt 10980
aaatagtctt aaattactgt ataaagagta tgcaggcata ggccacaaat taaaaggaac 11040
tgagacttat atatcaagag atatgcaatt tatgagtaaa acaattcaac ataacggtgt 11100
atattaccca gctagtataa agaaagtcct aagagtggga ccgtggataa acactatact 11160
tgatgatttc aaagtgagtc tagaatctat aggtagtttg acacaagaat tagaatatag 11220
aggagaaagt ctattatgca gtttaatatt tagaaatgta tggttatata atcaaattgc 11280
tttacaacta aaaaatcatg cattatgtaa caataaatta tatttggaca tattaaaggt 11340
tctgaaacac ttaaaaacct tttttaatct tgataatatt gatacagcat taacattgta 11400
tatgaatttg cccatgttat ttggtggtgg tgatcccaac ttgttatatc gaagtttcta 11460
tagaagaact cctgatttcc tcacagaggc tatagttcac tctgtgttca tacttagtta 11520
ttatacaaac catgatttaa aagataaact tcaagatctg tcagatgata gattgaataa 11580
gttcttaaca tgcataatca catttgacaa aaaccctaat gctgaattcg taacattgat 11640
gagagatcct caagctttag ggtctgagag acaagctaaa attactagcg aaatcaatag 11700
actggcagtt actgaggttt tgagcacagc tccaaacaaa atattctcca aaagtgcaca 11760
acactatacc actacagaga tagatctaaa tgatattatg caaaatatag aacctacata 11820
tcctcacggg ctaagagttg tttatgaaag tttacccttt tataaagcag agaaaatagt 11880
aaatcttata tccggtacaa aatctataac taacatactg gaaaagactt ctgccataga 11940
cttaacagat attgatagag ccactgagat gatgaggaaa aacataactt tgcttataag 12000
gatatttcca ttagattgta acagagataa aagggaaata ttgagtatgg aaaacctaag 12060
tattactgaa ttaagcaaat atgttaggga aagatcttgg tctttatcca atatagttgg 12120
tgttacatca cctagtatca tgtatacaat ggacatcaaa tatacaacaa gcactatagc 12180
tagtggcata atcatagaga aatataatgt taacagttta acacgtggtg agagaggacc 12240
cactaaacca tgggttggtt catctacaca agagaaaaaa acaatgccag tttataatag 12300
acaagtttta accaaaaaac agagagatca aatagatcta ttagcaaaat tggattgggt 12360
gtatgcatct atagataaca aggatgaatt catggaagaa cttagcatag gaattcttgg 12420
gttaacatat gagaaagcca aaaaattatt tccacaatat ttaagtgtta actatttgca 12480
tcgccttaca gtcagtagta gaccatgtga attccctgca tcaataccag cttatagaac 12540
tacaaattat cactttgata ctagccctat taatcgcata ttaacagaaa agtatggtga 12600
tgaagatatt gatatagtat tccaaaactg tataagcttt ggccttagct taatgtcagt 12660
agtagaacaa tttactaatg tatgtcctaa cagaattatt cttataccta agcttaatga 12720
gatacattta atgaaacctc ccatattcac aggtgatgtt gatattcaca agttaaaaca 12780
agtgatacaa aaacagcata tgtttttacc agacaaaata agtttgactc aatatgtgga 12840
attattctta agtaataaaa cactcaaatc tggatctcat gttaattcta atttaatatt 12900
ggcgcataag atatctgact attttcataa tacttacatt ttaagtacta atttagctgg 12960
acattggatt ctgattatac aacttatgaa agattctaag ggtatttttg aaaaagattg 13020
gggagaggga tatataactg atcatatgtt cattaatttg aaagttttct tcaatgctta 13080

-continued

```
taagacctat ctcttgtgtt ttcataaagg ttacggcaga gcaaagctgg agtgtgatat  13140
gaatacttca gatctcctat gtgtattgga attaatagac agtagttatt ggaagtctat  13200
gtctaaggta tttttagaac aaaaagttat caaatacatt cttagccagg atgcaagttt  13260
acatagagta aaaggatgtc atagcttcaa actatggttt cttaaacgtc ttaatgtagc  13320
agaattcaca gtttgccctt gggttgttaa catagattat catccaacac atatgaaagc  13380
aatattaact tatatagatc ttgttagaat gggattgata aatatagata aaatatacat  13440
taaaaataaa cacaaattca atgatgaatt ttatacttct aatctctttt acattaatta  13500
taacttctca gataatactc atctattaac taaacatata aggattgcta attctgaatt  13560
agaaaataat tacaacaaat tatatcatcc tacaccagaa accctagaaa atatactaac  13620
caatccggtt aaatgtaatg acaaaaagac actgaatgac tattgtatag gtaaaaatgt  13680
tgactcaata atgttaccat tgttatctaa taagaagctt attaaatcgc ctacaatgat  13740
tagaaccaat tacagcaaac aagatttgta taatttattt cctacggttg tgattgataa  13800
aattatagat cattcaggta atacagccaa atctaaccaa ctttacacta ctacttctca  13860
tcaaatacct ttagtgcaca atagcacatc actttattgc atgcttcctt ggcatcatat  13920
taatagattc aattttgtat ttagttctac aggttgtaaa attagtatag agtatatttt  13980
aaaagacctt ataattaaag atcctaattg tatagcattc ataggtgaag gagcagggaa  14040
tttattattg cgtacagtag tggaacttca tcccgatata agatatattt acagaagtct  14100
gaaggattgc aatgatcata gtttacctat tgagttttta aggctgtaca atggacatat  14160
caacattgat tatggtgaaa atttgaccat tcctgctaca gatgcaacca acaacattca  14220
ttggtcttat ttacatataa agtttgctga acctatcagt ctttttgtct gtgatgctga  14280
attgcctgta acagtcaact ggagtaaaat tataatagag tggagcaagc atgtaagaaa  14340
atgcaagtac tgttcctcag ttaataaatg tacgttaata gtaaaatatc atgctcaaga  14400
tgatatcgat ttcaaattag acaatataac tatattaaaa acttatgtat gcttaggcag  14460
taagttaaag gggtctgaag tttacttagt ccttacaata ggtcctgcaa atgtgttccc  14520
agtatttaat gtagtacaaa atgctaaatt gatactatca agaaccaaaa atttcatcat  14580
gcctaagaag gctgataaag agtctattga tgcaaatatt aaaagtttga taccctttct  14640
ttgttaccct ataacaaaaa aaggaattaa tactgcattg tcaaaactaa agagtgttgt  14700
tagtggagat atactatcat attctatagc aggacgtaat gaagttttca gcaataaact  14760
tataaatcat aagcatatga acatcttaaa atggttcaat catgttttaa atttcagatc  14820
aacagaacta aactataatc atttatatat ggtagaatct acatatcctt atctaagtga  14880
attgttaaac agcttgacaa ctaatgaact taaaaaactg attaaaatca caggtagttt  14940
gttatacaac tttcataatg aataatgaat aaaaatctta tattaaaaat tcccatagct  15000
acacactaac actgtattca attatagtta tttaaaatta aaaattatat aattttttaa  15060
taacttttag tgaactaatc ctaaaattat cattttgatc taggaggaat aaatttaaat  15120
ccaaatctaa ttggtttata tgtatattaa ctaaactacg agatattagt tttgacact  15180
tttttctcg t                                                   15191
```